United States Patent
Lim et al.

(10) Patent No.: US 9,023,865 B2
(45) Date of Patent: May 5, 2015

(54) COMPOUNDS THAT ARE ERK INHIBITORS

(71) Applicants: Jongwon Lim, Lexington, MA (US);
Elizabeth Helen Kelley, Cambridge, MA (US); Joey L. Methot, Westwood, MA (US); Hua Zhou, Acton, MA (US); Alessia Petrocchi, Houston, TX (US); Umar Faruk Mansoor, Framingham, MA (US); Christian Fischer, Natick, MA (US); Brendan O'Boyle, Pittsburgh, PA (US); David Joseph Guerin, Natick, MA (US); Corey E. Bienstock, Natick, MA (US); Christopher W. Boyce, Flemington, NJ (US); Matthew H. Daniels, Somerville, MA (US); Danielle Falcone, Brookline, MA (US); Ronald D. Ferguson, Scotch Plains, NJ (US); Salem Fevrier, Cranford, NJ (US); Xianhai Huang, Warren, NJ (US); Kathryn Ann Lipford, Boston, MA (US); David L. Sloman, Brookline, MA (US); Kevin Wilson, Boston, MA (US); Wei Zhou, Scotch Plains, NJ (US); David Witter, Norfolk, MA (US); Milana M. Maletic, Summit, NJ (US); Phieng Siliphaivanh, Newton, MA (US)

(72) Inventors: Jongwon Lim, Lexington, MA (US); Elizabeth Helen Kelley, Cambridge, MA (US); Joey L. Methot, Westwood, MA (US); Hua Zhou, Acton, MA (US); Alessia Petrocchi, Houston, TX (US); Umar Faruk Mansoor, Framingham, MA (US); Christian Fischer, Natick, MA (US); Brendan O'Boyle, Pittsburgh, PA (US); David Joseph Guerin, Natick, MA (US); Corey E. Bienstock, Natick, MA (US); Christopher W. Boyce, Flemington, NJ (US); Matthew H. Daniels, Somerville, MA (US); Danielle Falcone, Brookline, MA (US); Ronald D. Ferguson, Scotch Plains, NJ (US); Salem Fevrier, Cranford, NJ (US); Xianhai Huang, Warren, NJ (US); Kathryn Ann Lipford, Boston, MA (US); David L. Sloman, Brookline, MA (US); Kevin Wilson, Boston, MA (US); Wei Zhou, Scotch Plains, NJ (US); David Witter, Norfolk, MA (US); Milana M. Maletic, Summit, NJ (US); Phieng Siliphaivanh, Newton, MA (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 14/353,381

(22) PCT Filed: Oct. 25, 2012

(86) PCT No.: PCT/US2012/061836
§ 371 (c)(1),
(2) Date: Apr. 22, 2014

(87) PCT Pub. No.: WO2013/063214
PCT Pub. Date: May 2, 2013

(65) Prior Publication Data
US 2014/0296203 A1    Oct. 2, 2014

Related U.S. Application Data

(60) Provisional application No. 61/552,194, filed on Oct. 27, 2011.

(51) Int. Cl.
C07D 401/14    (2006.01)
A61K 31/437    (2006.01)

(52) U.S. Cl.
CPC ............ *C07D 471/04* (2013.01); *C07D 519/00* (2013.01); *A61K 31/437* (2013.01); *A61K 31/444* (2013.01); *A61K 31/4545* (2013.01); *A61K 31/4709* (2013.01); *A61K 31/496* (2013.01); *A61K 31/501* (2013.01); *A61K 31/506* (2013.01); *A61K 31/5377* (2013.01); *A61K 45/06* (2013.01)

(58) Field of Classification Search
CPC ............................ C07D 401/14; A61K 31/437
USPC ............................................ 514/303; 546/119
See application file for complete search history.

(56) References Cited

U.S. PATENT DOCUMENTS

2009/0163488 A1*    6/2009    Oguro et al. ............... 514/233.2

FOREIGN PATENT DOCUMENTS

WO    2011041152 A1    4/2011

* cited by examiner

*Primary Examiner* — Niloofar Rahmani
(74) *Attorney, Agent, or Firm* — Richard S. Parr; Laura M. Ginkel

(57)    ABSTRACT

Disclosed are the ERK inhibitors of formula (1): and the pharmaceutically acceptable salts thereof. Also disclosed are methods of treating cancer using the compounds of formula (1).

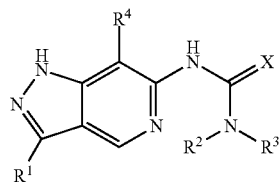

(1)

20 Claims, No Drawings

(51) Int. Cl.
*C07D 471/04* (2006.01)
*C07D 519/00* (2006.01)
*A61K 31/444* (2006.01)
*A61K 31/4545* (2006.01)
*A61K 31/4709* (2006.01)
*A61K 31/496* (2006.01)
*A61K 31/501* (2006.01)
*A61K 31/506* (2006.01)
*A61K 31/5377* (2006.01)
*A61K 45/06* (2006.01)

COMPOUNDS THAT ARE ERK INHIBITORS

BACKGROUND

The processes involved in tumor growth, progression, and metastasis are mediated by signaling pathways that are activated in cancer cells. The ERK pathway plays a central role in regulating mammalian cell growth by relaying extracellular signals from ligand-bound cell surface tyrosine kinase receptors such as erbB family, PDGF, FGF, and VEGF receptor tyrosine kinase. Activation of the ERK pathway is via a cascade of phosphorylation events that begins with activation of Ras. Activation of Ras leads to the recruitment and activation of Raf, a serine-threonine kinase. Activated Raf then phosphorylates and activates MEK½, which then phosphorylates and activates ERK½. When activated, ERK½ phosphorylates several downstream targets involved in a multitude of cellular events including cytoskeletal changes and transcriptional activation. The ERK/MAPK pathway is one of the most important for cell proliferation, and it is believed that the ERK/MAPK pathway is frequently activated in many tumors. Ras genes, which are upstream of ERK½, are mutated in several cancers including colorectal, melanoma, breast and pancreatic tumors. The high Ras activity is accompanied by elevated ERK activity in many human tumors. In addition, mutations of BRAF, a serine-threonine kinase of the Raf family, are associated with increased kinase activity. Mutations in BRAF have been identified in melanomas (60%), thyroid cancers (greater than 40%) and colorectal cancers. These observations indicate that the ERK½ signalling pathway is an attractive pathway for anticancer therapies in a broad spectrum of human tumours.

Therefore, a welcome contribution to the art would be small-molecules (i.e., compounds) that inhibit ERK activity (ERK2 activity), which small-molecules would be useful for treating a broad spectrum of cancers, such as, for example, melanoma, pancreatic cancer, thyroid cancer, colorectal cancer, lung cancer, breast cancer, and ovarian cancer. Such a contribution is provided by this invention.

SUMMARY OF THE INVENTION

This invention provides compounds that inhibit the activity of ERK2.

Thus, this invention provides compounds that are ERK inhibitors (i.e., ERK2 inhibitors), said compounds being of the formula (1):

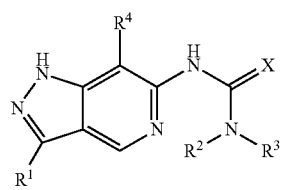

(1)

or the pharmaceutically acceptable salts, esters, solvates, and prodrugs thereof, wherein $R^1$, $R^2$, $R^3$, $R^4$ and X are defined below.

This invention provides: (1) compounds of formula (1); (2) compounds of formula (1) in pure or isolated form; (3) pharmaceutically acceptable salts of the compounds of formula (1); (4) solvates of the compounds of formula (1); (5) compounds of formula (1) wherein from one to all of the hydrogens are deuterium; (6) compounds of formula (1) wherein at least one H is deuterium; (7) compounds of formula (1) wherein 1 to 5H are deuterium; (8) compounds of formula (1) wherein 1 to 2H are deuterium; and (9) compounds of formula (1) wherein one H is deuterium.

This invention also provides the final compounds of Examples 1 to 95, and 116 to 701.

This invention also provides the final compounds of Examples 1 to 95.

This invention also provides the final compounds of Examples 116 to 701.

This invention also provides a pharmaceutical composition comprising an effective amount of at least one (e.g., 1) compound of formula (1) and a pharmaceutically acceptable carrier. This invention also provides a pharmaceutical composition comprising an effective amount of at least one (e.g., 1) compound of formula (1) and an effective amount of at least one (e.g., 1) other pharmaceutically active ingredient (such as, for example, a chemotherapeutic agent), and a pharmaceutically acceptable carrier.

This invention also provides a method of inhibiting ERK (i.e., inhibiting the activity of ERK2) in a patient in need of such treatment comprising administering to said patient an effective amount of at least one (e.g., 1) compound of formula (1).

This invention also provides a method for treating cancer in a patient in need of such treatment, said method comprising administering to said patient an effective amount of at least one (e.g., 1) compound of formula (1). This invention also provides a method for treating cancer in a patient in need of such treatment, said method comprising administering to said patient an effective amount of at least one (e.g., 1) compound of formula (1), in combination with an effective amount of at least one chemotherapeutic agent. The methods of this invention include the administration of a pharmaceutical composition comprising at least one (e.g., 1) compound of this invention and a pharmaceutically acceptable carrier. This invention also provides any of the above methods of treating cancer wherein the cancer is colorectal. This invention also provides any of the above methods of treating cancer wherein the cancer is melanoma.

The methods of treating cancers described herein can optionally include the administration of an effective amount of radiation (i.e., the methods of treating cancers described herein optionally include the administration of radiation therapy).

DETAILED DESCRIPTION OF THE INVENTION

All patents, publications and pending patent applications identified herein are hereby incorporated by reference.

As described herein, unless otherwise indicated, the use of a drug or compound in a specified period is per treatment cycle. For example, once a day means once per day of each day of the treatment cycle, and once a week means one time per week during the treatment cycle.

The following abbreviations have the following meanings unless defined otherwise: DCM is dichloromethane; DMF is N,N-dimethylformamide; Dppf is 1,1'-bis(diphenyl-phosphino)ferrocene; Me is methyl; MeOH is methanol; RT is room temperature; Tr is triphenyl methane; TFA is trifluoroacetic acid; TEA is triethylamine; CDI is 1,1'-carbonyldiimidazole; DIEA is diisopropylethylamine; and DMA is N,N-dimethylacetamide; SFC is Supercritical fluid chromatography; DEAD is diethyl azodicarboxylate; and HATU is N,N,N',N'-tetramethyl-O-(7-azabenzotriazol-1-yl) uroniumhexafluorophosphate As used herein, unless otherwise specified, the terms below have the meaning indicated.

The term "composition" is intended to encompass a product comprising the specified ingredients in the specified amounts, as well as any product which results, directly or indirectly, from combination of the specified ingredients in the specified amounts.

The term "anti-cancer agent" means a drug (medicament or pharmaceutically active ingredient) for treating cancer.

The term "antineoplastic agent" means a drug (medicament or pharmaceutically active ingredient) for treating cancer (i.e., a chemotherapeutic agent).

The term "at least one" means one or more than one. In one example "at least one" means 1-4, and in another example 1-3, and in another example 1-2, and in another example 1. The meaning of "at least one" with reference to the number of compounds of this invention is independent of the meaning with reference to the number of chemotherapeutic agents.

The term "chemotherapeutic agent" means a drug (medicament or pharmaceutically active ingredient) for treating cancer (i.e., and antineoplastic agent);

The term "compound" with reference to the antineoplastic agents, includes the agents that are antibodies.

The term "consecutively" means one following the other.

The term "effective amount" means a "therapeutically effective amount". The term "therapeutically effective amount" means that amount of active compound or pharmaceutical agent that elicits the biological or medicinal response in a tissue, system, animal or human that is being sought by a researcher, veterinarian, medical doctor or other clinician. Thus, for example, in the methods of treating cancer described herein "effective amount" (or "therapeutically effective amount") means, the amount of the compound (or drug), or radiation, that results in: (a) the reduction, alleviation or disappearance of one or more symptoms caused by the cancer, (b) the reduction of tumor size, (c) the elimination of the tumor, and/or (d) long-term disease stabilization (growth arrest) of the tumor. Also, for example, an effective amount, or a therapeutically effective amount of the ERK inhibitor (i.e., a compound of this invention) is that amount which results in the reduction in ERK (ERK2) activity and phosphorylation. The reduction in ERK activity may be determined by the analysis of pharmacodynamic markers such as phosphorylated RSK1,2 using techniques well known in the art.

The term "treating cancer" or "treatment of cancer" refers to administration to a mammal afflicted with a cancerous condition and refers to an effect that alleviates the cancerous condition by killing the cancerous cells, and also refers to an effect that results in the inhibition of growth and/or metastasis of the cancer.

The term "one or more" has the same meaning as "at least one".

The term "patient" means an animal, such as a mammal (e.g., a human being, and preferably a human being).

The term sequentially-represents (1) administration of one component of the method ((a) compound of the invention, or (b) chemotherapeutic agent, signal transduction inhibitor and/or radiation therapy) followed by administration of the other component or components. After administration of one component, the next component can be administered substantially immediately after the first component, or the next component can be administered after an effective time period after the first component. The effective time period is the amount of time given for realization of maximum benefit from the administration of the first component.

The term "solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like; "hydrate" is a solvate wherein the solvent molecule is $H_2O$.

The term "fused" with reference to, for example, two fused rings, means that the two rings have two atoms in common.

The term "monocyclic", as used to describe a ring, means the ring is a single ring (i.e., the ring is not a fused ring). Thus, for example, a "monocyclic heteroaryl ring" means a single heteroaryl ring. A bridged monocyclic ring means a monocyclic ring wherein two atoms in the ring are connected by a bridge. Thus, for example, a "bridged monocyclic heterocycloalkyl ring" means a monocyclic heterocycloalkyl ring wherein two atoms in the ring are connected by a bridge.

The term "administration" and variants thereof (e.g., "administering" a compound) in reference to a compound of the invention means introducing the compound or a prodrug of the compound into the system of the animal in need of treatment. When a compound of the invention or prodrug thereof is provided in combination with one or more other active agents (e.g., a cytotoxic agent, etc.), "administration" and its variants are each understood to include concurrent and sequential introduction of the compound or prodrug thereof and other agents.

As used herein, unless otherwise specified, the terms below have the meanings indicated, and unless otherwise specified, the definitions of each term (i.e, moiety or substituent) apply when that term is used individually or as a component of another term (e.g., the definition of aryl is the same for aryl and for the aryl portion of arylheterocycloalkyl, and the like).

The term "alkenyl" means an aliphatic hydrocarbon group (chain) comprising at least one carbon to carbon double bond, wherein the chain can be straight or branched, and wherein said group comprises about 2 to about 15 carbon atoms; Preferred alkenyl groups comprise about 2 to about 12 carbon atoms in the chain; and more preferably about 2 to about 6 carbon atoms in the chain; branched means that one or more lower alkyl groups, such as methyl, ethyl or propyl, or alkenyl groups are attached to a linear alkenyl chain; non-limiting examples of suitable alkenyl groups include ethenyl, propenyl, n-butenyl, 3-methylbut-2-enyl, n-pentenyl, octenyl and decenyl.

The term "alkoxy" means an alkyl-O— group (i.e., the bond to the parent moiety is through the ether oxygen) in which the alkyl group is as defined below. Non-limiting examples of suitable alkoxy groups include methoxy, ethoxy, n-propoxy, isopropoxy, n-butoxy and heptoxy.

The term "alkyl" (including the alkyl portions of other moieties, such as alkoxy) means an aliphatic hydrocarbon group (chain) that can be straight or branched wherein said group comprises about 1 to about 20 carbon atoms in the chain. In one example said alkyl group comprises about 1 to about 12 carbon atoms in the chain, in another example about 1 to about 6 carbon atoms in the chain; in another example 1 to about 4 carbon atoms in the chain; and in another example 1 to about 2 carbon atoms in the chain. Branched alkyl means that one or more lower alkyl groups, such as methyl, ethyl or propyl, are attached to a linear alkyl chain. "Lower alkyl" means a group comprising about 1 to about 6 carbon atoms in the chain, and said chain can be straight or branched.

The term "alkylene" (including the alkylene portions of other moieties, such as -alkylene-aryl) means a chain comprising at least one —(CH$_2$)— group. Examples of alkylene chains include, but are not limited to: —(CH$_2$)$_{1-6}$—, —(CH$_2$)$_{1-4}$—, —(CH$_2$)$_{1-2}$— and —(CH$_2$)—.

The term "amino" means an —NH$_2$ group.

The term "aryl" (sometimes abbreviated "ar") (including the aryl portion of fused heteroarylaryl and fused arylheterocycloalkyl) means an aromatic monocyclic or multicyclic ring system comprising about 6 to about 14 carbon atoms, preferably about 6 to about 10 carbon atoms. Non-limiting examples of suitable aryl groups include phenyl and naphthyl.

The term "arylalkyl" (or aralkyl) means an aryl-alkyl-group (i.e., the bond to the parent moiety is through the alkyl group) wherein the aryl and alkyl moieties are as defined above; preferred arylalkyls comprise a lower alkyl group; non-limiting examples of suitable aralkyl groups include benzyl, 2-phenethyl and naphthalenylmethyl.

The term "cycloalkyl" means a non-aromatic mono- or multicyclic ring system comprising about 3 to about 7 carbon atoms, preferably about 3 to about 6 carbon atoms. Non-limiting examples of suitable monocyclic cycloalkyls include cyclopropyl, cyclopentyl, cyclohexyl, cycloheptyl and the like. Non-limiting examples of suitable multicyclic cycloalkyls include 1-decalin, norbornyl, adamantyl and the like.

The term "cycloalkylalkyl" means a cycloalkyl-alkyl-group (i.e., the bond to the parent moiety is through the alkyl group) wherein the cycloalkyl and alkyl moieties are as defined above.

The term "cycloalkylalkenyl" means a cycloalkyl-alkenyl-group (i.e., the bond to the parent moiety is through the alkenyl group) wherein the cycloalkyl and alkenyl moieties are as defined above.

The term "halo" means fluoro, chloro, bromo, or iodo groups. Preferred halos are fluoro, chloro or bromo, and more preferred are fluoro and chloro.

The term "halogen" means fluorine, chlorine, bromine, or iodine. Preferred halogens are fluorine, chlorine and bromine.

The term "heteroaryl" means an aromatic monocyclic or multicyclic ring system (e.g., a fused ring system) comprising about 5 to about 14 ring atoms, preferably about 5 to about 10 ring atoms, in which one or more of the ring atoms is an element other than carbon, for example nitrogen, oxygen or sulfur, alone or in combination. Preferred heteroaryls comprise about 5 to about 6 ring atoms. The prefix aza, oxa or thia before the heteroaryl root name means that at least a nitrogen, oxygen or sulfur atom, respectively, is present as a ring atom. A nitrogen atom of a heteroaryl can be optionally oxidized to the corresponding N-oxide. The heteroaryl multicyclic ring system includes two rings fused together (i.e., there are two atoms common to both rings). Examples of the heteroaryl multicyclic ring system include fused heteroarylaryl rings (i.e., a heteroaryl ring fused to an aryl ring), and fused heteroarylheteroaryl rings (i.e., a heteroaryl ring fused to a heteroaryl ring). Non-limiting examples of suitable heteroaryls include pyridyl, pyrazinyl, furanyl, thienyl, pyrimidyl, isoxazolyl, isothiazolyl, oxazolyl, thiazolyl, pyrazolyl, furazanyl, pyrrolyl, pyrazolyl, triazolyl, 1,2,4-thiadiazolyl, pyrazinyl, pyridazinyl, quinoxalinyl, phthalazinyl, imidazo[1,2-a]pyridinyl, imidazo[2,1-b]thiazolyl, benzofurazanyl, indolyl, azaindolyl, benzimidazolyl, benzothienyl, benzopyrazolyl, quinolinyl, imidazolyl, thienopyridyl, quinazolinyl, thienopyrimidyl, pyrrolopyridyl, imidazopyridyl, isoquinolinyl, benzoazaindolyl, 1,2,4-triazinyl, benzothiazolyl, furopyridine

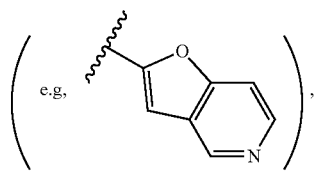

and the like.

The term "heteroarylalkyl" (or heteroaralkyl) means a heteroaryl-alkyl-group (i.e., the bond to the parent moiety is through the alkyl group) in which the heteroaryl and alkyl moieties are as defined above; preferred heteroarylalkyls comprise an alkyl group that is a lower alkyl group; non-limiting examples of suitable aralkyl groups include pyridyl-CH$_2$—, pyrimidinyl-CH$_2$—, imidazolyl-CH$_2$; pyrazinyl-CH$_2$—, and thiazolyl-CH$_2$—.

The term "fused heteroarylaryl" means a monocyclic heteroaryl ring fused to an aryl ring (i.e., the heteroaryl ring and the aryl ring have two atoms in common).

The term "fused (substituted heteroarylaryl)" means a monocyclic heteroaryl ring fused to an aryl ring (i.e., the heteroaryl ring and the aryl ring have two atoms in common) wherein one or both rings are substituted.

The term "fused heteroarylheteroaryl" means a monocyclic heteroaryl ring fused to a monocyclic heteroaryl ring (i.e., one heteroaryl ring has two atoms in common with the other heteroaryl ring), and each heteroaryl ring is independently selected.

The term "substituted fused heteroarylheteroaryl" (or "fused (substituted heteroarylheteroaryl)") means a monocyclic heteroaryl ring fused to a monocyclic heteroaryl ring (i.e., one heteroaryl ring has two atoms in common with the other heteroaryl ring), wherein one or both rings are substituted. Each heteroaryl ring is independently selected.

The term "fused arylheteroaryl" means an aryl ring fused to a monocyclic heteroaryl ring (i.e., the aryl ring and the heteroaryl ring have two atoms in common).

The term "fused (substituted arylheteroaryl)" means an aryl ring fused to a monocyclic heteroaryl ring (i.e., the aryl ring and the heteroaryl ring have two atoms in common) wherein one or both rings are substituted.

The term "fused cycloalkylheteroaryl" means a cycloalkyl ring fused to a monocyclic heteroaryl ring (i.e., the cycloalkyl ring and the heteroaryl ring have two atoms in common).

The term "substituted fused cycloalkylheteroaryl" means a cycloalkyl ring fused to a monocyclic heteroaryl ring (i.e., the cycloalkyl ring and the heteroaryl ring have two atoms in common), wherein one or both rings are substituted.

The term "fused heterocycloalkylaryl" means a heterocycloalkyl ring fused to an aryl ring (i.e., the heterocycloalkyl ring and the aryl ring have two atoms in common).

The term "substituted fused heterocycloalkylaryl" means a heterocycloalkyl ring fused to an aryl ring (i.e., the heterocycloalkyl ring and the aryl ring have two atoms in common), wherein one or both rings are substituted.

The term "fused cycloalkylaryl" means a cycloalkyl ring fused to an aryl ring (i.e., the cycloalkyl ring and the aryl ring have two atoms in common).

The term "substituted fused cycloalkylaryl" means a cycloalkyl ring fused to an aryl ring (i.e., the cycloalkyl ring and the aryl ring have two atoms in common), wherein one or both rings are substituted.

The term "heterocycloalkenyl" (or "heterocyclenyl") means a non-aromatic monocyclic or multicyclic ring system comprising about 3 to about 10 ring atoms, preferably about 5 to about 10 ring atoms, in which one or more of the atoms in the ring system is an element other than carbon (for example one or more heteroatoms independently selected from the group consisting of nitrogen, oxygen and sulfur atom), and which contains at least one carbon-carbon double bond or carbon-nitrogen double bond; there are no adjacent oxygen and/or sulfur atoms present in the ring system. Preferred heterocyclenyl rings contain about 5 to about 6 ring atoms. The prefix aza, oxa or thia before the heterocyclenyl root name means that at least a nitrogen, oxygen or sulfur atom, respectively, is present as a ring atom. The nitrogen or sulfur atom of the heterocyclenyl can be optionally oxidized to the corresponding N-oxide, S-oxide or S,S-dioxide. Non-limiting examples of suitable monocyclic azaheterocyclenyl groups include 1,2,3,4-tetrahydropyridine, 1,2-dihydropyridyl, 1,4-dihydropyridyl, 1,2,3,6-tetrahydropyridine, 1,4,5, 6-tetrahydropyrimidine, 2-pyrrolinyl, 3-pyrrolinyl, 2-imidazolinyl, 2-pyrazolinyl, and the like. Non-limiting examples of suitable oxaheterocyclenyl groups include 3,4-dihydro-2H-pyran, dihydrofuranyl, fluorodihydrofuranyl, and the like. A non-limiting example of a suitable multicyclic oxaheterocyclenyl group is 7-oxabicyclo[2.2.1]heptenyl; non-limiting examples of suitable monocyclic thiaheterocyclenyl rings include dihydrothiophenyl, dihydrothiopyranyl, and the like.

The term "heterocycloalkyl" (or "heterocyclyl") means a non-aromatic saturated monocyclic or multicyclic ring system comprising about 3 to about 10 ring atoms, preferably about 5 to about 10 ring atoms, in which one or more of the atoms in the ring system is an element other than carbon, for example nitrogen, oxygen or sulfur, alone or in combination. There are no adjacent oxygen and/or sulfur atoms present in the ring system. Preferred heterocyclyls contain about 5 to about 6 ring atoms. The prefix aza, oxa or thia before the heterocyclyl root name means that at least a nitrogen, oxygen or sulfur atom respectively is present as a ring atom. The nitrogen or sulfur atom of the heterocyclyl can be optionally oxidized to the corresponding N-oxide, S-oxide or S,S-dioxide. Non-limiting examples of suitable monocyclic heterocyclyl rings include azetidinyl, piperidyl, pyrrolidinyl, piperazinyl, morpholinyl, thiomorpholinyl, thiazolidinyl, 1,3-dioxolanyl, 1,4-dioxanyl, tetrahydrofuranyl, tetrahydrothiophenyl, tetrahydrothiopyranyl, and the like. The heterocycloalkyl rings of this invention can be "bridged heterocycloalkyl rings. The term "bridged heterocycloalkyl"" (or "bridged heterocyclyl") means a heterocycloalkyl group as defined above having an alkylene chain (generally a 1 or 2 carbon alkylene chain, not counting the atoms in the ring to which the alkylene chain is bound to) bridging two carbon atoms in the ring.

Any carbon or heteroatom with unsatisfied valences in the text, schemes, examples, structural formulae, and any tables herein is assumed to have the hydrogen atom or atoms to satisfy the valences. And any one or more of these hydrogen atoms can be deuterium.

Those skilled the art will appreciate that formulas showing a bond that does not have a substituent at the end of the bond represents a methyl group. Thus, for example,

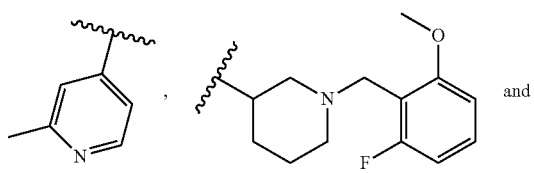

and

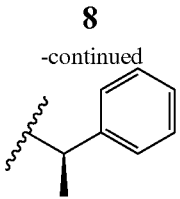

are the same moieties as:

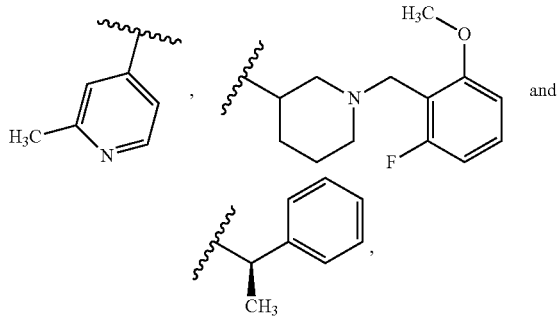

respectively.

One or more compounds of the invention may also exist as, or be optionally converted to, a solvate. Preparation of solvates is generally known. Thus, for example, M. Caira et al, *J. Pharmaceutical Sci.*, 93(3), 601-611 (2004) describe the preparation of the solvates of the antifungal fluconazole in ethyl acetate as well as from water. Similar preparations of solvates, hemisolvate, hydrates and the like are described by E. C. van Tonder et al, *AAPS PharmSciTech.*, 5(1), article 12 (2004); and A. L. Bingham et al, *Chem. Commun.*, 603-604 (2001). A typical, non-limiting, process involves dissolving the inventive compound in desired amounts of the desired solvent (organic or water or mixtures thereof) at a higher than ambient temperature, and cooling the solution at a rate sufficient to form crystals which are then isolated by standard methods. Analytical techniques such as, for example I. R. spectroscopy, show the presence of the solvent (or water) in the crystals as a solvate (or hydrate).

The term "pharmaceutical composition" is also intended to encompass both the bulk composition and individual dosage units comprised of more than one (e.g., two) pharmaceutically active agents such as, for example, a compound of the present invention and an additional agent selected from the lists of the additional agents described herein, along with any pharmaceutically inactive excipients. The bulk composition and each individual dosage unit can contain fixed amounts of the afore-said "more than one pharmaceutically active agents". The bulk composition is material that has not yet been formed into individual dosage units. An illustrative dosage unit is an oral dosage unit such as tablets, capsules, pills and the like. Similarly, the herein-described methods of treating a patient by administering a pharmaceutical composition of the present invention is also intended to encompass the administration of the afore-said bulk composition and individual dosage units.

The compounds of the present invention may have asymmetric centers, chiral axes, and chiral planes (as described in: E. L. Eliel and S. H. Wilen, Stereochemistry of Carbon Compounds, John Wiley & Sons, New York, 1994, pages 1119-1190), and occur as racemates, racemic mixtures, and as individual diastereomers, with all possible isomers and mixtures thereof, including optical isomers, being included in the present invention. In addition, the compounds disclosed herein may exist as tautomers and both tautomeric forms are intended to be encompassed by the scope of the invention, even though only one tautomeric structure is depicted. Also, for example, all keto-enol and imine-enamine forms of the compounds are included in the invention.

Tautomeric forms such as, for example, the moieties:

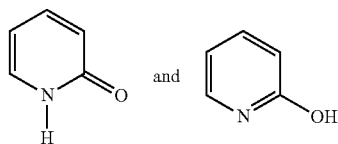 [SMILES: O=c1cccc[nH]1 ; Oc1ccccn1]

are considered equivalent in certain embodiments of this invention.

Thus, all stereoisomers (for example, geometric isomers, optical isomers and the like) of the present compounds (including those of the salts, solvates and prodrugs of the compounds as well as the salts and solvates of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention. Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the IUPAC 1974 Recommendations. The use of the terms "salt", "solvate" "prodrug" and the like, is intended to equally apply to the salt, solvate and prodrug of enantiomers, stereoisomers, rotamers, tautomers, racemates or prodrugs of the inventive compounds.

Diasteromeric mixtures can be separated into their individual diastereomers on the basis of their physical chemical differences by methods well known to those skilled in the art, such as, for example, by chromatography and/or fractional crystallization. Enantiomers can be separated by converting the enantiomeric mixture into a diasteromeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Also, some of the compounds of Formula (1) may be atropisomers and are considered as part of this invention. Enantiomers can also be separated by use of chiral HPLC column.

When any variable occurs more than one time in any constituent, its definition on each occurrence is independent at every other occurrence. Also, combinations of substituents and variables are permissible only if such combinations result in stable compounds. Lines drawn into the ring systems from substituents indicate that the indicated bond may be attached to any of the substitutable ring atoms. If the ring system is bicyclic, it is intended that the bond be attached to any of the suitable atoms on either ring of the bicyclic moiety.

It is understood that substituents and substitution patterns on the compounds of the instant invention can be selected by one of ordinary skill in the art to provide compounds that are chemically stable and that can be readily synthesized by techniques known in the art, as well as those methods set forth below, from readily available starting materials. If a substituent is itself substituted with more than one group, it is understood that these multiple groups may be on the same carbon or on different carbons, so long as a stable structure results. Also, "optionally substituted" means optional substitution with the specified groups, radicals or moieties.

It is understood that one or more silicon (Si) atoms can be incorporated into the compounds of the instant invention in place of one or more carbon atoms by one of ordinary skill in the art to provide compounds that are chemically stable and that can be readily synthesized by techniques known in the art from readily available starting materials. Carbon and silicon differ in their covalent radius leading to differences in bond distance and the steric arrangement when comparing analogous C-element and Si-element bonds. These differences lead to subtle changes in the size and shape of silicon-containing compounds when compared to carbon. One of ordinary skill in the art would understand that size and shape differences can lead to subtle or dramatic changes in potency, solubility, lack of off target activity, packaging properties, and so on. (Diass, J. O. et al. Organometallics (2006) 5:1188-1198; Showell, G. A. et al. Bioorganic & Medicinal Chemistry Letters (2006) 16:2555-2558).

Prodrugs of the compounds of the invention are also contemplated herein. The term "prodrug", as employed herein, denotes a compound that is a drug precursor which, upon administration to a subject, undergoes chemical conversion by metabolic or chemical processes to yield a compound of formula (1) or a salt and/or solvate thereof. A discussion of prodrugs is provided in T. Higuchi and V. Stella, *Pro-drugs as Novel Delivery Systems* (1987) 14 of the A.C.S. Symposium Series, and in *Bioreversible Carriers in Drug Design*, (1987) Edward B. Roche, ed., American Pharmaceutical Association and Pergamon Press, both of which are incorporated herein by reference thereto.

This invention also includes the compounds of this invention in isolated and purified form.

Polymorphic forms of the compounds of formula (1), and of the salts, solvates and prodrugs of the compounds of formula (1), are intended to be included in the present invention.

The pharmaceutically acceptable salts of the instant compounds can be synthesized from the compounds of this invention which contain a basic or acidic moiety by conventional chemical methods. Generally, the salts of the basic compounds are prepared either by ion exchange chromatography or by reacting the free base with stoichiometric amounts or with an excess of the desired salt-forming inorganic or organic acid in a suitable solvent or various combinations of solvents. Similarly, the salts of the acidic compounds are formed by reactions with the appropriate inorganic or organic base.

Thus, pharmaceutically acceptable salts of the compounds of this invention include the conventional non-toxic salts of the compounds of this invention as formed by reacting a basic instant compound with an inorganic or organic acid. For example, conventional non-toxic salts include those derived from inorganic acids such as hydrochloric, hydrobromic, sulfuric, sulfamic, phosphoric, nitric and the like, as well as salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxy-benzoic, fumaric, toluenesulfonic, methanesulfonic, ethane disulfonic, oxalic, isethionic, trifluoroacetic (TFA) and the like.

When the compound of the present invention is acidic, suitable "pharmaceutically acceptable salts" refers to salts prepared form pharmaceutically acceptable non-toxic bases including inorganic bases and organic bases. Salts derived from inorganic bases include aluminum, ammonium, calcium, copper, ferric, ferrous, lithium, magnesium, manganic salts, manganous, potassium, sodium, zinc and the like. Particularly preferred are the ammonium, calcium, magnesium, potassium and sodium salts. Salts derived from pharmaceutically acceptable organic non-toxic bases include salts of primary, secondary and tertiary amines, substituted amines including naturally occurring substituted amines, cyclic amines and basic ion exchange resins, such as arginine, betaine caffeine, choline, N,N$^1$-dibenzylethylenediamine, diethylamin, 2-diethylaminoethanol, 2-dimethylaminoethanol, ethanolamine, ethylenediamine, N-ethylmorpholine, N-ethylpiperidine, glutamine, glucosamine, histidine, hydrabamine, isopropylamine, lysine, methylglucamine, morpholine, piperazine, piperidine, polyamine resins, procaine, purines, theobromine, triethylamine, trimethylamine tripropylamine, tromethamine and the like.

The preparation of the pharmaceutically acceptable salts described above and other typical pharmaceutically acceptable salts is more fully described by Berg et al., "Pharmaceutical Salts," *J. Pharm. Sci.,* 1977:66:1-19.

It will also be noted that the compounds of the present invention are potentially internal salts or zwitterions, since under physiological conditions a deprotonated acidic moiety in the compound, such as a carboxyl group, may be anionic, and this electronic charge might then be balanced off internally against the cationic charge of a protonated or alkylated basic moiety, such as a quaternary nitrogen atom.

All such acid and base salts are intended to be pharmaceutically acceptable salts within the scope of the invention and all acid and base salts are considered equivalent to the free forms of the corresponding compounds for purposes of the invention.

In hetero-atom containing ring systems of this invention, there are no hydroxyl groups on carbon atoms adjacent to a N, O or S, and there are no N or S groups on carbon adjacent to another heteroatom. Thus, for example, in the ring:

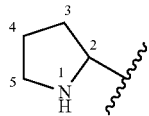

there is no —OH attached directly to carbons marked 2 and 5.

The term "purified", "in purified form" or "in isolated and purified form" for a compound refers to the physical state of said compound after being isolated from a synthetic process or natural source or combination thereof. Thus, the term "purified", "in purified form" or "in isolated and purified form" for a compound refers to the physical state of said compound after being obtained from a purification process or processes described herein or well known to the skilled artisan, in sufficient purity to be characterizable by standard analytical techniques described herein or well known to the skilled artisan.

When a functional group in a compound is termed "protected", this means that the group is in modified form to preclude undesired side reactions at the protected site when the compound is subjected to a reaction. Suitable protecting groups will be recognized by those with ordinary skill in the art as well as by reference to standard textbooks such as, for example, T. W. Greene et al, *Protective Groups in organic Synthesis* (1991), Wiley, New York.

The present invention also embraces isotopically-labelled compounds of the present invention which are identical to those recited herein, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorus, fluorine, chlorine, and iodine, such as $^2$H, $^3$H, $^{11}$C, $^{13}$C, $^{14}$C, $^{15}$N, $^{18}$O, $^{17}$O, $^{31}$P, $^{32}$P, $^{35}$S, $^{18}$F, $^{36}$Cl, and $^{123}$I, respectively.

Certain isotopically-labelled compounds of formula (1) (e.g., those labeled with $^3$H and $^{14}$C) are useful in compound and/or substrate tissue distribution assays. Tritiated (i.e., $^3$H) and carbon-14 (i.e., $^{14}$C) isotopes are particularly preferred for their ease of preparation and detectability. Certain isotopically-labelled compounds of Formula (1) can be useful for medical imaging purposes. E.g., those labeled with positron-emitting isotopes like $^{11}$C or $^{18}$F can be useful for application in Positron Emission Tomography (PET) and those labeled with gamma ray emitting isotopes like $^{123}$I can be useful for application in Single photon emission computed tomography (SPECT). Further, substitution with heavier isotopes such as deuterium (i.e., $^2$H) may afford certain therapeutic advantages resulting from greater metabolic stability (e.g., increased in vivo half-life or reduced dosage requirements) and hence may be preferred in some circumstances. Isotopically labeled compounds of Formula (I), in particular those containing isotopes with longer half lives (T½>1 day), can generally be prepared by following procedures analogous to those disclosed in the Schemes and/or in the Examples herein below, by substituting an appropriate isotopically labeled reagent for a non-isotopically labeled reagent.

This invention provides compounds of formula (1):

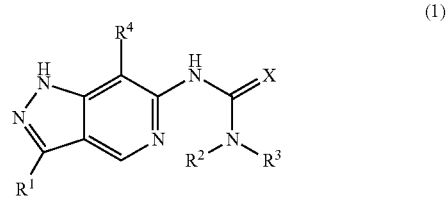

or a pharmaceutically acceptable salt thereof, wherein:

X is S or O;

R$^1$ is selected from the group consisting of: H, halo, —CF$_3$, —CN, (C$_1$-C$_6$)alkyl, substituted (C$_1$-C$_6$)alkyl, (C$_1$-C$_6$)alkenyl, (C$_3$-C$_6$)cycloalkyl, substituted (C$_3$-C$_6$)cycloalkyl, heteroaryl, substituted heteroaryl, heterocycloalkenyl-, substituted heterocycloalkenyl, —(C$_1$-C$_6$)alkyl-O—(C$_1$-C$_6$)alkyl, aryl, substituted aryl, —C(O)NH(C$_1$-C$_6$)alkyl, —C(O)N ((C$_1$-C$_6$)alkyl)$_2$ wherein each alkyl is independently selected, —C(O)—(C$_1$-C$_6$)alkyl-C(O)—(C$_1$-C$_6$)alkyl, —(C$_1$-C$_4$) alkyl-C(O)—O—(C$_1$-C$_4$)alkyl, —N((C$_1$-C$_6$)alkyl)-S(O)$_2$—(C$_1$-C$_6$)alkyl, —N((C$_1$-C$_6$)alkyl)-(C$_1$-C$_6$)alkyl-O—(C$_1$-C$_6$) alkyl, —C(O)NH—(C$_1$-C$_2$)alkyl-fused heteroarylheteroaryl, —C(O)NH—(C$_1$-C$_2$)alkyl-(substituted fused heteroarylheteroaryl), —C(O)NH—(C$_1$-C$_2$)alkyl-(C$_3$-C$_6$)cycloalkyl-N (R$^6$)$_2$, —C(O)NH—(C$_1$-C$_2$)alkyl-(substituted (C$_3$-C$_6$)cycloalkyl)-N(R$^6$)$_2$, —C(O)NH—(C$_1$-C$_2$) alkylheterocycloalkyl, —C(O)NH—(C$_1$-C$_2$)alkyl (substituted heterocycloalkyl), —C(O)NH—(C$_1$-C$_2$) alkylheteroaryl, —C(O)NH—(C$_1$-C$_2$)alkyl(substituted heteroaryl), —C(O)NH—(C$_1$-C$_6$)alkyl-(C$_3$-C$_6$)cycloalkyl, —C(O)NH—(C$_1$-C$_6$)alkyl-(substituted (C$_3$-C$_6$)cycloalkyl), —C(O)NH—(C$_1$-C$_6$)alkyl-O—(C$_1$-C$_6$)alkyl, —C(O)NH—(C$_1$-C$_6$)alkylheterocycloalkyl, —C(O)NH—(C$_1$-C$_6$)alkyl (substituted heterocycloalkyl), —C(O)NH—(C$_1$-C$_2$)-(bridged multicyclic cycloalkyl) (e.g., —C(O)NH—(C$_1$-C$_2$)-

(bridged tricyclic cycloalkyl), —C(O)NH—($C_1$-$C_2$)-(substituted bridged multicyclic cycloalkyl) (e.g., —C(O)NH—($C_1$-$C_2$)-(substituted bridged tricyclic cycloalkyl), —C(O)-heterocycloalkyl-S—($C_1$-$C_6$)alkyl, —C(O)-(substituted heterocycloalkyl-S—($C_1$-$C_6$)alkyl, —C(O)-heterocloalkyl, —C(O)-(substituted heterocycloalkyl), fused arylheteroaryl, fused (substituted arylheteroaryl), fused heteroarylheteroaryl, fused (substituted heteroarylheteroaryl), —($C_1$-$C_4$)alkyl-S(O)$_2$—($C_1$-$C_6$)alkyl, and —($C_1$-$C_4$)alkyl-NH—($C_1$-$C_6$)alkyl;

and wherein said substituted $R^1$ groups, other than said substituted ($C_1$-$C_6$)alkyl, are substituted with 1 to 3 substituents independently selected from the group consisting of: —($C_1$-$C_6$)alkyl, —($C_1$-$C_6$)alkoxy, halo, CN, —OH, —$CF_3$, =O, —$NH_2$, —NH($C_1$-$C_6$)alkyl, —S(O)$_2$($C_1$-$C_6$)alkyl, —($C_3$-$C_6$)cycloalkyl, —(($C_1$-$C_6$)alkyl)OH, —($C_3$-$C_6$)cycloalkyl-S—($C_3$-$C_6$)cycloalkyl, —N(($C_1$-$C_6$)alkyl)$_2$ wherein each alkyl is independently selected, —C(O)O—($C_1$-$C_6$)alkyl, —C(O)OH, —$OCF_3$, —C(O)NH($C_1$-$C_6$)alkyl, heteroaryl, —($C_1$-$C_6$)alkyl)-O—($C_1$-$C_6$)alkyl, fused heteroarylaryl-, heterocycloalkyl, and heterocycloalkenyl;

and wherein said substituted ($C_1$-$C_6$)alkyl $R^1$ group is substituted with 1 to 3 substituents independently selected from the group consisting of: —($C_1$-$C_6$)alkoxy, halo, CN, —OH, =O, —$CF_3$, —$NH_2$, —NH($C_1$-$C_6$)alkyl, —S(O)$_2$($C_1$-$C_6$)alkyl, fused heteroarylaryl-, heterocycloalkyl, and heterocycloalkenyl;

and wherein the alkyl moieties of the $R^1$ groups, other than ($C_1$-$C_6$)alkyl and substituted ($C_1$-$C_6$)alkyl, are optionally substituted with 1 to 3 substituents independently selected from the group consisting of: —($C_1$-$C_6$)alkoxy, halo, CN, —OH, =O, —$CF_3$, —$NH_2$, —NH($C_1$-$C_6$)alkyl, —S(O)$_2$($C_1$-$C_6$)alkyl, fused heteroarylaryl-, heterocycloalkyl, and heterocycloalkenyl;

$R^2$ is selected from the group consisting of: H, ($C_1$-$C_6$)alkyl, —($C_1$-$C_3$)alkyl-O—($C_1$-$C_2$)alkyl, aryl, arylalkyl-, heteroaryl, heteroarylalkyl-, substituted —($C_1$-$C_6$)alkyl, substituted aryl, substituted arylalkyl-, substituted heteroaryl, and substituted heteroarylalkyl-; wherein said substituted aryl, substituted arylalkyl, substituted heteroaryl and substituted heteroarylalkyl are substituted with 1 to 3 substitutents independently selected from the group consisting of aryl, substituted aryl, arylalkyl-, substituted arylalkyl-, halo, —OH, —C(O)N($R^6$)$_2$, —($C_1$-$C_6$)alkyl, —($C_1$-$C_6$)alkoxy, —$CF_3$, —($C_1$-$C_6$)alkyl-OH, —($C_1$-$C_6$)alkyl-$NH_2$, —NH—($CH_2$)$_{1-4}$—($C_6$-$C_{10}$)aryl; and wherein said $R^2$ which is substituted —($C_1$-$C_6$)alkyl is substituted with 1-3 substituents independently selected from the group consisting of: aryl, substituted aryl, arylalkyl-, substituted arylalkyl-, halo, —OH, —C(O)N($R^6$)$_2$, —($C_1$-$C_6$)alkoxy, —$CF_3$, —$NH_2$ and —NH—($CH_2$)$_{1-4}$—($C_6$-$C_{10}$)aryl;

$R^3$ is selected from the group consisting of: H, —($C_1$-$C_6$)alkyl, substituted —($C_1$-$C_6$)alkyl, heterocycloalkyl-, substituted heterocycloalkyl-, aryl, substituted aryl, arylalkyl-, substituted arylalkyl-, heteroaryl, substituted heteroaryl, heteroarylalkyl-, substituted heteroarylalkyl-, cycloalkyl, substituted cycloalkyl, cycloalkylalkyl, substituted cycloalkylalkyl-, cycloalkylalkenyl-, substituted cycloalkenyl, heterocycloalkylalkyl-, substituted heterocycloalkylalkyl, —($C_1$-$C_6$)alkyl($CF_3$)—C(O)O—($C_1$-$C_6$)alkyl, cycloalkenylalkyl-, substituted cycloalkenyl, fused cycloalkylheteroaryl, substituted fused cycloalkylheteroaryl, fused heterocycloalkylaryl, substituted fused heterocycloalkylaryl, fused cycloalkylaryl, substituted fused cycloalkylaryl, fused heteroarylaryl, substituted fused heteroarylaryl, —($C_1$-$C_6$)alkylheterocycloalkenyl, —($C_1$-$C_6$)alkyl(substituted heterocyloalkenyl), —($C_1$-$C_6$)alkylcyloalkyl-N—(—($C_1$-$C_6$)alkyl)$_2$ (wherein each alkyl is independently selected), —($C_1$-$C_6$)alkylheterocycloalkyl, —($C_1$-$C_6$)alkyl(substituted heterocycloalkyl), —($C_1$-$C_6$)alkylcycloalkylaryl, substituted —($C_1$-$C_6$)alkyl(substituted cycloalkylaryl), —($C_1$-$C_6$)alkyl-(fused arylheteroaryl), —($C_1$-$C_6$)alkyl-(substituted fused arylheteroaryl), an oxygen bridged ($C_3$-$C_6$) cycloalkyl ring (i.e., a cycloalkyl ring having an oxygen bridge between two carbon atoms in the ring), a substituted oxygen bridged ($C_3$-$C_6$) cycloalkyl ring (i.e., a cycloalkyl ring having an oxygen bridge between two carbon atoms in the ring, wherein said ring is substituted), —($C_1$-$C_6$)alkyl)-(fused heterocycloalkylaryl), —($C_1$-$C_6$)alkyl)-(substituted fused heterocycloalkylaryl), —($C_1$-$C_6$)alkyl)-(fused heteroarylaryl), —($C_1$-$C_6$)alkyl)-(substituted fused heteroarylaryl), —($C_1$-$C_6$)alkyl)-C(O)—NH-aryl, —($C_1$-$C_6$)alkyl)-C(O)—NH-(substituted aryl), —($C_3$-$C_6$)cycloalkyl-O-aryl, —($C_3$-$C_6$)cycloalkyl-O-(substituted aryl), a 5 and 4 membered heterocycloalkyl spiro ring, a substituted 5 and 4 membered heterocycloalkyl spiro ring, and —($C_1$-$C_6$)alkyl-O—($C_1$-$C_6$)alkyl;

and wherein said $R^3$ 5 and 4 membered heterocycloalkyl spiro ring comprises a 5 membered (including the carbon common to both rings) ring comprising one nitrogen, and a 4 membered (including the carbon common to both rings) ring comprising one oxygen atom;

and wherein said substituted $R^3$ groups, other than substituted —($C_1$-$C_6$)alkyl, are substituted with 1 to 3 substituents independently selected from the group consisting of: aryl, substituted aryl, arylalkyl-, substituted arylalkyl-, halo, —OH, —C(O)N($R^6$)$_2$, —($C_1$-$C_6$)alkyl, —($C_1$-$C_6$)alkoxy, —$CF_3$, —($C_1$-$C_6$)alkyl-OH, —($C_1$-$C_6$)alkyl-$NH_2$, —NH—($CH_2$)$_{1-4}$—($C_6$-$C_{10}$)aryl, —$NH_2$, =O, —CN, —$OCHF_2$, —$OCF_3$, —($C_3$-$C_6$)cycloalkyl, heterocycloalkyl, —($C_1$-$C_6$)alkyl-$CF_3$, —O—C(O)($C_1$-$C_6$)alkyl, —NHS(O)$_2$($C_1$-$C_6$)alkyl, —S(O)$_2$($C_1$-$C_6$)alkyl, —NHaryl, heteroaryl, —($C_1$-$C_6$)alkyl-N(($C_1$-$C_6$)alkyl)$_2$ wherein each alkyl is independently selected, —($C_1$-$C_6$)alkyl-O—($C_1$-$C_6$)alkyl, —N(($C_1$-$C_6$)alkyl)$_2$ (wherein each alkyl is independently selected), —($C_1$-$C_6$)alkyl-S(O)$_2$—($C_1$-$C_6$)alkyl, —(($C_1$-$C_6$)alkyl)(halo)$_{1-3}$, —S($C_1$-$C_6$)alkyl, —($C_1$-$C_6$)alkyl-O—($C_1$-$C_6$)alkyl-($C_3$-$C_6$)cycloalkyl, —($C_1$-$C_6$)alkyl-O—($C_1$-$C_6$)alkyl-O—($C_1$-$C_6$)alkyl, and —($C_1$-$C_6$)alkyl-O—($C_1$-$C_6$)alkyl(halo)$_{1-3}$;

and wherein said $R^3$ substituted —($C_1$-$C_6$)alkyl group is substituted with 1-3 substituents independently selected from the group consisting of: aryl, substituted aryl, arylalkyl-, substituted arylalkyl-, halo, —OH, —C(O)N($R^6$)$_2$, —($C_1$-$C_6$)alkoxy, —$CF_3$, —$NH_2$ and —NH—($CH_2$)$_{1-4}$—($C_6$-$C_{10}$)aryl, —N(($C_1$-$C_6$)alkyl)$_2$ (wherein each alkyl is independently selected), —C(O)O($C_1$-$C_6$)alkyl, —C(O)OH, —CN, —O-phenyl;

or said $R^2$ and said $R^3$, taken together with the nitrogen to which they are bonded to, form a 4-6 membered heterocycloalkyl ring, said ring optionally comprising an additional heteroatom selected from the group consisting of: N and O, and wherein said ring is optionally substituted with 1-3 substituents independently selected from the group consisting of: $C_1$-$C_6$)alkyl (e.g., methyl), aryl (e.g., phenyl), and substituted aryl (e.g., substituted phenyl) wherein said substituted aryl (e.g., substituted phenyl) is substituted with 1-3 substituents independently selected from the group consisting of halo (e.g., F);

$R^4$ is selected from the group consisting of: H, halo, —($C_1$-$C_6$)alkyl, —OH and —$NH_2$; and Each $R^6$ is independently selected from the group consisting of: H and —($C_1$-$C_6$)alkyl.

One embodiment of this invention is directed to compounds of formula (1), or a pharmaceutically acceptable salt thereof, wherein:

X is S or O;

$R^1$ is selected from the group consisting of: H, halo, $(C_1$-$C_6)$alkyl, $(C_1$-$C_6)$alkenyl, $(C_3$-$C_6)$cycloalkyl, heteroaryl, substituted heteroaryl, heterocycloalkenyl-, substituted heterocycloalkenyl, —$(C_1$-$C_6)$alkyl-O—$(C_1$-$C_6)$alkyl, aryl, and substituted aryl, and wherein said substituted heteroaryl, substituted heterocycloalkenyl, and substituted aryl are substituted with 1 to 3 substituents independently selected from the group consisting of: —$(C_1$-$C_6)$alkyl, —$(C_1$-$C_6)$alkoxy, halo, CN, =O, —$NH_2$, —NH$(C_1$-$C_6)$alkyl, —$S(O)_2(C_1$-$C_6)$alkyl, fused heteroarylaryl-, heterocycloalkyl, and heterocycloalkenyl;

$R^2$ is selected from the group consisting of: H, $(C_1$-$C_6)$alkyl, —$(C_1$-$C_3)$alkyl-O—$(C_1$-$C_2)$alkyl, aryl, arylalkyl-, heteroaryl, heteroarylalkyl-, substituted —$(C_1$-$C_6)$alkyl, substituted aryl, substituted arylalkyl-, substituted heteroaryl, and substituted heteroarylalkyl-; wherein said substituted aryl, substituted arylalkyl, substituted heteroaryl and substituted heteroarylalkyl are substituted with 1 to 3 substitutents independently selected from the group consisting of: aryl, substituted aryl, arylalkyl-, substituted arylalkyl-, halo, —OH, —C(O)N$(R^6)_2$, —$(C_1$-$C_6)$alkoxy, —$CF_3$, —$(C_1$-$C_6)$alkyl-OH, —$(C_1$-$C_6)$alkyl-$NH_2$, and —NH—$(CH_2)_{1-4}$—$(C_6$-$C_{10})$aryl; and wherein said $R^2$ which is substituted —$(C_1$-$C_6)$alkyl is substituted with 1-3 substituents independently selected from the group consisting of aryl, substituted aryl, arylalkyl-, substituted arylalkyl-, halo, —OH, —C(O)N$(R^6)_2$, —$(C_1$-$C_6)$alkoxy, —$CF_3$, —$NH_2$ and —NH—$(CH_2)_{1-4}$—$(C_6$-$C_{10})$aryl;

$R^3$ is selected from the group consisting of: H, —$(C_1$-$C_6)$alkyl, substituted —$(C_1$-$C_6)$alkyl, heterocycloalkyl-, substituted heterocycloalkyl-, aryl, substituted aryl, arylalkyl-, substituted arylalkyl-, heteroaryl, substituted heteroaryl, heteroarylalkyl-, substituted heteroarylalkyl-, cycloalkyl, substituted cycloalkyl, cycloalkylalkyl, substituted cycloalkylalkyl-, cycloalkylalkenyl-, substituted cycloalkenyl, and -alkyl-O-alkyl; and wherein said substituted heteroaryl, substituted heterocycloalkyl, substituted aryl, substituted arylalkyl, substituted heteroarylalkyl, substituted cycloalkyl, substituted cycloalkylalkyl, and substituted cycloalkenyl $R^3$ moieties are substituted with 1 to 3 substituents independently selected from the group consisting of aryl, substituted aryl, arylalkyl-, substituted arylalkyl-, halo, —OH, —C(O)N$(R^6)_2$, —$(C_1$-$C_6)$alkyl, —$(C_1$-$C_6)$alkoxy, —$CF_3$, —$(C_1$-$C_6)$alkyl-OH, —$(C_1$-$C_6)$alkyl-$NH_2$, and —NH—$(CH_2)_{1-4}$-$(C_6$-$C_{10})$aryl; and wherein said $R^3$ which is substituted —$(C_1$-$C_6)$alkyl is substituted with 1-3 substituents independently selected from the group consisting of aryl, substituted aryl, arylalkyl-, substituted arylalkyl-, halo, —OH, —C(O)N$(R^6)_2$, —$(C_1$-$C_6)$alkoxy, —$CF_3$, —$NH_2$ and —NH—$(CH_2)_{1-4}$—$(C_6$-$C_{10})$aryl;

$R^4$ is selected from the group consisting of: H, halo, —$(C_1$-$C_6)$alkyl, —OH and —$NH_2$; and Each $R^6$ is independently selected from the group consisting of: —$(C_1$-$C_6)$alkyl.

Examples of the ($C_1$ to $C_6$)alkyl substituent on the $R^1$ substituted heteroaryl, substituted heterocycloalkenyl, and substituted aryl groups include, but are not limited to ($C_1$-$C_3$) alkyl, and in one example methyl. Examples of the ($C_1$ to $C_6$)alkoxy substituent on the $R^1$ substituted heteroaryl, substituted heterocycloalkenyl, and substituted aryl groups include, but are not limited to ($C_1$-$C_3$)alkoxy. Examples of the halo substituent on the $R^1$ substituted heteroaryl, substituted heterocycloalkenyl, and substituted aryl groups include, but are not limited to F and Cl. Examples of the —$S(O)_2(C_1$-$C_6)$ alkyl substituent on the $R^1$ substituted heteroaryl, substituted heterocycloalkenyl, and substituted aryl groups include, but are not limited to —$S(O)_2(C_1$-$C_2)$alkyl, and in one example —$S(O)_2CH_3$.

The fused heteroarylaryl substituent on the $R^1$ substituted heteroaryl, substituted heterocycloalkenyl, and substituted aryl groups is a heteroaryl multicyclic ring system wherein a heteroaryl ring is fused to a aryl ring.

Examples of heteroaryls, as used in the definitions of $R^1$, include, for example: (i) a 5 or 6 membered ring comprising 1 to 3 heteroatoms independently selected from the group consisting of O, S, and N, and wherein the remaining ring atoms are carbon, (ii) a 5 or 6 membered ring comprising one nitrogen, and wherein the remaining ring atoms are carbon, (iii) a 5 or 6 membered ring comprising two nitrogens, and wherein the remaining ring atoms are carbon, (iv) a 9 to 10 membered two ring system (i.e., the two rings are fused together) comprising 1 to 3 heteroatoms independently selected from the group consisting of: O, S, and N, and wherein the remaining ring atoms are carbon, (v) a 9 to 10 membered two ring system (i.e., the two rings are fused together) comprising 1 to 3 heteroatoms independently selected from the group consisting of: S, and N, and wherein the remaining ring atoms are carbon.

Examples of the ($C_1$ to $C_6$)alkyl substituent on said $R^2$ substituted aryl, substituted arylalkyl, substituted heteroaryl and substituted heteroarylalkyl groups include, but are not limited to —$(C_1$-$C_4)$alkyl and —$(C_1$-$C_2)$alkyl. Examples of the ($C_1$ to $C_6$)alkoxy substituent on the $R^2$ substituted aryl, substituted arylalkyl, substituted heteroaryl and substituted heteroarylalkyl groups include, but are not limited to —$(C_1$-$C_4)$alkoxy and —$(C_1$-$C_2)$alkoxy. Examples of the —$(C_1$-$C_6)$alkyl-OH substituent on the $R^2$ substituted aryl, substituted arylalkyl, substituted heteroaryl and substituted heteroarylalkyl groups include, but are not limited to —$(C_1$-$C_4)$alkyl-OH and —$(C_1$-$C_2)$alkyl-OH. Examples of the —$(C_1$-$C_6)$alkyl-$NH_2$ substituent on the $R^2$ substituted aryl, substituted arylalkyl, substituted heteroaryl and substituted heteroarylalkyl groups include, but are not limited to —$(C_1$-$C_4)$alkyl-$NH_2$ and —$(C_1$-$C_2)$alkyl-$NH_2$.

Examples of the ($C_1$ to $C_6$)alkoxy substituent on the $R^2$ substituted —$(C_1$-$C_6)$alkyl groups include, but are not limited to —$(C_1$-$C_4)$alkoxy and —$(C_1$-$C_2)$alkoxy.

Examples of the ($C_1$ to $C_6$)alkyl substituent on said $R^3$ substituted heteroaryl, substituted heterocycloalkyl, substituted aryl, substituted arylalkyl, substituted heteroarylalkyl, substituted cycloalkyl, substituted cycloalkylalkyl, and substituted cycloalkenyl groups include, but are not limited to —$(C_1$-$C_4)$alkyl and —$(C_1$-$C_2)$alkyl. Examples of the ($C_1$ to $C_6$)alkoxy substituent on the $R^3$ substituted heteroaryl, substituted heterocycloalkyl, substituted aryl, substituted arylalkyl, substituted heteroarylalkyl, substituted cycloalkyl, substituted cycloalkylalkyl, and substituted cycloalkenyl groups include, but are not limited to —$(C_1$-$C_4)$alkoxy and —$(C_1$-$C_2)$alkoxy. Examples of the —$(C_1$-$C_6)$alkyl-OH substituent on the $R^3$ substituted heteroaryl, substituted heterocycloalkyl, substituted aryl, substituted arylalkyl, substituted heteroarylalkyl, substituted cycloalkyl, substituted cycloalkylalkyl, and substituted cycloalkenyl groups include, but are not limited to —$(C_1$-$C_4)$alkyl-OH and —$(C_1$-$C_2)$alkyl-OH. Examples of the —$(C_1$-$C_6)$alkyl-$NH_2$ substituent on the $R^3$ substituted heteroaryl, substituted heterocycloalkyl, substituted aryl, substituted arylalkyl, substituted heteroarylalkyl, substituted cycloalkyl, substituted cycloalkylalkyl, and substituted cycloalkenyl groups include, but are not limited to —$(C_1$-$C_4)$alkyl-$NH_2$ and —$(C_1$-$C_2)$alkyl-$NH_2$.

Examples of the ($C_1$ to $C_6$)alkoxy substituent on the $R^3$ substituted —($C_1$-$C_6$)alkyl groups include, but are not limited to —($C_1$-$C_4$)alkoxy and —($C_1$-$C_2$)alkoxy.

Examples of the $R^4$ halo groups include but are not limited to: Cl and F). Examples of the $R^4$—($C_1$-$C_6$)alkyl groups include, but are not limited to: —($C_1$-$C_4$)alkyl and —($C_1$-$C_2$)alkyl).

Examples of the $R^6$—($C_1$-$C_6$)alkyl groups include, but are not limited to: —($C_1$-$C_4$)alkyl and —($C_1$-$C_2$)alkyl).

The fused heteroarylaryl substituent on the $R^1$ substituted heteroaryl, substituted heterocycloalkenyl, and substituted aryl groups is a heteroaryl multicyclic ring system wherein a heteroaryl ring is fused to a aryl ring. Examples of these fused heteroarylaryl-substitutents include heteroaryl-phenyl-. The heteroaryl moiety, in one example, is a 5 to 6 membered heteroaryl ring comprising 1 to 3 heteroatoms selected from the group consisting of O, S and N, wherein the remaining atoms are carbon. Examples of fused heteroarylaryl-substitutents include, but are not limited to: benzopyrazolyl, benzothiazolyl and benzoimidazolyl.

Examples of the heterocycloalkyl substitutents on the substituted $R^1$ moietes include 4 to 6 membered heterocycloalkyl rings comprising 1 to 3 heteroatoms independently selected from the group consisting of O, S and N, and wherein the remaining atoms are carbon. Examples of heterocycloalkyl substitutents include, but are not limited to: pyrrolidinyl, oxetanyl, piperidinyl, piperazinyl and morpholinyl.

Examples of the heterocycloalkenyl substitutents on the substituted $R^1$ moieties include 5 to 6 membered heterocycloalkenyl rings comprising 1 to 3 (and in one example one) heteroatoms independently selected from the group consisting of O, S and N, and wherein the remaining atoms are carbon, and wherein there is at least one double bond in the ring. Examples of heterocycloalkenyl substitutents include but are not limited to: dihydropyranyl.

In one embodiment of this invention the $R^2$ group in formula (1) is in the trans position to X (i.e. the S or O atom). In another embodiment of this invention the $R^3$ group in formula (1) is in the cis position to X (i.e. the S or O atom). In another embodiment of this invention the $R^2$ group in formula (1) is in the trans position to X (i.e. the S or O atom) and the $R^3$ group in formula (1) is in the cis position to X (i.e. the S or O atom). Thus, in one embodiment of this invention the compounds of formula (1) are compounds of formula (1A):

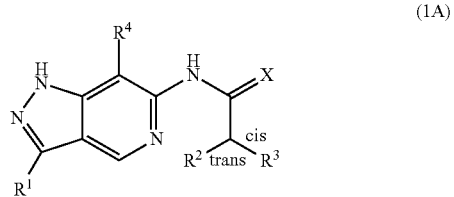

(1A)

One embodiment of this invention is directed to a pharmaceutically acceptable salt of the compounds of formula (1).

Another embodiment of this invention is directed to a pharmaceutically acceptable salt of the compounds of formula (1A).

Another embodiment of this invention is directed to the compounds of formula (1), that is the free base form of the compounds of formula (1).

Another embodiment of this invention is directed to the compounds of formula (1A), that is the free base form of the compounds of formula (1A).

In one embodiment of this invention X is O.
In another embodiment of this invention X is S.
Examples of $R^1$ include but are not limited to:

(a) halo, such as, for example, (i) Br: (ii) Cl and (iii) F;

(b) ($C_1$-$C_6$)alkyl, such as, for example: (i) ($C_1$-$C_4$)alkyl, (ii) ($C_1$-$C_3$)alkyl, and (iv) ($C_1$-$C_2$)alkyl;

(c) ($C_1$-$C_6$)alkenyl, such as, for example: (i) ($C_2$-$C_4$)alkenyl, and (ii) ($C_2$-$C_3$)alkenyl;

(d) ($C_3$-$C_6$)cycloalkyl, such as, for example: (i) ($C_3$-$C_6$) cycloalkyl, and (ii) ($C_3$-$C_5$)cycloalkyl;

(e) heteroaryl, such as, for example: (i) a 5 or 6 membered ring comprising 1 to 3 heteroatoms independently selected from the group consisting of: O, S, and N, and wherein the remaining ring atoms are carbon, (ii) a 5 or 6 membered ring comprising one nitrogen, and wherein the remaining ring atoms are carbon, (iii) a 5 or 6 membered ring comprising two nitrogens, and wherein the remaining ring atoms are carbon, (iv) a 9 to 10 membered two ring system (i.e., the two rings are fused together) comprising 1 to 3 heteroatoms independently selected from the group consisting of: O, S, and N, and wherein the remaining ring atoms are carbon, (v) a 9 to 10 membered two ring system (i.e., the two rings are fused together) comprising 1 to 3 heteroatoms independently selected from the group consisting of: S, and N, and wherein the remaining ring atoms are carbon;

(f) substituted heteroaryl, such as, for example: (i) a substituted 5 or 6 membered ring comprising 1 to 3 heteroatoms independently selected from the group consisting of: O, S, and N, and wherein the remaining ring atoms are carbon, (ii) a substituted 5 or 6 membered ring comprising one nitrogen, and wherein the remaining ring atoms are carbon, (iii) a substituted 5 or 6 membered ring comprising two nitrogens, and wherein the remaining ring atoms are carbon, (iv) a substituted 9 to 10 membered two ring system (i.e., the two rings are fused together) comprising 1 to 3 heteroatoms independently selected from the group consisting of: O, S, and N, and wherein the remaining ring atoms are carbon, (v) a substituted 9 to 10 membered two ring system (i.e., the two rings are fused together) comprising 1 to 3 heteroatoms independently selected from the group consisting of: S, and N, and wherein the remaining ring atoms are carbon, and (vi) any one of the substituted heteroaryl moieties described in (f)(i)-(v) substituted with 1 to 3 substitutents independently selected from the group consisting of: ($C_1$-$C_6$)alkyl (e.g., methyl), halo (e.g., F and Cl) and ($C_1$-$C_3$)alkoxy (e.g., isopropyloxy-);

(g) heterocycloalkenyl, such as, for example: (i) a 5 or 6 membered ring comprising one or two double bonds and comprising 1 to 3 heteroatoms selected from the group consisting of: O, S, and N, (ii) a 5 or 6 membered ring comprising one or two double bonds and comprising 1 heteroatom selected from the group consisting of: O, and N, (iii) a 6 membered ring comprising one or two double bonds and comprising 1 N, (iv) a 6 membered ring comprising two double bonds and comprising one N, (v) a 6 membered ring comprising one double bond and comprising one O;

(h) substituted heterocycloalkenyl, such as, for example: (i) a substituted 5 or 6 membered ring comprising one or two double bonds and comprising 1 to 3 heteroatoms selected from the group consisting of O, S, and N, (ii) a substituted 5 or 6 membered ring comprising one or two double bonds and comprising 1 heteroatom selected from the group consisting of: O, and N, (iii) a substituted 6 membered ring comprising one or two double bonds and comprising 1 N, (iv) a substituted 6 membered ring comprising two double bonds and comprising one N, (v) a 6 substituted membered ring comprising one double bond and comprising one O, and (vi) any one of the substituted heterocycloalkenyl moieties described in (h)(i)-(v) substituted with 1 to 3 substituents independently selected from the group consisting of: ($C_1$ to $C_6$)alkyl (e.g., ($C_1$-$C_3$)alkyl, and in one example methyl) and =O;

(i) —($C_1$-$C_6$)alkyl-O—($C_1$-$C_6$)alkyl, such as, for example: (i) a —($C_1$-$C_4$)alkyl-O—($C_1$-$C_3$)alkyl, and (ii) a-($C_1$-$C_3$)alkyl-O—($C_1$-$C_2$)alkyl);

(j) aryl, such as, for example: (i) a ($C_6$ to $C_{10}$) aryl, (ii) a ($C_6$ to $C_{10}$) multicyclic ring system (i.e., a fused ring system having two atoms common to both rings), wherein at least one ring is a ($C_6$ to $C_{10}$) aryl, and the remaining rings are selected from the group consisting of ($C_6$ to $C_{10}$) aryl heterocyloalkyl (as defined above), cycloalkyl (as defined above), and heterocyloalkenyl (as defined above), and (iii) wherein examples include, but are not limited to: phenyl, naphthyl and dihydrobenzodioxinyl, and in one example, phenyl and dihydrobenzodioxinyl; and (k) substituted aryl, such as, for example: (i) a substituted ($C_6$ to $C_{10}$) aryl, and (ii) a substituted ($C_6$ to $C_{10}$) multicyclic ring system (i.e., a fused ring system having two atoms common to both rings), wherein at least one ring is a ($C_6$ to $C_{10}$) aryl, and the remaining rings are selected from the group consisting of: ($C_6$ to $C_{10}$) aryl heterocyloalkyl (as defined above), cycloalkyl (as defined above), and heterocyloalkenyl (as defined above), and wherein examples include, but are not limited to: substituted phenyl (e.g., phenyl substituted with 1-3 substitutents independently selected from the group consisting of: halo (e.g., F and Cl), CN, and —S(O)$_2$($C_1$-$C_6$)alkyl (e.g., —S(O)$_2$($C_1$-$C_2$)alkyl, and —S(O)$_2$CH$_3$).

In one embodiment of this invention $R^1$ is selected from the group consisting of: propyl, pyridyl, pyridyl-N$^+$—O$^-$, 2-methylpyridyl, dihydropyran, pyrazolyl, N-methylpyrazolyl, fluorophenyl, phenyl, 2,6-dimethylpyridyl, fluoropyridyl, N-methylpyrazolyl-, N-methylpyrazolyl, N-methylindazolyl-, cyanophenyl, propenyl, Br, methyloxodihydropyridyl, pyrazolyl, chloropyridyl, aminopyrimindinyl, methylbenzothiazolyl, dihydrobenzodioxinyl, CH$_3$SO$_2$phenyl-, and methylpyridazinyl.

In another embodiment of this invention $R^1$ is selected from the group consisting of (1) —(CH$_2$)$_3$—O—CH$_3$, (2) CH$_3$CH$_2$CH$_2$—, (3) cyclopropyl, (4) CH$_3$CH=CH—, (5) Br, (6)

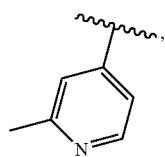

(7)

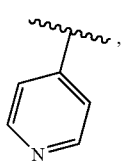

(8)

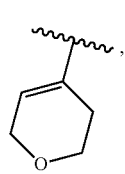

(9)

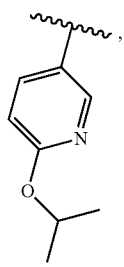

(10)

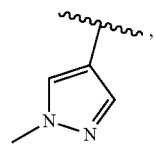

(11)

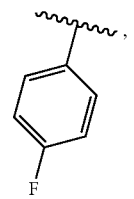

(12)

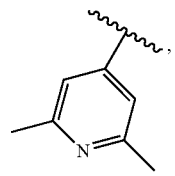

(13)

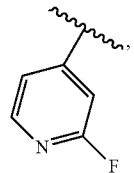

(14)

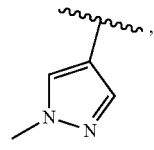

(15)

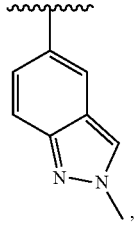

(16)

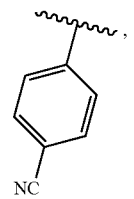

(17) 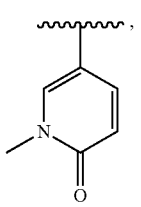

(18) 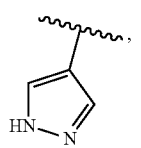

(19) 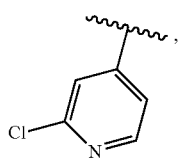

(20) 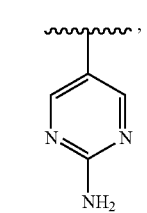

(21) 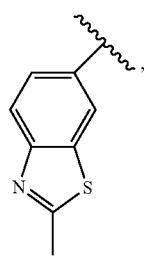

(22) 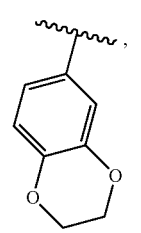

(23) 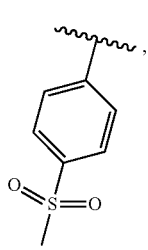

(24) 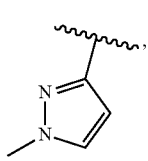

(25) 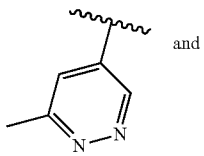
and

(26) 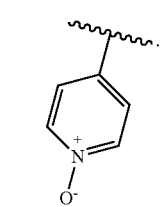

Examples $R^2$ include but are not limited to:
(a) H;
(b) $(C_1-C_6)$alkyl, such as, for example: (i) a $(C_1-C_4)$alkyl, (ii) a $(C_1-C_3)$alkyl, and (iii) a $(C_1-C_2)$alkyl, and (iv) in one example methyl; and
(c) —$(C_1-C_3)$alkyl-O—$(C_1-C_2)$alkyl, such as, for example: a —$CH_2CH_2OCH_3$.

Examples of $R^2$ also include the substituted arylalkyl- and substituted heteroarylalkyl-moieties substituted with 1 to 3 substitutents independently selected from the group consisting of: halo, —$(C_1-C_6)$alkoxy (e.g., —$(C_1-C_4)$alkoxy, and —$(C_1-C_2)$alkoxy), —$(C_1-C_6)$alkyl-OH (e.g., —$(C_1-C_4)$alkyl-OH and —$(C_1-C_2)$alkyl-OH), and —$(C_1-C_6)$alkyl-$NH_2$ (e.g., —$(C_1-C_4)$alkyl-$NH_2$ and —$(C_1-C_2)$alkyl-$NH_2$).

Examples of $R^2$ also include the substituted —$(C_1-C_6)$ alkyl moiety substituted with 1 to 3 substitutents independently selected from the group consisting of: halo, —$(C_1-C_6)$ alkoxy (e.g., —$(C_1-C_4)$alkoxy, and —$(C_1-C_2)$alkoxy), —OH, and $NH_2$.

Examples of the independently selected substitutents that are on the $R^2$ substituted groups (i.e., the groups that the substituted $R^2$ moiety is substituted with) include but are not limited to:
(a) aryl, such as, for example: (i) a $(C_6-C_{10})$aryl, and (ii) phenyl;
(b) substituted aryl, such as, for example: (i) a substituted a $(C_6-C_{10})$aryl, (ii) a substituted phenyl, and (iii) wherein the substituted aryl in (b)(i)-(ii) is substituted with 1-3 substituents independently selected from the group consisting of: halo (e.g., F and Cl);
(c) arylalkyl, such as, for example, (i) a single or multicyclic ring ($C_6$ to $C_{10}$)aryl($C_1-C_4$)alkyl-, (ii) a single or multicyclic ring ($C_6$ to $C_{10}$)aryl($C_1-C_3$)alkyl-), (iii) a phenyl-($C_1$-$C_4$)alkyl-, (iv) a phenyl-($C_1-C_3$)alkyl; (v) a phenyl-($C_1-C_2$) alkyl; (vi) a naphthyl-($C_1-C_4$)alkyl, (vii) a naphthyl-($C_1-C_2$) alkyl, (viii) and in one example benzyl;
(d) substituted arylalkyl-, such as, for example: (i) a substituted single or multicyclic ring ($C_6$ to $C_{10}$)aryl($C_1-C_4$) alkyl-, (ii) a substituted single or multicyclic ring ($C_6$ to $C_{10}$) aryl($C_1-C_3$)alkyl-), (iii) a substituted phenyl-($C_1-C_4$)alkyl-, (iv) a substituted phenyl-($C_1-C_3$)alkyl; (v) a substituted phenyl-($C_1-C_2$)alkyl; (vi) a substituted naphthyl-($C_1-C_4$)alkyl, (vii) a substituted naphthyl-($C_1-C_2$)alkyl, (viii) and in one example a substituted benzyl, and (ix) wherein the (d)(i)-(viii) are substituted with 1 to 3 substituents independently selected from the group consisting of: halo (e.g., F and Cl), and ($C_1-C_4$)alkoxy (e.g., ($C_1-C_3$) alkoxy, and in one example, —$OCH_3$)), and (x) in one example said substituted arylalkyl- is the substituted benzyl:

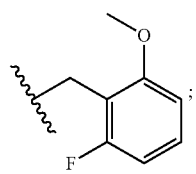 [SMILES: *Cc1c(F)cccc1OC]

(e) halo, such as, for example: F and Cl;

(f) alkyl, such as, for example: ($C_1$ to $C_3$) alkyl, and ($C_1$-$C_2$)alkyl;

(g) alkoxy, such as, for example; ($C_1$-$C_4$)alkoxy (e.g., ($C_1$-$C_3$) alkoxy, and in one example, —$OCH_3$)); and (h) —NH—$(CH_2)_{1-4}$—($C_6$-$C_{10}$)aryl, such as, for example: —NH—$(CH_2)_{1-4}$-phenyl, and —NH—$(CH_2)_{1-2}$-phenyl).

Examples of the $R^3$ heteroaryl groups include, but are not limited to: pyridyl, imidazolyl, thiazolyl, pyrimidinyl, pyrazinyl, pyrrolyl, oxazolyl, and triazinyl. Examples of the $R^3$ substituted heteroaryl groups include, but are not limited to: substituted pyridyl, substituted imidazolyl, substituted thiazolyl, substituted pyrimidinyl, substituted pyrazinyl, substituted pyrrolyl, substituted oxazolyl, and substituted triazinyl. Examples of the $R^3$ heteroaryl groups also include fused ring systems (fused ring heteroaryls), such as, for example, benzopyrazolyl, benzothiazolyl and benzoimidazolyl. Examples of the $R^3$ substituted heteroaryl groups also include substituted fused ring systems (fused ring heteroaryls), such as, for example, substituted benzopyrazolyl, substituted benzothiazolyl and substituted benzoimidazolyl.

Examples of $R^3$ include the substituted heterocycloalkyl, substituted aryl, substituted arylalkyl-, substituted heteroarylalkyl-, substituted cycloalkyl, substituted cycloalkylalkyl, and substituted cycloalkenyl moieties substituted with 1 to 3 substitutents independently selected from the group consisting of halo, —($C_1$-$C_6$)alkoxy (e.g., —($C_1$-$C_4$)alkoxy, and —($C_1$-$C_2$)alkoxy), —OH, —($C_1$-$C_6$)alkyl-OH (e.g., —($C_1$-$C_4$)alkyl-OH and —($C_1$-$C_2$)alkyl-OH), and —($C_1$-$C_6$)alkyl-$NH_2$ (e.g., —($C_1$-$C_4$)alkyl-$NH_2$ and —($C_1$-$C_2$)alkyl-$NH_2$).

Examples of $R^3$ also include the substituted —($C_1$-$C_6$) alkyl moiety substituted with 1 to 3 substitutents independently selected from the group consisting of: halo, —($C_1$-$C_6$) alkoxy (e.g., —($C_1$-$C_4$)alkoxy, and —($C_1$-$C_2$)alkoxy), —OH, and $NH_2$.

Examples of the independently selected substitutents that are on the $R^3$ substituted groups (i.e., the groups that the substituted $R^3$ moiety is substituted with) include but are not limited to:

(a) aryl, such as, for example: (i) a ($C_6$-$C_{10}$)aryl, and (ii) phenyl;

(b) substituted aryl, such as, for example: (i) a substituted a ($C_6$-$C_{10}$)aryl, (ii) a substituted phenyl, and (iii) wherein the substituted aryl in (b)(i)-(ii) is substituted with 1-3 substituents independently selected from the group consisting of: halo (e.g., F and Cl), —$CF_3$, —($C_1$-$C_6$)alkyl (e.g., —($C_1$-$C_4$) alkyl, —($C_1$-$C_2$)alkyl, and methyl), and —($C_1$-$C_6$)alkoxy (e.g., —($C_1$-$C_4$)alkoxy, —($C_1$-$C_2$)alkoxy, and methoxy);

(c) arylalkyl, such as, for example, (i) a single or multicyclic ring ($C_6$ to $C_{10}$)aryl($C_1$-$C_4$)alkyl-, (ii) a single or multicyclic ring ($C_6$ to $C_{10}$)aryl($C_1$-$C_3$)alkyl-), (iii) a phenyl-($C_1$-$C_4$)alkyl-, (iv) a phenyl-($C_1$-$C_3$)alkyl; (v) a phenyl-($C_1$-$C_2$) alkyl; (vi) a naphthyl-($C_1$-$C_4$)alkyl, (vii) a naphthyl-($C_1$-$C_2$) alkyl, (viii) and in one example benzyl;

(d) substituted arylalkyl-, such as, for example: (i) a substituted single or multicyclic ring ($C_6$ to $C_{10}$)aryl($C_1$-$C_4$) alkyl-, (ii) a substituted single or multicyclic ring ($C_6$ to $C_{10}$) aryl($C_1$-$C_3$)alkyl-), (iii) a substituted phenyl-($C_1$-$C_4$)alkyl-, (iv) a substituted phenyl-($C_1$-$C_3$)alkyl; (v) a substituted phenyl-($C_1$-$C_2$)alkyl; (vi) a substituted naphthyl-($C_1$-$C_4$)alkyl, (vii) a substituted naphthyl-($C_1$-$C_2$)alkyl, (viii) and in one example a substituted benzyl, and (ix) wherein the (d)(i)-(viii) are substituted with 1 to 3 substitutents independently selected from the group consisting of: halo (e.g., F and CO, and ($C_1$-$C_4$)alkoxy (e.g., ($C_1$-$C_3$) alkoxy, and in one example, —$OCH_3$)), and (x) in one example said substituted arylalkyl- is the substituted benzyl:

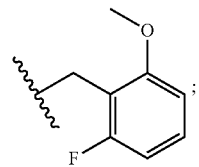 [SMILES: *Cc1c(F)cccc1OC]

(e) halo, such as, for example: F and Cl;

(f) alkyl, such as, for example: ($C_1$ to $C_3$) alkyl, and ($C_1$-$C_2$)alkyl;

(g) alkoxy, such as, for example; ($C_1$-$C_4$)alkoxy (e.g., ($C_1$-$C_3$) alkoxy, and in one example, —$OCH_3$)); and (h) —NH—$(CH_2)_{1-4}$—($C_6$-$C_{10}$)aryl, such as, for example: —NH—$(CH_2)_{1-4}$-phenyl, and —NH—$(CH_2)_{1-2}$-phenyl).

Examples $R^3$ include but are not limited to:

(a) H;

(b) —($C_1$-$C_6$)alkyl, such as, for example: a —($C_1$-$C_4$) alkyl;

(c) heterocycloalkyl, such as, for example: (i) a 4 to 6 membered ring comprising 1 to 3 heteroatoms selected from the group consisting of O, N and S wherein the remaining ring atoms are carbon; and (ii) a 4 to 6 membered ring comprising 1 to 3 N atoms wherein the remaining ring atoms are carbon;

(d) substituted heterocycloalkyl-, such as, for example: (i) a substituted 4 to 6 membered ring comprising 1 to 3 heteroatoms selected from the group consisting of O, N and S wherein the remaining ring atoms are carbon; (ii) a substituted 4 to 6 membered ring comprising 1 to 3 N atoms wherein the remaining ring atoms are carbon, (iii) any one of substituted heterocycloalkyls in (d)(i)-(ii) substituted with 1 to 3 substituents selected from the group consisting of: benzyl, and substituted benzyl, wherein said substituted benzyl is substituted with 1-3 substitutents independently selected from the group consisting of: halo (e.g., F), alkoxy (e.g., $C_1$-$C_3$alkoxy, and in one example —$OCH_3$), and (iv) any one of substituted heterocycloalkyls in (d)(i)-(ii) substituted with 1 substitutent selected from the group consisting of: aryl (e.g., phenyl), substituted aryl (e.g., substituted phenyl, such as phenyl substituted with 1-3 independently selected halos (such as F and Cl)), benzyl, and substituted benzyl, and wherein said substituted benzyl is substituted with 1-2 substituents independently selected from the group consisting of: halo (e.g., F), alkoxy (e.g., $C_1$-$C_3$alkoxy, and in one example —$OCH_3$);

(e) aryl, such as, for example: (i) a $C_6$ to $C_{10}$ single or multicyclic ring aryl (i.e., a fused ring system), (ii) phenyl, and (iii) naphthyl, and (iv) wherein a multicyclic ring aryl moiety comprises one ring that is aryl, and the remaining ring is selected from the group consisting of: aryl (e.g., phenyl) and ($C_3$ to $C_6$)cycloalkyl (e.g., ($C_3$ to $C_6$)cycloalkyl, such as, for example, pentyl), and the bond to the rest of the molecule can be through either ring;

(f) arylalkyl-, such as, for example: (i) a single or multicyclic ring ($C_6$ to $C_{10}$)aryl($C_1$-$C_4$)alkyl-, (ii) a single or multicyclic ring ($C_6$ to $C_{10}$)aryl($C_1$-$C_3$)alkyl-), (iii) a phenyl-($C_1$-

$C_4$)alkyl-, (iv) a phenyl-($C_1$-$C_3$)alkyl; (v) a phenyl-($C_1$-$C_2$) alkyl; (vi) a naphthyl-($C_1$-$C_4$)alkyl, and (vii) a naphthyl-($C_1$-$C_2$)alkyl;

(g) substituted arylalkyl-, such as, for example: (i) a substituted single or multicyclic ring ($C_6$ to $C_{10}$)aryl($C_1$-$C_4$) alkyl-, (ii) a substituted single or multicyclic ring ($C_6$ to $C_{10}$) aryl($C_1$-$C_3$)alkyl-), (iii) a substituted phenyl-($C_1$-$C_4$)alkyl-, (iv) a substituted phenyl-($C_1$-$C_3$)alkyl; (v) a substituted phenyl-($C_1$-$C_2$)alkyl; (vi) a substituted naphthyl-($C_1$-$C_4$)alkyl, and (vii) a substituted naphthyl-($C_1$-$C_2$)alkyl, and (viii) any one of (g)(i)-(vii) substituted with 1-3 substituents independently selected from the group consisting of: halo (e.g., F and Cl), —OH, —$CF_3$, and —($C_1$-$C_4$)alkoxy (e.g., —($C_1$-$C_3$) alkoxy, —($C_1$-$C_2$)alkoxy, and in one example —$OCH_3$), and (ix) wherein said substituted arylalkyl moieties in (viii) can be substituted on the aryl portion or the alkyl portion of the moiety;

(h) heteroarylalkyl-, such as, for example: (i) heteroaryl ($C_1$-$C_2$)alkyl-, (ii) heteroaryl($C_1$-$C_2$)alkyl- wherein said heteroaryl moiety comprises 5 to 6 ring atoms wherein 1 to 4 ring atoms are independently selected from the group consisting of: O, S and N, and the remaining ring atoms are carbon; (iii) heteroaryl($C_1$-$C_2$)alkyl- wherein said heteroaryl moiety comprises 5 to 6 ring atoms wherein 1 to 4 ring atoms are independently selected from the group consisting of: O, S and N, and the remaining ring atoms are carbon; (iv) heteroaryl($C_1$-$C_2$)alkyl- wherein said heteroaryl moiety comprises 5 ring atoms wherein 1 to 3 ring atoms are independently selected from the group consisting of O, N and S, and the remaining ring atoms are carbon, (v) heteroaryl($C_1$-$C_2$)alkyl- wherein said heteroaryl moiety comprises 5 ring atoms wherein 1 to 3 ring atoms are independently selected from the group consisting of O and N, and the remaining ring atoms are carbon, (vi) heteroaryl($C_1$-$C_2$)alkyl- wherein said heteroaryl moiety comprises 5 ring atoms wherein 1 to 3 ring atoms are independently selected from the group consisting of S and N, and the remaining ring atoms are carbon, (viii) heteroaryl($C_1$-$C_2$) alkyl- wherein said heteroaryl moiety comprises 5 ring atoms wherein 1 to 4 ring atoms are N, and the remaining ring atoms are carbon, (ix) heteroaryl($C_1$-$C_2$)alkyl- wherein said heteroaryl moiety comprises 5 ring atoms wherein 1 to 3 ring atoms are N, and the remaining ring atoms are carbon, (x) heteroaryl($C_1$-$C_2$)alkyl- wherein said heteroaryl moiety comprises 6 ring atoms wherein 1 to 3 ring atoms are independently selected from the group consisting of O, N and S, and the remaining ring atoms are carbon, (xi) heteroaryl($C_1$-$C_2$) alkyl- wherein said heteroaryl moiety comprises 6 ring atoms wherein 1 to 2 ring atoms are N, and the remaining ring atoms are carbon, (xii) heteroaryl($C_1$-$C_2$)alkyl- wherein said heteroaryl moiety comprises 6 ring atoms wherein 2 ring atoms are N, and the remaining ring atoms are carbon, and (xiii) heteroaryl($C_1$-$C_2$)alkyl- wherein said heteroaryl moiety comprises 6 ring atoms wherein 1 ring atom is N, and the remaining ring atoms are carbon;

(i) substituted heteroarylalkyl-, such as, for example: (i) substituted heteroaryl($C_1$-$C_2$)alkyl-, (ii) substituted heteroaryl($C_1$-$C_2$)alkyl- wherein said heteroaryl moiety comprises 5 to 6 ring atoms wherein 1 to 4 ring atoms are independently selected from the group consisting of: O, S and N, and the remaining ring atoms are carbon; (iii) substituted heteroaryl($C_1$-$C_2$)alkyl- wherein said heteroaryl moiety comprises 5 to 6 ring atoms wherein 1 to 4 ring atoms are independently selected from the group consisting of: O, S and N, and the remaining ring atoms are carbon; (iv) substituted heteroaryl($C_1$-$C_2$)alkyl- wherein said heteroaryl moiety comprises 5 ring atoms wherein 1 to 3 ring atoms are independently selected from the group consisting of O, N and S, and the remaining ring atoms are carbon, (v) substituted heteroaryl($C_1$-$C_2$)alkyl- wherein said heteroaryl moiety comprises 5 ring atoms wherein 1 to 3 ring atoms are independently selected from the group consisting of O and N, and the remaining ring atoms are carbon, (vi) substituted heteroaryl ($C_1$-$C_2$)alkyl- wherein said heteroaryl moiety comprises 5 ring atoms wherein 1 to 3 ring atoms are independently selected from the group consisting of S and N, and the remaining ring atoms are carbon, (vii) substituted heteroaryl($C_1$-$C_2$) alkyl- wherein said heteroaryl moiety comprises 5 ring atoms wherein 1 to 4 ring atoms are N, and the remaining ring atoms are carbon, (viii) substituted heteroaryl($C_1$-$C_2$)alkyl- wherein said heteroaryl moiety comprises 5 ring atoms wherein 1 to 3 ring atoms are N, and the remaining ring atoms are carbon, (ix) substituted heteroaryl($C_1$-$C_2$)alkyl- wherein said heteroaryl moiety comprises 6 ring atoms wherein 1 to 3 ring atoms are independently selected from the group consisting of O, N and S, and the remaining ring atoms are carbon, (x) substituted heteroaryl($C_1$-$C_2$)alkyl- wherein said heteroaryl moiety comprises 6 ring atoms wherein 1 to 2 ring atoms are N, and the remaining ring atoms are carbon, (xi) substituted heteroaryl($C_1$-$C_2$)alkyl- wherein said heteroaryl moiety comprises 6 ring atoms wherein 2 ring atoms are N, and the remaining ring atoms are carbon, (xii) substituted heteroaryl ($C_1$-$C_2$)alkyl- wherein said heteroaryl moiety comprises 6 ring atoms wherein 1 ring atom is N, and the remaining ring atoms are carbon, and (xiii) wherein any one of said (i)(i)-(xii) is substituted with 1 to 3 substitutents independently selected from the group consisting of: —($C_1$-$C_6$)alkyl (such as, for example: —($C_1$-$C_4$)alkyl and —($C_1$-$C_2$)alkyl, and in one example, methyl), halo (e.g., F and Cl and in one example F), and —NH—($CH_2$)$_{1-4}$—($C_6$-$C_{10}$)aryl (e.g., —NH—($CH_2$)$_{1-4}$-phenyl, and —NH—($CH_2$)$_{1-2}$-phenyl);

(j) cycloalkylalkyl- such as, for example: (i) a ($C_3$-$C_6$) cycloalkyl-($C_1$-$C_6$)alkyl-, and (ii) a ($C_3$-$C_5$)cycloalkyl-($C_1$-$C_2$)alkyl-;

(k) substituted cycloalkylalkyl-, such as, for example: (i) a substituted ($C_3$-$C_6$)cycloalkyl-($C_1$-$C_6$)alkyl-, (ii) a substituted ($C_3$-$C_5$)cycloalkyl-($C_1$-$C_2$)alkyl-, (iii) wherein (k)(i)-(ii) are substituted with 1 to 3 substituents independently selected from the group consisting of: —OH, halo, and —$CF_3$, (iv) where the substitutents in (iii) can be bound to the cycloalkyl moiety or the alkyl moiet, and (v) in one example said cycloalkyl moiety is cyclopropyl;

(l) cycloalkyl, such as, for example: a (i)($C_3$-$C_6$)cycloalkyl, (ii) a ($C_3$-$C_5$)cycloalkyl, and (iii) in one example, a cyclopropyl;

(m) cycloalkylalkenyl-, such as, for example: (i) a ($C_3$-$C_6$) cycloalkyl-($C_2$-$C_6$)alkenyl-, and (ii) a ($C_3$-$C_5$)cycloalkyl-($C_2$)alkenyl- (wherein one of the carbon atoms of the alkenyl group can be common to the cycloalkyl group), and (n)-alkyl-O-alkyl, such as, for example: (i) a —($C_1$-$C_4$)alkyl-O—($C_1$-$C_3$)alkyl, and (ii) a —($C_1$-$C_3$)alkyl-O—($C_1$-$C_2$)alkyl.

Examples of $R^3$ include, but are not limited to, the $R^3$ substitutents in the final compounds of Examples 1-95. Examples of $R^3$ also include, but are not limited to, the $R^3$ substitutents in the final compounds of Examples 116 to 701.

Examples of $R^3$ include, but are not limited to: (a) piperidinyl, (b) substituted piperidinyl, such as, for example (i) a N-substituted piperidinyl, (ii) a N-benzylpiperidinyl-, (iii) a N-(substituted benzyl)piperidinyl, and (iv) a N-(alkoxy, halobenzyl)piperidinyl), (c) —$CH_2$-phenyl, (d) substituted —$CH_2$-phenyl such as, for example: (i) a —$CH_2$— (monohalo substituted)phenyl, such as, for example, fluorophenyl-$CH_2$—, chlorophenyl-$CH_2$—, (ii) a —$CH_2$-(dihalo substituted)phenyl, such as, for example, dichlorophenyl-$CH_2$—, difluorophenyl-CH₂—, and chlorofluorophenyl-CH₂—, (iii) a —CH₂— (di(C₁-C₃)alkoxy substituted)phenyl, and (iv) a —CH₂—((C₁-C₃)alkoxy substituted)phenyl), (e) —(CH₂)-2-phenyl, (f) a hydroxy substituted —CH(CH₃)-phenyl, such as, for example, —CH(CH₂OH)-phenyl, (g) a monohalo substituted —CH(CH₃)-phenyl, such as, for example, chlorophenyl-CH(CH₃)—, and fluorophenyl-CH(CH₃)—, (h) a dihalo substituted —CH(CH₃)-phenyl, such as, for example, chlorofluorophenyl-CH(CH₃)—, (i) —CH₂-pyridyl, (j) —CH₂-oxadiazolyl, (k) substituted —CH₂-oxadiazolyl (e.g., C₁-C₂alkyl substituted oxadiazolyl), (l) —CH₂-naphthyl, (m) —CH₂-cyclopropyl, (n) t-butyl, (o) cyclopropylmethanol, (p) cyclopropylmethylene-, (q) azetidinyl, (r) methoxyethyl, (s) cyclopropyl-CH(CF₃)—, (t) N-methylimidazolyl-CH₂—, (u) methylthiazolyl-CH₂—, (v) (w) pyridyl-CH₂—, (x) pyridyl-(CH₂)₂—, (y) pyrazinyl-CH₂—, (z) pyridyl-CH(CH₃)—, (aa) fluoropyridyl-CH₂—, (ab) phenylethylaminopyridazinyl-, (ac) phenyl, (ad) chlorophenyl-C(CH₃)₂—, (ae) chlorophenyltetrahydropyranyl-, (af) dihydroindenyl, (ag) phenyl-CH(CH₃)—, and (ah) chlorophenylcyclopropyl-.

Examples of R³ also include, but are not limited to: (27) t-butyl, (28) —(CH₂)₂—O—CH₃,

(29)
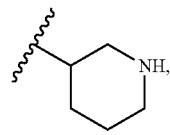

(30)
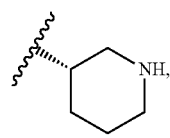

(31)
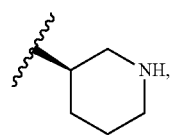

(32)
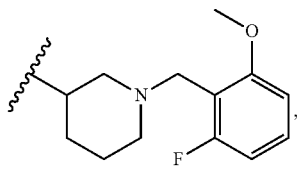

(33)
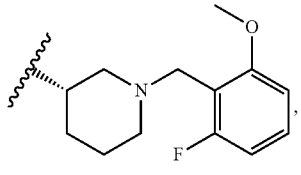

(34)
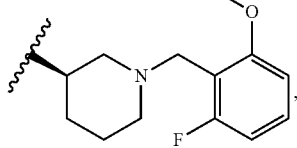

-continued

(35)
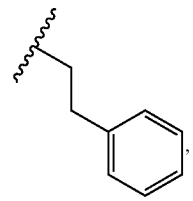

(36)
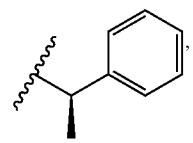

(37)
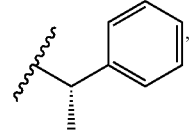

(38)
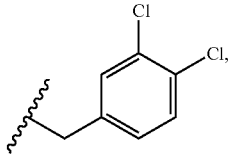

(39)
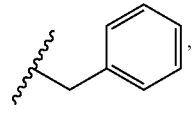

(40)
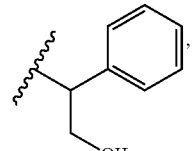

(41)
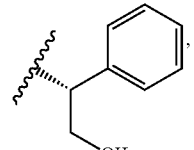

(42)
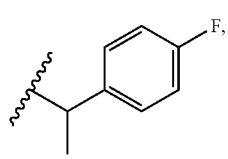

(43)
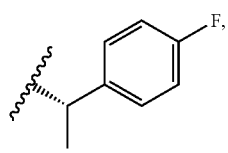

(44)
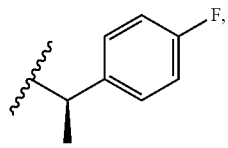

-continued
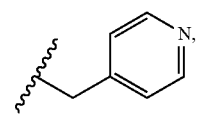 (45)
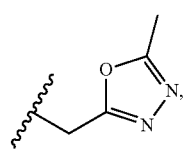 (46)
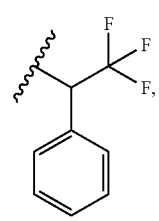 (47)
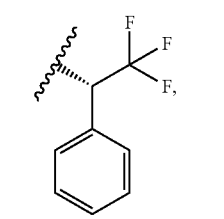 (48)
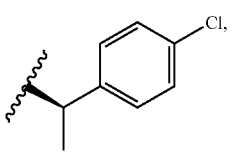 (49)
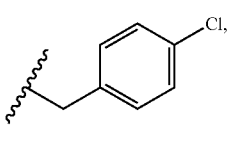 (50)
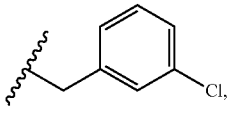 (51)
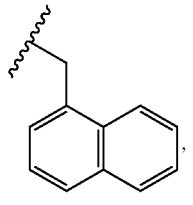 (52)
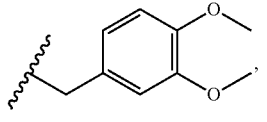 (53)
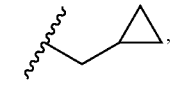 (54)
-continued
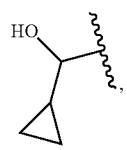 (55)
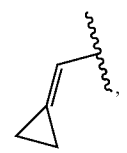 (56)
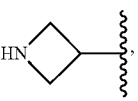 (57)
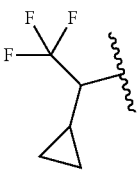 (58)
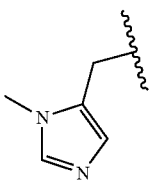 (59)
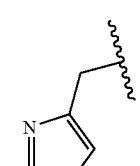 (60)
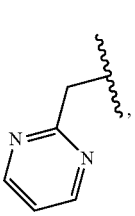 (61)
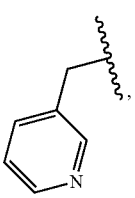 (62)
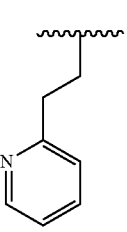 (63)

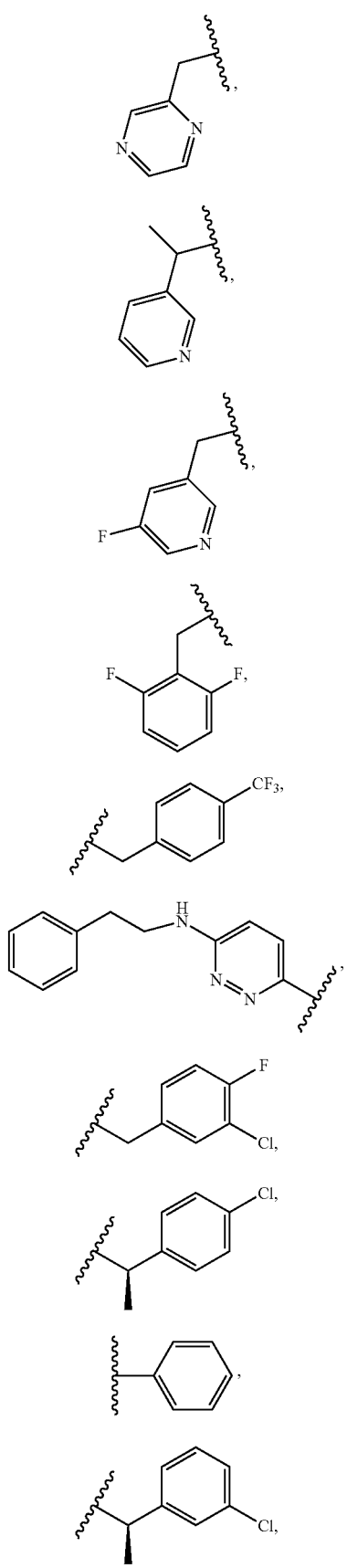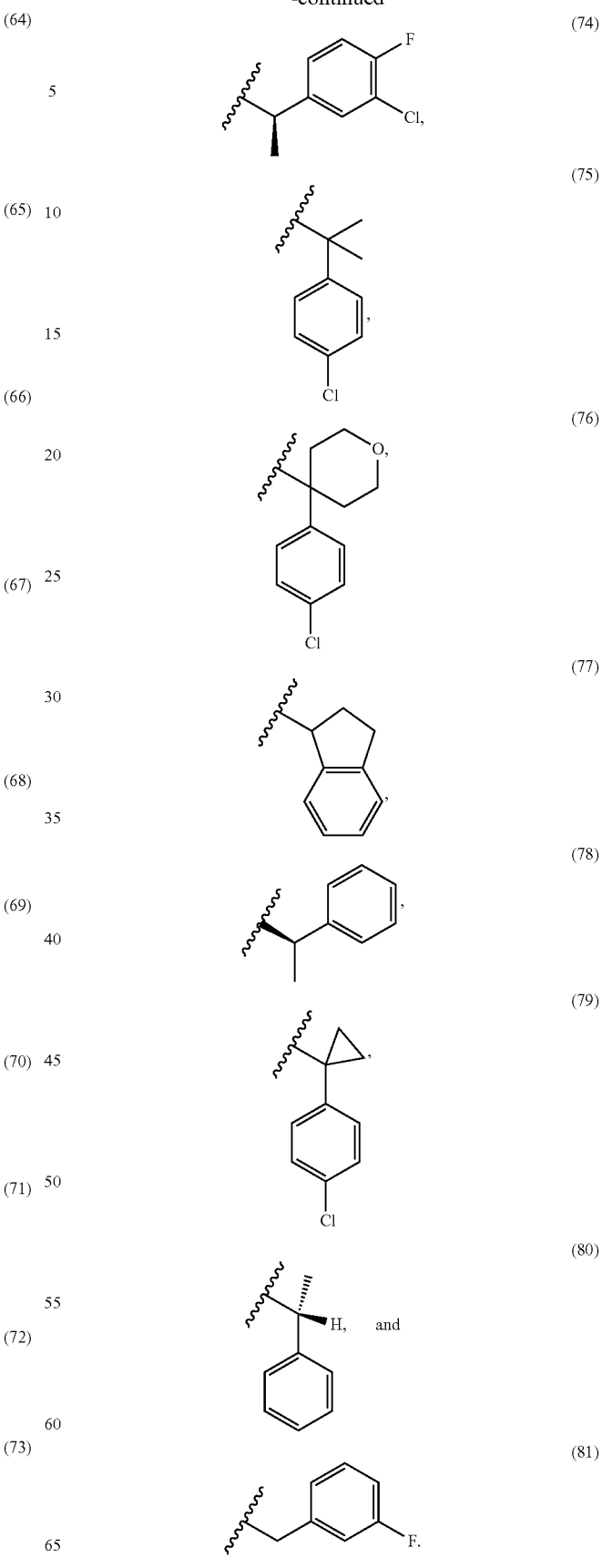

Examples of $R^4$ include but are not limited to: H, Cl and F. In one embodiment of this invention $R^4$ is H. In another embodiment of this invention $R^4$ is Cl. In another embodiment of this invention $R^4$ is F.

In one embodiment of this invention $R^2$ is H, $R^3$ is other than H (for example, $R^3$ is as described in any one of the embodiments below directed to $R^3$), $R^4$ is H, and X is O.

In another embodiment of this invention $R^2$ is H, $R^3$ is other than H (for example, $R^3$ is as described in any one of the embodiments below directed to $R^3$), $R^4$ is H, and X is S.

In one embodiment of this invention $R^2$ is H, $R^3$ is other than H (for example, $R^3$ is as described in any one of the embodiments below directed to $R^3$), $R^4$ is Cl, and X is O.

In another embodiment of this invention $R^2$ is H, $R^3$ is other than H (for example, $R^3$ is as described in any one of the embodiments below directed to $R^3$), $R^4$ is Cl, and X is S.

In one embodiment of this invention $R^2$ is H, $R^3$ is other than H (for example, $R^3$ is as described in any one of the embodiments below directed to $R^3$), $R^4$ is F, and X is O.

In another embodiment of this invention $R^2$ is H, $R^3$ is other than H (for example, $R^3$ is as described in any one of the embodiments below directed to $R^3$), $R^4$ is F, and X is S.

In another embodiment of this invention $R^1$ is a substituted heteroaryl.

In another embodiment of this invention $R^1$ is a substituted heteroaryl substituted with 1 to 3 independently selected ($C_1$-$C_6$)alkyl groups.

In another embodiment of this invention $R^1$ is a substituted heteroaryl substituted with 1 ($C_1$-$C_6$)alkyl group, and in one example, said alkyl group is —$CH_3$.

In another embodiment of this invention $R^1$ is a substituted heteroaryl substituted with 2 ($C_1$-$C_6$)alkyl groups, and in one example, said alkyl groups are each —$CH_3$.

Examples of $R^1$ include, but are not limited to, any of the $R^1$ substituents in the final compounds of Examples 1-95. Examples of $R^1$ also include, but are not limited to, the $R^1$ substitutents in the final compounds of Examples 116 to 701.

In another embodiment of this invention $R^1$ is selected from the group consisting of: 2-methylpyridyl, dihydropyran, propyl, N-methylpyrazolyl, fluorophenyl, 2,6-dimethylpyridyl, N-methylindazolyl-, propenyl, methyloxodihydropyridyl, pyrazolyl, cyanophenyl, and methylbenzothiazolyl.

In another embodiment of this invention $R^1$ is selected from the group consisting of:

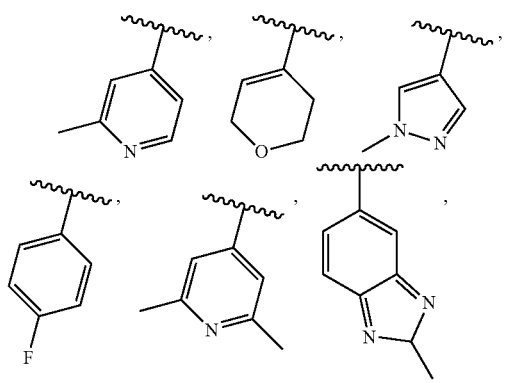

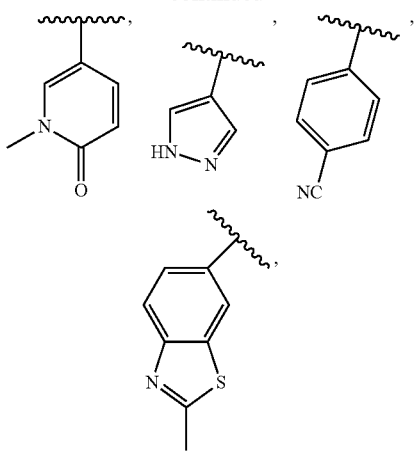

$CH_3CH_2CH_2$—, and $CH_3CH$=CH—.

In another embodiment $R^1$ is (1). In another embodiment $R^1$ is (2). In another embodiment $R^1$ is (3). In another embodiment $R^1$ is (4). In another embodiment $R^1$ is (5). In another embodiment $R^1$ is (6). In another embodiment $R^1$ is (7). In another embodiment $R^1$ is (8). In another embodiment $R^1$ is (9). In another embodiment $R^1$ is (10). In another embodiment $R^1$ is (11). In another embodiment $R^1$ is (12). In another embodiment $R^1$ is (13). In another embodiment $R^1$ is (14). In another embodiment $R^1$ is (15). In another embodiment $R^1$ is (16). In another embodiment $R^1$ is (17). In another embodiment $R^1$ is (18). In another embodiment $R^1$ is (19). In another embodiment $R^1$ is (20). In another embodiment $R^1$ is (21). In another embodiment $R^1$ is (22). In another embodiment 1e is (23). In another embodiment $R^1$ is (24). In another embodiment $R^1$ is (25). In another embodiment $R^1$ is (26).

In one embodiment of this invention $R^2$ is H.

In another embodiment of this invention $R^2$ is H and $R^3$ is other than H.

In another embodiment of this invention $R^2$ is H, and $R^1$ is selected from the group consisting of: 2-methylpyridyl, dihydropyran, propyl, N-methylpyrazolyl, fluorophenyl, 2,6-dimethylpyridyl, N-methylindazolyl-, propenyl, methyloxodihydropyridyl, pyrazolyl, cyanophenyl, and methylbenzothiazolyl.

In another embodiment of this invention $R^2$ is H, and $R^1$ is selected from the group consisting of: $R^1$ groups (1) to (26).

In another embodiment of this invention $R^2$ is H, and $R^1$ is selected from the group consisting of: $R^1$ groups (2), (4), (6), (8), (10), (11), (12), (15), (16), (17), (18), and (21).

In another embodiment of this invention $R^3$ is a substituted heterocycloalkyl.

In another embodiment of this invention $R^3$ is a substituted heterocycloalkyl comprising a 4 to 6 membered ring comprising 1 to 3 N atoms wherein the remaining ring atoms are carbon, and said heterocycloalkyl is substituted with 1 to 3 substitutents independently selected from the group consisting of: benzyl, and substituted benzyl, and wherein said substituted benzyl is substituted with 1-3 substituents independently selected from the group consisting of: halo (e.g., F), and alkoxy (e.g., $C_1$-$C_3$alkoxy, and in one example —$OCH_3$).

In another embodiment of this invention $R^3$ is an arylalkyl-.

In another embodiment of this invention $R^3$ is an arylalkyl- wherein said arylalkyl- is a phenyl-($C_1$-$C_4$)alkyl-. In another embodiment said $R^3$ is a phenyl-($C_1$-$C_3$)alkyl. In another embodiment said $R^3$ is a phenyl-($C_1$-$C_2$)alkyl.

In another embodiment of this invention $R^3$ is substituted arylalkyl-.

In another embodiment of this invention $R^3$ is a substituted arylalkyl- wherein said substituted arylalkyl- is a substituted phenyl-$(C_1-C_2)$alkyl.

In another embodiment of this invention $R^3$ is a substituted arylalkyl- wherein said substituted arylalkyl- is a substituted phenyl-$(C_1-C_2)$alkyl substituted with 1 to 3 substituents independently selected from the group consisting of halo (e.g., F and Cl) and —OH.

In another embodiment of this invention $R^3$ is substituted heteroarylalkyl-.

In another embodiment of this invention $R^3$ is substituted heteroarylalkyl wherein said substituted heteroarylalkyl- is heteroaryl$(C_1-C_2)$alkyl- wherein said heteroaryl moiety comprises 5 ring atoms wherein 1 to 3 ring atoms are independently selected from the group consisting of S and N, and the remaining ring atoms are carbon.

In another embodiment of this invention $R^3$ is substituted heteroarylalkyl wherein said substituted heteroarylalkyl- is a substituted heteroaryl$(C_1-C_2)$alkyl- wherein said heteroaryl moiety comprises 5 ring atoms wherein 1 to 3 ring atoms are independently selected from the group consisting of S and N, and the remaining ring atoms are carbon, and said substituted heteroaryl$(C_1-C_2)$alkyl- is substituted with 1 to 3 independently selected —$(C_1-C_6)$alkyl groups (such as, for example: —$(C_1-C_2)$alkyl) In one example, said substituted heteroaryl$(C_1-C_2)$alkyl-is substituted with one methyl group.

In another embodiment of this invention $R^3$ is a substituted piperidinyl.

In another embodiment of this invention $R^3$ is a substituted piperidinyl and said substituted piperidinyl is a N-substituted piperidinyl.

In another embodiment of this invention $R^3$ is a substituted piperidinyl and said substituted piperidinyl is a N-benzylpiperidinyl-.

In another embodiment of this invention $R^3$ is a substituted piperidinyl and said substituted piperidinyl is a N-(substituted benzyl)piperidinyl-.

In another embodiment of this invention $R^3$ is a substituted piperidinyl and said substituted piperidinyl is a N-(alkoxy, halo-benzyl)piperidinyl).

In another embodiment of this invention $R^3$ is —$CH_2$-phenyl (i.e., benzyl).

In another embodiment of this invention $R^3$ is a substituted —$CH_2$-phenyl.

In another embodiment of this invention $R^3$ is a substituted —$CH_2$-phenyl wherein said substituted —$CH_2$-phenyl is a —$CH_2$-(monohalo)phenyl.

In another embodiment of this invention $R^3$ is a substituted —$CH_2$-phenyl wherein said substituted —$CH_2$-phenyl is a —$CH_2$— (dihalo)phenyl.

In another embodiment of this invention $R^3$ is —$(CH_2)_2$-phenyl.

In another embodiment of this invention $R^3$ is a hydroxy substituted —$CH(CH_3)$-phenyl.

In another embodiment of this invention $R^3$ is a monohalo substituted —$CH(CH_3)$— phenyl.

In another embodiment of this invention $R^3$ is a dihalo substituted —$CH(CH_3)$-phenyl.

In another embodiment of this invention $R^3$ is a methylthiazolyl-$CH_2$—.

In another embodiment of this invention $R^3$ is phenyl-CH$(CH_3)$—.

In another embodiment of this invention $R^3$ is selected from the group consisting of: (32), (35), (36), (38), (39), (40), (41), (42), (44), (49), (50), (51), (60), (67), (70), (71), (74), and (81).

In another embodiment of this invention $R^3$ is (27). In another embodiment of this invention $R^3$ is (28). In another embodiment of this invention $R^3$ is (29). In another embodiment of this invention $R^3$ is (30). In another embodiment of this invention $R^3$ is (31). In another embodiment of this invention $R^3$ is (32). In another embodiment of this invention $R^3$ is (33). In another embodiment of this invention $R^3$ is (34). In another embodiment of this invention $R^3$ is (35). In another embodiment of this invention $R^3$ is (36). In another embodiment of this invention $R^3$ is (37). In another embodiment of this invention $R^3$ is (38). In another embodiment of this invention $R^3$ is (39). In another embodiment of this invention $R^3$ is (40). In another embodiment of this invention $R^3$ is (41). In another embodiment of this invention $R^3$ is (42). In another embodiment of this invention $R^3$ is (43). In another embodiment of this invention $R^3$ is (44). In another embodiment of this invention $R^3$ is (45). In another embodiment of this invention $R^3$ is (46). In another embodiment of this invention $R^3$ is (47). In another embodiment of this invention $R^3$ is (48). In another embodiment of this invention $R^3$ is (49). In another embodiment of this invention $R^3$ is (50). In another embodiment of this invention $R^3$ is (51). In another embodiment of this invention $R^3$ is (52). In another embodiment of this invention $R^3$ is (53). In another embodiment of this invention $R^3$ is (54). In another embodiment of this invention $R^3$ is (55). In another embodiment of this invention $R^3$ is (56). In another embodiment of this invention $R^3$ is (57). In another embodiment of this invention $R^3$ is (58). In another embodiment of this invention $R^3$ is (59). In another embodiment of this invention $R^3$ is (60). In another embodiment of this invention $R^3$ is (61). In another embodiment of this invention $R^3$ is (62). In another embodiment of this invention $R^3$ is (63). In another embodiment of this invention $R^3$ is (64). In another embodiment of this invention $R^3$ is (65). In another embodiment of this invention $R^3$ is (66). In another embodiment of this invention $R^3$ is (67). In another embodiment of this invention $R^3$ is (68). In another embodiment of this invention $R^3$ is (69). In another embodiment of this invention $R^3$ is (70). In another embodiment of this invention $R^3$ is (71). In another embodiment of this invention $R^3$ is (72). In another embodiment of this invention $R^3$ is (73). In another embodiment of this invention $R^3$ is (74). In another embodiment of this invention $R^3$ is (75). In another embodiment of this invention $R^3$ is (76). In another embodiment of this invention $R^3$ is (77). In another embodiment of this invention $R^3$ is (78). In another embodiment of this invention $R^3$ is (79). In another embodiment of this invention $R^3$ is (80). In another embodiment of this invention $R^3$ is (81). In another embodiment of this invention $R^3$ is any one of (27) to (81) and $R^2$ is H.

In another embodiment of this invention $R^3$ is selected from the group consisting of $R^3$ groups (27) to (81), and $R^1$ is selected from the group consisting of $R^1$ groups (1) to (26).

In another embodiment of this invention $R^3$ is selected from the group consisting of $R^3$ groups (27) to (81), $R^1$ is selected from the group consisting of $R^1$ groups (1) to (26), and $R^2$ is H.

In another embodiment of this invention $R^3$ is selected from the group consisting of $R^3$ groups (27) to (81), $R^1$ is selected from the group consisting of $R^1$ groups (1) to (26), $R^2$ is H, and $R^4$ is H.

In another embodiment of this invention $R^3$ is selected from the group consisting of $R^3$ groups (27) to (81), $R^1$ is selected from the group consisting of $R^1$ groups (1) to (26), $R^2$ is H, $R^4$ is H, and X is O.

In another embodiment of this invention $R^3$ is selected from the group consisting of: $R^3$ groups (32), (35), (36), (38), (39), (40), (41), (42), (44), (49), (50), (51), (60), (67), (70), (71), (74) and (81), and $R^1$ is selected from the group consisting of $R^1$ groups (2), (4), (6), (8), (10), (11), (12), (14), (15), (18), and (21).

In another embodiment of this invention $R^3$ is selected from the group consisting of: $R^3$ groups (32), (35), (36), (38), (39), (40), (41), (42), (44), (49), (50), (51), (60), (67), (70), (71), (74) and (81), $R^1$ is selected from the group consisting of $R^1$ groups (2), (4), (6), (8), (10), (11), (12), (14), (15), (18), and (21), and $R^2$ is H.

In another embodiment of this invention $R^3$ is selected from the group consisting of: $R^3$ groups (32), (35), (36), (38), (39), (40), (41), (42), (44), (49), (50), (51), (60), (67), (70), (71), (74) and (81), $R^1$ is selected from the group consisting of $R^1$ groups (2), (4), (6), (8), (10), (11), (12), (14), (15), (18), and (21), $R^2$ is H, and $R^4$ is H.

In another embodiment of this invention $R^3$ is selected from the group consisting of $R^3$ groups (32), (35), (36), (38), (39), (40), (41), (42), (44), (49), (50), (51), (60), (67), (70), (71), (74) and (81), $R^1$ is selected from the group consisting of $R^1$ groups (2), (4), (6), (8), (10), (11), (12), (14), (15), (18), and (21), $R^2$ is H, $R^4$ is H, and X is O.

In another embodiment of this invention $R^1$ is $R^1$ group (6).

In another embodiment of this invention $R^3$ is selected from the group consisting of; $R^3$ groups (36) and (71).

In another embodiment of this invention $R^1$ is $R^1$ group (6), and $R^3$ is selected from the group consisting of: $R^3$ groups (36) and (71).

In another embodiment of this invention $R^1$ is $R^1$ group (6), $R^3$ is selected from the group consisting of: $R^3$ groups (36) and (71), and $R^4$ is H.

In another embodiment of this invention $R^1$ is $R^1$ group (6), $R^2$ is H, $R^3$ is selected from the group consisting of: $R^3$ groups (36) and (71), and $R^4$ is H.

In another embodiment of this invention $R^1$ is $R^1$ group (6), $R^2$ is H, $R^3$ is selected from the group consisting of: $R^3$ groups (36) and (71), $R^4$ is H, and X is O.

Other embodiments of this invention are directed to any one of the embodiments described above wherein $R^2$ is in the trans position to X, and $R^3$ is in the cis position to X.

Other embodiments of this invention are directed to any one of the embodiments described above wherein the compounds are in the free base form.

In another embodiment of this invention the compounds of formula (1) are selected from the group consisting of the final compounds of Examples 1-95, and 116 to 701. In another embodiment of this invention the compounds of formula (1) are selected from the group consisting of the final compounds of Examples 1-95. In another embodiment of this invention the compounds of formula (1) are selected from the group consisting of the final compounds of Examples 116 to 701.

In another embodiment of this invention the compounds of formula (1) are selected from the group consisting of the final compounds of Examples 1 to 95.

The compounds of Examples 1, 15, 16, 19-69, 71-85, and 87-95 are the trifluoroacetic acid salts of the free base. Thus, another embodiment of this invention is directed to the free base form of the compounds of Examples 1, 15, 16, 19-69, 71-85, and 87-95.

Thus another embodiment of this invention is directed to the final compounds of Examples 2-14, 17, 18, 70, 86, 92, and the free base form of the compounds of Examples 1, 1, 16, 19-69, 71-85, 87-91, and 93-95.

In another embodiment of this invention the compounds of formula (1) are selected from the group consisting of the final compounds of Examples 2, 4, 5, 6, 8, 9, 10, 11, 14, 15, 19, 20, 22, 25, and 26.

In another embodiment of this invention the compounds of formula (1) are selected from the group consisting of the final compounds of Examples 2, 4, 5, 6, 8, 9, 10, 11, and 14, and the free base form of the final compounds of Examples 15, 19, 20, 22, 25, and 26.

In another embodiment of this invention the compounds of formula (1) are selected from the group consisting of the final compounds of Examples 27, 29, 30, 31, 34, 43, 49, 51, 52, 53, 56, 57, 58, 59, 60, 62, 63, 64, 65, 66, 67, 69, 71, 72, 74, 87, 88, 89, 91, 93, and 95.

In another embodiment of this invention the compounds of formula (1) are selected from the group consisting of the free base form of the final compounds of Examples 27, 29, 30, 31, 34, 43, 49, 51, 52, 53, 56, 57, 58, 59, 60, 62, 63, 64, 65, 66, 67, 69, 71, 72, 74, 87, 88, 89, 91, 93, and 95

Another embodiment of this invention is directed to the pharmaceutically acceptable salts of the compounds of formula (1). Thus, other embodiments of this invention are directed to any one of the embodiments described above wherein the compound of formula (1) is in the form of a pharmaceutically acceptable salt.

Another embodiment of this invention is directed to pharmaceutically acceptable salts of the final compounds of Examples 2-14, 17, 18, 70, 86, 92, and of the free base form of the compounds of Examples 1, 15, 16, 19-69, 71-85, 87-91, and 93-95.

Another embodiment of this invention is directed to the pharmaceutically acceptable salts of the compounds of Examples 2, 4, 5, 6, 8, 9, 10, 11, and 14, and of the free base forms of the final compounds of Examples 15, 19, 20, 22, 25, and 26.

Another embodiment of this invention is directed to the pharmaceutically acceptable salts of the compounds of Examples 27, 29, 30, 31, 34, 43, 49, 51, 52, 53, 56, 57, 58, 59, 60, 62, 63, 64, 65, 66, 67, 69, 71, 72, 74, 87, 88, 89, 91, 93, and 95.

Another embodiment is directed to the compound of Example 1. Another embodiment is directed to the compound of Example 2. Another embodiment is directed to the compound of Example 3. Another embodiment is directed to the compound of Example 4. Another embodiment is directed to the compound of Example 5. Another embodiment is directed to the compound of Example 6. Another embodiment is directed to the compound of Example 7. Another embodiment is directed to the compound of Example 8. Another embodiment is directed to the compound of Example 9. Another embodiment is directed to the compound of Example 10. Another embodiment is directed to the compound of Example 11. Another embodiment is directed to the compound of Example 12. Another embodiment is directed to the compound of Example 13. Another embodiment is directed to the compound of Example 14. Another embodiment is directed to the compound of Example 15. Another embodiment is directed to the compound of Example 16. Another embodiment is directed to the compound of Example 17. Another embodiment is directed to the compound of Example 18. Another embodiment is directed to the compound of Example 19. Another embodiment is directed to the compound of Example 20. Another embodiment is directed to the compound of Example 21. Another embodiment is directed to the compound of Example 22. Another embodiment is directed to the compound of Example 23. Another embodiment is directed to the compound of Example 24. Another embodiment is directed to the compound of Example 25. Another embodiment is directed to the compound of Example 26. Another embodiment is directed to the compound of Example 27. Another embodiment is directed to the compound of Example 28. Another embodiment is directed to the compound of Example 29. Another embodiment is directed to the compound of Example 30. Another embodiment is directed to the compound of Example 31. Another embodiment is directed to the compound of Example 32. Another embodiment is directed to the compound of Example 33. Another embodiment is directed to the compound of Example 34. Another embodiment is directed to the compound of Example 35. Another embodiment is directed to the compound of Example 36. Another embodiment is directed to the compound of Example 37. Another embodiment is directed to the compound of Example 38. Another embodiment is directed to the compound of Example 39. Another embodiment is directed to the compound of Example 40. Another embodiment is directed to the compound of Example 41. Another embodiment is directed to the compound of Example 42. Another embodiment is directed to the compound of Example 43. Another embodiment is directed to the compound of Example 44. Another embodiment is directed to the compound of Example 45. Another embodiment is directed to the compound of Example 46. Another embodiment is directed to the compound of Example 47. Another embodiment is directed to the compound of Example 48. Another embodiment is directed to the compound of Example 49. Another embodiment is directed to the compound of Example 50. Another embodiment is directed to the compound of Example 51. Another embodiment is directed to the compound of Example 52. Another embodiment is directed to the compound of Example 53. Another embodiment is directed to the compound of Example 54. Another embodiment is directed to the compound of Example 55. Another embodiment is directed to the compound of Example 56. Another embodiment is directed to the compound of Example 57. Another embodiment is directed to the compound of Example 58. Another embodiment is directed to the compound of Example 59. Another embodiment is directed to the compound of Example 60. Another embodiment is directed to the compound of Example 61. Another embodiment is directed to the compound of Example 62. Another embodiment is directed to the compound of Example 63. Another embodiment is directed to the compound of Example 64. Another embodiment is directed to the compound of Example 65. Another embodiment is directed to the compound of Example 66. Another embodiment is directed to the compound of Example 67. Another embodiment is directed to the compound of Example 68. Another embodiment is directed to the compound of Example 69. Another embodiment is directed to the compound of Example 70. Another embodiment is directed to the compound of Example 71. Another embodiment is directed to the compound of Example 72. Another embodiment is directed to the compound of Example 73. Another embodiment is directed to the compound of Example 74. Another embodiment is directed to the compound of Example 75. Another embodiment is directed to the compound of Example 76. Another embodiment is directed to the compound of Example 77. Another embodiment is directed to the compound of Example 78. Another embodiment is directed to the compound of Example 79. Another embodiment is directed to the compound of Example 80. Another embodiment is directed to the compound of Example 81. Another embodiment is directed to the compound of Example 82. Another embodiment is directed to the compound of Example 83. Another embodiment is directed to the compound of Example 84. Another embodiment is directed to the compound of Example 85. Another embodiment is directed to the compound of Example 86. Another embodiment is directed to the compound of Example 87. Another embodiment is directed to the compound of Example 88. Another embodiment is directed to the compound of Example 89. Another embodiment is directed to the compound of Example 90. Another embodiment is directed to the compound of Example 91. Another embodiment is directed to the compound of Example 92. Another embodiment is directed to the compound of Example 93. Another embodiment is directed to the compound of Example 94. Another embodiment is directed to the compound of Example 95. Other embodiments of this invention are directed to the pharmaceutically acceptable salts of any one of the compounds of any one of the Examples described in this paragraph.

Other embodiments of this invention are directed to each compound of Examples 116-701 such that there is one embodiment for each compound of each example. Other embodiments of this invention are directed to the pharmaceutically acceptable salts of any one of the compounds of Examples 116-701.

Another embodiment of this invention is directed to the free base form of the compound of Example 1. Another embodiment is directed to the free base form of the compound of Example 15. Another embodiment is directed to the free base form of the compound of Example 16. Another embodiment is directed to the free base form of the compound of Example 19. Another embodiment is directed to the free base form of the compound of Example 20. Another embodiment is directed to the free base form of the compound of Example 21. Another embodiment is directed to the free base form of the compound of Example 22. Another embodiment is directed to the free base form of the compound of Example 23. Another embodiment is directed to the free base form of the compound of Example 24. Another embodiment is directed to the free base form of the compound of Example 25. Another embodiment is directed to the free base form of the compound of Example 26. Another embodiment is directed to the free base form of the compound of Example 27. Another embodiment is directed to the free base form of the compound of Example 28. Another embodiment is directed to the free base form of the compound of Example 29. Another embodiment is directed to the free base form of the compound of Example 30. Another embodiment is directed to the free base form of the compound of Example 31. Another embodiment is directed to the free base form of the compound of Example 32. Another embodiment is directed to the free base form of the compound of Example 33. Another embodiment is directed to the free base form of the compound of Example 34. Another embodiment is directed to the free base form of the compound of Example 35. Another embodiment is directed to the free base form of the compound of Example 36. Another embodiment is directed to the free base form of the compound of Example 37. Another embodiment is directed to the free base form of the compound of Example 38. Another embodiment is directed to the free base form of the compound of Example 39. Another embodiment is directed to the free base form of the compound of Example 40. Another embodiment is directed to the free base form of the compound of Example 41. Another embodiment is directed to the free base form of the compound of Example 42. Another embodiment is directed to the free base form of the compound of Example 43. Another embodiment is directed to the free base form of the compound of Example 44. Another embodiment is directed to the free base form of the compound of Example 45. Another embodiment is directed to the free base form of the compound of Example 46. Another embodiment is directed to the free base form of the compound of Example 47. Another embodiment is directed to the free base form of the compound of Example 48. Another embodiment is directed to the free base form of the compound of Example 49. Another embodiment is directed to the free base form of the compound of Example 50. Another embodiment is directed to the free base form of the compound of Example 51. Another embodiment is directed to the free base form of the compound of Example 52. Another embodiment is directed to the free base form of the compound of Example 53. Another embodiment is directed to the free base form of the compound of Example 54. Another embodiment is directed to the free base form of the compound of Example 55. Another embodiment is directed to the free base form of the compound of Example 56. Another embodiment is directed to the free base form of the compound of Example 57. Another embodiment is directed to the free base form of the compound of Example 58. Another embodiment is directed to the free base form of the compound of Example 59. Another embodiment is directed to the free base form of the compound of Example 60. Another embodiment is directed to the free base form of the compound of Example 61. Another embodiment is directed to the free base form of the compound of Example 62. Another embodiment is directed to the free base form of the compound of Example 63. Another embodiment is directed to the free base form of the compound of Example 64. Another embodiment is directed to the free base form of the compound of Example 65. Another embodiment is directed to the free base form of the compound of Example 66. Another embodiment is directed to the free base form of the compound of Example 67. Another embodiment is directed to the free base form of the compound of Example 68. Another embodiment is directed to the free base form of the compound of Example 69. Another embodiment is directed to the free base form of the compound of Example 71. Another embodiment is directed to the free base form of the compound of Example 72. Another embodiment is directed to the free base form of the compound of Example 73. Another embodiment is directed to the free base form of the compound of Example 74. Another embodiment is directed to the free base form of the compound of Example 75. Another embodiment is directed to the free base form of the compound of Example 76. Another embodiment is directed to the free base form of the compound of Example 77. Another embodiment is directed to the free base form of the compound of Example 78. Another embodiment is directed to the free base form of the compound of Example 79. Another embodiment is directed to the free base form of the compound of Example 80. Another embodiment is directed to the free base form of the compound of Example 81. Another embodiment is directed to the free base form of the compound of Example 82. Another embodiment is directed to the free base form of the compound of Example 83. Another embodiment is directed to the free base form of the compound of Example 84. Another embodiment is directed to the free base form of the compound of Example 85. Another embodiment is directed to the free base form of the compound of Example 87. Another embodiment is directed to the free base form of the compound of Example 88. Another embodiment is directed to the free base form of the compound of Example 89. Another embodiment is directed to the free base form of the compound of Example 90. Another embodiment is directed to the free base form of the compound of Example 91. Another embodiment is directed to the free base form of the compound of Example 93. Another embodiment is directed to the free base form of the compound of Example 94. Another embodiment is directed to the free base form of the compound of Example 95. Other embodiments of this invention are directed to the pharmaceutically acceptable salts of any one of the compounds of any one of the Examples described in this paragraph.

Other embodiments of this invention are directed to any one of the embodiments above directed to the compounds of Examples 1-95, and 116-701 (free base form or pharmaceutically acceptable salt thereof) wherein the $R^2$ group is in the trans position to X and the $R^3$ group is in the cis position to X.

Other embodiments of this invention are directed to any one of the embodiments above directed to the compounds of Examples 1 to 95 (free base form or pharmaceutically acceptable salt thereof) wherein the $R^2$ group is in the trans position to X and the $R^3$ group is in the cis position to X.

Other embodiments of this invention are directed to any one of the embodiments above directed to the compounds of Examples 116 to 701 (free base form or pharmaceutically acceptable salt thereof) wherein the $R^2$ group is in the trans position to X and the $R^3$ group is in the cis position to X.

Another embodiment of this invention is directed to the solvates of the compounds of formula (1).

Other embodiments of this invention are directed to any one of the embodiments of formula (1) wherein the compound is in pure and isolated form. Other embodiments of this invention are directed to any one of the embodiments of formula (1) wherein the compound is in pure form. Other embodiments of this invention are directed to any one of the embodiments of formula (1) wherein the compound is in isolated form.

Another embodiment of this invention is directed to a pharmaceutical composition comprising an effective amount of at least one compound (e.g., 1, 2 or 3, or 1 or 2, or 1, and usually 1) of formula (1), or a pharmaceutically acceptable salt thereof, and a pharmaceutically acceptable carrier. Another embodiment of this invention is directed to a pharmaceutical composition comprising an effective amount of a compound of formula (1), or a pharmaceutically acceptable salt thereof, and a pharmaceutically acceptable carrier.

Another embodiment of this invention is directed to a pharmaceutical composition comprising an effective amount of at least one compound selected from the group consisting of the compounds of Examples 1-95, and 116-701 (e.g., the free base form of the compounds of Examples 1-95, and 116-701), or a pharmaceutically acceptable salt thereof, and a pharmaceutically acceptable carrier.

Another embodiment of this invention is directed to a pharmaceutical composition comprising an effective amount of at least one compound selected from the group consisting of the compounds of Examples 2-14, 17, 18, 70, 86, 92, and the free base form of the compounds of Examples 1, 15, 16, 19-69, 71-85, 87-91, and 93-95, or a pharmaceutically acceptable salt thereof, and a pharmaceutically acceptable carrier.

Another embodiment of this invention is directed to a pharmaceutical composition comprising an effective amount of at least one compound selected from the group consisting of the compounds of Examples 2, 4, 5, 6, 8, 9, 10, 11, and 14, and the free base forms of the compounds of Examples 15, 19, 20, 22, 25, and 26, a pharmaceutically acceptable carrier, and a pharmaceutically acceptable carrier.

Another embodiment of this invention is directed to a pharmaceutical composition comprising an effective amount of at least one compound selected from the group consisting of the free base form of the compounds of Examples 27, 29, 30, 31, 34, 43, 49, 51, 52, 53, 56, 57, 58, 59, 60, 62, 63, 64, 65, 66, 67, 69, 71, 72, 74, 87, 88, 89, 91, 93, and 95, a pharmaceutically acceptable carrier, and a pharmaceutically acceptable carrier.

Another embodiment of this invention is directed to a pharmaceutical composition comprising an effective amount of a compound of formula (1), a chemotherapeutic agent, and a pharmaceutically acceptable carrier.

The compounds of the invention are useful in preparing a medicament that is useful in treating cancer.

The compounds of this invention inhibit the activity of ERK2 Thus, this invention further provides a method of inhibiting ERK in mammals, especially humans, by the administration of an effective amount of one or more (e.g., one) compounds of this invention. The administration of the compounds of this invention to patients, to inhibit ERK2, is useful in the treatment of cancer.

In any of the methods of treating cancer described herein, unless stated otherwise, the methods can optionally include the administration of an effective amount of one or more (e.g., 1, 2 or 3, or 1 or 2, or 1) chemotherapeutic agents. The chemotherapeutic agents can be administered currently or sequentially with the compounds of this invention. In the treatment of breast cancer, the compounds of formula (1) can be be administered in a treatment protocol which also includes the administration of an effective amount of at least one (e.g., 1-3, or 1-2, or 1) antihormonal agent (i.e., the methods of treating breast cancer can include hormonal therapies).

The methods of treating cancer described herein include methods wherein a combination of drugs (i.e., compounds, or pharmaceutically active ingredients, or pharmaceutical compositions) are used (i.e., the methods of treating cancer of this invention include combination therapies). Those skilled in the art will appreciate that the drugs are generally administered individually as a pharmaceutical composition. The use of a pharmaceutical composition comprising more than one drug is within the scope of this invention.

The methods of treating cancer described herein include methods of treating cancer that comprise administering a therapeutically effective amount of a compound of the instant invention in combination with radiation therapy and/or in combination with a second compound selected from: an estrogen receptor modulator, an androgen receptor modulator, a retinoid receptor modulator, a cytotoxicytostatic agent, an antiproliferative agent, a prenyl-protein transferase inhibitor, an HMG-CoA reductase inhibitor, an HIV protease inhibitor, a reverse transcriptase inhibitor, an angiogenesis inhibitor, PPAR-γ agonists, PPAR-δ agonists, an inhibitor of inherent multidrug resistance, an anti-emetic agent, an agent useful in the treatment of anemia, an agent useful in the treatment of neutropenia, an immunologic-enhancing drug, an inhibitor of cell proliferation and survival signaling, a bisphosphonate, an aromatase inhibitor, an siRNA therapeutic, γ-secretase and/or NOTCH inhibitors, agents that interfere with receptor tyrosine kinases (RTKs), an agent that interferes with a cell cycle checkpoint, and any of the therapeutic agents listed herein.

In any of the methods of treating cancer described herein, unless stated otherwise, the methods can optionally include the administration of an effective amount of radiation therapy. For radiation therapy, γ-radiation is preferred.

Thus, another embodiment of this invention is directed to a method of treating cancer in a patient in need of such treatment, said method comprising administering an effective amount of a compound of formula (1). Another embodiment of this invention is directed to a method of treating cancer in a patient in need of such treatment, said method comprising administering to said patient an effective amount of a compound of formula (1), and an effective amount of at least one (e.g., 1-3, 1-2, or 1) chemotherapeutic agent.

The compounds, compositions and methods provided herein are useful for the treatment of cancer. Cancers that may be treated by the compounds, compositions and methods of the invention include, but are not limited to: (1) Cardiac: sarcoma (angiosarcoma, fibrosarcoma, rhabdomyosarcoma, liposarcoma), myxoma, rhabdomyoma, fibroma, lipoma and teratoma; (2) Lung: bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hamartoma, mesothelioma, non-small cell; (3) Gastrointestinal: esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel (adenocarcinoma, lymphoma, carcinoid tumors, Karposi's sarcoma, leiomyoma, hemangioma, lipoma, neurofibroma, fibroma), large bowel (adenocarcinoma, tubular adenoma, villous adenoma, hamartoma, leiomyoma), colon, colorectal, rectal; (4) Genitourinary tract: kidney (adenocarcinoma, Wilm's tumor [nephroblastoma], lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); (5) Liver: hepatoma (hepatocellular carcinoma), cholangiocarcinoma, hepatoblastoma, angio sarcoma, hepatocellular adenoma, hemangioma; (6) Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors; (7) Nervous system: skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma [pinealoma], glioblastoma multiform, oligodendroglioma, schwannoma, retinoblastoma, congenital tumors), spinal cord neurofibroma, meningioma, glioma, sarcoma); (8) Gynecological: uterus (endometrial carcinoma), cervix (cervical carcinoma, pre-tumor cervical dysplasia), ovaries (ovarian carcinoma [serous cystadenocarcinoma, mucinous cystadenocarcinoma, unclassified carcinoma], granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), fallopian tubes (carcinoma), breast; (9) Hematologic: blood (myeloid leukemia [acute and chronic], acute lymphoblastic leukemia, chronic lymphocytic leukemia, chronic myelomonocytic (CMML), myeloproliferative diseases, multiple myeloma, myelodysplastic syndrome), Hodgkin's disease, non-Hodgkin's lymphoma [malignant lymphoma]; (10) Skin: malignant melanoma, basal cell carcinoma, squamous cell carcinoma, Karposi's sarcoma, moles dysplastic nevi, lipoma, angioma, dermatofibroma, keloids, psoriasis; and (11) Adrenal glands: neuroblastoma. Examples of cancer that may be treated by the compounds, compositions and methods of the invention include thyroid cancer, anaplastic thyroid carcinoma, epidermal cancer, head and neck cancer (e.g., squamous cell cancer of the head and neck), sarcoma, tetracarcinoma, hepatoma and multiple myeloma. Thus, the term "cancerous cell" as provided herein, includes a cell afflicted by any one of the above-identified conditions.

In the treatment of breast cancer (e.g., postmenopausal and premenopausal breast cancer, e.g., hormone-dependent breast cancer) the compound of formula (1) may be used with an effective amount of at least one antihormonal agent selected from the group consisting of: (a) aromatase inhibitors, (b) antiestrogens, and (c) LHRH analogues; and optionally an effective amount of at least one chemotherapeutic agent. Examples of aromatase inhibitors include but are not limited to: Anastrozole (e.g., Arimidex), Letrozole (e.g., Femara), Exemestane (Aromasin), Fadrozole and Formestane (e.g., Lentaron). Examples of antiestrogens include but are not limited to: Tamoxifen (e.g., Nolvadex), Fulvestrant (e.g., Faslodex), Raloxifene (e.g., Evista), and Acolbifene. Examples of LHRH analogues include but are not limited to: Goserelin (e.g., Zoladex) and Leuprolide (e.g., Leuprolide Acetate, such as Lupron or Lupron Depot). Examples of chemotherapeutic agents include but are not limited to: Trastuzumab (e.g., Herceptin), Gefitinib (e.g., Iressa), Erlotinib (e.g., Erlotinib HCl, such as Tarceva), Bevacizumab (e.g., Avastin), Cetuximab (e.g., Erbitux), and Bortezomib (e.g., Velcade).

In one embodiment of this invention the cancer treated is colo-rectal cancer (such as, for example, colon adenocarcinoma and colon adenoma). Thus, another embodiment of this invention is directed to a method of treating colo-rectal cancer in a patient in need of such treatment, said method comprising administering an effective of a compound of formula (1) (in one example, a compound of Examples 1-95, and 116-701, and in another example a compound of Examples 1 to 95, and in another example a compound of Examples 116-701), or a pharmaceutically acceptable salt thereof, to said patient. Another embodiment is directed to a method of treating colo-rectal cancer in a patient in need of such treatment, said method comprising administering to said patient an effective amount of a compound selected from the group consisting of compounds of Examples 2, 5, 6, 8, 9, 10, 11, 15, 19, 20, 22, 26, 27, 29, 30, 31, 43, 52, 53, 56, 59, 60, 62, 63, 64, 65, 67, 69, 71, 72, 74, 83 and 87, or a pharmaceutically acceptable salt thereof. Another embodiment of this invention is directed to a method of treating colo-rectal cancer in a patient in need of such treatment, said method comprising administering to said patient an effective amount of a compound of formula (1) (in one example, a compound of Examples 1-95, and 116-701, and in another example a compound of Examples 1 to 95, and in another example a compound of Examples 116-701), or a pharmaceutically acceptable salt thereof, and an effective amount of at least one (e.g., 1-3, or 1-2, or 1) chemotherapeutic agent.

In one embodiment of this invention the cancer treated is melanoma. Thus, another embodiment of this invention is directed to a method of treating melanoma in a patient in need of such treatment, said method comprising administering an effective amount of a compound of formula (1) (in one example, a compound of Examples 1-95, and 116-701, and in another example, a compound of Examples 1 to 95, and in another example a compound of Examples 116-701), or a pharmaceutically acceptable salt thereof, to said patient. Another embodiment is directed to a method of treating melanoma in a patient in need of such treatment, said method comprising administering to said patient an effective amount of a compound selected from the group consisting of the compounds of Examples 2, 5, 6, 8, 9, 10, 11, 15, 19, 20, 22, 26, 27, 29, 30, 31, 43, 52, 53, 56, 59, 60, 62, 63, 64, 65, 67, 69, 71, 72, 74, 83 and 87, or a pharmaceutically acceptable carrier thereof. Another embodiment of this invention is directed to a method of treating melanoma in a patient in need of such treatment, said method comprising administering to said patient an effective amount of a compound of formula (1) (in one example, a compound of Examples 1-95, and 116-701, and in another example a compound of Examples 1 to 95, and in another example a compound of Examples 116-701), or a pharmaceutically acceptable salt thereof, and an effective amount of at least one (e.g., 1-3, or 1-2, or 1) chemotherapeutic agent.

The compounds of the invention are also useful in preparing a medicament that is useful in treating cancer.

The compounds of this invention may be administered to mammals, including humans, either alone or, in combination with pharmaceutically acceptable carriers, excipients or diluents, in a pharmaceutical composition, according to standard pharmaceutical practice. The compounds can be administered orally or parenterally, including the intravenous, intramuscular, intraperitoneal, subcutaneous, rectal and topical routes of administration.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, microcrystalline cellulose, sodium crosscarmellose, corn starch, or alginic acid; binding agents, for example starch, gelatin, polyvinyl-pyrrolidone or acacia, and lubricating agents, for example, magnesium stearate, stearic acid or talc. The tablets may be uncoated or they may be coated by known techniques to mask the unpleasant taste of the drug or delay disintegration and absorption in the gastrointestinal tract and thereby provide a sustained action over a longer period. For example, a water soluble taste masking material such as hydroxypropylmethyl-cellulose or hydroxypropylcellulose, or a time delay material such as ethyl cellulose, cellulose acetate buryrate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water soluble carrier such as polyethyleneglycol or an oil medium, for example peanut oil, liquid paraffin, or olive oil.

Aqueous suspensions contain the active material in admixture with excipients suitable for the manufacture of aqueous suspensions. Such excipients are suspending agents, for example sodium carboxymethylcellulose, methylcellulose, hydroxypropylmethyl-cellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethylene-oxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose, saccharin or aspartame.

Oily suspensions may be formulated by suspending the active ingredient in a vegetable oil, for example arachis oil, olive oil, sesame oil or coconut oil, or in mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as butylated hydroxyanisol or alpha-tocopherol.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present. These compositions may be preserved by the addition of an anti-oxidant such as ascorbic acid.

The pharmaceutical compositions of the invention may also be in the form of an oil-in-water emulsion. The oily phase may be a vegetable oil, for example olive oil or arachis oil, or a mineral oil, for example liquid paraffin or mixtures of these. Suitable emulsifying agents may be naturally-occurring phosphatides, for example soy bean lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening, flavouring agents, preservatives and antioxidants.

Syrups and elixirs may be formulated with sweetening agents, for example glycerol, propylene glycol, sorbitol or sucrose. Such formulations may also contain a demulcent, a preservative, flavoring and coloring agents and antioxidant.

The pharmaceutical compositions may be in the form of sterile injectable aqueous solutions. Among the acceptable vehicles and solvents that may be employed are water, Ringer's solution and isotonic sodium chloride solution.

The sterile injectable preparation may also be a sterile injectable oil-in-water microemulsion where the active ingredient is dissolved in the oily phase. For example, the active ingredient may be first dissolved in a mixture of soybean oil and lecithin. The oil solution then introduced into a water and glycerol mixture and processed to form a microemulsion.

The injectable solutions or microemulsions may be introduced into a patient's blood-stream by local bolus injection. Alternatively, it may be advantageous to administer the solution or microemulsion in such a way as to maintain a constant circulating concentration of the instant compound. In order to maintain such a constant concentration, a continuous intravenous delivery device may be utilized. An example of such a device is the Deltec CADD-PLUS™ model 5400 intravenous pump.

The pharmaceutical compositions may be in the form of a sterile injectable aqueous or oleagenous suspension for intramuscular and subcutaneous administration. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Compounds of the instant invention may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials include cocoa butter, glycerinated gelatin, hydrogenated vegetable oils, mixtures of polyethylene glycols of various molecular weights and fatty acid esters of polyethylene glycol.

For topical use, creams, ointments, jellies, solutions or suspensions, etc., containing the compound of the instant invention are employed. (For purposes of this application, topical application shall include mouth washes and gargles.)

The compounds for the present invention can be administered in intranasal form via topical use of suitable intranasal vehicles and delivery devices, or via transdermal routes, using those forms of transdermal skin patches well known to those of ordinary skill in the art. To be administered in the form of a transdermal delivery system, the dosage administration will, of course, be continuous rather than intermittent throughout the dosage regimen. Compounds of the present invention may also be delivered as a suppository employing bases such as cocoa butter, glycerinated gelatin, hydrogenated vegetable oils, mixtures of polyethylene glycols of various molecular weights and fatty acid esters of polyethylene glycol.

When a composition according to this invention is administered into a human subject, the daily dosage will normally be determined by the prescribing physician with the dosage generally varying according to the age, weight, and response of the individual patient, as well as the severity of the patient's symptoms.

The dosage regimen utilizing the compounds of the instant invention can be selected in accordance with a variety of factors including type, species, age, weight, sex and the type of cancer being treated; the severity (i.e., stage) of the cancer to be treated; the route of administration; the renal and hepatic function of the patient; and the particular compound or salt thereof employed. An ordinarily skilled physician or veterinarian can readily determine and prescribe the effective amount of the drug required to treat, for example, to prevent, inhibit (fully or partially) or arrest the progress of the disease. Compounds of this invention can be administered in a total daily dose of 10 mg to 3000 mg. For example, compounds of the instant invention can be administered in a total daily dose of up to 3000 mg. Compounds of the instant invention can be administered once daily (QD), or divided into multiple daily doses such as twice daily (BID), and three times daily (TID). Compounds of the instant invention can be administered at a total daily dosage of up to 3000 mg, e.g., 200 mg, 300 mg, 400 mg, 600 mg, 800 mg, 1000 mg, 2000 mg or 3000 mg, which can be administered in one daily dose or can be divided into multiple daily doses as described above.

In addition, the administration can be continuous, i.e., every day, or intermittently. The terms "intermittent" or "intermittently" as used herein means stopping and starting at either regular or irregular intervals. For example, intermittent administration of a compound of the instant invention may be administration one to six days per week or it may mean administration in cycles (e.g. daily administration for two to eight consecutive weeks, then a rest period with no administration for up to one week) or it may mean administration on alternate days. The compounds of this invention may be administered discontinuously rather than continuously during the treatment cycle. Thus, the compounds of this invention may be administered daily for one or more weeks during the cycle and discontinued for one or more weeks during the cycle, with this pattern of administration repeating during the treatment cycle (e.g., administration for a week and then discontinued for a week). This discontinuous treatment may also be based upon numbers of days rather than a full week. The number of days (or weeks) that the compounds of this invention are not dosed do not have to equal the number of days (or weeks) wherein the compounds of this invention are dosed. Usually, if a discontinuous dosing protocol is used, the number of days or weeks that the compounds of this invention are dosed is at least equal to or greater than the number of days or weeks that the compounds of this invention are not dosed.

In addition, the compounds of the instant invention may be administered according to any of the schedules described above, consecutively for a few weeks, followed by a rest period. For example, the compounds of the instant invention may be administered according to any one of the schedules described above from two to eight weeks, followed by a rest period of one week, or twice daily at a dose of 100-500 mg for three to five days a week. In another particular embodiment, the compounds of the instant invention may be administered three times daily for two consecutive weeks, followed by one week of rest.

Any one or more of the specific dosages and dosage schedules of the compounds of the instant invention, may also be applicable to any one or more of the therapeutic agents to be used in the combination treatment (hereinafter referred to as the "second therapeutic agent").

Moreover, the specific dosage and dosage schedule of this second therapeutic agent can further vary, and the optimal dose, dosing schedule and route of administration will be determined based upon the specific second therapeutic agent that is being used.

Of course, the route of administration of the compounds of the instant invention is independent of the route of administration of the second therapeutic agent. In an embodiment, the administration for a compound of the instant invention is oral administration. In another embodiment, the administration for a compound of the instant invention is intravenous administration. Thus, in accordance with these embodiments, a compound of the instant invention is administered orally or intravenously, and the second therapeutic agent can be administered orally, parenterally, intraperitoneally, intravenously, intraarterially, transdermally, sublingually, intramuscularly, rectally, transbuccally, intranasally, liposomally, via inhalation, vaginally, intraoccularly, via local delivery by catheter or stent, subcutaneously, intraadiposally, intraarticularly, intrathecally, or in a slow release dosage form.

In addition, a compound of the instant invention and second therapeutic agent may be administered by the same mode of administration, i.e. both agents administered e.g. orally, by IV. However, it is also within the scope of the present invention to administer a compound of the instant invention by one mode of administration, e.g. oral, and to administer the second therapeutic agent by another mode of administration, e.g. IV or any other ones of the administration modes described hereinabove.

The first treatment procedure, administration of a compound of the instant invention, can take place prior to the second treatment procedure, i.e., the second therapeutic agent, after the treatment with the second therapeutic agent, at the same time as the treatment with the second therapeutic agent, or a combination thereof. For example, a total treatment period can be decided for a compound of the instant invention. The second therapeutic agent can be administered prior to onset of treatment with a compound of the instant invention or following treatment with a compound of the instant invention. In addition, anti-cancer treatment can be administered during the period of administration of a compound of the instant invention but does not need to occur over the entire treatment period of a compound of the instant invention.

The instant compounds are also useful in combination with therapeutic, chemotherapeutic and anti-cancer agents. Combinations of the presently disclosed compounds with therapeutic, chemotherapeutic and anti-cancer agents are within the scope of the invention. Examples of such agents can be found in *Cancer Principles and Practice of Oncology* by V. T. Devita and S. Hellman (editors), $6^{th}$ edition (Feb. 15, 2001), Lippincott Williams & Wilkins Publishers. A person of ordinary skill in the art would be able to discern which combinations of agents would be useful based on the particular characteristics of the drugs and the cancer involved. Such agents include the following: estrogen receptor modulators, androgen receptor modulators, retinoid receptor modulators, cytotoxic/cytostatic agents, antiproliferative agents, prenyl-protein transferase inhibitors, HMG-CoA reductase inhibitors and other angiogenesis inhibitors, HIV protease inhibitors, reverse transcriptase inhibitors, inhibitors of cell proliferation and survival signaling, bisphosphonates, aromatase inhibitors, siRNA therapeutics, γ-secretase inhibitors, agents that interfere with receptor tyrosine kinases (RTKs) and agents that interfere with cell cycle checkpoints. The instant compounds are particularly useful when co-administered with radiation therapy.

"Estrogen receptor modulators" refers to compounds that interfere with or inhibit the binding of estrogen to the receptor, regardless of mechanism. Examples of estrogen receptor modulators include, but are not limited to, tamoxifen, raloxifene, idoxifene, LY353381, LY117081, toremifene, fulvestrant, 4-[7-(2,2-dimethyl-1-oxopropoxy-4-methyl-2-[4-[2-(1-piperidinyl)ethoxy]phenyl]-2H-1-benzopyran-3-yl]-phenyl-2,2-dimethylpropanoate, 4,4'-dihydroxybenzophenone-2,4-dinitrophenyl-hydrazone, and SH646.

"Androgen receptor modulators" refers to compounds which interfere or inhibit the binding of androgens to the receptor, regardless of mechanism. Examples of androgen receptor modulators include finasteride and other 5α-reductase inhibitors, nilutamide, flutamide, bicalutamide, liarozole, and abiraterone acetate.

"Retinoid receptor modulators" refers to compounds which interfere or inhibit the binding of retinoids to the receptor, regardless of mechanism. Examples of such retinoid receptor modulators include bexarotene, tretinoin, 13-cis-retinoic acid, 9-cis-retinoic acid, α-difluoromethylornithine, ILX23-7553, trans-N-(4'-hydroxyphenyl) retinamide, and N-4-carboxyphenyl retinamide.

"Cytotoxic/cytostatic agents" refer to compounds which cause cell death or inhibit cell proliferation primarily by interfering directly with the cell's functioning or inhibit or interfere with cell myosis, including alkylating agents, tumor necrosis factors, intercalators, hypoxia activatable compounds, microtubule inhibitors/microtubule-stabilizing agents, inhibitors of mitotic kinesins, histone deacetylase inhibitors, inhibitors of kinases involved in mitotic progression, inhibitors of kinases involved in growth factor and cytokine signal transduction pathways, antimetabolites, biological response modifiers, hormonal/anti-hormonal therapeutic agents, haematopoietic growth factors, monoclonal antibody targeted therapeutic agents, topoisomerase inhibitors, proteosome inhibitors, ubiquitin ligase inhibitors, and aurora kinase inhibitors.

Examples of cytotoxic/cytostatic agents include, but are not limited to, sertenef, cachectin, ifosfamide, tasonermin, lonidamine, carboplatin, altretamine, prednimustine, dibromodulcitol, ranimustine, fotemustine, nedaplatin, oxaliplatin, temozolomide, heptaplatin, estramustine, improsulfan tosilate, trofosfamide, nimustine, dibrospidium chloride, pumitepa, lobaplatin, satraplatin, profiromycin, cisplatin, irofulven, dexifosfamide, cis-aminedichloro(2-methyl-pyridine)platinum, benzylguanine, glufosfamide, GPX100, (trans, trans, trans)-bis-mu-(hexane-1,6-diamine)-mu-[diamine-platinum(II)]bis[diamine(chloro)platinum (II)]tetrachloride, diarizidinylspermine, arsenic trioxide, 1-(11-dodecylamino-10-hydroxyundecyl)-3,7-dimethylxanthine, zorubicin, idarubicin, daunorubicin, bisantrene, mitoxantrone, pirarubicin, pinafide, valrubicin, amrubicin, antineoplaston, 3'-deamino-3'-morpholino-13-deoxo-10-hydroxycaminomycin, annamycin, galarubicin, elinafide, MEN10755, 4-demethoxy-3-deamino-3-aziridinyl-4-methylsulphonyl-daunorubicin (see WO 00/50032), Raf kinase inhibitors (such as Bay43-9006) and mTOR inhibitors (such as Wyeth's CCI-779).

An example of a hypoxia activatable compound is tirapazamine.

Examples of proteosome inhibitors include but are not limited to lactacystin and MLN-341 (Velcade).

Examples of microtubule inhibitors/microtubule-stabilising agents include paclitaxel, vindesine sulfate, 3',4'-didehydro-4'-deoxy-8'-norvincaleukoblastine, docetaxol, rhizoxin, dolastatin, mivobulin isethionate, auristatin, cemadotin, RPR109881, BMS184476, vinflunine, cryptophycin, 2,3,4,5,6-pentafluoro-N-(3-fluoro-4-methoxyphenyl)benzene sulfonamide, anhydrovinblastine, N,N-dimethyl-L-valyl-L-valyl-N-methyl-L-valyl-L-prolyl-L-proline-t-butylamide, TDX258, the epothilones (see for example U.S. Pat. Nos. 6,284,781 and 6,288,237) and BMS188797. In an embodiment the epothilones are not included in the microtubule inhibitors/microtubule-stabilising agents.

Some examples of topoisomerase inhibitors are topotecan, hycaptamine, irinotecan, rubitecan, 6-ethoxypropionyl-3',4'-O-exo-benzylidene-chartreusin, 9-methoxy-N,N-dimethyl-5-nitropyrazolo[3,4,5-kl]acridine-2-(6H) propanamine, 1-amino-9-ethyl-5-fluoro-2,3-dihydro-9-hydroxy-4-methyl-1H,12H-benzo[de]pyrano[3',4':b,7]-indolizino[1,2b]quinoline-10,13(9H,15H)dione, lurtotecan, 7-[2-(N-isopropylamino)ethyl]-(20S)camptothecin, BNP1350, BNPI1100, BN80915, BN80942, etoposide phosphate, teniposide, sobuzoxane, 2'-dimethylamino-2'-deoxy-etoposide, GL331, N-[2-(dimethylamino)ethyl]-9-hydroxy-5,6-dimethyl-6H-pyrido[4,3-b]carbazole-1-carboxamide, asulacrine, (5a, 5aB, 8aa,9b)-9-[2-[N-[2-(dimethylamino)ethyl]-N-methylamino] ethyl]-5-[4-hydro0xy-3,5-dimethoxyphenyl]-5,5a,6,8,8a,9-hexohydrofuro(3',4':6,7)naphtho(2,3-d)-1,3-dioxol-6-one, 2,3-(methylenedioxy)-5-methyl-7-hydroxy-8-methoxybenzo[c]-phenanthridinium, 6,9-bis[(2-aminoethyl)amino] benzo[g]isoquinoline-5,10-dione, 5-(3-aminopropylamino)-7,10-dihydroxy-2-(2-hydroxyethylaminomethyl)-6H-pyrazolo[4,5,1-de]acridin-6-one, N-[1-[2(diethylamino) ethylamino]-7-methoxy-9-oxo-9H-thioxanthen-4-ylmethyl] formamide, N-(2-(dimethylamino)ethyl)acridine-4-carboxamide, 6-[[2-(dimethylamino)ethyl]amino]-3-hydroxy-7H-indeno[2,1-c]quinolin-7-one, and dimesna.

Examples of inhibitors of mitotic kinesins, and in particular the human mitotic kinesin KSP, are described in Publications WO03/039460, WO03/050064, WO03/050122, WO03/049527, WO03/049679, WO03/049678, WO04/039774, WO03/079973, WO03/099211, WO03/105855, WO03/106417, WO04/037171, WO04/058148, WO04/058700, WO04/126699, WO05/018638, WO05/019206, WO05/019205, WO05/018547, WO05/017190, US2005/0176776. In an embodiment inhibitors of mitotic kinesins include, but are not limited to inhibitors of KSP, inhibitors of MKLP1, inhibitors of CENP-E, inhibitors of MCAK and inhibitors of Rab6-KIFL.

Examples of "histone deacetylase inhibitors" include, but are not limited to, SAHA, TSA, oxamflatin, PXD101, MG98 and scriptaid. Further reference to other histone deacetylase inhibitors may be found in the following manuscript; Miller, T. A. et al. *J. Med. Chem.* 46(24):5097-5116 (2003).

"Inhibitors of kinases involved in mitotic progression" include, but are not limited to, inhibitors of aurora kinase, inhibitors of Polo-like kinases (PLK; in particular inhibitors of PLK-1), inhibitors of bub-1 and inhibitors of bub-R1. An example of an "aurora kinase inhibitor" is VX-680.

"Antiproliferative agents" includes antisense RNA and DNA oligonucleotides such as G3139, ODN698, RVASK-RAS, GEM231, and INX3001, and antimetabolites such as enocitabine, carmofur, tegafur, pentostatin, doxifluridine, trimetrexate, fludarabine, capecitabine, galocitabine, cytarabine ocfosfate, fosteabine sodium hydrate, raltitrexed, paltitrexid, emitefur, tiazofurin, decitabine, nolatrexed, pemetrexed, nelzarabine, 2'-deoxy-2'-methylidenecytidine, 2'-fluoromethylene-2'-deoxycytidine, N-[5-(2,3-dihydrobenzofuryl)sulfonyl]-N'-(3,4-dichlorophenyl)urea, N6-[4-deoxy-4-[N2-[2(E),4(E)-tetradecadienoyl]glycylamino]-L-glycero-B-L-manno-heptopyranosyl]adenine, aplidine, ecteinascidin, troxacitabine, 4-[2-amino-4-oxo-4,6,7,8-tetrahydro-3H-pyrimidino[5,4-b][1,4]thiazin-6-yl-(S)-ethyl]-2,5-thienoyl-L-glutamic acid, aminopterin, 5-fluorouracil, alanosine, 11-acetyl-8-(carbamoyloxymethyl)-4-formyl-6-methoxy-14-oxa-1,11-diazatetracyclo(7.4.1.0.0)-tetradeca-2,4,6-trien-9-yl acetic acid ester, swainsonine, lometrexol, dexrazoxane, methioninase, 2'-cyano-2'-deoxy-N4-palmitoyl-1-B-D-arabino furanosyl cytosine, 3-aminopyridine-2-carboxaldehyde thiosemicarbazone and trastuzumab.

Examples of monoclonal antibody targeted therapeutic agents include those therapeutic agents which have cytotoxic agents or radioisotopes attached to a cancer cell specific or target cell specific monoclonal antibody. Examples include Bexxar.

"HMG-CoA reductase inhibitors" refers to inhibitors of 3-hydroxy-3-methylglutaryl-CoA reductase. Examples of HMG-CoA reductase inhibitors that may be used include but are not limited to lovastatin (MEVACOR®; see U.S. Pat. Nos. 4,231,938, 4,294,926 and 4,319,039), simvastatin (ZOCOR®; see U.S. Pat. Nos. 4,444,784, 4,820,850 and 4,916,239), pravastatin (PRAVACHOL®; see U.S. Pat. Nos. 4,346,227, 4,537,859, 4,410,629, 5,030,447 and 5,180,589), fluvastatin (LESCOL®; see U.S. Pat. Nos. 5,354,772, 4,911,165, 4,929,437, 5,189,164, 5,118,853, 5,290,946 and 5,356,896), atorvastatin (LIPITORe; see U.S. Pat. Nos. 5,273,995, 4,681,893, 5,489,691 and 5,342,952) and cerivastatin (also known as rivastatin and BAYCHOL®; see U.S. Pat. No. 5,177,080). The structural formulas of these and additional HMG-CoA reductase inhibitors that may be used in the instant methods are described at page 87 of M. Yalpani, "Cholesterol Lowering Drugs", Chemistry & Industry, pp. 85-89 (5 Feb. 1996) and U.S. Pat. Nos. 4,782,084 and 4,885,314. The term HMG-CoA reductase inhibitor as used herein includes all pharmaceutically acceptable lactone and open-acid forms (i.e., where the lactone ring is opened to form the free acid) as well as salt and ester forms of compounds which have HMG-CoA reductase inhibitory activity, and therefor the use of such salts, esters, open-acid and lactone forms is included within the scope of this invention.

"Prenyl-protein transferase inhibitor" refers to a compound which inhibits any one or any combination of the prenyl-protein transferase enzymes, including farnesyl-protein transferase (FPTase), geranylgeranyl-protein transferase type I (GGPTase-I), and geranylgeranyl-protein transferase type-II (GGPTase-II, also called Rab GGPTase).

Examples of prenyl-protein transferase inhibitors can be found in the following publications and patents: WO 96/30343, WO 97/18813, WO 97/21701, WO 97/23478, WO 97/38665, WO 98/28980, WO 98/29119, WO 95/32987, U.S. Pat. Nos. 5,420,245, 5,523,430,5,532,359,5,510,510, 5,589,485, 5,602,098, European Patent Publ. 0 618 221, European Patent Publ. 0 675 112, European Patent Publ. 0 604 181, European Patent Publ. 0 696 593, WO 94/19357, WO 95/08542, WO 95/11917, WO 95/12612, WO 95/12572, WO 95/10514, U.S. Pat. No. 5,661,152, WO 95/10515, WO 95/10516, WO 95/24612, WO 95/34535, WO 95/25086, WO 96/05529, WO 96/06138, WO 96/06193, WO 96/16443, WO 96/21701, WO 96/21456, WO 96/22278, WO 96/24611, WO 96/24612, WO 96/05168, WO 96/05169, WO 96/00736, U.S. Pat. No. 5,571,792, WO 96/17861, WO 96/33159, WO 96/34850, WO 96/34851, WO 96/30017, WO 96/30018, WO 96/30362, WO 96/30363, WO 96/31111, WO 96/31477, WO 96/31478, WO 96/31501, WO 97/00252, WO 97/03047, WO 97/03050, WO 97/04785, WO 97/02920, WO 97/17070, WO 97/23478, WO 97/26246, WO 97/30053, WO 97/44350, WO 98/02436, and U.S. Pat. No. 5,532,359. For an example of the role of a prenyl-protein transferase inhibitor on angiogenesis see *European J. of Cancer*, Vol. 35, No. 9, pp. 1394-1401 (1999).

"Angiogenesis inhibitors" refers to compounds that inhibit the formation of new blood vessels, regardless of mechanism. Examples of angiogenesis inhibitors include, but are not limited to, tyrosine kinase inhibitors, such as inhibitors of the tyrosine kinase receptors Flt-1 (VEGFR1) and Flk-1/KDR (VEGFR2), inhibitors of epidermal-derived, fibroblast-derived, or platelet derived growth factors, MMP (matrix metalloprotease) inhibitors, integrin blockers, interferon-α, interleukin-12, pentosan polysulfate, cyclooxygenase inhibitors, including nonsteroidal anti-inflammatories (NSAIDs) like aspirin and ibuprofen as well as selective cyclooxygenase-2 inhibitors like celecoxib and rofecoxib (PNAS, Vol. 89, p. 7384 (1992); *JNCI, Vol.* 69, p. 475 (1982); *Arch. Opthalmol., Vol.* 108, p. 573 (1990); *Anat. Rec.*, Vol. 238, p. 68 (1994); *FEBS Letters*, Vol. 372, p. 83 (1995); *Clin, Orthop.* Vol. 313, p. 76 (1995); *J. Mol. Endocrinol.*, Vol. 16, p. 107 (1996); *Jpn. J. Pharmacol.*, Vol. 75, p. 105 (1997); *Cancer Res.*, Vol. 57, p. 1625 (1997); *Cell*, Vol. 93, p. 705 (1998);*Intl. J. Mol. Med.*, Vol. 2, p. 715 (1998); *J. Biol. Chem.*, Vol. 274, p. 9116 (1999)), steroidal anti-inflammatories (such as corticosteroids, mineralocorticoids, dexamethasone, prednisone, prednisolone, methylpred, betamethasone), carboxyamidotriazole, combretastatin A-4, squalamine, 6-O-chloroacetyl-carbonyl)-fumagillol, thalidomide, angiostatin, troponin-1, angiotensin II antagonists (see Fernandez et al., *J Lab. Clin. Med.* 105:141-145 (1985)), and antibodies to VEGF (see, *Nature Biotechnology*, Vol. 17, pp. 963-968 (October 1999); Kim et al., Nature, 362, 841-844 (1993); WO 00/44777; and WO 00/61186).

Other therapeutic agents that modulate or inhibit angiogenesis and may also be used in combination with the compounds of the instant invention include agents that modulate or inhibit the coagulation and fibrinolysis systems (see review in *Clin. Chem. La. Med.* 38:679-692 (2000)). Examples of such agents that modulate or inhibit the coagulation and fibrinolysis pathways include, but are not limited to, heparin (see *Thromb. Haemost.* 80:10-23 (1998)), low molecular weight heparins and carboxypeptidase U inhibitors (also known as inhibitors of active thrombin activatable fibrinolysis inhibitor [TAFIa]) (see *Thrombosis Res.* 101:329-354 (2001)). TAFIa inhibitors have been described in U.S. Ser. Nos. 60/310,927 (filed Aug. 8, 2001) and 60/349,925 (filed Jan. 18, 2002).

"Agents that interfere with cell cycle checkpoints" refer to compounds that inhibit protein kinases that transduce cell cycle checkpoint signals, thereby sensitizing the cancer cell to DNA damaging agents. Such agents include inhibitors of ATR, ATM, the CHK1 and CHK2 kinases and cdk and cdc kinase inhibitors and are specifically exemplified by 7-hydroxystaurosporin, flavopiridol, CYC202 (Cyclacel) and BMS-387032.

"Agents that interfere with receptor tyrosine kinases (RTKs)" refer to compounds that inhibit RTKs and therefore mechanisms involved in oncogenesis and tumor progression. Such agents include inhibitors of c-Kit, Eph, PDGF, Flt3 and c-Met. Further agents include inhibitors of RTKs as described by Bume-Jensen and Hunter, *Nature,* 411:355-365, 2001.

"Inhibitors of cell proliferation and survival signalling pathway" refer to compounds that inhibit signal transduction cascades downstream of cell surface receptors. Such agents include inhibitors of serine/threonine kinases (including but not limited to inhibitors of Akt such as described in WO 02/083064, WO 02/083139, WO 02/083140, US 2004-0116432, WO 02/083138, US 2004-0102360, WO 03/086404, WO 03/086279, WO 03/086394, WO 03/084473, WO 03/086403, WO 2004/041162, WO 2004/096131, WO 2004/096129, WO 2004/096135, WO 2004/096130, WO 2005/100356, WO 2005/100344, US 2005/029941, US 2005/44294, US 2005/43361, 60/734,188, 60/652,737, 60/670,469), inhibitors of Raf kinase (for example BAY-43-9006), inhibitors of MEK (for example CI-1040 and PD-098059), inhibitors of mTOR (for example Wyeth CCI-779), and inhibitors of PI3K (for example LY294002).

As described above, the combinations with NSAID's are directed to the use of NSAID's which are potent COX-2 inhibiting agents. For purposes of this specification an NSAID is potent if it possesses an $IC_{50}$ for the inhibition of COX-2 of 1 μM or less as measured by cell or microsomal assays.

The invention also encompasses combinations with NSAID's which are selective COX-2 inhibitors. For purposes of this specification NSAID's which are selective inhibitors of COX-2 are defined as those which possess a specificity for inhibiting COX-2 over COX-1 of at least 100 fold as measured by the ratio of $IC_{50}$ for COX-2 over $IC_{50}$ for COX-1 evaluated by cell or microsomal assays. Such compounds include, but are not limited to those disclosed in U.S. Pat. Nos. 5,474,995, 5,861,419, 6,001,843, 6,020,343, 5,409,944, 5,436,265, 5,536,752, 5,550,142, 5,604,260, 5,698,584, 5,710,140, WO 94/15932, U.S. Pat. No. 5,344,991, 5,134,142, 5,380,738, 5,393,790, 5,466,823, 5,633,272 and U.S. Pat. No. 5,932,598, all of which are hereby incorporated by reference.

Inhibitors of COX-2 that are particularly useful in the instant method of treatment are: 3-phenyl-4-(4-(methylsulfonyl)phenyl)-2-(5H)-furanone; and 5-chloro-3-(4-methylsulfonyl)-phenyl-2-(2-methyl-5-pyridinyl)pyridine; or a pharmaceutically acceptable salt thereof.

Compounds that have been described as specific inhibitors of COX-2 and are therefore useful in the present invention include, but are not limited to, the following: parecoxib, BEXTRA® and CELEBREX® or a pharmaceutically acceptable salt thereof.

Other examples of angiogenesis inhibitors include, but are not limited to, endostatin, ukrain, ranpirnase, IM862, 5-methoxy-4-[2-methyl-3-(3-methyl-2-buteny)oxiranyl]-1-oxaspiro[2,5]oct-6-yl(chloroacetyl)carbamate, acetyldinanaline, 5-amino-1-[[3,5-dichloro-4-(4-chlorobenzoyl)phenyl]methyl]-1H-1,2,3-triazole-4-carboxamide, CM101, squalamine, combretastatin, RPI4610, NX31838, sulfated mannopentaose phosphate, 7,7-(carbonyl-bis[imino-N-methyl-4,2-pyrrolocarbonylimino[N-methyl-4,2-pyrrole]-carbonylimino]-bis-(1,3-naphthalene disulfonate), and 3-[(2,4-dimethylpyrrol-5-yl)methylene]-2-indolinone (SU5416).

As used above, "integrin blockers" refers to compounds which selectively antagonize, inhibit or counteract binding of a physiological ligand to the $\alpha_v\beta_3$ integrin, to compounds which selectively antagonize, inhibit or counteract binding of a physiological ligand to the $\alpha v\beta 5$ integrin, to compounds which antagonize, inhibit or counteract binding of a physiological ligand to both the $\alpha_v\beta_3$ integrin and the $\alpha_v\beta_5$ integrin, and to compounds which antagonize, inhibit or counteract the activity of the particular integrin(s) expressed on capillary endothelial cells. The term also refers to antagonists of the $\alpha_v\beta_6$, $\alpha_v\beta_8$, $\alpha_2\beta_1$, $\alpha_5\beta_1$, $\alpha_6\beta_1$ and $\alpha_6\beta_4$ integrins. The term also refers to antagonists of any combination of $\alpha_v\beta_3$, $\alpha_v\beta_5$, $\alpha_v\beta_6$, $\alpha_v\beta_8$, $\alpha_1\beta_1$, $\alpha_2\beta_1$, $\alpha_5\beta_1$, $\alpha_6\beta_1$ and $\alpha_6\beta_4$ integrins.

Some specific examples of tyrosine kinase inhibitors include N-(trifluoromethylphenyl)-5-methylisoxazol-4-carboxamide, 3-[(2,4-dimethylpyrrol-5-yl)methylidenyl]indolin-2-one, 17-(allylamino)-17-demethoxygeldanamycin, 4-(3-chloro-4-fluorophenylamino)-7-methoxy-6-[3-(4-morpholinyl)propoxyl]quinazoline, N-(3-ethynylphenyl)-6,7-bis(2-methoxyethoxy)-4-quinazolinamine, BIBX1382, 2,3,9,10,11,12-hexahydro-10-(hydroxymethyl)-10-hydroxy-9-methyl-9,12-epoxy-1H-diindolo[1,2,3-fg:3',2',1'-kl]pyrrolo[3,4-i][1,6]benzodiazocin-1-one, SH268, genistein, STI571, CEP2563, 4-(3-chlorophenylamino)-5,6-dimethyl-7H-pyrrolo[2,3-d]pyrimidinemethane sulfonate, 4-(3-bromo-4-hydroxyphenyl)amino-6,7-dimethoxyquinazoline, 4-(4'-hydroxyphenyl)amino-6,7-dimethoxyquinazoline, SU6668, STI571A, N-4-chlorophenyl-4-(4-pyridylmethyl)-1-phthalazinamine, and EMD121974.

Combinations with compounds other than anti-cancer compounds are also encompassed in the instant methods. For example, combinations of the instantly claimed compounds with PPAR-γ (i.e., PPAR-gamma) agonists and PPAR-δ (i.e., PPAR-delta) agonists are useful in the treatment of certain malignancies. PPAR-γ and PPAR-δ are the nuclear peroxisome proliferator-activated receptors γ and δ. The expression of PPAR-γ on endothelial cells and its involvement in angiogenesis has been reported in the literature (see J. Cardiovasc. Pharmacol. 1998; 31:909-913; J. Biol. Chem. 1999; 274: 9116-9121; Invest. Ophthalmol Vis. Sci. 2000; 41:2309-2317). More recently, PPAR-γ agonists have been shown to inhibit the angiogenic response to VEGF in vitro; both troglitazone and rosiglitazone maleate inhibit the development of retinal neovascularization in mice. (Arch. Ophthamol. 2001; 119:709-717). Examples of PPAR-γ agonists and PPAR-γ/α agonists include, but are not limited to, thiazolidinediones (such as DRF2725, CS-011, troglitazone, rosiglitazone, and pioglitazone), fenofibrate, gemfibrozil, clofibrate, GW2570, SB219994, AR-H039242, JTT-501, MCC-555, GW2331, GW409544, NN2344, KRP297, NP0110, DRF4158, NN622, GI262570, PNU182716, DRF552926, 2-[(5,7-dipropyl-3-trifluoromethyl-1,2-benzisoxazol-6-yl)oxy]-2-methylpropionic acid (disclosed in U.S. Ser. No. 09/782,856), and 2(R)-7-(3-(2-chloro-4-(4-fluorophenoxy)phenoxy)propoxy)-2-ethylchroman-2-carboxylic acid (disclosed in U.S. Ser. No. 60/235,708 and 60/244,697).

Another embodiment of the instant invention is the use of the presently disclosed compounds in combination with gene therapy for the treatment of cancer. For an overview of genetic strategies to treating cancer see Hall et al (Am. J. Hum. Genet. 61:785-789, 1997) and Kufe et al (Cancer Medicine, 5th Ed, pp 876-889, BC Decker, Hamilton 2000). Gene therapy can be used to deliver any tumor suppressing gene. Examples of such genes include, but are not limited to, p53, which can be delivered via recombinant virus-mediated gene transfer (see U.S. Pat. No. 6,069,134, for example), a uPA/uPAR antagonist ("Adenovirus-Mediated Delivery of a uPA/uPAR Antagonist Suppresses Angiogenesis-Dependent Tumor Growth and Dissemination in Mice," Gene Therapy, August 1998; 5(8):1105-13), and interferon gamma (J. Immunol. 2000; 164:217-222).

The compounds of the instant invention may also be administered in combination with an inhibitor of inherent multidrug resistance (MDR), in particular MDR associated with high levels of expression of transporter proteins. Such MDR inhibitors include inhibitors of p-glycoprotein (P-gp), such as LY335979, XR9576, OC144-093, R101922, VX853 and PSC833 (valspodar).

A compound of the present invention may be employed in conjunction with anti-emetic agents to treat nausea or emesis, including acute, delayed, late-phase, and anticipatory emesis, which may result from the use of a compound of the present invention, alone or with radiation therapy. For the prevention or treatment of emesis, a compound of the present invention may be used in conjunction with other anti-emetic agents, especially neurokinin-1 receptor antagonists, 5HT3 receptor antagonists, such as ondansetron, granisetron, tropisetron, and zatisetron, GABAB receptor agonists, such as baclofen, a corticosteroid such as Decadron (dexamethasone), Kenalog, Aristocort, Nasalide, Preferid, Benecorten or others such as disclosed in U.S. Pat. Nos. 2,789,118, 2,990,401, 3,048,581, 3,126,375, 3,929,768, 3,996,359, 3,928,326 and 3,749,712, an antidopaminergic, such as the phenothiazines (for example prochlorperazine, fluphenazine, thioridazine and mesoridazine), metoclopramide or dronabinol. In another embodiment, conjunctive therapy with an anti-emesis agent selected from a neurokinin-1 receptor antagonist, a 5HT3 receptor antagonist and a corticosteroid is disclosed for the treatment or prevention of emesis that may result upon administration of the instant compounds.

Neurokinin-1 receptor antagonists of use in conjunction with the compounds of the present invention are fully described, for example, in U.S. Pat. Nos. 5,162,339, 5,232,929, 5,242,930, 5,373,003, 5,387,595, 5,459,270, 5,494,926, 5,496,833, 5,637,699, 5,719,147; European Patent Publication Nos. EP 0 360 390, 0 394 989, 0 428 434, 0 429 366, 0 430 771, 0 436 334, 0 443 132, 0 482 539, 0 498 069, 0 499 313, 0 512 901, 0 512 902, 0 514 273, 0 514 274, 0 514 275, 0 514 276, 0 515 681, 0 517 589, 0 520 555, 0 522 808, 0 528 495, 0 532 456, 0 533 280, 0 536 817, 0 545 478, 0 558 156, 0 577 394, 0 585 913, 0 590 152, 0 599 538, 0 610 793, 0 634 402, 0 686 629, 0 693 489, 0 694 535, 0 699 655, 0 699 674, 0 707 006, 0 708 101, 0 709 375, 0 709 376, 0 714 891, 0 723 959, 0 733 632 and 0 776 893; PCT International Patent Publication Nos. WO 90/05525, 90/05729, 91/09844, 91/18899, 92/01688, 92/06079, 92/12151, 92/15585, 92/17449, 92/20661, 92/20676, 92/21677, 92/22569, 93/00330, 93/00331, 93/01159, 93/01165, 93/01169, 93/01170, 93/06099, 93/09116, 93/10073, 93/14084, 93/14113, 93/18023, 93/19064, 93/21155, 93/21181, 93/23380, 93/24465, 94/00440, 94/01402, 94/02461, 94/02595, 94/03429, 94/03445, 94/04494, 94/04496, 94/05625, 94/07843, 94/08997, 94/10165, 94/10167, 94/10168, 94/10170, 94/11368, 94/13639, 94/13663, 94/14767, 94/15903, 94/19320, 94/19323, 94/20500, 94/26735, 94/26740, 94/29309, 95/02595, 95/04040, 95/04042, 95/06645, 95/07886, 95/07908, 95/08549, 95/11880, 95/14017, 95/15311, 95/16679, 95/17382, 95/18124, 95/18129, 95/19344, 95/20575, 95/21819, 95/22525, 95/23798, 95/26338, 95/28418, 95/30674, 95/30687, 95/33744, 96/05181, 96/05193, 96/05203, 96/06094, 96/07649, 96/10562, 96/16939, 96/18643, 96/20197, 96/21661, 96/29304, 96/29317, 96/29326, 96/29328, 96/31214, 96/32385, 96/37489, 97/01553, 97/01554, 97/03066, 97/08144, 97/14671, 97/17362, 97/18206, 97/19084, 97/19942 and 97/21702; and in British Patent Publication Nos. 2 266 529, 2 268 931, 2 269 170, 2 269 590, 2 271 774, 2 292 144, 2 293 168, 2 293 169, and 2 302 689. The preparation of such compounds is fully described in the aforementioned patents and publications, which are incorporated herein by reference.

In an embodiment, the neurokinin-1 receptor antagonist for use in conjunction with the compounds of the present invention is selected from: 2-(R)-(1-(R)-(3,5-bis(trifluoromethyl)phenyl)ethoxy)-3-(S)-(4-fluorophenyl)-4-(3-(5-oxo-1H,4H-1,2,4-triazolo)methyl)morpholine, or a pharmaceutically acceptable salt thereof, which is described in U.S. Pat. No. 5,719,147.

A compound of the instant invention may also be administered with an agent useful in the treatment of anemia. Such an anemia treatment agent is, for example, a continuous erythropoiesis receptor activator (such as epoetin alfa).

A compound of the instant invention may also be administered with an agent useful in the treatment of neutropenia. Such a neutropenia treatment agent is, for example, a hematopoietic growth factor which regulates the production and function of neutrophils such as a human granulocyte colony stimulating factor, (G-CSF). Examples of a G-CSF include filgrastim.

A compound of the instant invention may also be administered with an immunologic-enhancing drug, such as levamisole, isoprinosine and Zadaxin.

A compound of the instant invention may also be useful for treating or preventing cancer in combination with P450 inhibitors including: xenobiotics, quinidine, tyramine, ketoconazole, testosterone, quinine, metyrapone, caffeine, phenelzine, doxorubicin, troleandomycin, cyclobenzaprine, erythromycin, cocaine, furafyline, cimetidine, dextromethorphan, ritonavir, indinavir, amprenavir, diltiazem, terfenadine, verapamil, cortisol, itraconazole, mibefradil, nefazodone and nelfinavir.

A compound of the instant invention may also be useful for treating or preventing cancer in combination with Pgp and/or BCRP inhibitors including: cyclosporin A, PSC833, GF120918, cremophorEL, fumitremorgin C, Ko132, Ko134, Iressa, Imatnib mesylate, EKI-785, C11033, novobiocin, diethylstilbestrol, tamoxifen, resperpine, VX-710, tryprostatin A, flavonoids, ritonavir, saquinavir, nelfinavir, omeprazole, quinidine, verapamil, terfenadine, ketoconazole, nifidepine, FK506, amiodarone, XR9576, indinavir, amprenavir, cortisol, testosterone, LY335979, OC144-093, erythromycin, vincristine, digoxin and talinolol.

A compound of the instant invention may also be useful for treating or preventing cancer, including bone cancer, in combination with bisphosphonates (understood to include bisphosphonates, diphosphonates, bisphosphonic acids and diphosphonic acids). Examples of bisphosphonates include but are not limited to: etidronate (Didronel), pamidronate (Aredia), alendronate (Fosamax), risedronate (Actonel), zoledronate (Zometa), ibandronate (Boniva), incadronate or cimadronate, clodronate, EB-1053, minodronate, neridronate, piridronate and tiludronate including any and all pharmaceutically acceptable salts, derivatives, hydrates and mixtures thereof.

A compound of the instant invention may also be useful for treating or preventing breast cancer in combination with aromatase inhibitors. Examples of aromatase inhibitors include but are not limited to: anastrozole, letrozole and exemestane.

A compound of the instant invention may also be useful for treating or preventing cancer in combination with siRNA therapeutics.

The compounds of the instant invention may also be administered in combination with γ-secretase inhibitors and/or inhibitors of NOTCH signaling. Such inhibitors include compounds described in WO 01/90084, WO 02/30912, WO 01/70677, WO 03/013506, WO 02/36555, WO 03/093252, WO 03/093264, WO 03/093251, WO 03/093253, WO 2004/039800, WO 2004/039370, WO 2005/030731, WO 2005/014553, U.S. Ser. No. 10/957,251, WO 2004/089911, WO 02/081435, WO 02/081433, WO 03/018543, WO 2004/031137, WO 2004/031139, WO 2004/031138, WO 2004/101538, WO 2004/101539 and WO 02/47671 (including LY-450139).

A compound of the instant invention may also be useful for treating or preventing cancer in combination with PARP inhibitors.

A compound of the instant invention may also be useful for treating cancer in combination with the following therapeutic agents: abarelix (Plenaxis Depot®); aldesleukin (Prokine®); Aldesleukin (Proleukin®); Alemtuzumabb (Campath®); alitretinoin (Panretin®); allopurinol (Zyloprim®); altretamine (Hexylen®); amifostine (Ethyol®); anastrozole (Arimidex®); arsenic trioxide (Trisenox®); asparaginase (Elspar®); azacitidine (Vidaza®); bevacuzimab (Avastin®); bexarotene capsules (Targretin®); bexarotene gel (Targretin®); bleomycin (Blenoxane®); bortezomib (Velcade®); busulfan intravenous (Busulfex®); busulfan oral (Myleran®); calusterone (Methosarb®); capecitabine (Xeloda®); carboplatin (Paraplatin®); carmustine (BCNU®, BiCNU®); carmustine (Gliadel®); carmustine with Polifeprosan 20 Implant (Gliadel Wafer®); celecoxib (Celebrex®); cetuximab (Erbitux®); chlorambucil (Leukeran®); cisplatin (Platinol®); cladribine (Leustatin®, 2-CdA®); clofarabine (Clolar®); cyclophosphamide (Cytoxan®, Neosar®); cyclophosphamide (Cytoxan Injection®); cyclophosphamide (Cytoxan Tablet®); cytarabine (Cytosar-U®); cytarabine liposomal (DepoCyt®); dacarbazine (DTIC-Dome®); dactinomycin, actinomycin D (Cosmegen®); Darbepoetin alfa (Aranesp®); daunorubicin liposomal (DanuoXome®); daunorubicin, daunomycin (Daunorubicin®); daunorubicin, daunomycin (Cerubidine®); Denileukin diftitox (Ontak®);

dexrazoxane (Zinecard®); docetaxel (Taxotere®); doxorubicin (Adriamycin PFS®); doxorubicin (Adriamycin®, Rubex®); doxorubicin (Adriamycin PFS Injection®); doxorubicin liposomal (Doxil®); DROMOSTANOLONE PROPIONATE (DROMOSTANOLONE®); DROMOSTANOLONE PROPIONATE (MASTERONE INJECTION®); Elliott's B Solution (Elliott's B Solution®); epirubicin (Ellence®); Epoetin alfa (Epogen®); erlotinib (Tarceva®); estramustine (Emcyt®); etoposide phosphate (Etopophos®); etoposide, VP-16 (Vepesid®); exemestane (Aromasin®); Filgrastim (Neupogen®); floxuridine (intraarterial) (FUDR®); fludarabine (Fludara®); fluorouracil, 5-FU (Adrucil®); fulvestrant (Faslodex®); gefitinib (Iressa®); gemcitabine (Gemzar®); gemtuzumab ozogamicin (Mylotarg®); goserelin acetate (Zoladex Implant®); goserelin acetate (Zoladex®); histrelin acetate (Histrelin Implant®); hydroxyurea (Hydrea®); Ibritumomab Tiuxetan (Zevalin®); idarubicin (Idamycin®); ifosfamide (IFEX®); imatinib mesylate (Gleevec®); interferon alfa 2a (Roferon A®); Interferon alfa-2b (Intron A®); irinotecan (Camptosar®); lenalidomide (Revlimid®); letrozole (Femara®); leucovorin (Wellcovorin®, Leucovorin®); Leuprolide Acetate (Eligard®); levamisole (Ergamisol®); lomustine, CCNU (CeeBU®); meclorethamine, nitrogen mustard (Mustargen®); megestrol acetate (Megace®); melphalan, L-PAM (Alkeran®); mercaptopurine, 6-MP (Purinethol®); mesna (Mesnex®); mesna (Mesnex Tabs®); methotrexate (Methotrexate®); methoxsalen (Uvadex®); mitomycin C (Mutamycin®); mitotane (Lysodren®); mitoxantrone (Novantrone®); nandrolone phenpropionate (Durabolin-50®); nelarabine (Arranon®); Nofetumomab (Verluma®); Oprelvekin (Neumega®); oxaliplatin (Eloxatin®); paclitaxel (Paxene®); paclitaxel (Taxol®); paclitaxel protein-bound particles (Abraxane®); palifermin (Kepivance®); pamidronate (Aredia®); pegademase (Adagen (Pegademase Bovine)®); pegaspargase (Oncaspar®); Pegfilgrastim (Neulasta®); pemetrexed disodium (Alimta®); pentostatin (Nipent®); pipobroman (Vercyte®); plicamycin, mithramycin (Mithracin®); porfimer sodium (Photofrin®); procarbazine (Matulane®); quinacrine (Atabrine®); Rasburicase (Elitek®); Rituximab (Rituxan®); Ridaforolimus; sargramostim (Leukine®); Sargramostim (Prokine®); sorafenib (Nexavar®); streptozocin (Zanosar®); sunitinib maleate (Sutent®); talc (Sclerosol®); tamoxifen (Nolvadex®); temozolomide (Temodar®); teniposide, VM-26 (Vumon®); testolactone (Teslac®); thioguanine, 6-TG (Thioguanine®); thiotepa (Thioplex®); topotecan (Hycamtin®); toremifene (Fareston®); Tositumomab (Bexxar®); Tositumomab/1-131 tositumomab)(Bexxar®; Trastuzumab (Herceptin®); tretinoin, ATRA (Vesanoid®); Uracil Mustard (Uracil Mustard Capsules®); valrubicin (Valstar®); vinblastine (Velban®); vincristine (Oncovin®); vinorelbine (Navelbine®); vorinostat (Zolinza®) and zoledronate (Zometa®).

In an embodiment, the angiogenesis inhibitor to be used as the second compound is selected from a tyrosine kinase inhibitor, an inhibitor of epidermal-derived growth factor, an inhibitor of fibroblast-derived growth factor, an inhibitor of platelet derived growth factor, an MMP (matrix metalloprotease) inhibitor, an integrin blocker, interferon-α, interleukin-12, pentosan polysulfate, a cyclooxygenase inhibitor, carboxyamidotriazole, combretastatin A-4, squalamine, 6-O-chloroacetyl-carbonyl)umagillol, thalidomide, angiostatin, troponin-1, or an antibody to VEGF. In an embodiment, the estrogen receptor modulator is tamoxifen or raloxifene.

Thus, the scope of the instant invention encompasses the use of the instantly claimed compounds in combination with a second compound selected from: an estrogen receptor modulator, an androgen receptor modulator, a retinoid receptor modulator, a cytotoxic/cytostatic agent, an antiproliferative agent, a prenyl-protein transferase inhibitor, an HMG-CoA reductase inhibitor, an HIV protease inhibitor, a reverse transcriptase inhibitor, an angiogenesis inhibitor, PPAR-γ agonists, PPAR-δ agonists, an inhibitor of inherent multidrug resistance, an anti-emetic agent, an agent useful in the treatment of anemia, an agent useful in the treatment of neutropenia, an immunologic-enhancing drug, an inhibitor of cell proliferation and survival signaling, a bisphosphonate, an aromatase inhibitor, an siRNA therapeutic, γ-secretase and/or NOTCH inhibitors, agents that interfere with receptor tyrosine kinases (RTKs), an agent that interferes with a cell cycle checkpoint, and any of the therapeutic agents listed above.

Also included in the scope of the claims is a method of treating cancer that comprises administering a therapeutically effective amount of a compound of the instant invention in combination with radiation therapy and/or in combination with a second compound selected from: an estrogen receptor modulator, an androgen receptor modulator, a retinoid receptor modulator, a cytotoxiccytostatic agent, an antiproliferative agent, a prenyl-protein transferase inhibitor, an HMG-CoA reductase inhibitor, an HIV protease inhibitor, a reverse transcriptase inhibitor, an angiogenesis inhibitor, PPAR-γ agonists, PPAR-δ agonists, an inhibitor of inherent multidrug resistance, an anti-emetic agent, an agent useful in the treatment of anemia, an agent useful in the treatment of neutropenia, an immunologic-enhancing drug, an inhibitor of cell proliferation and survival signaling, a bisphosphonate, an aromatase inhibitor, an siRNA therapeutic, γ-secretase and/or NOTCH inhibitors, agents that interfere with receptor tyrosine kinases (RTKs), an agent that interferes with a cell cycle checkpoint, and any of the therapeutic agents listed above.

And yet another embodiment of the invention is a method of treating cancer that comprises administering a therapeutically effective amount of a compound of the instant invention in combination with paclitaxel or trastuzumab.

The invention further encompasses a method of treating or preventing cancer that comprises administering a therapeutically effective amount of a compound of the instant invention in combination with a COX-2 inhibitor.

The instant invention also includes a pharmaceutical composition useful for treating or preventing cancer that comprises a therapeutically effective amount of a compound of the instant invention and a second compound selected from: an estrogen receptor modulator, an androgen receptor modulator, a retinoid receptor modulator, a cytotoxic/cytostatic agent, an antiproliferative agent, a prenyl-protein transferase inhibitor, an HMG-CoA reductase inhibitor, an HIV protease inhibitor, a reverse transcriptase inhibitor, an angiogenesis inhibitor, a PPAR-γ agonist, a PPAR-δ agonist, an inhibitor of cell proliferation and survival signaling, a bisphosphonate, an aromatase inhibitor, an siRNA therapeutic, γ-secretase and/or NOTCHinhibitors, agents that interfere with receptor tyrosine kinases (RTKs), an agent that interferes with a cell cycle checkpoint, and any of the therapeutic agents listed above.

Methods for the safe and effective administration of most of these chemotherapeutic agents are known to those skilled in the art. In addition, their administration is described in the standard literature. For example, the administration of many of the chemotherapeutic agents is described in the "Physicians' Desk Reference" (PDR), e.g., 1996 edition (Medical Economics Company, Montvale, N.J. 07645-1742, USA), the Physicians' Desk Reference, $56^{th}$ Edition, 2002 (published by Medical Economics company, Inc. Montvale, N.J. 07645-1742), the Physicians' Desk Reference, 57th Edition, 2003 (published by Thompson PDR, Montvale, N.J. 07645-1742), the Physicians' Desk Reference, 60th Edition, 2006 (published by Thompson PDR, Montvale, N.J. 07645-1742), and the Physicians' Desk Reference, 64th Edition, 2010 (published by PDR Network, LLC at Montvale, N.J. 07645-1725); the disclosures of which are incorporated herein by reference thereto.

If the patient is responding, or is stable, after completion of the therapy cycle, the therapy cycle can be repeated according to the judgment of the skilled clinician. Upon completion of the therapy cycles, the patient can be continued on the compounds of this invention at the same dose that was administered in the treatment protocol. This maintenance dose can be continued until the patient progresses or can no longer tolerate the dose (in which case the dose can be reduced and the patient can be continued on the reduced dose).

Those skilled in the art will recognize that the actual dosages and protocols for administration employed in the methods of this invention may be varied according to the judgment of the skilled clinician. The actual dosage employed may be varied depending upon the requirements of the patient and the severity of the condition being treated. Determination of the proper dosage for a particular situation is within the skill of the art. A determination to vary the dosages and protocols for administration may be made after the skilled clinician takes into account such factors as the patient's age, condition and size, as well as the severity of the cancer being treated and the response of the patient to the treatment.

The amount and frequency of administration of the compound of formula (1) and the chemotherapeutic agents will be regulated according to the judgment of the attending clinician (physician) considering such factors as age, condition and size of the patient as well as severity of the cancer being treated.

The chemotherapeutic agent can be administered according to therapeutic protocols well known in the art. It will be apparent to those skilled in the art that the administration of the chemotherapeutic agent can be varied depending on the cancer being treated and the known effects of the chemotherapeutic agent on that disease. Also, in accordance with the knowledge of the skilled clinician, the therapeutic protocols (e.g., dosage amounts and times of administration) can be varied in view of the observed effects of the administered therapeutic agents on the patient, and in view of the observed responses of the cancer to the administered therapeutic agents.

The initial administration can be made according to established protocols known in the art, and then, based upon the observed effects, the dosage, modes of administration and times of administration can be modified by the skilled clinician.

The particular choice of chemotherapeutic agent will depend upon the diagnosis of the attending physicians and their judgement of the condition of the patient and the appropriate treatment protocol.

The determination of the order of administration, and the number of repetitions of administration of the chemotherapeutic agent during a treatment protocol, is well within the knowledge of the skilled physician after evaluation of the cancer being treated and the condition of the patient.

Thus, in accordance with experience and knowledge, the practicing physician can modify each protocol for the administration of a chemotherapeutic agent according to the individual patient's needs, as the treatment proceeds. All such modifications are within the scope of the present invention.

The attending clinician, in judging whether treatment is effective at the dosage administered, will consider the general well-being of the patient as well as more definite signs such as relief of cancer-related symptoms (e.g., pain), inhibition of tumor growth, actual shrinkage of the tumor, or inhibition of metastasis. Size of the tumor can be measured by standard methods such as radiological studies, e.g., CAT or MRI scan, and successive measurements can be used to judge whether or not growth of the tumor has been retarded or even reversed. Relief of disease-related symptoms such as pain, and improvement in overall condition can also be used to help judge effectiveness of treatment.

The compounds of this invention may be prepared by employing reactions as shown in the following Reaction Schemes, in addition to other standard manipulations that are known in the literature or exemplified in the experimental procedures. The illustrative Reaction Schemes below, therefore, are not limited by the compounds listed or by any particular substituents employed for illustrative purposes. Substituent numbering as shown in the Reaction Schemes do not necessarily correlate to that used in the claims and often, for clarity, a single substituent is shown attached to the compound where multiple substituents are optionally allowed under the definitions of formula (1) hereinabove.

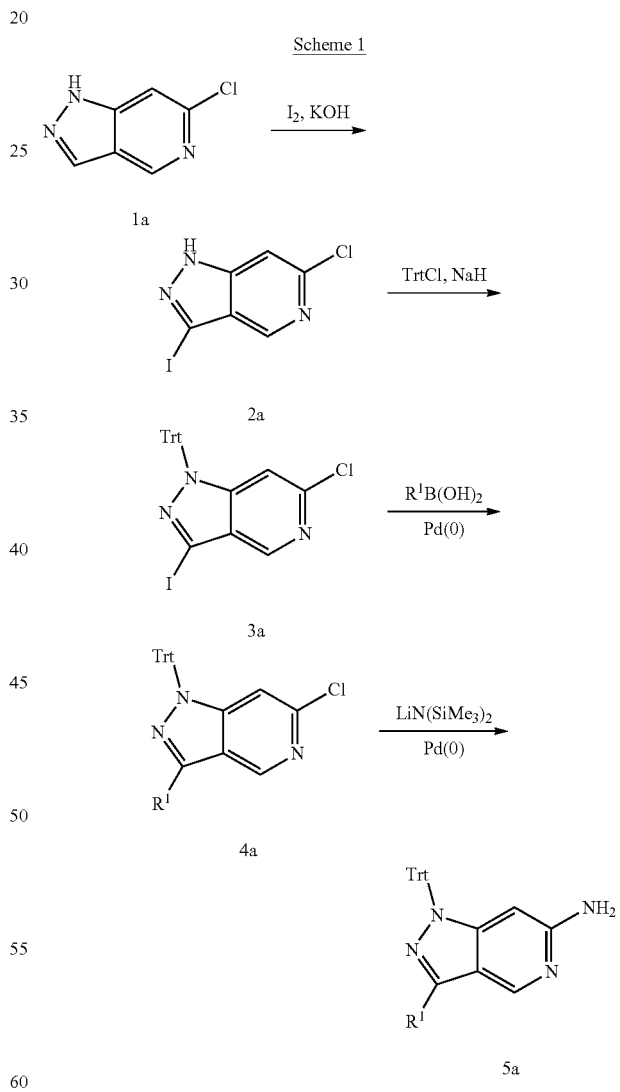

Step 1: 6-chloro-3-iodo-1H-pyrazolo[4,3-c]pyridine (2a)

A flask was charged with 6-chloro-1H-pyrazolo[4,3-c]pyridine (3 g, 19.54 mmol), iodine (13.11 g, 51.7 mmol), KOH (3.29 g, 58.6 mmol) and DMF (60 mL) (Note: heat generated during adding DMF). The mixture was heated at 40° C. for 16 h and then additional iodine (7.8 g, 30.7 mmol) and KOH (1.6 g, 28.4 mmol) were added. The mixture was heated at 70° C. for 3 h and then quenched with 1N $Na_2S_2O_3$ and extracted with EtOAc. The organic phase was washed with water, brine and dried ($Na_2SO_4$). After evaporation of volatiles DCM was added. A solid precipitated and filtrated off to yield 6-chloro-3-iodo-1H-pyrazolo[4,3-c]pyridine (3.2 g, 11.51 mmol, 59%), which was carried out in the next step without further purification. MS ESI calc'd. for $C_6H_4ClIN_3$ [M+1]$^+$ 280, found 280.

Step 2: 6-chloro-3-iodo-1-trityl-1H-pyrazolo[4,3-c]pyridine (3a)

A solution of 6-chloro-3-iodo-1H-pyrazolo[4,3-c]pyridine (1.874 g, 6.71 mmol) in THF (20 mL) was treated with NaH (60% in mineral oil; 0.402 g, 10.06 mmol) at 0° C. and the mixture was stirred for 50 min. Trityl chloride (2.244 g, 8.05 mmol) was added at the same temperature and the mixture was stirred for 16 h at room temperature, quenched with saturated $NH_4Cl$ and extracted with EtOAc. The organic phase was washed with water, brine, dried ($Na_2SO_4$) and concentrated in vacuo to afford a residue, which was purified by chromatography on silica gel (SNAP 50 g, from 0 to 10% EtOAc in hexanes, 5 CV; 10% EtOAc in hexanes, 15 CV) to yield 6-chloro-3-iodo-1-trityl-1H-pyrazolo[4,3-c]pyridine (3.26 g, 6.25 mmol, 93%) as a light yellow solid. MS ESI calc'd. for $C_{25}H_{18}ClIN_3$[M+1]$^+$522, found 522.

Step 3: 6-chloro-3-(2-methylpyridin-4-yl)-1-trityl-1H-pyrazolo[4,3-c]pyridine (4a) (R$^1$=2-methyl pyridine)

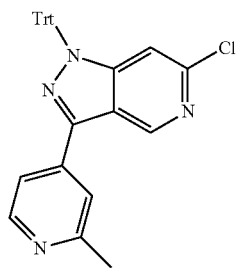

6-chloro-3-iodo-1-trityl-1H-pyrazolo[4,3-c]pyridine (2.465 g, 4.72 mmol), 2-methylpyridine-4-boronic acid (0.966 g, 7.05 mmol), $PdCl_2$(dppf)-$CH_2Cl_2$Adduct (0.579 g, 0.709 mmol) and $K_2CO_3$ (1.959 g, 14.17 mmol) were dissolved in a mixture of 1,4-dioxane (10 mL)/$H_2O$ (2.5 mL). The reaction mixture was degassed for 5 min, heated to 80° C. overnight, cooled to RT and diluted with EtOAc. Reaction was filtered through Celite and then partitioned between EtOAc and saturated $NaHCO_3$. The organic layer was extracted with EtOAc (3×) and the combined organic layers were dried ($Na_2SO_4$) and concentrated in vacuo. The residue was purified by chromatography on silica gel over a gradient of 0-75% EtOAc in hexanes to yield 6-chloro-3-(2-methylpyridin-4-yl)-1-trityl-1H-pyrazolo[4,3-c]pyridine (1.02 g, 2.09 mmol, 44%) as a solid. MS ESI calc'd. for $C_{31}H_{24}ClN_4$ [M+1]$^+$487, found 487.

Step 4: 3-(2-methylpyridin-4-yl)-1-trityl-1H-pyrazolo[4,3-c]pyridin-6-amine (5a) (R$^1$=2-methyl pyridine)

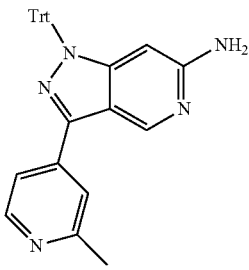

$Pd_2$(dba)$_3$ (0.192 g, 0.209 mmol), biphenyl-2-yl(dicyclohexyl)phosphane (0.073 g, 0.209 mmol), and 6-chloro-3-(2-methylpyridin-4-yl)-1-trityl-1H-pyrazolo[4,3-c]pyridine (1.02 g, 2.094 mmol) were placed in a microwave vial under nitrogen and dissolved in THF (11 mL) The reaction mixture was degassed for 5 min, LiHMDS (2.51 mL, 2.51 mmol, 1M in THF) was added via syringe and then heated to 65° C. overnight. The mixture was cooled to RT and $Pd_2$(dba)$_3$ (0.096 g, 0.1 mmol), biphenyl-2-yl(dicyclohexyl)phosphane (0.036 g, 0.1 mmol) and LiHMDS (1.25 mL, 1.25 mmol, 1M in THF) were added again. The mixture was degassed for 5 min and heated to 80° C. for 3 h, cooled to RT and quenched with 1N HCl. The mixture was then concentrated and partitioned between DCM and 1N NaOH. The organic layer was extracted with DCM (3×) and the combined organic layers were dried ($Na_2SO_4$) and concentrated in vacuo. The residue was purified by chromatography on silica gel over a gradient of 0-100% EtOAc in hexanes and then over a gradient of 0-30% (1:2=MeOH:EtOAc) in DCM to yield 3-(2-methylpyridin-4-yl)-1-trityl-1H-pyrazolo[4,3-c]pyridin-6-amine (549 mg, 2.09 mmol, 56%) as a solid. MS ESI calc'd. for $C_{31}H_{26}N_5$ [M+1]$^+$468, found 468.

Scheme 2

Step 1: Methyl 3-bromo-1-trityl-1H-pyrazolo[4,3-c]pyridine-6-carboxylate

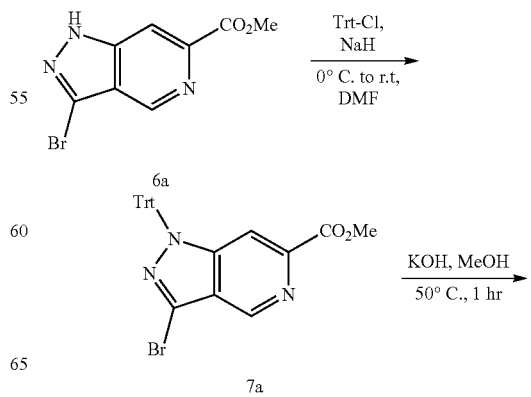

-continued

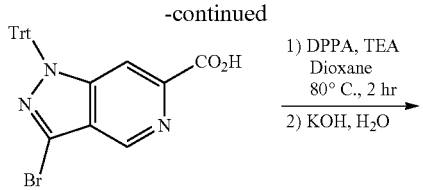

8a

1) DPPA, TEA
Dioxane
80° C., 2 hr
───────────→
2) KOH, H₂O

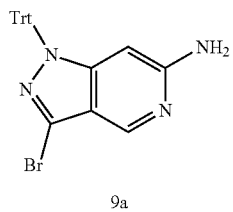

9a (7a)

At 0° C., to a brown suspension of methyl 3-bromo-1H-pyrazolo[4,3-c]pyridine-6-carboxylate (5 g, 19.53 mmol) in DMF (50 mL), 60% of NaH (1.172 g, 29.3 mmol) was added in portions. After addition, the reaction mixture was stirred at the same temperature for 30 min, then a solution of triphenylmethyl chloride (6.53 g, 23.43 mmol) in 50 mL of DMF was added dropwise. The treated reaction mixture was slowly warmed up to room temperature overnight and then quenched with H₂O. The reaction mixture was extracted with EtOAc. The combined organic layer was washed with brine and then dried (Na₂SO₄). After filtration and removal of solvent, the residue was purified by column chromatography on silica gel 120 g, eluting with 20% EtOAc in hexane to give the product 7a as a white solid (6.0 g, 12.04 mmol, 62%). MS ESI calc'd. for $C_{27}H_{21}BrN_3O_2$ [M+H]⁺ 498, found 498.

Step 2: 3-bromo-1-trityl-1H-pyrazolo[4,3-c]pyridine-6-carboxylic acid (8a)

To a suspension of methyl 3-bromo-1-trityl-1H-pyrazolo[4,3-c]pyridine-6-carboxylate (6.0 g, 12.04 mmol) in MeOH (60 mL), 1N KOH (42.1 mL, 42.1 mmol) was added. The reaction mixture was heated to 50° C. for 1 h. After cooling down to room temperature, 1N HCl was added to pH=4. The product 8a was collected by filtration and washed with H₂O (5.3 g, 10.95 mmol, 91%). MS ESI calc'd. for $C_{26}H_{19}BrN_3O_2$ [M+H]⁺ 484, found 484.

Step 3: 3-bromo-1-trityl-1H-pyrazolo[4,3-c]pyridin-6-amine (9a)

To a suspension of 3-bromo-1-trityl-1H-pyrazolo[4,3-c]pyridine-6-carboxylic acid (1.95 g, 4.03 mmol) in 1,4-dioxane (19.50 mL) and diphenylphosphoryl azide (DPPA) (1.047 mL, 4.83 mmol), TEA (0.842 mL, 6.04 mmol) in 10 mL of 1,4-dioxane was added dropwise over 5 min. The clear solution was heated to 80° C. for 2 h and a yellow clear solution was obtained. A solution of 1N KOH (20.13 mL, 20.13 mmol) was added at the same temperature. The reaction mixture was heated to 80° C. overnight. After cooling down to room temperature, the reaction mixture was extracted with EtOAc. The combined organic layer was washed with brine and then dried (Na₂SO₄). After filtration and removal of solvent, the residue was purified by column chromatography on silica gel 50 g, eluting with 50% EtOAc in hexane to give the product 9a as an off white solid (0.61 g, 1.34 mmol, 33%). MS ESI calc'd. for $C_{25}H_{20}BrN_4$ [M+H]⁺ 455, found 455.

Scheme 3

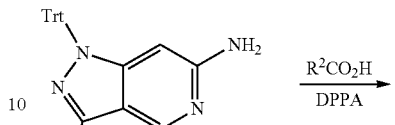

5a

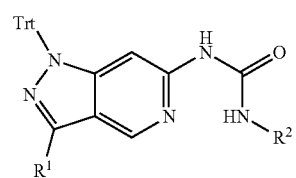

TFA
───→

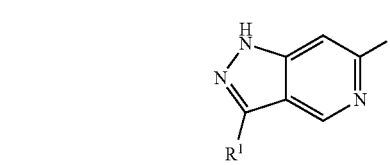

Urea derivatives have been prepared by heating at 100° C. the appropriate acid in presence of diphenylphosphoryl azide and TEA in toluene to form the isocyanate, which was then trapped in situ by intermediate 5a. After overnight heating at 100° C. and purification by chromatography on silica gel, the residue was directly treated with TFA in DCM to yield the desired product after purification via reverse phase HPLC.

Scheme 4

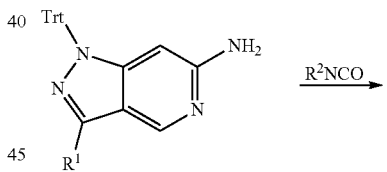

5a

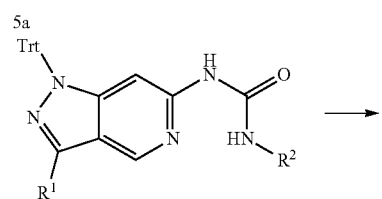

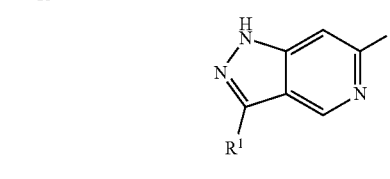

Urea derivatives have been prepared by overnight heating at 60° C. in 1,4-dioxane intermediate 5a and the appropriate isocyanate. After chromatography on silica gel, the residue was treated with TFA in DCM (with or without triethylsilane) to yield the desired product after purification via reverse phase HPLC.

Scheme 5

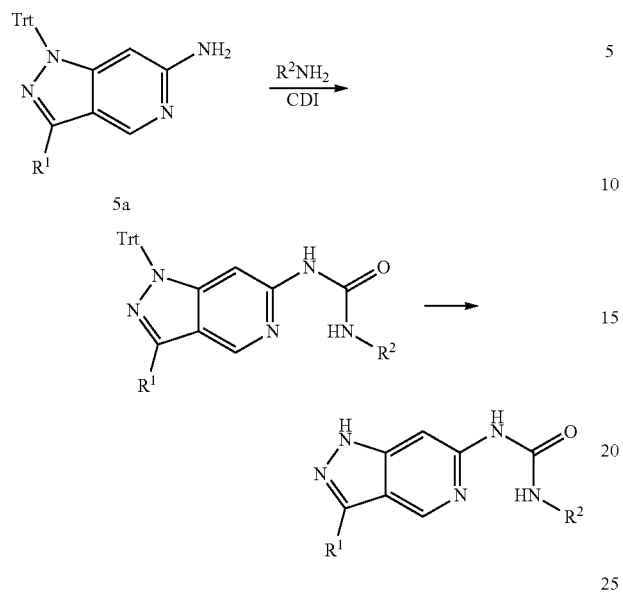

Urea derivatives have been prepared by adding intermediate 5a and imidazole to a solution of CDI in DCM, dioxane or THF. After stirring 3 h at RT, the appropriate amine was added and the mixture was left (from 30 min to 16 h) at the same temperature. After chromatography on silica gel, the residue was treated with TFA in DCM (with or without triethylsilane) to yield the desired product after purification via reverse phase HPLC.

Scheme 6

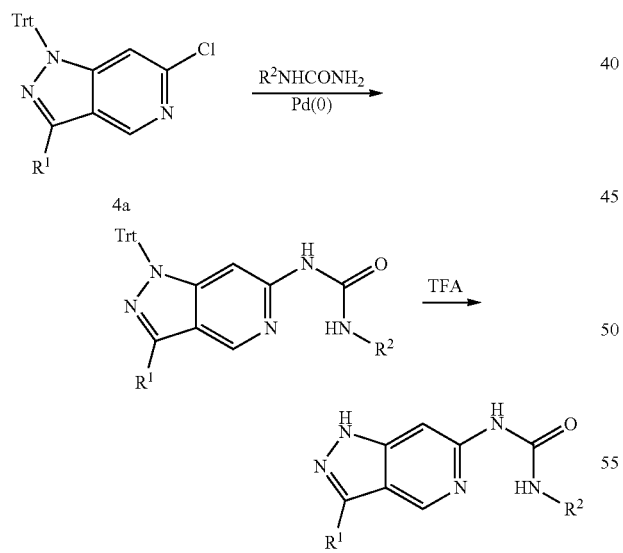

Urea derivatives have been prepared by heating at 100° C. (from 1 h to 16 h) intermediate 4a with the appropriate primary urea, $Cs_2CO_3$, BrettPhos precatalyst in DMA or dioxane. After chromatography on silica gel, the residue was treated with TFA in DCM (with or without triethylsilane) to yield the desired product after purification via reverse phase HPLC.

Scheme 7

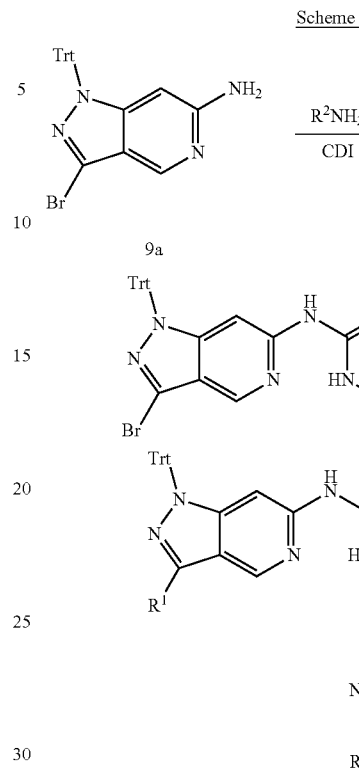

Urea derivatives have been prepared by adding intermediate 9a and imidazole to a solution of CDI in DCM, dioxane or THF. After stirring 16 h at RT, the appropriate amine was added and the mixture was left (from 30 min to 16 h) at the same temperature. After chromatography on silica gel, the urea was heated at 80° C. for 1 h in presence of the appropriate boronic acid or ester, $Na_2CO_3$, $PdCl_2$(dppf)-$CH_2Cl_2$ adduct in 1,4-dioxane. After aqueous work-up, the residue was treated with TFA in DCM (with or without triethylsilane) to yield the desired product after purification via reverse phase HPLC.

Scheme 8

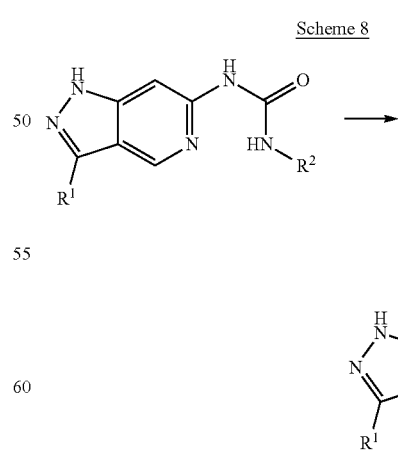

Bromination of the urea has been accomplished by reacting for 1 h the appropriate urea in MeCN in presence of NBS and purifying by chromatography on silica gel.

Scheme 20

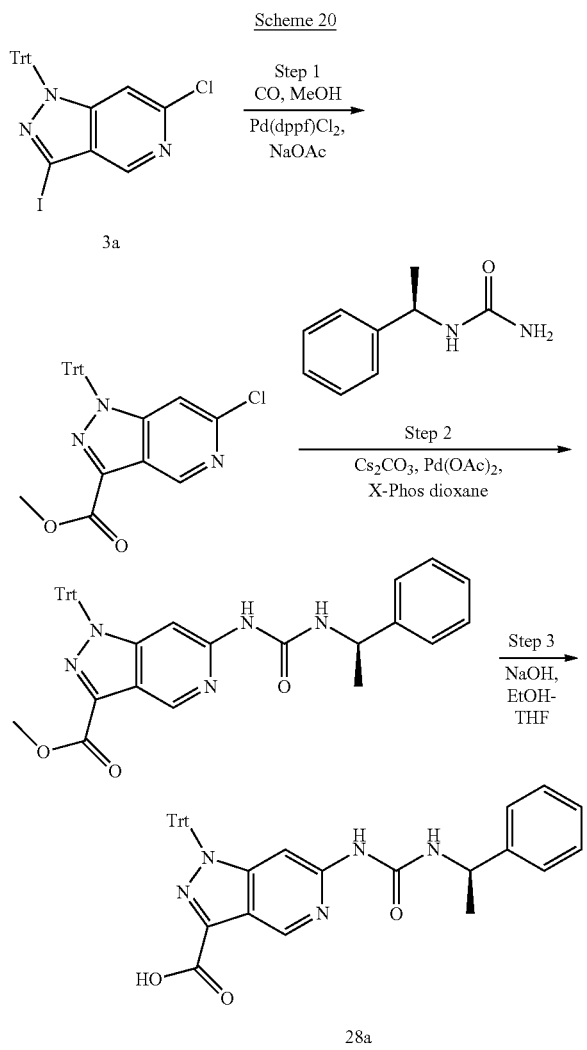

Step 1: Preparation of methyl 6-chloro-1-trityl-1H-pyrazolo[4,3-c]pyridine-3-carboxylate A suspension of NaOAc (1.415 g, 17.25 mmol), Pd(dppf)Cl2 (0.841 g, 1.150 mmol) and 6-chloro-3-iodo-1-trityl-1H-pyrazolo[4,3-c]pyridine (6 g, 11.50 mmol) in MeOH (30 ml) was stirred under CO (120 psi) at 65° C. for 3 days. After reaction, the reaction mixture was diluted with DCM and dry loaded on silica column and purified by column chromatography on silica gel 120 g, eluting with 1:3 EA in Hexane to give the desired product as an off white solid 4.74 g (91% yield). MS ESI calc'd. for $C_{27}H_{20}ClN_3O_2$ [M+1]$^+$ 454, found 454.

Step 2: Preparation of (R)-methyl 6-(3-(1-phenylethyl)ureido)-1-trityl-1H-pyrazolo[4,3-c]pyridine-3-carboxylate A mixture of methyl 6-chloro-1-trityl-1H-pyrazolo[4,3-c]pyridine-3-carboxylate (1.05 g, 2.313 mmol), Pd(OAc)₂ (0.104 g, 0.463 mmol), Cs₂CO₃ (1.884 g, 5.78 mmol), 4,5-bis(diphenylphosphino)-9,9-dimethylxanthene (XanPhos) (0.402 g, 0.694 mmol) and (R)-(+)-alpha-phenethylurea (0.570 g, 3.47 mmol) in 1,4-Dioxane (10 ml) was degassed and then heated to 80° C. for 16 hr. After cooling down to r.t, the reaction mixture was filtered through celite and concentrated down. The residue was purified by column chromatography on silica gel 120 g, eluting with 1:1 EA in Hexane to give the desired product as a yellow solid 580 mg (43% yield). MS ESI calc'd. for $C_{36}H_{31}N_5O_3$ [M+1]$^+$ 582, found 582.

Step 3: Preparation of (R)-6-(3-(1-phenylethyl)ureido)-1-trityl-1H-pyrazolo[4,3-c]pyridine-3-carboxylic acid (28a)

A solution of (R)-methyl 6-(3-(1-phenylethyl)ureido)-1-trityl-1H-pyrazolo[4,3-c]pyridine-3-carboxylate (0.58 g, 0.997 mmol) in Ethanol (10 ml) and THF (2 ml), 1.0M of aq. NaOH (2.99 ml, 2.99 mmol) was added. The reaction solution was heated to 50° C. for 15mins. After removal of the most solvent under vacuum, the reaction mixture was diluted with water and Ethyl acetate. 1N HCl was added to pH=4 and then the reaction mixture was extracted with ethyl acetate. The combined organic layer was washed with brine, dried over Na2SO4 and concentrated to give the pure product as a white solid 560 mg (99% yield). MS ESI calc'd. for $C_{35}H_{29}N_5O_3$ [M+1]$^+$ 568, found 568.

Scheme 21

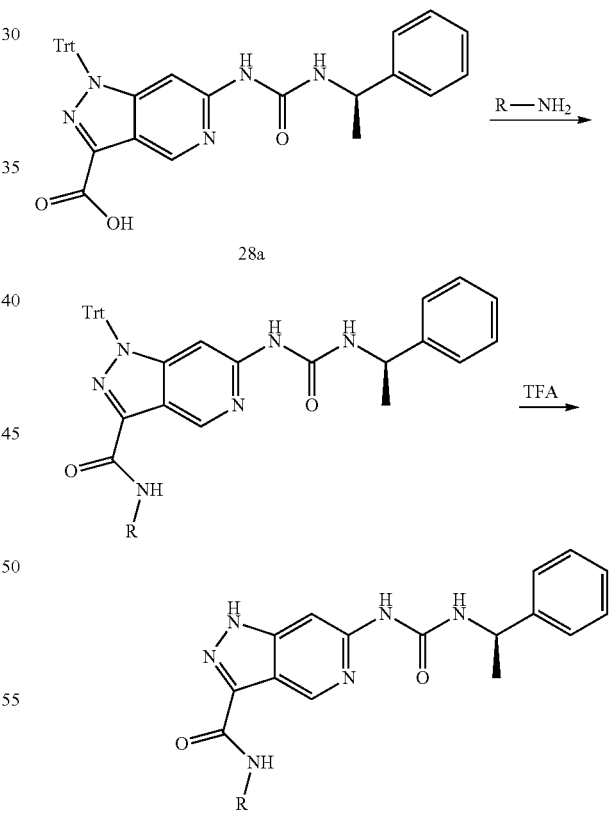

Urea derivatives have been prepared by adding intermediate 28a and the appropriate amine to a solution of HATU, DIEA, and DMA. After stirring 16 h at 60° C., the reaction mixture was dried under reduced pressure. The residue was treated with TFA and triethylsilane to yield the desired product after purification via reverse phase HPLC.

Scheme 22
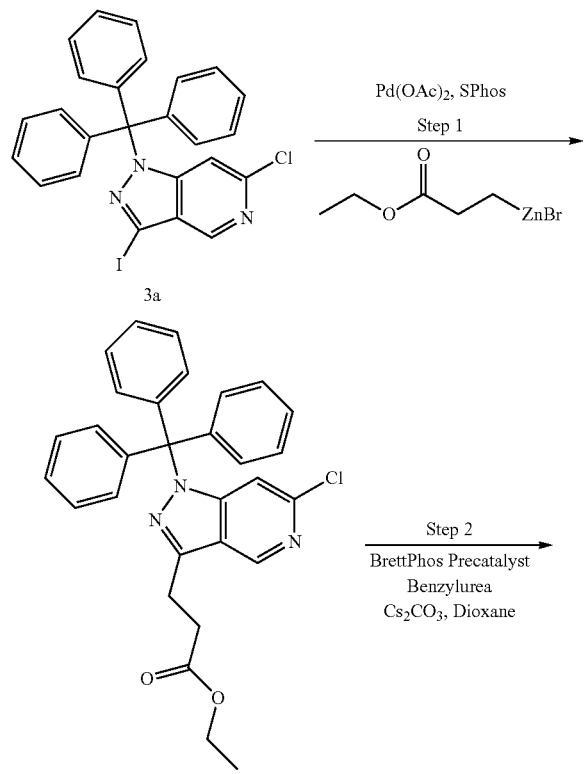
Scheme 23
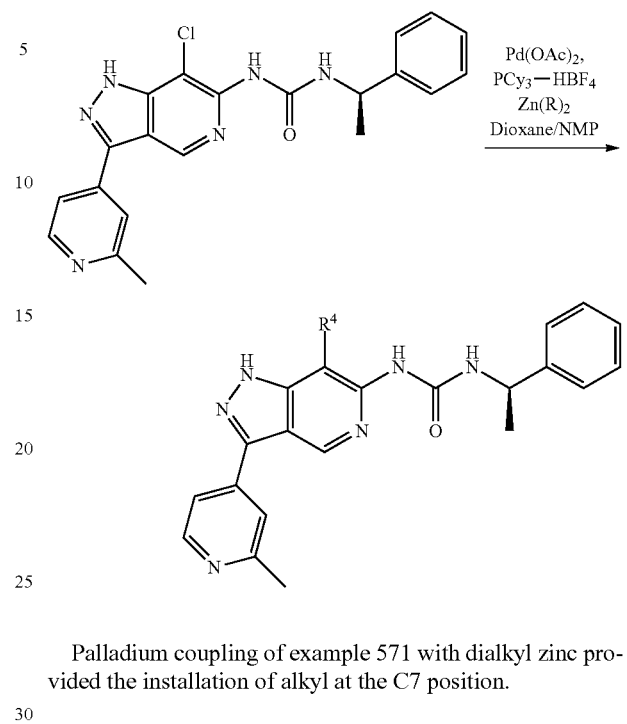
Palladium coupling of example 571 with dialkyl zinc provided the installation of alkyl at the C7 position.
Scheme 24
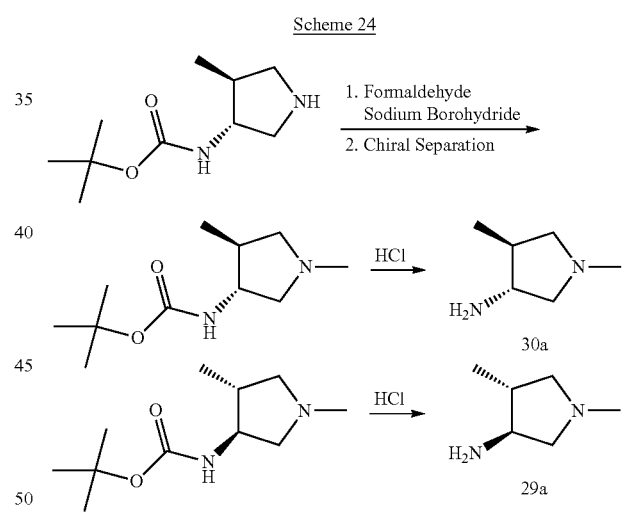
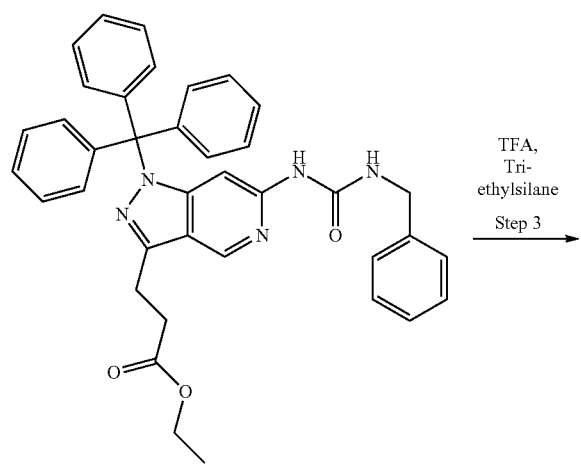
Intermediates 29a 30a
(3S,4R)-1,4-Dimethylpyrrolidin-3-amine (29a) and
(3R,4S)-1,4-Dimethylpyrrolidin-3-amine (30a)
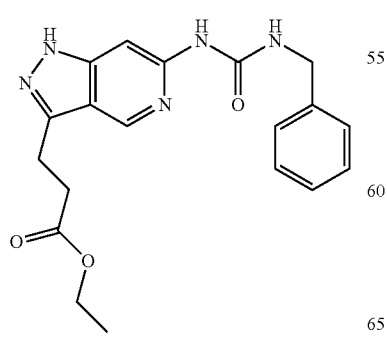
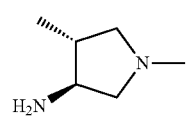

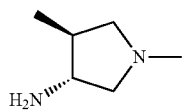

30a

Step 1: racemic tert-Butyl ((3S,4R) and (3R,4S)-1,4-dimethylpyrrolidin-3-yl)carbamate Racemic tert-Butyl ((3R,4R) and (3S,4S)-4-methylpyrrolidin-3-yl)carbamate (800 mg, 3.99 mmol) and formaldehyde (0.833 mL, 11.18 mmol) were dissovled in MeOH (40 mL) and treated with sodium borohydride (453 mg, 11.98 mmol) and the reaction was stirred at room temperature for one hour. The crude reaction mixture was diluted with EtOAc and washed with water and brine. The aqueous layer was extracted with EtOAc and the combined organic layers were dried over sodium sulfate, filtered, and concentrated in vacuo while loading onto silica gel. Purification by flash chromatography (0-20% $CH_2Cl_2$/MeOH with 1% ammonia) gave racemic tert-butyl ((3R,4R) and (3S,4S)-1,4-dimethylpyrrolidin-3-yl)carbamate (470 mg, 2.2 mmol, 47.5%). MS ESI calc'd. For $C_{11}H_{22}N_2O_2$ [M+1]$^+$ 215, found 215.

Step 2: tert-Butyl ((3S,4R)-1,4-dimethylpyrrolidin-3-yl)carbamate and tert-Butyl ((3R,4S)-1,4-dimethylpyrrolidin-3-yl)carbamate The enantiomers of tert-butyl ((3S and R,4R and S)-1,4-dimethylpyrrolidin-3-yl)carbamate (470 mg, 2.2 mmol) were separated by SFC (Berger Multigram II SFC, column: Phenomenex Lux, 2.1×25 cm, 5 uM mobile phase: 10% to 90% 2-propanol+0.25% dimethyl ethylamine $CO_{2(1)}$, flow rate: 70 mL/min, 5 min run time). The fractions were collected and the solvent evaporated in vacuo to afford tert-butyl ((3R,4S)-1,4-dimethylpyrrolidin-3-yl)carbamate (141.8 mg, 0.662 mmol, 33%) and tert-butyl ((3S,4R)-1,4-dimethylpyrrolidin-3-yl)carbamate (204.7 mg, 0.955 mmol, 48%). MS ESI calc'd. For $C_{11}H_{22}N_2O_2$ [M+1]$^+$ 215, found 215. MS ESI calc'd. For $C_{11}H_{22}N_2O_2$ [M+1]$^+$ 215, found 215.

Step 3: (3S,4R)-1,4-Dimethylpyrrolidin-3-amine tert-Butyl ((3S,4R)-1,4-dimethylpyrrolidin-3-yl)carbamate (205 mg, 0.957 mmol) was dissolved in Methanolic HCl (3N, 6 mL) and heated to 50° C. for two hours. The crude reaction mixture was concentrated in vacuo, dissolved in ACN/Water and lyophilized to give (3S,4R)-1,4-dimethylpyrrolidin-3-amine (182.9 mg, 0.978 mmol, 102%) as the HCl salt, which was carried onto the next step without further purification.

Step 3: (3R,4S)-1,4-Dimethylpyrrolidin-3-amine tert-Butyl ((3R,4S)-1,4-dimethylpyrrolidin-3-yl)carbamate (141 mg, 0.658 mmol) was dissolved in Methanolic HCl (3N, 4.5 mL) and heated to 50° C. for two hours. The crude reaction mixture was concentrated in vacuo, dissolved in ACN/Water and lyophilized to give (3R,4S)-1,4-dimethylpyrrolidin-3-amine (120 mg, 0.643 mmol, 98%) as the HCl salt.

Scheme 25

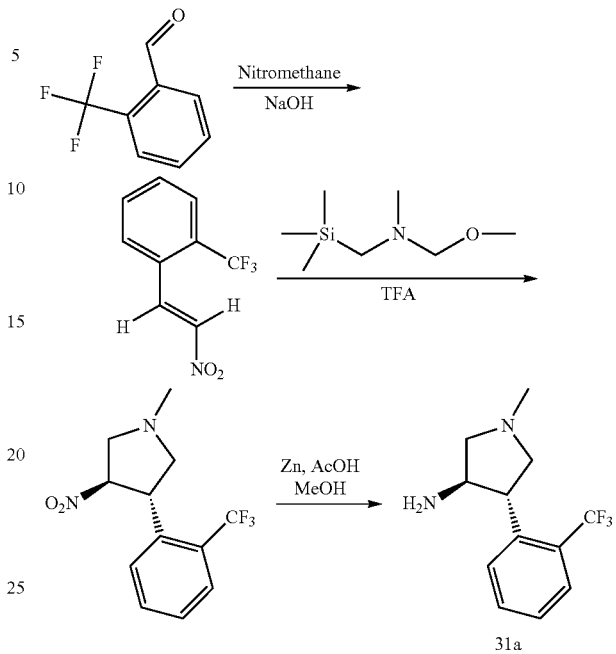

31a

Intermediate 31a

Racemic (3R,4S) and (3S,4R)-1-Methyl-4-(2-(trifluoromethyl)phenyl)pyrrolidin-3-amine

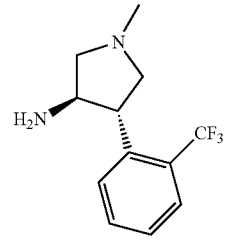 [SMILES: CN1C[C@H](c2ccccc2C(F)(F)F)[C@@H](N)C1]

Step 1: (E)-1-(2-Nitrovinyl)-2-(trifluoromethyl)benzene 2-(Trifluoromethyl)benzaldehyde (0.758 mL, 5.74 mmol) was dissolved in MeOH (5 mL) and nitromethane (0.370 mL, 6.89 mmol) was added. The mixture was cooled to −10° C. and a solution of NaOH (0.241 g, 6.03 mmol) in Water (2 mL) was added slowly keeping the temperature below −5° C. The mixture stirred at −5° C. for 15 minutes then warmed to 0° C. and stirred for two hours. Ice water (6 mL) was added followed by HCl (6 N, 3 mL). The mixture was extracted with DCM (×2) and washed with brine. The combined organic layers were dried over sodium sulfate, filtered, and concentrated in vacuo to give (E)-1-(2-nitrovinyl)-2-(trifluoromethyl)benzene (1.12 g, 2.373 mmol, 41%).

Step 2: Racemic (3R,4S) and (3S,4R)-1-Methyl-3-nitro-4-(2-(trifluoromethyl)phenyl)-pyrrolidine (E)-1-(2-Nitrovinyl)-2-(trifluoromethyl)benzene (230.8 mg, 1.063 mmol) and methyl-methoxymethyltrimethylsilanyl-methylamine (206 mg, 1.275 mmol) was dissolved in DCM (4 mL) and cooled to 0° C. under nitrogen. Trifluoroacetic acid (8.19 µL, 0.106 mmol) was then added and the reaction mixture was stirred at 0° C. for 30 minutes then warmed to room temperature and stirred for two hours. The reaction mixture was diluted with DCM and washed with brine. The organic layer was dried over sodium sulfate, filtered, and concentrated in vacuo while loading onto silica gel. The residue was purified by flash chromatography (7-60% EtOAc/isohexane) to racemic (3R,4S) and (3S,4R)-1-methyl-3-nitro-4-(2-(trifluoromethyl)phenyl)pyrrolidine (124 mg, 0.452 mmol, 42.5%).

Step 3: racemic (3R,4S) and (3S,4R)-1-Methyl-4-(2-(trifluoromethyl)phenyl)pyrrolidin-3-amine Racemic (3R,4S) and (3S,4R)-1-Methyl-3-nitro-4-(2-(trifluoromethyl)phenyl)-pyrrolidine (296.8 mg, 1.082 mmol) was dissolved in MeOH (5 mL) and Acetic Acid (5 mL) then zinc (354 mg, 5.41 mmol) was added at 0° C. The reaction mixture was warmed to room temperature and stirred under nitrogen overnight. The suspension was filtered over celite and washed with methanol. The filtrate was concentrated in vacuo and the residue was suspended in ethyl acetate, cooled in an ice bath, and basified with conc. NH$_4$OH. The organic phase was separated and washed with brine. The organic layers were combined and dried over sodium sulfate, filtered, and concentrated in vacuo to give racemic (3R,4S) and (3S,4R)-1-methyl-4-(2-(trifluoromethyl)phenyl)pyrrolidin-3-amine (230.9 mg, 0.945 mmol, 87%), which was carried onto the next step without further purification. MS ESI calc'd. For $C_{12}H_{15}F_3N_2$ [M+1]$^+$ 245, found 245.

Intermediates 32a-35a were prepared following similar procedures described for Intermediate 31a using the appropriate aldehyde or alkene, which can be achieved by those of ordinary skill in the art of organic synthesis.

| Intermediate | Structure | IUPAC Name | Exact Mass [M + H]+ |
|---|---|---|---|
| 32a | | racemic (3R,4S) and (3S,4R)-4-(2-fluorophenyl)-1-methylpyrrolidin-3-amine | Calc'd 195, Found 195 |
| 33a | | racemic (3R,4S) and (3S,4R)-1-methyl-4-(o-tolyl)pyrrolidin-3-amine | Calc'd 191, Found 191 |
| 34a | 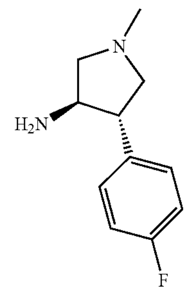 | racemic (3R,4S) and (3S,4R)-4-(4-fluorophenyl)-1-methylpyrrolidin-3-amine | Calc'd 195, Found 195 |
| 35a | 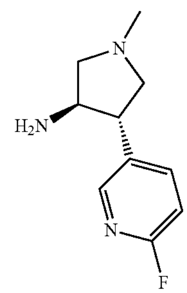 | racemic (3R,4S) and (3S,4R)-4-(6-fluoropyridin-3-yl)-1-methylpyrrolidin-3-amine | Calc'd 196, Found 196 |
| 36a | 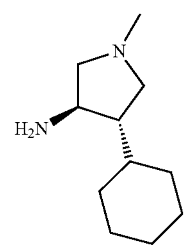 | racemic (3R,4S) and (3S,4R)-4-cyclohexyl-1-methylpyrrolidin-3-amine | — |
| 37a | 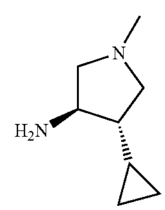 | racemic (3R,4S) and (3S,4R)-4-cyclopropyl-1-methylpyrrolidin-3-amine | — |
| 38a | 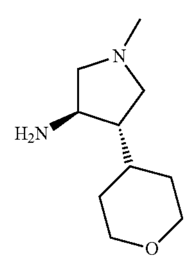 | racemic (3R,4S) and (3S,4R)-1-methyl-4-(tetrahydro-2H-pyran-4-yl)pyrrolidin-3-amine | — |

Scheme 26

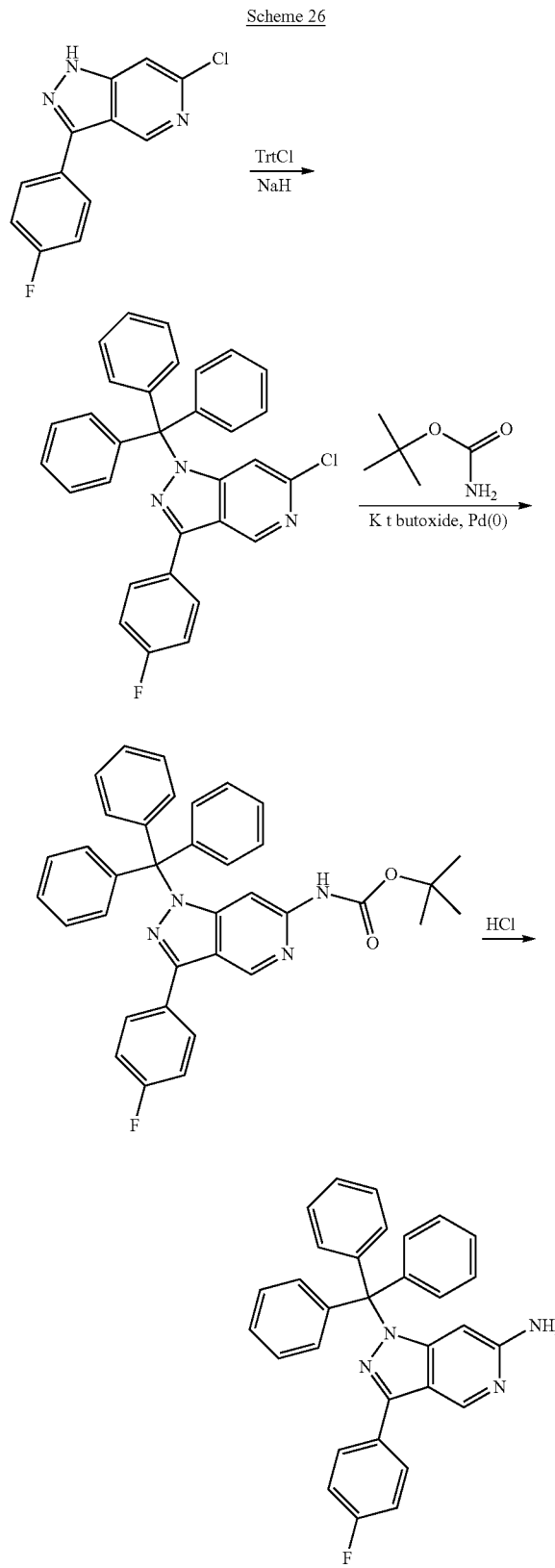

Intermediate 39a 3-(4-Fluorophenyl)-1-trityl-1H-pyrazolo[4,3-c]pyridin-6-amine

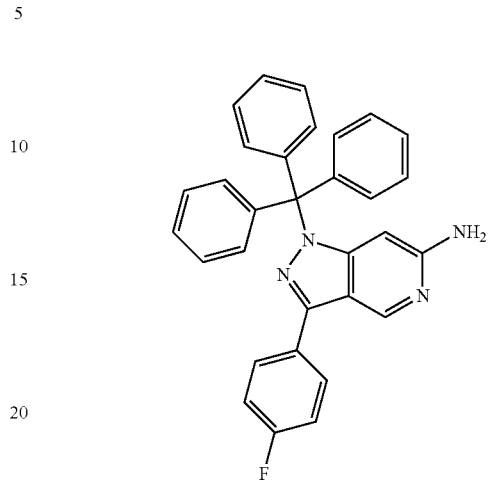

Step 1: 6-Chloro-3-(4-fluorophenyl)-1-trityl-1H-pyrazolo[4,3-c]pyridine

6-Chloro-3-(4-fluorophenyl)-1H-pyrazolo[4,3-c]pyridine (1 g, 4.04 mmol) was dissolved in DMF (20 mL) and cooled to 0° C. Sodium hydride (0.242 g, 6.06 mmol) was then added and the reaction mixture stirred for one hour. Trityl chloride (1.351 g, 4.85 mmol) was then added and the reaction mixture warmed to room temperature and stirred for 1.5 hours. The reaction mixture was diluted with water and stirred at 0° C. for one hour to promote perception. The solid was filtered and rinsed with water. The solid was diluted with DCM and concentrated in vacuo while loading onto silica gel. The residue was purified by flash chromatography (2-30% EtOAc/isohexane) to give 6-chloro-3-(4-fluorophenyl)-1-trityl-1H-pyrazolo[4,3-c]pyridine (1.63 g, 3.33 mmol, 82%). MS ESI calc'd. For $C_{31}H_{21}ClFN_3$ [M+1]$^+$ 490, found 490.

Step 2: tert-Butyl (3-(4-fluorophenyl)-1-trityl-1H-pyrazolo[4,3-c]pyridin-6-yl)carbamate 6-Chloro-3-(4-fluorophenyl)-1-trityl-1H-pyrazolo[4,3-c]pyridine (1.48 g, 3.02 mmol), tert-butyl carbamate (1.062 g, 9.06 mmol), and chloro(2-di-t-butylphosphino-2',4',6'-tri-i-propyl-1,1'-biphenyl)[2-(2-aminoethyl)phenyl]palladium (II) (0.249 g, 0.362 mmol) was dissolved in THF (30 mL) then potassium tert-butoxide (6.65 mL, 6.65 mmol, 1 M in THF) was added. The reaction mixture was purged under argon for five minutes then heated to 80° C. and stirred overnight. The reaction mixture was diluted with DCM and washed with NaOH (1 N) and brine. The organic layer was dried over sodium sulfate, filtered, and concentrated in vacuo while loading onto silica gel. The residue was purified by flash chromatography (2-20% EtOAc/isohexane) to give tert-butyl (3-(4-fluorophenyl)-1-trityl-1H-pyrazolo[4,3-c]pyridin-6-yl)carbamate (403 mg, 0.706 mmol, 23%). MS ESI calc'd. For $C_{36}H_{31}FN_4O_2$ [M+1]$^+$ 571, found 571.

Step 3: 3-(4-Fluorophenyl)-1-trityl-1H-pyrazolo[4,3-c]pyridin-6-amine tent-Butyl (3-(4-fluorophenyl)-1-trityl-1H-pyrazolo[4,3-c]pyridin-6-yl)carbamate (403 mg, 0.706 mmol) was dissolved in HCl (4 M in dioxane, 6 mL) and stirred at room temperature for four hours. The reaction mixture was diluted with ethyl acetate and washed with NaOH (1 N) and brine. The aqueous layer was reextracted with 3:1 chloroform/IPA and the combined organic layers were dried over sodium sulfate, filtered, and concentrated in vacuo to give 3-(4-fluorophenyl)-1-trityl-1H-pyrazolo[4,3-c]pyridin-6-amine (359.1 mg, 0.672 mmol, 95%), which was carried onto the next step without further purification. MS ESI calc'd. For $C_{31}H_{23}FN_4$ [M+1]$^+$ 471, found 471.

Intermediate 40a

Racemic (3R,4S) and (3S,4R)-4-phenyl-1-(2,2,2-trifluoroethyl)pyrrolidin-3-amine

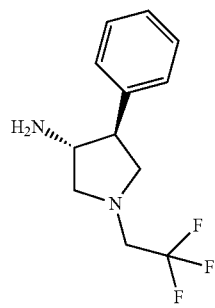

Step 1: racemic tert-butyl (3R,4S) and (3S,4R)-4-phenyl-1-(2,2,2-trifluoroethyl)-pyrrolidin-3-yl)carbamate

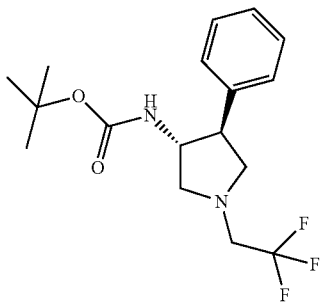 [SMILES: CC(C)(C)OC(=O)N[C@H]1CN(CC(F)(F)F)C[C@@H]1c1ccccc1]

Racemic tert-butyl (3R,4S) and (3S,4R)-4-phenylpyrrolidin-3-ylcarbamate (260 mg, 0.991 mmol) was taken up in DMF (5 ml) and cooled to 0° C. NaH (59.5 mg, 1.487 mmol) was added slowly. The reaction was allowed to stir for 10 minutes at 0° C. before adding 2,2,2-trifluoroethyl trifluoromethanesulfonate (345 mg, 1.487 mmol). The reaction continued to stir at 0° C. for 1 hour and was then allowed to reach room temperature and continue stirring for 16 hours. LC/MS in showed full conversion to desired product. Saturated NH$_4$Cl was added slowly. EtOAc and water were added. Our products were extracted into EtOAc (3×). The combined organic layers were then washed with brine, dried over MgSO$_4$, and concentrated in vacuo. Purification by MPLC SNAP 25 g 0-25% EtOAc/hexanes gave racemic tert-butyl (3R,4S) and (3S,4R)-4-phenyl-1-(2,2,2-trifluoroethyl)pyrrolidin-3-yl)carbamate (258 mg, 0.749 mmol, 76% yield). MS ESI calc'd. For $C_{17}H_{24}F_3N_2O_2$ [M+1]$^+$ 345, found 345.

Step 2 racemic (3R,4S) and (3S,4R)-4-phenyl-1-(2,2,2-trifluoroethyl)pyrrolidin-3-amine, 2HCl

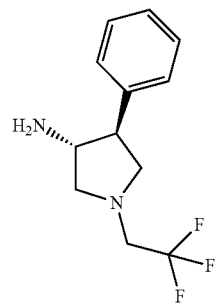 [SMILES: N[C@H]1CN(CC(F)(F)F)C[C@@H]1c1ccccc1]

tert-butyl ((3S and R,4R and S)-4-phenyl-1-(2,2,2-trifluoroethyl)pyrrolidin-3-yl)carbamate (258 mg, 0.749 mmol) was taken up in 1,4-Dioxane (2 ml) and 2N HCl (2 ml) was added. The reaction was allowed to stir at ambient temperature for 2 hours followed by heating to 45° C. and stirring for 16 hours. Full deprotection was observed by LCMS. The reaction mixture was concentrated in vacuo to give racemic (3R,4S) and (3S,4R)-4-phenyl-1-(2,2,2-trifluoroethyl)pyrrolidin-3-amine, 2HCl (272 mg, 0.858 mmol, 114% yield). MS ESI calc'd. For $C_{12}H_{16}F_3N_2$ [M+1]$^+$245, found 245.

Scheme 27

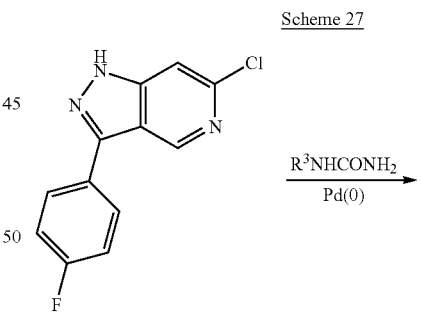

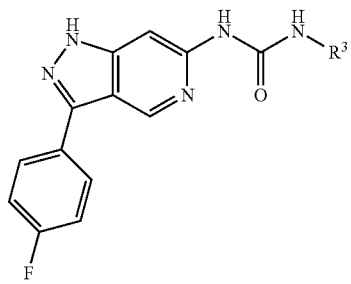

6-Chloro-3-(4-fluorophenyl)-1H-pyrazolo[4,3-c]pyridine undergoes palladium coupling with appropriate urea to provide the desired product.

Intermediate 41a 7-fluoro-3-(2-methylpyridin-4-yl)-1-trityl-1H-pyrazolo[4,3-c]pyridin-6-amine

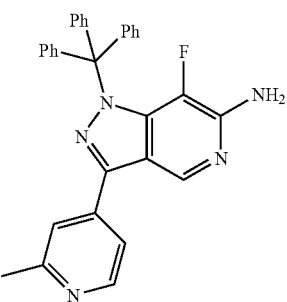 [SMILES: Cc1cc(-c2nn(C(c3ccccc3)(c3ccccc3)c3ccccc3)c3c(F)c(N)ncc23)ccn1]

A 200 mL round bottom flask was charged with 3-(2-methylpyridin-4-yl)-1-trityl-1H-pyrazolo[4,3-c]pyridin-6-amine (0.76 g, 1.625 mmol) and the flask was put under an atmosphere of argon. The reaction was charged with 10 mL THF and the slurry was cooled to 0° C. in an ice bath. Xenon Difluoride (0.056 ml, 1.418 mmol) was added with vigorous stirring in several portions. Then stirring was continued with warming to ambient temperature.

The reaction was stirred for 16 hours at ambient temperature. It was then quenched while cold with sodium thiosulfate. Additional bubbling occurred. The reaction was then transferred to a separatory funnel and diluted with 300 mL EtOAc. The organic phase was separated and washed with water and then brine (150 mL portions). The organic phase was dried over magnesium sulfate, filtered and concentrated to dryness. The resulting crude solid was purified first by reversed phase HPLC (Gilson, 20-60% ACN/water). The active fractions were pooled and concentrated to dryness yielding the product (275 mg, 35%). MS ESI calc'd. for $C_{31}H_{24}FN_5$ [M+H]$^+$ 468, found 468. $^1$H NMR (500 MHz, CDCl$_3$) δ 8.71 (s, 1H), 8.53 (d, J=2.0 Hz, 1H), 7.55 (br, s, 1H), 7.50 (m, 1H), 4.35 (s, 2H), 2.58 (s, 3H) ppm.

Intermediate 42a (R)-1-(3-chloro-7-fluoro-1H-pyrazolo[4,3-c]pyridin-6-yl)-3-(1-phenylethyl)urea

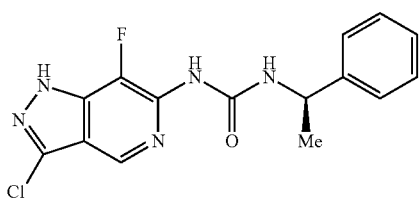 [SMILES: C[C@@H](NC(=O)Nc1ncc2c(Cl)n[nH]c2c1F)c1ccccc1]

A flask containing (R)-1-(3-chloro-1H-pyrazolo[4,3-c]pyridin-6-yl)-3-(1-phenylethyl)urea (1.30 g, 4.12 mmoles) was charged with dimethylacetamide (3 mL) and methanol (3 mL). To this solution was added 1-chloromethyl-4-fluoro-1,4-diazoniabicyclo[2.2.2]octane bis tetrafluoroborate (1.459 g, 4.12 mmoles). The resulting suspension was stirred for 18 hours at ambient temperature. No conversion was observed by LC/MS analysis and the reaction was then warmed to 60° C. for three hours. The reaction conversion appeared to slow at this point and the reaction was diluted with water and ethyl acetate. The organic phase was separated, dried over magnesium sulfate, filtered and concentrated.

Silica gel chromatography purification (5-15% MeOH/DCM) was performed and the desired fractions were concentrated to dryness. The resulting solid (486 mg, 35%) was analyzed by proton NMR and LC/MS. MS ESI calc'd. for $C_{15}H_{13}ClFN_5O$ [M+H]$^+$ 334, found 334. $^1$H NMR (500 MHz, CDCl$_3$) δ 10.45 (s, 1H), 9.60 (d, J=6.7 Hz, 1H), 8.51 (s, 1H), 7.40-7.10 (dt, J=4.1, 7.0 Hz 5H), 5.15 (m, 1H), 1.59 (d, J=6.7 Hz, 3H) ppm.

Scheme 28

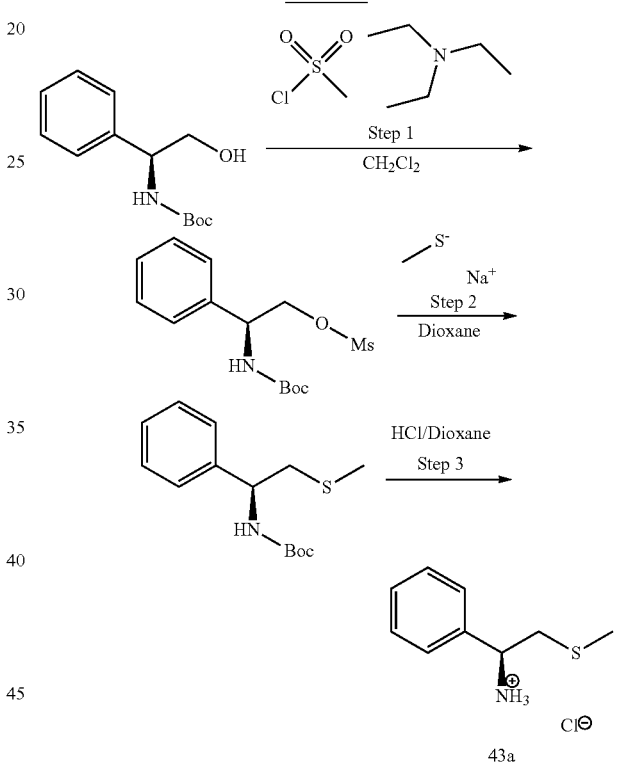

Step 1

(S)-2-((tert-butoxycarbonyl)amino)-2-phenylethyl methanesulfonate

To an ice-cooled solution of (S)-tert-butyl (2-hydroxy-1-phenylethyl)carbamate (1020 mg, 4.30 mmol) and TEA (0.659 ml, 4.73 mmol) in DCM (12 ml), a solution of Mesyl-Cl (0.368 ml, 4.73 mmol) in DCM (6 ml) was added dropwise during 30 min, After completion of the reaction (monitored by TLC), the solvent was evaporated under reduced pressure and ethyl acetate and water were added to the residue. The organic layer was washed with aqueous 5% NaHCO3 and brine, dried over Na2SO4 and evaporated to give (S)-2-((tert-butoxycarbonyl)amino)-2-phenylethyl methanesulfonate (1300 mg, 4.12 mmol, 96% yield) as a white solid. (Procedure From Angew Chem. Int. Ed. 2010 49 (26) pages 4467-4470)

Step 2

(S)-tert-butyl (2-(methylthio)-1-phenylethyl)carbamate (S)-2-((tert-butoxycarbonyl)amino)-2-phenylethyl methanesulfonate (600 mg, 1.902 mmol) and sodium thiomethoxide (593 mg, 7.61 mmol) were added to a 20 mL microwave tube equipped with mechanical stir bar and charged with Dioxane (10 ml). The reaction was allowed to heat overnight at 45° C. The reaction was poured into 5 mL MeOH and 5 g silica, and the solvents were evaporated in vacuo. The dry-loaded crude product was purified on 50 g SNAP column 10-50% EtOAc/hexanes to provide (S)-tert-butyl (2-(methylthio)-1-phenylethyl)carbamate (387 mg, 1.447 mmol, 76% yield).

Step 3

(S)-2-(methylthio)-1-phenylethanaminium chloride (S)-tert-butyl (2-(methylthio)-1-phenylethyl)carbamate (380 mg, 1.421 mmol) was dissolved in HCl (1066 µl, 4.26 mmol) in dioxane and allowed to stir for 30 minutes at rt. The solvents were removed in vacuo to provide (S)-2-(methylthio)-1-phenylethanaminium chloride (275 mg, 1.350 mmol, 95% yield).

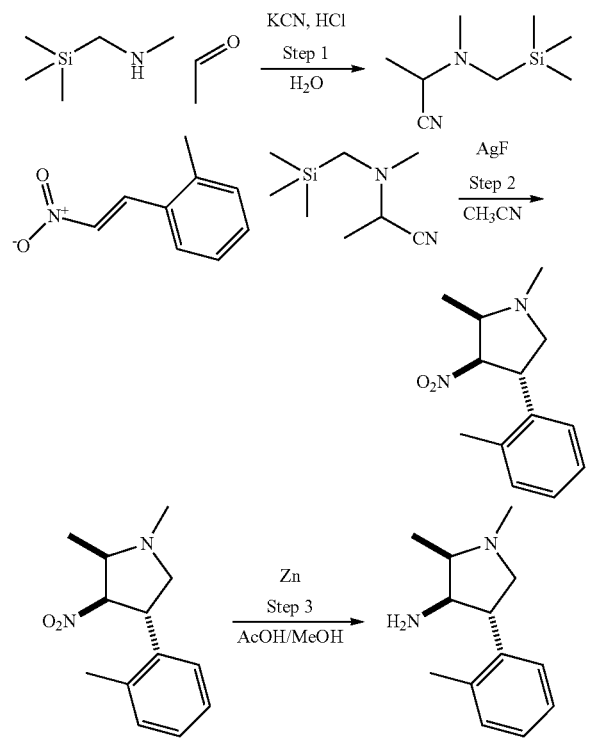

Scheme 29

44a

Step 1

2-(methyl((trimethylsilyl)methyl)amino)propanenitrile

N-methyl-1-(trimethylsilyl)methanamine (2200 mg, 17.82 mmol) was dissolved in HCl (53.5 ml, 53.5 mmol) and THF (20 ml), charged with potassium cyanide (4642 mg, 71.3 mmol) and ACETALDEHYDE (6.04 ml, 107 mmol) and allowed to stir overnight at rt. The reaction was poured into 100 mL water and extracted 2×100 mL ether. The combined organics were washed with water (50 mL), brine, dried over sodium sulfate, filtered and concentrated in vacuo to provide a crude pale yellow oil which contained 20-30% Et2O and THF (concentrated at 15° C. in case product was volatile). The reaction was purified 1% Et2O/DCM to provide Product 1 (2450 mg, 11.51 mmol, 64.6% yield) as a clear oil. Some THF seen in product.

Step 2

(2R,3R,4S)+(2S,3S,4R)-1,2-dimethyl-3-nitro-4-(o-tolyl)pyrrolidine (E)-1-methyl-2-(2-nitrovinyl)benzene (500 mg, 3.06 mmol) and Reactant 2 (848 mg, 3.98 mmol) were added to a 20 mL amber vial, dissolved in Acetonitrile (10 ml), charged with silver(I) fluoride (389 mg, 3.06 mmol) and allowed to stir overnight at rt. The reaction was diluted with 5 mL DCM, filtered through a pad of celite and the solvents were removed in vacuo. The residue was purified 5-30% EtOAc/hexanes to provide 4 products, +200 mg recovered mixture of diastereomers. Impure fractions were re-purified 2-20% EtOAc/DCM. (2R,3R,4S)+(2S,3S,4R)-1,2-dimethyl-3-nitro-4-(o-tolyl)pyrrolidine was isolated as a clear oil (100 mg, 11.51 mmol, 13.9% yield)

Step 3

(2R,3R,4S)+(2S,3S,4R)-1,2-dimethyl-4-(o-tolyl)pyrrolidin-3-amine (2R,3R,4S)+(2S,3S,4R)-1,2-dimethyl-3-nitro-4-(o-tolyl)pyrrolidine (28 mg, 0.12 mmol) was dissolved in 1 ml MeOH and Acetic Acid (2.0 ml) and charged with ZINC (39.1 mg, 0.598 mmol). The reaction was allowed to stir overnight at rt. The solution was filtered through celite and concentrated in vacuo. The residue was dissolved in 2 mL MeOH and desalted on ps-bicarb. The solvents were removed in vacuo to afford (2R,3R,4S)+(2S,3S,4R)-1,2-dimethyl-4-(o-tolyl)pyrrolidin-3-amine (17 mg, 0.08 mmol, 70% yield). LC/MS M+H 205.2

| Intermediate | Structure | Name | Mass [M + H]+ |
|---|---|---|---|
| 45a | 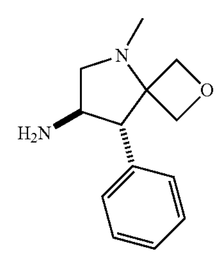 [SMILES: CN1C[C@H](N)[C@@H](c2ccccc2)C12COC2] | (7R,8R) + (7S,8S)-5-methyl-8-phenyl-2-oxa-5-azaspiro[3.4]octan-7-amine | Calc'd 219, found 219 |

85
-continued

| Intermediate | Structure | Name | Mass [M + H]+ |
|---|---|---|---|
| 46a | 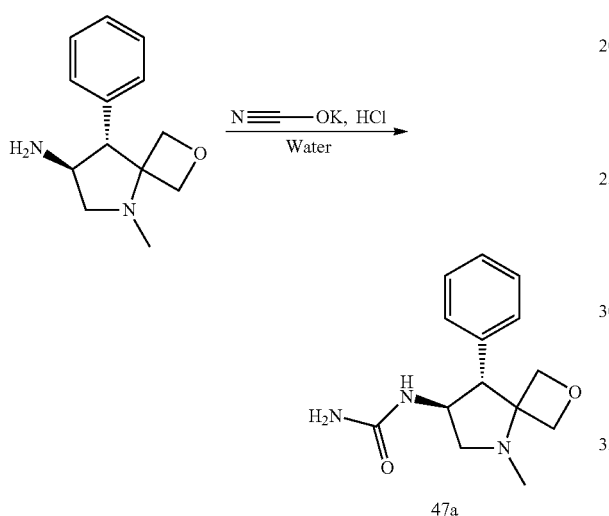 | (2R,3R,4S) + (2S,3S,4R)-1,2-dimethyl-4-phenylpyrrolidin-3-amine | Calc'd 191, found 191 |

Scheme 30

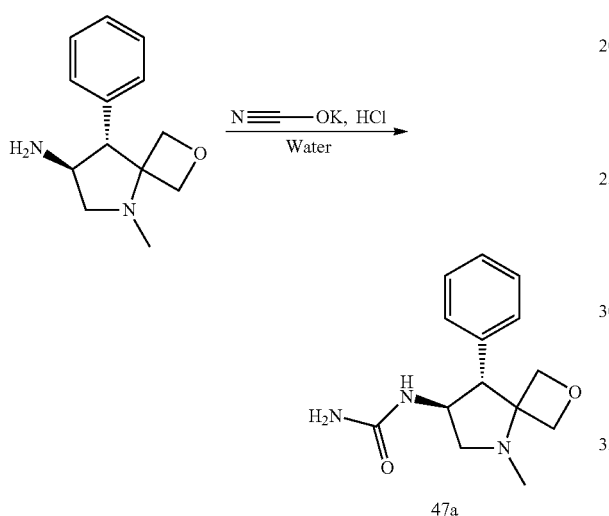

1-((7S,8S)+(7R,8R)-5-methyl-8-phenyl-2-oxa-5-azaspiro[3.4]octan-7-yl)urea

To a solution of (7S,8S)(+7R,8R)-5-methyl-8-phenyl-2-oxa-5-azaspiro[3.4]octan-7-amine (150 mg, 0.687 mmol) in water (1247 µl), HCl (701 µl, 0.701 mmol) 1N and potassium cyanate (279 mg, 3.44 mmol) were added. System was heated @ 80° C. in a micro wave reactor for 1 h. LC/MS indicates product formation. Solvent was evaporated in vacuo and residue was partioned between EtOAc/sat. aq. NaHCO₃. Organic was washed w/sat. aq. NaHCO₃ and brine, dried over Na₂SO₄, and evaporated in vacuo affording (7S,8S)+(7R,8R)-5-methyl-8-phenyl-2-oxa-5-azaspiro[3.4]octan-7-yl) urea (44 mg, 0.168 mmol, 24.50% yield). MS ESI Calc'd for C14H19N3O2 [M+H]⁺ 262, found 262.

Scheme 31

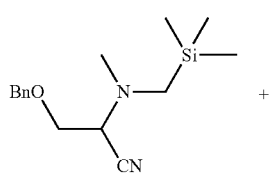 +

86
-continued

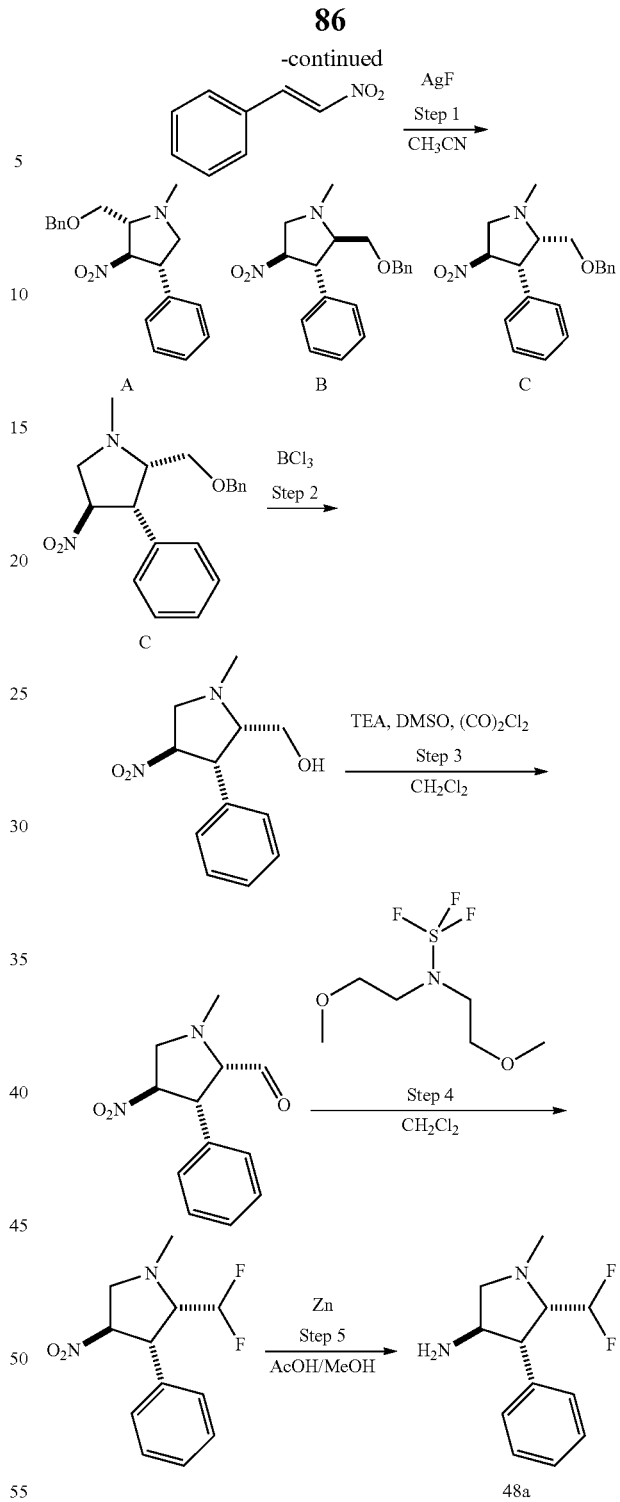

Step 1

A,B,C-(E)-(2-nitrovinyl)benzene (2.291 g, 15.36 mmol) and 3-(benzyloxy)-2-(methyl((trimethylsilyl)methyl)amino) propanenitrile (3.86 g, 13.96 mmol) were added to a 20 mL amber vial, dissolved in Acetonitrile (100 ml), charged with silver (I) fluoride (1.771 g, 13.96 mmol) and allowed to stir overnight at for 3 h. The reaction was diluted with 20 mL DCM, filtered through a pad of celite and the solvents were removed in vacuo. The residue was purified 2-10% EtOAc./ DCM to provide a mixture of products (see below).

The mixture of diastereomers was separated by achiral SFC followed by a third purification on silica gel 2-10% EtOAc./DCM to provide:

A (2R,3R,4S)+(2S,3S,4R)-2-((benzyloxy)methyl)-1-methyl-3-nitro-4-phenylpyrrolidine: $^1$H NMR (600 MHz, CDCl$_3$) δ 7.36-7.25 (m, 9H), 7.23-7.21 (m, 1H), 4.99 (dd, J=4.9, 6.6, 1H), 4.59-4.51 (m, 2H), 3.84 (ddd, J=3.4, 4.8, 8.3, 1H), 3.72-3.62 (m, 2H), 3.22 (dd, J=3.3, 9.7, 1H), 3.14 (dt, J=4.3, 6.7, 1H), 3.07 (dd, J=8.4, 9.7, 1H), 2.45 (s, 3H).

B (2R,3S,4R)+(2S,3R,4S)-2-((benzyloxy)methyl)-1-methyl-4-nitro-3-phenylpyrrolidine: $^1$H NMR (600 MHz, CDCl$_3$) δ 7.28 (m, 6H), 7.24-7.11 (m, 4H), 4.84 (ddd, J=1.7, 5.3, 7.3, OH), 4.57-4.36 (m, 2H), 3.94-3.87 (m, 1H), 3.82 (dt, J=7.9, 15.8, 1H), 3.58-3.52 (m, 1H), 3.45 (dd, J=4.6, 10.4, 1H), 2.89 (dd, J=7.8, 11.8, 1H), 2.55 (ddd, J=3.0, 4.5, 9.4, 1H), 2.45 (s, 3H).

C (2S,3S,4R)+(2R,3R,4S)-2-((benzyloxy)methyl)-1-methyl-4-nitro-3-phenylpyrrolidine: $^1$H NMR (500 MHz, CDCl$_3$) δ 7.35-7.27 (m, 8H), 7.16 (d, J=7.2, 2H), 5.26-5.18 (m, 1H), 4.22-4.11 (m, 2H), 4.05 (dt, J=6.9, 13.8, 1H), 3.76 (dt, J=11.1, 22.2, 1H), 3.27-3.16 (m, 2H), 3.13 (dd, J=5.2, 9.0, 1H), 3.01 (dt, J=6.7, 13.6, 1H), 2.47 (s, 3H).

Step 2

((2S,3S,4R+(3R,3R,RS))-1-methyl-4-nitro-3-phenylpyrrolidin-2-yl)methanol (2R,3R,4S)+(2S,3S,4R)-2-((benzyloxy)methyl)-1-methyl-3-nitro-4-phenylpyrrolidine (369 mg, 1.131 mmol) was dissolved in DCM (10 ml), cooled to −78° C. and charged with BORON TRICHLORIDE (3.39 ml, 3.39 mmol) (solution in DCM). The reaction was allowed to stir for 1 h, charged with 2 mL MeOH, warmed to rt and allowed to stir for a further 30 minutes. The solvents were evaporated in vacuo and the residue was purified on silica gel 2-8% to provide ((2S,3S,4R+(3R,3R,RS))-1-methyl-4-nitro-3-phenylpyrrolidin-2-yl)methanol (177 mg, 0.52 mmol, 45% yield)

Step 3

((2S,3S,4R+(3R,3R,RS))-1-methyl-4-nitro-3-phenylpyrrolidine-2-carbaldehyde

Took DMSO (0.107 ml, 1.498 mmol) and 30 ml DCM to −76 in acetone/dry ice. Added Oxalyl Chloride (0.131 ml, 1.498 mmol) dropwise and let stir 30 minutes. ((2S,3S,4R+(3R,3R,RS))-1-methyl-4-nitro-3-phenylpyrrolidin-2-yl)methanol (177 mg, 0.749 mmol) in 5 ml DCM and let stir 20 minutes. Added TEA (0.418 ml, 3.00 mmol) and let warm to room temp. Quenched with water and extracted ethyl acetate. Washed 2× with water followed by brine, and dried over magnesium sulfate to provide crude Product 1 (163 mg, 0.696 mmol, 93% yield) suitable for use in the next step.

Step 4

((2S,3S,4R+(3R,3R,RS))-2-(difluoromethyl)-1-methyl-4-nitro-3-phenylpyrrolidine ((2S,3S,4R+(3R,3R,RS))-1-methyl-4-nitro-3-phenylpyrrolidine-2-carbaldehyde (160 mg, 0.683 mmol) was dissolved in DCM (3 ml), cooled to 0° C. and charged with DEOXOFLUOR (0.277 ml, 1.503 mmol) and allowed to stir for 1 h. TLC revealed consumption of SM. Quenched with ice and sodium bicarbonate aq., diluted with DCM, washed with brine, dried over sodium sulfate. Purified 2-20% EtOAc/hexanes to provide ((2S,3S,4R+(3R,3R,RS))-2-(difluoromethyl)-1-methyl-4-nitro-3-phenylpyrrolidine (67 mg, 0.261 mmol, 38.3% yield) as a white solid.

Step 5

((3R,4R,5S)+(3S,4S,5R))-5-(difluoromethyl)-1-methyl-4-phenylpyrrolidin-3-amine ((2S,3S,4R+(3R,3R,RS))-2-(difluoromethyl)-1-methyl-4-nitro-3-phenylpyrrolidine (67 mg, 0.261 mmol) was dissolved in Acetic Acid and MeOH, charged with zinc (86 mg, 1.307 mmol), and allowed to stir overnight under vigorous stirring. The suspension was filtered through a whatman filter (0.2 uM), and the solvents were evaporated on the V-10. The white residue was dissolved in 3 mL MeOH, and passed through a PS-bicarb cartridge. The solvents were evaporated in vacuo to provide ((3R,4R,5S)+(3S,4S,5R))-5-(difluoromethyl)-1-methyl-4-phenylpyrrolidin-3-amine (55 mg, 0.243 mmol, 93% yield) which was used without further purification. MS ESI Calc'd for C12H16F2N2 [M+H]$^+$ 227, found 227.

| Intermediate | Structure | Name | Exact Mass [M + H]+ |
|---|---|---|---|
| 49a | 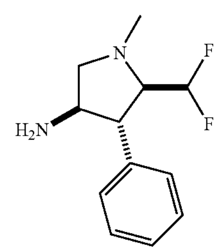 [SMILES: CN1C[C@H](N)[C@@H](c2ccccc2)[C@@H]1C(F)F] | (3R,4R,5R) + (3S,4S,5S)-5-(difluoromethyl)-1-methyl-4-phenylpyrrolidin-3-amine | Calc'd 227, found 227 |

Scheme 32

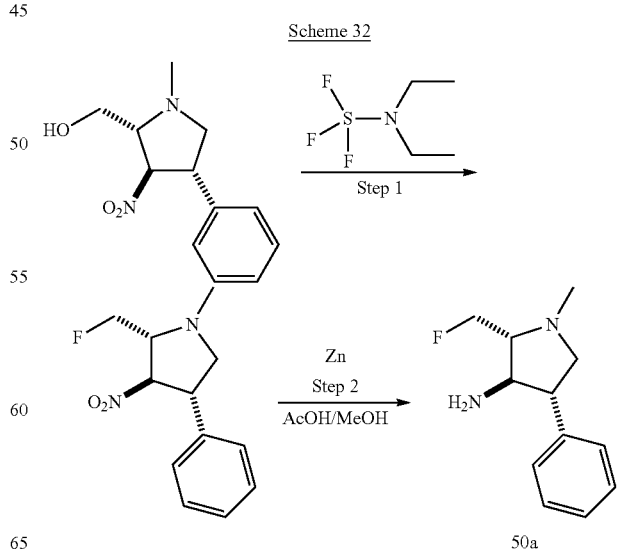

50a

Step 1

(2R,3R,4S)+(2S,3S,4R)-2-(fluoromethyl)-1-methyl-3-nitro-4-phenylpyrrolidine ((2R,3R,4S)+2S,3S,4R)-1-methyl-3-nitro-4-phenylpyrrolidin-2-yl)methanol, compound is made from intermediate A and debenzylation similar to step 2 in scheme 31, (165 mg, 0.698 mmol) was dissolved in DCM and charged with DAST (101 µl, 0.768 mmol) and allowed to stir for 20 min at rt. LC/MS revealed product formation, quenched with 1 mL sat. aq. sodium bicarbonate and loaded directly onto silica. Purification, 2-10% MeOH/NH3/DCM provided racemic (2R,3R,4S)+(2S,3S,4R)-2-(fluoromethyl)-1-methyl-3-nitro-4-phenylpyrrolidine (41 mg, 0.172 mmol, 24.64% yield).

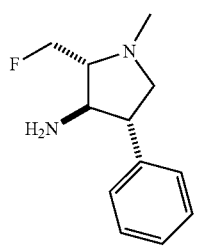

Step 2

(2R,3R,4S)+(2S,3S,4R)-2-(fluoromethyl)-1-methyl-4-phenylpyrrolidin-3-amine (2R,3R,4S)+4S,3S,4R-2-(fluoromethyl)-1-methyl-3-nitro-4-phenylpyrrolidine (40 mg, 0.168 mmol) was dissolved in MeOH, Acetic Acid, charged with ZINC (54.9 mg, 0.839 mmol) and allowed to stir vigorously overnight. The reaction was filtered through 0.2 uM whatman filter and the solvents were evaporated in vacuo on the V-10 (very hi). The residue was re-dissolved in MeOH and filtered through a ps-bicarbonate cartridge 500 mg. The solvents were removed in vacuo to provide (2R,3R,4S)+(2S,3S,4R)-2-(fluoromethyl)-1-methyl-4-phenylpyrrolidin-3-amine (30 mg, 0.144 mmol, 86% yield) as an AcOH salt. MS ESI Calc'd for $C_{12}H_{17}FN_2$ [M+H]+ 209, found 209.

Scheme 33

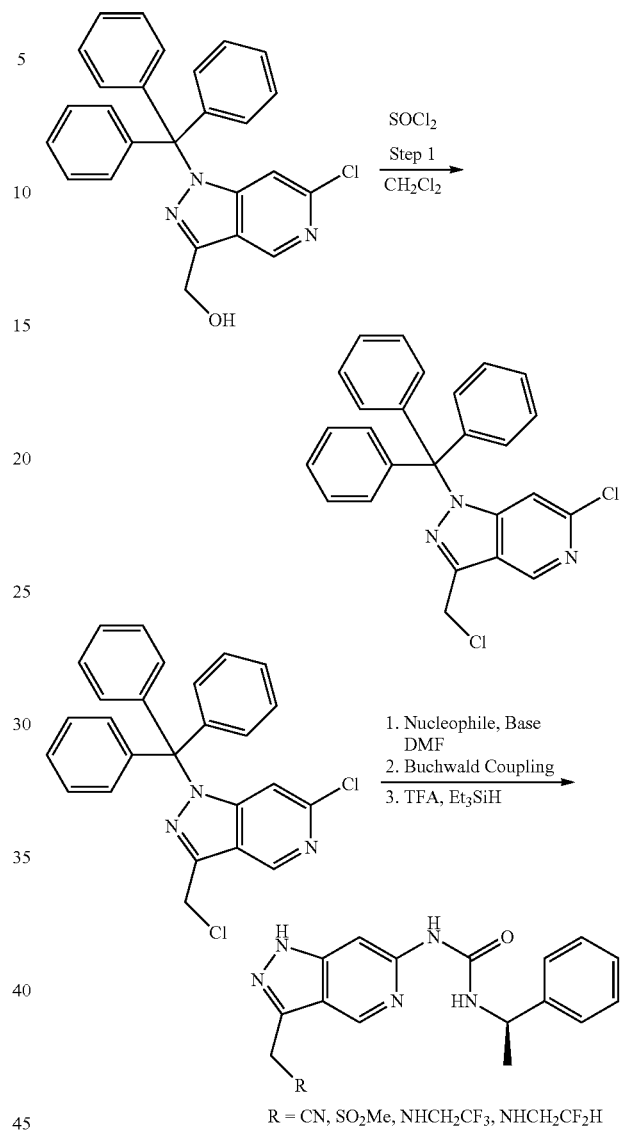

R = CN, $SO_2Me$, $NHCH_2CF_3$, $NHCH_2CF_2H$

Scheme 34

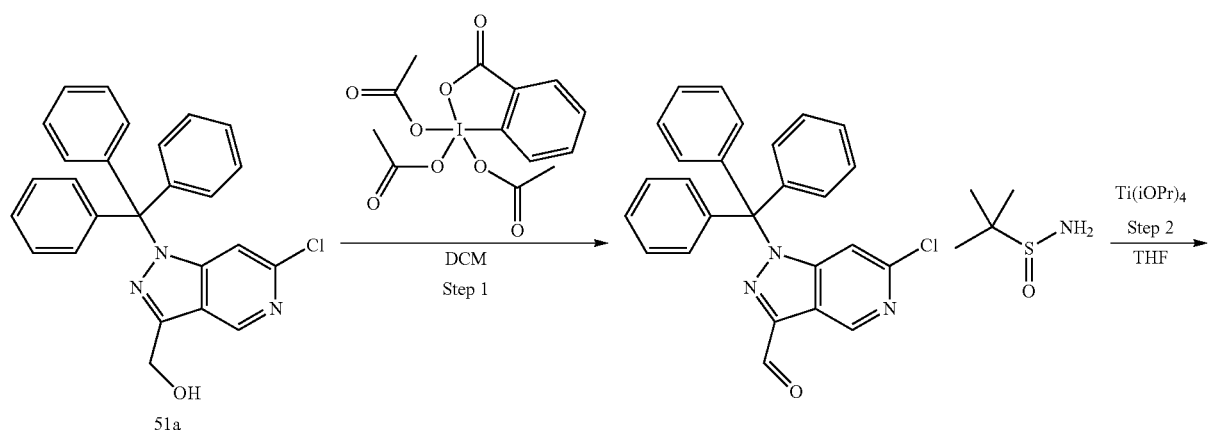

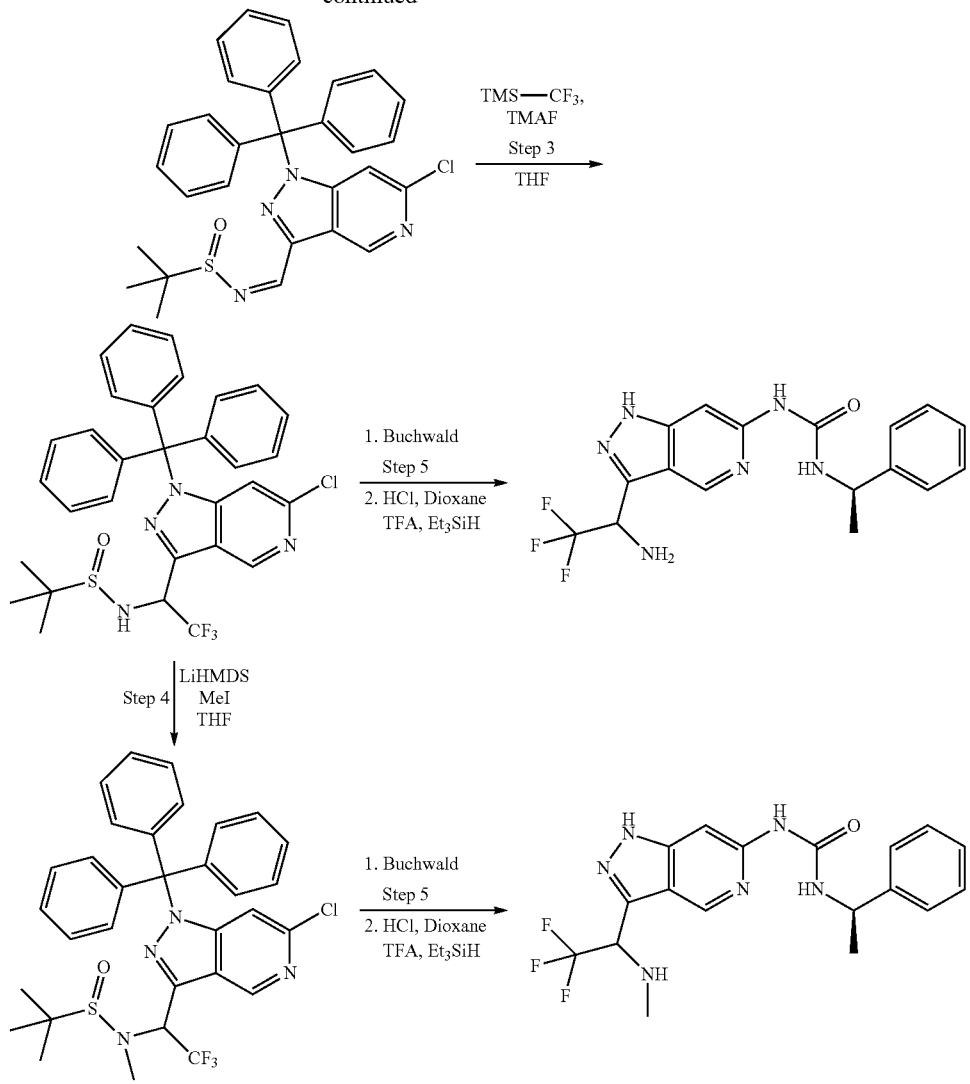

Step 1

(6-chloro-1-trityl-1H-pyrazolo[4,3-c]pyridin-3-yl)methanol 53a (1100 mg, 2.58 mmol) was dissolved in wet DCM (30 ml), charged with Dess-MartinPeriodinane (1315 mg, 3.10 mmol) and allowed to stir 1 h at rt. The reaction was quenched 30 mL 1:1 1M sodium thiosulfate and conc. sodium bicarbonate and allowed to stir until both aq and organic were clear (~1 h). The organic layer was separated, dried over sodium sulfate, filtered and concentrated in vacuo to provide the aldehyde (1.05 g, 2.477 mmol, 96% yield).

Step 2

(E/Z)—N4(6-chloro-1-trityl-1H-pyrazolo[4,3-c]pyridin-3-yl)methylene)-2-methylpropane-2-sulfinamide Dissolved 6-chloro-1-trityl-1H-pyrazolo[4,3-c]pyridine-3-carbaldehyde (500 mg, 1.180 mmol) in THF (10 ml) and added 2-methylpropane-2-sulfinamide (286 mg, 2.359 mmol), cooled to 0° C. Added titanium (IV) isopropoxide (1.382 ml, 4.72 mmol) slowly and let warm to RT over 6 hrs. Worked up with conc. NaCl, filtered and pardoned with ethyl acetate. Dried over magnesiumsulfate. Purified on silica gel, 0-10% EtOAc/hexanes to provide (E/Z)—N-((6-chloro-1-trityl-1H-pyrazolo[4,3-c]pyridin-3-yl)methylene)-2-methylpropane-2-sulfinamide (529 mg, 1.0 mmol, 85% yield) MS ESI Calc'd for [M+H]$^+$ 527, found 527.

Step 3

N-(1-(6-chloro-1-trityl-1H-pyrazolo[4,3-c]pyridin-3-yl)-2,2,2-trifluoroethyl)-2-methylpropane-2-sulfinamide TMS-CF3 (0.130 ml, 0.882 mmol) was added to a stirred, cooled 0° C. mixture of (E/Z)—N-((6-chloro-1-trityl-1H-pyrazolo[4,3-c]pyridin-3-yl)methylene)-2-methylpropane-2-sulfonamide (310 mg, 0.588 mmol) in THF (5 ml). TMAF (82 mg, 0.882 mmol) was added 1 min later. Reaction was stirred until SM was consumed by LC/MS (~30 min at 0° C.). Sat. NH4Cl was added, and organics were extracted using EtOAc (3×). Combined organics were dried over MgSO4, filtered, and concentrated. The residue was purified on SNAP 25 g silica cartridge, 5-30% EtOAc/DCM to provide N-(1-

(6-chloro-1-trityl-1H-pyrazolo[4,3-c]pyridin-3-yl)-2,2,2-trifluoroethyl)-2-methylpropane-2-sulfonamide 230 mg, 0.39 mmol, 66% yield) MS ESI Calc'd for [M+H]⁺ 597, found 597.

Intermediate 52a

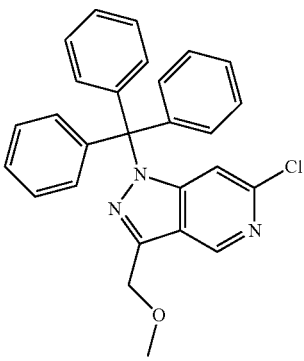 [SMILES: COCc1nn(C(c2ccccc2)(c2ccccc2)c2ccccc2)c2cc(Cl)ncc12]

6-chloro-3-(methoxymethyl)-1-trityl-1H-pyrazolo[4,3-c]pyridine

Under Argon, the solution of 6-chloro-3-iodo-1-trityl-1H-pyrazolo[4,3-c]pyridine (52 mg, 0.100 mmol), potassium methoxymethyltrifluoroborate (16.66 mg, 0.110 mmol), palladium(II) acetate (0.671 mg, 2.99 μmol), (2-DICYCLO-HEXYLPHOSPHINO-2',6'-DIISOPROPYL-1,1'-BIPHE-NYL)[2-(2-AMINOETHYL)PHENYL)]PALLADIUM(II) (4.36 mg, 5.98 μmol and cesium carbonate (0.024 ml, 0.299 mmol) in 1,4-Dioxane (0.9 ml) and Water (0.1 ml) was allowed to stir at 100° C. for 24 h. LC-MS showed the desired product's mass. EtOAc was added into the mixture and the organic layer was washed by water and brine. After drying over Na₂SO₄ the organic layer was evaporated under reduced pressure yielding 6-chloro-3-(methoxymethyl)-1-trityl-1H-pyrazolo[4,3-c]pyridine, 52a. The intermediate was taken to the next reaction without further purification. MS ESI Calc'd for $C_{27}H_{22}ClN_3O$ [M+H]⁺ 440, found 440.

Scheme 35

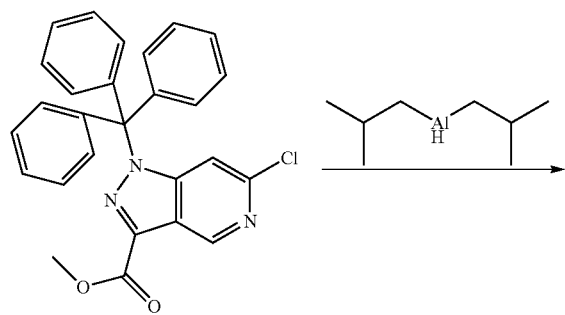

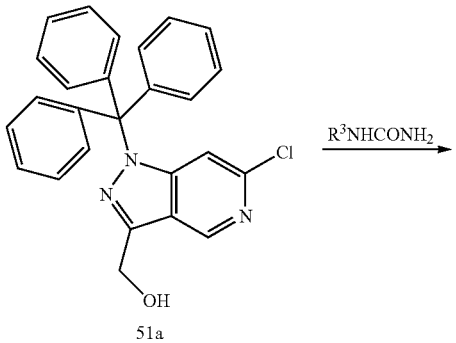

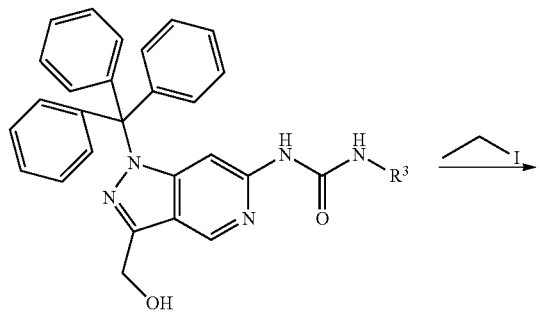

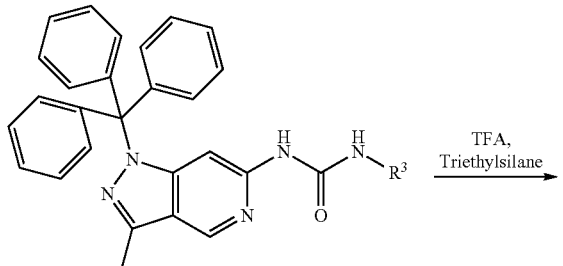

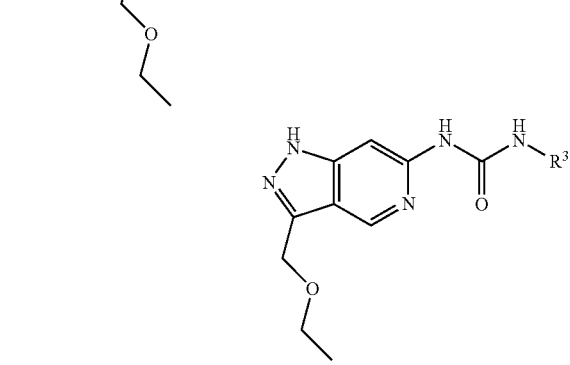

Scheme 36

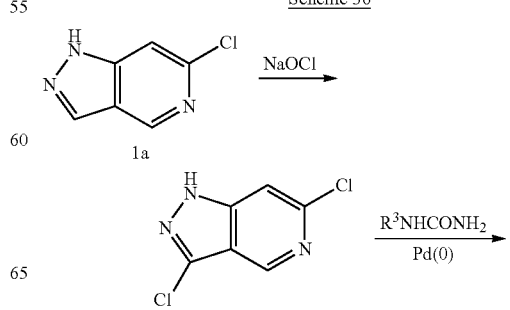

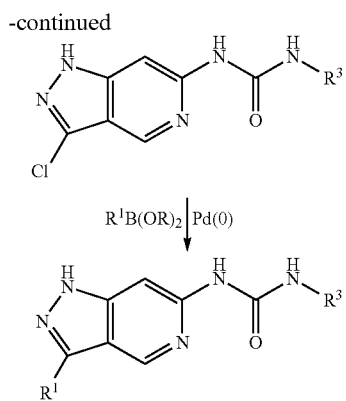

The example numbers below refer to the compounds in Table 1 below.

EXAMPLE 1

3-({[3-(2-methylpyridin-4-yl)-1H-pyrazolo[4,3-c]pyridin-6-yl]carbamoyl}amino-piperidinium trifluoroacetate

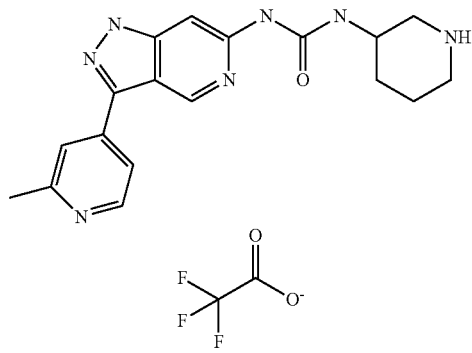

A sealed vial was charged with 1-(tert-butoxycarbonyl)piperidine-3-carboxylic acid (51.4 mg, 0.224 mmol), and TEA (0.125 mL, 0.897 mmol) in toluene (2.5 mL). Diphenylphosphoryl azide (0.058 mL, 0.269 mmol) was added and the mixture was stirred at 100° C. After 3 h the mixture was cooled to RT and added to a suspension of 3-(2-methylpyridin-4-yl)-1-trityl-1H-pyrazolo[4,3-c]pyridin-6-amine (intermediate 5a; 115 mg, 0.198 mmol) in toluene (1.5 mL). After overnight heating at 100° C., the mixture was cooled down to RT and treated again with a solution in toluene (1 mL) of 1-(tert-butoxycarbonyl)piperidine-3-carboxylic acid (114 mg, 0.497 mmol) and TEA (0.625 ml, 4.485 mmol), previously treated with diphenylphosphoryl azide (0.125 mL, 0.578 mmol) and heated at 100° C. for 1 h. After 2 h the mixture was cooled to RT and taken up in EtOAc. The organic phase was washed with saturated NaHCO$_3$ and the aqueous phase was back-extracted with EtOAc (3×). Combined organic layers were dried (Na$_2$SO$_4$) and volatiles were evaporated in vacuo. The residue was purified by chromatography on silica gel over a gradient of 0-100% EtOAc in hexanes to yield 32 mg of a solid which was directly dissolved in DCM (1 mL) and treated with TFA (0.1 mL). The mixture was stirred at RT for 2.5 h and then concentrated in vacuo. Crude material was purified via reverse phase HPLC over a gradient of 5-60% MeCN in water with 0.1% TFA to yield 3-({[3-(2-methylpyridin-4-yl)-1H-pyrazolo[4,3-c]pyridin-6-yl] carbamoyl}amino)piperidinium trifluoroacetate (5 mg, 0.01 mmol, 23%). MS ESI calc'd. for C$_{18}$H$_{22}$N$_7$O [M+1]$^+$ 352, found 352.

$^1$H NMR (600 MHz, DMSO-d$_6$) δ 13.96 (s, 1H), 9.34 (s, 1H), 9.26 (s, 1H), 8.73 (d, J=5.9 Hz, 1H), 8.72 (br s, 1H), 8.65-8.55 (m, 1H), 8.33 (s, 1H), 8.24 (d, J=5.9 Hz, 1H), 7.85 (s, 1H), 7.26 (br s, 1H), 3.89-3.81 (m, 1H), 3.31 (d, J=11.5, 1H), 3.15 (d, J=11.5 Hz, 1H), 2.88-2.72 (m, 2H), 2.72 (s, 3H), 1.95-1.87 (m, 1H), 1.87-1.79 (m, 1H), 1.72-1.61 (m, 1H), 1.52-1.42 (m, 1H).

Preparation of
3-carboxy-1-(2-fluoro-6-methoxybenzyl)piperidinium
2,2,2-trifluoroacetate Nipecotic acid (1.05 g, 8.13 mmol) and 2-fluoro-6-methoxybenzaldehyde (1.509 g, 9.79 mmol) were dissolved in MeOH (30 ml) and DCM (5 ml). AcOH (0.465 ml, 8.13 mmol) was added and the reaction mixture stirred at room temperature for 15 minutes. Sodium triacetoxyborohydride (5.51 g, 26.0 mmol) was added in three batches to avoid bubbling and the mixture was stirred overnight. Additional AcOH (0.465 mL) and sodium triacetoxyborohydride (2.3 g, 10.8 mmol) were added and the mixture was left for 5 h, then the mixture was filtered and concentrated and purified by via reverse phase HPLC over a gradient of 15-50% MeCN with 0.1% TFA to yield 3-carboxy-1-(2-fluoro-6-methoxybenzyl)-piperidinium 2,2,2-trifluoroacetate as a white solid. (1.15 g, 3.01 mmol, 37%). MS ESI calc'd. for C$_{14}$H$_{19}$FNO$_3$ [M+1]$^+$ 268, found 268.

3-Carboxy-1-(2-fluoro-6-methoxybenzyl)piperidinium 2,2,2-trifluoroacetate was used for the preparation of Examples 2-4.

EXAMPLE 11

1-[(1S)-1-(4-fluorophenyl)ethyl]-3-[3-(2-methylpyridin-4-yl)-1H-pyrazolo[4,3-c]pyridin-6-yl]urea

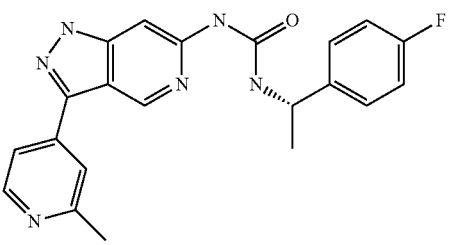 [SMILES: Cc1cc(-c2n[nH]c3cc(NC(=O)N[C@@H](C)c4ccc(F)cc4)ncc23)ccn1]

A mixture of 3-(2-methylpyridin-4-yl)-1-trityl-1H-pyrazolo[4,3-c]pyridin-6-amine (intermediate 5a; 50 mg, 0.107 mmol) and 1-fluoro-4-[(1R)-1-isocyanatoethyl]-benzene (75 mg, 0.454 mmol) in 1,4-dioxane (1 mL) was heated to 60° C. overnight, then cooled down to RT and concentrated in vacuo. The residue was suspended in DCM and purified by chromatography on silica gel (0-50% MeOH/DCM) to yield a solid, which was directly dissolved in DCM (1 mL) and treated with TFA (1 mL). The mixture was stirred at RT for 3 h, then concentrated in vacuo and purified via reverse phase HPLC over a gradient of 20-55% MeCN with 0.1% TFA. The collected fractions were then partitioned between DCM/MeOH and 1N NaOH. The organic layer was dried (Na$_2$SO$_4$) and concentrated in vacuo to provide 1-[(1S)-1-(4-fluorophenyl)ethyl]-3-[3-(2-methylpyridin-4-yl)-1H-pyrazolo[4,3-c]pyridin-6-yl]urea as a solid (13 mg, 0.033 mmol, 31%). MS ESI calc'd. for C$_{21}$H$_{20}$N$_6$OF. [M+1]$^+$ 391, found 391.

¹H NMR (600 MHz, CD₃OD) δ 9.15 (s, 1H) 8.51 (d, J=5.3 Hz, 1H), 7.91 (s, 1H), 7.85 (d, J=5.3 Hz, 1H), 7.48 (s, 1H), 7.39 (dd, J=8.5, 5.3 Hz, 2H), 7.05 (t, J=8.8 Hz, 2H), 4.98 (q, J=7.0 Hz, 1H), 2.62 (s, 3H), 1.50 (d, J=7.0 Hz, 3H)

EXAMPLE 12

2-methyl-4-(6-{[(pyridin-4-ylmethyl)carbamoyl]amino}-1H-pyrazolo[4,3-c]pyridin-3-yl)pyridinium trifluoroacetate

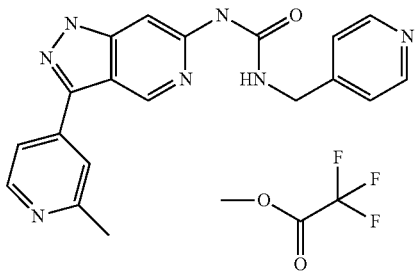

A suspension of 3-(2-methylpyridin-4-yl)-1-trityl-1H-pyrazolo[4,3-c]pyridin-6-amine (intermediate 5a; 33.4 mg, 0.071 mmol) and imidazole (14.59 mg, 0.214 mmol) in DCM (0.5 mL) was added to a solution of CDI (69.5 mg, 0.429 mmol) in DCM (0.5 mL) and the mixture was stirred at RT. After 3 h, 4-(aminomethyl)pyridine (0.062 mL, 0.571 mmol) was added and the mixture was left at the same temperature for additional 30 min. Volatiles were removed in vacuo and the residue was purified by chromatography on silica gel over a gradient of 0-50% (20% MeOH in EtOAc) in DCM to yield a solid, which was directly dissolved in DCM (1 mL), treated with triethylsilane (0.011 mL, 0.071 mmol) and TFA (0.1 mL, 1.298 mmol). After overnight stirring at RT the volatiles were concentrated in vacuo. The residue was purified via reverse phase HPLC over a gradient of 5-20% MeCN in H₂O with 0.1% TFA to yield 2-methyl-4-(6-{[(pyridin-4-ylmethyl)carbamoyl]amino}-1H-pyrazolo[4,3-c]pyridin-3-yl)pyridinium trifluoroacetate (9 mg, 0.026 mmol, 36%) as a solid. MS ESI calc'd. for $C_{19}H_{18}N_7O$ [M+1]⁺ 360, found 360.

¹H NMR (600 MHz, DMSO-d₆) δ 13.5 (br s, 1H), 9.37 (s, 1H), 9.19 (s, 1H), 8.50 (d, J=5.0 Hz, 1H), 8.48 (d, J=5.8 Hz, 2H), 7.89 (br s, 1H), 7.84 (s, 1H), 7.77 (d, J=4.9 Hz, 1H), 7.70 (s, 1H), 7.27 (d, J=5.4 Hz, 2H), 4.39 (d, J=5.8 Hz, 2H), 2.53 (s, 3H)

EXAMPLE 21, 22, and 67

(R)-1-(3-(3-methoxypropyl)-1H-pyrazolo[4,3-c]pyridin-6-yl)-3-(1-phenylethyl)urea (21)

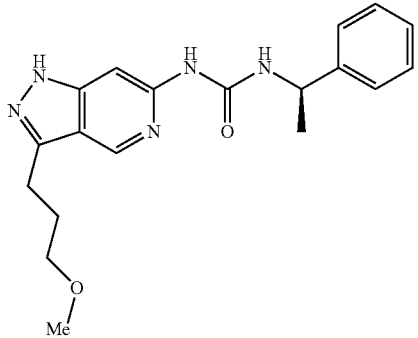 [SMILES: COCCCc1n[nH]c2cc(NC(=O)N[C@H](C)c3ccccc3)ncc12]

(R)-1-(1-phenylethyl)-3-(3-propyl-1H-pyrazolo[4,3-c]pyridin-6-yl)urea (22)

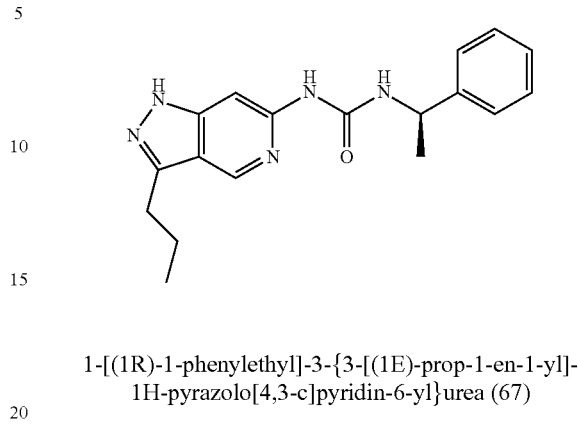

1-[(1R)-1-phenylethyl]-3-{3-[(1E)-prop-1-en-1-yl]-1H-pyrazolo[4,3-c]pyridin-6-yl}urea (67)

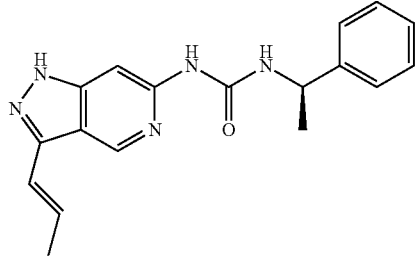 [SMILES: C/C=C/c1n[nH]c2cc(NC(=O)N[C@H](C)c3ccccc3)ncc12]

Step 1

6-chloro-3-iodo-1-trityl-1H-pyrazolo[4,3-c]pyridine (Intermediate 2a, 200 mg, 0.383 mmol), PdCl₂(dppf)-CH₂Cl₂ adduct (47.0 mg, 0.057 mmol), 1-4-dioxane (1 mL), trans-3-methoxy-1-propenylboronic acid pinacol ester (0.15 mL, 0.707 mmol) and Na₂CO₃ (0.48 mL, 0.960 mmol, 2M) were charged in a vial. The mixture was evacuated and purged with nitrogen six times and heated at 80° C. for 35 min. The mixture was diluted with EtOAc and the organic phase was washed with water, brine, dried (Na₂SO₄) and concentrated in vacuo to afford a residue, which was purified by column chromatography on silica gel (10 g, EtOAc in hexane, 0-10%, 10 CV; 10-20%, 20CV) to afford (E)-6-chloro-3-(3-methoxyprop-1-en-1-yl)-1-trityl-1H-pyrazolo[4,3-c]pyridine (147 mg, 0.315 mmol, 82% yield) as a light yellow solid. MS ESI calc'd. for $C_{29}H_{25}ClN_3O$ [M+H]⁺ 466, found 466.

Step 2

(E)-6-chloro-3-(3-methoxyprop-1-en-1-yl)-1-trityl-1H-pyrazolo[4,3-c]pyridine (111 mg, 0.239 mmol), (R)-1-(1-phenylethyl)urea (59 mg, 0.359 mmol), Cs₂CO₃ (194 mg, 0.597 mmol), BrettPhos precatalyst (19.06 mg, 0.024 mmol) and DMA (1.5 ml). The mixture was evacuated and purged with nitrogen six times and heated at 100° C. for 35 min. The mixture was diluted with EtOAc and washed with water, brine, dried (Na₂SO₄) and concentrated to afford crude (R,E)-1-(3-(3-methoxyprop-1-en-1-yl)-1-trityl-1H-pyrazolo[4,3-c]pyridin-6-yl)-3-(1-phenylethyl)urea, which was used in the next step. MS ESI calc'd. for $C_{38}H_{36}N_5O_2$ [M+H]⁺ 594, found 594.

Step 3

To the solution of crude (R,E)-1-(3-(3-methoxyprop-1-en-1-yl)-1-trityl-1H-pyrazolo[4,3-c]pyridin-6-yl)-3-(1-phenylethyl)urea (142 mg, 0.239 mmol) in DCM (0.8 mL) TFA (0.3 mL) and triethylsilane (0.1 mL) were added. The mixture was stirred at room temperature for 30 min and additional TFA (0.5 mL) and triethylsilane (0.3 mL) were added. The mixture was stirred at room temperature for 30 min, evaporated in vacuo and purified by MS-directed reverse phase preparative-HPLC (C-18 stationary phase, eluting with a H$_2$O/MeCN gradient with 0.1% TFA), to afford (R)-1-(3-(3-methoxypropyl)-1H-pyrazolo[4,3-c]pyridin-6-yl)-3-(1-phenylethyl)urea (21.7 mg, 0.046 mmol, 19%). MS ESI calc'd. for C$_{19}$H$_{24}$N$_5$O$_2$ [M+H]$^+$ 354, found 354. $^1$H NMR (600 MHz, DMSO-d$_6$) δ 12.92 (s, 1H), 9.38 (s, 1H), 8.80 (s, 1H), 7.88 (s, 1H), 7.46 (s, 1H), 7.38-7.15 (m, 5H), 4.85 (m, 1H), 3.33 (t, J=6.3 Hz, 2H), 3.19 (s, 3H), 2.91 (t, J=7.6 Hz, 2H), 1.99-1.85 (m, 2H), 1.39 (d, J=6.9 Hz, 3H), (R)-1-(1-phenylethyl)-3-(3-propyl-1H-pyrazolo[4,3-c]pyridin-6-yl)urea (42 mg, 0.097 mmol, 40%). MS ESI calcd. For C$_{18}$H$_{22}$N$_5$O [M+H]$^+$ 324, found 324. $^1$H NMR (600 MHz, DMSO-d$_6$) δ 12.92 (s, 1H), 9.37 (s, 1H), 8.82 (s, 1H), 7.88 (s, 1H), 7.45 (s, 1H), 7.31 (dd, J=8.6, 5.2 Hz, 4H), 7.21 (m, 1H), 4.85 (m, J=7.0, 1H), 2.86 (t, J=7.5 Hz, 2H), 1.80-1.62 (m, 2H), 1.39 (d, J=6.9 Hz, 3H), 0.90 (t, J=7.3 Hz, 3H), and 1-[(1R)-1-phenylethyl]-3-{3-[(1E)-prop-1-en-1-yl]-1H-pyrazolo[4,3-c]pyridin-6-yl}urea (7.9 mg, 0.018 mmol, 8%). MS ESI calc'd. for C$_{18}$H$_{19}$N$_5$O [M+H]$^+$ 322, found 322

EXAMPLE 23

1-(3-(2-methylpyridin-4-yl)-1H-pyrazolo[4,3-c]pyridin-6-yl)urea

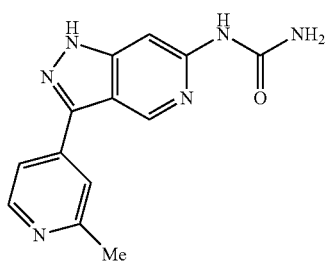 [SMILES: Cc1cc(-c2n[nH]c3cc(NC(N)=O)ncc23)ccn1]

A crude mixture of 1-(4-methoxybenzyl)-3-(3-(2-methylpyridin-4-yl)-1-trityl-1H-pyrazolo[4,3-c]pyridin-6-yl)urea prepared according to Scheme 6 (35 mg, 0.055 mmol) in 1,4-dioxane (0.25 mL) was treated at room temperature with TFA (0.25 mL) and the reaction mixture stirred for 5 h, then additional TFA (0.25 mL) was added and the reaction mixture stirred for 16 h at room temperature and then concentrated in vacuo. The residue was purified by MS-directed reverse phase preparative-HPLC (C-18 stationary phase, eluting with a H$_2$O/MeCN gradient with 0.1% TFA), to give 1-(3-(2-methylpyridin-4-yl)-1H-pyrazolo[4,3-c]pyridin-6-yl)urea TFA salt as a yellow solid (4 mg, 0.01 mmol, 19%). MS ESI calc'd. for C$_{13}$H$_{13}$N$_6$O [M+H]$^+$ 269, found 269. $^1$H NMR (600 MHz, DMSO-d$_6$) δ 13.82 (br s, 1H), 9.31 (s, 1H), 9.19 (s, 1H), 8.70 (s, 1H), 8.30-8.15 (m, 2H), 7.88 (s, 1H), 2.70 (s, 3H).

EXAMPLE 24

1-[(1R)-1-(4-fluorophenyl)ethyl]-3-(1H-pyrazolo[4,3-c]pyridin-6-yl)urea

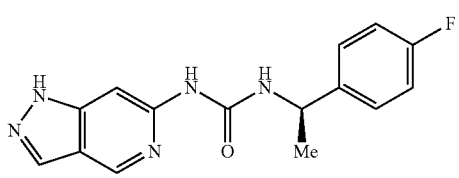 [SMILES: C[C@@H](NC(=O)Nc1cc2[nH]ncc2cn1)c1ccc(F)cc1]

Step 1

Under ice-cooling, a solution of 6-chloro-1H-pyrazolo[4,3-c]pyridine (1 g, 6.51 mmol) in THF (40 mL), was treated with NaH (60% in mineral oil; 438 mg, 10.95 mmol) and the mixture was stirred for 1 h. Trityl chloride (2.17 g, 7.81 mmol) was added and the mixture was stirred at the same temperature for 1 h and further stirred at room temperature for 3 h. The mixture was quenched with saturated NH$_4$Cl and then extracted with EtOAc. The organic layer was washed with water, brine, dried (MgSO$_4$) and concentrated in vacuo. To the residue was added 10 ml of DCM, some solid precipitated out. After filtration, some yellow solid was afforded. The filtrate was purified by chromatography on silica gel (0-30% EtOAc in hexane) to isolate 6-chloro-1-trityl-1H-pyrazolo[4,3-c]pyridine (1.375 g, 3.47 mmol, 53% overall) as a yellow solid. MS ESI calc'd. for C$_{25}$H$_{19}$ClN$_3$ [M+H]$^+$ 396, found 396.

Step 2

A microwave vial was charged with 6-chloro-1-trityl-1H-pyrazolo[4,3-c]pyridine (1.02 g, 2.58 mmol), Pd$_2$(dba)$_3$ (0.24 g, 0.262 mmol), 2-(dicyclohexylphosphino) biphenyl (0.1 g, 0.285 mmol) and THF (11 mL). The mixture was evacuated and purged with nitrogen 5 times. Lithium bis(trimethylsilyl) amide (4.0 ml, 4.0 mmol, 1M in THF) was added dropwise and the mixture was heated at 70° C. for 2 h. Pd$_2$(dba)$_3$ (0.12 g, 0.131 mmol), 2-(dicyclohexylphosphino) biphenyl (0.05 g, 0.142 mmol) and LiHMDS (2.0 ml, 2.0 mmol, 1M in THF) were added again. After 16 h, the mixture was quenched with saturated NH$_4$Cl and extracted with 2-methyltetrahydrofuran. The organic phase was washed with water, brine, dried (Na$_2$SO$_4$) and concentrated in vacuo to afford a residue, which was purified by chromatography on silica gel (MeOH in DCM, 0-8% 15 CV, 8-10% 10 CV) to afford 1-trityl-1H-pyrazolo[4,3-c]pyridin-6-amine (0.813 g, 2.16 mmol, 84%). MS ESI calc'd. for C$_{25}$H$_{21}$N$_4$ [M+H]$^+$ 377, found 377.

Step 3

1-trityl-1H-pyrazolo[4,3-c]pyridin-6-amine (301 mg, 0.8 mmol), CDI (519 mg, 3.2 mmol), DIEA (0.5 ml, 2.87 mmol and 1,4-dioxane (5 mL) were charged in a microwave vial. The mixture was stirred at 50° C. for 4.5 h. Additional CDI (519 mg, 3.2 mmol) and imidazole (218 mg, 3.20 mmol) were added, the mixture was stirred at 50° C. for 16 h and then treated with (R)-1-(4-fluorophenyl)ethanamine (536 mg, 3.85 mmol). The mixture was stirred at 50° C. for 2 h and then diluted with EtOAc washed with water, brine, dried (Na$_2$SO$_4$) and concentrated in vacuo to afford a residue, which was purified by chromatography on silica gel (0-40% EtOAc in hexane, 25 CV; 40-100% EtOAc in hexane, 20 CV) to afford (R)-1-(1-(4-fluorophenyl)ethyl)-3-(1-trityl-1H-pyrazolo[4,3-c]pyridin-6-yl)urea (154 mg, 0.229 mmol, 28%) as a yellow solid. MS ESI calc'd. for C$_{34}$H$_{29}$FN$_5$O [M+H]$^+$ 542, found 542.

Step 4

A solution of (R)-1-(1-(4-fluorophenyl)ethyl)-3-(1-trityl-1H-pyrazolo[4,3-c]pyridin-6-yl)urea (157 mg, 0.291 mmol) in DCM (0.8 mL) was treated with TFA (0.2 mL) and triethylsilane (0.1 mL). The mixture was stirred at room temperature for 1.5 h. Additional TFA (0.2 mL) and triethylsilane (0.1 mL) were added and the mixture was stirred for 1.5 h and then evaporated in vacuo to afford a residue, which was purified by MS-directed reverse phase preparative-HPLC (C-18 stationary phase, eluting with a H$_2$O/MeCN gradient with 0.1% TFA), to yield (R)-1-(1-(4-fluorophenyl)ethyl)-3-(1H-pyrazolo[4,3-c]pyridin-6-yl)urea (14 mg, 0.034 mmol, 12%). MS ESI calc'd. for C$_{15}$H$_{15}$FN$_5$O [M+H]$^+$ 300, found 300. $^1$H NMR (600 MHz, DMSO-d$_6$) δ 9.22 (s, 1H), 8.15 (s, 1H), 7.92 (s, 1H), 7.32 (dd, J=8.5, 5.6 Hz, 2H), 7.12 (t, J=8.9 Hz, 2H), 7.07 (s, 1H), 6.78 (s, 1H), 4.79 (m, 1H), 1.35 (d, J=7.0 Hz, 3H).

EXAMPLE 30

1-[3-(4-fluorophenyl)-1H-pyrazolo[4,3-c]pyridin-6-yl]-3-[(1R)-1-phenylethyl]urea

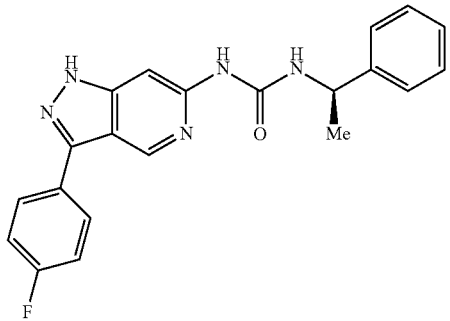 [SMILES: C[C@@H](NC(=O)Nc1cc2[nH]nc(-c3ccc(F)cc3)c2cn1)c1ccccc1]

Preparation of (R)-1-(1-Phenylethyl)urea

A mixture of (R)-1-phenylethylamine (1.00 g, 8.25 mmol) in water (4 mL) was treated with a 1 M solution of HCl in water (8.5 mL, 8.5 mmol) followed by potassium cyanate (3.35 g, 41.2 mmol). The reaction mixture was warmed to 80° C. for 1 hour and cooled. The mixture was neutralized with saturated NaHCO$_3$ and extracted with ethyl acetate and 2-methyltetrahydrofuran. The combined organic phase was dried (Na$_2$SO$_4$), filtered and concentrated. Chromatography on SiO$_2$ (0-10% MeOH/DCM) gave the desired urea product (1.32 g, 8.04 mmol; 97%) as a white solid. MS ESI calc'd for C$_9$H$_{12}$N$_2$O [M+H]$^+$ 165, found 165. $^1$H NMR (600 MHz, DMSO-d$_6$) δ 7.23-7.28 (m, 4 H), 7.17 (t, J=6.7 Hz, 1 H), 6.38 (d, J=7.9 Hz, 1 H), 5.38 (br s, 2 H), 4.65 (m, 1 H), 1.26 (d, J=7.1 Hz, 3 H).

Step 1

6-chloro-3-(4-fluorophenyl)-1-trityl-1H-pyrazolo[4,3-c]pyridine (Intermediate 4a, 73 mg, 0.147 mmol), (R)-1-(1-phenylethyl)urea (37 mg, 0.225 mmol), Cs$_2$CO$_3$ (120 mg, 0.367 mmol), BrettPhos precatalyst (11.7 mg, 0.015 mmol) and DMA (1.1 mL) were charged in a vial. The mixture was evacuated and purged with nitrogen six times and heated at 100° C. for 55 min. The mixture was diluted with EtOAc and washed with water, brine, dried (Na$_2$SO$_4$) and concentrated to afford a residue, which was purified by chromatography on silica gel (0-100% ethyl acetate in hexane, 20 CV) to afford (R)-1-(3-(4-fluorophenyl)-1-trityl-1H-pyrazolo[4,3-c]pyridin-6-yl)-3-(1-phenylethyl)urea (85 mg, 0.136 mmol, 92%) as a yellow solid. MS ESI calcd. For C$_{40}$H$_{32}$FN$_5$O [M+H]$^+$ 618, found 618.

Step 2

To the solution of (R)-1-(3-(4-fluorophenyl)-1-trityl-1H-pyrazolo[4,3-c]pyridin-6-yl)-3-(1-phenylethyl)urea (61 mg, 0.10 mmol) in DCM (0.5 mL) was added TFA (0.5 mL) and triethylsilane (0.05 mL, 0.313 mmol). The mixture was stirred at room temperature for 10 min, concentrated in vacuo and purified on reversed phase HPLC to afford (R)-1-(3-(4-fluorophenyl)-1H-pyrazolo[4,3-c]pyridin-6-yl)-3-(1-phenylethyl)urea (40 mg, 0.083 mmol, 83%) as a yellow solid. MS ESI calcd. for C$_{21}$H$_{19}$FN$_5$O [M+H]$^+$ 376, found 376. $^1$H NMR (600 MHz, DMSO-d$_6$) δ 13.24 (s, 1H), 9.12 (s, 1H), 9.06 (s, 1H), 8.04 (dd, J=8.8, 5.5 Hz, 2H), 7.75 (s, 1H), 7.65 (s, 1H), 7.39-7.27 (m, 6H), 7.22-7.18 (m, 1H), 4.86 (m, 1H), 1.39 (d, J=6.9 Hz, 3H).

EXAMPLE 33 and 34

1-(3,4-dimethoxybenzyl)-3-(3-(4-fluorophenyl)-1H-pyrazolo[4,3-c]pyridin-6-yl)urea (33) and 1-O-(4-fluorophenyl)-1H-pyrazolo[4,3-c]pyridin-6-yl)urea (34)

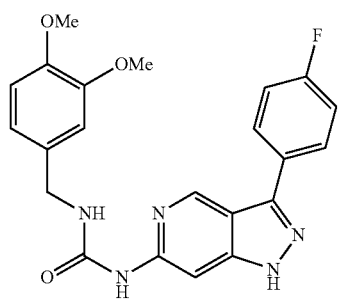

103

-continued (34)

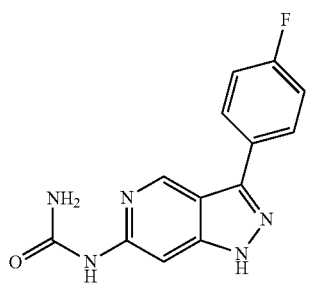

Step 1

6-chloro-3-(4-fluorophenyl)-1H-pyrazolo[4,3-c]pyridine (50 mg, 0.202 mmol) and DMAP (2.4 mg, 0.020 mmol) were added to a 10-mL flask and MeCN (2 mL), DIEA (0.123 mL, 0.707 mmol) and di-tert-butyl dicarbonate (0.262 mL, 0.262 mmol, 1M in THF) were added. The yellow solution was stirred for 16 h at room temperature, then brine was added and the reaction mixture extracted with DCM (3×). The combined organic layers were dried ($MgSO_4$), filtered and the volatiles were evaporated in vacuo to yield a yellow oil which was used as such in Step 2.

Step 2

$Cs_2CO_3$ (122 mg, 0.374 mmol), xantphos (21.6 mg, 0.037 mmol), $Pd(OAc)_2$ (4.2 mg, 0.019 mmol), 1-(3,4-dimethoxybenzyl)urea (43.2 mg, 0.206 mmol) were added to the crude product from Step 1 in 1,4-dioxane (2 mL) in a 4-mL vial under $N_2$. The reaction mixture was heated to 90° C. for 16 h and then filtered through $MgSO_4$/Celite with DCM. Solvents were evaporated in vacuo to give an oil which was used as such in Step 3.

Step 3

The crude oil from Step 2 was dissolved in DCM (1 mL) and TFA (1 mL) was added. The yellow reaction mixture was stirred for 16 h at room temperature, then additional TFA (1 mL) was added and the reaction stirred for another 24 h. The residue was purified by MS-directed reverse phase preparative-HPLC (C-18 stationary phase, eluting with a $H_2O$/MeCN gradient with 0.1% TFA), to give 1-(3-(4-fluorophenyl)-1H-pyrazolo[4,3-c]pyridin-6-yl)urea trifluoroacetate salt (0.4 mg, 0.01 mmol, 0.5%) and 1-(3,4-dimethoxybenzyl)-3-(3-(4-fluorophenyl)-1H-pyrazolo[4,3-c]pyridin-6-yl)urea trifluoroacetate salt (56 mg, 0.1 mmol, 56%) as colorless solids.

(33) 1-(3,4-dimethoxybenzyl)-3-(3-(4-fluorophenyl)-1H-pyrazolo[4,3-c]pyridin-6-yl)urea MS ESI calc'd. for $C_{22}H_{21}FN_5O_3$ [M+H]$^+$ 422, found 422. $^1$H NMR (600 MHz, DMSO-$d_6$) δ 13.25 (s, 1H), 9.23 (s, 1H), 9.04 (s, 1H), 8.04 (m, 2H), 7.70 (s, 1H), 7.61 (br s, 1H), 7.31 (m, 2H), 6.90 (m, 2H), 6.82 (m, 1H), 4.27 (m, 2H), 3.71 (s, 3H), 3.69 (s, 3H).

104

(34) 1-(3-(4-fluorophenyl)-1H-pyrazolo[4,3-c]pyridin-6-yl)urea: MS ESI calc'd. for $C_{13}H_{11}FN_5O$ [M+H]$^+$ 272, found 272.

EXAMPLE 55

1-[3-(2-methylpyridin-4-yl)-1H-pyrazolo[4,3-c]pyridin-6-yl]-3-{6-[(2-phenylethyl)amino]pyridazin-3-yl}urea Example 55 was prepared according to Scheme 6 by using intermediate 10a.

1-(6-(phenethylamino)pyridazin-3-yl)urea (10a)

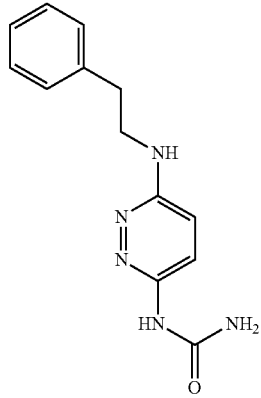

10a

Step 1

$Cs_2CO_3$ (139 mg, 0.428 mmol), xantphos (24.7 mg, 0.043 mmol), $Pd(OAc)_2$ (4.8 mg, 0.021 mmol), 1-(4-methoxybenzyl)urea (46.3 mg, 0.257 mmol) and 6-chloro-N-phenethylpyridazin-3-amine (50 mg, 0.214 mmol) in 1,4-dioxane (2 mL) were added to a 4-mL vial under $N_2$. The reaction mixture was heated to 90° C. for 16 h. The reaction mixture was filtered through a $MgSO_4$/Celite plug with DCM and the solvents were evaporated in vacuo. The crude oil was used as such in Step 2.

Step 2

The crude product from Step 1 was dissolved in DCM (1 mL) and TFA (1 mL) was added. The brownish reaction mixture was stirred at room temperature for 40 h, then additional TFA (1 mL) was added and the reaction mixture stirred for another 32 h. MeOH (10 mL) was added and after evaporation in vacuo the residue was purified by preparative HPLC Reverse phase (C-18) over a gradient of 0-100% MeCN in $H_2O$ with 0.1% TFA to give 1-(6-(phenethylamino)pyridazin-3-yl)urea trifluoroacetate salt (45 mg, 0.121 mmol, 47%×2 steps) as a yellow oil. MS ESI calc'd. for $C_{13}H_{16}N_5O$ $[M+H]^+$ 258, found 258.

EXAMPLE 86

1-[7-bromo-3-(2-methylpyridin-4-yl)-1H-pyrazolo[4,3-c]pyridin-6-yl]-3-[(1R)-1-(4-chlorophenyl)ethyl]urea

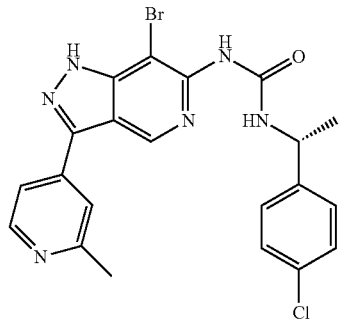 [SMILES: Cc1cc(-c2n[nH]c3c(Br)c(NC(=O)N[C@H](C)c4ccc(Cl)cc4)ncc23)ccn1]

To a stirred solution of 1-[(1R)-1-(4-chlorophenyl)ethyl]-3-[3-(2-methylpyridin-4-yl)-1H-pyrazolo[4,3-c]pyridin-6-yl]urea (Example 19; 82 mg, 0.202 mmol) in MeCN (2 mL) was added NBS (47 mg, 0.262 mmol). The mixture was left to stir for 1 h at room temperature and then treated with 1N $Na_2S_2O_3$, and extracted with chloroform:iPrOH (3:1, x3). The combined organics were dried ($Na_2SO_4$), concentrated in vacuo and purified by column chromatography on silica gel to yield 1-[7-bromo-3-(2-methylpyridin-4-yl)-1H-pyrazolo[4,3-c]pyridin-6-yl]-3-[(1R)-1-(4-chlorophenyl)ethyl]urea (42 mg, 0.086 mmol, 43%). MS ESI calc'd. for $C_{21}H_{19}BrClN_6O$ $[M+1]^+$ 485, found 485.

$^1$H NMR (600 MHz, DMSO-$d_6$) δ 9.29 (s, 1H), 9.04 (s, 1H), 8.55 (d, J=5.0 Hz, 1H), 8.08 (s, 1H), 7.88 (s, 1H), 7.81 (s, 1H), 7.37 (s, 4H), 4.97-4.90 (m, 1H), 2.56 (s, 3H), 1.43 (d, J=6.8 Hz, 3H)

EXAMPLE 90

1-[3-(1-methyl-1H-pyrazol-3-yl)-1H-pyrazolo[4,3-c]pyridin-6-yl]-3-[(1R)-1-phenylethyl]urea

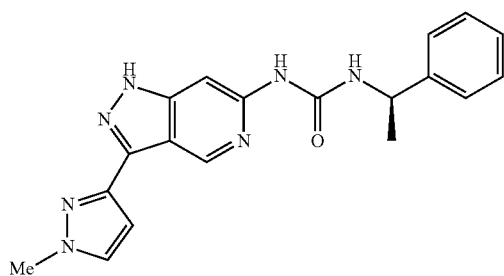 [SMILES: C[C@@H](NC(=O)Nc1cc2[nH]nc(-c3ccn(C)n3)c2cn1)c1ccccc1]

Step 1

3-bromo-1-trityl-1H-pyrazolo[4,3-c]pyridin-6-amine (Intermediate 9a, 500 mg, 1.098 mmol), CDI (356 mg, 2.196 mmol), imidazole (150 mg, 2.196 mmol) and DCM (11 mL) were charged in a flask. The mixture was stirred at room temperature for 16 h and then treated with (R)-1-phenylethanamine (272 mg, 2.245 mmol). The mixture was stirred at room temperature for 1 h and then purified by chromatography on silica gel (EtOAc in hexane, 0-40%, 25 CV) to afford (R)-1-(3-bromo-1-trityl-1H-pyrazolo[4,3-c]pyridin-6-yl)-3-(1-phenylethyl)urea (582 mg, 0.966 mmol, 88%) as a white solid. MS ESI calcd. For $C_{34}H_{29}BrN_5O$ $[M+H]^+$ 602, found 602.

Step 2

(R)-1-(3-bromo-1-trityl-1H-pyrazolo[4,3-c]pyridin-6-yl)-3-(1-phenylethyl)urea (36 mg, 0.060 mmol), 1-methyl-3-(4,4,5,5-tetramethyl-1,3,2-dioxaborolan-2-yl)-1H-pyrazole (18.6 mg, 0.090 mmol), $PdCl_2$(dppf)-$CH_2Cl_2$ adduct (7.3 mg, 8.96 μmol), 1,4-dioxane (0.6 mL) and $Na_2CO_3$ (0.08 mL, 0.160 mmol, 2M) were charged in a vial. The mixture was evacuated and purged with nitrogen six times and heated at 80° C. for 1 h. The mixture was diluted with EtOAc, washed with water, brine, dried ($Na_2SO_4$) and concentrated in vacuo to afford crude (R)-1-(3-(1-methyl-1H-pyrazol-3-yl)-1-trityl-1H-pyrazolo[4,3-c]pyridin-6-yl)-3-(1-phenylethyl)urea, which was used as such in the next step. MS ESI calcd. For $C_{38}H_{34}N_7O$ $[M+H]^+$ 604, found 604.

Step 3

A solution of crude (R)-1-(3-(1-methyl-1H-pyrazol-3-yl)-1-trityl-1H-pyrazolo[4,3-c]pyridin-6-yl)-3-(1-phenylethyl)urea (36 mg, 0.060 mmol) in DCM (1 mL) was treated with TFA (0.2 mL) and triethylsilane (0.02 mL, 0.125 mmol). The mixture was stirred at room temperature for 5.5 h, evaporated in vacuo and purified on reversed phase HPLC to afford (R)-1-(3-(1-methyl-1H-pyrazol-3-yl)-1H-pyrazolo[4,3-c]pyridin-6-yl)-3-(1-phenylethyl)urea (15.7 mg, 0.033 mmol, 55%) as a white solid. MS ESI calcd. For $C_{19}H_{20}N_7O$ $[M+H]^+$ 362, found 362. $^1$H NMR (600 MHz, DMSO-$d_6$) δ 13.06 (s, 1H), 9.16 (s, 1H), 9.12 (s, 1H), 7.84-7.79 (m, 1H), 7.78 (d, J=2.2 Hz, 1H), 7.57 (s, 1H), 7.35-7.27 (m, 4H), 7.21 (ddd, J=8.7, 5.8, 2.6 Hz, 1H), 6.68 (d, J=2.2 Hz, 1H), 4.97-4.71 (m, 1H), 3.93 (s, 3H), 1.39 (d, J=7.0 Hz, 3H).

EXAMPLE 92

1-benzyl-3-[7-chloro-3-(2-methylpyridin-4-yl)-1H-pyrazolo[4,3-c]pyridin-6-yl]urea

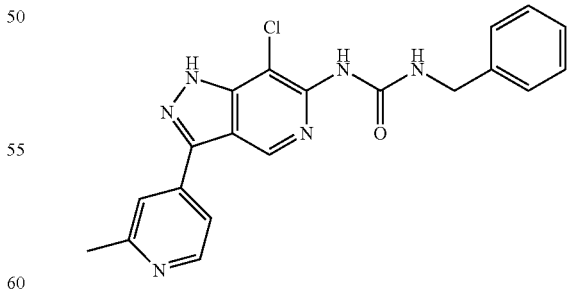

A vial was charged with 1-benzyl-3-(7-chloro-3-(2-methylpyridin-4-yl)-1H-pyrazolo[4,3-c]pyridin-6-yl)urea (Example 9; 25 mg, 0.070 mmol) and a second vial was charged with xenon difluoride (78 mg, 0.46 mmol). The second vial was put under an atmosphere of argon and 1,2-dichloroethane (3 mL) was injected.

A portion of this solution (0.7 mL) was transferred into the flask containing the substrate. After 3 h the remaining xenon difluoride solution was injected into the reaction flask. Stirring was continued for 16 h. The reaction was filtered, concentrated under reduced pressure and the crude residue was purified by MS-directed reverse phase preparative-HPLC (C-18 stationary phase, eluting with a H₂O/MeCN gradient with 0.1% TFA) to yield 1-benzyl-3-[7-chloro-3-(2-methylpyridin-4-yl)-1H-pyrazolo[4,3-c]pyridin-6-yl]urea as a white solid (5.6 mg, 0.014 mmol, 20%)

MS ESI calc'd. for $C_{20}H_{18}ClN_6O$ [M+H]⁺ 393, found 393. ¹H NMR (500 MHz, DMSO-d₆) δ 9.35 (s, 1H), 8.75 (d, J=4.0 Hz, 1H), 8.63 (s, 1H), 8.37 (s, 1H), 8.28 (d, J=4.0 Hz, 1H), 7.38-7.22 (m, 5H), 4.42 (d, J=6.1 Hz, 2H), 2.73 (s, 3H).

EXAMPLE 94

6-[(benzylcarbamothioyl)amino]-3-(2-methylpyridin-4-yl)-1H-pyrazolo[4,3-c]pyridin-5-ium trifluoroacetate

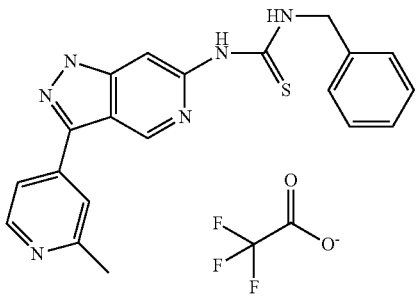 [SMILES: Cc1cc(-c2n[nH]c3cc(NC(=S)NCc4ccccc4)ncc23)ccn1 ; O=C([O-])C(F)(F)F]

A suspension of 3-(2-methylpyridin-4-yl)-1-trityl-1H-pyrazolo[4,3-c]pyridin-6-amine (intermediate 5a; 25 mg, 0.05 mmol) in toluene (1 mL) was treated with (isothiocyanatomethyl)benzene (15 mg, 0.1 mmol) and the mixture was heated at 100° C. overnight. The volatiles were concentrated in vacuo and the residue was directly dissolved in DCM (0.8 mL), treated with TFA (0.2 mL) and triethylsilane (0.008 mL, 0.051 mmol) and left under stirring for 5 h, then concentrated in vacuo and purified by MS-directed reverse phase preparative-HPLC (C-18 stationary phase, eluting with a H₂O/MeCN gradient with 0.1% TFA) to yield 6-[(benzylcarbamothioyl)amino]-3-(2-methylpyridin-4-yl)-1H-pyrazolo[4,3-c]pyridin-5-ium trifluoroacetate as a yellow solid (7 mg, 0.014 mmol, 27%). MS ESI calc'd. for $C_{20}H_{19}N_6S$ [M+1]⁺ 375, found 375.

¹H NMR (600 MHz, DMSO-d₆) δ 11.95 (br s, 1H), 10.77 (s, 1H), 9.35 (s, 1H), 8.69 (d, J=5.0 Hz, 1H), 8.27 (s, 1H), 8.18 (br s, 1H), 7.55-7.24 (m, 5H), 7.14-7.10 (m, 1H), 4.92 (d, J=5.3 Hz, 2H), 2.67 (s, 3H).

EXAMPLE 95

1-[7-fluoro-3-(2-methylpyridin-4-yl)-1H-pyrazolo[4,3-c]pyridin-6-yl]-3-[(1R)-1-phenylethyl]urea

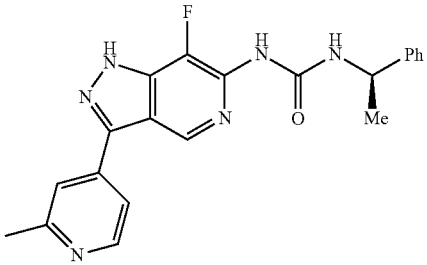 [SMILES: Cc1cc(-c2n[nH]c3c(F)c(NC(=O)N[C@H](C)c4ccccc4)ncc23)ccn1]

Step 1

A vial was charged with 3-(2-methylpyridin-4-yl)-1-trityl-1H-pyrazolo[4,3-c]pyridin-6-amine (intermediate 5a, 50 mg, 0.107 mmol) and xenon difluoride (23 mg, 0.139 mmol). The reaction was put under an atmosphere of argon and THF (1 mL) was injected. The reaction was stirred at room temperature for 16 h. The resulting solution was diluted with EtOAc (5 mL) and 50% NaHCO₃ (3 mL). The organic phase was separated, dried (MgSO₄), filtered and concentrated in vacuo. The residue was purified by column chromatography on silica gel (DCM/EtOAc, 20-100%) to yield a solid (20 mg, 0.041 mmol, 39%).

MS ESI calc'd. for $C_{31}H_{25}FN_5$ [M+H]⁺486, found 486. ¹H NMR (500 MHz, CDCl₃) δ 8.71 (s, 1H), 8.53 (d, J=5.1 Hz, 1H), 7.55 (s, 1H), 7.50 (d, J=5.1 Hz, 1H), 7.37-7.17 (m, 15H), 4.35 (s, 2H), 2.58 (s, 3H). ¹⁹F NMR (500 MHz, CDCl₃) δ-151.5

Step 2

A flask was charged with the mono-TFA salt of 7-fluoro-3-(2-methylpyridin-4-yl)-1-trityl-1H-pyrazolo[4,3-c]pyridin-6-amine (30.0 mg, 0.050 mmol), 1,1'-carbonyldiimidazole (48.7 mg, 0.30 mmol) and imidazole (17.0 mg, 0.25 mmol). The flask was put under an atmosphere of argon and 1,2-dichloroethane was injected (1 mL). The mixture was stirred 3 h at room temperature, warmed to 40° C. for 16 h, allowed to cool to room temperature and treated with (R)-methyl-benzylamine (0.1 mL). The reaction was stirred for 2 hours at room temperature and then diluted with 50% NaHCO₃ (3 mL) and EtOAc (5 mL). The organic phase was separated, dried (MgSO₄), filtered and concentrated in vacuo. The resulting residue was dissolved in a mixture of DCM, TFA and triethylsilane (3:2:0.1 mL). After 2 h the reaction was filtered, concentrated under reduced pressure and the crude residue was purified by MS-directed reverse phase preparative-HPLC (C-18 stationary phase, eluting with a H₂O/MeCN gradient with 0.1% TFA) to yield 1-[7-fluoro-3-(2-methylpyridin-4-yl)-1H-pyrazolo[4,3-c]pyridin-6-yl]-3-[(1R)-1-phenylethyl]urea as a white solid (9 mg, 0.019 mmol, 37%).

MS ESI calc'd. for $C_{21}H_{20}FN_6O$ [M+H]⁺391, found 391. ¹H NMR (500 MHz, MeOH-d₄) δ 9.21 (s, 1H), 8.72 (d, J=6.3, 1H), 8.56 (s, 1H), 8.50 (dd, J=1.4, 6.1, 1H), 7.42-7.22 (m, 5H), 5.06 (dd, J=6.9, 13.9, 1H), 2.88 (s, 3H), 1.57 (d, J=6.8, 3H). ¹⁹F NMR (500 MHz, dr MeOH) δ −156.4.

Table 1 below provides data for the compounds of the Examples above, and provides additional examples. The compounds in Table 1 were prepared following procedures similar to those in the indicated Example in the "Route Used" column. No example number in the "Route Used" column means that the preparation is described in the written examples above. The compounds of Examples 1, 15, 16, 19-69, 71-85, 87-91, and 93-95 were obtained as the trifluoroacetic acid salt of the compound.

TABLE 1

| Example | Structure and IUPAC Name | Exact Mass [M + H]+ | Route Used |
|---|---|---|---|
| 1 | 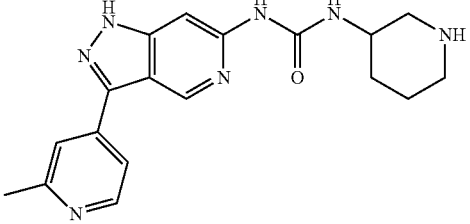<br>1-[3-(2-methylpridin-4-yl)-1H-pyrazolo[4,3-c]pyridin-6-yl]-3-piperidin-3-ylurea | Calc'd 352, found 352 | — |
| 2 | 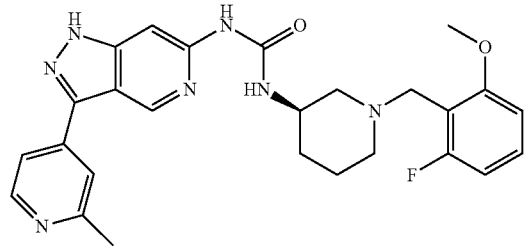 [SMILES: COc1cccc(F)c1CN1CCC[C@@H](NC(=O)Nc2cc3[nH]nc(-c4ccnc(C)c4)c3cn2)C1]<br>1-[(3R)-1-(2-fluoro-6-methoxybenzyl)-piperidin-3-yl]-3-[3-(2-methylpyridin-4-yl)-1H-pyrazolo[4,3-c]pyridin-6-yl]urea | Calc'd 490, found 490 | 1 |
| 3 | 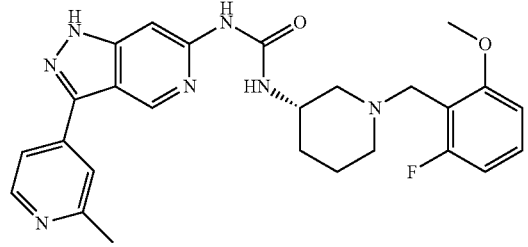 [SMILES: COc1cccc(F)c1CN1CCC[C@H](NC(=O)Nc2cc3[nH]nc(-c4ccnc(C)c4)c3cn2)C1]<br>1-[(3S)-1-(2-fluoro-6-methoxybenzyl)-piperidin-3-yl]-3-[3-(2-methylpyridin-4-yl)-1H-pyrazolo[4,3-c]pyridin-6-yl]urea | Calc'd 490, found 490 | 1 |
| 4 | 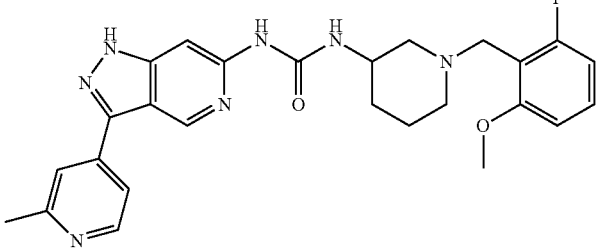<br>1-[1-(2-fluoro-6-methoxybenzyl)-piperidin-3-yl]-3-[3-(2-methylpyridin-4-yl)-1H-pyrazolo[4,3-c]pyridin-6-yl]urea | Calc'd 490, found 490 | 1 |

TABLE 1-continued

| Example | Structure and IUPAC Name | Exact Mass [M + H]+ | Route Used |
|---|---|---|---|
| 5 | 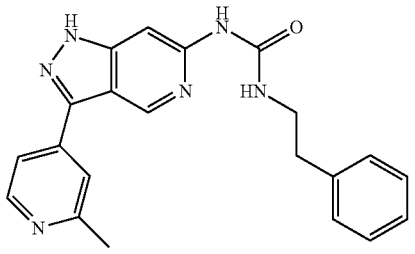 [SMILES: Cc1cc(-c2n[nH]c3cc(NC(=O)NCCc4ccccc4)ncc23)ccn1]<br>1-[3-(2-methylpyridin-4-yl)-1H-pyrazolo[4,3-c]pyridin-6-yl]-3-(2-phenylethyl)urea | Calc'd 373, found 373 | 11 |
| 6 | 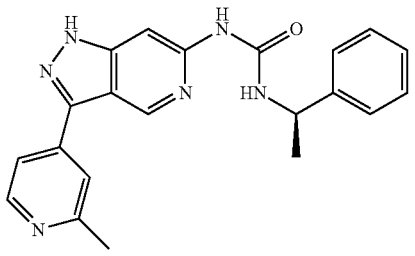 [SMILES: Cc1cc(-c2n[nH]c3cc(NC(=O)N[C@H](C)c4ccccc4)ncc23)ccn1]<br>1-[3-(2-methylpyridin-4-yl)-1H-pyrazolo[4,3-c]pyridin-6-yl]-3-[(1R)-1-phenylethyl]urea | Calc'd 373, found 373 | 11 |
| 7 | 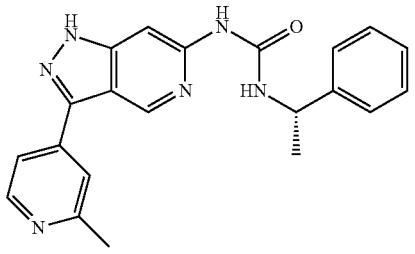 [SMILES: Cc1cc(-c2n[nH]c3cc(NC(=O)N[C@@H](C)c4ccccc4)ncc23)ccn1]<br>1-[3-(2-methylpyridin-4-yl)-1H-pyrazolo[4,3-c]pyridin-6-yl]-3-[(1S)-1-phenylethyl]urea | Calc'd 373, found 373 | 11 |
| 8 | 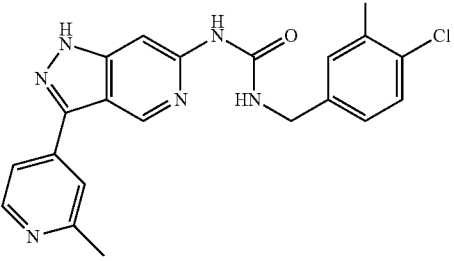<br>1-(3,4-dichlorobenzyl)-3-[3-(2-methylpyridin-4-yl)-1H-pyrazolo[4,3-c]pyridin-6-yl]urea | Calc'd 427, found 427 | 11 |
| 9 | 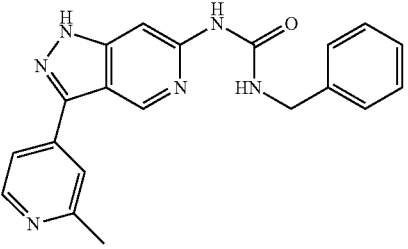<br>1-benzyl-3-[3-(2-methylpyridin-4-yl)-1H-pyrazolo[4,3-c]pyridin-6-yl]urea | Calc'd 359, found 359 | 11 |

TABLE 1-continued

| Example | Structure and IUPAC Name | Exact Mass [M + H]+ | Route Used |
|---|---|---|---|
| 10 | 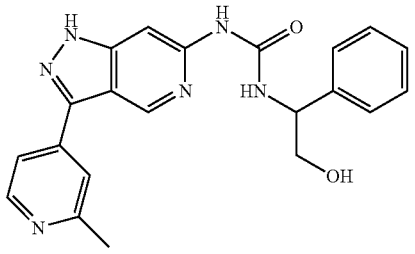 [SMILES: Cc1cc(-c2n[nH]c3cc(NC(=O)NC(CO)c4ccccc4)ncc23)ccn1]<br>1-(2-hydroxy-1-phenylethyl)-3-[3-(2-methylpyridin-4-yl)-1H-pyrazolo[4,3-c]pyridin-6-yl]urea | Calc'd 389, found 389 | 1 |
| 11 | 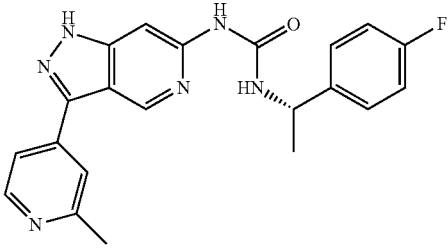 [SMILES: Cc1cc(-c2n[nH]c3cc(NC(=O)N[C@@H](C)c4ccc(F)cc4)ncc23)ccn1]<br>1-[(1S)-1-(4-fluorophenyl)ethyl]-3-[3-(2-methylpyridin-4-yl)-1H-pyrazolo[4,3-c]pyridin-6-yl]urea | Calc'd 391, found 391 | — |
| 12 | 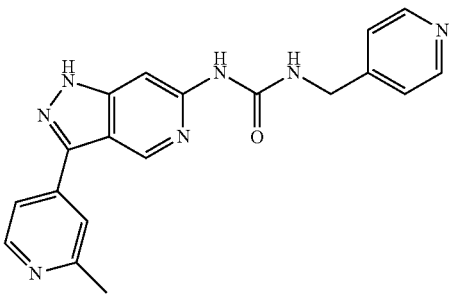 [SMILES: Cc1cc(-c2n[nH]c3cc(NC(=O)NCc4ccncc4)ncc23)ccn1]<br>1-[3-(2-methylpyridin-4-yl)-1H-pyrazolo[4,3-c]pyridin-6-yl]-3-(pyridin-4-ylmethyl)urea | Calc'd 360, found 360 | — |
| 13 | 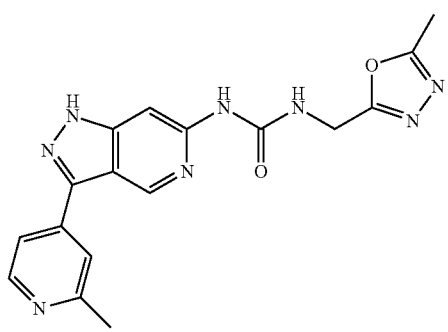 [SMILES: Cc1cc(-c2n[nH]c3cc(NC(=O)NCc4nnc(C)o4)ncc23)ccn1]<br>1-[(5-methyl-1,3,4-oxadiazol-2-yl)methyl]-3-[3-(2-methylpyridin-4-yl)-1H-pyrazolo[4,3 | Calc'd 365, found 365 | 12 |

TABLE 1-continued

| Example | Structure and IUPAC Name | Exact Mass [M + H]+ | Route Used |
|---|---|---|---|
| 14 | 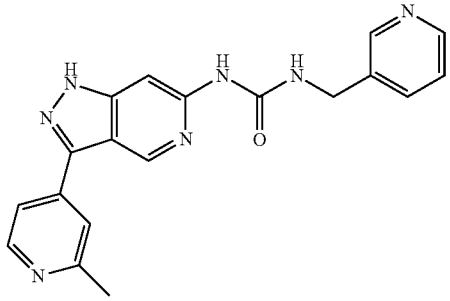 [SMILES: Cc1cc(-c2n[nH]c3cc(NC(=O)NCc4cccnc4)ncc23)ccn1]<br>1-[3-(2-methylpyridin-4-yl)-1H-pyrazolo[4,3-c]pyridin-6-yl]-3-(pyridin-3-ylmethyl)urea | Calc'd 360, found 360 | 12 |
| 15 | 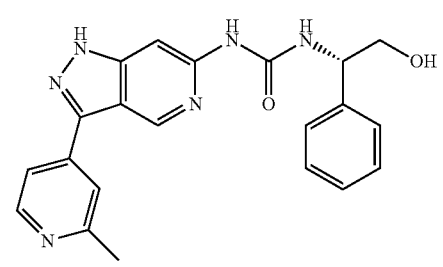 [SMILES: Cc1cc(-c2n[nH]c3cc(NC(=O)N[C@H](CO)c4ccccc4)ncc23)ccn1]<br>1-[(1S)-2-hydroxy-1-phenylethyl]-3-[3-(2-methylpyridin-4-yl)-1H-pyrazolo[4,3-c]pyridin-6-yl]urea | Calc'd 389, found 389 | 12 |
| 16 | 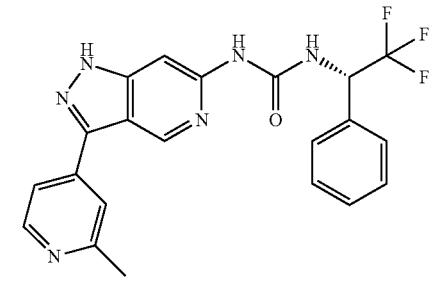 [SMILES: Cc1cc(-c2n[nH]c3cc(NC(=O)N[C@@H](c4ccccc4)C(F)(F)F)ncc23)ccn1]<br>1-[3-(2-methylpyridin-4-yl)-1H-pyrazolo[4,3-c]pyridin-6-yl]-3-[(1S)-2,2,2-trifluoro-1-phenylethyl]urea | Calc'd 427, found 427 | 12 |
| 17 | 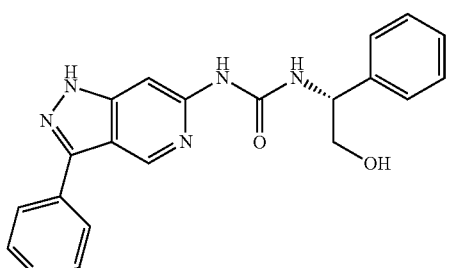<br>1-[(1R)-2-hydroxy-1-phenylethyl]-3-[3-(2-methylpyridin-4-yl)-1H-pyrazolo[4,3-c]pyridin-6-yl]urea | Calc'd 389, found 389 | 12 |

TABLE 1-continued

| Example | Structure and IUPAC Name | Exact Mass [M + H]+ | Route Used |
|---|---|---|---|
| 18 | 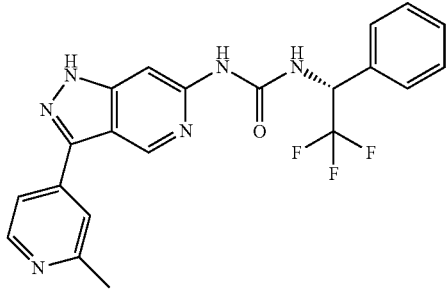 [SMILES: Cc1cc(-c2n[nH]c3cc(NC(=O)N[C@H](c4ccccc4)C(F)(F)F)ncc23)ccn1]<br>1-[3-(2-methylpyridin-4-yl)-1H-pyrazolo[4,3-c]pyridin-6-yl]-3-[(1R)-2,2,2-trifluoro-1-phenylethyl]urea | Calc'd 427, found 427 | 12 |
| 19 | 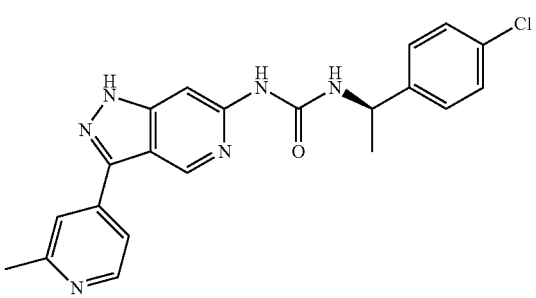 [SMILES: Cc1cc(-c2n[nH]c3cc(NC(=O)N[C@H](C)c4ccc(Cl)cc4)ncc23)ccn1]<br>1-[(1R)-1-(4-chlorophenyl)ethyl]-3-[3-(2-methylpyridin-4-yl)-1H-pyrazolo[4,3-c]pyridin-6-yl]urea | Calc'd 407, found 407 | 11 |
| 20 | 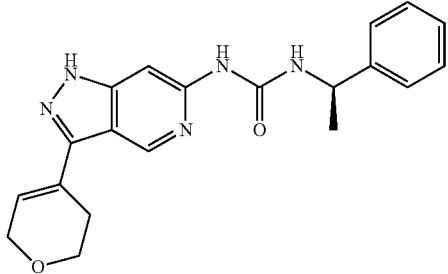 [SMILES: C[C@@H](NC(=O)Nc1cc2[nH]nc(C3=CCOCC3)c2cn1)c1ccccc1]<br>1-[3-(3,6-dihydro-2H-pyran-4-yl)-1H-pyrazolo[4,3-c]pyridin-6-yl]-3-[(1R)-1-phenylethyl]urea | Calc'd 364, found 364 | 30 |
| 21 | 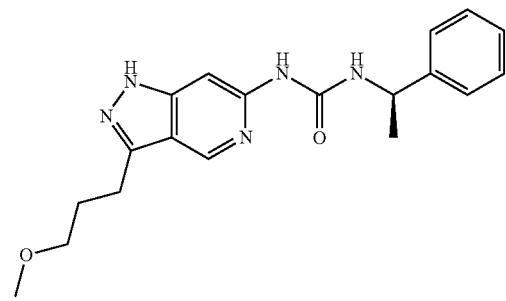 [SMILES: COCCCc1n[nH]c2cc(NC(=O)N[C@H](C)c3ccccc3)ncc12]<br>1-[3-(3-methoxypropyl)-1H-pyrazolo[4,3-c]pyridin-6-yl]-3-[(1R)-1-phenylethyl]urea | Calc'd 354, found 354 | — |

TABLE 1-continued

| Example | Structure and IUPAC Name | Exact Mass [M + H]+ | Route Used |
|---|---|---|---|
| 22 | 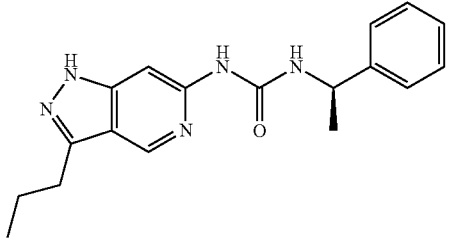 [SMILES: CCCc1n[nH]c2cc(NC(=O)N[C@H](C)c3ccccc3)ncc12]<br>1-[(1R)-1-phenylethyl]-3-(3-propyl-1H-pyrazolo[4,3-c]pyridin-6-yl)urea | Calc'd 324, found 324 | — |
| 23 | 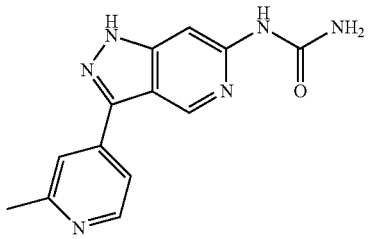 [SMILES: Cc1cc(-c2n[nH]c3cc(NC(N)=O)ncc23)ccn1]<br>1-[3-(2-methylpyridin-4-yl)-1H-pyrazolo[4,3-c]pyridin-6-yl]urea | Calc'd 269, found 269 | — |
| 24 | 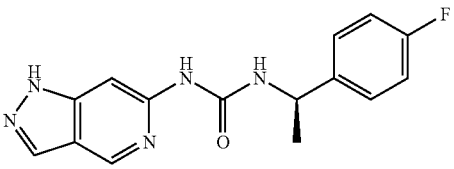 [SMILES: C[C@@H](NC(=O)Nc1cc2[nH]ncc2cn1)c1ccc(F)cc1]<br>1-[(1R)-1-(4-fluorophenyl)ethyl]-3-(1H-pyrazolo[4,3-c]pyridin-6-yl)urea | Calc'd 300, found 300 | — |
| 25 | 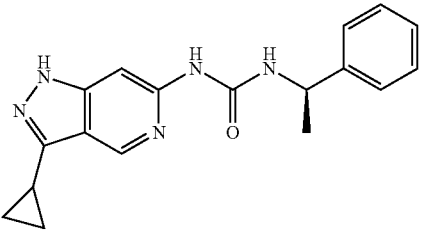 [SMILES: C[C@@H](NC(=O)Nc1cc2[nH]nc(C3CC3)c2cn1)c1ccccc1]<br>1-(3-cyclopropyl-1H-pyrazolo[4,3-c]pyridin-6-yl)-3-[(1R)-1-phenylethyl]urea | Calc'd 322, found 322 | 30 |
| 26 | 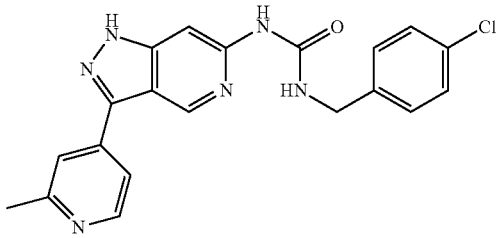 [SMILES: Cc1cc(-c2n[nH]c3cc(NC(=O)NCc4ccc(Cl)cc4)ncc23)ccn1]<br>1-(4-chlorobenzyl)-3-[3-(2-methylpyridin-4-yl)-1H-pyrazolo[4,3-c]pyridin-6-yl]urea | Calc'd 393, found 393 | 11 |

TABLE 1-continued

| Example | Structure and IUPAC Name | Exact Mass [M + H]+ | Route Used |
|---|---|---|---|
| 27 | 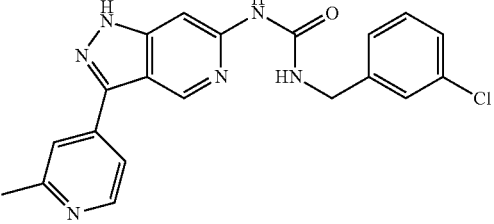<br>1-(3-chlorobenzyl)-3-[3-(2-methylpyridin-4-yl)-1H-pyrazolo[4,3-c]pyridin-6-yl]urea | Calc'd 393, found 393 | 12 |
| 28 | 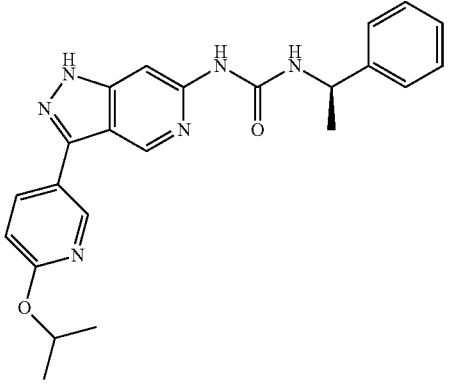 [SMILES: CC(C)Oc1ccc(-c2n[nH]c3cc(NC(=O)N[C@H](C)c4ccccc4)ncc23)cn1]<br>1-{3-[6-(1-methylethoxy)pyridin-3-yl]-1H-pyrazolo[4,3-c]pyridin-6-yl}-3-[(1R)-1-phenylethyl]urea | Calc'd 417, found 417 | 30 |
| 29 | 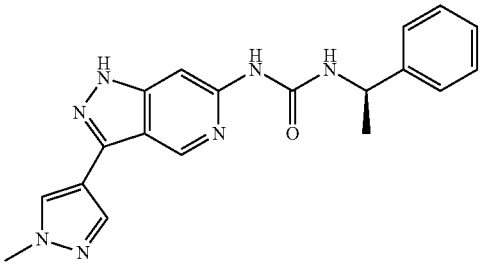 [SMILES: C[C@@H](NC(=O)Nc1cc2[nH]nc(-c3cnn(C)c3)c2cn1)c1ccccc1]<br>1-[3-(1-methyl-1H-pyrazol-4-yl)-1H-pyrazolo[4,3-c]pyridin-6-yl]-3-[(1R)-1-phenylethyl]urea | Calc'd 362, found 362 | 30 |
| 30 | 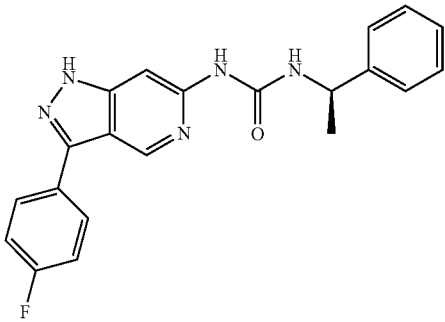 [SMILES: C[C@@H](NC(=O)Nc1cc2[nH]nc(-c3ccc(F)cc3)c2cn1)c1ccccc1]<br>1-[3-(4-fluorophenyl)-1H-pyrazolo[4,3-c]pyridin-6-yl]-3-[(1R)-1-phenylethyl]urea | Calc'd 376, found 376 | — |

TABLE 1-continued

| Example | Structure and IUPAC Name | Exact Mass [M + H]+ | Route Used |
|---|---|---|---|
| 31 | 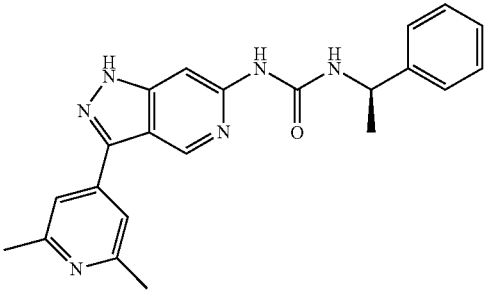 [SMILES: Cc1cc(-c2n[nH]c3cc(NC(=O)N[C@H](C)c4ccccc4)ncc23)cc(C)n1]<br>1-[3-(2,6-dimethylpyridin-4-yl)-1H-pyrazolo[4,3-c]pyridin-6-yl]-3-[(1R)-1-phenylethyl]urea | Calc'd 387, found 387 | 30 |
| 32 | 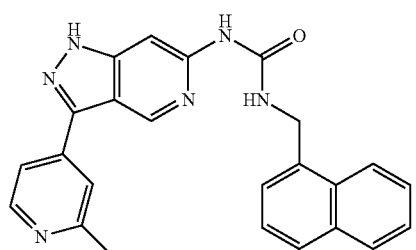<br>1-[3-(2-methylpyridin-4-yl)-1H-pyrazolo[4,3-c]pyridin-6-yl]-3-(naphthalen-1-ylmethyl)urea | Calc'd 409, found 409 | 12 |
| 33 | 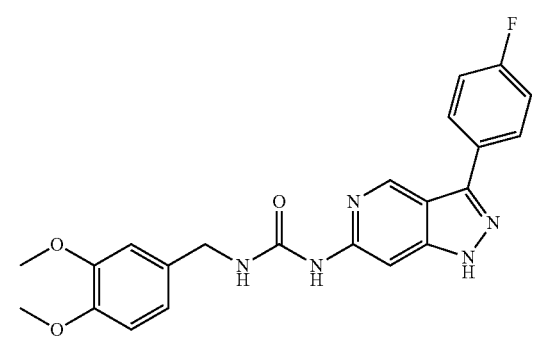 [SMILES: COc1ccc(CNC(=O)Nc2cc3[nH]nc(-c4ccc(F)cc4)c3cn2)cc1OC]<br>1-(3,4-dimethoxybenzyl)-3-[3-(4-fluorophenyl)-1H-pyrazolo[4,3-c]pyridin-6-yl]urea | Calc'd 422, found 422 | — |
| 34 | 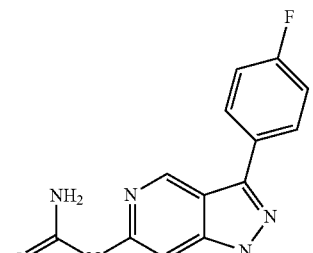<br>1-[3-(4-fluorophenyl)-1H-pyrazolo[4,3-c]pyridin-6-yl]urea | Calc'd 272, found 272 | — |

TABLE 1-continued

| Example | Structure and IUPAC Name | Exact Mass [M + H]+ | Route Used |
|---|---|---|---|
| 35 | 1-(cyclopropylmethyl)-3-[3-(2-methylpyridin-4-yl)-1H-pyrazolo[4,3-c]pyridin-6-yl]urea | Calc'd 323, found 323 | 12 |
| 36 | 1-tert-butyl-3-[3-(2-methylpyridin-4-yl)-1H-pyrazolo[4,3-c]pyridin-6-yl]urea | Calc'd 325, found 325 | 12 |
| 37 | hydroxycyclopropyl)methyl]-3-[3-(2-methylpyridin-4-yl)-1H-pyrazolo[4,3-c]pyridin-6-yl]urea | Calc'd 339, found 339 | 12 |

TABLE 1-continued

| Example | Structure and IUPAC Name | Exact Mass [M + H]+ | Route Used |
|---|---|---|---|
| 38 | 1-(cyclopropylidenemethyl)-3-[3-(2-methylpyridin-4-yl)-1H-pyrazolo[4,3-c]pyridin-6-yl]urea | Calc'd 321, found 321 | 12 |
| 39 | 1-azetidin-3-yl-3-[3-(2-methylpyridin-4-yl)-1H-pyrazolo[4,3-c]pyridin-6-yl]urea | Calc'd 324, found 324 | 12 |
| 40 | 1-(2-methoxyethyl)-3-[3-(2-methylpyridin-4-yl)-1H-pyrazolo[4,3-c]pyridin-6-yl]urea | Calc'd 327, found 327 | 12 |

TABLE 1-continued
| Example | Structure and IUPAC Name | Exact Mass [M + H]+ | Route Used |
|---|---|---|---|
| 41 | 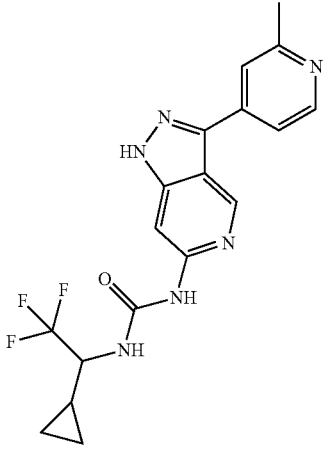 [SMILES: Cc1cc(-c2n[nH]c3cc(NC(=O)NC(C4CC4)C(F)(F)F)ncc23)ccn1]<br>1-(1-cyclopropyl-2,2,2-trifluoroethyl)-3-[3-(2-methylpyridin-4-yl)-1H-pyrazolo[4,3-c]pyridin-6-yl]urea | Calc'd 391, found 391 | 12 |
| 42 | <br>1-[(1-methyl-1H-imidazol-5-yl)methyl]-3-[3-(2-methylpyridin-4-yl)-1H-pyrazolo[4,3-c]pyridin-6-yl]urea | Calc'd 363, found 363 | 12 |
| 43 | 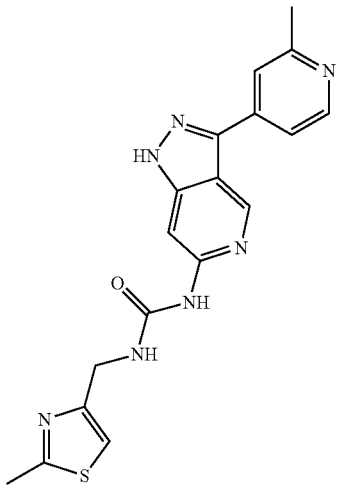 [SMILES: Cc1cc(-c2n[nH]c3cc(NC(=O)NCc4csc(C)n4)ncc23)ccn1]<br>1-[3-(2-methylpyridin-4-yl)-1H-pyrazolo[4,3-c]pyridin-6-yl]-3-[(2-methyl-1,3-thiazol-4-yl)methyl]urea | Calc'd 380, found 380 | 12 |

US 9,023,865 B2
TABLE 1-continued
| Example | Structure and IUPAC Name | Exact Mass [M + H]+ | Route Used |
|---------|--------------------------|---------------------|------------|
| 44 | 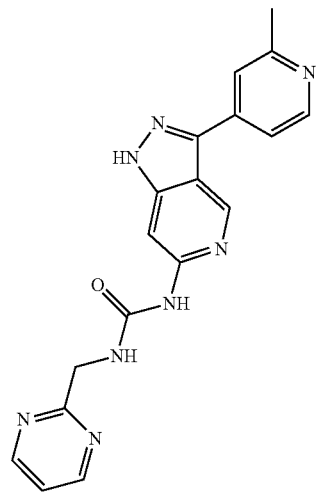 [SMILES: Cc1cc(-c2n[nH]c3cc(NC(=O)NCc4ncccn4)ncc23)ccn1]<br>1-[3-(2-methylpyridin-4-yl)-1H-pyrazolo[4,3-c]pyridin-6-yl]-3-(pyrimidin-2-ylmethyl)urea | Calc'd 361, found 361 | 12 |
| 45 | 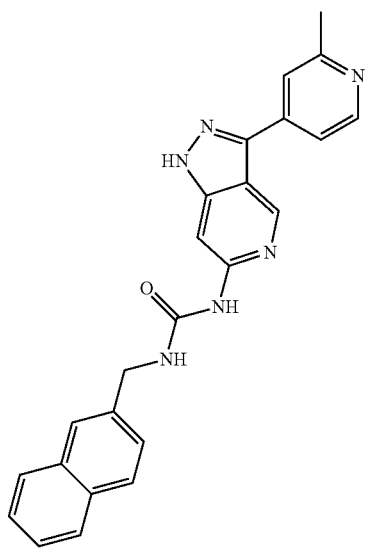 [SMILES: Cc1cc(-c2n[nH]c3cc(NC(=O)NCc4ccc5ccccc5c4)ncc23)ccn1]<br>1-[3-(2-methylpyridin-4-yl)-1H-pyrazolo[4,3-c]pyridin-6-yl]-3-(naphthalen-2-ylmethyl)urea | Calc'd 409, found 409 | 12 |

TABLE 1-continued
| Example | Structure and IUPAC Name | Exact Mass [M + H]+ | Route Used |
|---|---|---|---|
| 46 | 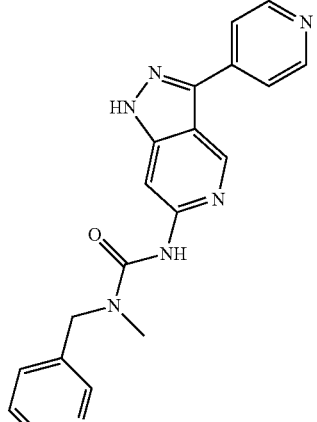<br>1-methyl-3-[3-(2-methylpyridin-4-yl)-1H-pyrazolo[4,3-c]pyridin-6-yl]-1-(pyridin-3-ylmethyl)urea | Calc'd 374, found 374 | 12 |
| 47 | 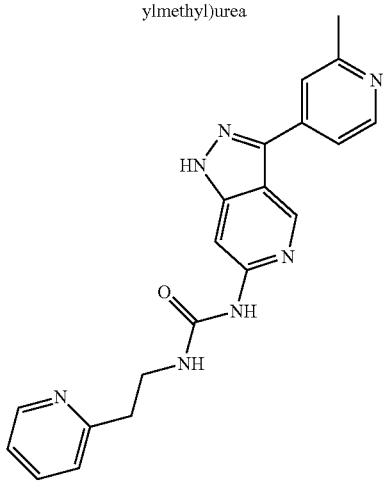<br>1-[3-(2-methylpyridin-4-yl)-1H-pyrazolo[4,3-c]pyridin-6-yl]-3-(2-pyridin-2-ylethyl)urea | Calc'd 374, found 374 | 12 |
| 48 | 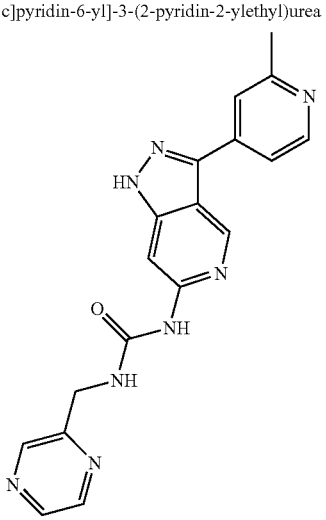<br>1-[3-(2-methylpyridin-4-yl)-1H-pyrazolo[4,3-c]pyridin-6-yl]-3-(pyrazin-2-ylmethyl)urea | Calc'd 361, found 361 | 12 |

TABLE 1-continued
| Example | Structure and IUPAC Name | Exact Mass [M + H]+ | Route Used |
|---|---|---|---|
| 49 | 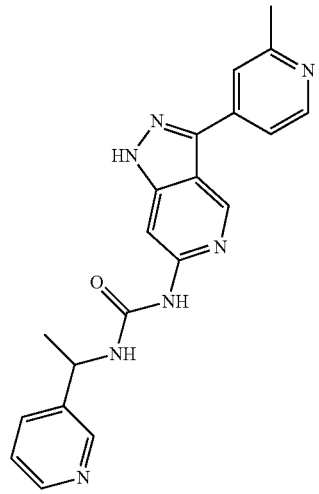 [SMILES: Cc1cc(-c2n[nH]c3cc(NC(=O)NC(C)c4cccnc4)ncc23)ccn1]<br>1-[3-(2-methylpyridin-4-yl)-1H-pyrazolo[4,3-c]pyridin-6-yl]-3-(1-pyridin-3-ylethyl)urea | Calc'd 374, found 374 | 12 |
| 50 | 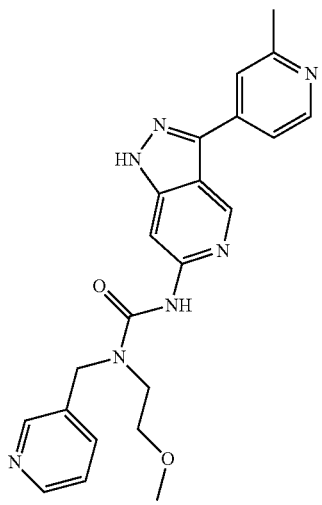 [SMILES: COCCN(Cc1cccnc1)C(=O)Nc1cc2[nH]nc(-c3ccnc(C)c3)c2cn1]<br>1-(2-methoxyethyl)-3-[3-(2-methylpyridin-4-yl)-1H-pyrazolo[4,3-c]pyridin-6-yl]-1-(pyridin-3-ylmethyl)urea | Calc'd 418, found 418 | 12 |

TABLE 1-continued
| Example | Structure and IUPAC Name | Exact Mass [M + H]+ | Route Used |
|---|---|---|---|
| 51 | 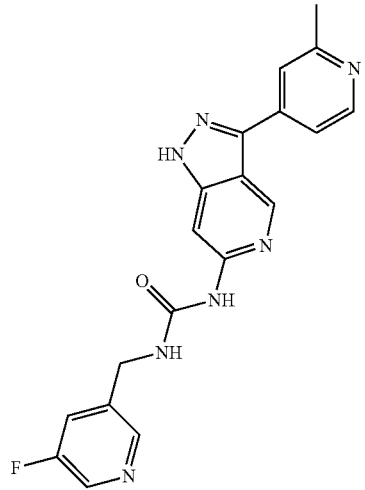 [SMILES: Cc1cc(-c2n[nH]c3cc(NC(=O)NCc4cncc(F)c4)ncc23)ccn1]<br>1-[(5-fluoropyridin-3-yl)methyl]-3-[3-(2-methylpyridin-4-yl)-1H-pyrazolo[4,3-c]pyridin-6-yl]urea | Calc'd 378, found 378 | 12 |
| 52 | 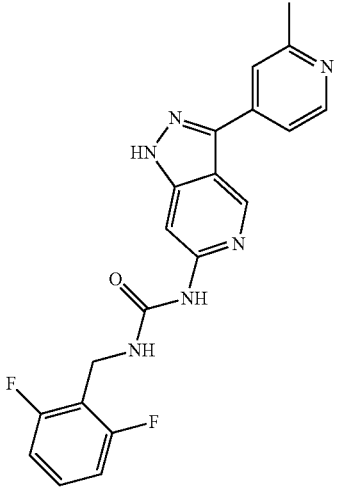 [SMILES: Cc1cc(-c2n[nH]c3cc(NC(=O)NCc4c(F)cccc4F)ncc23)ccn1]<br>1-(2,6-difluorobenzyl)-3-[3-(2-methylpyridin-4-yl)-1H-pyrazolo[4,3-c]pyridin-6-yl]urea | Calc'd 395, found 395 | 12 |
| 53 | 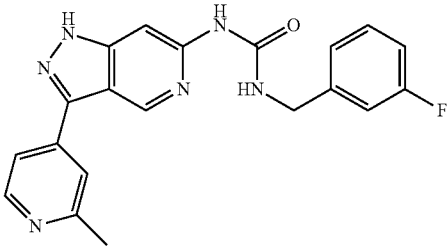 [SMILES: Cc1cc(-c2n[nH]c3cc(NC(=O)NCc4cccc(F)c4)ncc23)ccn1]<br>1-(3-fluorobenzyl)-3-[3-(2-methylpyridin-4-yl)-1H-pyrazolo[4,3-c]pyridin-6-yl]urea | Calc'd 377, found 377 | 11 |

TABLE 1-continued

| Example | Structure and IUPAC Name | Exact Mass [M + H]+ | Route Used |
|---|---|---|---|
| 54 | 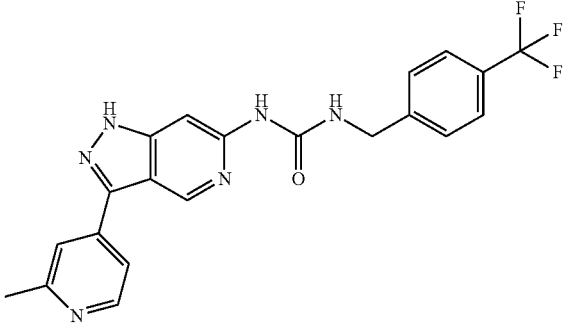 [SMILES: Cc1cc(-c2n[nH]c3cc(NC(=O)NCc4ccc(C(F)(F)F)cc4)ncc23)ccn1]<br>1-[3-(2-methylpyridin-4-yl)-1H-pyrazolo[4,3-c]pyridin-6-yl]-3-[4-(trifluoromethyl)-benzyl]urea | Calc'd 427, found 427 | 11 |
| 55 | 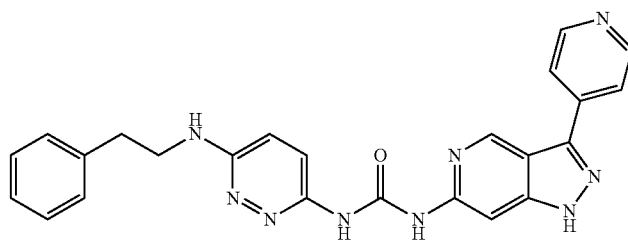<br>1-[3-(2-methylpyridin-4-yl)-1H-pyrazolo[4,3-c]pyridin-6-yl]-3-{6-[(2-phenylethyl)-amino]pyridazin-3-yl}urea | Calc'd 466 found 466 | — |
| 56 | 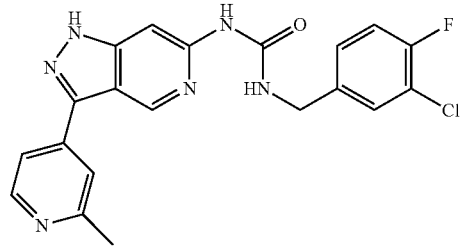 [SMILES: Cc1cc(-c2n[nH]c3cc(NC(=O)NCc4ccc(F)c(Cl)c4)ncc23)ccn1]<br>1-(3-chloro-4-fluorobenzyl)-3-[3-(2-methylpyridin-4-yl)-1H-pyrazolo[4,3-c]pyridin-6-yl]urea | Calc'd 411, found 411 | 30 |
| 57 | 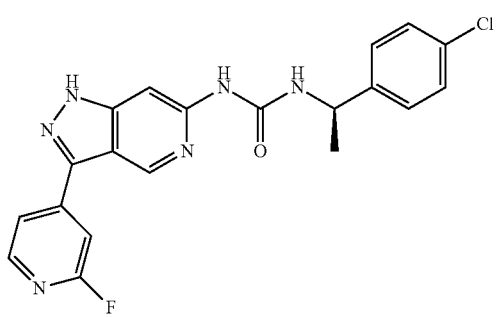 [SMILES: C[C@@H](NC(=O)Nc1cc2[nH]nc(-c3ccnc(F)c3)c2cn1)c1ccc(Cl)cc1]<br>1-[(1R)-1-(4-chlorophenyl)ethyl]-3-[3-(2-fluoropyridin-4-yl)-1H-pyrazolo[4,3-c]pyridin-6-yl]urea | Calc'd 411, found 411 | 30 |

TABLE 1-continued

| Example | Structure and IUPAC Name | Exact Mass [M + H]+ | Route Used |
|---|---|---|---|
| 58 | 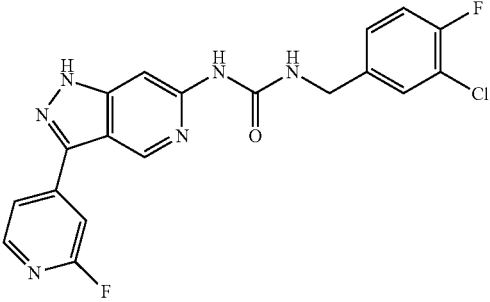 [SMILES: O=C(NCc1ccc(F)c(Cl)c1)Nc1cc2[nH]nc(-c3ccnc(F)c3)c2cn1]<br>1-(3-chloro-4-fluorobenzyl)-3-[3-(2-fluoropyridin-4-yl)-1H-pyrazolo[4,3-c]pyridin-6-yl]urea | Calc'd 415, found 415 | 30 |
| 59 | 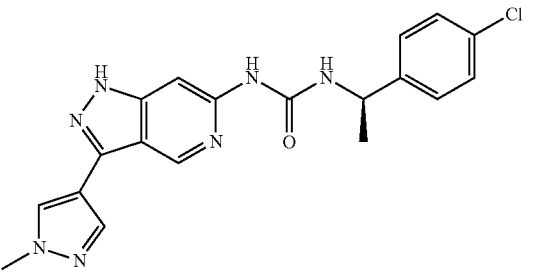 [SMILES: C[C@@H](NC(=O)Nc1cc2[nH]nc(-c3cnn(C)c3)c2cn1)c1ccc(Cl)cc1]<br>1-[(1R)-1-(4-chlorophenyl)ethyl]-3-[3-(1-methyl-1H-pyrazol-4-yl)-1H-pyrazolo[4,3-c]pyridin-6-yl]urea | Calc'd 396, found 396 | 30 |
| 60 | 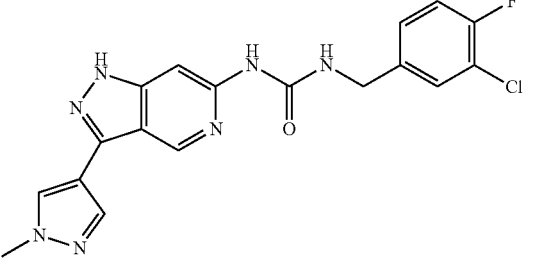<br>1-(3-chloro-4-fluorobenzyl)-3-[3-(1-methyl-1H-pyrazol-4-yl)-1H-pyrazolo[4,3-c]pyridin-6-yl]urea | Calc'd 400, found 400 | 30 |
| 61 | 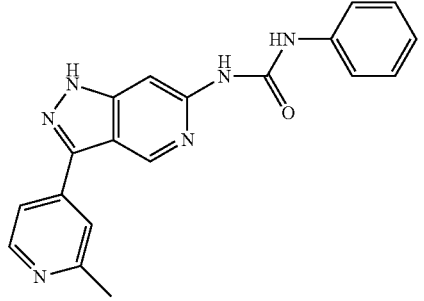 [SMILES: Cc1cc(-c2n[nH]c3cc(NC(=O)Nc4ccccc4)ncc23)ccn1]<br>1-[3-(2-methylpyridin-4-yl)-1H-pyrazolo[4,3-c]pyridin-6-yl]-3-phenylurea | Calc'd 345, found 345 | 30 |

TABLE 1-continued
| Example | Structure and IUPAC Name | Exact Mass [M + H]+ | Route Used |
|---|---|---|---|
| 62 | 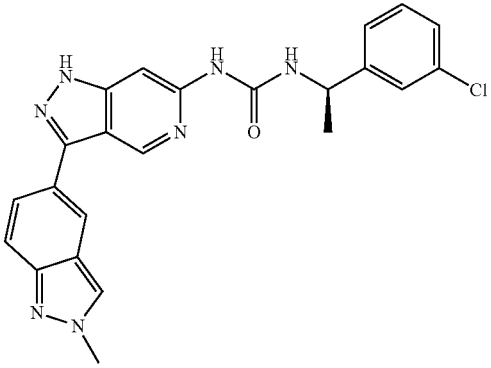 [SMILES: C[C@@H](NC(=O)Nc1cc2[nH]nc(-c3ccc4nn(C)cc4c3)c2cn1)c1cccc(Cl)c1]<br>1-[(1R)-1-(3-chlorophenyl)ethyl]-3-[3-(2-methyl-2H-indazol-5-yl)-1H-pyrazolo[4,3-c]pyridin-6-yl]urea | Calc'd 446, found 446 | 30 |
| 63 | 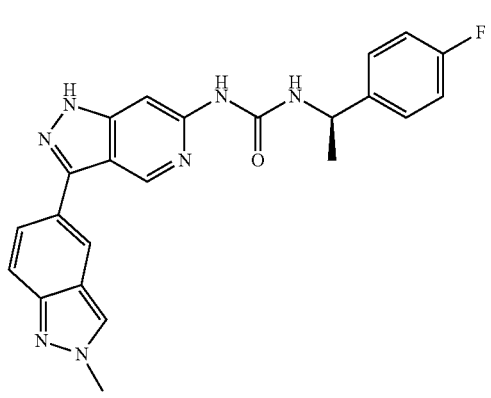 [SMILES: C[C@@H](NC(=O)Nc1cc2[nH]nc(-c3ccc4nn(C)cc4c3)c2cn1)c1ccc(F)cc1]<br>1-[(1R)-1-(4-fluorophenyl)ethyl]-3-[3-(2-methyl-2H-indazol-5-yl)-1H-pyrazolo[4,3-c]pyridin-6-yl]urea | Calc'd 430, found 430 | 30 |
| 64 | 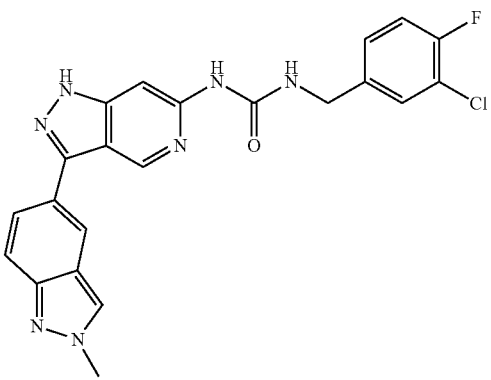 [SMILES: Cn1cc2cc(-c3n[nH]c4cc(NC(=O)NCc5ccc(F)c(Cl)c5)ncc34)ccc2n1]<br>1-(3-chloro-4-fluorobenzyl)-3-[3-(2-methyl-2H-indazol-5-yl)-1H-pyrazolo[4,3-c]pyridin-6-yl]urea | Calc'd 450, found 450 | 30 |

TABLE 1-continued

| Example | Structure and IUPAC Name | Exact Mass [M + H]+ | Route Used |
|---|---|---|---|
| 65 | 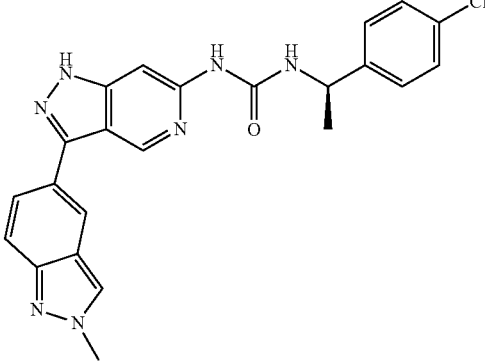<br>1-[(1R)-1-(4-chlorophenyl)ethyl]-3-[3-(2-methyl-2H-indazol-5-yl)-1H-pyrazolo[4,3-c]pyridin-6-yl]urea | Calc'd 446, found 446 | 30 |
| 66 | 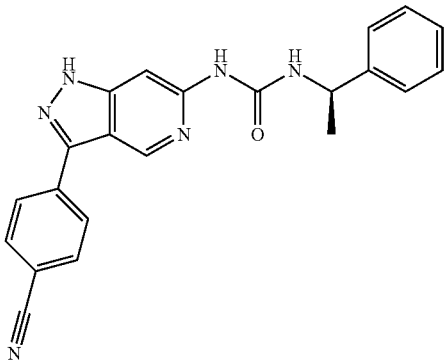 [SMILES: C[C@@H](NC(=O)Nc1cc2[nH]nc(-c3ccc(C#N)cc3)c2cn1)c1ccccc1]<br>1-[3-(4-cyanophenyl)-1H-pyrazolo[4,3-c]pyridin-6-yl]-3-[(1R)-1-phenylethyl]urea | Calc'd 383, found 383 | 30 |
| 67 | 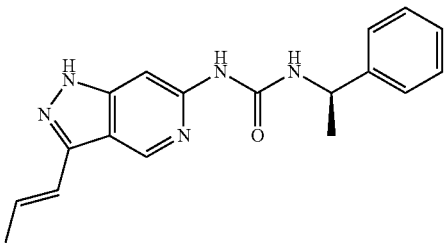 [SMILES: C/C=C/c1n[nH]c2cc(NC(=O)N[C@H](C)c3ccccc3)ncc12]<br>1-[(1R)-1-phenylethyl]-3-{3-[(1E)-prop-1-en-1-yl]-1H-pyrazolo[4,3-c]pyridin-6-yl}urea | Calc'd 322 found 322 | — |
| 68 | 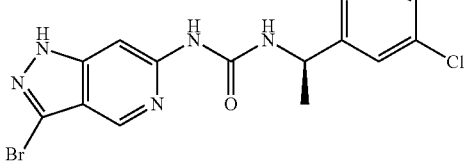<br>1-(3-bromo-1H-pyrazolo[4,3-c]pyridin-6-yl)-3-[(1R)-1-(3-chloro-4-fluorophenyl)ethyl]urea | Calc'd 412, found 412 | 90 |

TABLE 1-continued

| Example | Structure and IUPAC Name | Exact Mass [M + H]+ | Route Used |
|---|---|---|---|
| 69 | 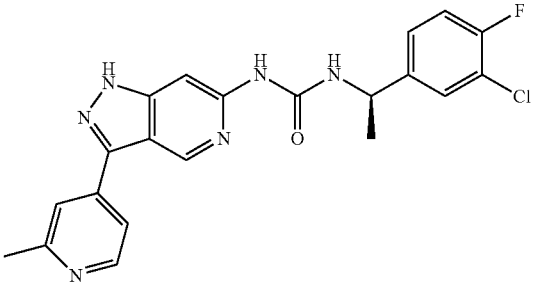 [SMILES: Cc1cc(-c2n[nH]c3cc(NC(=O)N[C@H](C)c4ccc(F)c(Cl)c4)ncc23)ccn1]<br>1-[(1R)-1-(3-chloro-4-fluorophenyl)ethyl]-3-[3-(2-methylpyridin-4-yl)-1H-pyrazolo[4,3-c]pyridin-6-yl]urea | Calc'd 425, found 425 | 90 |
| 70 | 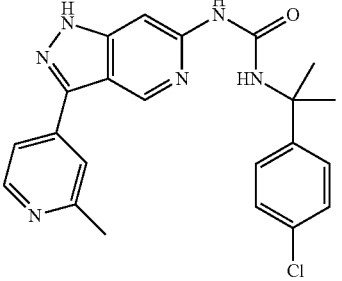<br>1-[1-(4-chlorophenyl)-1-methylethyl]-3-[3-(2-methylpyridin-4-yl)-1H-pyrazolo[4,3-c]pyridin-6-yl]urea | Calc'd 421, found 421 | 12 |
| 71 | 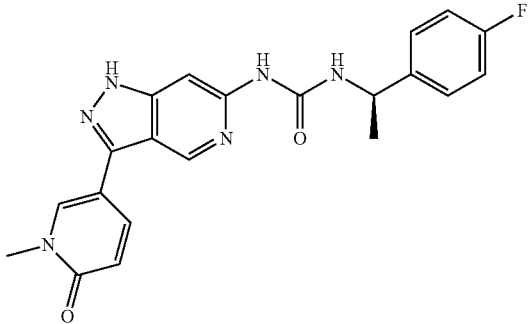 [SMILES: C[C@@H](NC(=O)Nc1cc2[nH]nc(-c3ccc(=O)n(C)c3)c2cn1)c1ccc(F)cc1]<br>1-[(1R)-1-(4-fluorophenyl)ethyl]-3-[3-(1-methyl-6-oxo-1,6-dihydropyridin-3-yl)-1H-pyrazolo[4,3-c]pyridin-6-yl]urea | Calc'd 407, found 407 | 30 |
| 72 | 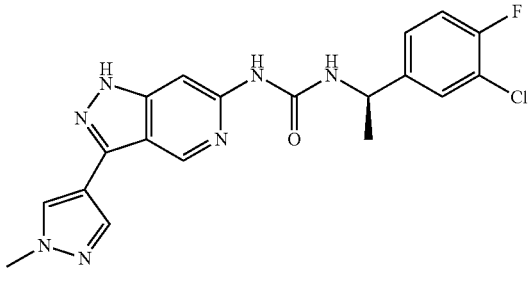 [SMILES: C[C@@H](NC(=O)Nc1cc2[nH]nc(-c3cnn(C)c3)c2cn1)c1ccc(F)c(Cl)c1]<br>1-[(1R)-1-(3-chloro-4-fluorophenyl)ethyl]-3-[3-(1-methyl-1H-pyrazol-4-yl)-1H-pyrazolo[4,3-c]pyridin-6-yl]urea | Calc'd 414, found 414 | 90 |

TABLE 1-continued

| Example | Structure and IUPAC Name | Exact Mass [M + H]+ | Route Used |
|---|---|---|---|
| 73 | 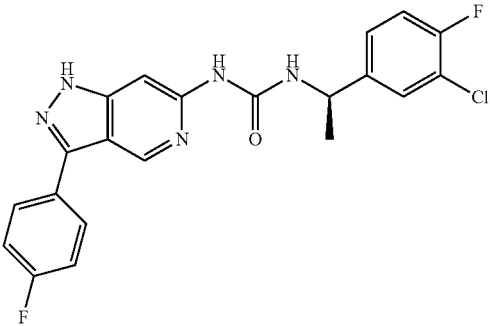 [SMILES: C[C@@H](NC(=O)Nc1cc2[nH]nc(-c3ccc(F)cc3)c2cn1)c1ccc(F)c(Cl)c1]

1-[(1R)-1-(3-chloro-4-fluorophenyl)ethyl]-3-[3-(4-fluorophenyl)-1H-pyrazolo[4,3-c]pyridin-6-yl]urea | Calc'd 428, found 428 | 90 |
| 74 | 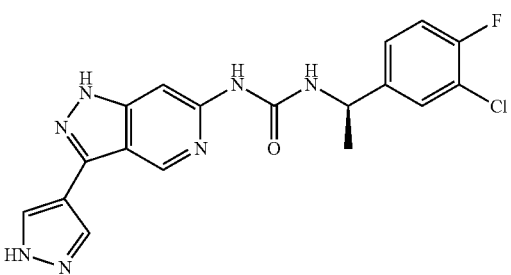 [SMILES: C[C@@H](NC(=O)Nc1cc2[nH]nc(-c3cn[nH]c3)c2cn1)c1ccc(F)c(Cl)c1]

1-[(1R)-1-(3-chloro-4-fluorophenyl)ethyl]-3-[3-(1H-pyrazol-4-yl)-1H-pyrazolo[4,3-c]pyridin-6-yl]urea | Calc'd 400, found 400 | 90 |
| 75 | 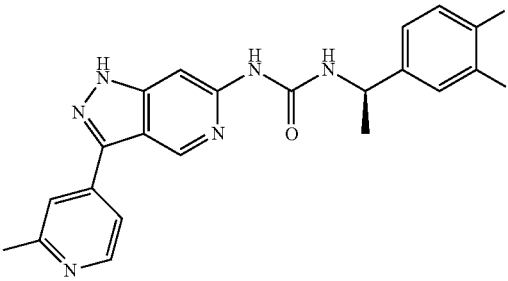

1-[(1R)-1-(3-chloro-4-fluorophenyl)ethyl]-3-[3-(2-chloropyridin-4-yl)-1H-pyrazolo[4,3-c]pyridin-6-yl]urea | Calc'd 445, found 445 | 90 |
| 76 | 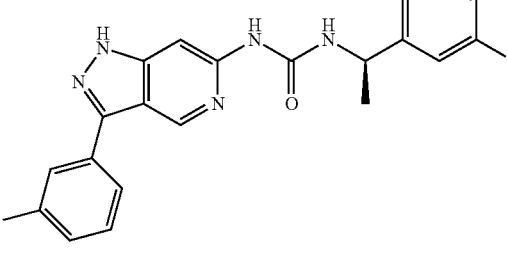

1-[(1R)-1-(3-chloro-4-fluorophenyl)ethyl]-3-[3-(3-chlorophenyl)-1H-pyrazolo[4,3-c]pyridin-6-yl]urea | Calc'd 444, found 444 | 90 |

TABLE 1-continued

| Example | Structure and IUPAC Name | Exact Mass [M + H]+ | Route Used |
|---|---|---|---|
| 77 | 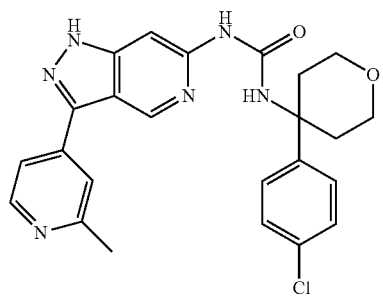 [SMILES: Cc1cc(-c2n[nH]c3cc(NC(=O)NC4(c5ccc(Cl)cc5)CCOCC4)ncc23)ccn1]<br>1-[4-(4-chlorophenyl)tetrahydro-2H-pyran-4-yl]-3-[3-(2-methylpyridin-4-yl)-1H-pyrazolo[4,3-c]pyridin-6-yl]urea | Calc'd 463, found 463 | 12 |
| 78 | 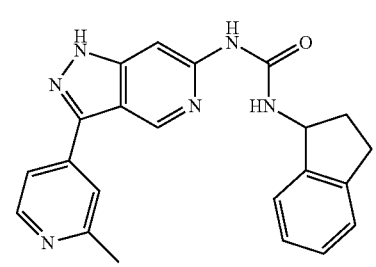 [SMILES: Cc1cc(-c2n[nH]c3cc(NC(=O)NC4CCc5ccccc54)ncc23)ccn1]<br>1-(2,3-dihydro-1H-inden-1-yl)-3-[3-(2-methylpyridin-4-yl)-1H-pyrazolo[4,3-c]pyridin-6-yl]urea | Calc'd 385, found 385 | 12 |
| 79 | 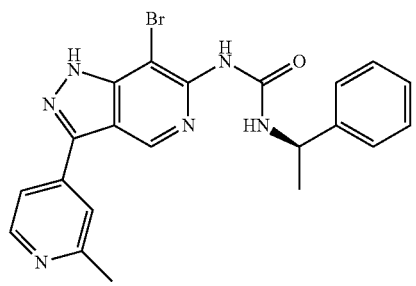 [SMILES: Cc1cc(-c2n[nH]c3c(Br)c(NC(=O)N[C@H](C)c4ccccc4)ncc23)ccn1]<br>1-[7-bromo-3-(2-methylpyridin-4-yl)-1H-pyrazolo[4,3-c]pyridin-6-yl]-3-[(1R)-1-phenylethyl]urea | Calc'd 451, found 451 | 86 |
| 80 | 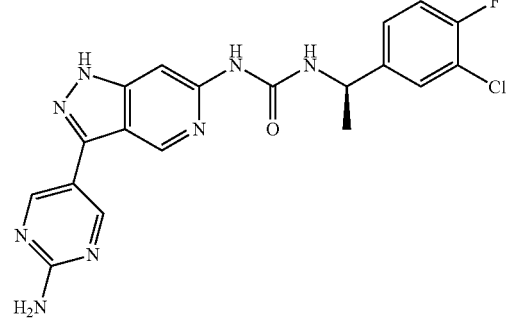<br>1-[3-(2-aminopyridin-5-yl)-1H-pyrazolo[4,3-c]pyridin-6-yl]-3-[(1R)-1-(3-chloro-4-fluorophenyl)ethyl]urea | Calc'd 427, found 427 | 90 |

TABLE 1-continued

| Example | Structure and IUPAC Name | Exact Mass [M + H]+ | Route Used |
|---|---|---|---|
| 81 | 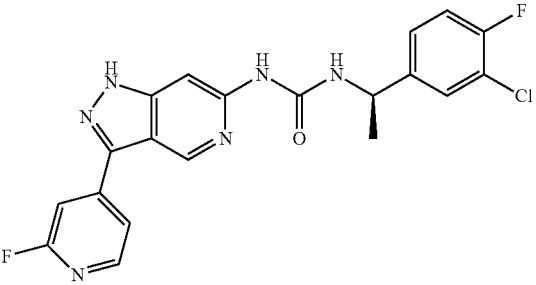 [SMILES: C[C@@H](NC(=O)Nc1cc2[nH]nc(-c3ccnc(F)c3)c2cn1)c1ccc(F)c(Cl)c1]<br>1-[(1R)-1-(3-chloro-4-fluorophenyl)ethyl]-3-[3-(2-fluoropyridin-4-yl)-1H-pyrazolo[4,3-c]pyridin-6-yl]urea | Calc'd 429, found 429 | 90 |
| 82 | 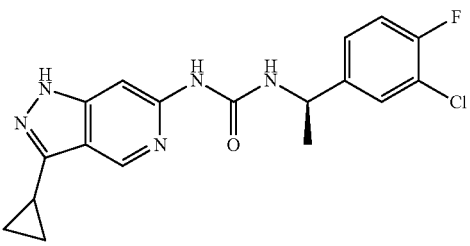 [SMILES: C[C@@H](NC(=O)Nc1cc2[nH]nc(C3CC3)c2cn1)c1ccc(F)c(Cl)c1]<br>1-[(1R)-1-(3-chloro-4-fluorophenyl)ethyl]-3-(3-cyclopropyl-1H-pyrazolo[4,3-c]pyridin-6-yl)urea | Calc'd 374, found 374 | 90 |
| 83 | 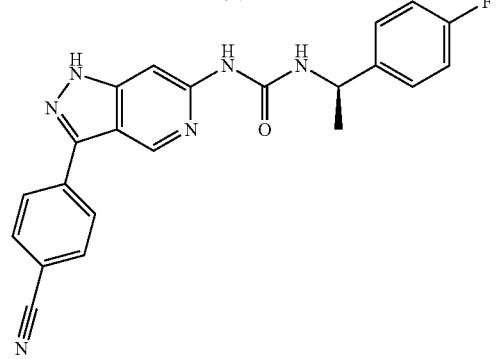<br>1-[3-(4-cyanophenyl)-1H-pyrazolo[4,3-c]pyridin-6-yl]-3-[(1R)-1-(4-fluorophenyl)ethyl]urea | Calc'd 401, found 401 | 30 |
| 84 | 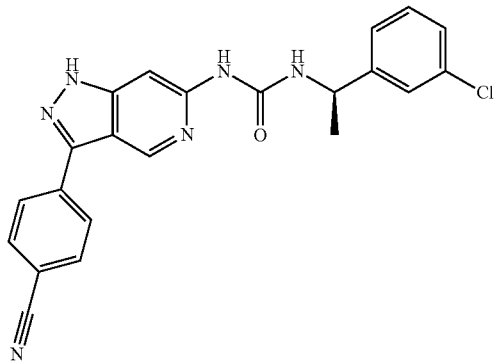 [SMILES: C[C@@H](NC(=O)Nc1cc2[nH]nc(-c3ccc(C#N)cc3)c2cn1)c1cccc(Cl)c1]<br>1-[(1R)-1-(3-chlorophenyl)ethyl]-3-[3-(4-cyanophenyl)-1H-pyrazolo[4,3-c]pyridin-6-yl]urea | Calc'd 417, found 417 | 30 |

TABLE 1-continued

| Example | Structure and IUPAC Name | Exact Mass [M + H]+ | Route Used |
|---|---|---|---|
| 85 | 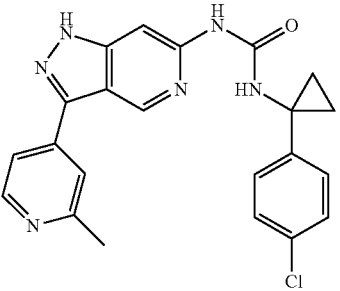 [SMILES: Cc1cc(-c2n[nH]c3cc(NC(=O)NC4(c5ccc(Cl)cc5)CC4)ncc23)ccn1]<br>1-[1-(4-chlorophenyl)cyclopropyl]-3-[3-(2-methylpyridin-4-yl)-1H-pyrazolo[4,3-c]pyridin-6-yl]urea | Calc'd 419, found 419 | 12 |
| 86 | 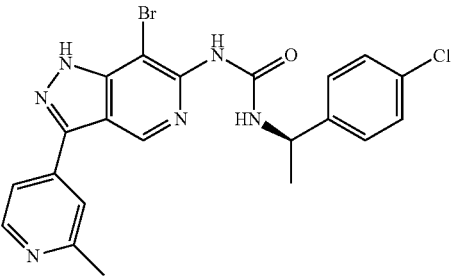 [SMILES: Cc1cc(-c2n[nH]c3c(Br)c(NC(=O)N[C@H](C)c4ccc(Cl)cc4)ncc23)ccn1]<br>1-[7-bromo-3-(2-methylpyridin-4-yl)-1H-pyrazolo[4,3-c]pyridin-6-yl]-3-[(1R)-1-(4-chlorophenyl)ethyl]urea | Calc'd 485, found 485 | — |
| 87 | 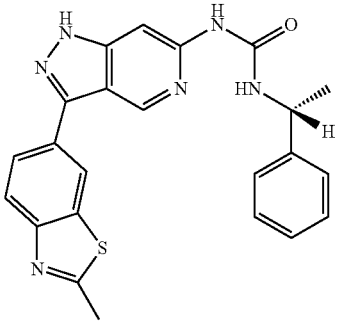 [SMILES: Cc1nc2ccc(-c3n[nH]c4cc(NC(=O)N[C@H](C)c5ccccc5)ncc34)cc2s1]<br>1-[3-(2-methyl-1,3-benzothiazol-6-yl)-1H-pyrazolo[4,3-c]pyridin-6-yl]-3-[(1R)-1-phenylethyl]urea | Calc'd 429, found 429 | 90 |
| 88 | 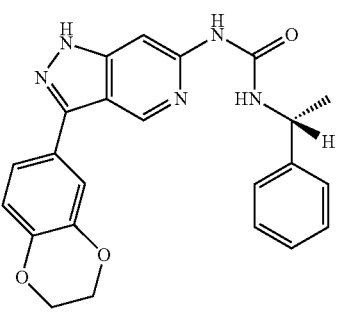 [SMILES: C[C@@H](NC(=O)Nc1cc2[nH]nc(-c3ccc4c(c3)OCCO4)c2cn1)c1ccccc1]<br>1-[3-(2,3-dihydro-1,4-benzodioxin-6-yl)-1H-pyrazolo[4,3-c]pyridin-6-yl]-3-[(1R)-1-phenylethyl]urea | Calc'd 416, found 416 | 90 |

TABLE 1-continued

| Example | Structure and IUPAC Name | Exact Mass [M + H]+ | Route Used |
|---|---|---|---|
| 89 | 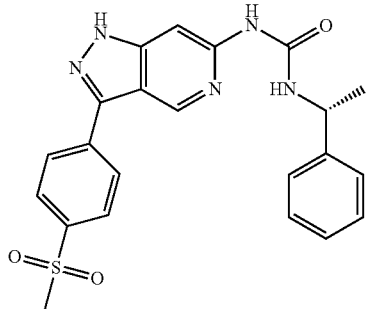 [SMILES: C[C@@H](NC(=O)Nc1cc2[nH]nc(-c3ccc(S(C)(=O)=O)cc3)c2cn1)c1ccccc1]<br>1-{3-[4-(methylsulfonyl)phenyl]-1H-pyrazolo[4,3-c]pyridin-6-yl}-3-[(1R)-1-phenylethyl]urea | Calc'd 436, found 436 | 90 |
| 90 | 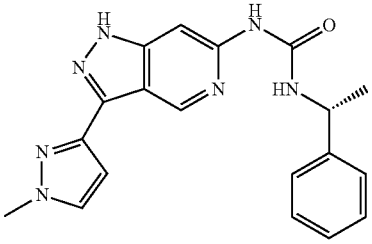 [SMILES: C[C@@H](NC(=O)Nc1cc2[nH]nc(-c3ccn(C)n3)c2cn1)c1ccccc1]<br>1-[3-(1-methyl-1H-pyrazol-3-yl)-1H-pyrazolo[4,3-c]pyridin-6-yl]-3-[(1R)-1-phenylethyl]urea | Calc'd 362, found 362 | — |
| 91 | 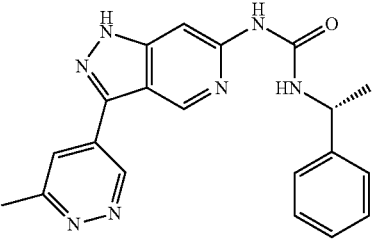 [SMILES: Cc1cc(-c2n[nH]c3cc(NC(=O)N[C@H](C)c4ccccc4)ncc23)cnn1]<br>1-[3-(6-methylpyridazin-4-yl)-1H-pyrazolo[4,3-c]pyridin-6-yl]-3-[(1R)-1-phenylethyl]urea | Calc'd 374, found 374 | 90 |
| 92 | 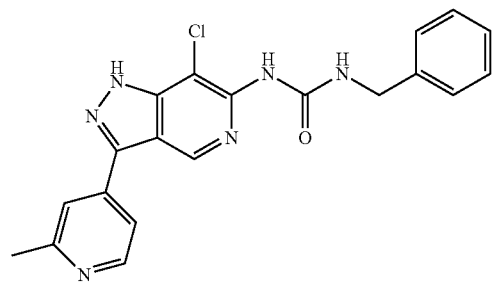 [SMILES: Cc1cc(-c2n[nH]c3c(Cl)c(NC(=O)NCc4ccccc4)ncc23)ccn1]<br>1-benzyl-3-[7-chloro-3-(2-methylpyridin-4-yl)-1H-pyrazolo[4,3-c]pyridin-6-yl]urea | Calc'd 393, found 393 | — |

TABLE 1-continued

| Example | Structure and IUPAC Name | Exact Mass [M + H]+ | Route Used |
|---|---|---|---|
| 93 | 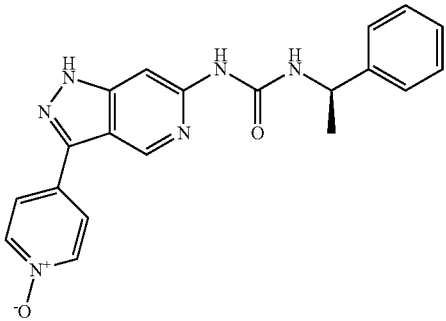<br>1-[3-(1-oxidopyridin-4-yl)-1H-pyrazolo[4,3-c]pyridin-6-yl]-3-[(1R)-1-phenylethyl]urea | Calc'd 375, found 375 | 90 |
| 94 | 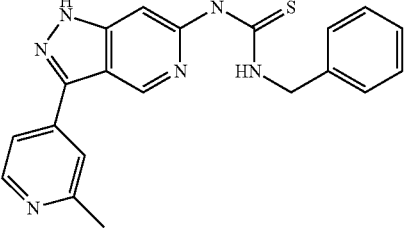<br>1-benzyl-3-[3-(2-methylpyridin-4-yl)-1H-pyrazolo[4,3-c]pyridin-6-yl]thiourea | Calc'd 375, found 375 | — |
| 95 | 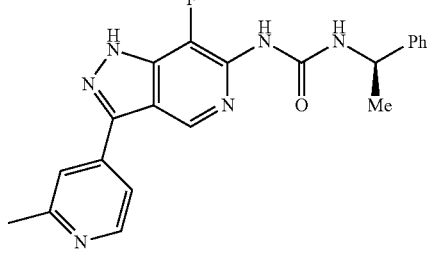<br>1-[7-fluoro-3-(2-methylpyridin-4-yl)-1H-pyrazolo[4,3-c]pyridin-6-yl]-3-[(1R)-1-phenylethyl]urea | Calc'd 391, found 391 | — |

EXAMPLE 116

N-(2-methoxyethyl)-6-({[(1R)-1-phenylethyl]carbamoyl}amino)-1H-pyrazolo[4,3-c]pyridine-3-carboxamide

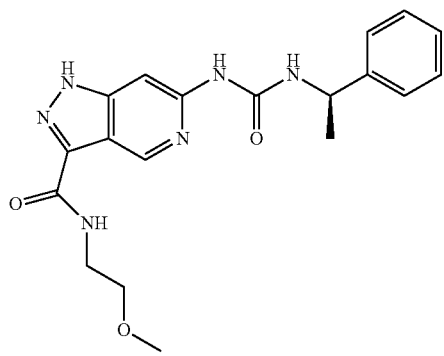 [SMILES: COCCNC(=O)c1n[nH]c2cc(NC(=O)N[C@H](C)c3ccccc3)ncc12]

A sealed vial was charged with N-(2-methoxyethyl)-6-({[(1R)-1-phenylethyl]carbamoyl}amino)-1H-pyrazolo[4,3-c]pyridine-3-carboxamide (20 mg, 0.035 mmol), 2-Methoxyethylamine (3.03 µl, 0.035 mmol), HATU (16.08 mg, 0.042 mmol), DIEA (18 0.103 mmol), and DMA (1 ml). The reaction was stirred at 60° C. for 16 hours. The reaction mixture was dried under reduced pressure. TFA (1 ml) was added and the reaction was stirred at room temperature for 1 hour. Triethylsilane (5.63 0.035 mmol) was added and the reaction was stirred at RT for an additional 5 minutes. The reaction mixture was then dried under reduced pressure. The reaction was then diluted with 1.0 mL DMSO and purified by mass-triggered reverse phase HPLC, eluting with a 1% trifluoroacetic acid buffered water/acetonitrile gradient over a Waters X-Bridge C-18 column, to afford N-(2-methoxyethyl)-6-({[(1R)-1-phenylethyl]carbamoyl}amino)-1H-pyrazolo[4,3-c]pyridine-3-carboxamide (4 mg, 0.01 mmol, 29.7%). MS ESI calc'd. for $C_{19}H_{22}N_6O_3$ [M+1]+383, found 383.

EXAMPLE 140

1-(3-cyclopropyl-1H-pyrazolo[4,3-c]pyridin-6-yl)-3-(4-fluorobenzyl)urea

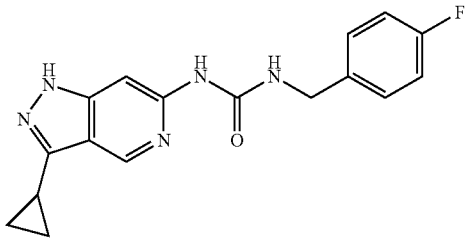 [SMILES: O=C(NCc1ccc(F)cc1)Nc1cc2[nH]nc(C3CC3)c2cn1]

Step 1

To a flask were added 6-chloro-3-iodo-1-trityl-1H-pyrazolo[4,3-c]pyridine (3a, 2 g, 3.83 mmol), cyclopropylboronic acid (0.560 g, 6.52 mmol)), potassium carbonate (1.3 g, 9.6 mmol), 1,1'-bis(diphenylphosphino)ferrocene-palladium(ii) dichloride dichloromethane complex (0.157 g, 0.192 mmol), dioxane (10 ml), and water (5 ml). The mixture was Vac/N2 purged 6 times and heated at 60° C. After 5 h, the reaction was treated further with cyclopropylboronic acid (0.560 g, 6.52 mmol)), potassium carbonate (1.3 g, 9.6 mmol), 1,1'-bis(diphenylphosphino)ferrocene-palladium(ii)dichloride dichloromethane complex (0.157 g, 0.192 mmol), then degassed, and then heated at 80° C. overnight. The mixture was diluted with DCM and water and then filtered through celite. The organic phase was separated and concentrated to afford a dark residue, which was purified on silica gel (40 g, 0-20% ethyl acetate/hexanes) to afford 6-chloro-3-cyclopropyl-1-trityl-1H-pyrazolo[4,3-c]pyridine (1.4 g, 84% yield) as a white foam. MS ESI calc'd. for $C_{28}H_{22}Cl_1N_3[M+1]^+$ 436, found 436.

Step 2

A mixture of 6-chloro-3-cyclopropyl-1-trityl-1H-pyrazolo[4,3-c]pyridine (60 mg, 0.138 mmol), 1-(4-fluorobenzyl)urea (69 mg, 0.413 mmol), palladium(II) acetate (6 mg, 0.028 mmol), Xantphos (4,5-bis(diphenylphosphino)-9,9-dimethyxanthene, 24 mg, 0.041 mmol), and cesium carbonate (112 mg, 0.028 mmol) in dioxane (1 mL) was degassed and refilled with nitrogen (3 times) and then heated at 80° C. overnight. The mixture was diluted with dichloromethane (5 mL) and water (1 mL), and then was filtered through celite. The DCM layer was evaporated under reduced pressure and purified by column chromatography on silica gel (eluting with 0-30% EtOAc/hexanes) to give 1-(3-cyclopropyl-1-trityl-1H-pyrazolo[4,3-c]pyridin-6-yl)-3-(4-fluorobenzyl)urea (70 mg, 90% yield) as a clear-white film. MS ESI calc'd. for $C_{36}H_{30}FN_5O[M+1]^+$ 568, found 568.

Step 3

A mixture of 1-(3-cyclopropyl-1-trityl-1H-pyrazolo[4,3-c]pyridin-6-yl)-3-(4-fluorobenzyl)urea (70 mg, 0.123 mmol), TFA (1900 24.66 mmol), and triethylsilane (19.70 μl, 0.123 mmol) was stirred at room temperature. The reaction was concentrated, taken up in DMSO (2 mL) and purified by preparative HPLC (Reverse phase C-18, Waters SunFire PrepODB, 150×19 mm, 5u, eluting with 10-95% Acetonitrile/Water+0.1% TFA (20 mL/min) over 10 min.) to give 1-(3-cyclopropyl-1H-pyrazolo[4,3-c]pyridin-6-yl)-3-(4-fluorobenzyl)urea (23 mg, 0.052 mmol, 42.5% yield) as an off-white solid. MS ESI calc'd. for $C_{17}H_{16}FN_5O$ $[M+1]^+$ 326, found 326.

EXAMPLE 143

1-butyl-3-(3-cyclobutyl-1H-pyrazolo[4,3-c]pyridin-6-yl)urea

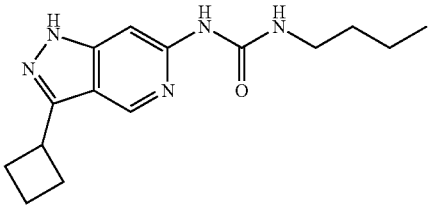 [SMILES: CCCCNC(=O)Nc1cc2[nH]nc(C3CCC3)c2cn1]

Step 1

Reference: PCT Int. Appl., 2010056631, 2010. To a solution of zinc chloride (1.5 ml, 3.591 mmol, 1.9M in 2-methyl THF) at 0° C. was added a solution of cyclobutyl magnesium chloride in (9.20 ml, 4.60 mmol, 0.5 M in 2-methyl-THF). The reaction solution was stirred at 0° C. to r.t for 1 hr, and then transferred into a mixture of 6-chloro-3-iodo-1-trityl-1H-pyrazolo[4,3-c]pyridine (3a, 1 g, 1.917 mmol), Pd(OAc)$_2$ (0.043 g, 0.192 mmol) and S-Phos (2-dicyclohexylphosphino-2',6'-dimethoxybiphenyl, 0.118 g, 0.287 mmol) at r.t. The result dark suspension was stirred at r.t for 3 hr and then was quenched with water and extracted with ethyl acetate. The organic layer was concentrated and purified by column chromatography on silica gel (50 g, eluting with 20% ethyl acetate/hexanes) to give 6-chloro-3-cyclobutyl-1-trityl-1H-pyrazolo[4,3-c]pyridine (483 mg, 56%) as a light yellow solid. MS ESI calc'd. for $C_{29}H_{24}Cl_1N_3[M+1]^+$ 450, found 450.

Steps 2-3

In a manner similar to that described in Scheme 6 and Example 30, 6-chloro-3-cyclobutyl-1-trityl-1H-pyrazolo[4,3-c]pyridine was reacted with 1-butylurea, (Xantphos, Pd(OAc)$_2$, Cs$_2$CO$_3$, dioxane, 80° C., overnight) and then deprotected with TFA to provide 1-butyl-3-(3-cyclobutyl-1H-pyrazolo[4,3-c]pyridin-6-yl)urea. MS ESI calc'd. for $C_{15}H_{21}N_5O[M+1]^+$ 288, found 288.

EXAMPLE 159

1-[3-(2,2-difluoro-1-methylcyclopropyl)-1H-pyrazolo[4,3-c]pyridin-6-yl]-3-[(1R)-1-(4-fluorophenyl)ethyl]urea

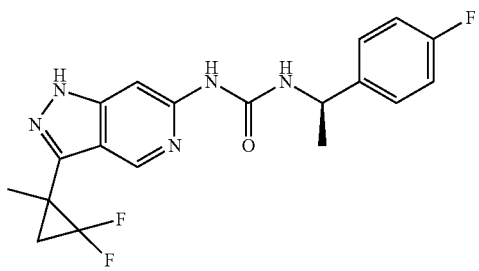 [SMILES: C[C@@H](NC(=O)Nc1cc2[nH]nc(C3(C)CC3(F)F)c2cn1)c1ccc(F)cc1]

Step 1

In a manner similar to that described in Scheme 1 (Step 3), 6-chloro-3-iodo-1-trityl-1H-pyrazolo[4,3-c]pyridine (3a) was coupled with isopropenylboronic acid pinacol ester to provide 6-chloro-3-(prop-1-en-2-yl)-1-trityl-1H-pyrazolo[4,3-c]pyridine. MS ESI calc'd. for $C_{28}H_{22}ClN_3$ $[M+1]^+$ 436, found 436.

Step 2

Reference: Angew. Chemie Int. Ed., 2011, 50(31), 7153. To a 2 dram pressure vial charged with a magnetic stir bar was added anhydrous NaI (3.4 mg, 0.023 mmol), THF (1 ml), and 6-chloro-3-(prop-1-en-2-yl)-1-trityl-1H-pyrazolo[4,3-c]pyridine (50 mg, 0.115 mmol) under nitrogen. To this was added (trifluoromethyl)trimethylsilane (0.042 ml, 0.287 mmol). The reaction vessel was sealed and heated to 65° C. in an oil bath for a period of 2.5 hours. LCMS and TLC indicated product and remaining starting material. Additional sodium iodide (3.4 mg, 0.023 mmol) and (trifluoromethyl)-trimethylsilane (0.042 ml, 0.287 mmol) were added and the reaction was heated overnight at 65° C. The reaction mixture was concentrated and taken up in ether (15 ml). The organic layer was washed with water (15 ml), saturated sodium thiosulfate solution (15 ml), saturated sodium bicarbonate solution (15 ml), and water (15 ml), in that order. The ethereal layer dried over anhydrous magnesium sulfate, concentrated, and purified (12 g silica gel, eluting with 0-10% tOAc/hexanes) to give 6-chloro-3-(2,2-difluoro-1-methylcyclopropyl)-1-trityl-1H-pyrazolo[4,3-c]pyridine (60 mg, 0.123 mmol) as a beige foam. MS ESI calc'd. for $C_{29}H_{22}ClF_2N_3[M+1]^+$ 486, found 486.

Steps 3-4

In a manner similar to that described in Scheme 6 and Example 30, 6-chloro-3-(2,2-difluoro-1-methylcyclopropyl)-1-trityl-1H-pyrazolo[4,3-c]pyridine was reacted with (R)-1-(1-(4-fluorophenyl)ethyl)urea (Xantphos, Pd(OAc)$_2$, Cs$_2$CO$_3$, dioxane, 80° C., overnight) and then deprotected with TFA to provide (R)-1-(3-(2,2-difluoro-1-methylcyclopropyl)-1H-pyrazolo[4,3-c]pyridin-6-yl)-3-(1-(4-fluorophenyl)ethyl)urea 2,2,2-trifluoroacetate. MS ESI calc'd. for $C_{19}H_{18}F_3N_5O[M+1]^+$ 390, found 390.

EXAMPLE 167

1-[(1S)-2-methoxy-1-phenylethyl]-3-[3-(trifluoromethyl)-1H-pyrazolo[4,3-c]pyridin-6-yl]urea

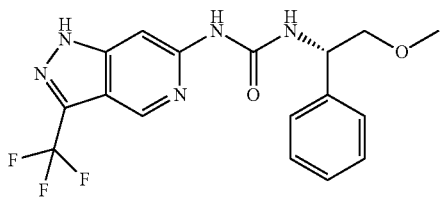 [SMILES: COC[C@@H](NC(=O)Nc1cc2[nH]nc(C(F)(F)F)c2cn1)c1ccccc1]

Step 1

Ref: PCT Int. Appl., 2010086251, 2010. To a suspension of 6-chloro-1H-pyrazolo[4,3-c]pyridine (1a, 1 g, 6.51 mmol), sodium trifluoromethanesulfinate (3.05 g, 19.54 mmol) in 10 mL of DCM and 4 mL of H$_2$O, 70% tert-butyl hydroperoxide (4.19 g, 32.6 mmol) aqueous solution was added. The heterogeneous reaction mixture was stirred vigorously at r.t. After 28 hr, LCMS analysis showed partial conversion. Additional sodium trifluoromethanesulfinate (3.05 g, 19.54 mmol) and tert-butyl hydroperoxide (4.19 g, 32.6 mmol) was added and the reaction mixture was stirred over the weekend. Water, DCM and aqueous Na$_2$S$_2$O$_3$ was added. A yellow solid was filtered off and the filtrate was extracted with DCM. The organic layer was concentrated and purified (50 g silica gel, eluting with 1:30 MeOH/DCM) to give 6-chloro-3-(trifluoromethyl)-1H-pyrazolo[4,3-c]pyridine as a yellow solid, which was further purified by recrystallization from MeOH/DCM/Hexane (200 mg, 13%). MS ESI calc'd. for $C_7H_3ClF_3N_3[M+1]^+$ 222, found 222.

Step 2

In a manner similar to that described in Example 30 (Step 1), 6-chloro-3-(trifluoromethyl)-1H-pyrazolo[4,3-c]pyridine was reacted with (S)-1-(2-methoxy-1-phenylethyl)urea (BrettPhos precatalyst, KOtBu, dioxane, 90° C., overnight) to provide 1-[(1S)-2-methoxy-1-phenylethyl]-3-[3-(trifluoromethyl)-1H-pyrazolo[4,3-c]pyridin-6-yl]urea. MS ESI calc'd. for $C_{17}H_{16}F_3N_5O_2[M+1]^+$ 380, found 380.

EXAMPLE 170

(1S,2S)—N-ethyl-2-(6-(3-((S)-2-methoxy-1-phenylethyl)ureido)-1H-pyrazolo[4,3-c]pyridin-3-yl)cyclopropanecarboxamide

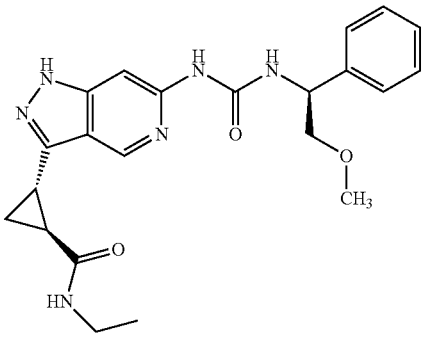 [SMILES: CCNC(=O)[C@H]1C[C@@H]1c1n[nH]c2cc(NC(=O)N[C@H](COC)c3ccccc3)ncc12]

Step 1

A mixture of 6-chloro-1-trityl-3-vinyl-1H-pyrazolo[4,3-c]pyridine (100 mg, 0.237 mmol, derived from 3a and vinylboronic acid pinacol ester as described in Scheme 1, Step 3) in toluene (2 ml) under nitrogen was treated with ethyl diazoacetate (0.074 ml, 0.711 mmol) and heated at 100° C. overnight to give a yellow solution. The reaction was cooled to room temperature and then diluted with aqueous sodium hydrogen carbonate and dichloromethane. The organic layer was concentrated and purified by column chromatography on silica gel (24 g, eluting with 0-20% EtOAc/hexanes) to give two products: trans-ethyl 2-(6-chloro-1-trityl-1H-pyrazolo[4,3-c]pyridin-3-yl)cyclopropanecarboxylate (77 mg, 64% yield) and cis-ethyl 2-(6-chloro-1-trityl-1H-pyrazolo[4,3-c]pyridin-3-yl)cyclopropanecarboxylate (37 mg, 31% yield). MS ESI calc'd. for $C_{31}H_{26}ClN_3O_2[M+1]^+$ 508, found 508.

Steps 2-4

In a manner similar to that described in Example 30 (Step 1), trans-ethyl 2-(6-chloro-1-trityl-1H-pyrazolo[4,3-c]pyridin-3-yl)cyclopropanecarboxylate was reacted with (S)-1-(2-methoxy-1-phenylethyl)urea (BrettPhos precatalyst, KOtBu, dioxane, 80° C.) to provide trans-2-(6-(3-((S)-2-methoxy-1-phenylethyl)ureido)-1-trityl-1H-pyrazolo[4,3-c]pyridin-3-yl)cyclopropanecarboxylic acid. MS ESI calc'd. for $C_{39}H_{35}N_5O_4[M+1]^+$ 638, found 638.

A mixture of trans-2-(6-(3-((S)-2-methoxy-1-phenylethyl)ureido)-1-trityl-1H-pyrazolo[4,3-c]pyridin-3-yl)cyclopropanecarboxylic acid (13 mg, 0.020 mmol), 1-propanephosphonic acid cyclic anhydride (50% in EtOAc, 18.20 μl, 0.031 mmol), DIEA (10.68 μl, 0.061 mmol) and ethylamine (2M in THF) (102 μl, 0.204 mmol) in DCM (0.5 ml) was stirred at room temperature overnight and then concentrated. The residue was treated with TFA (500 μl, 6.49 mmol) and triethylsilane (7 μl, 0.044 mmol). The mixture was stirred at room temperature for 6 h and then concentrated. The residue was purified by preparative HPLC (Reverse phase C-18, Waters SunFire PrepODB, 150×19 mm, 5u), eluting with 10-90% Acetonitrile/Water+0.1% TFA (20 mL/min) over 15 min. to give trans-N-ethyl-2-(6-(3-((S)-2-methoxy-1-phenylethyl)ureido)-1H-pyrazolo[4,3-c]pyridin-3-yl)cyclopropanecarboxamide (4.5 mg, 52% yield). MS ESI calc'd. for $C_{22}H_{26}N_6O_3[M+1]^+$ 423, found 423. MS ESI calc'd. for $C_{22}H_{26}N_6O_3[M-1]^-$ 421, found 421.

EXAMPLE 173

Ethyl 3-(6-(3-benzylureido)-1H-pyrazolo[4,3-c]pyridin-3-yl)propanoate

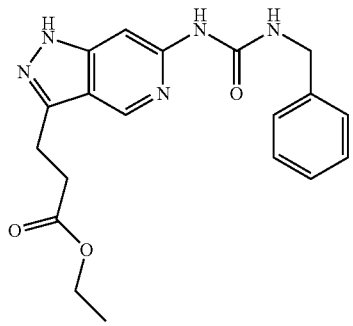 [SMILES: CCOC(=O)CCc1n[nH]c2cc(NC(=O)NCc3ccccc3)ncc12]

Step 1: Ethyl 3-(6-chloro-1-trityl-1H-pyrazolo[4,3-c]pyridin-3-yl)propanoate An oven-dried, nitrogen cooled 2 ml microwave vial was charged with 6-chloro-3-iodo-1-trityl-1H-pyrazolo[4,3-c]pyridine (Intermediate 3a, 103 mg, 0.197 mmol), palladium (II) acetate (2.2 mg, 9.80 μmol) and SPhos (8.2 mg, 0.020 mmol), sealed under an argon atmosphere, charged with (3-ethoxy-3-oxopropyl)zinc(II) bromide (0.5 M in THF, 0.5 ml, 0.250 mmol) and heated to 40° C. for 23 hr. Quenched with MeOH, filtered through celite, concentrated in vacuo and purified via flash chromatography (0-100% EtOAc/Hex). Obtained ethyl 3-(6-chloro-1-trityl-1H-pyrazolo[4,3-c]pyridin-3-yl)propanoate (32.6 mg, 0.066 mmol, 33.3% yield) as a yellow residue. MS ESI calc'd for $C_{30}H_{26}ClN_3O_2$ $[M+H]^+$=496, found 496.

Step 2: Ethyl 3-(6-(3-benzylureido)-1-trityl-1H-pyrazolo[4,3-c]pyridin-3-yl)propanoate An oven-dried, nitrogen cooled 2 ml microwave vial was charged with ethyl 3-(6-chloro-1-trityl-1H-pyrazolo[4,3-c]pyridin-3-yl)propanoate (59 mg, 0.119 mmol), BrettPhos precatalyst (5 mg, 6.26 μmol), cesium carbonate (122 mg, 0.374 mmol) and 1-benzylurea (32 mg, 0.213 mmol), sealed under a nitrogen atmosphere, charged with Dioxane (0.5 ml) and heated to 100° C. for 16 hr. Filtered through celite, eluted with EtOAc, concentrated in vacuo and purified via flash chromatography (0-20% MeOH/DCM) to provide ethyl 3-(6-(3-benzylureido)-1-trityl-1H-pyrazolo[4,3-c]pyridin-3-yl)propanoate (38.7 mg, 0.063 mmol, 53.4% yield) as a yellow solid. MS ESI calc'd for $C_{38}H_{35}N_5O_3$ $[M+H]^+$=610, found 610.

Step 3

A solution of ethyl 3-(6-(3-benzylureido)-1-trityl-1H-pyrazolo[4,3-c]pyridin-3-yl)propanoate (38.7 mg, 0.063 mmol) in TFA (1 ml) was charged with triethylsilane (12 μl, 0.075 mmol) and stirred at RT for 2 hr. LCMS shows conversion to the desired mass. Purified via mass-triggered reverse-phase HPLC to provide ethyl 3-(6-(3-benzylureido)-1H-pyrazolo[4,3-c]pyridin-3-yl)propanoate (8.4 mg, 0.017 mmol, 27.5% yield) as a white solid (TFA salt). MS ESI calc'd for $C_{19}H_{21}N_5O_3$ $[M+H]^+$=368, found 368. $^1$H NMR (500 MHz, DMSO-$d_6$) δ 9.53 (br s, 1H), 8.85 (s, 1H), 7.85 (s, 1H), 7.51 (s, 1H), 7.32 (m, 4H), 7.25 (m, 1H), 4.36 (d, J=5.9 Hz, 2H), 4.02 (q, J=7.1 Hz, 2H), 3.17 (t, J=7.3 Hz, 2H), 2.79 (t, J=7.3 Hz, 2H), 1.13 (t, J=7.1 Hz, 3H).

EXAMPLE 174

(R)-1-(7-Methyl-3-(2-methylpyridin-4-yl)-1H-pyrazolo[4,3-c]pyridin-6-yl)-3-(1-phenylethyl)urea

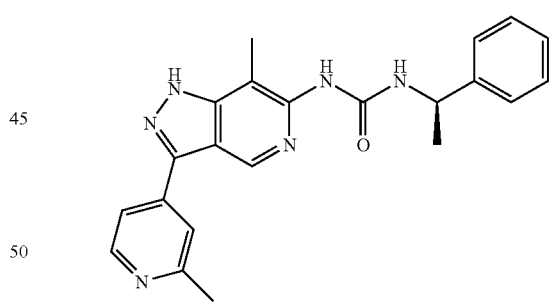

An oven-dried, nitrogen cooled 5 ml microwave vial was charged with (R)-1-(7-chloro-3-(2-methylpyridin-4-yl)-1H-pyrazolo[4,3-c]pyridin-6-yl)-3-(1-phenylethyl)urea (Example 571, 78.7 mg, 0.193 mmol), palladium (II) acetate (8.5 mg, 0.038 mmol) and tricyclohexylphosphonium tetrafluoroborate (36 mg, 0.098 mmol), sealed under a nitrogen atmosphere and charged with Dioxane (1.0 ml) and NMP (0.25 ml) followed by dropwise addition of dimethylzinc in toluene (1.6 ml, 1.920 mmol). Heated to 100° C. for 17 hr. Quenched with TFA until gas evolution ceased, and then poured into saturated aqueous sodium bicarbonate. Extracted 3× with DCM and filtered aqueous layer to remove precipitate. Extracted precipitate with DCM/MeOH. Concentrated combined organic extracts in vacuo and purified via flash chromatography (0-20% MeOH/DCM) followed by mass-triggered reverse-phase HPLC. Obtained (R)-1-(7-methyl-3-(2-methylpyridin-4-yl)-1H-pyrazolo[4,3-c]pyridin-6-yl)-3-(1-phenylethyl)urea (26.9 mg, 0.070 mmol, 36.0% yield) as a white solid. MS ESI calc'd for $C_{22}H_{22}N_6O$ [M+H]$^+$=387, found 387. $^1$H NMR (500 MHz, DMSO-$d_6$) δ 936 (br s, 1H), 9.16 (s, 1H), 8.52 (d, J=5.1 Hz, 1H), 8.27 (s, 1H), 7.89 (s, 1H), 7.82 (d, J=5.1 Hz, 1H), 7.37 (m, 4H), 7.21 (m, 1H), 4.97 (m, 1H), 2.56 (s, 3H), 2.48 (s, 1H), 1.45 (d, J=7.1 Hz, 3H).

EXAMPLE 178

1-((3R,4S)-1-Methyl-4-(2-(trifluoromethyl)phenyl)pyrrolidin-3-yl)-3-(3-(2-methylpyridin-4-yl)-1H-pyrazolo[4,3-c]pyridin-6-yl)urea

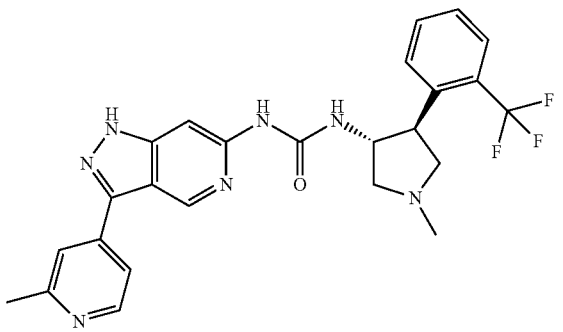 [SMILES: Cc1cc(-c2n[nH]c3cc(NC(=O)N[C@H]4CN(C)C[C@@H]4c4ccccc4C(F)(F)F)ncc23)ccn1]

3-(2-Methylpyridin-4-yl)-1-trityl-1H-pyrazolo[4,3-c]pyridin-6-amine (200 mg, 0.428 mmol) was dissolved in dioxane (4 mL). CDI (209 mg, 1.288 mmol) and imidazole (144 mg, 2.122 mmol) were added and the reaction mixture was stirred at room temperature overnight. (3R,4S)-1-methyl-4-(2-(trifluoromethyl)phenyl)pyrrolidin-3-amine (38.7 mg, 0.158 mmol) was dissolved in dioxane (0.5 mL) and added to the reaction mixture (1 mL, 50 mg, 0.107 mmol) followed by addition of triethylamine (0.075 mL, 0.535 mmol). The reaction mixture was stirred at room temperature for one hour.

After an hour, the reaction was diluted with ethyl acetate and washed with saturated sodium bicarbonate and brine. The organic layer was dried over sodium sulfate, filtered, and concentrated in vacuo.

Crude 1-((3R,4S)-1-methyl-4-(2-(trifluoromethyl)phenyl)pyrrolidin-3-yl)-3-(3-(2-methylpyridin-4-yl)-1-trityl-1H-pyrazolo[4,3-c]pyridin-6-yl) was dissolved in DCM (2 mL) then triethylsilane (0.034 mL) and TFA (0.5 mL) were added. The reaction mixture was stirred at room temperature overnight. The reaction was concentrated in vacuo, diluted with ethyl acetate, and washed with saturated sodium bicarbonate. The aqueous layer was reextracted with 3:1 chloroform/IPA. The organic layer was dried over sodium sulfate, filtered, and concentrated in vacuo. The residue was dissolved in DMSO (1.5 mL), filtered, and purified via mass-triggered reverse-phase HPLC. The fractions containing pure product were combined, concentrated in vacuo, dissolved in ACN/water, and lyophilized to give 1-((3R,4S)-1-methyl-4-(2-(trifluoromethyl)phenyl)pyrrolidin-3-yl)-3-(3-(2-methylpyridin-4-yl)-1H-pyrazolo[4,3-c]pyridin-6-yl)urea (13.7 mg, 0.019 mmol, 17.8%) as the TFA salt. MS ESI calc'd. For $C_{25}H_{24}F_3N_7O$ [M+1]$^+$ 496, found 496.

EXAMPLE 215 and 216

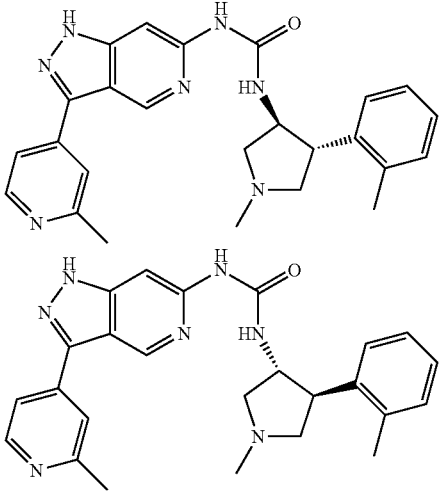

1-((3S,4R)-1-methyl-4-(o-tolyl)pyrrolidin-3-yl)-3-(3-(2-methylpyridin-4-yl)-1H-pyrazolo[4,3-c]pyridin-6-yl)urea (215) and 1-((3R,4S)-1-methyl-4-(o-tolyl)pyrrolidin-3-yl)-3-(3-(2-methylpyridin-4-yl)-1H-pyrazolo[4,3-e]pyridin-6-yl)urea (216)

30 mg of racemic 1-((3S,4R)+(3R,4S)-1-methyl-4-(o-tolyl)pyrrolidin-3-yl)-3-(3-(2-methylpyridin-4-yl)-1H-pyrazolo[4,3-c]pyridin-6-yl)urea was dissolved up in 2 mL methanol and subjected to chiral SFC purification. Injections of 0.5 mL were performed on the Berger Multigram II. Elution was observed at 8.23 min and 9.62 min. The two fractions were concentrated to a oil. Dissolved in 1:1 ACN/water and lyophilized to provided the two enantiomers.

EXAMPLE 242

1-[(1R)-1-(4-fluorophenyl)ethyl]-3-{3-[4-(1H-1,2,3-triazol-1-yl)phenyl]-1H-pyrazolo[4,3-c]pyridin-6-yl}urea

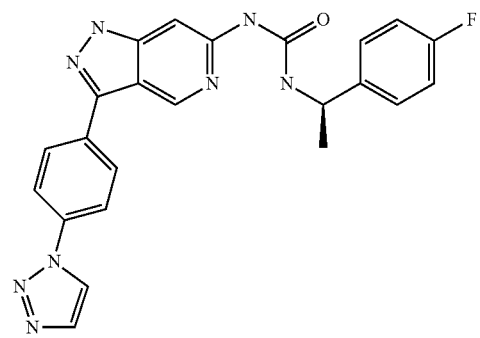 [SMILES: C[C@@H](NC(=O)Nc1cc2[nH]nc(-c3ccc(-n4ccnn4)cc3)c2cn1)c1ccc(F)cc1]

1-(3-bromo-1-trityl-1H-pyrazolo[4,3-c]pyridin-6-yl)-3-[(1R)-1-(4-fluorophenyl)ethyl]urea (10 mg, 0.016 mmol, 1 eq), potassium phosphate tribasic (21 mg 0.048 mmol in 0.1 mL of degassed water), 2-Dicyclohexylphosphino-2',4',6'-triisopropylbiphenyl (Xphos) (1.5 mg 3.2 umol, 0.2 eq) and Palladium(II) acetate (0.3 mg, 1.6 umol, 0.1 eq) all in in 0.5 mL THF (degassed) were added to 1-[4-(4,4,5,5-tetramethyl-1,3,2-dioxaborolan-2-yl)phenyl]-1H-1,2,3-triazole (7 mg, 0.024 mmol, 1.5 eq). The vial was purged with nitrogen gas, capped and stirred for 16 hours at 60°.

The solvents were removed in vacuo and the residue was dissolved in 1 mL of DCM. To this solution was added Silicycle SiliaMetS DMT resin (20 mg, 0.1 mmol, >5 eq. of Pd) and the solution was shaken at room temperature for 4 hours. The solution was filtered and TFA (1 mL) was added with triethylsilane (0.02 mL, 0.125 mmol). The mixture was stirred at room temperature for 6 h, evaporated in vacuo and purified on reversed phase HPLC to afford 1-[(1R)-1-(4-fluorophenyl)ethyl]-3-{3-[4-(1H-1,2,3-triazol-1-yl)phenyl]-1H-pyrazolo[4,3-c]pyridin-6-yl}urea 4.2 mg, 0.015 mmol (45%)

EXAMPLE 262

1-[3-(2-methylpyridin-4-yl)-1H-pyrazolo[4,3-c]pyridin-6-yl]-3-[(8R)-5,6,7,8-tetrahydroquinolin-8-yl]urea

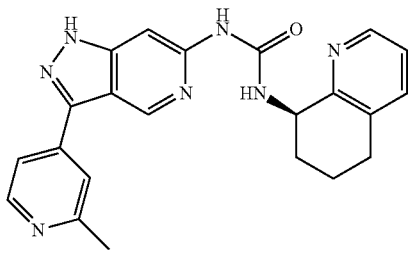 [SMILES: Cc1cc(-c2n[nH]c3cc(NC(=O)N[C@@H]4CCCc5cccnc54)ncc23)ccn1]

Step 1

In a 1 dram, 4 mL, vial were added 3-(2-methylpyridin-4-yl)-1-trityl-1H-pyrazolo[4,3-c]pyridin-6-amine, (25 mg, 0.053 mmol) and triethylamine (1 eq. 100 uL) with 1.5 mL of dry DCM which was purged with nitrogen gas. The solution was cooled to −20° C. while purging with N2 and a solution of bis(trichloromethyl)carbonate (triphosgene) (19.04 mg, 0.064 mmol) in 1 mL of dry DCM was added dropwise to the above stirred solution while maintaining the −20° C. temperature. The solution was stirred an additional 20 minutes at −20° C. then allowed to warm to room temperature.

Step 2

(8R)-8-5,6,7,8-tetrahyrdoquinolylamine HCl Salt (12 mg, 0.8 mmol, 1.5 eq.) and triethylamine (21.64 mg, 0.214 mmol, 4 eq.) in in 0.25 mL of dioxane was added slowly to the previously prepared vial which was stirred at 45° C. for 5 hours. The solvents were removed in vaccuo and DCM (1 mL), TFA (1 mL), and triethylsilane (0.02 mL, 0.125 mmol) were added to the vial. The mixture was stirred at room temperature for 6 h, evaporated in vacuo and purified on reversed phase HPLC to afford 1-[3-(2-methylpyridin-4-yl)-1H-pyrazolo[4,3-c]pyridin-6-yl]-3-[(8R)-5,6,7,8-tetrahydroquinolin-8-yl]urea (5 mg, 0.0078 mmol, 48%).

EXAMPLE 276

1-[(4S)-7-fluoro-3,4-dihydro-2H-chromen-4-yl]-3-[3-(2-methylpyridin-4-yl)-1H-pyrazolo[4,3-c]pyridin-6-yl]urea

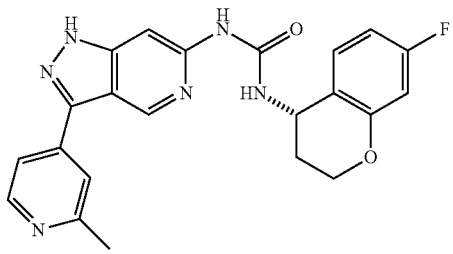

Step 1

In a vial 3-(2-methylpyridin-4-yl)-1-trityl-1H-pyrazolo[4,3-c]pyridin-6-amine (101.0 mg, 0.216 mmol) and CDI (77 mg, 0.475 mmol) were dissolved in THF (6.00 ml) before treatment with 1.0 M solution NaHMDS in THF (0.454 ml, 0.454 mmol). After stirring at RT for 1 h, a solution of (S)-7-fluorochroman-4-amine hydrochloride (97 mg, 0.475 mmol) and TEA (0.151 ml, 1.080 mmol) in THF (2.00 ml) were added. The resulting mixture was heated to 55° C. for 1 h. The mixture was cooled to RT and taken up in DCM. The organic phase was washed with saturated NaHCO₃ and the aqueous phase was back-extracted with DCM (2×). The combined organic layers were dried (Na₂SO₄) and volatiles were evaporated in vacuo. Crude material was purified via reverse phase HPLC over a gradient of 10-90% MeCN in water with 0.1% TFA to yield (S)-1-(7-fluorochroman-4-yl)-3-(3-(2-methylpyridin-4-yl)-1-trityl-1H-pyrazolo[4,3-c]pyridin-6-yl)urea (111 mg, 0.168 mmol, 78% yield). MS ESI calc'd. for $C_{41}H_{33}FN_6O_6$ [M+1]⁺ 661, found 661.

Step 2

In a manner similar to that described in Scheme 6 and Example 30, (S)-1-(7-fluorochroman-4-yl)-3-(3-(2-methylpyridin-4-yl)-1-trityl-1H-pyrazolo[4,3-c]pyridin-6-yl)urea was deprotected with TFA to afford 1-[(4S)-7-fluoro-3,4-dihydro-2H-chromen-4-yl]-3-[3-(2-methylpyridin-4-yl)-1H-pyrazolo[4,3-c]pyridin-6-yl]urea. MS ESI calc'd. for $C_{22}H_{19}FN_6O_2$[M+1]⁺ 419, found 419.

EXAMPLE 328 and 329

1-((3S,4S)-4-fluoro-1-methylpyrrolidin-3-yl)-3-(3-(2-methylpyridin-4-yl)-1H-pyrazolo[4,3-c]pyridin-6-yl)urea (328) and 1-((3R,4R)-4-fluoro-1-methylpyrrolidin-3-yl)-3-(3-(2-methylpyridin-4-yl)-1H-pyrazolo[4,3-c]pyridin-6-yl)urea (329)

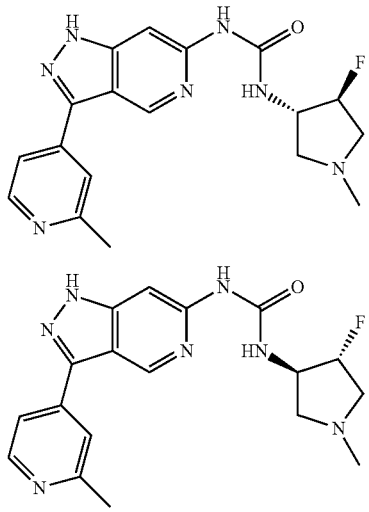

Step 1: ((3S,4S) and (3R,4R)-tert-butyl 3-fluoro-4-(3-(3-(2-methylpyridin-4-yl)-1-trityl-1H-pyrazolo[4,3-c]pyridin-6-yl)ureido)pyrrolidine-1-carboxylate

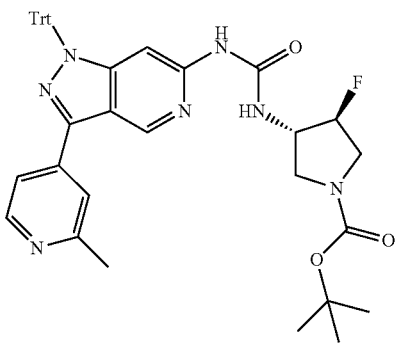

3-(2-methylpyridin-4-yl)-1-trityl-1H-pyrazolo[4,3-c]pyridin-6-amine 5a (200 mg, 0.428 mmol) was taken up in 1,4-Dioxane (8 ml). CDI (209 mg, 1.288 mmol) and imidazole (144 mg, 2.122 mmol) were added and the reaction mixture was allowed to stir at 45° C. overnight. Full conversion to the acyl imidazole intermediate was observed.

(3S and S,4R and R)-tert-butyl 3-amino-4-fluoropyrrolidin-1-carboxylate (135 mg, 0.462 mmol) and triethylamine (0.298 ml, 2.139 mmol) were added and the reaction was allowed to stir at 45° C. for 2 hours. No starting material remained. EtOAc and saturated NH₄Cl were added. The products were extracted into EtOAc (3×) and the combined organic layers were then washed with brine, dried over MgSO₄, and concentrated in vacuo. The yellow oil was taken up in 2 ml of DCM and loaded directly onto a SNAP 25 g column. Purification by MPLC 50-100% EtOAc/hexanes gave our product, racemic (3S,4S) and (3R,4R)-tert-butyl 3-fluoro-4-(3-(3-(2-methylpyridin-4-yl)-1-trityl-1H-pyrazolo[4,3-c]pyridin-6-yl)ureido)pyrrolidine-1-carboxylate. MS ESI calc'd. for $C_{38}H_{37}N_5O_2$ [M+H]⁺ 698, found 698.

Step 2: 1-((3S,4S) and (3R,4R)-4-fluoropyrrolidin-3-yl)-3-(3-(2-methylpyridin-4-yl)-1-trityl-1H-pyrazolo[4,3-c]pyridin-6-yl)urea HCl

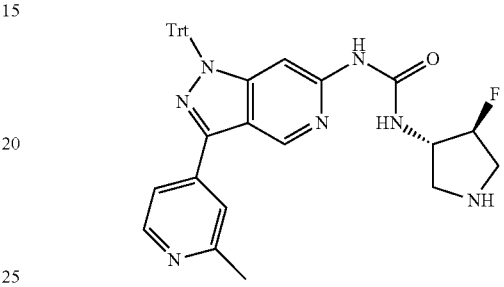

Racemic (3S,4S) and (3R,4R)-tert-butyl 3-fluoro-4-(3-(3-(2-methylpyridin-4-yl)-1-trityl-1H-pyrazolo[4,3-c]pyridin-6-yl)ureido)pyrrolidine-1-carboxylate (200 mg, 0.287 mmol) was taken up in 1,4-Dioxane (2 ml) and 4N HCl in Dioxane (0.2 ml) was added. The reaction was allowed to stir at ambient temperature for 16 hours. LCMS showed that Boc deprotection had occurred without loss of the trityl group. The reaction contents were concentrated in vacuo to give 1-((3S, 4S) and (3R,4R)-4-fluoropyrrolidin-3-yl)-3-(3-(2-methylpyridin-4-yl)-1-trityl-1H-pyrazolo[4,3-c]pyridin-6-yl)urea HCl. MS ESI calc'd. for $C_{36}H_{33}FN_7O$ [M+H]⁺ 598, found 598.

Step 3: Racemic 1-((3S,4S) and (3R,4R)-4-fluoro-1-methylpyrrolidin-3-yl)-3-(3-(2-methylpyridin-4-yl)-1H-pyrazolo[4,3-c]pyridin-6-yl)urea

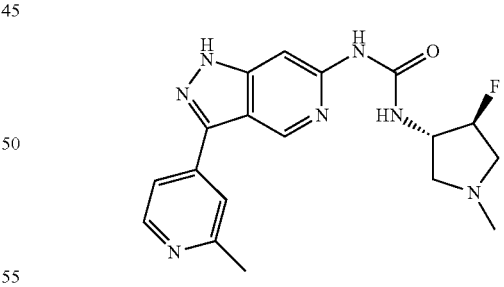

A mixture of 1-((3S,4S) and (3R,4R)-4-fluoropyrrolidin-3-yl)-3-(3-(2-methylpyridin-4-yl)-1-trityl-1H-pyrazolo[4,3-c]pyridin-6-yl)urea HCl (205 mg, 0.343 mmol) and Si-Cyanoborohydride (715 mg, 0.686 mmol) in DCM (2 ml) and MeOH (2 ml) was treated with formaldehyde (0.03 8 ml, 0.514 mmol). The reaction mixture was allowed to stir at ambient temperature for 2 hours. LC/MS showed full conversion to product. The reaction mixture was filtered through a phase separator eluting with MeOH/DCM and the solvent was evaporated in vacuo. TFA (2 ml) and triethylsilane (0.082 ml, 0.514 mmol) were added and the reaction was allowed to stir at ambient temperature for 16 hours, until complete by LC/MS. The mixture was purified by MS-directed reverse phase preparative-HPLC (C-18 stationary phase, eluting with a H$_2$O/MeCN gradient with 0.1% TFA), to yield desired product, 1-((3S,4S) and (3R,4R)-4-fluoro-1-methylpyrrolidin-3-yl)-3-(3-(2-methylpyridin-4-yl)-1H-pyrazolo[4,3-c]pyridin-6-yl)urea. MS ESI calc'd. for C$_{18}$H$_{21}$FN$_7$O [M+H]$^+$ 370, found 370.

The enantiomers of 1-((3S,4S) and (3R,4R)-4-fluoro-1-methylpyrrolidin-3-yl)-3-(3-(2-methylpyridin-4-yl)-1H-pyrazolo[4,3-c]pyridin-6-yl)urea (470 mg, 2.2 mmol) were separated by SFC (Berger Multigram II SFC, column: ES Industries IA 2.1×25 cm, 5 uM mobile phase: 40%/60% Methanol+0.25% dimethyl ethylamine/CO$_{20}$, flow rate: 70 mL/min, 13 min run time). The fractions were collected and the solvent evaporated in vacuo to afford:

1-((3R,4R)-4-fluoro-1-methylpyrrolidin-3-yl)-3-(3-(2-methylpyridin-4-yl)-1H-pyrazolo[4,3-c]pyridin-6-yl)urea 329 (16.9 mg, 0.046 mmol, 107% yield). MS ESI calc'd. For C$_{18}$H$_{21}$FN$_7$O [M+1]$^+$ 370, found 370. MS ESI calc'd. For C$_{18}$H$_{21}$FN$_7$O [M+1]$^+$ 370, found 370. $^1$H NMR (500 MHz, DMSO-d$_6$) δ 13.51 (br s, 1 H), 9.21 (s, 1 H), 9.17 (s, 1 H), 8.53 (d, J=5.0 Hz, 1 H), 7.87 (s, 1 H), 7.80 (d, J=5.1 Hz, 1 H), 7.78 (s, 1 H), 7.51 (br s, 1 H), 4.99-4.87 (m, 1 H), 4.22-4.16 (m, 1 H), 3.00-2.97 (m, 1H), 2.85-2.76 (m, 1 H), 2.71-2.64 (m, 1 H), 2.56 (s, 3 H), 2.28 (s, 3 H), 2.25-2.22 (m, 1 H).

1-((3S,4S)-4-fluoro-1-methylpyrrolidin-3-yl)-3-(3-(2-methylpyridin-4-yl)-1H-pyrazolo[4,3-c]pyridin-6-yl)urea 328(16.6 mg, 0.045 mmol, 105%) MS ESI calc'd. For C$_{18}$H$_{21}$FN$_7$O [M+1]$^+$ 370, found 370. MS ESI calc'd. For C$_{18}$H$_{21}$FN$_7$O [M+1]$^+$ 370, found 370. $^1$H NMR (500 MHz, DMSO-d$_6$) δ 13.51 (br s, 1 H), 9.21 (s, 1 H), 9.17 (s, 1 H), 8.53 (d, J=5.0 Hz, 1 H), 7.87 (s, 1 H), 7.80 (d, J=5.1 Hz, 1 H), 7.78 (s, 1 H), 7.51 (br s, 1 H), 4.99-4.87 (m, 1 H), 4.22-4.16 (m, 1 H), 3.00-2.97 (m, 1 H), 2.85-2.76 (m, 1 H), 2.71-2.64 (m, 1 H), 2.56 (s, 3 H), 2.28 (s, 3 H), 2.25-2.22 (m, 1 H).

EXAMPLE 537

(R)-1-(3-cyano-1H-pyrazolo[4,3-c]pyridin-6-yl)-3-(1-phenylethyl)urea

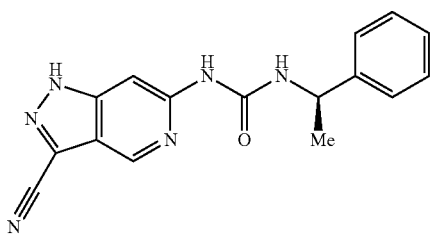 [SMILES: C[C@@H](NC(=O)Nc1cc2[nH]nc(C#N)c2cn1)c1ccccc1]

A flask containing (R)-1-(3-chloro-1H-pyrazolo[4,3-c]pyridin-6-yl)-3-(1-phenylethyl)urea (50.0 mg, 0.158 mmol), zinc cyanide (24.2 mg, 0.206 mmol), allylpalladium chloride dimer (1.7 mg, 4.8 μmol) and 2-(dicyclohexylphosphino-2',4',6'-triisopropylbiphenyl (4.5 mg, 9.5 μmmol) was put under nitrogen and DMA (500 μl) was injected.

The reaction was heated to 120° C. for a period of 14 hours and then allowed to cool. The reaction was diluted with 1.5 mL acetonitrile and stirred with quadrapure to scavenge Pd. The resulting solution was filtered and the filtrate was delivered to the purification group. Reversed phase mass triggered HPLC was performed and the active fractions were returned, frozen and concentrated to dryness on the lyophilizer.

The desired product was obtained in low yield (1.7 mg, 2.5%). MS ESI calc'd. for C$_{16}$H$_{14}$N$_6$O [M+H]$^+$ 307, found 307. $^1$H NMR (500 MHz, Methanol-d$_4$) δ 8.85 (s, 1H), 7.71 (s, 1H), 7.39-7.21 (m, 5H), 4.95 (dd, J=6.6, 13.7 Hz, 1H), 1.51 (d, J=7.1 Hz, 3H) ppm.

EXAMPLE 559

(R)-1-(3-(cyanomethyl)-1H-pyrazolo[4,3-c]pyridin-6-yl)-3-(1-phenylethyl)urea

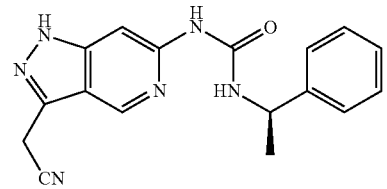 [SMILES: C[C@@H](NC(=O)Nc1cc2[nH]nc(CC#N)c2cn1)c1ccccc1]

Step 1

6-chloro-3-(chloromethyl)-1-trityl-1H-pyrazolo[4,3-c]pyridine (6-chloro-1-trityl-1H-pyrazolo[4,3-c]pyridin-3-yl)methanol (250 mg, 0.587 mmol) was dissolved in DCM (6 ml) and cooled to 0° C. Thionyl chloride (0.086 ml, 1.174 mmol) was added dropwise, the ice bath was removed and the reaction was allowed to stir at rt for 1 h. The reaction was quenched with aq. sodium bicarbonate, organics washed with brine, dried over sodium sulfate, filtered and concentrated to provide Product 1 (225 mg, 0.506 mmol, 86% yield) as a white solid. MS ESI Calc'd for C$_{26}$H$_{19}$Cl$_2$N$_3$ [M+H]+ 444, found 444.

Step 2

2-(6-chloro-1-trityl-1H-pyrazolo[4,3-c]pyridin-3-yl)acetonitrile 6-chloro-3-(chloromethyl)-1-trityl-1H-pyrazolo[4,3-c]pyridine (140 mg, 0.315 mmol) was dissolved in DMF, charged with potassium cyanide (61.5 mg, 0.945 mmol) and heated to 80° C. for 1 h. The solution was diluted with water, extracted 2×10 mL EtOAc, washed with brine, dried over sodium sulfate, filtered and concentrated in vacuo. The crude oil was purified on silica (SNAP 25 g) 10-50% EtOAc/DCM to provide (R)-1-(3-(cyanomethyl)-1H-pyrazolo[4,3-c]pyridin-6-yl)-3-(1-phenylethyl)urea (105 mg, 0.241 mmol, 77% yield). MS ESI Calc'd for C$_{27}$H$_{19}$ClN$_4$ [M+H]+ 435, found 435.

Step 3

(R)-1-(3-(cyanomethyl)-1-trityl-1H-pyrazolo[4,3-c]pyridin-6-yl)-3-(1-phenylethyl)urea 2-(6-chloro-1-trityl-1H-pyrazolo[4,3-c]pyridin-3-yl)acetonitrile (100 mg, 0.230 mmol), Reactant 3 (76 mg, 0.460 mmol), cesium carbonate (225 mg, 0.690 mmol) and CHLORO[2-(DICYCLOHEXYLPHOSPHINO)-3,6-DIMETHOXY-2'-4'-6'-TRI-I-PROPYL-1,1'-BIPHENYL][2-(2-AMINOETHYL)PHENYL]PALLADIUM(II) (12.86 mg, 0.016 mmol) were taken up in Dioxane (2299 μl) in a 1.5 mL microwave vial and the vial was evacuated and back-filled with N2 (x3). The reaction mixture was stirred at 100° C. for 2 hours. The reaction was complete by LCMS. The crude reaction mixture was diluted with methanol filtered through Si-Thiol 6 ml, 500 mg, cartridges (to remove the excess Pd). The filtrate was concentrated, and purified on silica gel 5-50% DCM/EtOAc to provide (R)-1-(3-(cyanomethyl)-1-trityl-1H-pyrazolo[4,3-c]pyridin-6-yl)-3-(1-phenylethyl)urea (82 mg, 0.146 mmol, 63.4% yield)

Step 4

(R)-1-(3-(cyanomethyl)-1H-pyrazolo[4,3-c]pyridin-6-yl)-3-(1-phenylethyl)urea (R)-1-(3-(cyanomethyl)-1-trityl-1H-pyrazolo[4,3-c]pyridin-6-yl)-3-(1-phenylethyl)urea (20 mg, 0.036 mmol) was dissolved in TFA (0.274 ml, 3.55 mmol) and stirred for 30 m at rt. The solvents were removed in vacuo and the residue purified by reverse-phase HPLC to provide pure (R)-1-(3-(cyanomethyl)-1H-pyrazolo[4,3-c]pyridin-6-yl)-3-(1-phenylethyl)urea (9 mg, 0.021 mmol, 58.3% yield). MS ESI Calc'd for $C_{17}H_{16}N_6O$ [M+H]$^+$ 321, found 321.

EXAMPLE 563

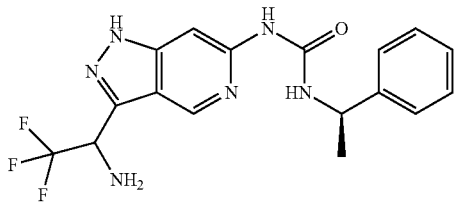 [SMILES: C[C@@H](NC(=O)Nc1cc2[nH]nc(C(N)C(F)(F)F)c2cn1)c1ccccc1]

1-amino-2,2,2-trifluoroethyl)-1H-pyrazolo[4,3-c]pyridin-6-yl)-3-((R)-1-phenylethyl)urea N-(1-(6-chloro-1-trityl-1H-pyrazolo[4,3-c]pyridin-3-yl)-2,2,2-trifluoroethyl)-2-methylpropane-2-sulfinamide (115 mg, 0.193 mmol), R-phenethylurea (63.3 mg, 0.385 mmol), cesium carbonate (188 mg, 0.578 mmol) and CHLORO[2-(DICYCLOHEXYLPHOSPHINO)-3,6-DIMETHOXY-2'-4'-6'-TRI-I-PROPYL-1,1'-BIPHENYL][2-(2-AMINOETHYL)PHENYL]PALLADIUM(II) (10.77 mg, 0.013 mmol) were taken up in Dioxane (1926 µl) in a 1.5 mL microwave vial and the vial was evacuated and back-filled with N2 (x3). The reaction mixture was stirred at 85° C. for 2 hours. The reaction was complete by LCMS. The crude reaction mixture was diluted with methanol filtered through Si-Thiol 6 ml, 500 mg, cartridges (to remove the excess Pd). The filtrate was concentrated, and purified on silica gel 5-50% DCM/EtOAc. The trityl material was taken up in 4.0M HCL/dioxane and stirred at rt for 1 h. Sulfinamide cleavage was seen by LC/MS, but no trityl deprotection. Added 1 eq. triethylsilane and 2 mL TFA and heated in a sealed vial to 60° C. for 45 minutes. The solvents were evaporated in vacuo and the solution was resuspended in DMSO/MeOH and submitted to the Purification Group for purification by reverse phase mass-triggered preparative HPLC. Pure fractions were evaporated in vacuo to provide pure 1-(3-(1-amino-2,2,2-trifluoroethyl)-1H-pyrazolo[4,3-c]pyridin-6-yl)-3-((R)-1-phenylethyl)urea (14 mg, 0.037 mmol, 19.21% yield). MS ESI Calc'd for $C_{17}H_{17}F_3N_6O$ [M+H]$^+$378, found 378. $^1$H NMR (500 MHz, cd3od) δ 8.90 (s, 1H), 7.48 (s, 1H), 7.43-7.29 (m, 4H), 7.29-7.19 (m, 1H), 5.92 (t, J=55.6, –1H), 4.98 (q, J=6.9, 1H, 1.52 (d, J=7.0, 3H).

LC/MS M+H=378.1 1H NMR (500 MHz, CD$_3$OD) δ 8.90 (s, 1H), 7.48 (s, 1H), 7.43-7.29 (m, 4H), 7.29-7.19 (m, 1H), 5.92 (t, J=55.6, –1H), 4.98 (q, J=6.9, 1H, 1.52 (d, J=7.0, 3H).

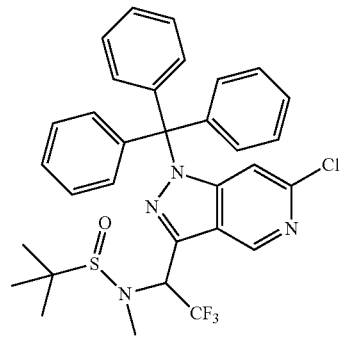 [SMILES: CN(C(c1nn(C(c2ccccc2)(c2ccccc2)c2ccccc2)c2cc(Cl)ncc12)C(F)(F)F)S(=O)C(C)(C)C]

N-(1-(6-chloro-1-trityl-1H-pyrazolo[4,3-c]pyridin-3-yl)-2,2,2-trifluoroethyl)-N,2-dimethylpropane-2-sulfinamide N-(1-(6-chloro-1-trityl-1H-pyrazolo[4,3-c]pyridin-3-yl)-2,2,2-trifluoroethyl)-2-methylpropane-2-sulfonamide (108 mg, 0.181 mmol) was cooled to 0° C. and charged with lithium bis(trimethylsilyl)amide (0.217 ml, 0.217 mmol) followed by iodomethahe (0.011 ml, 0.181 mmol) (~2 drops). The reaction was allowed to warm to rt overnight. Quenched excess LiHMDS with methanol and evaporated solvents on the V-10. The residue was purified on silica, 10-50% DCM/EtOAc to provide N-(1-(6-chloro-1-trityl-1H-pyrazolo[4,3-c]pyridin-3-yl)-2,2,2-trifluoroethyl)-N,2-dimethylpropane-2-sulfinamide (53 mg, 0.09 mmol, 48% yield) MS ESI Calc'd for $C_{32}H_{30}ClF_3N_4OS$ [M+H]$^+$ 611, found 611.

EXAMPLE 564

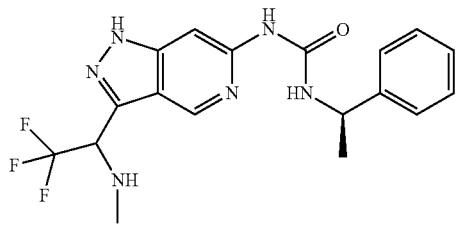 [SMILES: CNC(c1n[nH]c2cc(NC(=O)N[C@H](C)c3ccccc3)ncc12)C(F)(F)F]

1-((R)-1-phenylethyl)-3-(3-(2,2,2-trifluoro-1-(methylamino)ethyl)-1H-pyrazolo[4,3-c]pyridin-6-yl)urea Buchwald Coupling/deprotection sequence same as 1-amino-2,2,2-trifluoroethyl)-1H-pyrazolo[4,3-c]pyridin-6-yl)-3-((R)-1-phenylethyl)urea MS ESI Calc'd for C18H19F3N6O [M+H]$^+$ 393, found 393; $^1$H NMR (500 MHz, CD$_3$OD) δ 10.27 (s, 1H), 8.85 (d, J=4.4, 1H), 8.90-8.54

(m, 5H), 6.41-6.19 (m, 1H), 6.11-5.99 (m, 1H), 3.76 (d, J=2.2, 3H), 2.89 (dd, J=1.3, 7.0, 3H).

EXAMPLE 571

(R)-1-(7-chloro-3-(2-methylpyridin-4-yl)-1H-pyrazolo[4,3-c]pyridin-6-yl)-3-(1-phenylethyl)urea

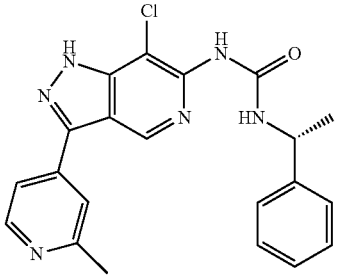 [SMILES: Cc1cc(-c2n[nH]c3c(Cl)c(NC(=O)N[C@H](C)c4ccccc4)ncc23)ccn1]

To the solution of (R)-1-(3-(2-methylpyridin-4-yl)-1H-pyrazolo[4,3-c]pyridin-6-yl)-3-(1-phenylethyl)urea, example 6, (70 mg, 0.188 mmol) in DMF (3.0 ml) was added N-chlorosuccinimide (25.10 mg, 0.188 mmol) at rt. The resulting solution was allowed to stir for 16 h.

The crude product was purified by by mass triggered, reverse phase prep-HPLC and a TFA salt was got. The TFA salt was taken in MeOH and filtered through NaHCO3 cartridge. The filtrate was lyophilized to give (R)-1-(7-chloro-3-(2-methylpyridin-4-yl)-1H-pyrazolo[4,3-c]pyridin-6-yl)-3-(1-phenylethyl)urea (32 mg, 0.079 mmol, 41.8% yield)).MS ESI calc'd. for $C_{21}H_{19}ClN_6O$ [M+H]$^+$ 407 found 407.

EXAMPLE 600

1-[(1R)-2-methoxy-1-phenylethyl]-3-[3-(1-methyl-1H-pyrazol-4-yl)-1H-pyrazolo[4,3-c]pyridin-6-yl]urea

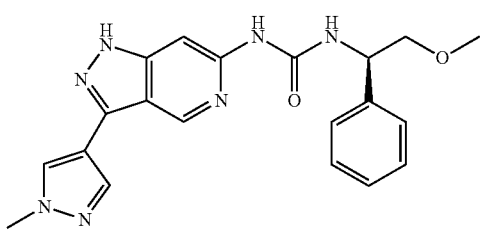

Step 1

To a vial were added 6-chloro-3-(1-methyl-1H-pyrazol-4-yl)-1-trityl-1H-pyrazolo[4,3-c]pyridine (47.6 mg, 0.100 mmol), (S)-1-(2-methoxy-1-phenylethyl)urea (38.8 mg, 0.200 mmol), cesium carbonate (0.024 ml, 0.300 mmol), CHLORO[2-(DICYCLOHEXYLPHOSPHINO)-3,6-DIMETHOXY-2',4',6'-TRI-I-PROPYL-1,1'-BIPHENYL][2-(2-AMINOETHYL)PHENYL]PALLADIUM(II) (15.98 mg, 0.020 mmol) and DMA (1.0 ml). The mixture was Vac/N2 purged 6 times and heated at 100° C. for 2 h. LC-MS showed complete conversion. The mixture was diluted with EtOAc and washed with water and brine. After dried over Na2SO4 the solution was concentrated to yield (S)-1-(2-methoxy-1-phenylethyl)-3-(3-(1-methyl-1H-pyrazol-4-yl)-1-trityl-1H-pyrazolo[4,3-c]pyridin-6-yl)urea (63.4 mg, 0.100 mmol, 100% yield) without purification.

Step 2

To the solution of (S)-1-(2-methoxy-1-phenylethyl)-3-(3-(1-methyl-1H-pyrazol-4-yl)-1-trityl-1H-pyrazolo[4,3-c]pyridin-6-yl)urea (63.4 mg, 0.100 mmol) and trifluoroacetic acid (0.383 ml, 5.00 mmol) in Dichloromethane (2.0 ml) was added triethylsilane (17.45 mg, 0.150 mmol). The resulting mixture was allowed to stir at rt for 18 h. LC-MS showed the completion of the reaction. After concentration the residue was purified by reverse phase HPLC to provide desired product (17.3 mg, 0.028 mmol, 27.9% yield). MS ESI Calc'd for $C_{20}H_{21}N_7O_2$ [M+H]$^+$ 392, found 392

EXAMPLE 620

1-[3-(ethoxymethyl)-1H-pyrazolo[4,3-c]pyridin-6-yl]-3-[(1R)-1-phenylethyl]urea

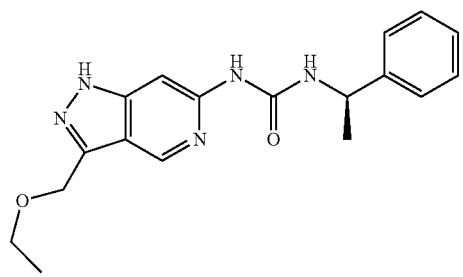 [SMILES: CCOCc1n[nH]c2cc(NC(=O)N[C@H](C)c3ccccc3)ncc12]

Step 1

At −78° C., to a solution of methyl 6-chloro-1-trityl-1H-pyrazolo[4,3-c]pyridine-3-carboxylate (1.5 g, 3.30 mmol) in DCM (12 ml), 1.0 M DIISOBUTYLALUMINUM HYDRIDE (7.27 ml, 7.27 mmol) in THF was added dropwise under N2. The reaction mixture was allowed to stir at −78° C. for 2 h.

EtOAc and Rochelle salt solution were added into the reaction mixture and the water layer was extracted by EtOAc for two more times. The organic layers were combined and washed by water and brine. The organic phase was dried over sodium sulfate and concentrated under reduced pressure. The residue was purified by MPLC (0-50% EtOAc/Haxanes) gave (6-chloro-1-trityl-1H-pyrazolo[4,3-c]pyridin-3-yl)methanol (1.022 g, 2.400 mmol, 72.6%). MS ESI calc'd. for $C_{26}H_{20}ClN_3O$ [M+H]$^+$ 426, found 426.

Step 2

To a vial were added (6-chloro-1-trityl-1H-pyrazolo[4,3-c]pyridin-3-yl)methanol (600 mg, 1.409 mmol), (R)-1-(1-phenylethyl)urea (463 mg, 2.82 mmol), cesium carbonate (0.33 8 ml, 4.23 mmol), CHLORO[2-(DICYCLOHEXYLPHOSPHINO)-3,6-DIMETHOXY-2'-4'-6'-TRI-I-PROPYL-1,1'-BIPHENYL][2-(2-AMINOETHYL)PHENYL]PALLADIUM(II) (225 mg, 0.282 mmol) and DMA (10 ml). The mixture was Vac/N2 purged 6 times and heated at 100° C. for 2 h.

The mixture was diluted with EtOAc and washed with water and brine. After dried over Na2SO4 the solution was concentrated. The crude product was purified by MPLC (0-80% EtOAc/Hexanes) gave (R)-1-(3-(hydroxymethyl)-1-trityl-1H-pyrazolo[4,3-c]pyridin-6-yl)-3-(1-phenylethyl)urea (328 mg, 0.592 mmol, 42.1% yield). MS ESI calc'd. for $C_{35}H_{31}N_5O_2$ [M+H]$^+$ 554, found 554.

Step 3

The solution of (R)-1-(3-(hydroxymethyl)-1-trityl-1H-pyrazolo[4,3-c]pyridin-6-yl)-3-(1-phenylethyl)urea (124 mg, 0.224 mmol), cesium carbonate (146 mg, 0.448 mmol) and iodoethane (26.9 μl, 0.336 mmol) in DMF was stirred at 60° C. for 24 h. Water was added into the solution and extracted with EtOAc for twice. The combined organic extracts were washed with water, brine and dried over Na2SO4. After concentration (R)-1-(3-(ethoxymethyl)-1-trityl-1H-pyrazolo[4,3-c]pyridin-6-yl)-3-(1-phenylethyl)urea (130 mg, 0.224 mmol, 100% yield) was yielded without purification.

MS ESI calc'd. for C37H35N5O2 [M+H]$^+$ 582, found 582.

Step 4

To the solution of (R)-1-(3-(ethoxymethyl)-1-trityl-1H-pyrazolo[4,3-c]pyridin-6-yl)-3-(1-phenylethyl)urea (130 mg, 0.223 mmol) and trifluoroacetic acid (0.856 ml, 11.17 mmol) in dichloromethane (2.0 ml) was added triethylsilane (39.0 mg, 0.335 mmol). The resulting mixture was allowed to stir at rt for 18 h. The reaction was concentrated in vacuo and submitted for reversed phase HPLC purification to provide the desired product (28.5 mg, 0.063 mmol, 28.1% yield). MS ESI calc'd. for $C_{18}H_{21}N_5O_2$ [M+H]$^+$ 340, found 340.

EXAMPLE 623

1-[3-(4-Fluorophenyl)-1H-pyrazolo[4,3-c]pyridin-6-yl]-3-(2-methoxyethyl)urea

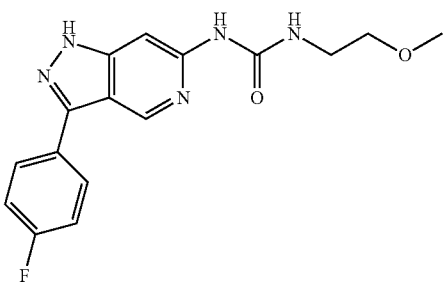 [SMILES: COCCNC(=O)Nc1cc2[nH]nc(-c3ccc(F)cc3)c2cn1]

6-Chloro-3-(4-fluorophenyl)-1H-pyrazolo[4,3-c]pyridine (433 mg, 1.748 mmol), 1-(2-methoxyethyl)urea (313 mg, 2.65 mmol) and chloro[2-(dicyclohexylphosphino)-3,6-dimethoxy-2'-4'-6'-tri-i-propyl-1,1'-biphenyl][2-(2-aminoethyl)phenyl]palladium(II) (97 mg, 0.121 mmol) were taken up in THF (10.5 mL) in a 20 mL microwave vial. 1 M potassium t-butoxide in THF (5.25 mL, 5.25 mmol) was added and the vial was evacuated and back-filled with N2 (x3). The reaction mixture was stirred at 60° C. for 18 hours. Room temperature was attained and the mixture filtered through Celite, eluting with MeOH. The filtrate was concentrated in vacuo and the residue purified by MPLC (0-10% MeOH-EtOAc). The product was then triturated in EtOH to give 1-(3-(4-fluorophenyl)-1H-pyrazolo[4,3-c]pyridin-6-yl)-3-(2-methoxyethyl)urea (237 mg, 0.720 mmol, 41.2% yield). MS ESI calc'd. for $C_{16}H_{17}FN_5O_2$ [M+H]$^+$ 330, found 330. $^1$H NMR (600 MHz, DMSO-d$_6$) δ 13.21 (s, 1H), 9.15 (s, 1H), 9.04 (s, 1H), 8.07-8.04 (m, 2H), 7.72 (s, 1H), 7.35-7.31 (m, 3H), 3.39 (t, J=5.5 Hz, 2H), 3.32-3.29 (m, 2H), 3.27 (s, 3H).

EXAMPLE 624

1-[3-(4-Cyanophenyl)-1H-pyrazolo[4,3-c]pyridin-6-yl]-3-(2-methoxyethyl)urea

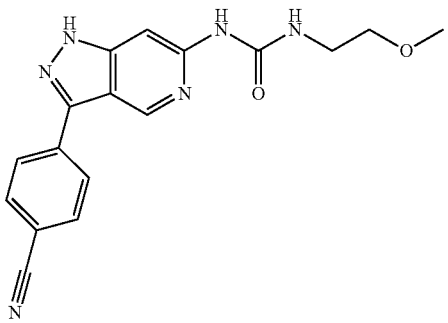

Step 1

Sodium hypochlorite (121 mL, 195 mmol) was gradually added to a suspension of 6-chloro-1H-pyrazolo[4,3-c]pyridine (10 g, 65.1 mmol) in EtOH (100 mL) at 0° C. The reaction mixture was then stirred at room temperature for 10 minutes. Water and sodium sulfite (24.62 g, 195 mmol) were added, forming a clear solution, and the mixture was extracted with EtOAc. The organic phase was concentrated in vacuo to give 3,6-dichloro-1H-pyrazolo[4,3-c]pyridine (11.6 g, 61.7 mmol, 95% yield). MS ESI calc'd. for $C_6H_4Cl_2N_3$ [M+H]$^+$ 188, found 188.

Step 2

A mixture of 3,6-dichloro-1H-pyrazolo[4,3-c]pyridine (583.6 mg, 3.10 mmol), 1-(2-methoxyethyl)urea (550 mg, 4.66 mmol), chloro[2-(dicyclohexylphosphino)-3,6-dimethoxy-2'-4'-6'-tri-1-propyl-1,1'-biphenyl][2-(2-aminoethyl)phenyl]palladium(II) (248 mg, 0.310 mmol) and 1.78 M KOtBu in THF (5231 μl, 9.31 mmol) was degassed and then THF (0.5 mL) was added. The reaction mixture was heated to 60° C. overnight. The reaction was diluted with ethyl acetate and washed with water. The combined organics were dried over magnesium sulfate and concentrated under reduced pressure. The residue was purified by MPLC (0-30% MeOH-DCM) gave 1-(3-chloro-1H-pyrazolo[4,3-c]pyridin-6-yl)-3-(2-methoxyethyl)urea (214 mg, 0.794 mmol, 25.6% yield). MS ESI calc'd. for $C_{10}H_{13}ClN_5O_2$ [M+H]$^+$ 270, found 270.

Step 3

1-(3-Chloro-1H-pyrazolo[4,3-c]pyridin-6-yl)-3-(2-methoxyethyl)urea (48 mg, 0.178 mmol), 4-cyanophenylboronic acid (103 mg, 0.701 mmol), potassium phosphate (77 mg, 0.363 mmol) and X-Phos biphenyl precatalyst (13.1 mg, 0.017 mmol) were taken up in n-pentanol (1.4 mL)/water (0.7 mL) in a 5 mL microwave vial. The vial was evacuated and back-filled with $N_2$ (x3) before heating to 120° C. for 20 minutes under microwave irradiation. The reaction mixture was diluted with MeOH and filtered through Celite, eluting with MeOH. The filtrate was concentrated in vacuo and the residue purified by MPLC (0-10% MeOH-EtOAc) to give 16 mg of product that required further purification. The crude product was taken up in 0.5 mL of DMF and the mixture was purified by mass triggered, reverse phase prep-HPLC. The product fraction was lyophilized to give the TFA salt of 1-(3-(4-cyanophenyl)-1H-pyrazolo[4,3-c]pyridin-6-yl)-3-(2-methoxyethyl)urea (7.6 mg, 0.017 mmol, 9.48% yield). MS ESI calc'd. for $C_{16}H_{17}FN_5O_2$ [M+H]$^+$ 337, found 337. $^1$H NMR (600 MHz, DMSO-$d_6$) δ 13.51 (s, 1H), 9.23 (s, 1H), 9.15 (s, 1H), 8.24-8.22 (m, 1H), 7.96-7.94 (m, 1H), 7.78 (s, 1H), 7.29 (br s, 1H), 3.39 (t, J=6.0 Hz, 2H), 3.32-3.29 (m, 2H), 3.27 (s, 3H).

Table 2 Below Summarizes the Examples Above and Provides Additional Examples. the "Route Used" Column Indicates the Example Followed to Obtain the Compound Listed in Table 2.

TABLE 2

| EX | Structure | Exact Mass [M + H]+ | Route Used |
|---|---|---|---|
| 116 | 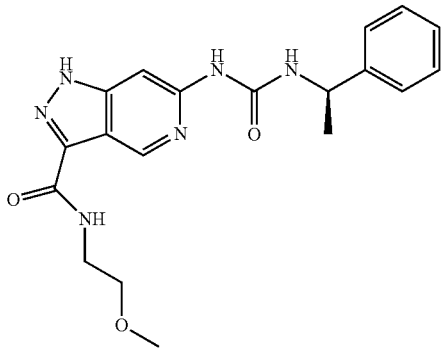<br>N-(2-methoxyethyl)-6-({[(1R)-1-phenylethyl]carbamoyl}amino)-1H-pyrazolo[4,3-c]pyridine-3-carboxamide | Calc'd 383, found 383 | |
| 117 | 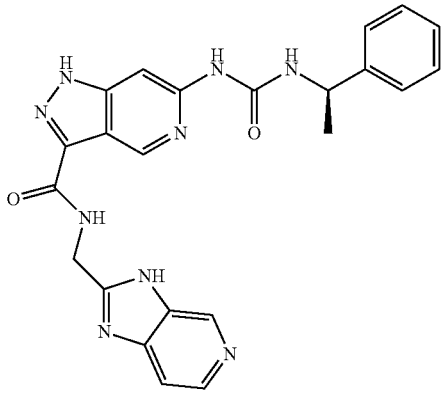<br>N-(3H-imidazo[4,5-c]pyridin-2-ylmethyl)-6-({[(1R)-1-phenylethyl]carbamoyl}amino)-1H-pyrazolo[4,3-c]pyridine-3-carboxamide | Calc'd 456, found 456 | 116 |
| 118 | 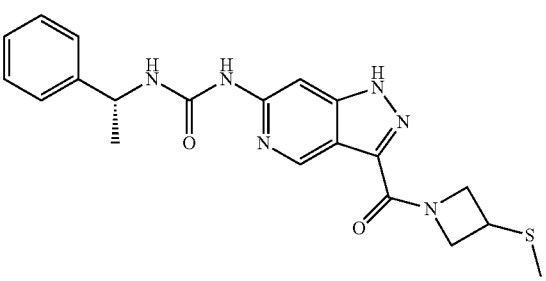<br>1-(3-{[3-(methylsulfanyl)azetidin-1-yl]carbonyl}-1H-pyrazolo[4,3-c]pyridine-6-yl)-3-[(1R)-1-phenylethyl]urea | Calc'd 411, found 411 | 116 |

TABLE 2-continued

| EX | Structure | Exact Mass [M + H]+ | Route Used |
|---|---|---|---|
| 119 | 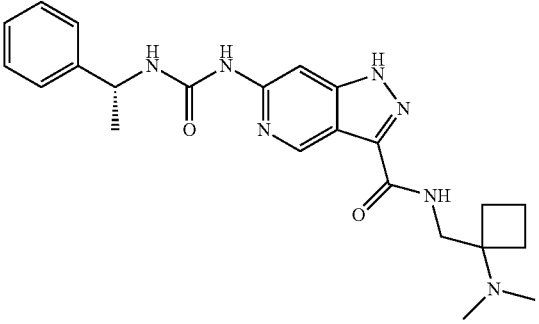<br>N-{[1-(dimethylamino)cyclobutyl]methyl}-6-({[(1R)-1-phenylethyl]carbamoyl}amino)-1H-pyrazolo[4,3-c]pyridine-3-carboxamide | Calc'd 436, found 436 | 116 |
| 120 | 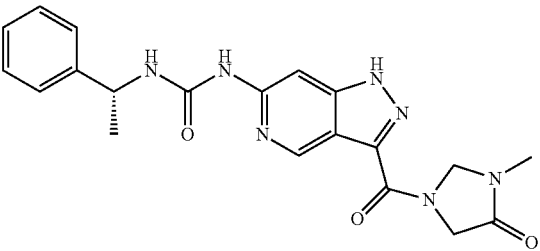<br>1-{3-[(3-methyl-4-oxoimidazolidin-1-yl)carbonyl]-1H-pyrazolo[4,3-c]pyridine-6-yl}-3-[(1R)-1-phenylethyl]urea | Calc'd 408, found 408 | 116 |
| 121 | 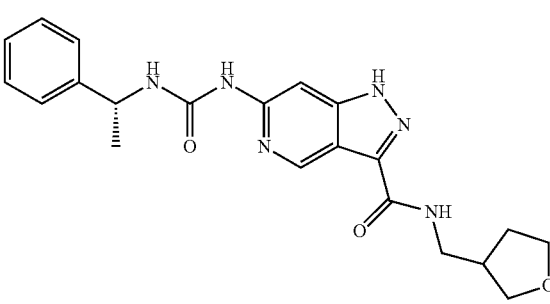<br>6-({[(1R)-1-phenylethyl]carbamoyl}amino)-N-(tetrahydrofuran-3-ylmethyl)-1H-pyrazolo[4,3-c]pyridine | Calc'd 409, found 409 | 116 |
| 122 | 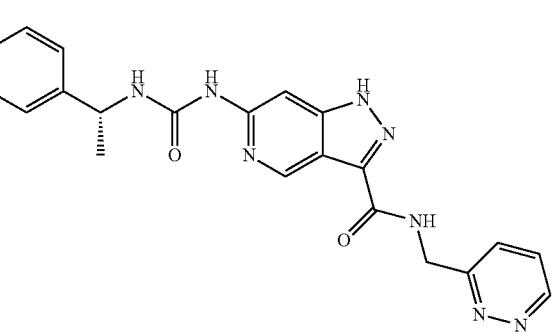<br>6-({[(1R)-1-phenylethyl]carbamoyl}amino)-N-(pyridazin-3-ylmethyl)-1H-pyrazolo[4,3-c]pyridine-3-carboxamide | Calc'd 417, found 417 | 116 |

TABLE 2-continued

| EX | Structure | Exact Mass [M + H]+ | Route Used |
|---|---|---|---|
| 123 | N-(3,3-difluoro-2-hydroxypropyl)-6-({[(1R)-1-phenylethyl]carbamoyl}amino)-1H-pyrazolo[4,3-c]pyridine-3-carboxamide | Calc'd 419, found 419 | 116 |
| 124 | N-(3,3-difluoro-2-hydroxypropyl)-6-({[(1R)-1-phenylethyl]carbamoyl}amino)-1H-pyrazolo[4,3-c]pyridine-3-carboxamide | Calc'd 395, found 395 | 116 |
| 125 | N-(2,2-difluoro-3-morpholin-4-ylpropyl)-6-({[(1R)-1-phenylethyl]carbamoyl}amino)-1H-pyrazolo[4,3-c]pyridine-3-carboxamide | Calc'd 488, found 488 | 116 |

TABLE 2-continued

| EX | Structure | Exact Mass [M + H]+ | Route Used |
|---|---|---|---|
| 126 | N-[2-(1-hydroxycyclopentyl)ethyl]-6-({[(1R)-1-phenylethyl]carbamoyl}amino)-1H-pyrazolo[4,3-c]pyridine-3-carboxamide | Calc'd 437, found 437 | 116 |
| 127 | N-[(4-hydroxytricyclo[3.3.1.1~3,7~]dec-1-yl)methyl]-6-({[(1R)-1-phenylethyl]carbamoyl}amino)-1H-pyrazolo[4,3-c]pyridine-3-carboxamide | Calc'd 489, found 489 | 116 |
| 128 | N-(2,2-difluoro-3-pyrrolidin-1-ylpropyl)-6-({[(1R)-1-phenylethyl]carbamoyl}amino)-1H-pyrazolo[4,3-c]pyridine-3-carboxamide | Calc'd 472, found 472 | 116 |

TABLE 2-continued

| EX | Structure | Exact Mass [M + H]+ | Route Used |
|---|---|---|---|
| 129 | N-[(1-cyclopropylpyrrolidin-3-yl)methyl]-6-({[(1R)-1-phenylethyl]carbamoyl}amino)-1H-pyrazolo[4,3-c]pyridine-3-carboxamide | Calc'd 448, found 448 | 116 |
| 130 | 1-(3-{[(3S,4S)-3-hydroxy-4-methoxypyrrolidin-1-yl]carbonyl}-1H-pyrazolo[4,3-c]pyridin-6-yl)-3-[(1R)-1-phenylethyl]urea | Calc'd 425, found 425 | 116 |
| 131 | N-[(2-methoxypropyl)-6-({[(1R)-1-phenylethyl]carbamoyl}amino)-1H-pyrazolo[4,3-c]pyridine-3-carboxamide | Calc'd 397, found 397 | 116 |

TABLE 2-continued

| EX | Structure | Exact Mass [M + H]+ | Route Used |
|---|---|---|---|
| 132 | 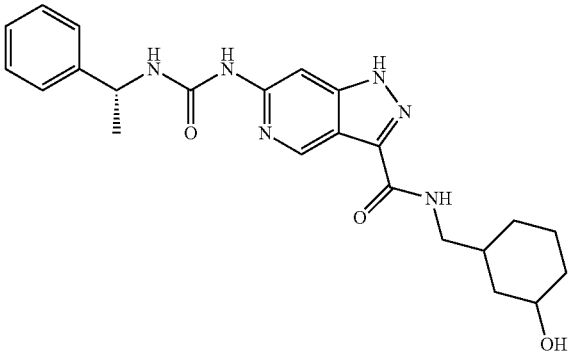<br>N-[(3-hydroxycyclohexyl)methyl]-6-({[(1R)-1-phenylethyl]carbamoyl}amino)-1H-pyrazolo[4,3-c]pyridine-3-carboxamide | Calc'd 437, found 437 | 116 |
| 133 | 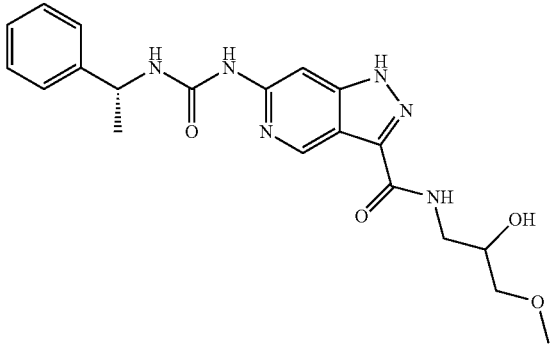<br>N-(2-hydroxy-3-methoxypropyl)-6-({[(1R)-1-phenylethyl]carbamoyl}amino)-1H-pyrazolo[4,3-c]pyridine-3-carboxamide | Calc'd 413, found 413 | 116 |
| 134 | 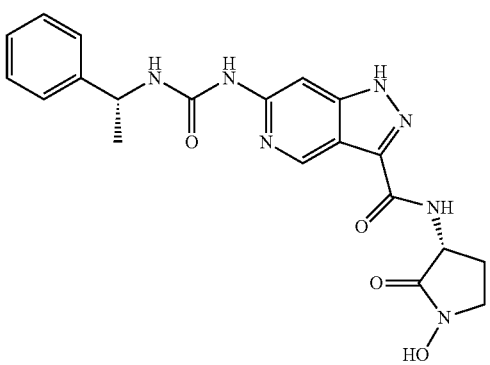<br>N-[(3R)-1-hydroxy-2-oxypyrrolidin-3-yl]-6-({[(1R)-1-phenylethyl]carbamoyl}amino)-1H-pyrazolo[4,3-c]pyridine-3-carboxamide | Calc'd 424, found 424 | 116 |

TABLE 2-continued

| EX | Structure | Exact Mass [M + H]+ | Route Used |
|---|---|---|---|
| 135 | N-(2-hydroxy-4-methypentyl)-6-({[(1R)-1-phenylethyl]carbamoyl}amino)-1H-pyrazolo[4,3-c]pyridine-3-carboxamide | Calc'd 425, found 425 | 116 |
| 136 | N-(1-hydroxycyclobutyl)methyl]-6-({[(1R)-1-phenylethyl]carbamoyl}amino)-1H-pyrazolo[4,3-c]pyridine-3-carboxamide | Calc'd 409, found 409 | 116 |
| 137 | N-methyl-6-({[(1R)-1-phenylethyl]carbamoyl}amino)-1H-pyrazolo[4,3-c]pyridine-3-carboxamide | Calc'd 339, found 339 | 116 |
| 138 | N-methyl-6-({[(1R)-1-phenylethyl]carbamoyl}amino)-1H-pyrazolo[4,3-c]pyridine-3-carboxamide | Calc'd 353, found 353 | 116 |

TABLE 2-continued

| EX | Structure | Exact Mass [M + H]+ | Route Used |
|---|---|---|---|
| 139 | 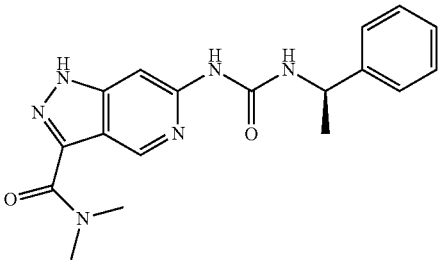<br>N,N-dimethyl-6-({[(1R)-1-phenylethyl]carbamoyl}amino)-1H-pyrazolo[4,3-c]pyridine-3-carboxamide | Calc'd 353, found 353 | 116 |
| 140 | 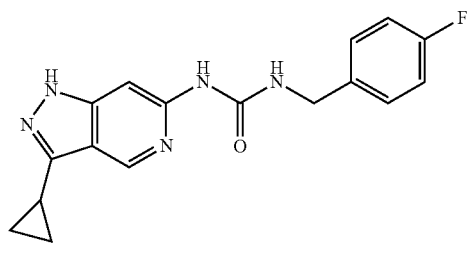<br>1-(3-cyclopropyl-1H-pyrazolo[4,3-c]pyridin-6-yl)-3-(4-fluorobenzyl)urea | Calc'd 326, found 326 | 140 |
| 141 | 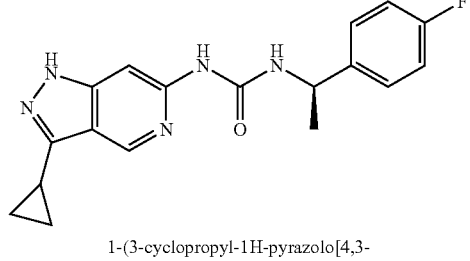<br>1-(3-cyclopropyl-1H-pyrazolo[4,3-c]pyridin-6-yl)-3-[(1R)-1-(4-fluorophenyl)ethyl]urea | Calc'd 340, found 340 | 140 |
| 142 | 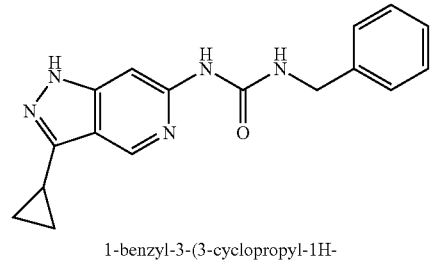<br>1-benzyl-3-(3-cyclopropyl-1H-pyrazolo[4,3-c]pyridin-6-yl)urea | Calc'd 308, found 308 | 140 |
| 143 | 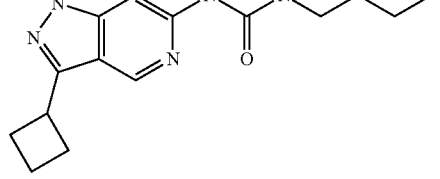<br>1-butyl-3-(3-cyclobutyl-1H-pyrazolo[4,3-c]pyridin-6-yl)urea | Calc'd 288, found 288 | ------ |

TABLE 2-continued

| EX | Structure | Exact Mass [M + H]+ | Route Used |
|---|---|---|---|
| 144 | 1-(3-cyclobutyl-1H-pyrazolo[4,3-c]pyridin-6-yl)-3-[(1R)-1-(4-fluorophenyl)ethyl]urea | Calc'd 354, found 354 | 143 |
| 145 | 1-(3-cyclobutyl-1H-pyrazolo[4,3-c]pyridin-6-yl)-3-[(1R)-1-phenylethyl]urea | Calc'd 336, found 336 | 143 |
| 146 | 1-(3-cyclobutyl-1H-pyrazolo[4,3-c]pyridin-6-yl)-3-(4-fluorobenzyl)urea | Calc'd 340, found 340 | 143 |
| 147 | 1-benzyl-3-(3-cyclobutyl-1H-pyrazolo[4,3-c]pyridin-6-yl)urea | Calc'd 322, found 322 | 143 |
| 148 | 1-(cyclopropylmethyl)-3-(3-cyclopropyl-1H-pyrazolo[4,3-c]pyridin-6-yl)urea | Calc'd 272, found 272 | 30 |

TABLE 2-continued

| EX | Structure | Exact Mass [M + H]+ | Route Used |
|---|---|---|---|
| 149 | 1-(3-cyclobutyl-1H-pyrazolo[4,3-c]pyridin-6-yl)-3-[(1R)-1-pyridine-2-ylethyl]urea | Calc'd 337.0, found | 30 |
| 150 | 1-[(1R)-1-(4-chlorophenyl)ethyl]-3-(3-cyclopropyl-1H-pyrazolo[4,3-c]pyridin-6-yl)urea | Calc'd 356, found 356 | 30 |
| 151 | 1-[(1R)-1-(4-chlorophenyl)ethyl]-3-(3-cyclobutyl-1H-pyrazolo[4,3-c]pyridin-6-yl)urea | Calc'd 370, found 370 | 30 |
| 152 | 1-(3-cyclopropyl-1H-pyrazolo[4,3-c]pyridine-6-yl)-3-[(1R)-1-pyridin-2-ylethyl]urea | Calc'd 323, found 323 | 30 |

TABLE 2-continued

| EX | Structure | Exact Mass [M + H]+ | Route Used |
|---|---|---|---|
| 153 | 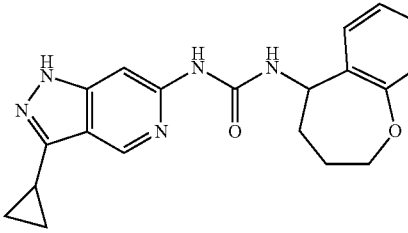<br>1-(3-cyclopropyl-1H-pyrazolo[4,3-c]pyridine-6-yl)-3-(2,3,4,5-tetrahydro-1-benzoxepin-5-yl)urea | Calc'd 364, found 364 | 140 |
| 154 | 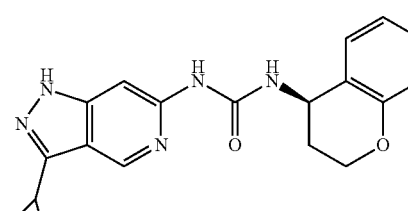<br>1-(3-cyclopropyl-1H-pyrazolo[4,3-c]pyridine-6-yl)-3-[(4R)-3,4,-dihydro-2H-chromen-4-yl]urea | Calc'd 350, found 350 | 140 |
| 155 | 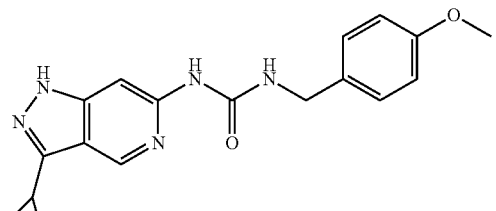<br>1-(3-cyclopropyl-1H-pyrazolo[4,3-c]pyridine-6-yl)-3-(4-methoxybenzyl)urea | Calc'd 338, found 338 | 140 |
| 156 | 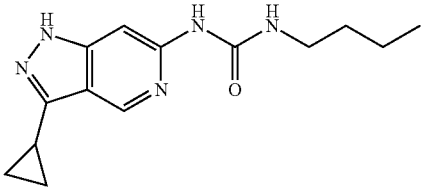<br>1-butyl-3-(3-cyclopropyl-1H-pyrazolo[4,3-c]pyridine-6-yl)urea | Calc'd 274, found 274 | 140 |
| 157 | 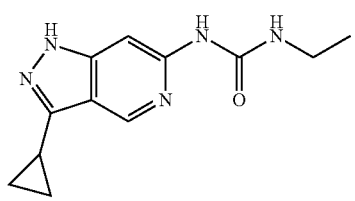<br>1-(3-cyclopropyl-1H-pyrazolo[4,3-c]pyridine-6-yl)-3-ethylurea | Calc'd 246, found 246 | 140 |

TABLE 2-continued

| EX | Structure | Exact Mass [M + H]+ | Route Used |
|---|---|---|---|
| 158 | 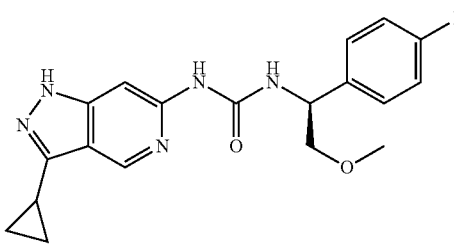 1-(3-cyclopropyl-1H-pyrazolo[4,3-c]pyridine-6-yl)-3-[(1S)-1-(4-fluorophenyl)-2-methoxyethyl]urea | Calc'd 370, found 370 | 140 |
| 159 | 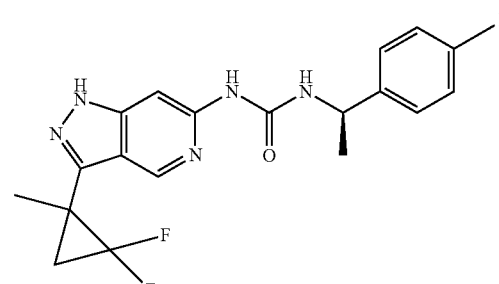 1-[3-(2,2-difluoro-1-methylcyclopropyl)-1H-pyrazolo[4,3-c]pyridin-6-yl]-3-[(1R)-1-(4-fluorophenyl)ethyl]urea | Calc'd 390, found 390 | 159 |
| 160 | 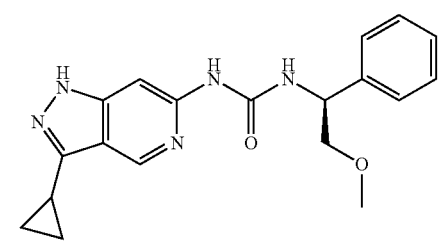 1-(3-cyclopropyl-1H-pyrazolo[4,3-c]pyridine-6-yl)-3-[(1S)-2-methoxy-1-phenylethyl]urea | Calc'd 352, found 352 | 30 |
| 161 | 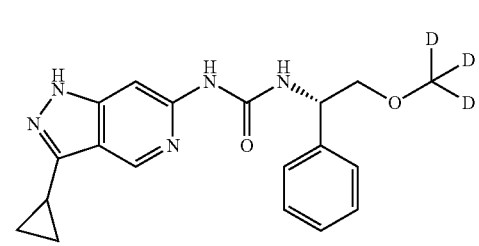 1-(3-cyclopropyl-1H-pyrazolo[4,3-c]pyridine-6-yl)-3-{(1S)-2-[(~2~H_3_)methloxy]-1-phenylethyl}urea | Calc'd 355, found 355 | 30 |

TABLE 2-continued

| EX | Structure | Exact Mass [M + H]+ | Route Used |
|---|---|---|---|
| 162 | 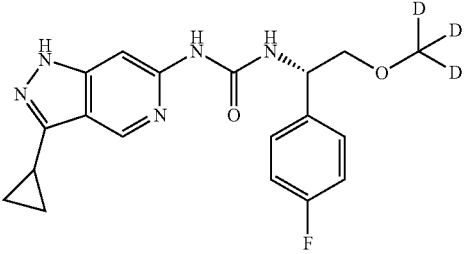<br>1-(3-cyclopropyl-1H-pyrazolo[4,3-c]pyridine-6-yl)-3-{(1S)-1-(4-fluorophenyl)-2-[(~2~H_3_)methyloxy]ethyl}urea | Calc'd 373, found 373 | 30 |
| 163 | 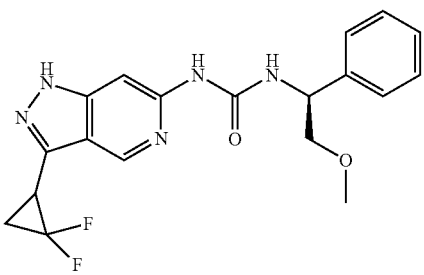<br>1-[3-(2,2-difluorocyclopropyl)-1H-pyrazolo[4,3-c]pyridine-6-yl]-3-[(1S)-2-methoxy-1-phenylethyl]urea | Calc'd 388, found 388 | 159 |
| 164 | 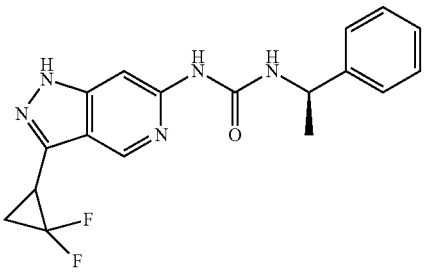<br>1-[3-(2,2-difluorocyclopropyl)-1H-pyrazolo[4,3-c]pyridine-6-yl]-3-[(1R)-1-phenylethyl]urea | Calc'd 358, found 358 | 159 |
| 165 | 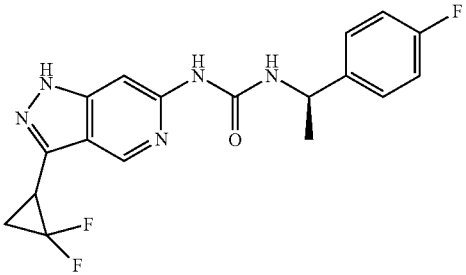<br>1-[3-(2,2-difluorocyclopropyl)-1H-pyrazolo[4,3-c]pyridine-6-yl]-3-[(1R)-1-(4-fluorophenyl)ethyl]urea | Calc'd 376, found 376 | 159 |

TABLE 2-continued

| EX | Structure | Exact Mass [M + H]+ | Route Used |
|---|---|---|---|
| 166 | 1-[3-(2,2-difluorocyclopropyl)-1H-pyrazolo[4,3-c]pyridine-6-yl]-3-[(1S)-1-(4-fluorophenyl)-2-methoxyethyl]urea | Calc'd 406, found 406 | 159 |
| 167 | 1-[(1S)-2-methoxy-1-phenylethyl]-3-[3-(trifluoromethyl)-1H-pyrazolo[4,3-c]pyridine-6-yl]urea | Calc'd 380, found 380 | 167 |
| 168 | 1-(3-cyclopropyl-1H-pyrazolo[4,3-c]pyridine-6-yl)-3-[(1S)-1-(4-fluorophenyl-2-yl)-2-methoxyethyl]urea | Calc'd 371, found 371 | 30 |
| 169 | (S)-1-(1-(4-fluoropyridin-2-yl)-2-methoxyethyl)-3-(3-(2-methylpyridin-4-yl)-1H-pyrazolo[4,3-c]pyridin-6-yl)urea | Calc'd 422, found 422 | 12 |

TABLE 2-continued

| EX | Structure | Exact Mass [M + H]+ | Route Used |
|---|---|---|---|
| 170 | 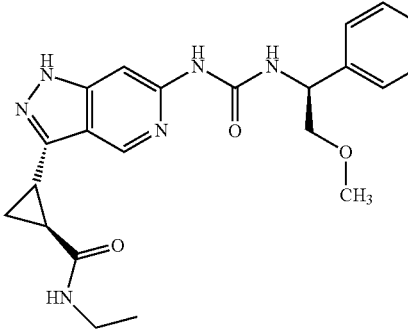 trans-N-ethyl-2-(6-(3-((S)-2-methoxy-1-phenylethyl)ureido)-1H-pyrazolo[4,3-c]pyridin-3-yl)cyclopropanecarboxamide | Calc'd 423, found 423 | |
| 171 | 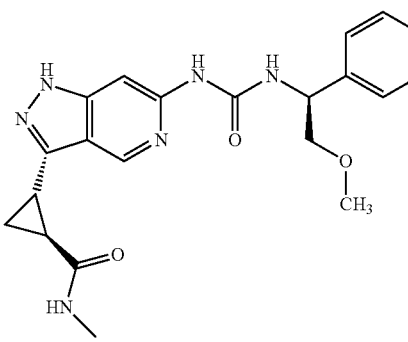 trans-2-(6-(3-((S)-2-methoxy-1-phenylethyl)ureido)-1H-pyrazolo[4,3-c]pyridin-3-yl)-N-methylcyclopropanecarboxamide | Calc'd 409, found 409 | 170 |
| 172 | 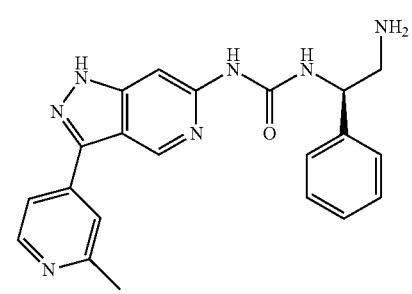 1-[(1R)-2-amino-1-phenylethyl]-3-[3-(2-methylpyridin-4-yl)-1H-pyrazolo[4,3-c]pyridin-6-yl]urea | Calc'd 388, found 388 | 12 |
| 173 | 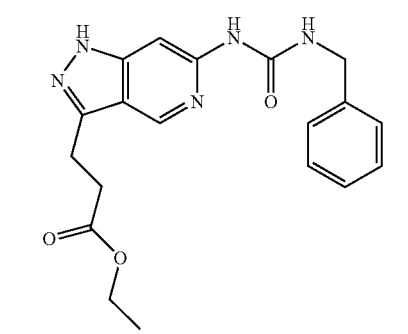 ethyl 3-{6-[(benzylcarbamoyl)amino]-1H-pyrazolo[4,3-c]pyridin-3-yl}propanoate | Calc'd 368, found 368 | 173 |

TABLE 2-continued
| EX | Structure | Exact Mass [M + H]+ | Route Used |
|---|---|---|---|
| 174 | 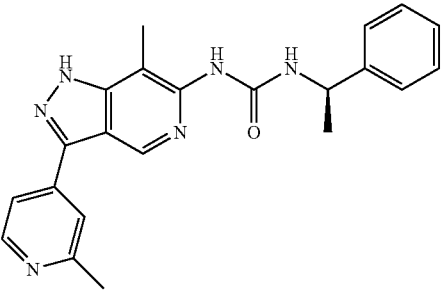 1-[7-methyl-3-(2-methylpyridin-4-yl)-1H-pyrazolo[4,3-c]pyridin-6-yl]-3-[(1R)-1-phenylethyl]urea | Calc'd 387, found 387 | 174 |
| 175 | 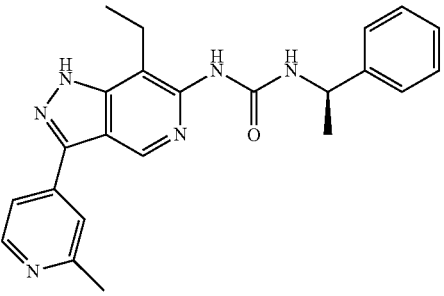 1-[7-ethyl-3-(2-methylpyridin-4-yl)-1H-pyrazolo[4,3-c]pyridin-6-yl]-3-[(1R)-1-phenylethyl]urea | Calc'd 401, found 401 | 174 |
| 176 | 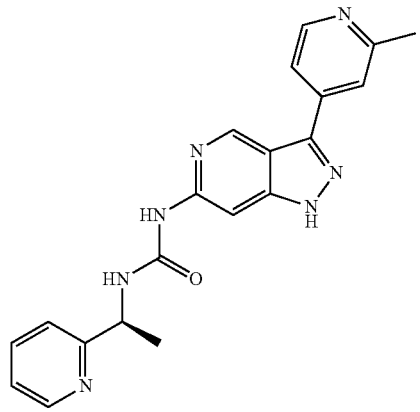 1-[3-(2-methylpyridin-4-yl)-1H-pyrazolo[4,3-c]pyridin-6-yl]-3-[(1S)-1-pyridin-2-ylethyl]urea | Calc'd 374, found 374 | 178 + SFC |

TABLE 2-continued

| EX | Structure | Exact Mass [M + H]+ | Route Used |
|---|---|---|---|
| 177 | 1-[3-(2-methylpyridin-4-yl)-1H-pyrazolo[4,3-c]pyridin-6-yl]-3-[(1R)-1-pyridin-2-ylethyl]urea | Calc'd 374, found 374 | 178 + SFC |
| 178 | 1-[3-(2-methylpyridin-4-yl)-1H-pyrazolo[4,3-c]pyridin-6-yl]-3-{(3R,4S)-1-methyl-4-[2-(trifluoromethyl)phenyl]pyrrolidin-3-yl}urea | Calc'd 496, found 496 | 178 |
| 179 | 1-[(3R,4S)-4-(6-fluoropyridin-3-yl)-1-methylpyrrolidin-3-yl]-3-[3-(2-methylpyridin-4-yl)-1H-pyrazolo[4,3-c]pyridin-6-yl]urea | Calc'd 447, found 447 | 178 |

TABLE 2-continued

| EX | Structure | Exact Mass [M + H]+ | Route Used |
|---|---|---|---|
| 180 | 1-[(3-(2-methylpyridin-4-yl)-1H-pyrazolo[4,3-c]pyridin-6-yl]-3-[(3S,4S)-4-phenylpyrrolidin-3-yl]urea | Calc'd 414, found 414 | 178 |
| 181 | 1-[(3R,4S)-1-methyl-4-phenylpyrrolidin-3-yl]-3-[3-(2-methylpyridin-4-yl)-1H-pyrazolo[4,3-c]pyridin-6-yl]urea | Calc'd 428, found 428 | 178 |
| 182 | 1-[(3R,4S)-1-methyl-4-phenylpyrrolidin-3-yl]-3-[3-(2-methylpyridin-4-yl)-1H-pyrazolo[4,3-c]pyridin-6-yl]urea | Calc'd 428, found 428 | 178 |

TABLE 2-continued

| EX | Structure | Exact Mass [M + H]+ | Route Used |
|---|---|---|---|
| 183 | Racemic 1-[(3R,4S) and (3S, 4R)-4-(2-fluorophenyl)-1-methylpyrrolidin-3-yl]-3-[3-(2-methylpyridin-4-yl)-1H-pyrazolo[4,3-c]pyridin-6-yl]urea | Calc'd 446, found 446 | 30 |
| 184 | 1-[(3S,4R)-4-(2-fluorophenyl)-1-methylpyrrolidin-3-yl]-3-[3-(2-methylpyridin-4-yl)-1H-pyrazolo[4,3-c]pyridin-6-yl]urea | Calc'd 446, found 446 | 30 |
| 185 | 1-[(3R,4S)-4-(2-fluorophenyl)-1-methylpyrrolidin-3-yl]-3-[3-(2-methylpyridin-4-yl)-1H-pyrazolo[4,3-c]pyridin-6-yl]urea | Calc'd 446, found 446 | 30 |
| 186 | N-methyl-N~2~-{[3-(2-methylpyridin-4-yl)-1H-pyrazolo[4,3-c]pyridin-6-yl]carbamoyl}glycinamide | Calc'd 340, found 340 | 178 |

TABLE 2-continued

| EX | Structure | Exact Mass [M + H]+ | Route Used |
|---|---|---|---|
| 187 | N,N-dimethyl-N~2~-{[3-(2-methylpyridin-4-yl)-1H-pyrazolo[4,3-c]pyridin-6-yl]carbamoyl}glycinamide | Calc'd 354, found 354 | 178 |
| 188 | 1-[(3S,4R)-4-hydroxytetrahydrofuran-3-yl]-3-[3-(2-methylpyridin-4-yl)-1H-pyrazolo[4,3-c]pyridin-6-yl]urea | Calc'd 355 found 355 | 178 |
| 189 | 1-(3,3-difluoro-2-hydroxypropyl)-3-[3-(2-methylpyridin-4-yl)-1H-pyrazolo[4,3-c]pyridin-6-yl]urea | Calc'd 363, found 363 | 178 |
| 190 | 1-(2,2-difluoro-3-hydroxypropyl)-3-[3-(2-methylpyridin-4-yl)-1H-pyrazolo[4,3-c]pyridin-6-yl]urea | Calc'd 363, found 363 | 178 |

TABLE 2-continued

| EX | Structure | Exact Mass [M + H]+ | Route Used |
|---|---|---|---|
| 191 | 1-[(3-methyl-4,5-dihydroisoxazol-5-yl)methyl]-3-[3-(2-methylpyridin-4-yl)-1H-pyrazolo[4,3-c]pyridin-6-yl]urea | Calc'd 366, found 366 | 178 |
| 192 | 1-[(3,5-dimethyl-4,5-dihydroisoxazol-5-yl)methyl]-3-[3-(2-methylpyridin-4-yl)-1H-pyrazolo[4,3-c]pyridin-6-yl]urea | Calc'd 380, found 380 | 178 |
| 193 | 1-{[1-(dimethylamino)cyclobutyl]methyl}-3-[3-(2-methylpyridin-4-yl)-1H-pyrazolo[4,3-c]pyridin-6-yl]urea | Calc'd 380, found 380 | 178 |
| 194 | 1-[3-(2-methylpyridin-4-yl)-1H-pyrazolo[4,3-c]pyridin-6-yl]-3-[2,2,2-trifluoro-1-(hydroxymethyl)ethyl]urea | Calc'd 381, found 381 | 178 |

TABLE 2-continued

| EX | Structure | Exact Mass [M + H]+ | Route Used |
|---|---|---|---|
| 195 | 1-[3-(2-methylpyridin-4-yl)-1H-pyrazolo[4,3-c]pyridin-6-yl]-3-(3,3,3-trifluoro-2-hydroxypropyl)urea | Calc'd 381, found 381 | 178 |
| 196 | 1-(2,2-dimethyltetrahydro-2H-pyran-4-yl)-3-[3-(2-methylpyridin-4-yl)-1H-pyrazolo[4,3-c]pyridin-6-yl]urea | Calc'd 381, found 381 | 178 |
| 197 | 1-{[3-(methylamino)tetrahydrofuran-3-yl]methyl}-3-[3-(2-methylpyridin-4-yl)-1H-pyrazolo[4,3-c]pyridin-6-yl]urea | Calc'd 382, found 382 | 178 |
| 198 | 1-[(4-methylmorpholin-2-yl)methyl]-3-[3-(2-methylpyridin-4-yl)-1H-pyrazolo[4,3-c]pyridin-6-yl]urea | Calc'd 382, found 382 | 178 |

TABLE 2-continued

| EX | Structure | Exact Mass [M + H]+ | Route Used |
|---|---|---|---|
| 199 | 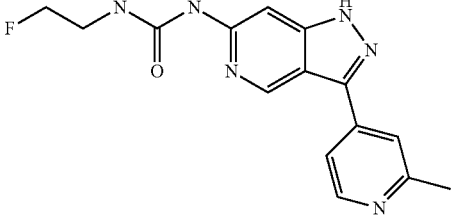<br>1-(2-fluoroethyl)-3-[3-(2-methylpyridin-4-yl)-1H-pyrazolo[4,3-c]pyridin-6-yl]urea | Calc'd 315, found 315 | 178 |
| 200 | 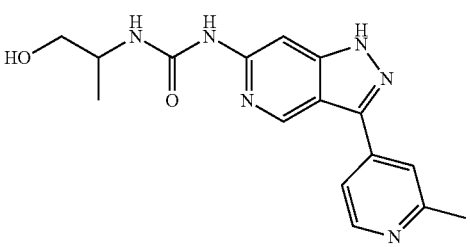<br>1-(2-hydroxy-1-methylethyl)-3-[3-(2-methylpyridin-4-yl)-1H-pyrazolo[4,3-c]pyridin-6-yl]urea | Calc'd 327, found 327 | 178 |
| 201 | 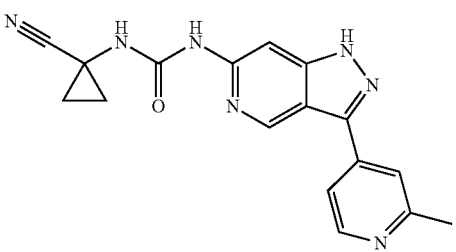<br>1-(1-cyanocyclopropyl)-3-[3-(2-methylpyridin-4-yl)-1H-pyrazolo[4,3-c]pyridin-6-yl]urea | Calc'd 334, found 334 | 178 |
| 202 | 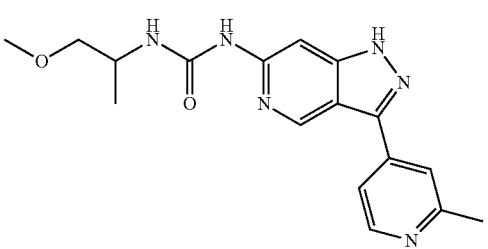<br>1-(2-methoxy-1-methylethyl)-3-[3-(2-methylpyridin-4-yl)-1H-pyrazolo[4,3-c]pyridin-6-yl]urea | Calc'd 341, found 341 | 178 |
| 203 | 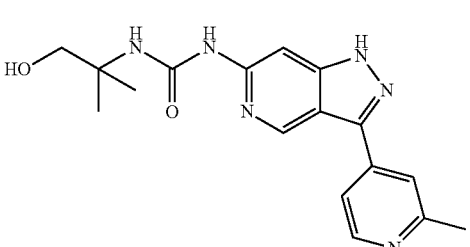<br>1-(2-hydroxy-1,1-dimethylethyl)-3-[3-(2-methylpyridin-4-yl)-1H-pyrazolo[4,3-c]pyridin-6-yl]urea | Calc'd 341, found 341 | 178 |

TABLE 2-continued

| EX | Structure | Exact Mass [M + H]+ | Route Used |
|---|---|---|---|
| 204 | 1-[(1R)-1-(hydroxymethyl)propyl]-3-[3-(2-methylpyridin-4-yl)-1H-pyrazolo[4,3-c]pyridin-6-yl]urea | Calc'd 341, found 341 | 178 |
| 205 | 1-[(3R,4S)-1,4-dimethylpyrrolidin-3-yl]-3-[3-(2-methylpyridin-4-yl)-1H-pyrazolo[4,3-c]pyridin-6-yl]urea | Calc'd 366, found 366 | 178 |
| 206 | 1-[(3S,4R)-1,4-dimethylpyrrolidin-3-yl]-3-[3-(2-methylpyridin-4-yl)-1H-pyrazolo[4,3-c]pyridin-6-yl]urea | Calc'd 366, found 366 | 178 |
| 207 | 1-[(3R,4S)-1-methyl-4-(2-methylphenyl)pyrrolidin-3-yl]-3-[3-(2-methylpyridin-4-yl)-1H-pyrazolo[4,3-c]pyridin-6-yl]urea | Calc'd 442, found 442 | 178 |

TABLE 2-continued

| EX | Structure | Exact Mass [M + H]+ | Route Used |
|----|-----------|---------------------|------------|
| 208 | 1-[(3R,4S)-4-cyclohexyl-1-methylpyrrolidin-3-yl]-3-[3-(2-methylpyridin-4-yl)-1H-pyrazolo[4,3-c]pyridin-6-yl]urea | Calc'd 434, found 434 | 178 |
| 209 | 1-[(3R,4S)-4-cyclohexyl-1-methylpyrrolidin-3-yl]-3-[3-(2-methylpyridin-4-yl)-1H-pyrazolo[4,3-c]pyridin-6-yl]urea | Calc'd 392, found 392 | 178 |
| 210 | 1-[3-(2-methylpyridin-4-yl)-1H-pyrazolo[4,3-c]pyridin-6-yl]-3-[(3R,4S)-1-methyl-4-(tetrahydro-2H-pyran-4-yl)pyrrolidin-3-yl]urea | Calc'd 436, found 436 | 178 |

TABLE 2-continued

| EX | Structure | Exact Mass [M + H]+ | Route Used |
|---|---|---|---|
| 211 | 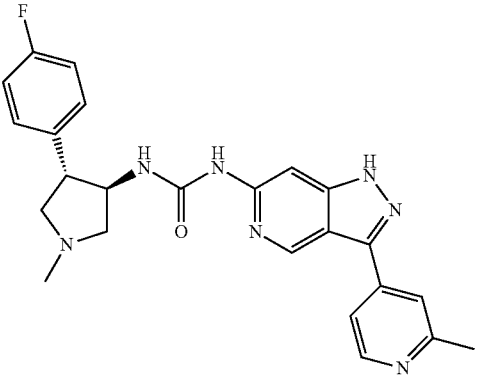 1-[(3R,4S)-4-(4-fluorophenyl)-1-methylpyrrolidin-3-yl]-3-[3-(2-methylpyridin-4-yl)-1H-pyrazolo[4,3-c]pyridin-6-yl]urea | Calc'd 446, found 446 | 178 |
| 212 | 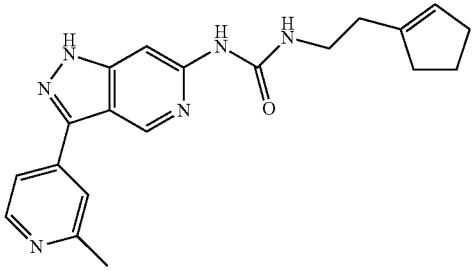 1-(2-cyclopent-1-en-1-ylethyl)-3-[3-(2-methylpyridin-4-yl)-1H-pyrazolo[4,3-c]pyridin-6-yl]urea | Calc'd 363, found 363 | 178 |
| 213 | 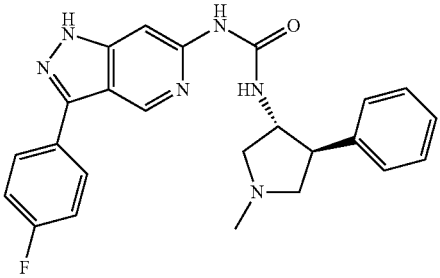 1-[3-(4-fluorophenyl)-1H-pyrazolo[4,3-c]pyridin-6-yl]-3-[(3R,4S)-1-methyl-4-phenylpyrrolin-3-yl]urea | Calc'd 431, found 431 | 30 |
| 214 | 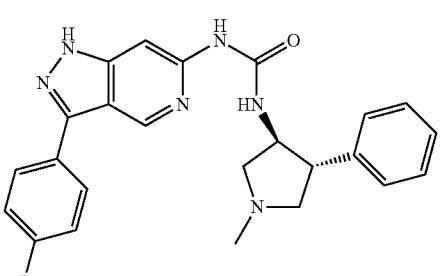 1-[3-(4-fluorophenyl)-1H-pyrazolo[4,3-c]pyridin-6-yl]-3-[(3S,4R)-1-methyl-4-phenylpyrrolin-3-yl]urea | Calc'd 431, found 431 | 30 |

TABLE 2-continued

| EX | Structure | Exact Mass [M + H]+ | Route Used |
|----|-----------|---------------------|------------|
| 215 | 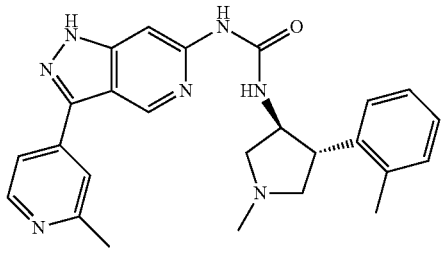<br>1-[(3S,4R)-1-methyl-4-(2-methylphenyl)pyrrolidin-3-yl]-3-[3-(2-methylpyridin-4-yl)-1H-pyrazolo[4,3-c]pyridin-6-yl]urea | Calc'd 442, found 442 | 215 |
| 216 | 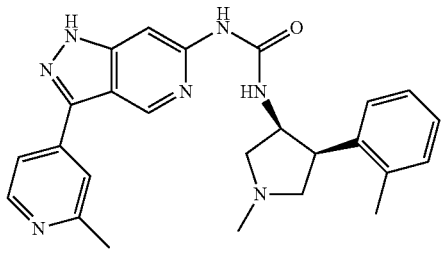<br>1-[(3R,4S)-1-methyl-4-(2-methylphenyl)pyrrolidin-3-yl]-3-[3-(2-methylpyridin-4-yl)-1H-pyrazolo[4,3-c]pyridin-6-yl]urea | Calc'd 442, found 442 | 216 |
| 217 | 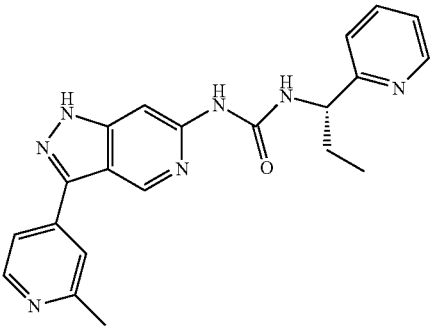<br>1-[3-(2-methylpyridin-4-yl)-1H-pyrazolo[4,3-c]pyridin-6-yl]-3-[(1S)-1-pyridin-2-ylpropyl]urea | Calc'd 388, found 388 | 215 |
| 218 | 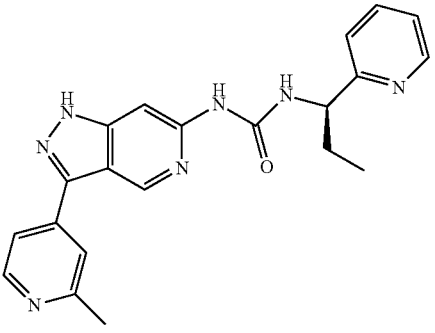<br>1-[3-(2-methylpyridin-4-yl)-1H-pyrazolo[4,3-c]pyridin-6-yl]-3-[(1R)-1-pyridin-2-ylpropyl]urea | Calc'd 388, found 388 | 215 |

TABLE 2-continued

| EX | Structure | Exact Mass [M + H]+ | Route Used |
|---|---|---|---|
| 219 | 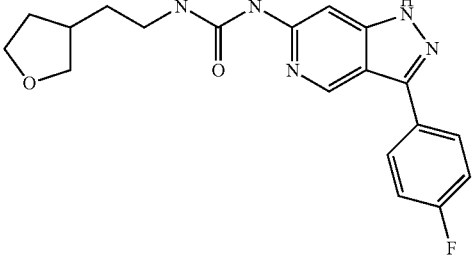<br>1-[3-(4-fluorophenyl)-1H-pyrazolo[4,3-c]pyridin-6-yl]-3-[2-(tetrahydrofuran-3-yl)ethyl]urea | Calc'd 370, found 370 | 178 |
| 220 | 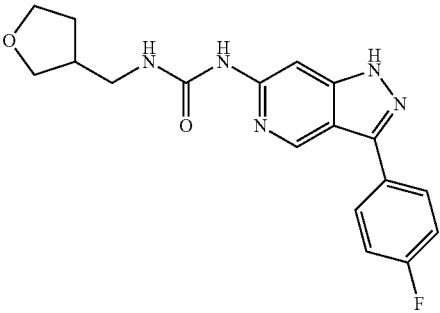<br>1-[3-(4-fluorophenyl)-1H-pyrazolo[4,3-c]pyridin-6-yl]-3-(tetrahydrofuran-3-ylmethyl)urea | Calc'd 356, found 356 | 178 |
| 221 | 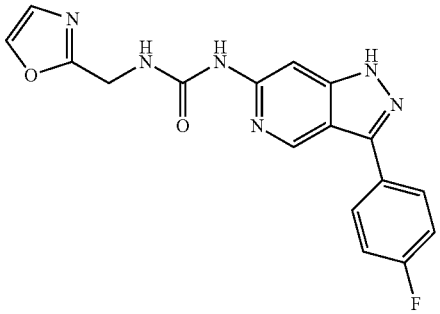<br>1-[3-(4-fluorophenyl)-1H-pyrazolo[4,3-c]pyridin-6-yl]-3-(1,3-oxazol-2-ylmethyl)urea | Calc'd 353, found 353 | 178 |
| 222 | 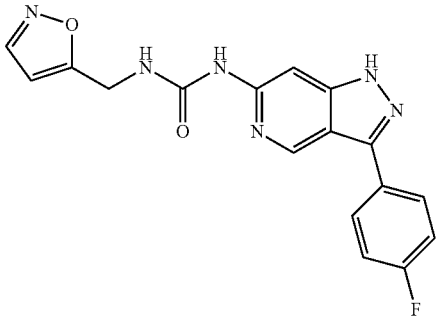<br>1-[3-(4-fluorophenyl)-1H-pyrazolo[4,3-c]pyridin-6-yl]-3-(isoxazol-5-ylmethyl)urea | Calc'd 353, found 353 | 178 |

TABLE 2-continued
| EX | Structure | Exact Mass [M + H]+ | Route Used |
|---|---|---|---|
| 223 | 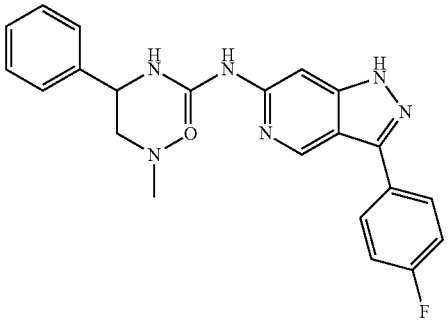<br>1-[2-(dimethylamino)-1-phenylethyl]-3-[3-(4-fluorophenyl)-1H-pyrazolo[4,3-c]pyridin-6-yl]urea | Calc'd 419, found 419 | 178 |
| 224 | 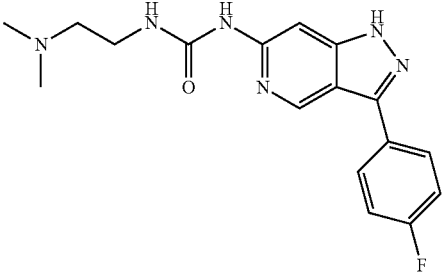<br>1-[2-(dimethylamino)ethyl]-3-[3-(4-fluorophenyl)-1H-pyrazolo[4,3-c]pyridin-6-yl]urea | Calc'd 343, found 343 | 178 |
| 225 | 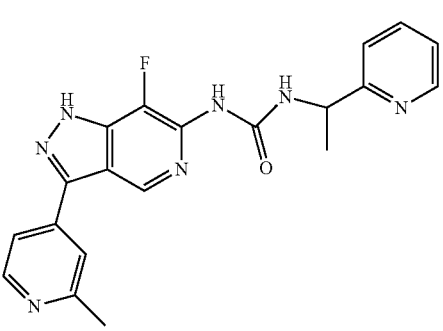<br>1-[7-fluoro-3-(2-methylpyridin-4-yl)-1H-pyrazolo[4,3-c]pyridin-6-yl]-3-(1-pyridin-2-ylethyl)urea | Calc'd 392, found 392 | 95 |

TABLE 2-continued
| EX | Structure | Exact Mass [M + H]+ | Route Used |
|---|---|---|---|
| 226 | 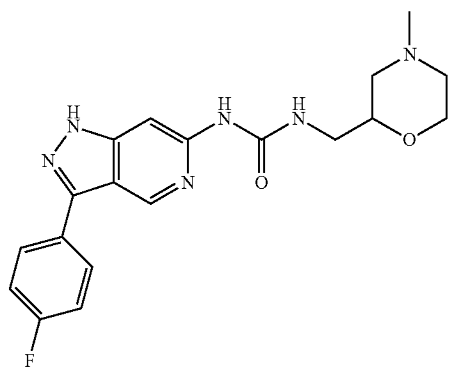 | Calc'd 385, found 385 | 178 |
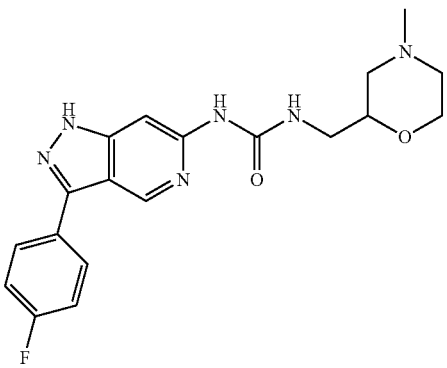
1-[3-(4-fluorophenyl)-1H-pyrazolo[4,3-c]pyridin-6-yl]-3-[(4-methylmorpholin-2-yl)methyl]urea
| 227 | | Calc'd 357, found 357 | 178 |
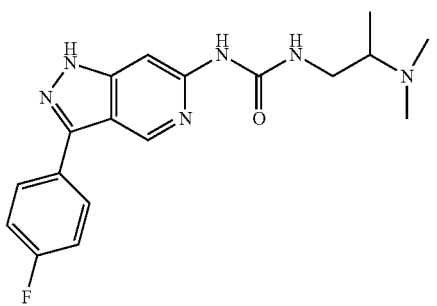
1-[2-(dimethylamino)propyl]-3-[3-(4-fluorophenyl)-1H-pyrazolo[4,3-c]pyridin-6-yl]urea
| 228 | | Calc'd 357, found 357 | 178 |
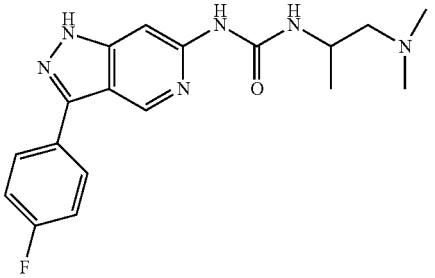
1-[2-(dimethylamino)-1-methylethyl]-3-[3-(4-fluorophenyl)-1H-pyrazolo[4,3-c]pyridin-6-yl]urea TABLE 2-continued

| EX | Structure | Exact Mass [M + H]+ | Route Used |
|----|-----------|---------------------|------------|
| 229 | 1-[(1R)-1-(4-chloropyridin-2-yl)ethyl]-3-[3-(2-methylpyridin-4-yl)-1H-pyrazolo[4,3-c]pyridin-6-yl]urea | Calc'd 408, found 408 | 178 |
| 230 | 1-[(1S)-1-(4-methoxypyridin-2-yl)ethyl]-3-[3-(2-methylpyridin-4-yl)-1H-pyrazolo[4,3-c]pyridin-6-yl]urea | Calc'd 404, found 404 | 178 |
| 231 | 1-[(1R)-1-(4-methoxypyridin-2-yl)ethyl]-3-[3-(2-methylpyridin-4-yl)-1H-pyrazolo[4,3-c]pyridin-6-yl]urea | Calc'd 404, found 404 | 178 |

TABLE 2-continued

| EX | Structure | Exact Mass [M + H]+ | Route Used |
|---|---|---|---|
| 232 | 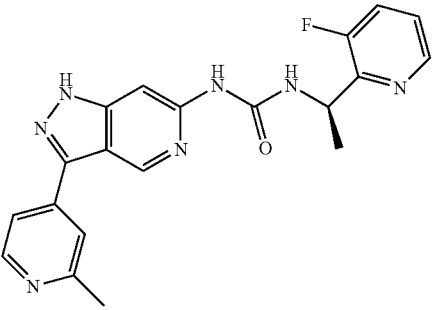<br>1-[(1R)-1-(3-fluoropyridin-2-yl)ethyl]-3-[3-(2-methylpyridin-4-yl)-1H-pyrazolo[4,3-c]pyridin-6-yl]urea | Calc'd 392, found 392 | 178 |
| 233 | 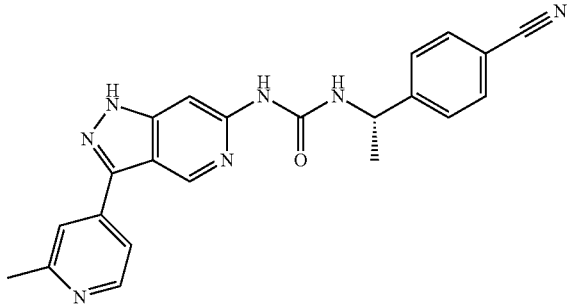<br>1-[(1S)-1-(4-cyanophenyl)ethyl]-3-[3-(2-methylpyridin-4-yl)-1H-pyrazolo[4,3-c]pyridin-6-yl]urea | Calc'd 398, found 398 | 178 |
| 234 | 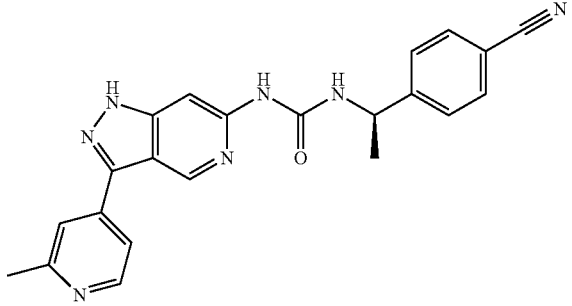<br>1-[(1R)-1-(4-cyanophenyl)ethyl]-3-[3-(2-methylpyridin-4-yl)-1H-pyrazolo[4,3-c]pyridin-6-yl]urea | Calc'd 398, found 398 | 178 |
| 235 | 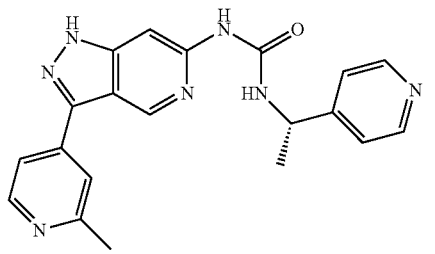<br>1-[3-(2-methylpyridin-4-yl)-1H-pyrazolo[4,3-c]pyridin-6-yl]-3-[(1S)-1-pyridin-4-ylethyl]urea | Calc'd 374, found 374 | 178 |

TABLE 2-continued

| EX | Structure | Exact Mass [M + H]+ | Route Used |
|---|---|---|---|
| 236 | 1-[3-(2-methylpyridin-4-yl)-1H-pyrazolo[4,3-c]pyridin-6-yl]-3-[(1R)-1-pyridin-4-ylethyl]urea | Calc'd 374, found 374 | 178 |
| 237 | 1-[3-(2-methylpyridin-4-yl)-1H-pyrazolo[4,3-c]pyridin-6-yl]-3-[phenyl(tetrahydrofuran-2-yl)methyl]urea | Calc'd 429, found 429 | 178 |
| 238 | 1-[(4-fluorophenyl)(tetrahydrofuran-2-yl)methyl]-3-[3-(2-methylpyridin-4-yl)-1H-pyrazolo[4,3-c]pyridin-6-yl]urea | Calc'd 447, found 447 | 178 |
| 239 | 1-[3-(2-methylpyridin-4-yl)-1H-pyrazolo[4,3-c]pyridin-6-yl]-3-[1-methyl-2-(tetrahydrofuran-2-yl)ethyl]urea | Calc'd 381, found 381 | 178 |

TABLE 2-continued

| EX | Structure | Exact Mass [M + H]+ | Route Used |
|---|---|---|---|
| 240 | 1-{2-methoxy-1-[5-(trifluoromethyl)pyridin-2-yl]ethyl}-3-[3-(2-methylpyridin-4-yl)-1H-pyrazolo[4,3-c]pyridin-6-yl]urea | Calc'd 472, found 472 | 178 |
| 241 | 1-[3-(2-methylpyridin-4-yl)-1H-pyrazolo[4,3-c]pyridin-6-yl]-3-propylurea | Calc'd 311, 311 | 262 |
| 242 | 1-[(1R)-1-(4-fluorophenyl)ethyl]-3-{3-[4-(1H-1,2,3-triazol-1-yl)phenyl]-1H-pyrazolo[4,3-c]pyridine-6-yl}urea | Calc'd 443, 443 | 242 |
| 243 | 1-[(1R)-1-(4-fluorophenyl)ethyl]-3-[3-(3-methylisoxazol-4-yl)-1H-pyrazolo[4,3-c]pyridine-6-yl]urea | Calc'd 381, 381 | 242 |

TABLE 2-continued

| EX | Structure | Exact Mass [M + H]+ | Route Used |
|---|---|---|---|
| 244 | 1-[(1R)-1-(4-fluorophenyl)ethyl]-3-[3-(6-piperidin-1-ylpyridin-3-yl)-1H-pyrazolo[4,3-c]pyridin-6-yl]urea | Calc'd 460, 460 | 242 |
| 245 | 1-[(1R)-1-(4-fluorophenyl)ethyl]-3-{3-[5-(trifluoromethyl)pyridin-3-yl]-1H-pyrazolo[4,3-c]pyridine-6-yl}urea | Calc'd 445, 445 | 242 |
| 246 | 1-[(1R)-1-(4-fluorophenyl)ethyl]-3-(3-[1,2,4]triazolo[4,3-a]pyridin-6-yl-1H-pyrazolo[4,3-c]pyridin-6-yl)urea | Calc'd 417, 417 | 242 |
| 247 | 1-[(1R)-1-(4-fluorophenyl)ethyl]-3-{3-[4-(2H-1,2,3-triazol-2-yl)phenyl]-1H-pyrazolo[4,3-c]pyridine-6-yl}urea | Calc'd 443, 443 | 242 |

| EX | Structure | Exact Mass [M + H]+ | Route Used |
|---|---|---|---|
| 248 | 1-[(1R)-1-(4-fluorophenyl)ethyl]-3-[3-(5-methylthiophen-2-yl)-1H-pyrazolo[4,3-c]pyridine-6-yl]urea | Calc'd 396, 396 | 242 |
| 249 | 2-{5-[6-({[(1R)-1-(4-fluorophenyl)ethyl]carbamoyl}amino)-1H-pyrazolo[4,3-c]pyridin-3-yl]pyridin-2-yl}-4-methyl-3H-1,3-thiazol-1-ium | Calc'd 475, 475 | 242 |
| 250 | 1-[(1R)-1-(4-fluorophenyl)ethyl]-3-{3-[6-(1-methylethoxy)pyridin-3-yl]-1H-pyrazolo[4,3-c]pyridin-6-yl}urea | Calc'd 435, 435 | 242 |
| 251 | 1-[(1R)-1-(4-fluorophenyl)ethyl]-3-[3-[6-methoxypyrazin-2-yl]-1H-pyrazolo[4,3-c]pyridin-6-yl}urea | Calc'd 408, 408 | 242 |

TABLE 2-continued

| EX | Structure | Exact Mass [M + H]+ | Route Used |
|---|---|---|---|
| 252 | 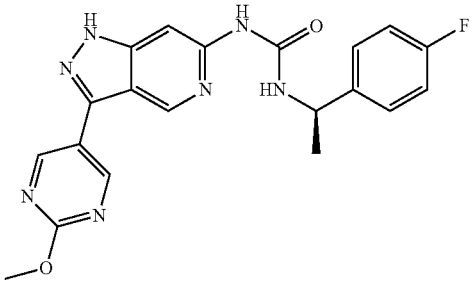<br>1-[(1R)-1-(4-fluorophenyl)ethyl]-3-[3-(2-methoxypyrimidin-5-yl)-1H-pyrazolo[4,3-c]pyridin-6-yl]urea | Calc'd 408, 408 | 242 |
| 253 | 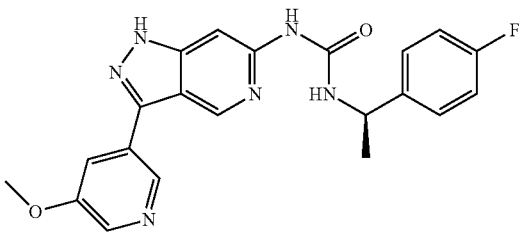<br>1-[(1R)-1-(4-fluorophenyl)ethyl]-3-[3-(5-methoxypyridin-3-yl)-1H-pyrazolo[4,3-c]pyridin-6-yl]urea | Calc'd 407, 407 | 242 |
| 254 | 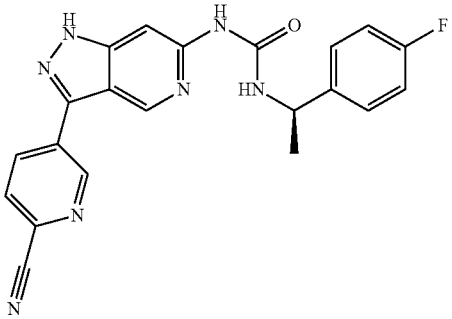<br>1-[3-(6-cyanopyridin-3-yl)-1H-pyrazolo[4,3-c]pyridin-6-yl]-3-[(1R)-1-(4-fluorophenyl)ethyl]urea | Calc'd 402, 402 | 242 |
| 255 | 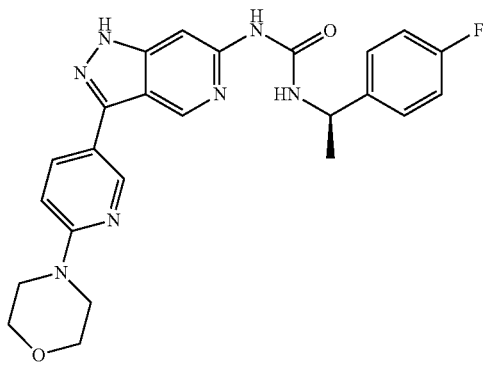<br>1-[(1R)-1-(4-fluorophenyl)ethyl]-3-[3-(6-morpholin-4-ylpyridin-3-yl)-1H-pyrazolo[4,3-c]pyridin-6-yl]urea | Calc'd 462, 462 | 242 |

TABLE 2-continued

| EX | Structure | Exact Mass [M + H]+ | Route Used |
|---|---|---|---|
| 256 | 1-[(1R)-1-(4-fluorophenyl)ethyl]-3-[3-(6-methylpyridin-3-yl)-1H-pyrazolo[4,3-c]pyridin-6-yl]urea | Calc'd 391, 391 | 242 |
| 257 | 1-[(1R)-1-(4-fluorophenyl)ethyl]-3-{3-[2-methoxy-6-(trifluoromethyl)pyridin-4-yl]-1H-pyrazolo[4,3-c]pyridin-6-yl}urea | Calc'd 475, 475 | 242 |
| 258 | 1-[3-(2-cyanopyridin-4-yl)-1H-pyrazolo[4,3-c]pyridin-6-yl]-3-[(1R)-1-(4-fluorophenyl)ethyl]urea | Calc'd 402, 402 | 242 |
| 259 | 1-[(1R)-1-(4-fluorophenyl)ethyl]-3-[3-(1-methyl)-1H-pyrazol-4-yl)-1H-pyrazolo[4,3-c]pyridin-6-yl]urea | Calc'd 380, 380 | 242 |

TABLE 2-continued

| EX | Structure | Exact Mass [M + H]+ | Route Used |
|---|---|---|---|
| 260 | 1-[(1R)-1-(4-fluorophenyl)ethyl]-3-[3-(1-methyl-1H-benzotriazol-6-yl)-1H-pyrazolo[4,3-c]pyridin-6-yl]urea | Calc'd 431, 431 | 242 |
| 261 | 1-[3-(2-methylpyridin-4-yl)-1H-pyrazolo[4,3-c]pyridin-6-yl]-3-[(5R)-5,6,7,8-tetrahydroquinolin-5-yl]urea | Calc'd 400, 400 | 242 |
| 262 | 1-[3-(2-methylpyridin-4-yl)-1H-pyrazolo[4,3-c]pyridin-6-yl]-3-[(8R)-5,6,7,8-tetrahydroquinolin-8-yl]urea | Calc'd 400, 400 | 262 |
| 263 | 1-[3-(2-methylpyridin-4-yl)-1H-pyrazolo[4,3-c]pyridin-6-yl]-3-[(8R)-5,6,7,8-tetrahydroquinolin-8-yl]urea | Calc'd 400, 400 | 262 |

TABLE 2-continued

| EX | Structure | Exact Mass [M + H]+ | Route Used |
|---|---|---|---|
| 264 | 1-[(4R)-3,4-dihydro-2H-thiochromen-4-yl]-3-[3-(2-methylpyridin-4-yl)-1H-pyrazolo[4,3-c]pyridin-6-yl]urea | Calc'd 417, 417 | 262 |
| 265 | 1-[3-(2-methylpyridin-4-yl)-1H-pyrazolo[4,3-c]pyridin-6-yl]-3-[(5R)-6,7,8,9-tetrahydro-5H-benzo[7]annulen-5-yl]urea | Calc'd 413, 413 | 262 |
| 266 | 1-[(4R)-7-cyano-3,4-dihydro-2H-chromen-4-yl]-3-[3-(2-methylpyridin-4-yl)-1H-pyrazolo[4,3-c]pyridin-6-yl]urea | Calc'd 426, 426 | 262 |
| 267 | 1-[(4R)-7-chloro-3,4-dihydro-2H-chromen-4-yl]-3-[3-(2-methylpyridin-4-yl)-1H-pyrazolo[4,3-c]pyridin-6-yl]urea | Calc'd 435, 435 | 262 |

TABLE 2-continued

| EX | Structure | Exact Mass [M + H]+ | Route Used |
|---|---|---|---|
| 268 | 1-[3-(2-methylpyridin-4-yl)-1H-pyrazole[4,3-c]pyridin-6-yl]-3-({1-[4-(trifluoromethoxy)phenyl]cyclopropyl}methyl)urea | Calc'd 483, 483 | 262 |
| 269 | 1-{[1-(4-fluorophenyl)cyclopropyl]methyl}-3-[3-(2-methylpyridin-4-yl)-1H-pyrazolo[4,3-c]pyridin-6-yl]urea | Calc'd 417, 417 | 262 |
| 270 | 1-[(1R)-6-fluoro-2,3-dihydro-1H-inden-1-yl]-3-[3-(2-methylpyridin-4-yl)-1H-pyrazolo[4,3-c]pyridin-6-yl]urea | Calc'd 403, 403 | 262 |
| 271 | 1-(2,2)-dimethyl-3,4-dihydro-2H-chromen-4-yl)-3-[3-(2-methylpyridin-4-yl)-1H-pyrazolo[4,3-c]pyridin-6-yl]urea | Calc'd 429, 429 | 262 |

TABLE 2-continued

| EX | Structure | Exact Mass [M + H]+ | Route Used |
|---|---|---|---|
| 272 | 1-(6,8-difluoro-3,4-dihydro-2H-chromen-4-yl)-3-[3-(2-methylpyridin-4-yl)-1H-pyrazolo[4,3-c]pyridin-6-yl]urea | Calc'd 437, 437 | 262 |
| 273 | 1-(4-fluorobenzyl)-3-[3-(2-methylpyridin-4-yl)-1H-pyrazolo[4,3-c]pyridin-6-yl]urea | Calc'd 377, found 377 | 30 |
| 274 | 1-[3-(2-methylpyridin-4-yl)-1H-pyrazolo[4,3-c]pyridin-6-yl]-3-(2,3,4,5-tetrahydro-1-benzoxepin-5-yl)urea | Calc'd 415, found 415 | 276 |
| 275 | 1-[(4R)-1,1-dioxido-3,4-dihydro-2H-thiochromen-4-yl]-3-[3-(2-methylpyridin-4-yl)-1H-pyrazolo[4,3-c]pyridin-6-yl]urea | Calc'd 449, found 449 | 276 |

TABLE 2-continued

| EX | Structure | Exact Mass [M + H]+ | Route Used |
|---|---|---|---|
| 276 | 1-[(4S)-7-fluoro-3,4-dihydro-2H-chromen-4-yl]-3-[3-(2-methylpyridin-4-yl)-1H-pyrazolo[4,3-c]pyridin-6-yl]urea | Calc'd 419, found 419 | 276 |
| 277 | 1-[3-(2-methylpyridin-4-yl)-1H-pyrazolo[4,3-c]pyridin-6-yl]-3-[1-(methylsulfonyl)-1,2,3,4-tetrahydroquinolin-4-yl]urea | Calc'd 478, found 478 | 276 |
| 278 | 3-(3-fluorophenyl)-N-[3-(2-methylpyridin-4-yl)-1H-pyrazolo[4,3-c]pyridin-6-yl]azetidine-1-carboxamide | Calc'd 403, found 403 | 276 |
| 279 | 1-[3-(2-methylpyridin-4-yl)-1H-pyrazolo[4,3-c]pyridin-6-yl]-3-[(1R)-2,2,2-trifluoro-1-(4-fluorophenyl)ethyl]urea | Calc'd 445, found 445 | 276 |

TABLE 2-continued

| EX | Structure | Exact Mass [M + H]+ | Route Used |
|---|---|---|---|
| 280 | 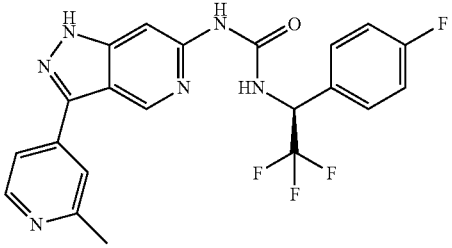 1-[3-(2-methylpyridin-4-yl)-1H-pyrazolo[4,3-c]pyridin-6-yl]-3-[(1S)-2,2,2-trifluoro-1-(4-fluorophenyl)ethyl]urea | Calc'd 445, found 445 | 276 |
| 281 | 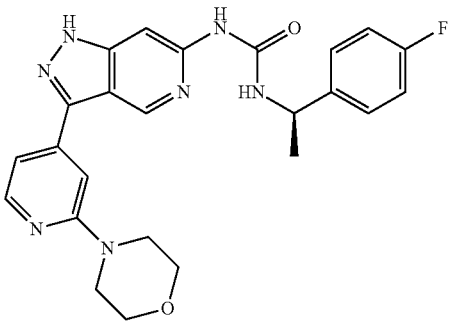 1-[(1R)-1-(4-fluorophenyl)ethyl]-3-[3-(2-morpholin-4-ylpyridin-4-yl)-1H-pyrazolo[4,3-c]pyridin-6-yl]urea | Calc'd 462, found 462 | 30 |
| 282 | 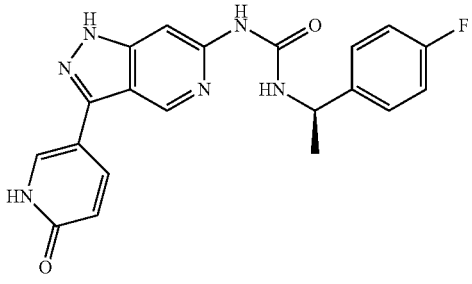 1-[(1R)-1-(4-fluorophenyl)ethyl]-3-[3-(6-oxo-1,6-dihydropyridin-3-yl)-1H-pyrazolo[4,3-c]pyridin-6-yl]urea | Calc'd 393, found 393 | 30 |
| 283 | 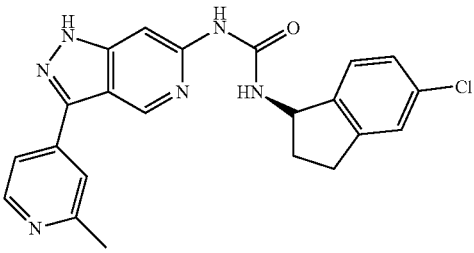 1-[(1R)-5-chloro-2,3-dihydro-1H-inden-1-yl]-3-[3-(2-methylpyridin-4-yl)-1H-pyrazolo[4,3-c]pyridin-6-yl]urea | Calc'd 419, found 419 | 276 |

TABLE 2-continued

| EX | Structure | Exact Mass [M + H]+ | Route Used |
|---|---|---|---|
| 284 | 1-[3-(2-methylpyridin-4-yl)-1H-pyrazolo[4,3-c]pyridin-6-yl]-3-[(5S)-2,3,4,5-tetrahydro-1-benzoxepin-5-yl]urea | Calc'd 415, found 415 | 276 |
| 285 | 1-[3-(2-methylpyridin-4-yl)-1H-pyrazolo[4,3-c]pyridin-6-yl]-3-[(5R)-2,3,4,5-tetrahydro-1-benzoxepin-5-yl]urea | Calc'd 415, found 415 | 276 |
| 286 | 1-[(4R)-7-fluoro-3,4-dihydro-2H-chromen-4-yl]-3-[3-(2-methylpyridin-4-yl)-1H-pyrazolo[4,3-c]pyridin-6-yl]urea | Calc'd 419, found 419 | 276 |
| 287 | 1-[(1S)-1-(4-fluorophenyl)-2-methoxyethyl]-3-[3-(2-fluoropyridin-4-yl)-1H-pyrazolo[4,3-c]pyridin-6-yl]urea | Calc'd 425, found 425 | 276 |

TABLE 2-continued

| EX | Structure | Exact Mass [M + H]+ | Route Used |
|---|---|---|---|
| 288 | (2R)-4-(4-fluorophenyl)-2-methyl-N-[3-(2-methylpyridin-4-yl)-1H-pyrazolo[4,3-c]pyridin-6-yl]piperazine-1-carboxamide | Calc'd 446, found 446 | 276 |
| 289 | 1-{3-[1-(2-methoxyethyl)-1H-pyrazol-4-yl]-1H-pyrazolo[4,3-c]pyridin-6-yl}-3-[(1R)-1-phenylethyl]urea | Calc'd 406, found 406 | 90 |
| 290 | 1-[3-(2-hydroxypyrimidin-5-yl)-1H-pyrazolo[4,3-c]pyridin-6-yl]-3-[(1R)-1-phenylethyl]urea | Calc'd 376, found 376 | 90 |

TABLE 2-continued

| EX | Structure | Exact Mass [M + H]+ | Route Used |
|---|---|---|---|
| 291 | 1-[(1R)-1-phenylethyl]-3-{3-[2-(1H-pyrazol-1-yl)-pyrimidin-5-yl]-1H-pyrazolo[4,3-c]pyridin-6-yl}urea | Calc'd 426, found 426 | 90 |
| 292 | N-methyl-N-{5-[6-({[(1R)-1-phenylethyl]carbamoyl}amino)-1H-pyrazolo[4,3-c]pyridin-3-yl]pyrimidin-2-yl}methanesulfonamide | Calc'd 467, found 467 | 90 |
| 293 | 1-(3-{2-[(2-methoxyethyl)(methyl)amino]pyrimidin-5-yl}-1H-pyrazolo[4,3-c]pyridin-6-yl)-3-[(1R)-1-phenylethyl]urea | Calc'd 447, found 447 | 90 |

TABLE 2-continued

| EX | Structure | Exact Mass [M + H]+ | Route Used |
|---|---|---|---|
| 294 | 1-[(1R)-1-phenylethyl]-3-(3-[1,2,4]triazolo[1,5-a]pyridin-7-yl-1H-pyrazolo[4,3-c]pyridin-6-yl}urea | Calc'd 399, found 399 | 90 |
| 295 | 1-(3-cyclopropyl-1H-pyrazolo[4,3-c]pyridin-6-yl)-3-[(5R)-2,3,4,5-tetrahydro-1-benzoxepin-5-yl]urea | Calc'd 364, found 364 | 30 |
| 296 | 1-[(1S)-1-(4-fluorophenyl)-2-methoxyethyl]-3-[3-(1-methyl-1H-pyrazol-4-yl)-1H-pyrazolo[4,3-c]pyridin-6-yl]urea | Calc'd 410, found 410 | 90 |
| 297 | 1-[(1S)-1-(4-fluorophenyl)-2-methoxyethyl]-3-[3-(6-morpholin-4-ylpyridin-3-yl)-1H-pyrazolo[4,3-c]pyridin-6-yl]urea | Calc'd 492, found 492 | 90 |

TABLE 2-continued

| EX | Structure | Exact Mass [M + H]+ | Route Used |
|----|-----------|---------------------|------------|
| 298 | 1-[(1S)-1-(4-fluorophenyl)-2-methoxyethyl]-3-[3-(2-morpholin-4-ylpyridin-3-yl)-1H-pyrazolo[4,3-c]pyridin-6-yl]urea | Calc'd 492, found 492 | 90 |
| 299 | 1-[(1S)-1-(4-fluorophenyl)-2-methoxyethyl]-3-[3-(2-methoxypyrimidin-5-yl)-1H-pyrazolo[4,3-c]pyridin-6-yl]urea | Calc'd 438, found 438 | 90 |
| 300 | 1-[(1S)-1-(4-fluorophenylethyl)-2-methoxyethyl]-3-(3-[1,2,4]triazolo[1,5-a]pyridin-7-yl-1H-pyrazolo[4,3-c]pyridin-6-yl)urea | Calc'd 447, found 447 | 90 |

TABLE 2-continued

| EX | Structure | Exact Mass [M + H]+ | Route Used |
|---|---|---|---|
| 301 | 1-[(1S)-1-(4-fluorophenylethyl)-2-methoxyethyl]-3-[3-(1-methyl-1H-benzotriazol-5-yl-1H-pyrazolo[4,3-c]pyridin-6-yl)urea | Calc'd 461, found 461 | 90 |
| 302 | 1-[(1S)-1-(4-fluorophenyl)-2-methoxyethyl]-3-[3-(5-methoxypyridin-3-yl)-1H-pyrazolo[4,3-c]pyridin-6-yl]urea | Calc'd 437, found 437 | 90 |
| 303 | 1-[3-(6-cyanopyridin-3-yl)-1H-pyrazolo[4,3-c]pyridin-6-yl]-3-[(1S)-1-(4-fluorophenyl)-2-methoxyethyl]urea | Calc'd 432, found 432 | 90 |
| 304 | 1-[3-(2-cyanopyridin-4-yl)-1H-pyrazolo[4,3-c]pyridin-6-yl]-3-[(1S)-1-(4-fluorophenyl)-2-methoxyethyl]urea | Calc'd 432, found 432 | 90 |

TABLE 2-continued

| EX | Structure | Exact Mass [M + H]+ | Route Used |
|---|---|---|---|
| 305 | 1-[(1S)-1-(4-fluorophenyl)-2-methoxyethyl]-3-{3-[6-(trifluoromethyl)pyridin-3-yl]-1H-pyrazolo[4,3-c]pyridin-6-yl}urea | Calc'd 475, found 475 | 90 |
| 306 | 1-[(1S)-1-(4-fluorophenyl)-2-methoxyethyl]-3-[3-(2-piperazin-1-ylpyridin-4-yl)-1H-pyrazolo[4,3-c]pyridin-6-yl]urea | Calc'd 491, found 491 | 90 |
| 307 | 1-[(1S)-1-(4-fluorophenyl)-2-methoxyethyl]-3-{3-[4-(1H-1,2,3-triazol-1-yl)phenyl]-1H-pyrazolo[4,3-c]pyridin-6-yl}urea | Calc'd 473, found 473 | 90 |

TABLE 2-continued

| EX | Structure | Exact Mass [M + H]+ | Route Used |
|---|---|---|---|
| 308 | 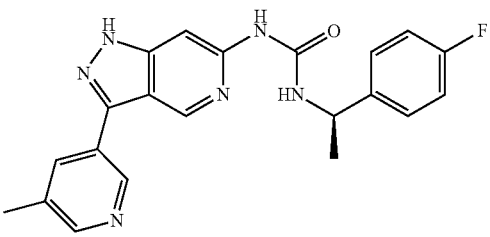<br>(R)-1-(1-(4-fluorophenyl)ethyl)-3-(3-(5-methylpyridin-3-yl)-1H-pyrazolo[4,3-c]pyridin-6-yl]urea | Calc'd 391, found 391 | 90 |
| 309 | 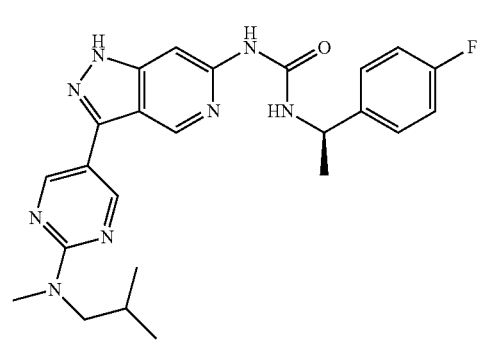<br>(R)-1-(1-(4-fluorophenyl)ethyl)-3-(3-(2-(isobutyl(methyl)amino)pyrimidin-5-yl)-1H-pyrazolo[4,3-c]pyridin-6-yl)urea | Calc'd 463, found 463 | 90 |
| 310 | 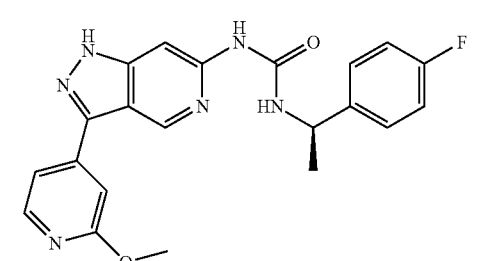<br>(R)-1-(1-(4-fluorophenyl)ethyl)-3-(3-(2-methoxypyridin-4-yl)-1H-pyrazolo[4,3-c]pyridin-6-yl]urea | Calc'd 407, found 407 | 90 |
| 311 | 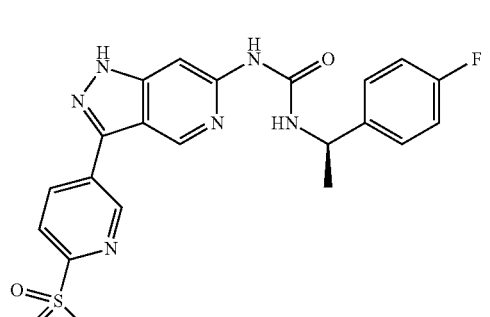<br>(R)-1-(3-(6-ethylsulfonyl)pyridin-3-yl)-1H-pyrazolo[4,3-c]pyridin-6-yl)-3-(1-(4-fluorophenyl)ethyl)urea | Calc'd 469, found 469 | 90 |

TABLE 2-continued

| EX | Structure | Exact Mass [M + H]+ | Route Used |
|---|---|---|---|
| 312 | (R)-1-(3-(2-methoxypyrimidin-5-yl)-1H-pyrazolo[4,3-c]pyridin-6-yl)-3-(2,3,4,5-tetrahydrobenzo[b]oxepin-5-yl)urea | Calc'd 432., found 432 | 30 |
| 313 | (R)-1-(3-(2-methoxypyrimidin-5-yl)-1H-pyrazolo[4,3-c]pyridin-6-yl)-3-(1-phenylethyl)urea | Calc'd 390, found 390 | 30 |
| 314 | (S)-1-(2-methoxy-1-phenylethyl)-3-(3-(2-methoxypyrimidin-5-yl)-1H-pyrazolo[4,3-c]pyridin-6-yl)urea | Calc'd 420, found 420 | 90 |
| 315 | 1-[(6-methylpyridin-2-yl)methyl)-3-[3-(2-methylpyridin-4-yl)-1H-pyrazolo[4,3-c]pyridin-6-yl]urea | Calc'd 374, found 374 | 12 |

TABLE 2-continued

| EX | Structure | Exact Mass [M + H]+ | Route Used |
|---|---|---|---|
| 316 | 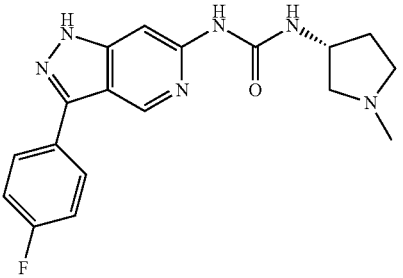<br>1-[3-(4-fluorophenyl)-1H-pyrazolo[4,3-c]pyridin-6-yl]-3-[(3R)-1-methylpyrrolidin-3-yl]urea | Calc'd 355, found 355 | 623 + SFC |
| 317 | 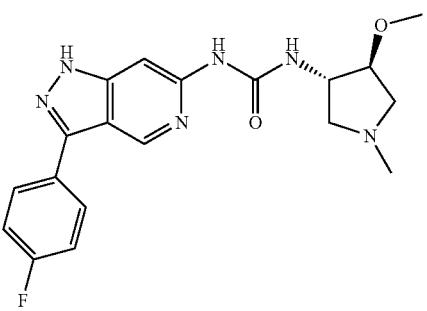<br>1-[3-(4-fluorophenyl)-1H-pyrazolo[4,3-c]pyridin-6-yl]-3-[(3S,4S)-4-methoxy-1-methylpyrrolidin-3-yl]urea | Calc'd 385, found 385 | 623 + SFC |
| 318 | 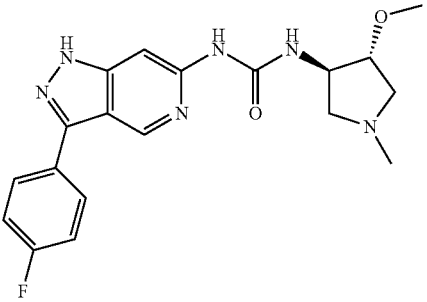<br>1-[3-(4-fluorophenyl)-1H-pyrazolo[4,3-c]pyridin-6-yl]-3-[(3R,4R)-4-methoxy-1-methylpyrrolidin-3-yl]urea | Calc'd 385, found 385 | 623 + SFC |
| 319 | 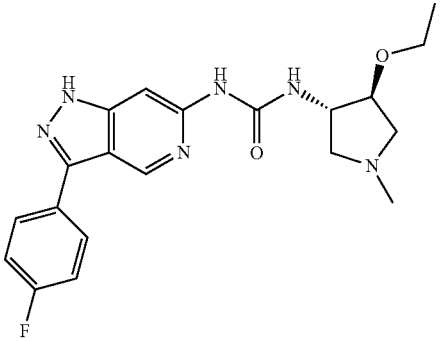<br>1-[(3S,4S)-4-ethoxy-1-methylpyrrolidin-3-yl]-3-[3-(4-fluorophenyl)-1H-pyrazolo[4,3-c]pyridin-6-yl]urea | Calc'd 399, found 399 | 623 + SFC |

TABLE 2-continued

| EX | Structure | Exact Mass [M + H]+ | Route Used |
|---|---|---|---|
| 320 | 1-[(3R,4R)-4-ethoxy-1-methylpyrrolidin-3-yl]-3-[3-(4-fluorophenyl)-1H-pyrazolo[4,3-c]pyridin-6-yl]urea | Calc'd 399, found 399 | 623 + SFC |
| 321 | 1-[3-(4-fluorophenyl)-1H-pyrazolo[4,3-c]pyridin-6-yl]-3-{[(3S)-1-methylpyrrolidin-3-yl]methyl}urea | Calc'd 369, found 369 | 623 + SFC |
| 322 | 1-[3-(4-fluorophenyl)-1H-pyrazolo[4,3-c]pyridin-6-yl]-3-{[(3R)-1-methylpyrrolidin-3-yl]methyl}urea | Calc'd 369, found 369 | 623 + SFC |
| 323 | 1-[(1R)-1-(4-fluorophenyl)-2-methoxyethyl]-3-[3-(2-methylpyridin-4-yl)-1H-pyrazolo[4,3-c]pyridin-6-yl]urea | Calc'd 421, found 421 | 178 + SFC |

TABLE 2-continued

| EX | Structure | Exact Mass [M + H]+ | Route Used |
|---|---|---|---|
| 324 | 1-[(1S)-1-(4-fluorophenyl)-2-methoxyethyl]-3-[3-(2-methylpyridin-4-yl)-1H-pyrazolo[4,3-c]pyridin-6-yl]urea | Calc'd 421, found 421 | 178 + SFC |
| 325 | 1-[(3R,4R)-4-fluoropyrrolidin-3-yl]-3-[3-(2-methylpyridin-4-yl)-1H-pyrazolo[4,3-c]pyridin-6-yl]urea | Calc'd 356, found 356 | 178 |
| 326 | 1-[3-(2-methylpyridin-4-yl)-1H-pyrazolo[4,3-c]pyridin-6-yl]-3-[(3R)-1-(2,2,2-trifluoroethyl)pyrrolidin-3-yl]urea | Calc'd 420, found 420 | 178 + SFC |
| 327 | 1-[3-(2-methylpyridin-4-yl)-1H-pyrazolo[4,3-c]pyridin-6-yl]-3-[(3S)-1-(2,2,2-trifluoroethyl)pyrrolidin-3-yl]urea | Calc'd 420, found 420 | 178 + SFC |

TABLE 2-continued

| EX | Structure | Exact Mass [M + H]+ | Route Used |
|---|---|---|---|
| 328 | 1-[(3S,4S)-4-fluoro-l-methylpyrrolidin-3-yl]-3-[3-(2-methylpyridin-4-yl)-1H-pyrazolo[4,3-c]pyridin-6-yl]urea | Calc'd 370, found 370 | 328 |
| 329 | 1-[(3R,4R)-4-fluoro-1-methylpyrrolidin-3-yl]-3-[3-(2-methylpyridin-4-yl)-1H-pyrazolo[4,3-c]pyridin-6-yl]urea | Calc'd 370, found 370 | 329 |
| 330 | Racemic 1-[3-(2-methylpyridin-4-yl)-1H-pyrazolo[4,3-c]pyridin-6-yl]-3-[(3S,4R) and (3R,4S)-4-phenyl-1-(2,2,2-trifluoroethyl)pyrrolidin-3-yl]urea | Calc'd 496, found 496 | 178 |

TABLE 2-continued
| EX | Structure | Exact Mass [M + H]+ | Route Used |
|---|---|---|---|
| 331 | 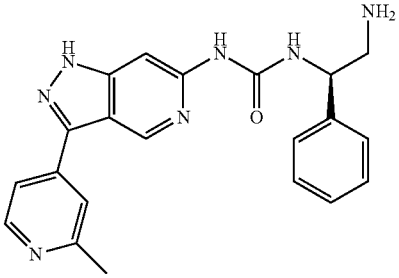<br>1-[(1R)-2-amino-1-phenylethyl]-3-[3-(2-methylpyridin-4-yl)-1H-pyrazolo[4,3-c]pyridin-6-yl]urea | Calc'd 388, found 388 | 12 |
| 332 | 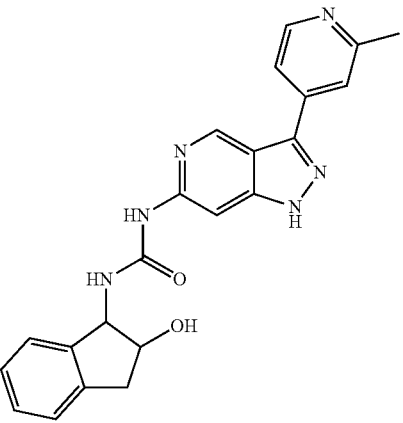<br>1-(2-hydroxy-2,3-dihydro-1H-inden-1-yl)-3-[3-(2-methylpyridin-4-yl)-1H-pyrazolo[4,3-c]pyridin-6-yl]urea | Calc'd 401, found 401 | 12 |
| 333 | 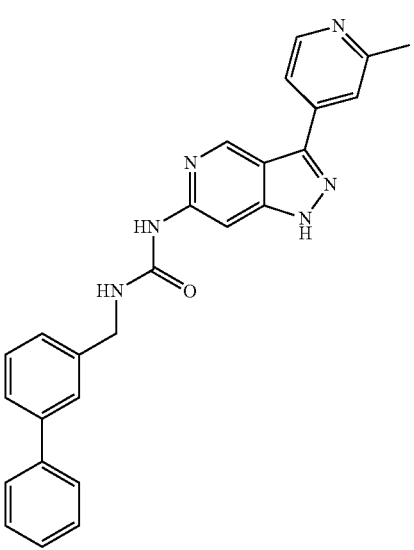<br>1-(biphenyl-3-ylmethyl)-3-[3-(2-methylpyridin-4-yl)-1H-pyrazolo[4,3-c]pyridin-6-yl]urea | Calc'd 435, found 435 | 12 |

TABLE 2-continued
| EX | Structure | Exact Mass [M + H]+ | Route Used |
|---|---|---|---|
| 334 | 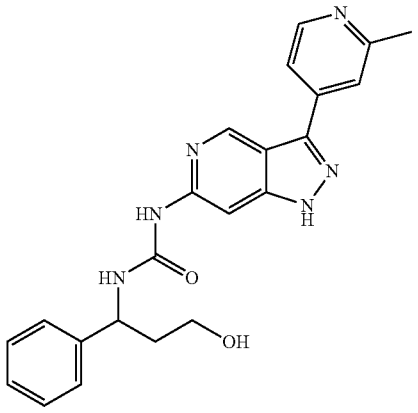 1-(3-hydroxy-1-phenylpropyl)-3-[3-(2-methylpyridin-4-yl)-1H-pyrazolo[4,3-c]pyridin-6-yl]urea | Calc'd 403, found 403 | 12 |
| 335 | 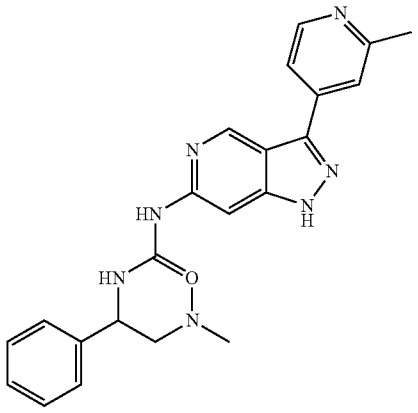 1-[2-(dimethylamino)-1-phenylethyl]-3-[3-(2-methylpyridin-4-yl)-1H-pyrazolo[4,3-c]pyridin-6-yl]urea | Calc'd 416, found 416 | 12 |
| 336 | 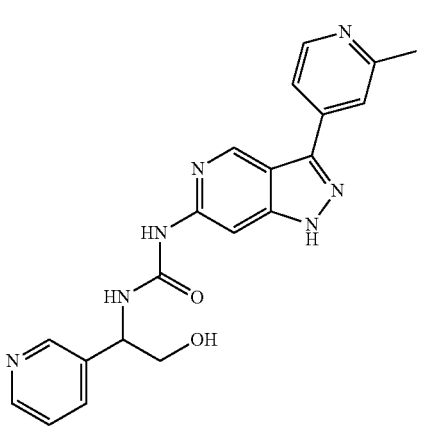 1-(2-hydroxy-1-pyridin-3-ylethyl)-3-[3-(2-methylpyridin-4-yl)-1H-pyrazolo[4,3-c]pyridin-6-yl]urea | Calc'd 390, found 390 | 12 |

TABLE 2-continued
| EX | Structure | Exact Mass [M + H]+ | Route Used |
|---|---|---|---|
| 337 | 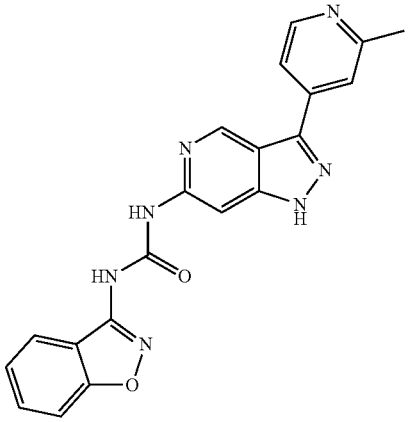<br>1-(1,2-benzisoxazol-3-yl)-3-[3-(2-methylpyridin-4-yl)-1H-pyrazolo[4,3-c]pyridin-6-yl]urea | Calc'd 386, found 386 | 12 |
| 338 | 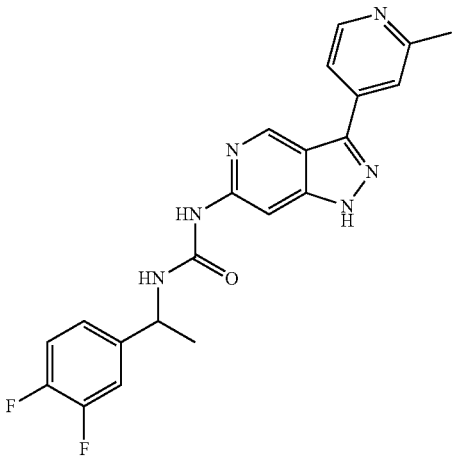<br>1-[1-(3,4-difluorophenyl)ethyl]-3-[3-(2-methylpyridin-4-yl)-1H-pyrazolo[4,3-c]pyridin-6-yl]urea | Calc'd 409, found 409 | 12 |
| 339 | 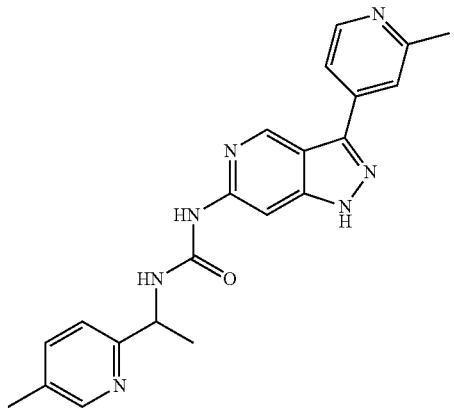<br>1-[1-(5-methylpyridin-2-yl)ethyl]-3-[3-(2-methylpyridin-4-yl)-1H-pyrazolo[4,3-c]pyridin-6-yl]urea | Calc'd 388, found 388 | 12 |

TABLE 2-continued
| EX | Structure | Exact Mass [M + H]+ | Route Used |
|---|---|---|---|
| 340 | 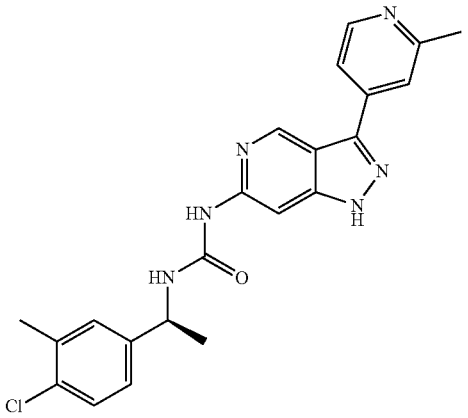<br>1-[(1S)-1-(4-chloro-3-methylphenyl)ethyl]-3-[3-(2-methylpyridin-4-yl)-1H-pyrazolo[4,3-c]pyridin-6-yl]urea | Calc'd 421, found 421 | 12 |
| 341 | 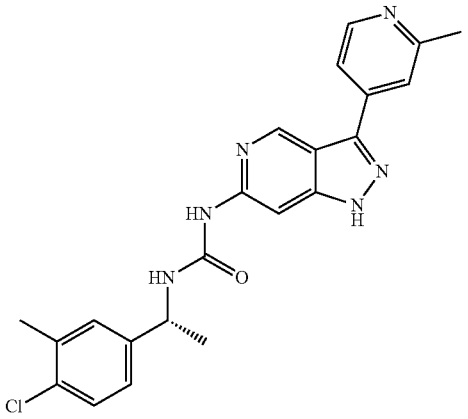<br>1-[(1R)-1-(4-chloro-3-methylphenyl)ethyl]-3-[3-(2-methylpyridin-4-yl)-1H-pyrazolo[4,3-c]pyridin-6-yl]urea | Calc'd 421, found 421 | 12 |
| 342 | 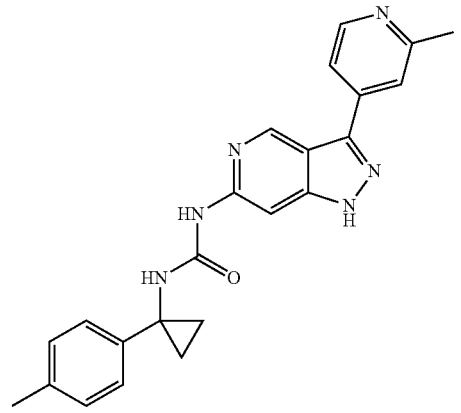<br>1-[1-(4-methylphenyl)cyclopropyl]-3-[3-(2-methylpyridin-4-yl)-1H-pyrazolo[4,3-c]pyridin-6-yl]urea | Calc'd 399, found 399 | 12 |

TABLE 2-continued
| EX | Structure | Exact Mass [M + H]+ | Route Used |
|---|---|---|---|
| 343 | 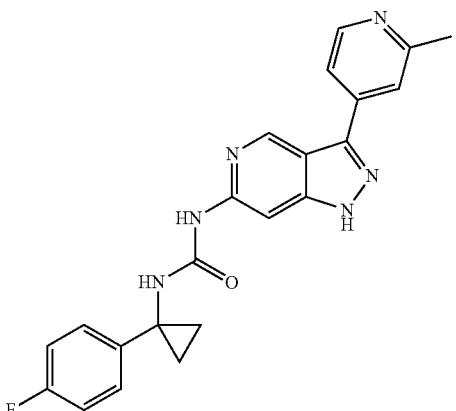<br>1-[1-(4-fluorophenyl)cyclopropyl]-3-[3-(2-methylpyridin-4-yl)-1H-pyrazolo[4,3-c]pyridin-6-yl]urea | Calc'd 403, found 403 | 12 |
| 344 | 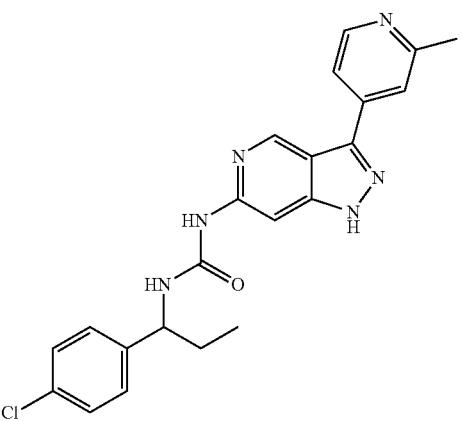<br>1-[1-(4-chlorophenyl)propyl]-3-[3-(2-methylpyridin-4-yl)-1H-pyrazolo[4,3-c]pyridin-6-yl]urea | Calc'd 421, found 421 | 12 |
| 345 | 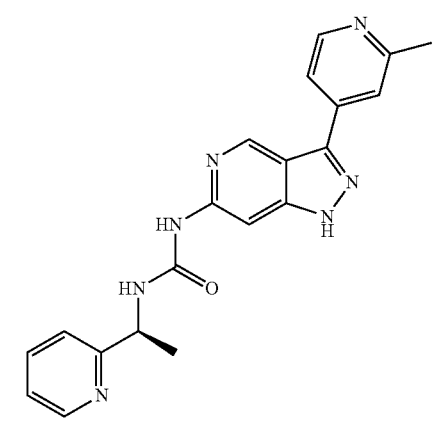<br>1-[3-(2-methylpyridin-4-yl)-1H-pyrazolo[4,3-c]pyridin-6-yl]-3-[(1S)-1-pyridin-2-ylethyl]urea | Calc'd 374, found 374 | 12 |

TABLE 2-continued
| EX | Structure | Exact Mass [M + H]+ | Route Used |
|---|---|---|---|
| 346 | 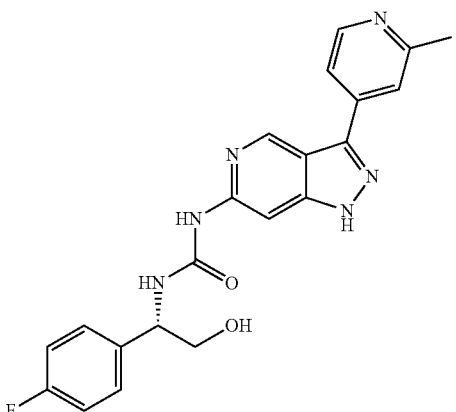 1-[(1S)-1-(4-fluorophenyl)-2-hydroxyethyl]-3-[3-(2-methylpyridin-4-yl)-1H-pyrazolo[4,3-c]pyridin-6-yl]urea | Calc'd 407, found 407 | 12 |
| 347 | 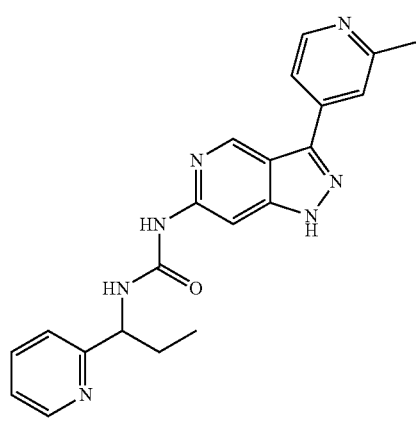 1-[3-(2-methylpyridin-4-yl)-1H-pyrazolo[4,3-c]pyridin-6-yl]-3-(1-pyridin-2-ylpropyl)urea | Calc'd 388, found 388 | 12 |
| 348 | 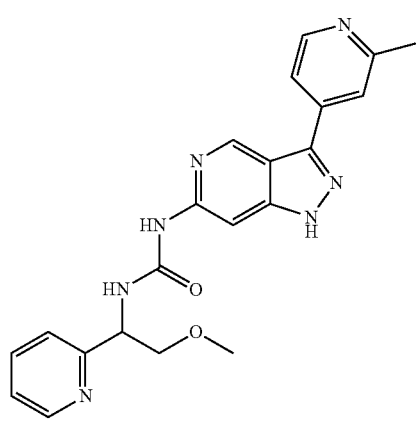 1-(2-methoxy-1-pyridin-2-ylethyl)-3-[3-(2-methylpyridin-4-yl)-1H-pyrazolo[4,3-c]pyridin-6-yl]urea | Calc'd 404, found 404 | 12 |

TABLE 2-continued

| EX | Structure | Exact Mass [M + H]+ | Route Used |
|---|---|---|---|
| 349 | 1-[1-(3-methylpyridin-2-yl)ethyl]-3-[3-(2-methylpyridin-4-yl)-1H-pyrazolo[4,3-c]pyridin-6-yl]urea | Calc'd 388, found 388 | 12 |
| 350 | 1-[3-(2-methylpyridin-4-yl)-1H-pyrazolo[4,3-c]pyridin-6-yl]-3-(1-phenylcyclopropyl)urea | Calc'd 385, found 385 | 12 |
| 351 | 1-[3-(2-methylpyridin-4-yl)-1H-pyrazolo[4,3-c]pyridin-6-yl]-3-(1-pyridin-2-ylcyclopropyl)urea | Calc'd 386, found 386 | 12 |

TABLE 2-continued
| EX | Structure | Exact Mass [M + H]+ | Route Used |
|---|---|---|---|
| 352 | 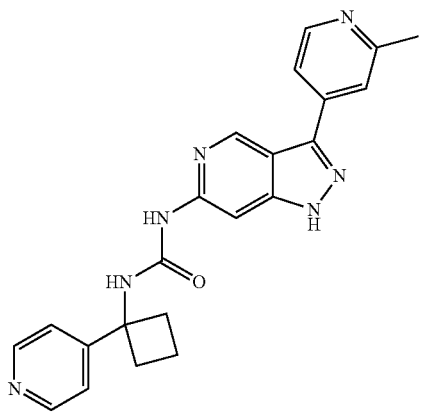<br>1-[3(2-methylpyridin-4-yl)-1H-pyrazolo[4,3-c]pyridin-6-yl]-3-(1-pyridin-4-ylcyclopropyl)urea | Calc'd 400, found 400 | 12 |
| 353 | 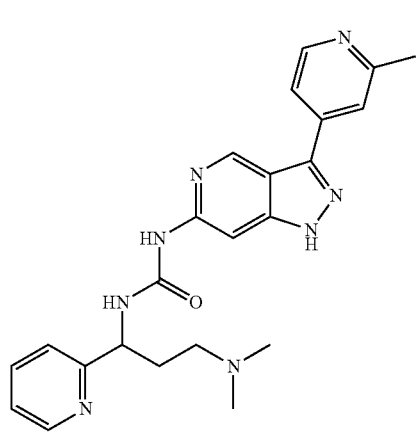<br>1-[(3-dimethylamino)-1-pyridin-2-ylpropyl]-3-[3-(2-methylpyridin-4-yl)-1H-pyrazolo[4,3-c]pyridin-6-yl]urea | Calc'd 431, found 431 | 12 |
| 354 | 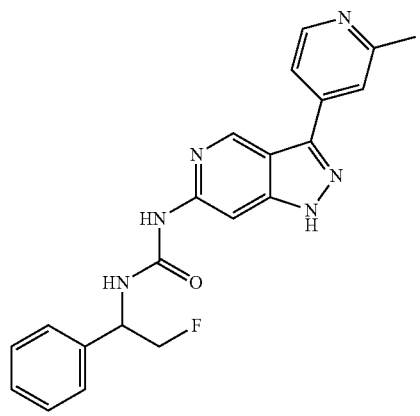<br>1-(2-fluoro-1-phenylethyl)-3-[3-(2-methylpyridin-4-yl)-1H-pyrazolo[4,3-c]pyridin-6-yl]urea | Calc'd 391.0, found 391 | 12 |

TABLE 2-continued
| EX | Structure | Exact Mass [M + H]+ | Route Used |
|---|---|---|---|
| 355 | 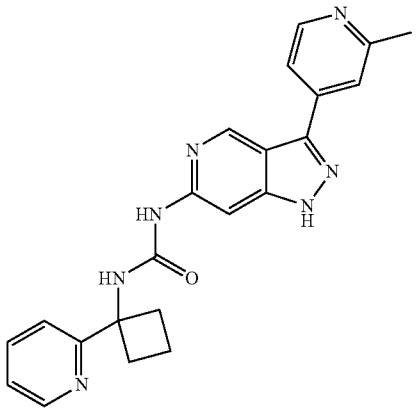<br>1-[3-(2-methylpyridin-4-yl)-1H-pyrazolo[4,3-c]pyridin-6-yl]-3-(1-pyridin-2-ylcyclopropyl)urea | Calc'd 400, found 400 | 12 |
| 356 | 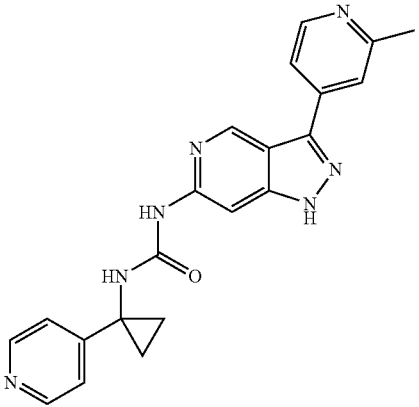<br>1-[3-(2-methylpyridin-4-yl)-1H-pyrazolo[4,3-c]pyridin-6-yl]-3-(1-pyridin-2-ylcyclopropyl)urea | Calc'd 386, found 386 | 12 |
| 357 | 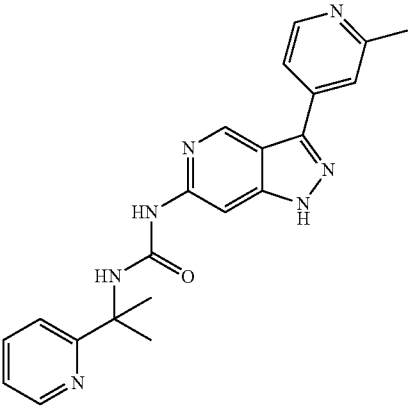<br>1-(1-methyl-1-pyridin-2-ylethyl)-3-[3-(2-methylpyridin-4-yl)-1H-pyrazolo[4,3-c]pyridin-6-yl]urea | Calc'd 388, found 388 | 12 |

TABLE 2-continued
| EX | Structure | Exact Mass [M + H]+ | Route Used |
|---|---|---|---|
| 358 | 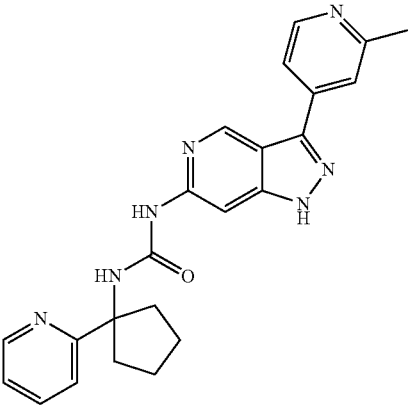<br>1-[3-(2-methylpyridin-4-yl)-1H-pyrazolo[4,3-c]pyridin-6-yl]-3-(1-pyridin-2-ylcyclopropyl)urea | Calc'd 414, found 414 | 12 |
| 359 | 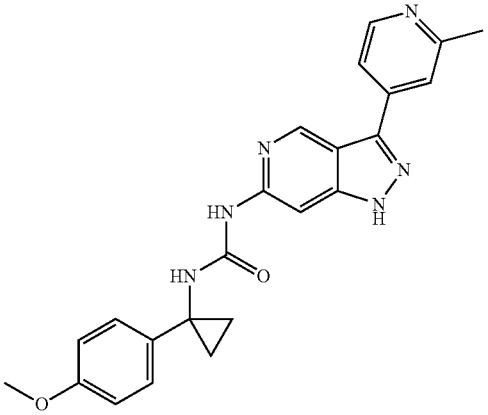<br>1-[1-(4-methoxyphenyl)cyclopropyl]-3-[3-(2-methylpyridin-4-yl)-1H-pyrazolo[4,3-c]pyridin-6-yl]urea | Calc'd 415, found 415 | 12 |
| 360 | 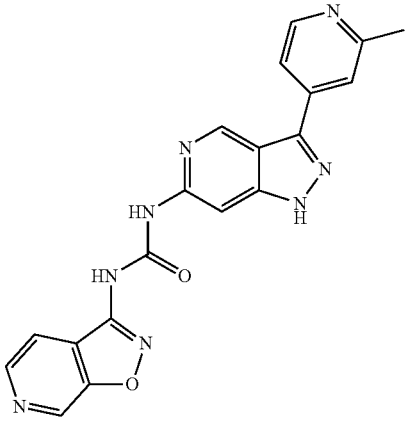<br>1-isoxazolo[5,4-c]pyridin-3-yl-3-[3-(2-methylpyridin-4-yl)-1H-pyrazolo[4,3-c]pyridin-6-yl]urea | Calc'd 387, found 387 | 12 |

TABLE 2-continued

| EX | Structure | Exact Mass [M + H]+ | Route Used |
|---|---|---|---|
| 361 | 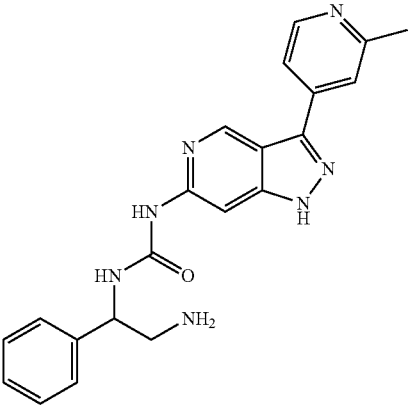 1-(2-amino-1-phenylethyl)-3-[3-(2-methylpyridin-4-yl)-1H-pyrazolo[4,3-c]pyridin-6-yl]urea | Calc'd 388, found 388 | 12 |
| 362 | 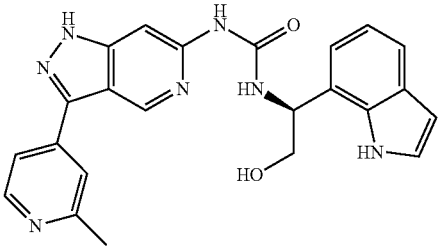 1-[(1S)-2-hydroxy-1-(1H-indol-7-yl)ethyl]-3-[3-(2-methylpyridin-4-yl)-1H-pyrazolo[4,3-c]pyridin-6-yl]urea | Calc'd 428, found 428 | 12 |
| 363 | 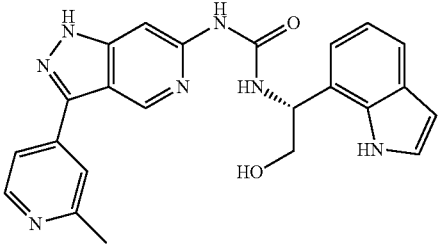 1-[(1S)-2-hydroxy-1-(1H-indol-7-yl)ethyl]-3-[3-(2-methylpyridin-4-yl)-1H-pyrazolo[4,3-c]pyridin-6-yl]urea | Calc'd 428, found 428 | 12 |
| 364 | 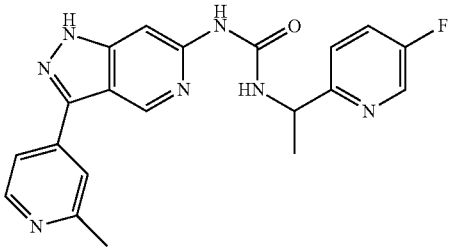 1-[1-(5-fluoropyridin-2-yl)ethyl]-3-[3-(2-methylpyridin-4-yl)-1H-pyrazolo[4,3-c]pyridin-6-yl]urea | Calc'd 392, found 392 | 12 |

TABLE 2-continued

| EX | Structure | Exact Mass [M + H]+ | Route Used |
|---|---|---|---|
| 365 | 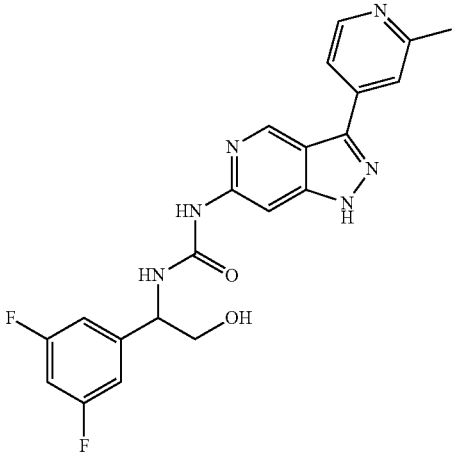<br>1-[1-(3,5-difluorophenyl)-2-hydroxyethyl]-3-[3-(2-methylpyridin-4-yl)-1H-pyrazolo[4,3-c]pyridin-6-yl]urea | Calc'd 425, found 425 | 12 |
| 366 | 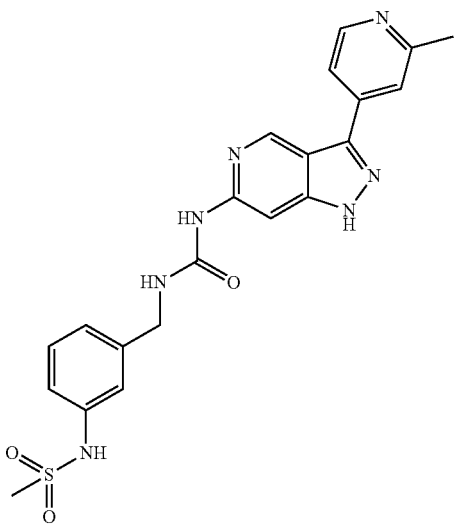<br>N-{3-[({[3-(2-methylpyridin-4-yl)-1H-pyrazolo[4,3-c]pyridin-6-yl]carbamoyl}amino)methyl]phenyl}methanesulfonamide | Calc'd 452, found 452 | 12 |
| 367 | 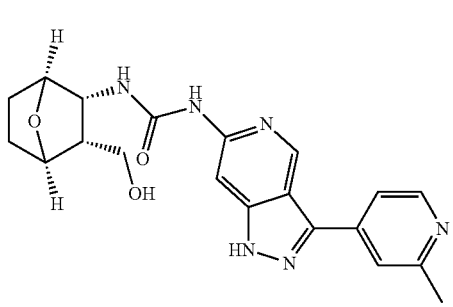<br>1-[(1S,2R,3R,4R)-3-(hydroxymethyl)-7-oxabicyclo[2.2.1]hept-2-yl]-3-[3-(2-methylpyridin-4-yl)-1H-pyrazolo[4,3-c]pyridin-6-yl]urea | Calc'd 395, found 395 | 12 |

TABLE 2-continued
| EX | Structure | Exact Mass [M + H]+ | Route Used |
|----|-----------|---------------------|------------|
| 368 | 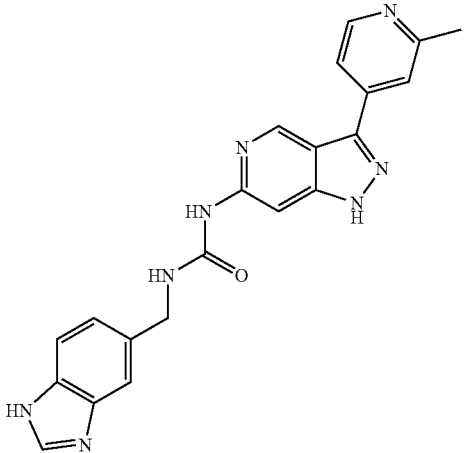<br>1-(1H-benzimidazol-5-ylmethyl)-3-[3-(2-methylpyridin-4-yl)-1H-pyrazolo[4,3-c]pyridin-6-yl]urea | Calc'd 399, found 399 | 12 |
| 369 | 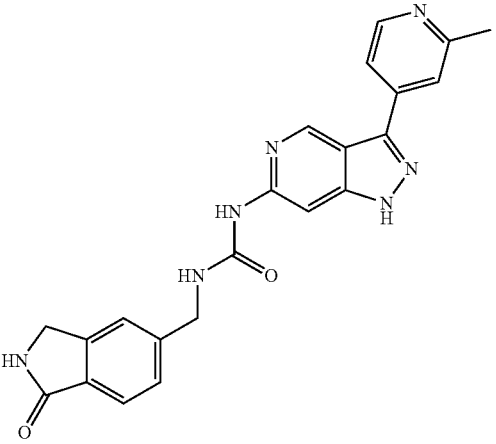<br>1-[3-(2-methylpyridin-4-yl)-1H-pyrazolo[4,3-c]pyridin-6-yl]-3-[(1-oxo-2,3-dihydro-1H-isoindol-5-yl)methyl]urea | Calc'd 414, found 414 | 12 |
| 370 | 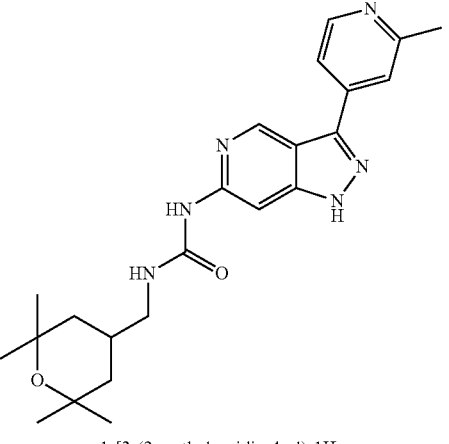<br>1-[3-(2-methylpyridin-4-yl)-1H-pyrazolo[4,3-c]pyridin-6-yl]-3-[(2,2,6,6-tetramethyltetrahydro-2H-pyran-4-yl)methyl]urea | Calc'd 423, found 423 | 12 |

TABLE 2-continued
| EX | Structure | Exact Mass [M + H]+ | Route Used |
|---|---|---|---|
| 371 | 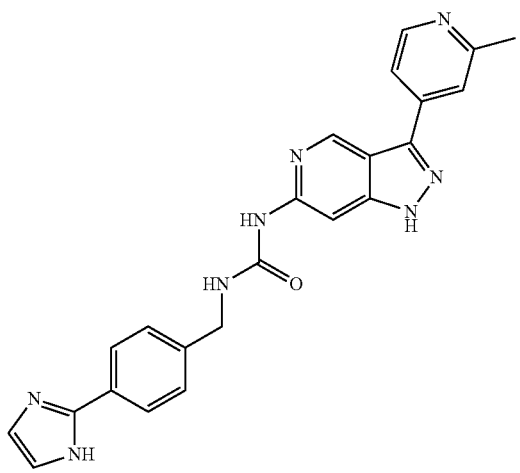 1-[4-(1H-imidazol-2-yl)benzyl)-3-[3-(2-methylpyridin-4-yl)-1H-pyrazolo[4,3-c]pyridin-6-yl]urea | Calc'd 425, found 425 | 12 |
| 372 | 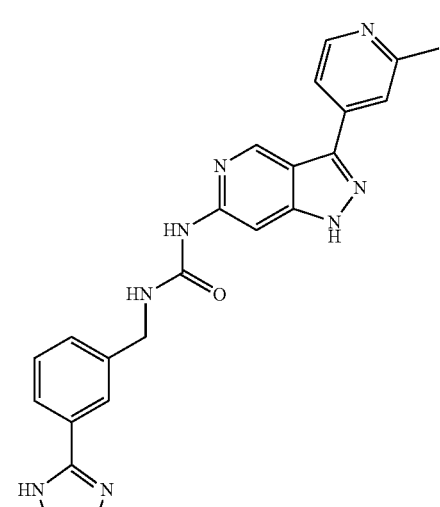 1-[3-(1H-imidazol-2-yl)benzyl)-3-[3-(2-methylpyridin-4-yl)-1H-pyrazolo[4,3-c]pyridin-6-yl]urea | Calc'd 425, found 425 | 12 |

TABLE 2-continued
| EX | Structure | Exact Mass [M + H]+ | Route Used |
|---|---|---|---|
| 373 | 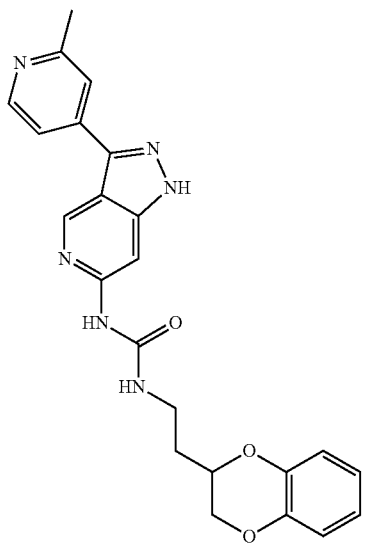<br>1-[2-(2,3-dihydro-1,4-benzodioxin-2-yl)ethyl]-3-[3-(2-methylpyridin-4-yl)-1H-pyrazolo[4,3-c]pyridin-6-yl]urea | Calc'd 431, found 431 | 12 |
| 374 | 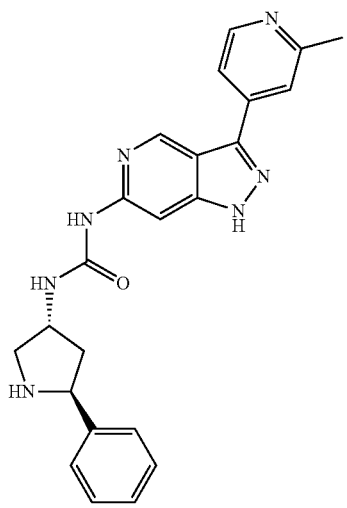<br>1-[3-(2-methylpyridin-4-yl)-1H-pyrazolo[4,3-c]pyridin-6-yl]-3-[(3R,5S)-5-phenylpyrrolidin-3-yl]urea | Calc'd 414, found 414 | 12 |

TABLE 2-continued
| EX | Structure | Exact Mass [M + H]+ | Route Used |
|---|---|---|---|
| 375 | 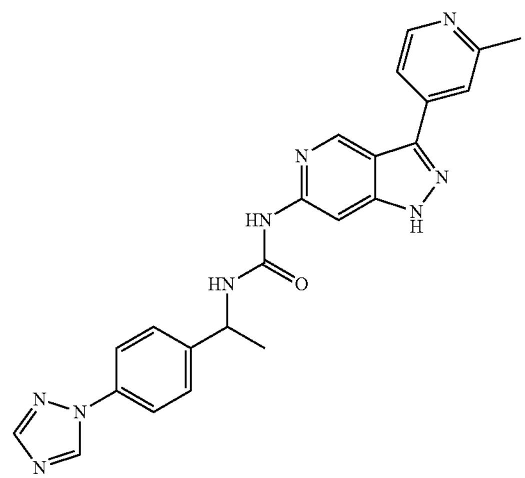 | Calc'd 440, found 440 | 12 |
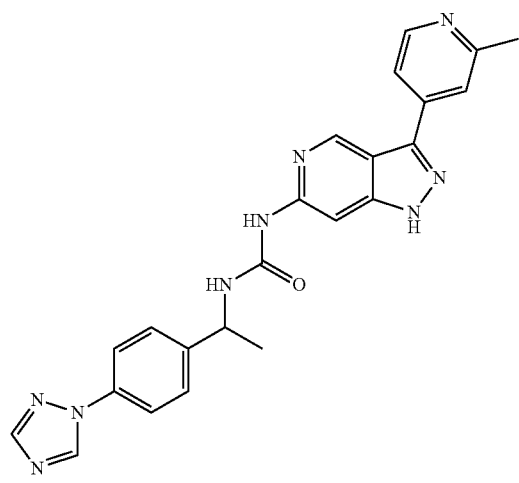
1-[3-(2-methylpyridin-4-yl)-1H-pyrazolo[4,3-c]pyridin-6-yl]-3-{1-[4-(1H-1,2,4-triazol-1-yl)phenyl]ethyl}urea
| 376 | | Calc'd 451, found 451 | 12 |
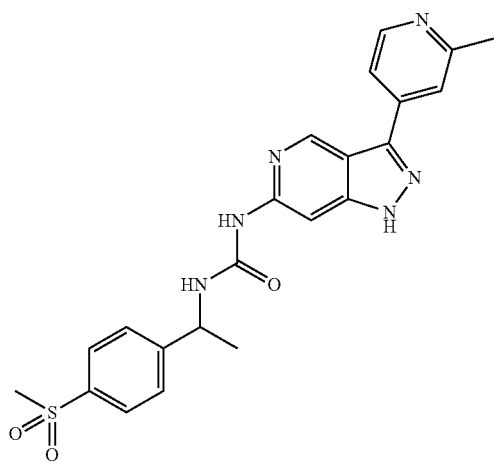
1-[3-(2-methylpyridin-4-yl)-1H-pyrazolo[4,3-c]pyridin-6-yl]-3-{1-[4-(methylsulfonyl)phenyl]ethyl}urea

TABLE 2-continued
| EX | Structure | Exact Mass [M + H]+ | Route Used |
|---|---|---|---|
| 377 | 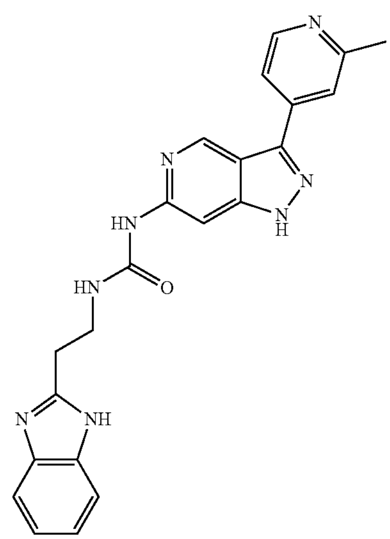 | Calc'd 413, found 413 | 12 |
1-[2-(1H-benzimidazol-2-yl)ethyl]-3-[3-(2-methylpyridin-4-yl)-1H-pyrazolo[4,3-c]pyridin-6-yl]urea
| 378 | | Calc'd 457, found 457 | 12 |
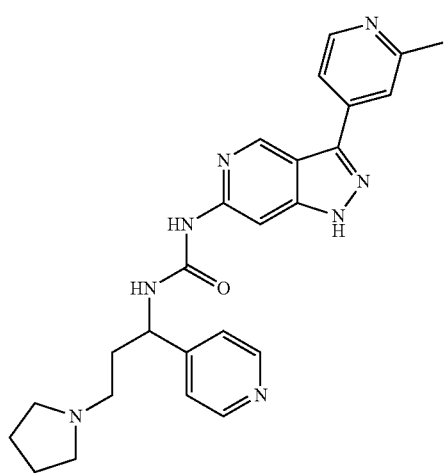
1-[3-(2-methylpyridin-4-yl)-1H-pyrazolo[4,3-c]pyridin-6-yl]-3-(1-pyridin-4-yl-3-pyrrolidin-1-ylpropyl)urea

TABLE 2-continued
| EX | Structure | Exact Mass [M + H]+ | Route Used |
|---|---|---|---|
| 379 | 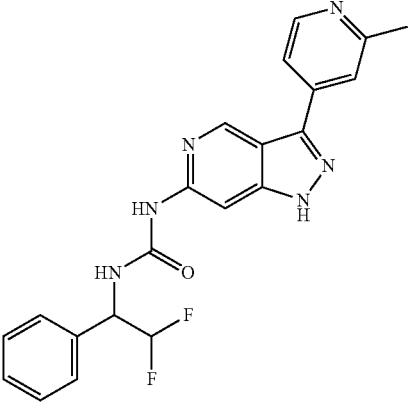 1-(2,2-difluoro-1-phenylethyl)-3-[3-(2-methylpyridin-4-yl)-1H-pyrazolo[4,3-c]pyridin-6-yl]urea | Calc'd 409, found 409 | 12 |
| 380 | 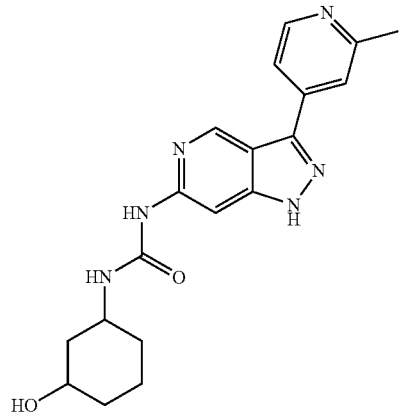 1-(3-hydroxycyclohexyl)-3-[3-(2-methylpyridin-4-yl)-1H-pyrazolo[4,3-c]pyridin-6-yl]urea | Calc'd 367, found 367 | 12 |
| 381 | 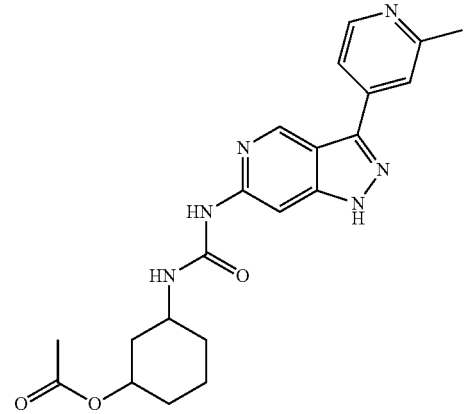 3-({[3-(2-methylpyridin-4-yl)-1H-pyrazolo[4,3-c]pyridin-6-yl]carbamoyl}amino)cyclohexyl acetate | Calc'd 409, found 409 | 12 |

TABLE 2-continued
| EX | Structure | Exact Mass [M + H]+ | Route Used |
|---|---|---|---|
| 382 | 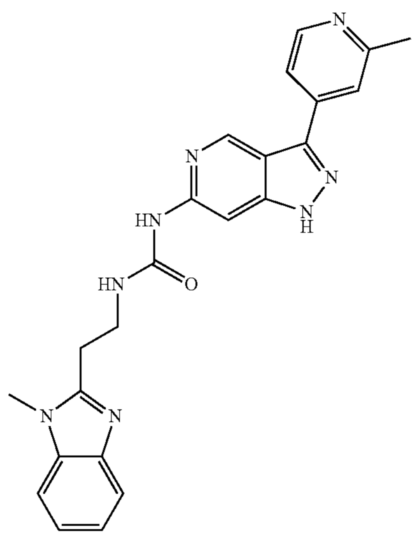 | Calc'd 427, found 427 | 12 |
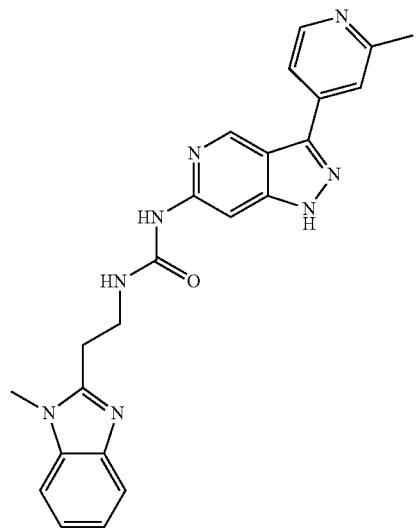
1-[2-(1-methyl-1H-benzimidazol-2-yl)ethyl]-3-[3-(2-methylpyridin-4-yl)-1H-pyrazolo[4,3-c]pyridin-6-yl]urea
| 383 | | Calc'd 403, found 403 | 12 |
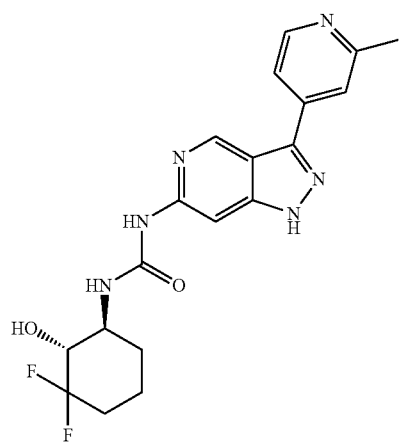
1-[(1S,2R)-3,3-difluoro-2-hydroxycyclohexyl]-3-[3-(2-methylpyridin-4-yl)-1H-pyrazolo[4,3-c]pyridin-6-yl]urea

TABLE 2-continued
| EX | Structure | Exact Mass [M + H]+ | Route Used |
|---|---|---|---|
| 384 | 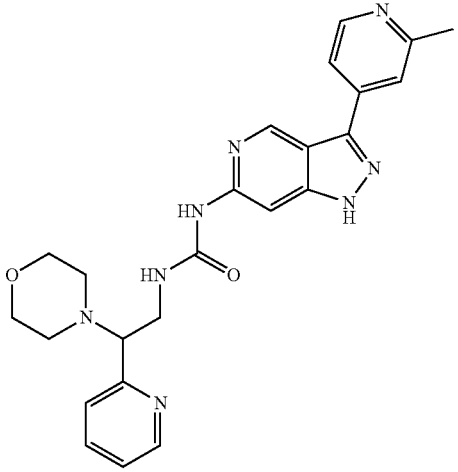<br>1-[3-(2-methylpyridin-4-yl)-1H-pyrazolo[4,3-c]pyridin-6-yl]-3-(2-morpholin-4-yl-2-pyridin-2-ylethyl)urea | Calc'd 459, found 459 | 12 |
| 385 | 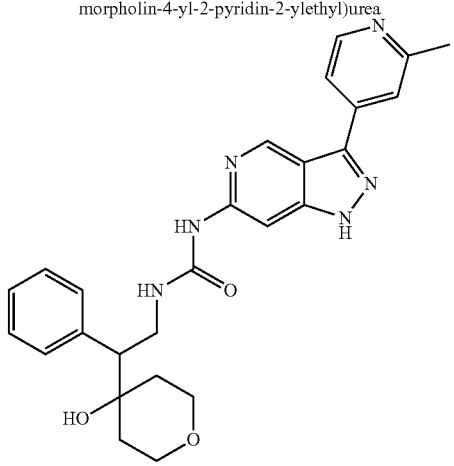<br>1-[2-(4-hydroxytetrahydro-2H-pyran-4-yl)-2-phenylethyl]-3-[3-(2-methylpyridin-4-yl)-1H-pyrazolo[4,3-c]pyridin-6-yl]urea | Calc'd 473, found 473 | 12 |
| 386 | 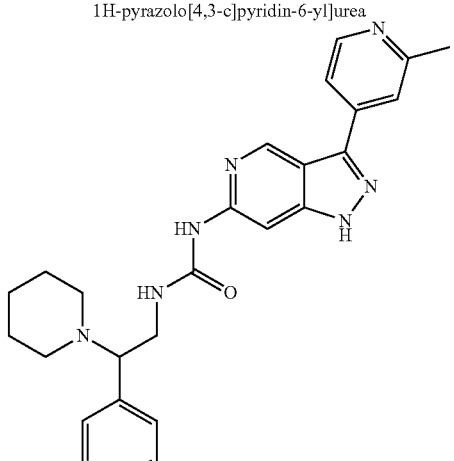<br>1-[3-(2-methylpyridin-4-yl)-1H-pyrazolo[4,3-c]pyridin-6-yl]-3-(2-phenyl-2-piperidin-1-ylethyl)urea | Calc'd 456, found 456 | 12 |

TABLE 2-continued
| EX | Structure | Exact Mass [M + H]+ | Route Used |
|---|---|---|---|
| 387 | 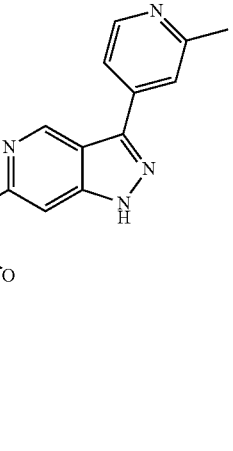<br>1-[3-(2-methylpyridin-4-yl)-1H-pyrazolo[4,3-c]pyridin-6-yl]-3-[2-(tetrahydrofuran-3-yl)ethyl]urea | Calc'd 367, found 367 | 12 |
| 388 | 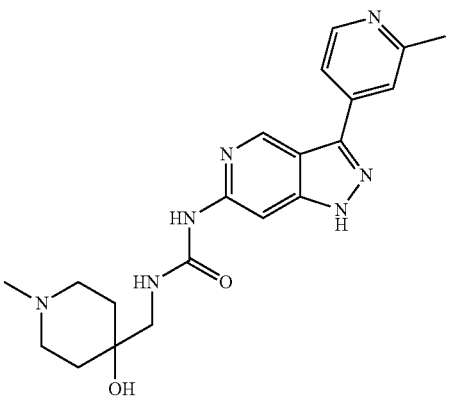<br>1-[(4-hydroxy-1-methylpiperidin-4-yl)methyl]-3-[3-(2-methylpyridin-4-yl)-1H-pyrazolo[4,3-c]pyridin-6-yl]urea | Calc'd 396, found 396 | 12 |
| 389 | 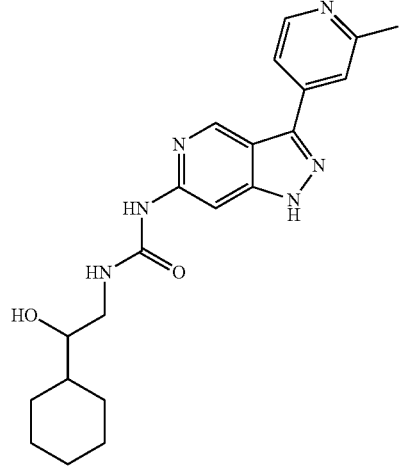<br>1-(2-cyclohexyl-2-hydroxyethyl)-3-[3-(2-methylpyridin-4-yl)-1H-pyrazolo[4,3-c]pyridin-6-yl]urea | Calc'd 395, found 395 | 12 |

| EX | Structure | Exact Mass [M + H]+ | Route Used |
|---|---|---|---|
| 390 | 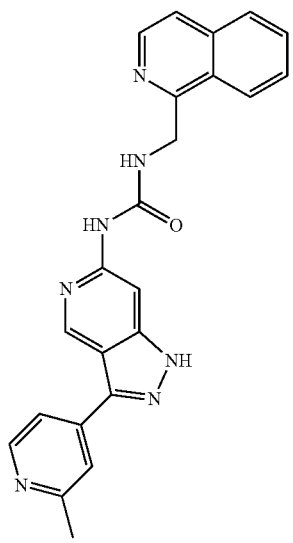 1-(isoquinolin-1-ylmethyl)-3-[3-(2-methylpyridin-4-yl)-1H-pyrazolo[4,3-c]pyridin-6-yl]urea | Calc'd 410, found 410 | 12 |
| 391 | 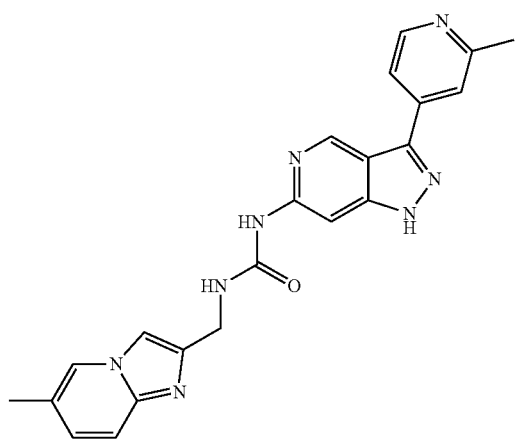 1-[(6-methylimidazo[1,2-a]pyridin-2-yl)methyl]-3-[3-(2-methylpyridin-4-yl)-1H-pyrazolo[4,3-c]pyridin-6-yl]urea | Calc'd 413, found 413 | 12 |

| EX | Structure | Exact Mass [M + H]+ | Route Used |
|---|---|---|---|
| 392 | 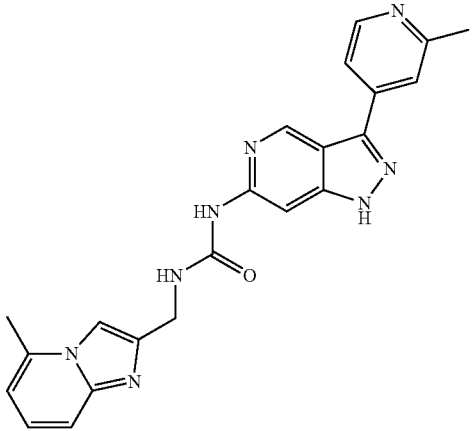<br>1-[(5-methylimidazo[1,2-a]pyridin-2-yl)methyl]-3-[3-(2-methylpyridin-4-yl)-1H-pyrazolo[4,3-c]pyridin-6-yl]urea | Calc'd 413, found 413 | 12 |
| 393 | 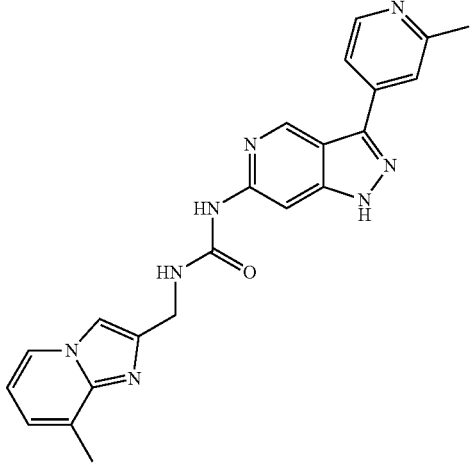<br>1-[(8-methylimidazo[1,2-a]pyridin-2-yl)methyl]-3-[3-(2-methylpyridin-4-yl)-1H-pyrazolo[4,3-c]pyridin-6-yl]urea | Calc'd 413, found 413 | 12 |
| 394 | 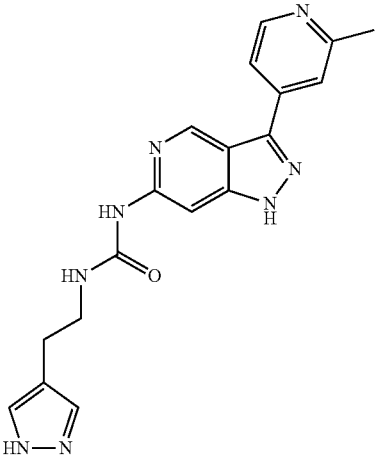<br>1-[3-(2-methylpyridin-4-yl)-1H-pyrazolo[4,3-c]pyridin-6-yl]-3-[2-(1H-pyrazol-4-yl)ethyl]urea | Calc'd 363, found 363 | 12 |

TABLE 2-continued
| EX | Structure | Exact Mass [M + H]+ | Route Used |
|---|---|---|---|
| 395 | 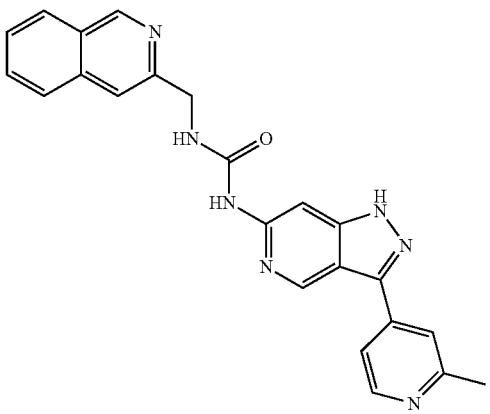<br>1-(isoquinolin-3-ylmethyl)-3-[3-(2-methylpyrindin-4-yl)-1H-pyrazolo[4,3-c]pyridin-6-yl]urea | Calc'd 410, found 410 | 12 |
| 396 | 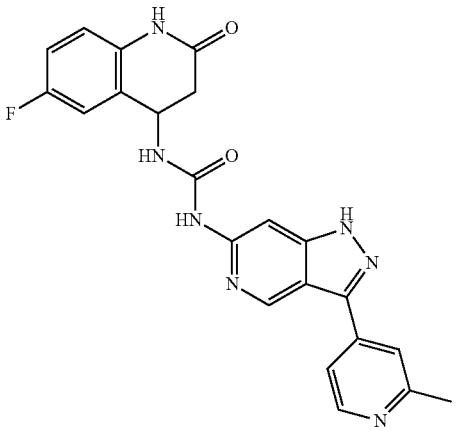<br>1-(6-fluoro-2-oxo-1,2,3,4-tetrahydroquinolin-4-yl)-3-[3-(2-methylpyrindin-4-yl)-1H-pyrazolo[4,3-c]pyridin-6-yl]urea | Calc'd 432, found 432 | 12 |
| 397 | 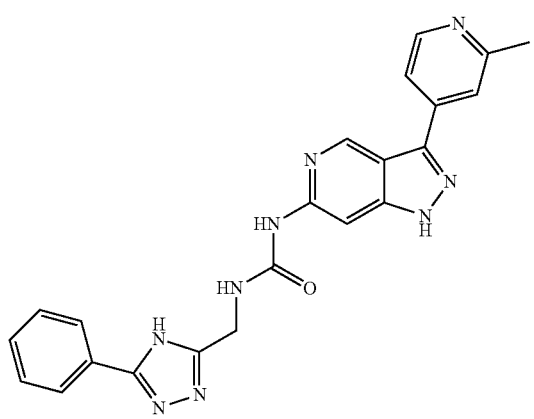<br>1-[3-(2-methylpyridin-4-yl)-1H-pyrazolo[4,3-c]pyridin-6-yl]-3-[(5-phenyl-4H-1,2,4-triazol-3-yl)methyl]urea | Calc'd 426, found 426 | 12 |

| EX | Structure | Exact Mass [M + H]+ | Route Used |
|---|---|---|---|
| 398 | 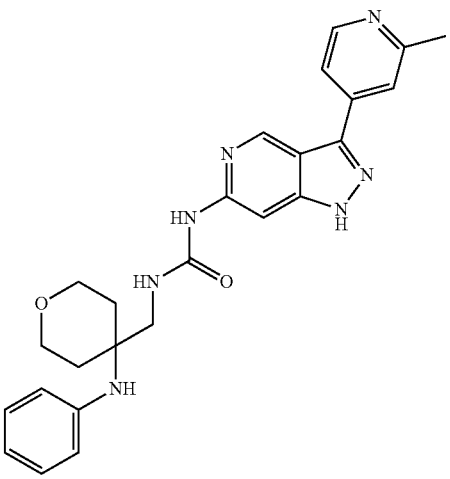 1-[3-(2-methylpyridin-4-yl)-1H-pyrazolo[4,3-c]pyridin-6-yl]-3-{[4-(phenylamino)tetrahydro-2H-pyran-4-yl]methyl}urea | Calc'd 458, found 458 | 12 |
| 399 | 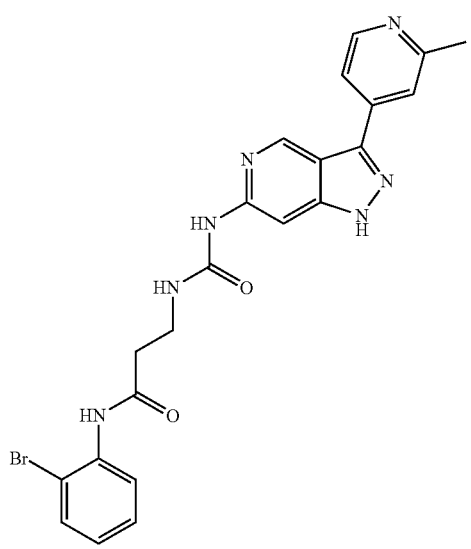 N-(2-bromophenyl)-N~3~-{[3-(2-methylpyridin-4-yl)-1H-pyrazolo[4,3-c]pyridin-6-yl]carbamoyl}-beta-alaninamide | Calc'd 494, found 494 | 12 |

TABLE 2-continued
| EX | Structure | Exact Mass [M + H]+ | Route Used |
|---|---|---|---|
| 400 | 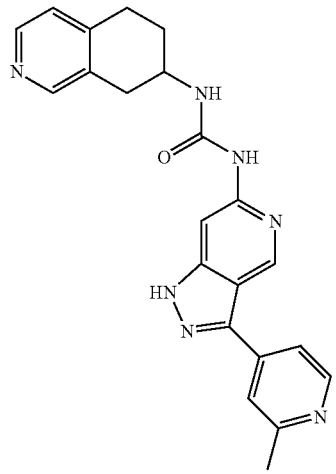<br>1-[3-(2-methylpyridin-4-yl)-1H-pyrazolo[4,3-c]pyridin-6-yl]-3-(5,6,7,8-tetrahydroisoquinolin-7-yl)urea | Calc'd 400, found 400 | 12 |
| 401 | 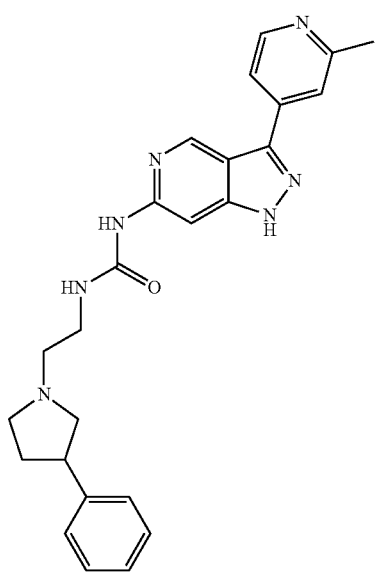<br>1-[3-(2-methylpyridin-4-yl)-1H-pyrazolo[4,3-c]pyridin-6-yl]-3-[2-(3-phenylpyrrolidin-1-yl)ethyl]urea | Calc'd 442, found 442 | 12 |

TABLE 2-continued
| EX | Structure | Exact Mass [M + H]+ | Route Used |
|---|---|---|---|
| 402 | 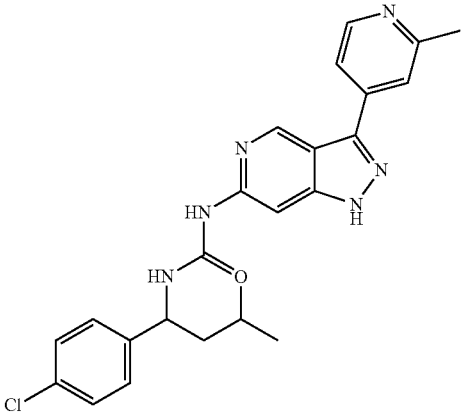<br>1-[1-(4-chlorophenyl)-3-methylbutyl]-3-[3-(2-methylpyridin-4-yl)-1H-pyrazolo[4,3-c]pyridin-6-yl]urea | Calc'd 449, found 449 | 12 |
| 403 | 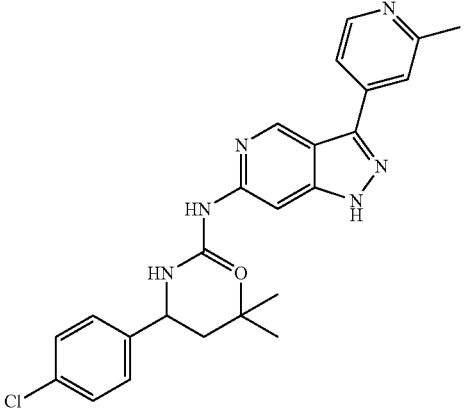<br>1-[1-(4-chlorophenyl)-3,3-dimethylbutyl]-3-[3-(2-methylpyridin-4-yl)-1H-pyrazolo[4,3-c]pyridin-6-yl]urea | Calc'd 463, found 463 | 12 |
| 404 | 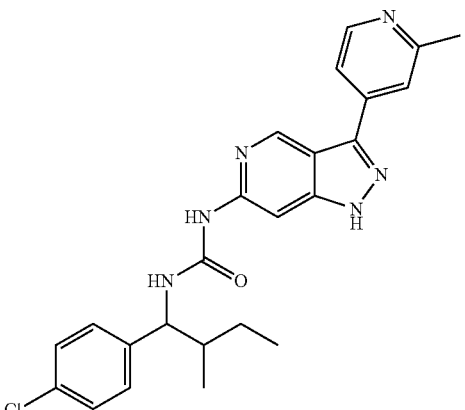<br>1-[1-(4-chlorophenyl)-2-methylbutyl]-3-[3-(2-methylpyridin-4-yl)-1H-pyrazolo[4,3-c]pyridin-6-yl]urea | Calc'd 449, found 449 | 12 |

TABLE 2-continued

| EX | Structure | Exact Mass [M + H]+ | Route Used |
|---|---|---|---|
| 405 | 1-[3-(2-methylpyridin-4-yl)-1H-pyrazolo[4,3-c]pyridin-6-yl]-3-[(3S,5S)-5-phenylpyrrolidin-3-yl]urea | Calc'd 414, found 414 | 12 |
| 406 | 1-[3-(diethylamino)-1-phenylpropyl]-3-[3-(2-methylpyridin-4-yl)-1H-pyrazolo[4,3-c]pyridin-6-yl]urea | Calc'd 458, found 458 | 12 |
| 407 | 1-[3-(2-methylpyridin-4-yl)-1H-pyrazolo[4,3-c]pyridin-6-yl]-3-(2-oxo-1,2,3,4-tetrahydroquinolin-4-yl)urea | Calc'd 414, found 414 | 12 |
| 408 | 1-(1H-benzimidazol-2-ylmethyl)-3-[3-(2-methylpyridin-4-yl)-1H-pyrazolo[4,3-c]pyridin-6-yl]urea | Calc'd 399, found 399 | 12 |

TABLE 2-continued

| EX | Structure | Exact Mass [M + H]+ | Route Used |
|---|---|---|---|
| 409 | 1-[3-(2-methylpyridin-4-yl)-1H-pyrazolo[4,3-c]pyridin-6-yl]-3-[(5-phenylpyrrolidin-3-yl)methyl]urea | Calc'd 428, found 428 | 12 |
| 410 | 1-[(1-benzylpyrrolidin-3-yl)methyl]-3-[3-(2-methylpyridin-4-yl)-1H-pyrazolo[4,3-c]pyridin-6-yl]urea | Calc'd 442, found 442 | 12 |
| 411 | 1-[(1S)-1-(3,4-difluorophenyl)ethyl]-3-[3-(2-methylpyridin-4-yl)-1H-pyrazolo[4,3-c]pyridin-6-yl]urea | Calc'd 409, found 409 | 12 |
| 412 | 1-[(1R)-1-(3,4-difluorophenyl)ethyl]-3-[3-(2-methylpyridin-4-yl)-1H-pyrazolo[4,3-c]pyridin-6-yl]urea | Calc'd 409, found 409 | 12 |

TABLE 2-continued

| EX | Structure | Exact Mass [M + H]+ | Route Used |
|---|---|---|---|
| 413 | 1-[(1S)-1-(4-chlorophenyl)propyl]-3-[3-(2-methylpyridin-4-yl)-1H-pyrazolo[4,3-c]pyridin-6-yl]urea | Calc'd 421, found 421 | 12 |
| 414 | 1-[(1R)-1-(4-chlorophenyl)propyl]-3-[3-(2-methylpyridin-4-yl)-1H-pyrazolo[4,3-c]pyridin-6-yl]urea | Calc'd 421, found 421 | 12 |
| 415 | 1-[(1R)-2-methoxy-1-pyridin-2-ylethyl]-3-[3-(2-methylpyridin-4-yl)-1H-pyrazolo[4,3-c]pyridin-6-yl]urea | Calc'd 404, found 404 | 12 |
| 416 | 1-[(1S)-2-methoxy-1-pyridin-2-ylethyl]-3-[3-(2-methylpyridin-4-yl)-1H-pyrazolo[4,3-c]pyridin-6-yl]urea | Calc'd 404, found 404 | 12 |

TABLE 2-continued
| EX | Structure | Exact Mass [M + H]+ | Route Used |
|---|---|---|---|
| 417 | 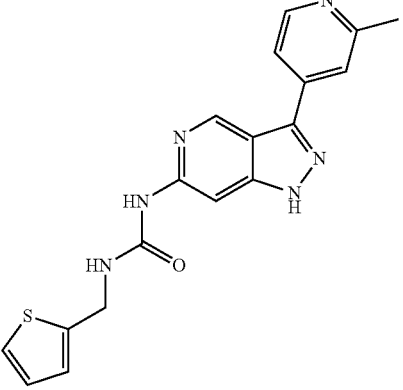 1-[3-(2-methylpyridin-4-yl)-1H-pyrazolo[4,3-c]pyridin-6-yl]-3-(thiophen-2-ylmethyl)urea | Calc'd 365, found 365 | 12 |
| 418 | 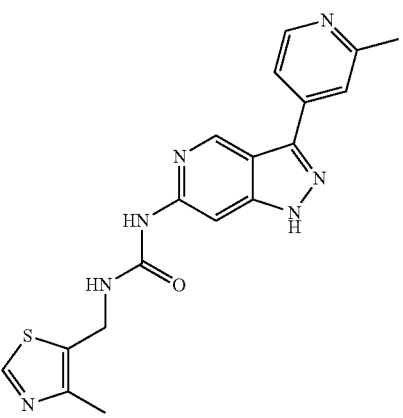 1-[3-(2-methylpyridin-4-yl)-1H-pyrazolo[4,3-c]pyridin-6-yl]-3-[(4-methyl-1,3-thiazol-5-yl)methyl]urea | Calc'd 380, found 380 | 12 |
| 419 | 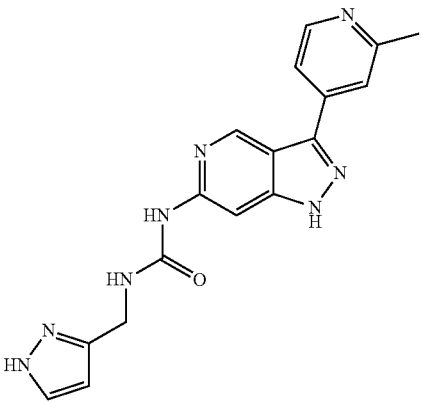 1-[3-(2-methylpyridin-4-yl)-1H-pyrazolo[4,3-c]pyridin-6-yl]-3-(1H-pyrazol-3-ylmethyl)urea | Calc'd 349, found 349 | 12 |

TABLE 2-continued
| EX | Structure | Exact Mass [M + H]+ | Route Used |
|---|---|---|---|
| 420 | 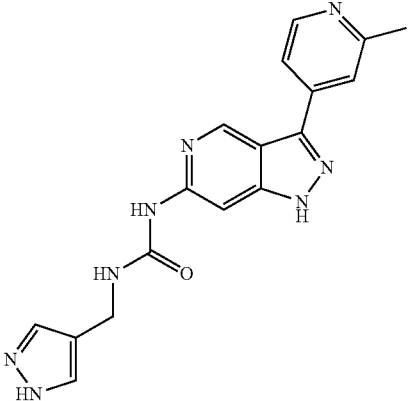<br>1-[3-(2-methylpyridin-4-yl)-1H-pyrazolo[4,3-c]pyridin-6-yl]-3-(1H-pyrazol-4-ylmethyl)urea | Calc'd 349, found 349 | 12 |
| 421 | 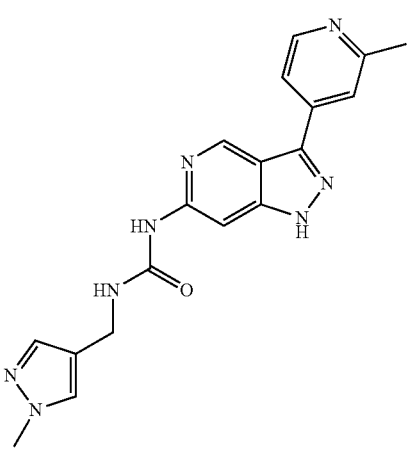<br>1-[(1-methyl-1H-pyrazol-4-yl)methyl]-3-[3-(2-methylpyridin-4-yl)-1H-pyrazolo[4,3-c]pyridin-6-yl]urea | Calc'd 363, found 363 | 12 |
| 422 | 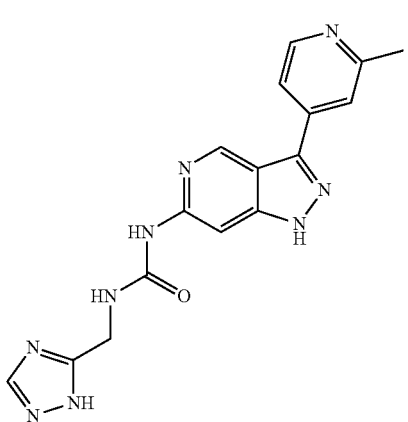<br>1-[3-(2-methylpyridin-4-yl)-1H-pyrazolo[4,3-c]pyridin-6-yl]-3-(1H-1,2,4-triazol-5-ylmethyl)urea | Calc'd 350, found 350 | 12 |

TABLE 2-continued
| EX | Structure | Exact Mass [M + H]+ | Route Used |
|---|---|---|---|
| 423 | 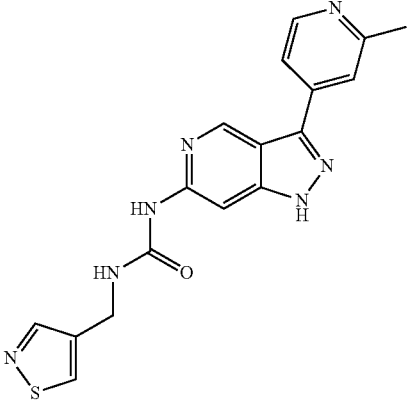<br>1-(isothiazol-4-ylmethyl)-3-[3-(2-methylpyridin-4-yl)-1H-pyrazolo[4,3-c]pyridin-6-yl]urea | Calc'd 366, found 366 | 12 |
| 424 | 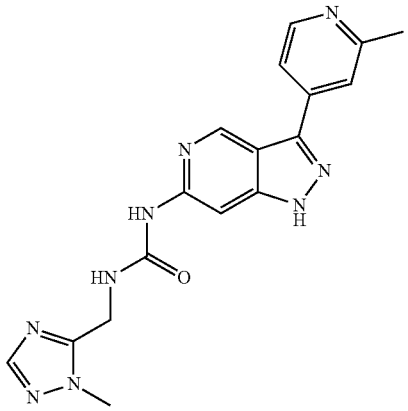<br>1-[3-(2-methylpyridin-4-yl)-1H-pyrazolo[4,3-c]pyridin-6-yl]-3-[(1-methyl-1H-1,2,4-triazol-5-yl)methyl]urea | Calc'd 364, found 364 | 12 |
| 425 | 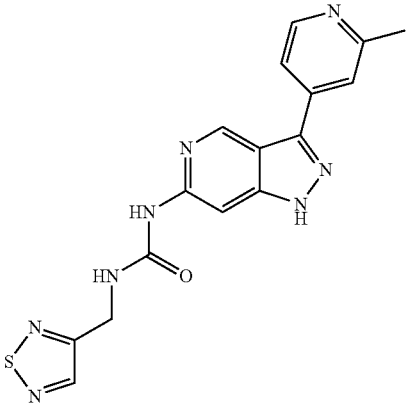<br>1-[3-(2-methylpyridin-4-yl)-1H-pyrazolo[4,3-c]pyridin-6-yl]-3-(1,2,5-thiadiazol-3-ylmethyl)urea | Calc'd 367, found 367 | 12 |

TABLE 2-continued
| EX | Structure | Exact Mass [M + H]+ | Route Used |
|----|-----------|---------------------|------------|
| 426 | 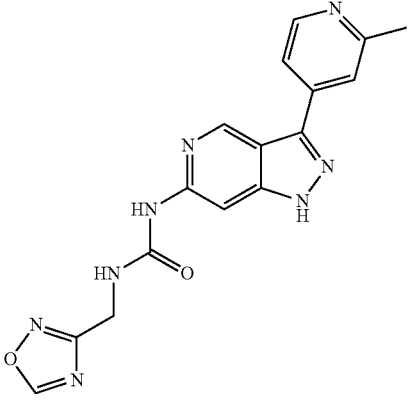<br>1-[3-(2-methylpyridin-4-yl)-1H-pyrazolo[4,3-c]pyridin-6-yl]-3-(1,2,4-oxadiazol-3-ylmethyl)urea | Calc'd 351, found 351 | 12 |
| 427 | 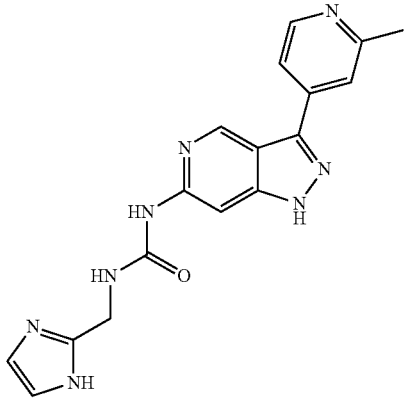<br>1-(1H-imidazol-2-ylmethyl)-3-[3-(2-methylpyridin-4-yl)-1H-pyrazolo[4,3-c]pyridin-6-yl]urea | Calc'd 349, found 349 | 12 |
| 428 | 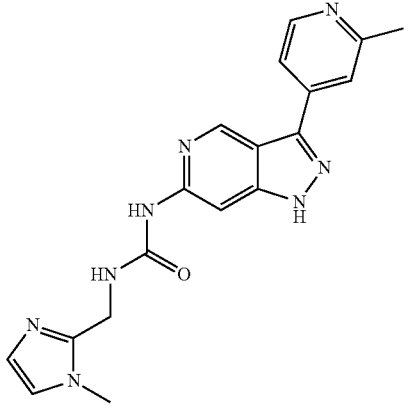<br>1-[(1-methyl-1H-imidazol-2-yl)methyl]-3-[3-(2-methylpyridin-4-yl)-1H-pyrazolo[4,3-c]pyridin-6-yl]urea | Calc'd 363, found 363 | 12 |

TABLE 2-continued

| EX | Structure | Exact Mass [M + H]+ | Route Used |
|---|---|---|---|
| 429 | 1-(isothiazol-5-ylmethyl)-3-[3-(2-methylpyridin-4-yl)-1H-pyrazolo[4,3-c]pyridin-6-yl]urea | Calc'd 366, found 366 | 12 |
| 430 | 1-[3-(2-methylpyridin-4-yl)-1H-pyrazolo[4,3-c]pyridin-6-yl]-3-(1,3-thiazol-5-ylmethyl)urea | Calc'd 366, found 366 | 12 |
| 431 | 1-[3-(2-methylpyridin-4-yl)-1H-pyrazolo[4,3-c]pyridin-6-yl]-3-(1H-1,2,3-triazol-4-ylmethyl)urea | Calc'd 350, found 350 | 12 |

TABLE 2-continued
| EX | Structure | Exact Mass [M + H]+ | Route Used |
|---|---|---|---|
| 432 | 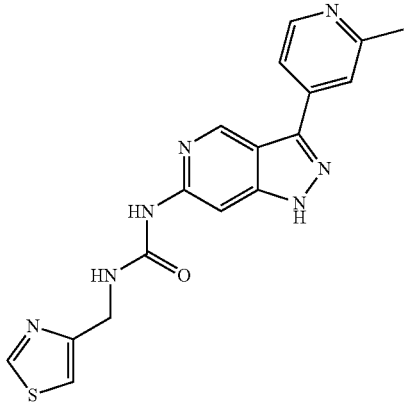
1-[3-(2-methylpyridin-4-yl)-1H-pyrazolo[4,3-c]pyridin-6-yl]-3-(1,3-thiazol-4-ylmethyl)urea | Calc'd 366, found 366 | 12 |
| 433 | 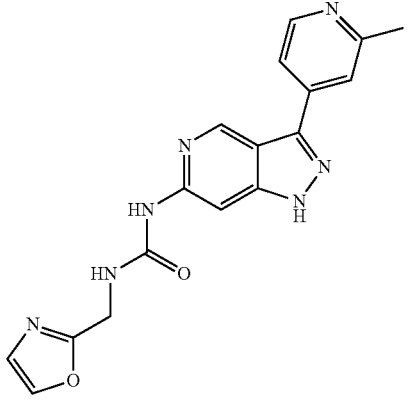
1-[3-(2-methylpyridin-4-yl)-1H-pyrazolo[4,3-c]pyridin-6-yl]-3-(1,3-thiazol-4-ylmethyl)urea | Calc'd 350, found 350 | 12 |
| 434 | 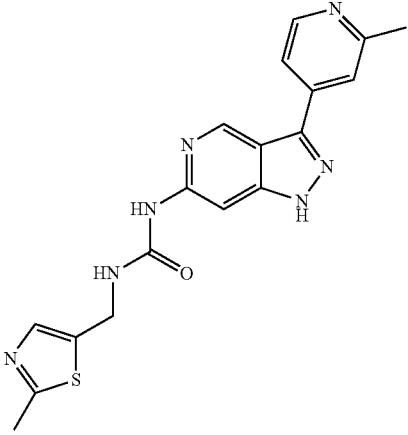
1-[3-(2-methylpyridin-4-yl)-1H-pyrazolo[4,3-c]pyridin-6-yl]-3-[(2-methyl-1,3-thiazol-5-yl)methyl]urea | Calc'd 380, found 380 | 12 |

TABLE 2-continued
| EX | Structure | Exact Mass [M + H]+ | Route Used |
|---|---|---|---|
| 435 | 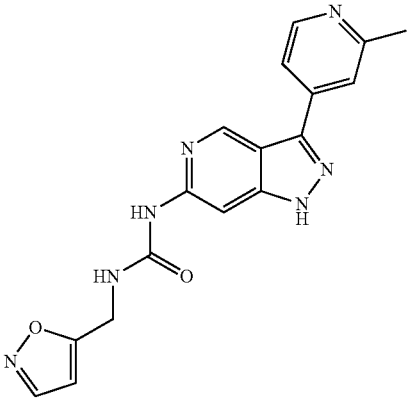<br>1-(isoxazol-5-ylmethyl)-3-[3-(2-methylpyridin-4-yl)-1H-pyrazolo[4,3-c]pyridin-6-yl]urea | Calc'd 350, found 350 | 12 |
| 436 | 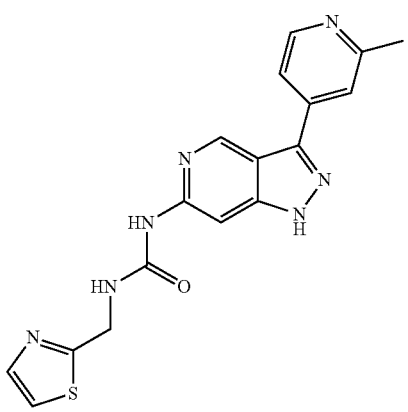<br>1-[3-(2-methylpyridin-4-yl)-1H-pyrazolo[4,3-c]pyridin-6-yl]-3-(1,3-thiazol-2-ylmethyl)urea | Calc'd 366, found 366 | 12 |
| 437 | 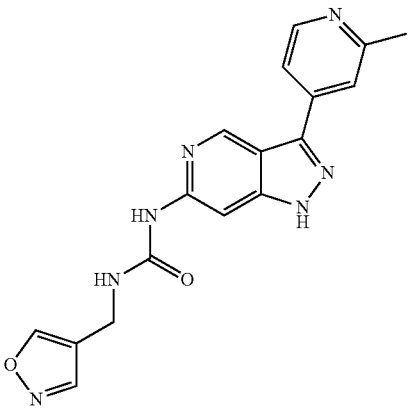<br>1-(isoxazol-4-ylmethyl)-3-[3-(2-methylpyridin-4-yl)-1H-pyrazolo[4,3-c]pyridin-6-yl]urea | Calc'd 350, found 350 | 12 |

TABLE 2-continued

| EX | Structure | Exact Mass [M + H]+ | Route Used |
|---|---|---|---|
| 438 | 1-[3-(2-methylpyridin-4-yl)-1H-pyrazolo[4,3-c]pyridin-6-yl]-3-(1,3,4-thiadiazol-2-ylmethyl)urea | Calc'd 367, found 367 | 12 |
| 439 | 1-(2-chlorobenzyl)-3-[3-(2-methylpyridin-4-yl)-1H-pyrazolo[4,3-c]pyridin-6-yl]urea | Calc'd 393, found 393 | 12 |
| 440 | 1-(2-chloro-6-fluorobenzyl)-3-[3-(2-methylpyridin-4-yl)-1H-pyrazolo[4,3-c]pyridin-6-yl]urea | Calc'd 411, found 411 | 12 |

TABLE 2-continued
| EX | Structure | Exact Mass [M + H]+ | Route Used |
|---|---|---|---|
| 441 | 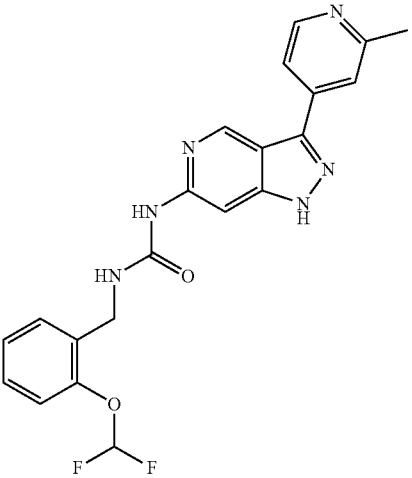<br>1-[2-(difluoromethoxy)benzyl]-3-[3-(2-methylpyridin-4-yl)-1H-pyrazolo[4,3-c]pyridin-6-yl]urea | Calc'd 425, found 425 | 12 |
| 442 | 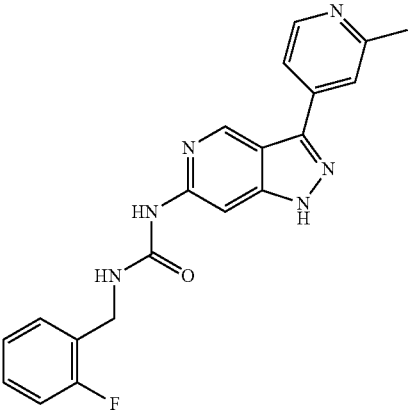<br>1-(2-fluorobenzyl)-3-[3-(2-methylpyridin-4-yl)-1H-pyrazolo[4,3-c]pyridin-6-yl]urea | Calc'd 377, found 377 | 12 |
| 443 | 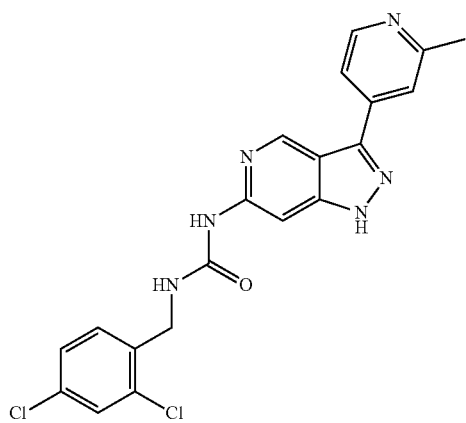<br>1-(2,4-dichlorobenzyl)-3-[3-(2-methylpyridin-4-yl)-1H-pyrazolo[4,3-c]pyridin-6-yl]urea | Calc'd 427, found 427 | 12 |

TABLE 2-continued
| EX | Structure | Exact Mass [M + H]+ | Route Used |
|---|---|---|---|
| 444 | 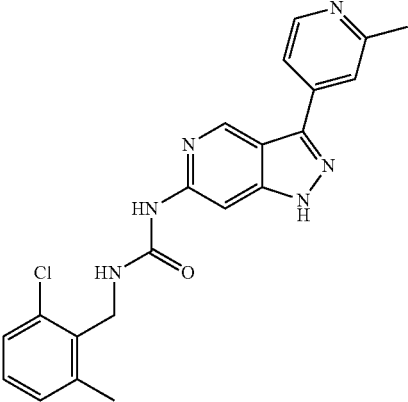<br>1-(2-chloro-6-methylbenzyl)-3-[3-(2-methylpyridin-4-yl)-1H-pyrazolo[4,3-c]pyridin-6-yl]urea | Calc'd 407, found 407 | 12 |
| 445 | 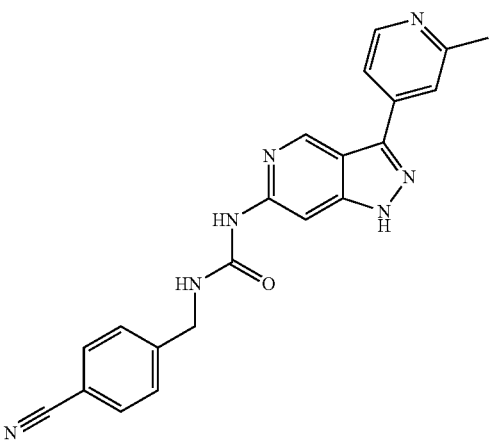<br>1-(4-cyanobenzyl)-3-[3-(2-methylpyridin-4-yl)-1H-pyrazolo[4,3-c]pyridin-6-yl]urea | Calc'd 384, found 384 | 12 |
| 446 | 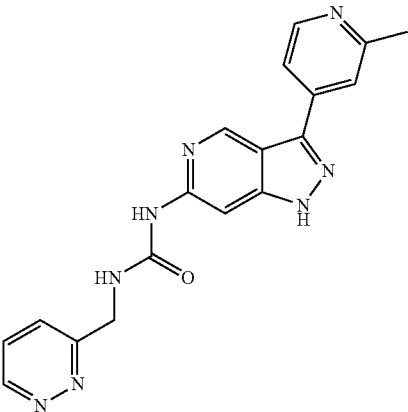<br>1-[3-(2-methylpyridin-4-yl)-1H-pyrazolo[4,3-c]pyridin-6-yl]-3-(pyridazin-3-ylmethyl)urea | Calc'd 361, found 361 | 12 |

TABLE 2-continued
| EX | Structure | Exact Mass [M + H]+ | Route Used |
|---|---|---|---|
| 447 | 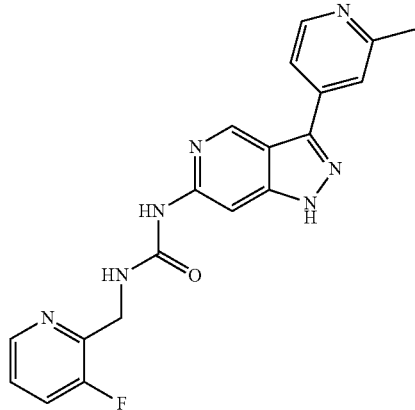<br>1-[(3-fluoropyridin-2-yl)methyl]-3-[3-(2-methylpyridin-4-yl)-1H-pyrazolo[4,3-c]pyridin-6-yl]urea | Calc'd 378, found 378 | 12 |
| 448 | 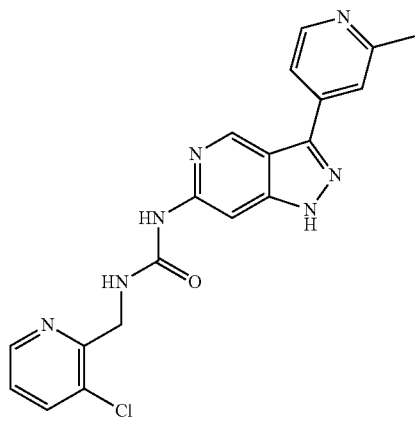<br>1-[(3-chloropyridin-2-yl)methyl]-3-[3-(2-methylpyridin-4-yl)-1H-pyrazolo[4,3-c]pyridin-6-yl]urea | Calc'd 394, found 394 | 12 |
| 449 | 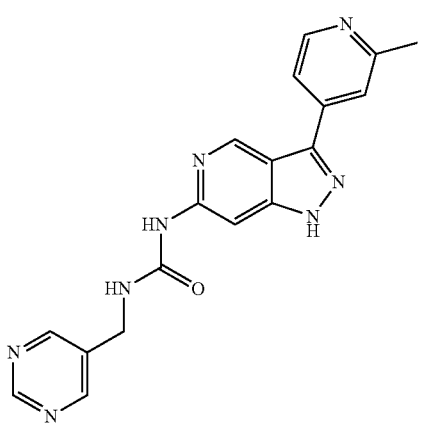<br>1-[3-(2-methylpyridin-4-yl)-1H-pyrazolo[4,3-c]pyridin-6-yl]-3-(pyrimidin-5-ylmethyl)urea | Calc'd 361, found 361 | 12 |

TABLE 2-continued

| EX | Structure | Exact Mass [M + H]+ | Route Used |
|---|---|---|---|
| 450 | 1-[(3,5-difluoropyridin-2-yl)methyl]-3-[3-(2-methylpyridin-4-yl)-1H-pyrazolo[4,3-c]pyridin-6-yl]urea | Calc'd 396, found 396 | 12 |
| 451 | 1-[2-(1-methylethoxy)ethyl]-3-[3-(2-methylpyridin-4-yl)-1H-pyrazolo[4,3-c]pyridin-6-yl]urea | Calc'd 355, found 355 | 12 |
| 452 | N-{[3-(2-methylpyridin-4-yl)-1H-pyrazolo[4,3-c]pyridin-6-yl]carbamoyl}-L-valine | Calc'd 369, found 369 | 12 |

TABLE 2-continued

| EX | Structure | Exact Mass [M + H]+ | Route Used |
|---|---|---|---|
| 453 | 1-[3-(2-methylpyridin-4-yl)-1H-pyrazolo[4,3-c]pyridin-6-yl]-3-(2-phenoxyethyl)urea | Calc'd 389, found 389 | 12 |
| 454 | N{[3-(2-methylpyridin-4-yl)-1H-pyrazolo[4,3-c]pyridin-6-yl]carbamoyl}-L-alanine | Calc'd 341, found 341 | 12 |
| 455 | methyl N{[3-(2-methylpyridin-4-yl)-1H-pyrazolo[4,3-c]pyridin-6-yl]carbamoyl}-L-alaninate | Calc'd 355, found 355 | 12 |

TABLE 2-continued
| EX | Structure | Exact Mass [M + H]+ | Route Used |
|---|---|---|---|
| 456 | 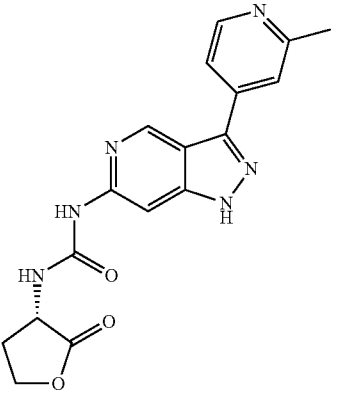 1-[3-(2-methylpyridin-4-yl)-1H-pyrazolo[4,3-c]pyridin-6-yl]-3-[(3S)-2-oxotetrahydrofuran-3-yl]urea | Calc'd 353, found 353 | 12 |
| 457 | 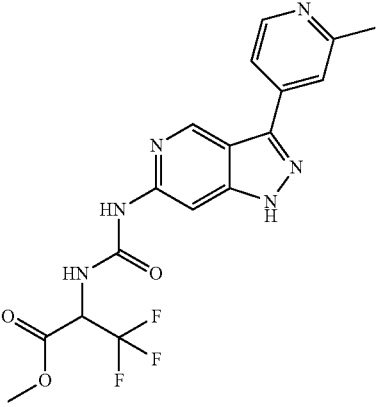 methyl 3,3,3-trifluoro-N-{[3-(2-methylpyridin-4-yl)-1H-pyrazolo[4,3-c]pyridin-6-yl]carbamoyl}alaninate | Calc'd 409, found 409 | 12 |
| 458 | 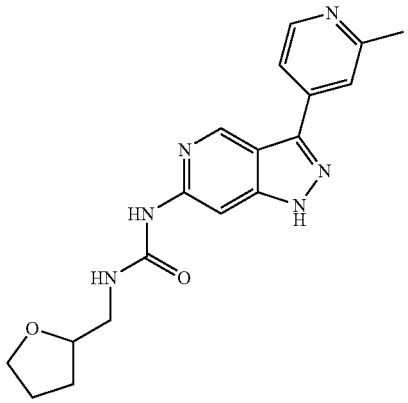 1-[3-(2-methylpyridin-4-yl)-1H-pyrazolo[4,3-c]pyridin-6-yl]-3-(tetrahydrofuran-2-ylmethyl)urea | Calc'd 353, found 353 | 12 |

TABLE 2-continued

| EX | Structure | Exact Mass [M + H]+ | Route Used |
|---|---|---|---|
| 459 | 1-(2,3-dihydro-1,4-benzodioxin-2-ylmethyl)-3-[3-(2-methylpyridin-4-yl)-1H-pyrazolo[4,3-c]pyridin-6-yl]urea | Calc'd 417, found 417 | 12 |
| 460 | methyl N-{[3-(2-methylpyridin-4-yl)-1H-pyrazolo[4,3-c]pyridin-6-yl]carbamoyl}-L-valinate | Calc'd 383, found 383 | 12 |
| 461 | methyl N-{[3-(2-methylpyridin-4-yl)-1H-pyrazolo[4,3-c]pyridin-6-yl]carbamoyl}-D-alaninate | Calc'd 355, found 355 | 12 |

TABLE 2-continued
| EX | Structure | Exact Mass [M + H]+ | Route Used |
|---|---|---|---|
| 462 | 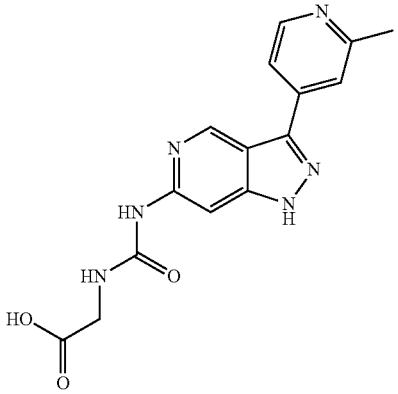<br>N-{[3-(2-methylpyridin-4-yl)-1H-pyrazolo[4,3-c]pyridin-6-yl]carbamoyl}glycine | Calc'd 327, found 327 | 12 |
| 463 | 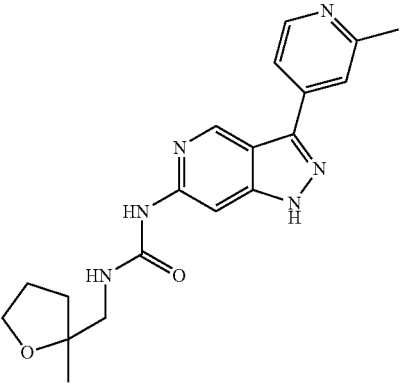<br>1-[3-(2-methylpyridin-4-yl)-1H-pyrazolo[4,3-c]pyridin-6-yl]-3-[(2-methyltetrahydrofuran-2-yl)methyl]urea | Calc'd 367, found 367 | 12 |
| 464 | 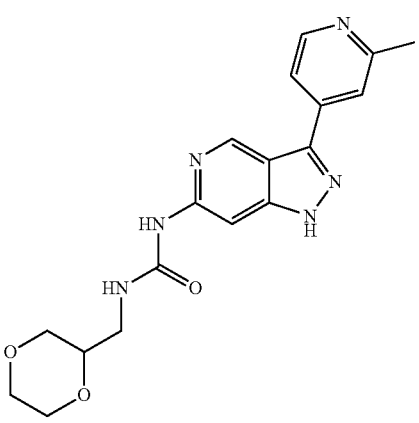<br>1-(1,4-dioxan-2-ylmethyl)-3-[3-(2-methylpyridin-4-yl)-1H-pyrazolo[4,3-c]pyridin-6-yl]urea | Calc'd 369, found 369 | 12 |

TABLE 2-continued
| EX | Structure | Exact Mass [M + H]+ | Route Used |
|---|---|---|---|
| 465 | 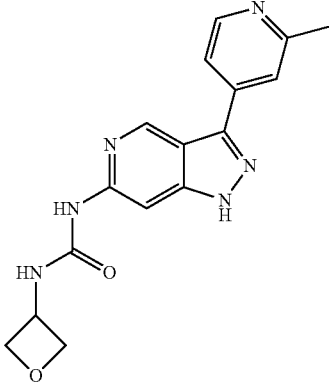 1-[3-(2-methylpyridin-4-yl)-1H-pyrazolo[4,3-c]pyridin-6-yl]-3-oxetan-3-ylurea | Calc'd 325, found 325 | 12 |
| 466 | 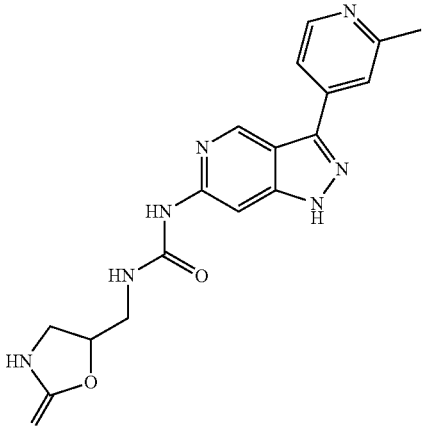 1-[3-(2-methylpyridin-4-yl)-1H-pyrazolo[4,3-c]pyridin-6-yl]-3-[(2-oxo-1,3-oxazolidin-5-yl)methyl]urea | Calc'd 368, found 368 | 12 |
| 467 | 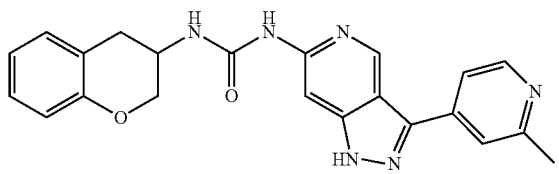 1-(3,4-dihydro-2H-chromen-3-yl)-3-[3-(2-methylpyridin-4-yl)-1H-pyrazolo[4,3-c]pyridin-6-yl]urea | Calc'd 401, found 401 | 12 |

TABLE 2-continued

| EX | Structure | Exact Mass [M + H]+ | Route Used |
|---|---|---|---|
| 468 | 1-[3-(2-methylpyridin-4-yl)-1H-pyrazolo[4,3-c]pyridin-6-yl]-3-(tetrahydro-2H-pyran-3-yl)urea | Calc'd 353, found 353 | 12 |
| 469 | 1-[3-(2-methylpyridin-4-yl)-1H-pyrazolo[4,3-c]pyridin-6-yl]-3-(tetrahydro-2H-pyran-2-ylmethyl)urea | Calc'd 367, found 367 | 12 |
| 470 | 1-[(5-methylisoxazol-3-yl)methyl]-3-[3-(2-methylpyridin-4-yl)-1H-pyrazolo[4,3-c]pyridin-6-yl]urea | Calc'd 364, found 364 | 12 |

TABLE 2-continued
| EX | Structure | Exact Mass [M + H]+ | Route Used |
|---|---|---|---|
| 471 | 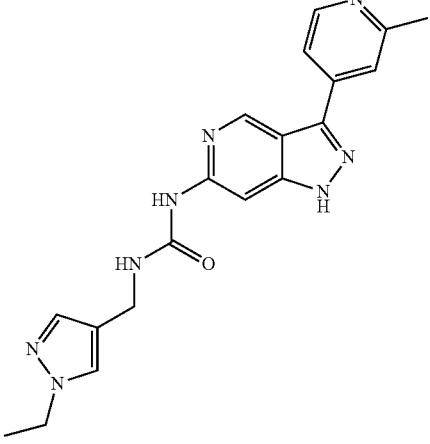<br>1-[(1-ethyl-1H-pyrazol-4-yl)methyl]-3-[3-(2-methylpyridin-4-yl)-1H-pyrazolo[4,3-c]pyridin-6-yl]urea | Calc'd 377, found 377 | 12 |
| 472 | 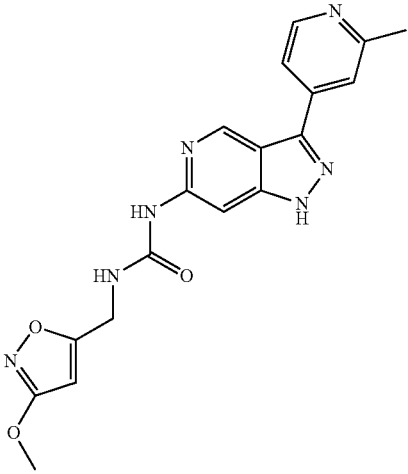<br>1-[(3-methoxyisoxazol-5-yl)methyl]-3-[3-(2-methylpyridin-4-yl)-1H-pyrazolo[4,3-c]pyridin-6-yl]urea | Calc'd 380, found 380 | 12 |
| 473 | 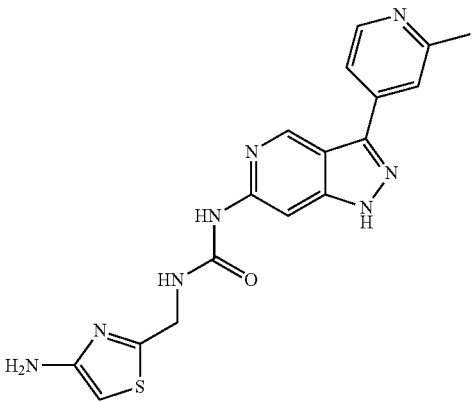<br>1-[(4-amino-1,3-thiazol-2-yl)methyl]-3-[3-(2-methylpyridin-4-yl)-1H-pyrazolo[4,3-c]pyridin-6-yl]urea | Calc'd 381, found 381 | 12 |

TABLE 2-continued

| EX | Structure | Exact Mass [M + H]+ | Route Used |
|---|---|---|---|
| 474 | 1-[3-(2-methylpyridin-4-yl)-1H-pyrazolo[4,3-c]pyridin-6-yl]-3-[(5-methyl-1,3,4-thiadiazol-2-yl)methyl]urea | Calc'd 381, found 381 | 12 |
| 475 | 1-[3-(2-methylpyridin-4-yl)-1H-pyrazolo[4,3-c]pyridin-6-yl]-3-(thiophen-3-ylmethyl)urea | Calc'd 365, found 365 | 12 |
| 476 | 1-(isothiazol-3-ylmethyl)-3-[3-(2-methylpyridin-4-yl)-1H-pyrazolo[4,3-c]pyridin-6-yl]urea | Calc'd 366, found 366 | 12 |
| 477 | 1-[3-(2-methylpyridin-4-yl)-1H-pyrazolo[4,3-c]pyridin-6-yl]-3-[(4-methyl-1,3-thiazol-2-yl)methyl]urea | Calc'd 380, found 380 | 12 |

TABLE 2-continued

| EX | Structure | Exact Mass [M + H]+ | Route Used |
|---|---|---|---|
| 478 | 1-[(5-chloropyridin-2-yl)methyl]-3-[3-(2-methylpyridin-4-yl)-1H-pyrazolo[4,3-c]pyridin-6-yl]urea | Calc'd 394, found 394 | 12 |
| 479 | 1-[3-(2-methylpyridin-4-yl)-1H-pyrazolo[4,3-c]pyridin-6-yl]-3-(pyridin-2-ylmethyl)urea | Calc'd 360, found 360 | 12 |
| 480 | 1-[(3-methylpyridin-2-yl)methyl]-3-[3-(2-methylpyridin-4-yl)-1H-pyrazolo[4,3-c]pyridin-6-yl]urea | Calc'd 374, found 374 | 12 |
| 481 | 1-[(1R)-2-(dimethylamino)-1-phenylethyl]-3-[3-(2-methylpyridin-4-yl)-1H-pyrazolo[4,3-c]pyridin-6-yl]urea | Calc'd 416, found 416 | 12 |

TABLE 2-continued

| EX | Structure | Exact Mass [M + H]+ | Route Used |
|---|---|---|---|
| 482 | 1-[(1S)-2-(dimethylamino)-1-phenylethyl]-3-[3-(2-methylpyridin-4-yl)-1H-pyrazolo[4,3-c]pyridin-6-yl]urea | Calc'd 416, found 416 | 12 |
| 483 | 1-[(1S)-2-amino-1-phenylethyl]-3-[3-(2-methylpyridin-4-yl)-1H-pyrazolo[4,3-c]pyridin-6-yl]urea | Calc'd 388, found 388 | 12 |
| 484 | 1-[3-(2-methylpyridin-4-yl)-1H-pyrazolo[4,3-c]pyridin-6-yl]-3-(oxetan-2-ylmethyl)urea | Calc'd 339, found 339 | 12 |
| 485 | 1-(2-fluoro-6-methoxybenzyl)-3-[3-(2-methylpyridin-4-yl)-1H-pyrazolo[4,3-c]pyridin-6-yl]urea | Calc'd 407, found 407 | 12 |

TABLE 2-continued
| EX | Structure | Exact Mass [M + H]+ | Route Used |
|---|---|---|---|
| 486 | 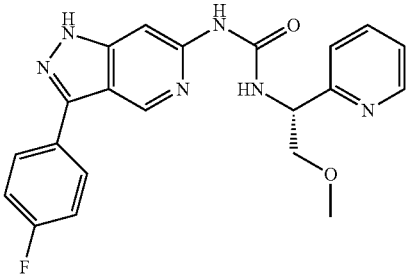<br>1-[3-(4-fluorophenyl)-1H-pyrazolo[4,3-c]pyridin-6-yl]-3-[(1R)-2-methoxy-1-pyridin-2-ylethyl]urea | Calc'd 407, found 407 | 90 |
| 487 | 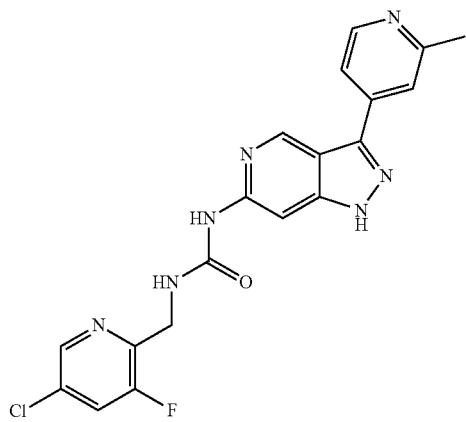<br>1-[(5-chloro-3-fluoropyridin-2-yl)methyl]-3-[3-(2-methylpyridin-4-yl)-1H-pyrazolo[4,3-c]pyridin-6-yl]urea | Calc'd 412, found 412 | 12 |
| 488 | 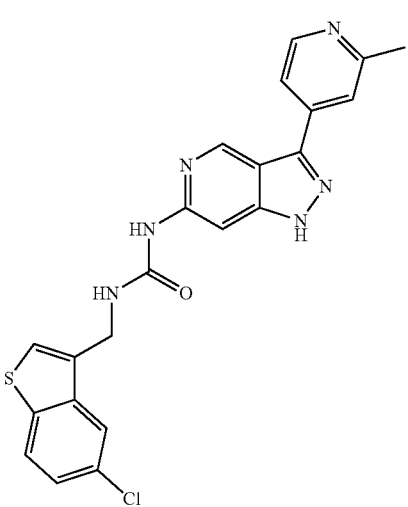<br>1-[(5-chloro-1-benzothiophen-3-yl)methyl]-3-[3-(2-methylpyridin-4-yl)-1H-pyrazolo[4,3-c]pyridin-6-yl]urea | Calc'd 449, found 449 | 12 |

TABLE 2-continued

| EX | Structure | Exact Mass [M + H]+ | Route Used |
|---|---|---|---|
| 489 | 1-[3-(2-methylpyridin-4-yl)-1H-pyrazolo[4,3-c]pyridin-6-yl]-3-(1,2,3,4-tetrahydroisoquinolin-4-yl)urea | Calc'd 400, found 400 | 12 |
| 490 | 1-[(1R,2R)-2-(dimethylamino)-2,3-dihydro-1H-inden-1-yl]-3-[3-(2-methylpyridin-4-yl)-1H-pyrazolo[4,3-c]pyridin-6-yl]urea | Calc'd 428, found 428 | 12 |
| 491 | 1-[(4-methylpyridin-3-yl)methyl]-3-[3-(2-methylpyridin-4-yl)-1H-pyrazolo[4,3-c]pyridin-6-yl]urea | Calc'd 374, found 374 | 12 |

TABLE 2-continued
| EX | Structure | Exact Mass [M + H]+ | Route Used |
|---|---|---|---|
| 492 | 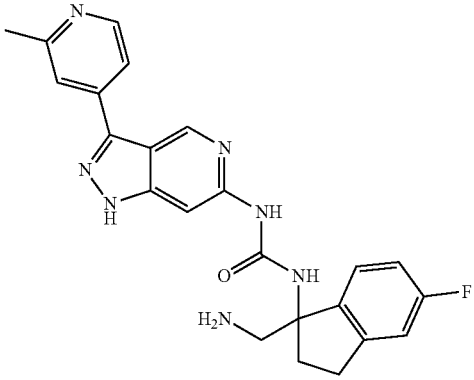<br>1-[1-(aminomethyl)-5-fluoro-2,3-dihydro-1H-inden-1-yl]-3-[3-(2-methylpyridin-4-yl)-1H-pyrazolo[4,3-c]pyridin-6-yl]urea | Calc'd 432, found 432 | 12 |
| 493 | 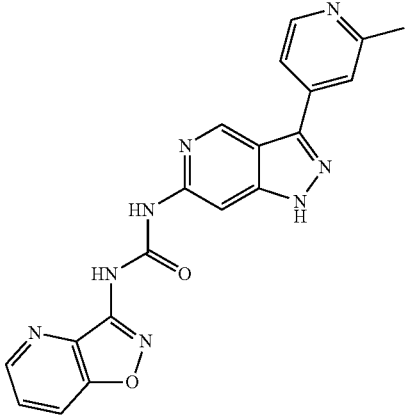<br>1-isoxazolo[4,5-b]pyridin-3-yl-3-[3-(2-methylpyridin-4-yl)-1H-pyrazolo[4,3-c]pyridin-6-yl]urea | Calc'd 387, found 387 | 12 |
| 494 | 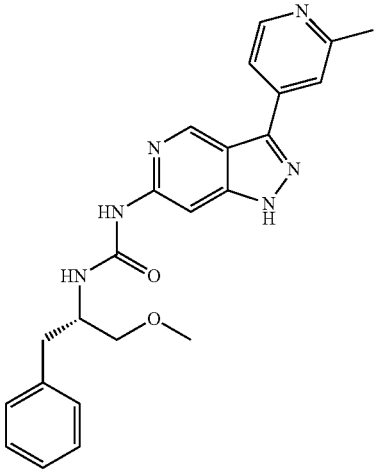<br>1-[(1S)-1-benzyl-2-methoxyethyl]-3-[3-(2-methylpyridin-4-yl)-1H-pyrazolo[4,3-c]pyridin-6-yl]urea | Calc'd 417, found 417 | 12 |

TABLE 2-continued
| EX | Structure | Exact Mass [M + H]+ | Route Used |
|---|---|---|---|
| 495 | 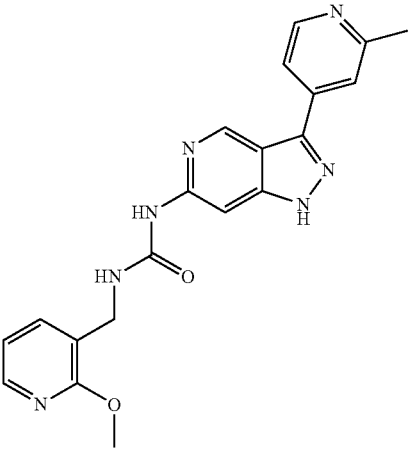<br>1-[(2-methoxypyridin-3-yl)methyl]-3-[3-(2-methylpyridin-4-yl)-1H-pyrazolo[4,3-c]pyridin-6-yl]urea | Calc'd 390, found 390 | 12 |
| 496 | 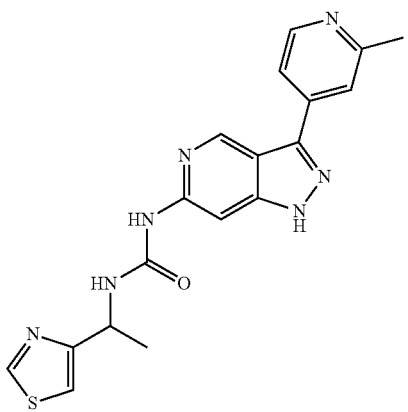<br>1-[3-(2-methylpyridin-4-yl)-1H-pyrazolo[4,3-c]pyridin-6-yl]-3-[1-(1,3-thiazol-4-yl)ethyl]urea | Calc'd 380, found 380 | 12 |
| 497 | 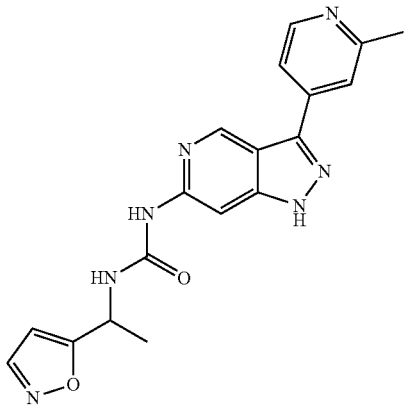<br>1-(1-isoxazol-5-ylethyl)-3-[3-(2-methylpyridin-4-yl)-1H-pyrazolo[4,3-c]pyridin-6-yl]urea | Calc'd 364, found 364 | 12 |

TABLE 2-continued

| EX | Structure | Exact Mass [M + H]+ | Route Used |
|---|---|---|---|
| 498 | 1-[1-(4-methylpyridin-2-yl)ethyl]-3-[3-(2-methylpyridin-4-yl)-1H-pyrazolo[4,3-c]pyridin-6-yl]urea | Calc'd 388, found 388 | 12 |
| 499 | 1-[1-(6-fluoropyridin-3-yl)ethyl]-3-[3-(2-methylpyridin-4-yl)-1H-pyrazolo[4,3-c]pyridin-6-yl]urea | Calc'd 392, found 392 | 12 |
| 500 | 1-[3-(4-fluorophenyl)-1H-pyrazolo[4,3-c]pyridin-6-yl]-3-[(1S)-2-methoxy-1-pyridin-2-ylethyl]urea | Calc'd 407, found 407 | 90 |

TABLE 2-continued

| EX | Structure | Exact Mass [M + H]+ | Route Used |
|---|---|---|---|
| 501 | 1-[3-(2-methylpyridin-4-yl)-1H-pyrazolo[4,3-c]pyridin-6-yl]-3-(1,2,3,4-tetrahydroquinolin-3-yl)urea | Calc'd 400, found 400 | 12 |
| 502 | 1-(1-benzothiophen-3-ylmethyl)-3-[3-(2-methylpyridin-4-yl)-1H-pyrazolo[4,3-c]pyridin-6-yl]urea | Calc'd 415, found 415 | 12 |
| 503 | 1-[(1R)-1-(5-fluoropyridin-2-yl)ethyl]-3-[3-(2-methylpyridin-4-yl)-1H-pyrazolo[4,3-c]pyridin-6-yl]urea | Calc'd 392, found 392 | 12 |
| 504 | 1-(2-amino-4,5,6,7-tetrahydro-1,3-benzothiazol-6-yl)-3-[3-(2-methylpyridin-4-yl)-1H-pyrazolo[4,3-c]pyridin-6-yl]urea | Calc'd 421, found 421 | 12 |

TABLE 2-continued

| EX | Structure | Exact Mass [M + H]+ | Route Used |
|---|---|---|---|
| 505 | 1-[3-(2-methylpyridin-4-yl)-1H-pyrazolo[4,3-c]pyridin-6-yl]-3-(5,6,7,8-tetrahydroquinolin-7-yl)urea | Calc'd 400, found 400 | 12 |
| 506 | 1-[3-(2-methylpyridin-4-yl)-1H-pyrazolo[4,3-c]pyridin-6-yl]-3-(4,5,6,7-tetrahydro-1H-indazol-5-yl)urea | Calc'd 389, found 389 | 12 |
| 507 | 1-[3-(2-methylpyridin-4-yl)-1H-pyrazolo[4,3-c]pyridin-6-yl]-3-(3-methyl-4,5,6,7-tetrahydro-1H-indazol-5-yl)urea | Calc'd 403, found 403 | 12 |
| 508 | 1-[3-(2-methylpyridin-4-yl)-1H-pyrazolo[4,3-c]pyridin-6-yl]-3-[(1-oxidopyridin-3-yl)methyl]urea | Calc'd 376, found 376 | 12 |

TABLE 2-continued

| EX | Structure | Exact Mass [M + H]+ | Route Used |
|---|---|---|---|
| 509 | 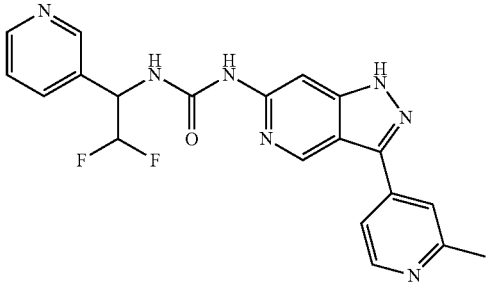<br>1-(2,2-difluoro-1-pyridin-3-ylethyl)-3-[3-(2-methylpyridin-4-yl)-1H-pyrazolo[4,3-c]pyridin-6-yl]urea | Calc'd 410, found 410 | 12 |
| 510 | 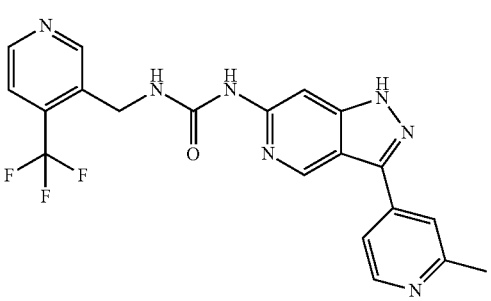<br>1-[3-(2-methylpyridin-4-yl)-1H-pyrazolo[4,3-c]pyridin-6-yl]-3-{[4-(trifluoromethyl)pyridin-3-yl]methyl}urea | Calc'd 428, found 428 | 12 |
| 511 | 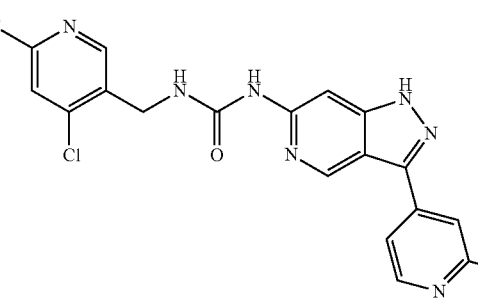<br>1-(2-chloro-4-fluorobenzyl)-3-[3-(2-methylpyridin-4-yl)-1H-pyrazolo[4,3-c]pyridin-6-yl]urea | Calc'd 411, found 411 | 12 |
| 512 | 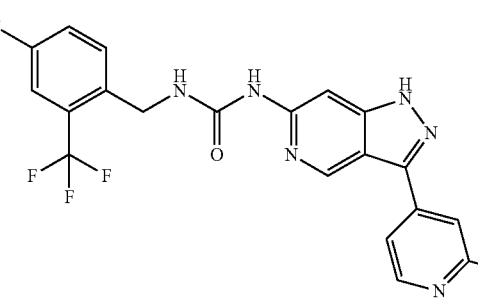<br>1-[4-fluoro-2-(trifluoromethyl)benzyl]-3-[3-(2-methylpyridin-4-yl)-1H-pyrazolo[4,3-c]pyridin-6-yl]urea | Calc'd 445, found 445 | 12 |

TABLE 2-continued

| EX | Structure | Exact Mass [M + H]+ | Route Used |
|---|---|---|---|
| 513 | 1-(2,4-difluorobenzyl)-3-[3-(2-methylpyridin-4-yl)-1H-pyrazolo[4,3-c]pyridin-6-yl]urea | Calc'd 395, found 395 | 12 |
| 514 | 1-(2,4-dichloro-6-methylbenzyl)-3-[3-(2-methylpyridin-4-yl)-1H-pyrazolo[4,3-c]pyridin-6-yl]urea | Calc'd 441, found 441 | 12 |
| 515 | 1-(4-chloro-2-methylbenzyl)-3-[3-(2-methylpyridin-4-yl)-1H-pyrazolo[4,3-c]pyridin-6-yl]urea | Calc'd 407, found 407 | 12 |
| 516 | 1-[(5-fluoropyridin-2-yl)methyl]-3-[3-(2-methylpyridin-4-yl)-1H-pyrazolo[4,3-c]pyridin-6-yl]urea | Calc'd 378, found 378 | 12 |

TABLE 2-continued

| EX | Structure | Exact Mass [M + H]+ | Route Used |
|---|---|---|---|
| 517 | 1-[(3-chloro-5-fluoropyridin-2-yl)methyl]-3-[3-(2-methylpyridin-4-yl)-1H-pyrazolo[4,3-c]pyridin-6-yl]urea | Calc'd 412, found 412 | 12 |
| 518 | 5-fluoro-N-methyl-2-[({[3-(2-methylpyridin-4-yl)-1H-pyrazolo[4,3-c]pyridin-6-yl]carbamoyl}amino)methyl]benzamide | Calc'd 434, found 434 | 12 |
| 519 | 1-[3-(2-methylpyridin-4-yl)-1H-pyrazolo[4,3-c]pyridin-6-yl]-3-(2,4,6-trifluorobenzyl)urea | Calc'd 413, found 413 | 12 |
| 520 | 1-(4-fluoro-2-methoxybenzyl)-3-[3-(2-methylpyridin-4-yl)-1H-pyrazolo[4,3-c]pyridin-6-yl]urea | Calc'd 407, found 407 | 12 |

TABLE 2-continued

| EX | Structure | Exact Mass [M + H]+ | Route Used |
|---|---|---|---|
| 521 | 1-(4-chloro-2-fluorobenzyl)-3-[3-(2-methylpyridin-4-yl)-1H-pyrazolo[4,3-c]pyridin-6-yl]urea | Calc'd 411, found 411 | 12 |
| 522 | 1-[2-amino-1-(4-fluorophenyl)ethyl]-3-[3-(2-methylpyridin-4-yl)-1H-pyrazolo[4,3-c]pyridin-6-yl]urea | Calc'd 406, found 406 | 12 |
| 523 | 1-[3-(2-methylpyridin-4-yl)-1H-pyrazolo[4,3-c]pyridin-6-yl]-3-[2-(trifluoromethoxy)benzyl]urea | Calc'd 443, found 443 | 12 |
| 524 | 1-[3-(2-methylpyridin-4-yl)-1H-pyrazolo[4,3-c]pyridin-6-yl]-3-{1-[2-(trifluoromethoxy)phenyl]ethyl}urea | Calc'd 457, found 457 | 12 |

TABLE 2-continued

| EX | Structure | Exact Mass [M + H]+ | Route Used |
|---|---|---|---|
| 525 | 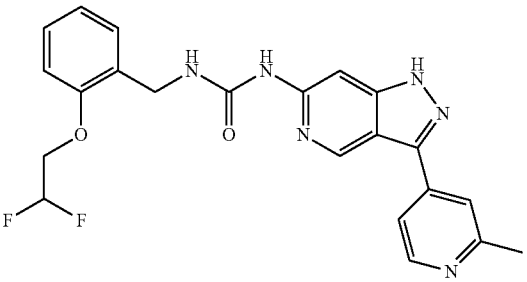<br>1-[2-(2,2-difluoroethoxy)benzyl]-3-[3-(2-methylpyridin-4-yl)-1H-pyrazolo[4,3-c]pyridin-6-yl]urea | Calc'd 439, found 439 | 12 |
| 526 | 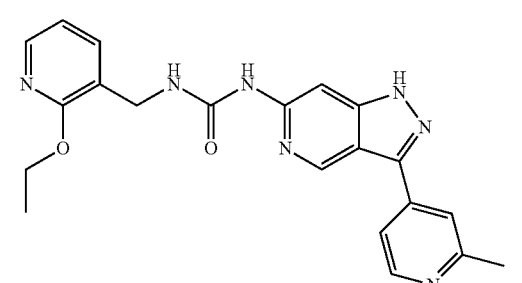<br>1-[(2-ethoxypyridin-3-yl)methyl]-3-[3-(2-methylpyridin-4-yl)-1H-pyrazolo[4,3-c]pyridin-6-yl]urea | Calc'd 404, found 404 | 12 |
| 527 | 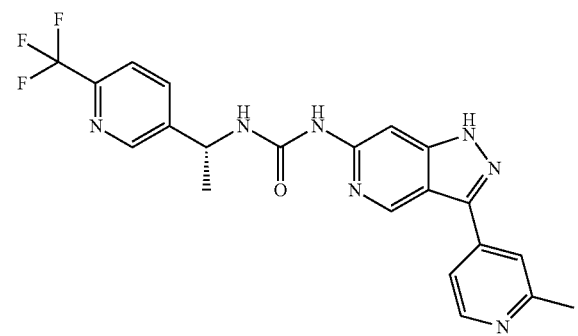<br>1-[3-(2-methylpyridin-4-yl)-1H-pyrazolo[4,3-c]pyridin-6-yl]-3-{(1R)-1-[6-(trifluoromethyl)pyridin-3-yl]ethyl}urea | Calc'd 442, found 442 | 12 |
| 528 | 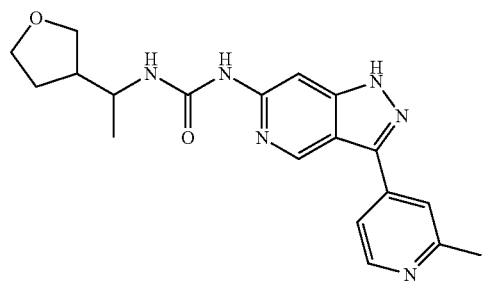<br>1-[3-(2-methylpyridin-4-yl)-1H-pyrazolo[4,3-c]pyridin-6-yl]-3-[1-(tetrahydrofuran-3-yl)ethyl]urea | Calc'd 367, found 367 | 12 |

TABLE 2-continued

| EX | Structure | Exact Mass [M + H]+ | Route Used |
|---|---|---|---|
| 529 | 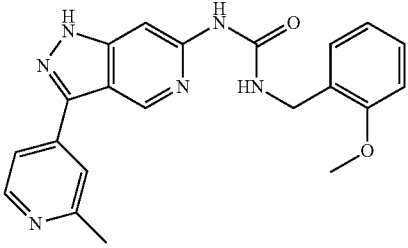<br>1-(2-methoxybenzyl)-3-[3-(2-methylpyridin-4-yl)-1H-pyrazolo[4,3-c]pyridin-6-yl]urea | Calc'd 389, found 389 | 12 |
| 530 | 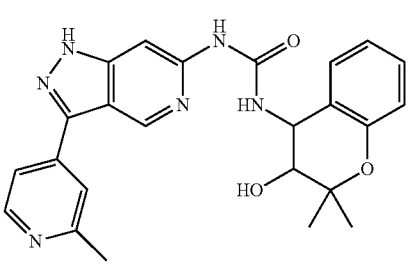<br>1-(3-hydroxy-2,2-dimethyl-3,4-dihydro-2H-chromen-4-yl)-3-[3-(2-methylpyridin-4-yl)-1H-pyrazolo[4,3-c]pyridin-6-yl]urea | Calc'd 445, found 445 | 12 |
| 531 | 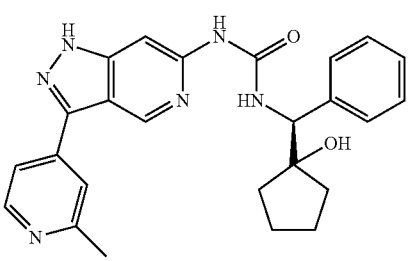<br>1-[(S)-(1-hydroxycyclopentyl)(phenyl)methyl]-3-[3-(2-methylpyridin-4-yl)-1H-pyrazolo[4,3-c]pyridin-6-yl]urea | Calc'd 443, found 443 | 12 |
| 532 | 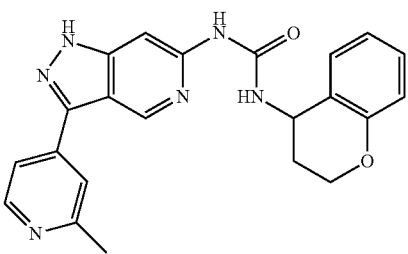<br>1-(3,4-dihydro-2H-chromen-4-yl)-3-[3-(2-methylpyridin-4-yl)-1H-pyrazolo[4,3-c]pyridin-6-yl]urea | Calc'd 401, found 401 | 12 |

TABLE 2-continued

| EX | Structure | Exact Mass [M + H]+ | Route Used |
|---|---|---|---|
| 533 | 1-(1H-indazol-3-yl)-3-[3-(2-methylpyridin-4-yl)-1H-pyrazolo[4,3-c]pyridin-6-yl]urea | Calc'd 439, found 439 | 12 |
| 534 | 1-[(1R)-1-(4-chlorophenyl)ethyl]-3-[7-fluoro-3-(2-methylpyridin-4-yl)-1H-pyrazolo[4,3-c]pyridin-6-yl]urea | Calc'd 425, found 425 | 12 |
| 535 | 1-[7-fluoro-3-(2-methylpyridin-4-yl)-1H-pyrazolo[4,3-c]pyridin-6-yl]-3-[(1R)-1-(4-fluorophenyl)ethyl]urea | Calc'd 409, found 409 | 12 |
| 536 | 1-benzyl-3-[7-fluoro-3-(2-methylpyridin-4-yl)-1H-pyrazolo[4,3-c]pyridin-6-yl]urea | Calc'd 377, found 377 | 12 |

TABLE 2-continued

| EX | Structure | Exact Mass [M + H]+ | Route Used |
|---|---|---|---|
| 537 | 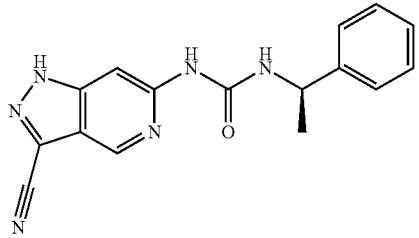
1-(3-cyano-1H-pyrazolo[4,3-c]pyridin-6-yl)-3-[(1R)-1-phenylethyl]urea | Calc'd 307, found 307 | 537 |
| 538 | 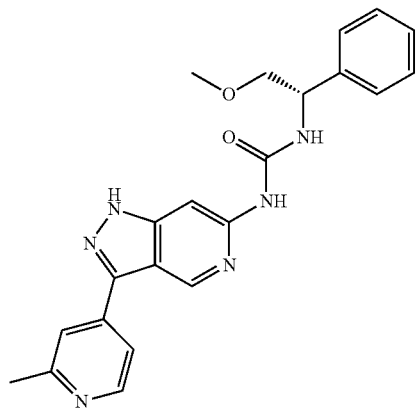
1-[(1S)-2-methoxy-1-phenylethyl]-3-[3-(2-methylpyridin-4-yl)-1H-pyrazolo[4,3-c]pyridin-6-yl]urea | Calc'd 403, found 403 | 30 |
| 539 | 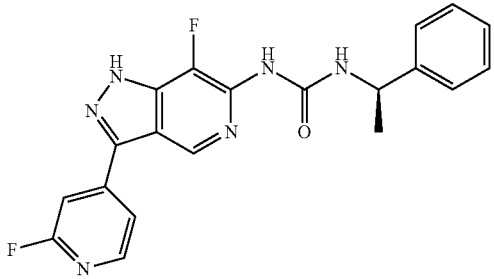
1-[7-fluoro-3-(2-fluoropyridin-4-yl)-1H-pyrazolo[4,3-c]pyridin-6-yl]-3-[(1R)-1-phenylethyl]urea | Calc'd 395, found 395 | Step 3 in ex 624 with Intermediate 42a |
| 540 | 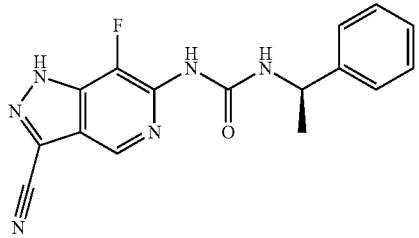
1-(3-cyano-7-fluoro-1H-pyrazolo[4,3-c]pyridin-6-yl)-3-[(1R)-1-phenylethyl]urea | Calc'd 325, found 325 | 95 |

TABLE 2-continued

| EX | Structure | Exact Mass [M + H]+ | Route Used |
|---|---|---|---|
| 541 | 1-[3-(4-fluorophenyl)-1H-pyrazolo[4,3-c]pyridin-6-yl]-3-[(1R)-2-methoxy-1-phenylethyl] | Calc'd 406, found 406 | 623 |
| 542 | 1-[7-fluoro-3-(2-methylpyridin-4-yl)-1H-pyrazolo[4,3-c]pyridin-6-yl]-3-[(1S)-2-methoxy-1-phenylethyl]urea | Calc'd 421, found 421 | 95 |
| 543 | 1-[7-fluoro-3-(2-fluoropyridin-4-yl)-1H-pyrazolo[4,3-c]pyridin-6-yl]-3-[(1S)-2-methoxy-1-phenylethyl]urea | Calc'd 425, found 425 | Intermediate 42a |
| 544 | 1-[7-fluoro-3-(2-methylpyridin-4-yl)-1H-pyrazolo[4,3-c]pyridin-6-yl]-3-[(1S)-2-hydroxy-1-phenylethyl]urea | Calc'd 407, found 407 | Intermediate 42a |

TABLE 2-continued

| EX | Structure | Exact Mass [M + H]+ | Route Used |
|---|---|---|---|
| 545 | 1-[(1S)-2-methoxy-1-phenylethyl]-3-(3-pyridin-4-yl-1H-pyrazolo[4,3-c]pyridin-6-yl)urea | Calc'd 389, found 389 | 90 |
| 546 | 1-[(1S)-2-hydroxy-1-phenylethyl]-3-(3-pyridin-4-yl-1H-pyrazolo[4,3-c]pyridin-6-yl)urea | Calc'd 375, found 375 | 90 |
| 547 | 1-(7-fluoro-3-pyridin-4-yl-1H-pyrazolo[4,3-c]pyridin-6-yl)-3-[(1S)-2-methoxy-1-phenylethyl]urea | Calc'd 407, found 407 | 95 |
| 548 | 1-(7-fluoro-3-pyridin-4-yl-1H-pyrazolo[4,3-c]pyridin-6-yl)-3-[(1S)-2-hydroxy-1-phenylethyl]urea | Calc'd 393, found 393 | 95 |

TABLE 2-continued

| EX | Structure | Exact Mass [M + H]+ | Route Used |
|---|---|---|---|
| 549 | 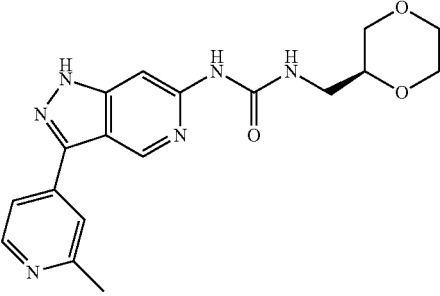<br>1-[(2S)-1,4-dioxan-2-ylmethyl]-3-[3-(2-methylpyridin-4-yl)-1H-pyrazolo[4,3-c]pyridin-6-yl]urea | Calc'd 369, found 369 | 30 |
| 550 | 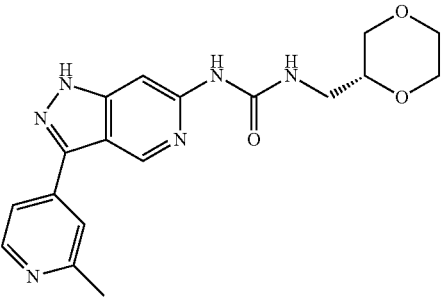<br>1-[(2S)-1,4-dioxan-2-ylmethyl]-3-[3-(2-methylpyridin-4-yl)-1H-pyrazolo[4,3-c]pyridin-6-yl]urea | Calc'd 369, found 369 | 30 |
| 551 | 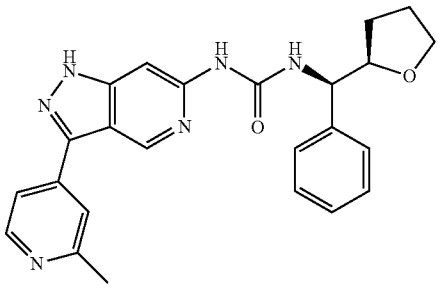<br>1-[3-(2-methylpyridin-4-yl)-1H-pyrazolo[4,3-c]pyridin-6-yl]-3-{(R)-phenyl[(2R)-tetrahydrofuran-2-yl]methyl}urea | Calc'd 429, found 429 | 178 |
| 552 | 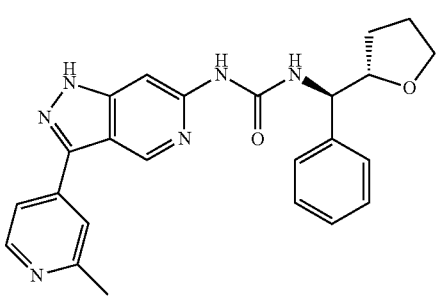<br>1-[3-(2-methylpyridin-4-yl)-1H-pyrazolo[4,3-c]pyridin-6-yl]-3-{(R)-phenyl[(2S)-tetrahydrofuran-2-yl]methyl}urea | Calc'd 429, found 429 | 178 |

TABLE 2-continued

| EX | Structure | Exact Mass [M + H]+ | Route Used |
|---|---|---|---|
| 553 | 1-[3-(2-methylpyridin-4-yl)-1H-pyrazolo[4,3-c]pyridin-6-yl]-3-{(S)-phenyl[(2R)-tetrahydrofuran-2-yl]methyl}urea | Calc'd 429, found 429 | 178 |
| 554 | 1-[3-(2-methylpyridin-4-yl)-1H-pyrazolo[4,3-c]pyridin-6-yl]-3-{(S)-phenyl[(2S)-tetrahydrofuran-2-yl]methyl}urea | Calc'd 429, found 429 | 178 |
| 555 | 1-[(2S,3S,4R)-1,2-dimethyl-4-(2-methylphenyl)pyrrolidin-3-yl]-3-[3-(2-methylpyridin-4-yl)-1H-pyrazolo[4,3-c]pyridin-6-yl] urea | Calc'd 456, found 456 | 178 |
| 556 | 1-[3-(2-methylpyridin-4-yl)-1H-pyrazolo[4,3-c]pyridin-6-yl]-3-[1-(1,3,4-oxadiazol-2-yl)ethyl]urea | Calc'd 365, found 365 | 178 |

TABLE 2-continued

| EX | Structure | Exact Mass [M + H]+ | Route Used |
|---|---|---|---|
| 557 | 1-[3-(4-fluorophenyl)-1H-pyrazolo[4,3-c]pyridin-6-yl]-3-[(7S,8S)-5-methyl-8-phenyl-2-oxa-5-azaspiro[3.4]oct-7-yl]urea | Calc'd 473, found 473 | 623 |
| 558 | 1-[(7R,8R)-5-methyl-8-phenyl-2-oxa-5-azaspiro[3.4]oct-7-yl]-3-[3-(2-methylpyridin-4-yl)-1H-pyrazolo[4,3-c]pyridin-6-yl]urea | Calc'd 470, found 470 | 178 |
| 559 | 1-[3-(cyanomethyl)-1H-pyrazolo[4,3-c]pyridin-6-yl]-3-[(1R)-1-phenylethyl]urea | Calc'd 321, found 321 | 559 |
| 560 | 1-{3-[(methylsulfonyl)methyl]-1H-pyrazolo[4,3-c]pyridin-6-yl}-3-[(1R)-1-phenylethyl]urea | Calc'd 374, found 374 | 559 |

TABLE 2-continued

| EX | Structure | Exact Mass [M + H]+ | Route Used |
|---|---|---|---|
| 561 | 1-[(1R)-1-phenylethyl]-3-(3-{[(2,2,2-trifluoroethyl)amino]methyl}-1H-pyrazolo[4,3-c]pyridin-6-yl)urea | Calc'd 393, found 393 | 559 |
| 562 | 1-(3-{[(2,2-difluoroethyl)amino]methyl}-1H-pyrazolo[4,3-c]pyridin-6-yl)-3-[(1R)-1-phenylethyl]urea | Calc'd 375, found 375 | 559 |
| 563 | 1-[3-(1-amino-2,2,2-trifluoroethyl)-1H-pyrazolo[4,3-c]pyridin-6-yl]-3-[(1R)-1-phenylethyl]urea | Calc'd 379.0, found | 563 |
| 564 | 1-[(1R)-1-phenylethyl]-3-{3-[2,2,2-trifluoro-1-(methylamino)ethyl]-1H-pyrazolo[4,3-c]pyridin-6-yl}urea | Calc'd 393.0, found | 564 |

TABLE 2-continued

| EX | Structure | Exact Mass [M + H]+ | Route Used |
|---|---|---|---|
| 565 | 1-[(2R,3R,4S)-2-(fluoromethyl)-1-methyl-4-phenylpyrrolidin-3-yl]-3-[3-(2-methylpyridin-4-yl)-1H-pyrazolo[4,3-c]pyridin-6-yl]urea | Calc'd 460, found 460 | 178 |
| 566 | 1-[3-(2-methylpyridin-4-yl)-1H-pyrazolo[4,3-c]pyridin-6-yl]-3-[2-(methylsulfonyl)-1-phenylethyl]urea | Calc'd 451, found 451 | 178 |
| 567 | 1-[(3R,4R,5R)-5-(difluoromethyl)-1-methyl-4-phenylpyrrolidin-3-yl]-3-[3-(2-methylpyridin-4-yl)-1H-pyrazolo[4,3-c]pyridin-6-yl] urea | Calc'd 478, found 478 | 178 |
| 568 | 1-[(2R,3R,4S)-1,2-dimethyl-4-phenylpyrrolidin-3-yl]-3-[3-(2-methylpyridin-4-yl)-1H-pyrazolo[4,3-c]pyridin-6-yl] urea | Calc'd 442, found 442 | 178 |

TABLE 2-continued

| EX | Structure | Exact Mass [M + H]+ | Route Used |
|---|---|---|---|
| 569 | 1-[(3R,4R,5S)-5-(difluoromethyl)-1-methyl-4-phenylpyrrolidin-3-yl]-3-[3-(2-methylpyridin-4-yl)-1H-pyrazolo[4,3-c]pyridin-6-yl] urea | Calc'd 478, found 478 | 178 |
| 570 | 1-[3-(2-methylpyridin-4-yl)-1H-pyrazolo[4,3-c]pyridin-6-yl]-3-[(1S)-2-(methylsulfanyl)-1-phenylethyl]urea | Calc'd 419, found 419 | 178 |
| 571 | 1-[7-chloro-3-(2-methylpyridin-4-yl)-1H-pyrazolo[4,3-c]pyridin-6-yl]-3-[(1R)-1-phenylethyl]urea | Calc'd 407, found 407 | 571 |
| 572 | 1-[3-(2-methylpyridin-4-yl)-1H-pyrazolo[4,3-c]pyridin-6-yl]-3-propylurea | Calc'd 311, found 311 | 12 |

TABLE 2-continued

| EX | Structure | Exact Mass [M + H]+ | Route Used |
|---|---|---|---|
| 573 | 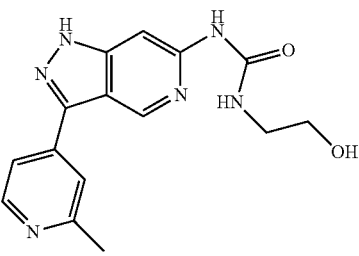  1-(2-hydroxyethyl)-3-[3-(2-methylpyridin-4-yl)-1H-pyrazolo[4,3-c]pyridin-6-yl]urea | Calc'd 313, found 313 | 12 |
| 574 | 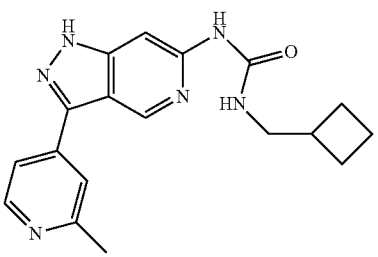  1-(cyclobutylmethyl)-3-[3-(2-methylpyridin-4-yl)-1H-pyrazolo[4,3-c]pyridin-6-yl]urea | Calc'd 337, found 337 | 12 |
| 575 | 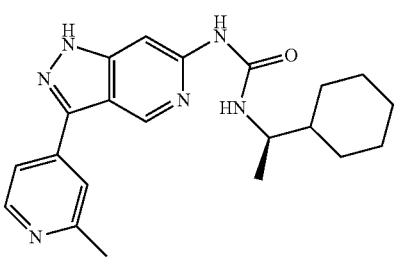  1-[(1R)-1-cyclohexylethyl)-3-[3-(2-methylpyridin-4-yl)-1H-pyrazolo[4,3-c]pyridin-6-yl]urea | Calc'd 379, found 379 | 12 |
| 576 | 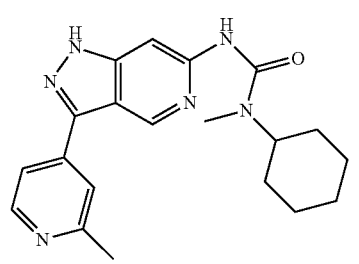  1-cyclohexyl-1-methyl-3-[3-(2-methylpyridin-4-yl)-1H-pyrazolo[4,3-c]pyridin-6-yl]urea | Calc'd 365, found 365 | 12 |

| EX | Structure | Exact Mass [M + H]+ | Route Used |
|---|---|---|---|
| 577 | 1-[3-(2-methylpyridin-4-yl)-1H-pyrazolo[4,3-c]pyridin-6-yl]-3-(tetrahydrofuran-3-yl)urea | Calc'd 339, found 339 | 12 |
| 578 | 1-(cyclohexylmethyl)-3-[3-(2-methylpyridin-4-yl)-1H-pyrazolo[4,3-c]pyridin-6-yl]urea | Calc'd 365.0, found | 12 |
| 579 | 1-[3-(2-methylpyridin-4-yl)-1H-pyrazolo[4,3-c]pyridin-6-yl]-3-pyrrolidin-3-ylurea | Calc'd 338, found 338 | 12 |
| 580 | 1-[3-(2-methylpyridin-4-yl)-1H-pyrazolo[4,3-c]pyridin-6-yl]-3-[(3S,4S)-4-phenyltetrahydrofuran-3-yl]urea | Calc'd 415, found 415 | 12 |

TABLE 2-continued

| EX | Structure | Exact Mass [M + H]+ | Route Used |
|---|---|---|---|
| 581 | 1-[(3S,4R)-4-(3-chlorophenyl)-1-methylpyrrolidin-3-yl]-3-[3-(2-methylpyridin-4-yl)-1H-pyrazolo[4,3-c]pyridin-6-yl]urea | Calc'd 462, found 462 | 12 |
| 582 | 1-[(3S,4R)-1-methyl-4-phenylpyrrolidin-3-yl]-3-[3-(2-methylpyridin-4-yl)-1H-pyrazolo[4,3-c]pyridin-6-yl]urea | Calc'd 428, found 428 | 12 |
| 583 | 1-[3-(2-methylpyridin-4-yl)-1H-pyrazolo[4,3-c]pyridin-6-yl]-3-[(1R,2S)-2-phenylcyclopropyl]urea | Calc'd 385, found 385 | 12 |
| 584 | 1-[3-(2-methylpyridin-4-yl)-1H-pyrazolo[4,3-c]pyridin-6-yl]-3-(2-phenylpropyl)urea | Calc'd 387, found 387 | 12 |

TABLE 2-continued

| EX | Structure | Exact Mass [M + H]+ | Route Used |
|---|---|---|---|
| 585 | 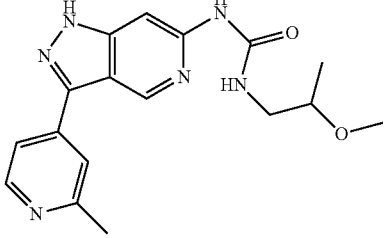<br>1-(2-methoxypropyl)-3-[3-(2-methylpyridin-4-yl)-1H-pyrazolo[4,3-c]pyridin-6-yl]urea | Calc'd 341, found 341 | 12 |
| 586 | 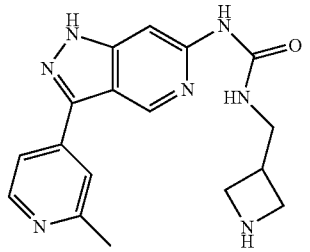<br>1-(azetidin-3-ylmethyl)-3-[3-(2-methylpyridin-4-yl)-1H-pyrazolo[4,3-c]pyridin-6-yl]urea | Calc'd 338, found 338 | 12 |
| 587 | 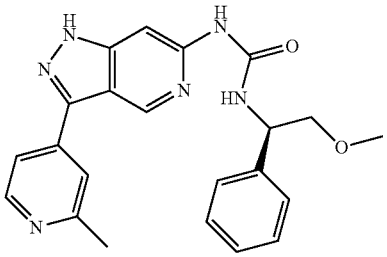<br>1-[(1R)-2-methoxy-1-phenylethyl]-3-[3-(2-methylpyridin-4-yl)-1H-pyrazolo[4,3-c]pyridin-6-yl]urea | Calc'd 403, found 403 | 12 |
| 588 | 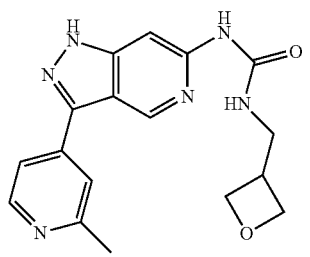<br>1-[3-(2-methylpyridin-4-yl)-1H-pyrazolo[4,3-c]pyridin-6-yl]-3-(oxetan-3-ylmethyl)urea | Calc'd 339, found 339 | 12 |

TABLE 2-continued

| EX | Structure | Exact Mass [M + H]+ | Route Used |
|----|-----------|---------------------|------------|
| 589 | 1-[(1R)-1-cyclohexylethyl]-3-[3-(1-methyl-1H-pyrazol-4-yl)-1H-pyrazolo[4,3-c]pyridin-6-yl]urea | Calc'd 368, found 368 | 600 |
| 590 | 1-(cyclobutylmethyl)-3-[3-(1-methyl-1H-pyrazol-4-yl)-1H-pyrazolo[4,3-c]pyridin-6-yl]urea | Calc'd 326, found 326 | 600 |
| 591 | 1-(cyclobutylmethyl)-3-[3-(2-fluoropyridin-4-yl)-1H-pyrazolo[4,3-c]pyridin-6-yl]urea | Calc'd 341, found 341 | 600 |
| 592 | 1-(cyclobutylmethyl)-3-[3-(4-fluorophenyl-1H-pyrazolo[4,3-c]pyridin-6-yl]urea | Calc'd 340, found 340 | 600 |

TABLE 2-continued

| EX | Structure | Exact Mass [M + H]+ | Route Used |
|---|---|---|---|
| 593 | 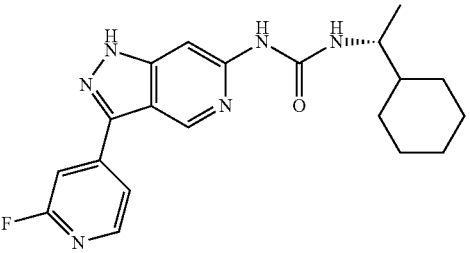<br>1-[(1R)-1-cyclohexylethyl]-3-[3-(2-fluoropyridin-4-yl)-1H-pyrazolo[4,3-c]pyridin-6-yl] urea | Calc'd 383, found 383 | 600 |
| 594 | 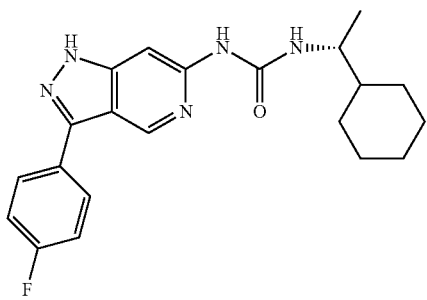<br>1-[(1R)-1-cyclohexylethyl]-3-[3-(4-fluorophenyl-1H-pyrazolo[4,3-c]pyridin-6-yl]urea | Calc'd 382, found 382 | 600 |
| 595 | 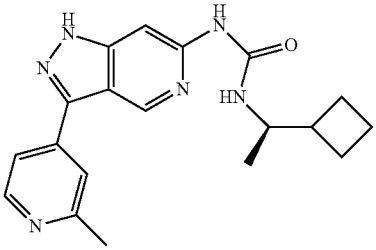<br>1-[(1R)-1-cyclobutylethyl]-3-[3-(2-methylpyridin-4-yl)-1H-pyrazolo[4,3-c]pyridin-6-yl]urea | Calc'd 351, found 351 | 12 |
| 596 | 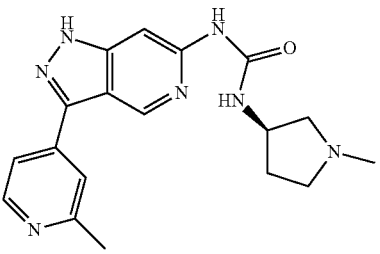<br>1-[3-(2-methylpyridin-4-yl)-1H-pyrazolo[4,3-c]pyridin-6-yl]-3-[(3R)-1-methylpyrrolidin-3-yl]urea | Calc'd 352, found 352 | 12 |

TABLE 2-continued

| EX | Structure | Exact Mass [M + H]+ | Route Used |
|---|---|---|---|
| 597 | 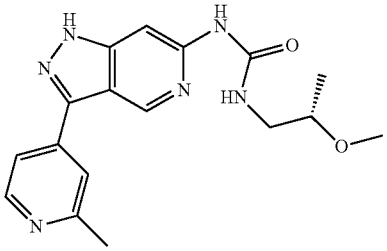<br>1-[(2S)-2-methoxypropyl]-3-[3-(2-methylpyridin-4-yl)-1H-pyrazolo[4,3-c]pyridin-6-yl]urea | Calc'd 341, found 341 | 12 |
| 598 | 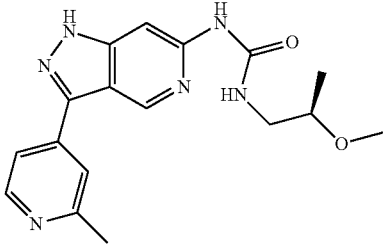<br>1-[(2R)-2-methoxypropyl]-3-[3-(2-methylpyridin-4-yl)-1H-pyrazolo[4,3-c]pyridin-6-yl]urea | Calc'd 341, found 341 | 12 |
| 599 | 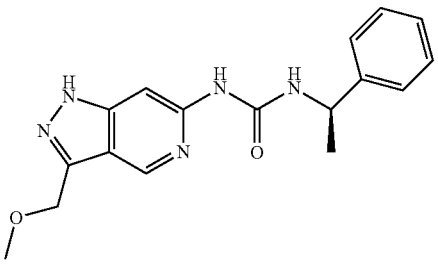<br>1-[3-(hydroxymethyl)-1H-pyrazolo[4,3-c]pyridin-6-yl]-1-methyl-3-[(1R)-1-phenylethyl]urea | Calc'd 326, found 326 | 600 |
| 600 | 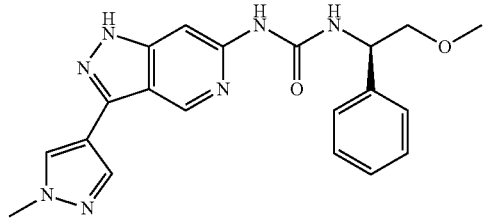<br>1-[(1R)-2-methoxy-1-phenylethyl-3-[3-(1-methyl-1H-pyrazol-4-yl)-1H-pyrazolo[4,3-c]pyridin-6-yl]urea | Calc'd 392, found 392 | 600 |

TABLE 2-continued

| EX | Structure | Exact Mass [M + H]+ | Route Used |
|---|---|---|---|
| 601 | 1-[3-(2-fluoropyridin-4-yl)-1H-pyrazolo[4,3-c]pyridin-6-yl]-3-[(1R)-2-methoxy-1-phenylethyl]urea | Calc'd 407, found 407 | 600 |
| 602 | 1-[3-(4-fluorophenyl)-1H-pyrazolo[4,3-c]pyridin-6-yl]-3-[(1R)-2-methoxy-1-phenylethyl]urea | Calc'd 406, found 406 | 600 |
| 603 | 1-ethyl-3-[3-(2-methylpyridin-4-yl)-1H-pyrazolo[4,3-c]pyridin-6-yl]urea | Calc'd 297, found 297 | 600 |
| 604 | 1-(2-methoxyethyl)-3-{3-[2-(1-methylethoxy)pyridin-4-yl]-1H-pyrazolo[4,3-c]pyridin-6-yl}urea | Calc'd 371, found 371 | 624 |

TABLE 2-continued

| EX | Structure | Exact Mass [M + H]+ | Route Used |
|---|---|---|---|
| 605 | 1-[3-(2-cyclopropylpyridin-4-yl)-1H-pyrazolo[4,3-c]pyridin-6-yl]-3-[(1S)-2-methoxy-1-phenylethyl]urea | Calc'd 429, found 429 | 600 |
| 606 | 1-[(1R)-1-methyl-2-phenylethyl]-3-[3-(2-methylpyridin-4-yl)-1H-pyrazolo[4,3-c]pyridin-6-yl]urea | Calc'd 387, found 387 | 12 |
| 607 | 1-[3-(4-cyanophenyl)-1H-pyrazolo[4,3-c]pyridin-6-yl]-3-[(1S)-2-methoxy-1-phenylethyl]urea | Calc'd 413, found 413 | 600 |
| 608 | 1-ethyl-3-[3-(4-fluorophenyl)-1H-pyrazolo[4,3-c]pyridin-6-yl]urea | Calc'd 300, found 300 | 623 |

TABLE 2-continued

| EX | Structure | Exact Mass [M + H]+ | Route Used |
|---|---|---|---|
| 609 | 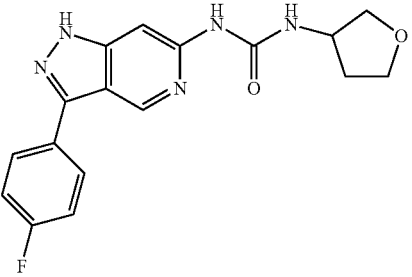<br>1-[3-(4-fluorophenyl)-1H-pyrazolo[4,3-c]pyridin-6-yl]-3-(tetrahydrofuran-3-yl)urea | Calc'd 342, found 342 | 623 |
| 610 | 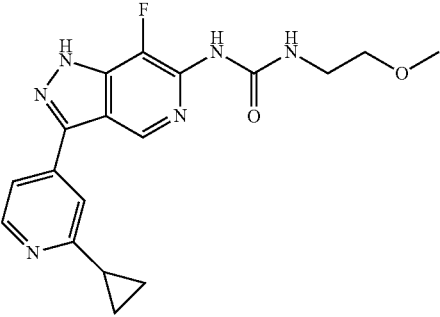<br>1-[3-(2-cyclopropylpyridin-4-yl)-7-fluoro-1H-pyrazolo[4,3-c]pyridin-6-yl]-3-(2-methoxyethyl)urea | Calc'd 371, found 371 | 624 |
| 611 | 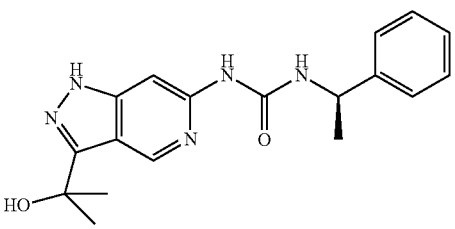<br>1-[3-(1-hydroxy-1-methylethyl)-1H-pyrazolo[4,3-c]pyridin-6-yl]-3-[(1R)-1-phenylethyl]urea | Calc'd 340, found 340 | 600 |
| 612 | 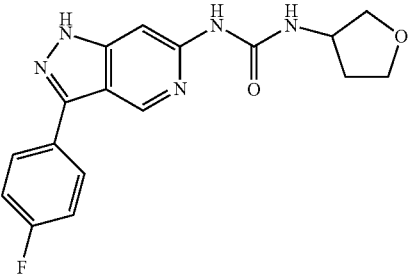<br>1-[3-(4-fluorophenyl)-1H-pyrazolo[4,3-c]pyridin-6-yl]-3-(tetrahydrofuran-3-yl)urea | Calc'd 342, found 342 | 623 |

TABLE 2-continued

| EX | Structure | Exact Mass [M + H]+ | Route Used |
|---|---|---|---|
| 613 | 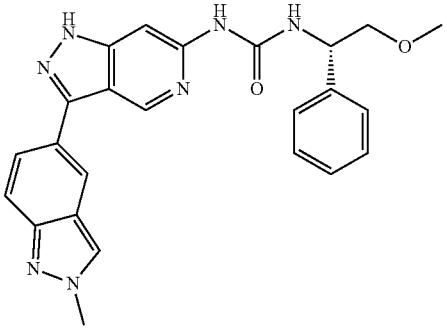

1-[(1S)-2-methoxy-1-phenylethyl]-3-[3-(2-methyl-2H-indazol-5-yl)-1H-pyrazolo[4,3-c]pyridin-6-yl]urea | Calc'd 442, found 442 | 600 |
| 614 | 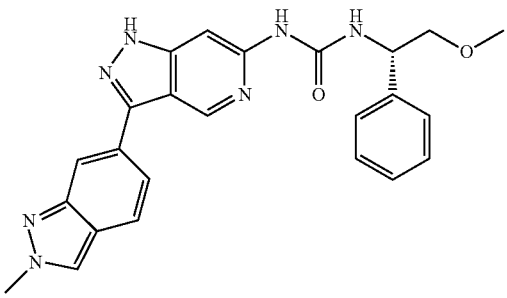

1-[(1S)-2-methoxy-1-phenylethyl]-3-[3-(2-methyl-2H-indazol-6-yl)-1H-pyrazolo[4,3-c]pyridin-6-yl]urea | Calc'd 442, found 442 | 600 |
| 615 | 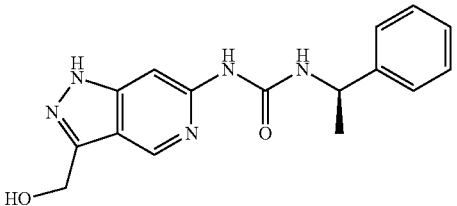

1-[3-(hydroxymethylethyl)-1H-pyrazolo[4,3-c]pyridin-6-yl]-3-[(1R)-1-phenylethyl]urea | Calc'd 312, found 312 | 600 |
| 616 | 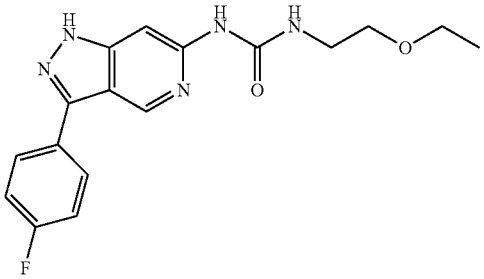

1-(2-ethoxyethyl)-3-[3-(4-fluorophenyl)-1H-pyrazolo[4,3-c]pyridin-6-yl]urea | Calc'd 344, found 344 | 623 |

TABLE 2-continued

| EX | Structure | Exact Mass [M + H]+ | Route Used |
|---|---|---|---|
| 617 | 1-(2-ethoxyethyl)-3-[3-(2-methylpyridin-4-yl)-1H-pyrazolo[4,3-c]pyridin-6-yl]urea | Calc'd 341, found 341 | 600 |
| 618 | 1-[3-(1-hydroxyethyl)-1H-pyrazolo[4,3-c]pyridin-6-yl]-3-[(1R)-1-phenylethyl]urea | Calc'd 326, found 326 | 600 |
| 619 | 1-[3-(2-methylpyridin-4-yl)-1H-pyrazolo[4,3-c]pyridin-6-yl]-3-[3-(methylsulfonyl)benzyl]urea | Calc'd 437, found 437 | 12 |
| 620 | 1-[3-(ethoxymethyl)-1H-pyrazolo[4,3-c]pyridin-6-yl]-3-[(1R)-1-phenylethyl]urea | Calc'd 340, found 340 | 620 |

TABLE 2-continued
| EX | Structure | Exact Mass [M + H]+ | Route Used |
|---|---|---|---|
| 621 | 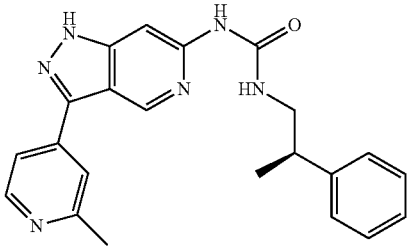<br>1-[3-(2-methylpyridin-4-yl)-1H-pyrazolo[4,3-c]pyridin-6-yl]-3-[(2R)-2-phenylpropyl]urea | Calc'd 387, found 387 | 30 |
| 622 | 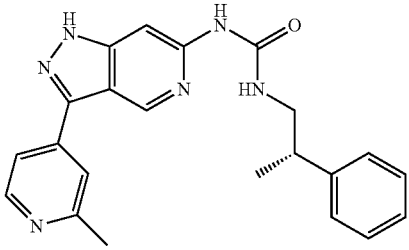<br>1-[3-(2-methylpyridin-4-yl)-1H-pyrazolo[4,3-c]pyridin-6-yl]-3-[(2S)-2-phenylpropyl]urea | Calc'd 387, found 387 | 30 |
| 623 | 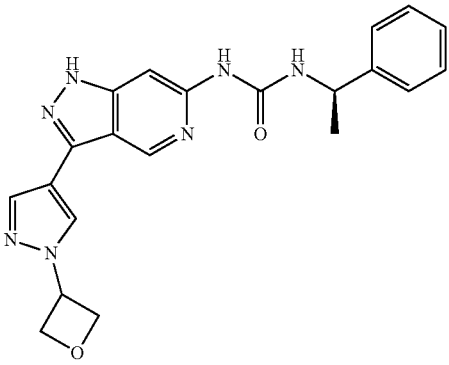<br>1-[3-(4-fluorophenyl)-1H-pyrazolo[4,3-c]pyridin-6-yl]-3-(2-methoxyethyl)urea | Calc'd 330, found 330 | 623 |
| 624 | 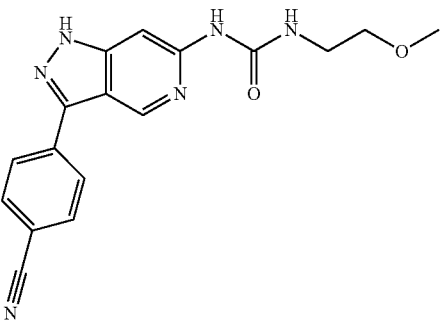 [SMILES: COCCNC(=O)Nc1cc2[nH]nc(-c3ccc(C#N)cc3)c2cn1]<br>1-[3-(4-cyanophenyl)-1H-pyrazolo[4,3-c]pyridin-6-yl]-3-(2-methoxyethyl)urea | Calc'd 337, found 337 | 624 |

TABLE 2-continued

| EX | Structure | Exact Mass [M + H]+ | Route Used |
|---|---|---|---|
| 625 | 1-(2-methoxyethyl)-3-[3-(2-methyl-2H-indazol-6-yl)-1H-pyrazolo[4,3-c]pyridin-6-yl]urea | Calc'd 366, found 366 | 624 |
| 626 | 1-(2-methoxyethyl)-3-[3-(2-methyl-2H-indazol-5-yl)-1H-pyrazolo[4,3-c]pyridin-6-yl]urea | Calc'd 366, found 366 | 624 |
| 627 | 1-(2-methoxyethyl)-3-(3-phenyl-1H-pyrazolo[4,3-c]pyridin-6-yl)urea | Calc'd 312, found 312 | 624 |
| 628 | 1-{3-[4-(1-cyano-1-methylethyl)phenyl]-1H-pyrazolo[4,3-c]pyridin-6-yl}-3-(2-methoxyethyl)urea | Calc'd 379, found 379 | 624 |

TABLE 2-continued

| EX | Structure | Exact Mass [M + H]+ | Route Used |
|---|---|---|---|
| 629 | 1-[3-(2-cyclopropylpyridin-4-yl)-1H-pyrazolo[4,3-c]pyridin-6-yl]-3-(2-methoxyethyl)urea | Calc'd 353, found 353 | 624 |
| 630 | 1-(2-methoxyethyl)-3-{3-[6-(1-methylethoxy)pyridin-3-yl]-1H-pyrazolo[4,3-c]pyridin-6-yl}urea | Calc'd 371, found 371 | 624 |
| 631 | 1-(2-methoxyethyl)-3-[3-(2-methoxy-6-methylpyridin-4-yl)-1H-pyrazolo[4,3-c]pyridin-6-yl]urea | Calc'd 357, found 357 | 624 |
| 632 | 1-[3-(4-fluorophenyl)-1H-pyrazolo[4,3-c]pyridin-6-yl]-3-[(1R)-2-methoxy-1-methylethyl]urea | Calc'd 344, found 344 | 623 |

TABLE 2-continued

| EX | Structure | Exact Mass [M + H]+ | Route Used |
|---|---|---|---|
| 633 | 1-[3-(4-fluorophenyl)-1H-pyrazolo[4,3-c]pyridin-6-yl]-3-[(1S)-2-methoxy-1-methylethyl]urea | Calc'd 344, found 344 | 623 |
| 634 | 1-[3-(4-fluorophenyl)-1H-pyrazolo[4,3-c]pyridin-6-yl]-3-[(2R)-2-methoxypropyl]urea | Calc'd 344, found 344 | 623 + SFC |
| 635 | 1-[3-(4-fluorophenyl)-1H-pyrazolo[4,3-c]pyridin-6-yl]-3-[(2S)-2-methoxypropyl]urea | Calc'd 344, found 344 | 623 + SFC |
| 636 | 1-[3-(2-fluoropyridin-4-yl)-1H-pyrazolo[4,3-c]pyridin-6-yl]-3-[(1R)-1-phenylethyl]urea | Calc'd 377, found 377 | 30 |

TABLE 2-continued

| EX | Structure | Exact Mass [M + H]+ | Route Used |
|---|---|---|---|
| 637 | 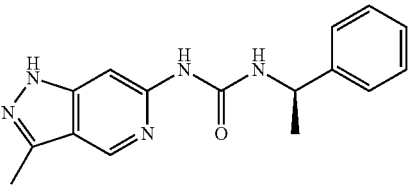<br>1-(3-methyl-1H-pyrazolo[4,3-c]pyridin-6-yl)-3-[(1R)-1-phenylethyl]urea | Calc'd 296, found 296 | 30 |
| 638 | 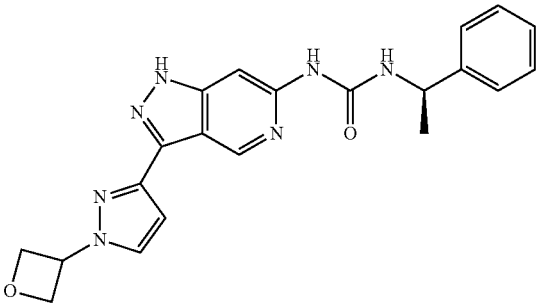<br>1-[3-(1-oxetan-3-yl-1H-pyrazol-3-yl)-1H-pyrazolo[4,3-c]pyridin-6-yl]-3-[(1R)-1-phenylethyl]urea | Calc'd 404, found 404 | 30 |
| 639 | 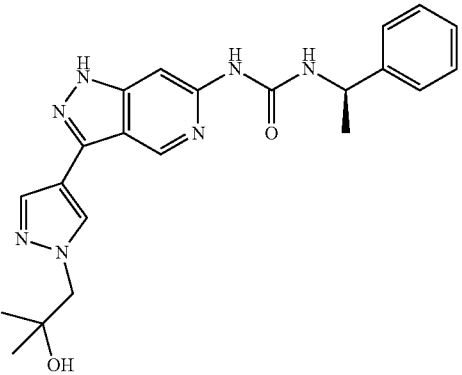<br>1-{3-[1-(2-hydroxy-2-methylpropyl)-1H-pyrazol-4-yl]-1H-pyrazolo[4,3-c]pyridin-6-yl}-3-[(1R)-1-phenylethyl]urea | Calc'd 420, found 420 | 90 |
| 640 | 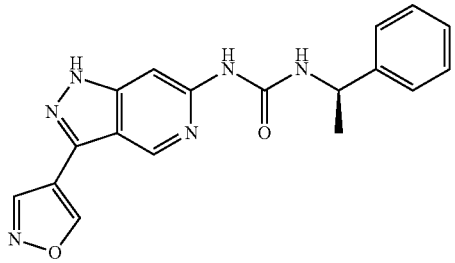<br>1-(3-isoxazol-4-yl-1H-pyrazolo[4,3-c]pyridin-6-yl)-3-[(1R)-1-phenylethyl]urea | Calc'd 349, found 349 | 90 |

TABLE 2-continued

| EX | Structure | Exact Mass [M + H]+ | Route Used |
|---|---|---|---|
| 641 | (1R, 2S), (1S, 2R), (1S, 2S) or (1R, 2R) methyl 2-[6-({[(1R)-1-phenylethyl]carbamoyl}amino)-1H-pyrazolo[4,3-c]pyridin-3-yl]cyclopropanecarboxylate | Calc'd 380, found 380 | 90 |
| 642 | (1S, 2R), (1R, 2S), (1S, 2S) or (1R, 2R) methyl 2-[6-({[(1R)-1-phenylethyl]carbamoyl}amino)-1H-pyrazolo[4,3-c]pyridin-3-yl]cyclopropanecarboxylate | Calc'd 380, found 380 | 90 |
| 643 | methyl 2-[6-({[(1R)-1-phenylethyl]carbamoyl}amino)-1H-pyrazolo[4,3-c]pyridin-3-yl]cyclopropanecarboxylate | Calc'd 380, found 380 | 30 |

TABLE 2-continued

| EX | Structure | Exact Mass [M + H]+ | Route Used |
|---|---|---|---|
| 644 | (1S, 2S), (1S, 2R), (1R, 2S) or (1R, 2R) methyl 2-[6-({[(1R)-1-phenylethyl]carbamoyl}amino)-1H-pyrazolo[4,3-c]pyridin-3-yl]cyclopropanecarboxylate | Calc'd 380, found 380 | 90 |
| 645 | 1-[(1R)-1-(4-fluorophenyl)ethyl]-3-[3-(2-fluoropyridin-4-yl)-1H-pyrazolo[4,3-c]pyridin-6-yl]urea | Calc'd 395, found 395 | 30 |
| 646 | 1-[3-(4-chloro-3-fluorophenoxy)cyclohexyl]-3-[3-(2-methylpyridin-4-yl)-1H-pyrazolo[4,3-c]pyridin-6-yl]urea | Calc'd 495, found 495 | 90 |

TABLE 2-continued

| EX | Structure | Exact Mass [M + H]+ | Route Used |
|---|---|---|---|
| 647 | 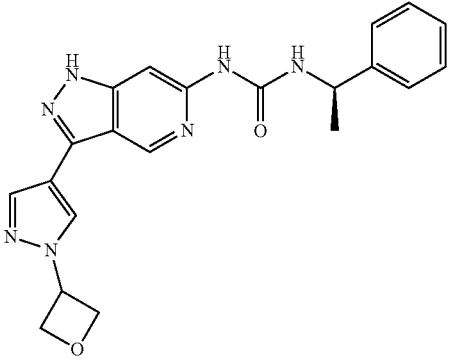<br>1-[3-(1-oxetan-3-yl-1H-pyrazol-4-yl)-1H-pyrazolo[4,3-c]pyridin-6-yl]-3-[(1R)-1-phenylethyl]urea | Calc'd 404, found 404 | 90 |
| 648 | 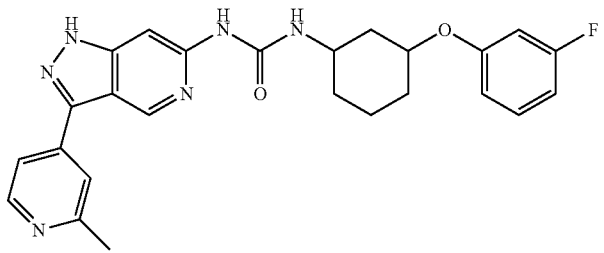<br>1-[3-(3-fluorophenoxy)cyclohexyl]-3-[3-(2-methylpyridin-4-yl)-1H-pyrazolo[4,3-c]pyridin-6-yl]urea | Calc'd 461, found 461 | 90 |
| 649 | 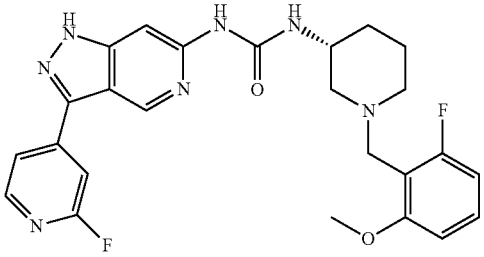<br>1-[(3R)-1-(2-fluoro-6-methoxybenzyl)piperidin-3-yl]-3-[3-(2-fluoropyridin-4-yl)-1H-pyrazolo[4,3-c]pyridin-6-yl]urea | Calc'd 494, found 494 | 30 |
| 650 | 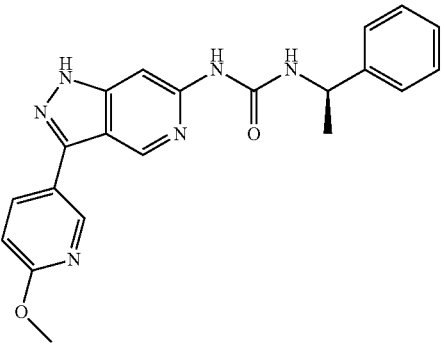<br>1-[3-(6-methoxypyridin-3-yl)-1H-pyrazolo[4,3-c]pyridin-6-yl]-3-[(1R)-1-phenylethyl]urea | Calc'd 389, found 389 | 90 |

TABLE 2-continued

| EX | Structure | Exact Mass [M + H]+ | Route Used |
|---|---|---|---|
| 651 | 1-[3-(2-methyl-2H-indazol-5-yl)-1H-pyrazolo[4,3-c]pyridin-6-yl]-3-[(1R)-1-phenylethyl]urea | Calc'd 412, found 412 | 90 |
| 652 | 1-[3-(2-methyl-1,3-benzoxazol-6-yl)-1H-pyrazolo[4,3-c]pyridin-6-yl]-3-[(1R)-1-phenylethyl]urea | Calc'd 413, found 413 | 90 |
| 653 | 1-(3-cyclopentyl-1H-pyrazolo[4,3-c]pyridin-6-yl)-3-[(1R)-1-phenylethyl]urea | Calc'd 350, found 350 | 30 |

TABLE 2-continued

| EX | Structure | Exact Mass [M + H]+ | Route Used |
|----|-----------|---------------------|------------|
| 654 | 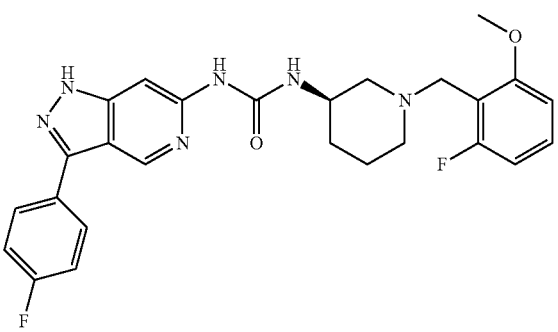<br>1-[(3R)-1-(2-fluoro-6-methoxybenzyl)piperidin-3-yl]-3-[3-(4-fluorophenyl)-1H-pyrazolo[4,3-c]pyridin-6-yl]urea | Calc'd 493, found 493 | 30 |
| 655 | 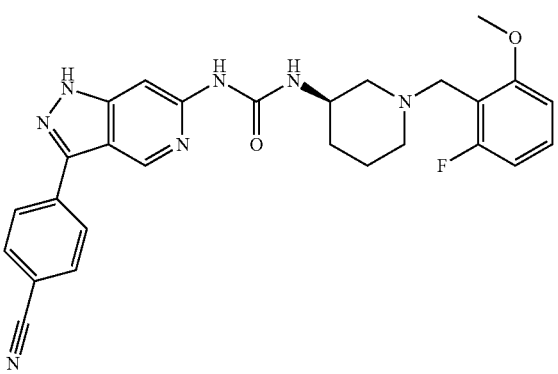<br>1-[3-(4-cyanophenyl)-1H-pyrazolo[4,3-c]pyridin-6-yl]-3-[(3R)-1-(2-fluoro-6-methoxybenzyl)piperidin-3-yl]urea | Calc'd 500, found 500 | 30 |
| 656 | 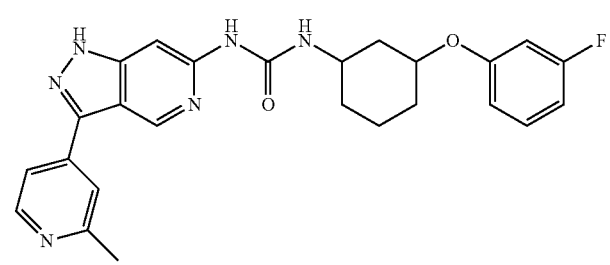<br>1-[3-(3-fluorophenoxy)cyclohexyl]-3-[3-(2-methylpyridin-4-yl)-1H-pyrazolo[4,3-c]pyridin-6-yl]urea | Calc'd 461, found 461 | 90 |
| 657 | 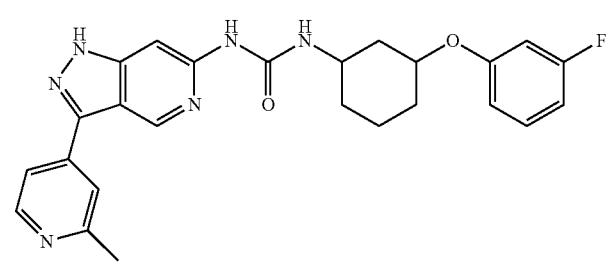<br>1-[3-(3-fluorophenoxy)cyclohexyl]-3-[3-(2-methylpyridin-4-yl)-1H-pyrazolo[4,3-c]pyridin-6-yl]urea | Calc'd 461, found 461 | 90 |

TABLE 2-continued

| EX | Structure | Exact Mass [M + H]+ | Route Used |
|---|---|---|---|
| 658 | 1-[3-(3-fluorophenoxy)cyclohexyl]-3-[3-(2-methylpyridin-4-yl)-1H-pyrazolo[4,3-c]pyridin-6-yl]urea | Calc'd 461, found 461 | 90 |
| 659 | 1-[3-(3-fluorophenoxy)cyclohexyl]-3-[3-(2-methylpyridin-4-yl)-1H-pyrazolo[4,3-c]pyridin-6-yl]urea | Calc'd 461, found 461 | 90 |
| 660 | 2-[6-({[(1R)-1-phenylethyl]carbamoyl}amino)-1H-pyrazolo[4,3-c]pyridin-3-yl]cyclopropanecarboxylic acid | Calc'd 366, found 366 | 30 |
| 661 | 1-[3-(2-methoxypyridin-4-yl)-1H-pyrazolo[4,3-c]pyridin-6-yl]-3-[(1R)-1-phenylethyl]urea | Calc'd 389, found 389 | 90 |

TABLE 2-continued

| EX | Structure | Exact Mass [M + H]+ | Route Used |
|---|---|---|---|
| 662 | 1-[(3R)-1-(2-fluoro-6-methoxybenzyl)piperidin-3-yl]-3-[3-(2-methyl-2H-indazol-5-yl)-1H-pyrazolo[4,3-c]pyridin-6-yl]urea | Calc'd 529, found 529 | 30 |
| 663 | 1-[3-(1,2-dihydropyrimidin-5-yl)-1H-pyrazolo[4,3-c]pyridin-6-yl]-3-[(1R)-1-(4-fluorophenyl)ethyl]urea | Calc'd 380, found 380 | 140 |
| 664 | 1-[(1R)-1-(4-fluorophenyl)ethyl]-3-[3-(5-fluoropyridin-3-yl)-1H-pyrazolo[4,3-c]pyridin-6-yl]urea | Calc'd 395, found 395 | 140 |
| 665 | 1-[3-(1,1-difluoroethyl)-1H-pyrazolo[4,3-c]pyridin-6-yl]-3-[(1R)-1-(4-fluorophenyl)ethyl]urea | Calc'd 364, found 364 | 140 |

TABLE 2-continued

| EX | Structure | Exact Mass [M + H]+ | Route Used |
|---|---|---|---|
| 666 | 1-[3-(1,1-difluoroethyl)-1H-pyrazolo[4,3-c]pyridin-6-yl]-3-[(1R)-1-phenylethyl]urea | Calc'd 346, found 346 | 140 |
| 667 | 1-benzyl-3-[3-(1,1-difluoroethyl)-1H-pyrazolo[4,3-c]pyridin-6-yl]urea | Calc'd 332, found 332 | 140 |
| 668 | 1-[3-(1,1-difluoroethyl)-1H-pyrazolo[4,3-c]pyridin-6-yl]-3-(4-fluorobenzyl)urea | Calc'd 350, found 350 | 140 |
| 669 | 1-[3-(difluoromethyl)-1H-pyrazolo[4,3-c]pyridin-6-yl]-3-[(1R)-1-(4-fluorophenyl)ethyl]urea | Calc'd 350, found 350 | 140 |
| 670 | 1-[3-(difluoromethyl)-1H-pyrazolo[4,3-c]pyridin-6-yl]-3-[(1R)-1-phenylethyl]urea | Calc'd 332, found 332 | 140 |

TABLE 2-continued

| EX | Structure | Exact Mass [M + H]+ | Route Used |
|---|---|---|---|
| 671 | 1-[(1R)-1-(4-fluorophenyl)ethyl]-3-(3-pyrimidin-5-yl-1H-pyrazolo[4,3-c]pyridin-6-yl)urea | Calc'd 378, found 378 | 140 |
| 672 | 1-[3-(3-cyanophenyl)-1H-pyrazolo[4,3-c]pyridin-6-yl]-3-[(1R)-1-phenylethyl]urea | Calc'd 383, found 383 | 140 |
| 673 | 1-[3-(3-cyanophenyl)-1H-pyrazolo[4,3-c]pyridin-6-yl]-3-(4-fluorobenzyl)urea | Calc'd 387, found 387 | 140 |

TABLE 2-continued
| EX | Structure | Exact Mass [M + H]+ | Route Used |
|---|---|---|---|
| 674 | 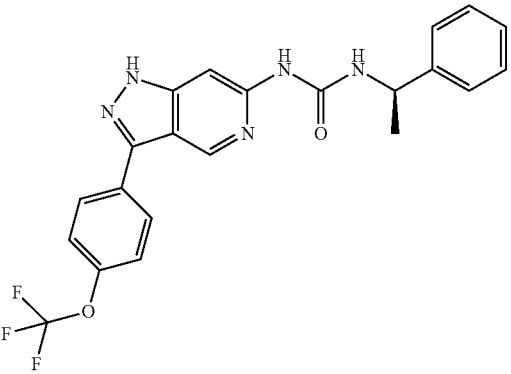 1-[(1R)-1-phenylethyl]-3-{3-[4-(trifluoromethoxy)phenyl]-1H-pyrazolo[4,3-c]pyridin-6-yl}urea | Calc'd 442, found 442 | 140 |
| 675 | 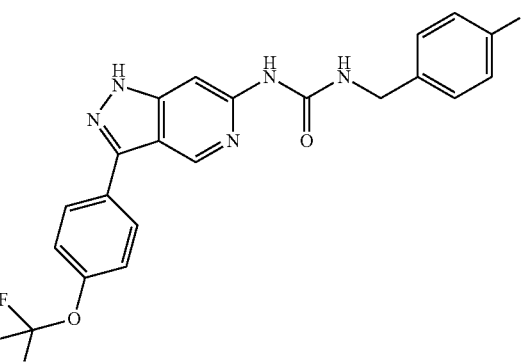 1-(4-fluorobenzyl)-3-{3-[4-(trifluoromethoxy)phenyl]-1H-pyrazolo[4,3-c]pyridin-6-yl}urea | Calc'd 446, found 446 | 140 |
| 676 | 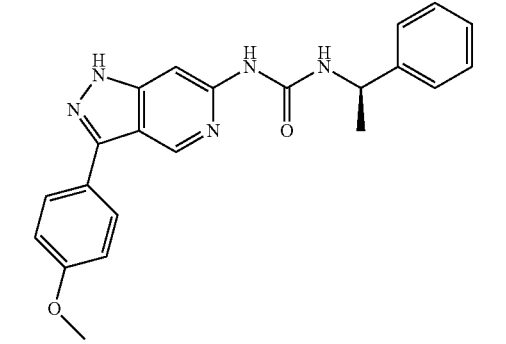 1-[3-(4-methoxyphenyl)-1H-pyrazolo[4,3-c]pyridin-6-yl]-3-[(1R)-1-phenylethyl]urea | Calc'd 388, found 388 | 140 |

TABLE 2-continued

| EX | Structure | Exact Mass [M + H]+ | Route Used |
|---|---|---|---|
| 677 | 1-(4-fluorobenzyl)-3-[3-(4-methoxyphenyl)-1H-pyrazolo[4,3-c]pyridin-6-yl]urea | Calc'd 392, found 392 | 140 |
| 678 | 1-[3-(difluoromethyl)-1H-pyrazolo[4,3-c]pyridin-6-yl]-3-[(1R)-1-pyridin-2-ylethyl]urea | Calc'd 333, found 333 | 140 |
| 679 | 1-{3-[5-(hydroxymethyl)isoxazol-3-yl-1H-pyrazolo[4,3-c]pyridin-6-yl}-3-[(1R)-1-phenylethyl]urea | Calc'd 379, found 379 | 140 |
| 680 | 1-[3-(difluoromethyl)-1H-pyrazolo[4,3-c]pyridin-6-yl]-3-[(1S)-1-(4-fluorophenyl)-2-methoxyethyl]urea | Calc'd 380, found 380 | 140 |

TABLE 2-continued

| EX | Structure | Exact Mass [M + H]+ | Route Used |
|---|---|---|---|
| 681 | 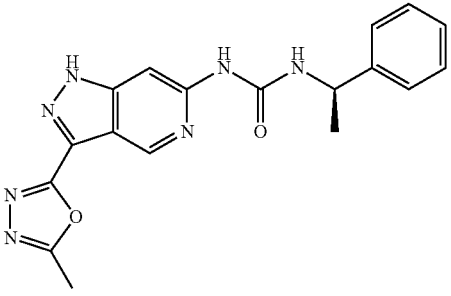<br>1-[3-(5-methyl-1,3,4-oxadiazol-2-yl)-1H-pyrazolo[4,3-c]pyridin-6-yl]-3-[(1R)-1-phenylethyl]urea | Calc'd 364, found 364 | 140 |
| 682 | 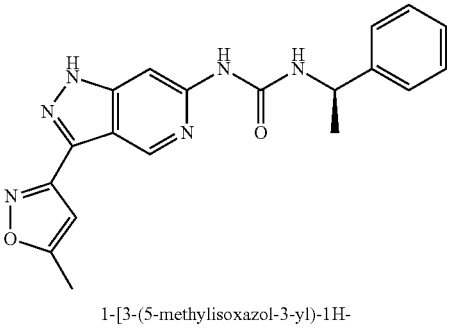<br>1-[3-(5-methylisoxazol-3-yl)-1H-pyrazolo[4,3-c]pyridin-6-yl]-3-[(1R)-1-phenylethyl]urea | Calc'd 363, found 363 | 140 |
| 683 | 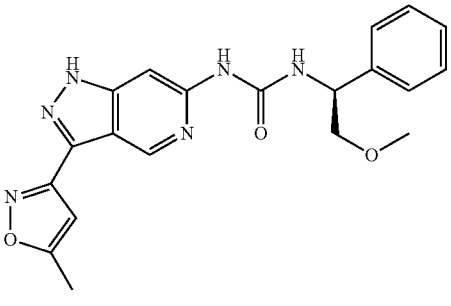<br>1-[(1S)-2-methoxy-1-phenylethyl]-3-[3-(5-methylisoxazol-3-yl)-1H-pyrazolo[4,3-c]pyridin-6-yl]urea | Calc'd 393, found 393 | 140 |
| 684 | 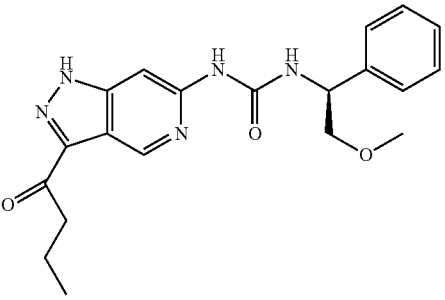<br>1-(3-butanoyl-1H-pyrazolo[4,3-c]pyridin-6-yl)-3-[(1S)-2-methoxy-1-phenylethyl]urea | Calc'd 382, found 382 | 140 |

TABLE 2-continued

| EX | Structure | Exact Mass [M + H]+ | Route Used |
|---|---|---|---|
| 685 | 1-(3-butanoyl-1H-pyrazolo[4,3-c]pyridin-6-yl)-3-[(1S)-1-(4-fluorophenyl)-2-methoxyethyl]urea | Calc'd 400, found 400 | 140 |
| 686 | 1-[(1S)-2-methoxy-1-phenylethyl]-3-[3-(5-methyl-4,5-dihydroisoxazol-3-yl)-1H-pyrazolo[4,3-c]pyridin-6-yl]urea | Calc'd 395, found 395 | 140 |
| 687 | 1-[3-(5-methyl-4,5-dihydroisoxazol-3-yl)-1H-pyrazolo[4,3-c]pyridin-6-yl]-3-[(1R)-1-phenylethyl]urea | Calc'd 365, found 365 | 140 |
| 688 | 1-[(1S)-1-(4-fluorophenyl)-2-methoxyethyl]-3-[3-(5-methylisoxazol-3-yl)-1H-pyrazolo[4,3-c]pyridin-6-yl]urea | Calc'd 411, found 411 | 140 |

TABLE 2-continued

| EX | Structure | Exact Mass [M + H]+ | Route Used |
|---|---|---|---|
| 689 | 1-[3-(5-methylisoxazol-3-yl)-1H-pyrazolo[4,3-c]pyridin-6-yl]-3-(2,3,4,5-tetrahydro-1-benzoxepin-5-yl)urea | Calc'd 405, found 405 | 140 |
| 690 | 1-[3-(5-methylisoxazol-3-yl)-1H-pyrazolo[4,3-c]pyridin-6-yl]-3-(2,3,4,5-tetrahydro-1-benzoxepin-5-yl)urea | Calc'd 405, found 405 | 140 |
| 691 | 1-[3-(difluoromethyl)-1H-pyrazolo[4,3-c]pyridin-6-yl]-3-[(1S)-2-methoxy-1-phenylethyl]urea | Calc'd 362, found 362 | 140 |
| 692 | 1-[3-(difluoromethyl)-1H-pyrazolo[4,3-c]pyridin-6-yl]-3-[(1S)-2-ethoxy-1-phenylethyl]urea | Calc'd 376, found 376 | 178 |

TABLE 2-continued

| EX | Structure | Exact Mass [M + H]+ | Route Used |
|---|---|---|---|
| 693 | 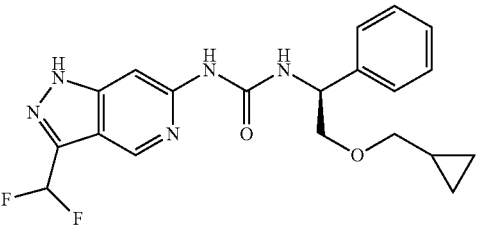<br>1-[(1S)-2-(cyclopropylmethoxy)-1-phenylethyl]-3-[3-(difluoromethyl)-1H-pyrazolo[4,3-c]pyridin-6-yl]urea | Calc'd 402, found 402 | 178 |
| 694 | 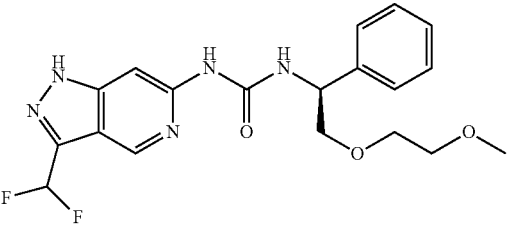<br>1-[3-(difluoromethyl)-1H-pyrazolo[4,3-c]pyridin-6-yl]-3-[(1S)-2-(2-methoxyethoxy)-1-phenylethyl]urea | Calc'd 406, found 406 | 178 |
| 695 | 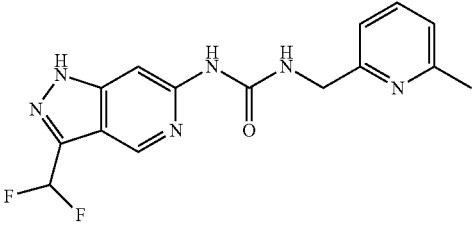<br>1-[3-(difluoromethyl)-1H-pyrazolo[4,3-c]pyridin-6-yl]-3-[(6-methylpyridin-2-yl)methyl]urea | Calc'd 333, found 333 | 178 |
| 696 | 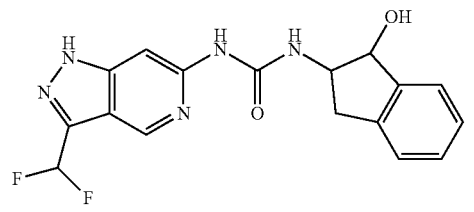<br>1-[3-(difluoromethyl)-1H-pyrazolo[4,3-c]pyridin-6-yl]-3-(1-hydroxy-2,3-dihydro-1H-inden-2-yl)urea | Calc'd 360, found 360 | 178 |

TABLE 2-continued

| EX | Structure | Exact Mass [M + H]+ | Route Used |
|---|---|---|---|
| 697 | 1-[(1S)-2-methoxy-1-phenylethyl]-3-[3-(1-methyl-1H-benzotriazol-6-yl)-1H-pyrazolo[4,3-c]pyridin-6-yl]urea | Calc'd 443, found 443 | 140 |
| 698 | 1-[(1S)-2-ethoxy-1-phenylethyl]-3-[3-(5-methylisoxazol-3-yl)-1H-pyrazolo[4,3-c]pyridin-6-yl]urea | Calc'd 407, found 407 | 178 |
| 699 | 1-[(1S)-2-(cyclopropylmethoxy)-1-phenylethyl]-3-[3-(5-methylisoxazol-3-yl)-1H-pyrazolo[4,3-c]pyridin-6-yl]urea | Calc'd 433, found 433 | 178 |
| 700 | 1-[(1S)-2-(2-methoxyethoxy)-1-phenylethyl]-3-[3-(5-methylisoxazol-3-yl)-1H-pyrazolo[4,3-c]pyridin-6-yl]urea | Calc'd 437, found 437 | 178 |

TABLE 2-continued

| EX | Structure | Exact Mass [M + H]+ | Route Used |
|---|---|---|---|
| 701 | 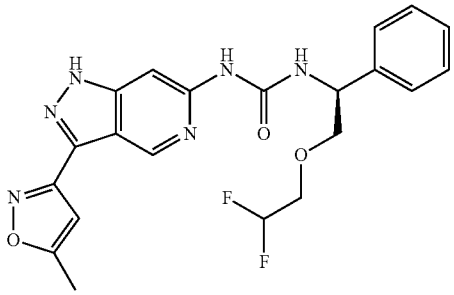<br>1-[(1S)-2-(2,2-difluoroethoxy)-1-phenylethyl]-3-[3-(5-methylisoxazol-3-yl)-1H-pyrazolo[4,3-c]pyridin-6-yl]urea | Calc'd 443, found 443 | 178 |

Assays
Active Human ERK2 (hERK2) Activity Assay:

Activated ERK2 activity was determined in an IMAP-FP assay (Molecular Devices). Using this assay format, the potency ($IC_{50}$) of each compound was determined from a 10 point (1:3 serial dilution, 3 µM starting compound concentration) titration curve using the following outlined procedure. To each well of a black Corning 384-well plate (Corning Catalog #3575), 7.5 mL of compound (3333 fold dilution in final assay volume of 25 µL) was dispensed, followed by the addition of 15 µL of kinase buffer (tween containing kinase buffer, Molecular Devices) containing 0.0364 ng/mL (0.833 nM) of phosphorylated active hERK2 enzyme. Following a 15 minute compound & enzyme incubation, each reaction was initiated by the addition of 10 µL kinase buffer containing 2.45 µM ERK2 IMAP substrate peptides (2.25 µM-unlabeled IPTTPITTTYFFFK—COOH and 200 nM-labeled IPTTPITTTYFFFK-5FAM (5-carboxyfluorescein)-COOH), and 75 µM ATP. The final reaction in each well of 25 µL consists of 0.5 nM hERK2, 900 nM unlabeled peptide, 80 nM labeled-peptide, and 30 µM ATP. Phosphorylation reactions were allowed to proceed for 60 minutes and were immediately quenched by the addition of 604 µL IMAP detection beads (1:1000 dilutions) in IMAP binding buffer (Molecular Devices) with 24 mM NaCl. Plates were read on EnVision reader after 60 minutes binding equilibration using Fluorescence Polarization protocol (Perkin Elmer).

Active Mouse ERK2 (mERK2) Activity Assay:

Activated ERK2 activity was determined in an IMAP-FP assay (Molecular Devices). Using this assay format, the potency ($IC_{50}$) of each compound was determined from a 10 point (1:3 serial dilution, 3 µM starting compound concentration) titration curve using the following outlined procedure. To each well of a black Corning 384-well plate (Corning Catalog #3575), 7.5 mL of compound (3333 fold dilution in final assay volume of 25 µL) was dispensed, followed by the addition of 15 µL of kinase buffer (tween containing kinase buffer, Molecular Devices) containing 0.0133 ng/mL (0.316 nM) of phosphorylated active mERK2 enzyme. Following a 15 minute compound & enzyme incubation, each reaction was initiated by the addition of 10 µL kinase buffer containing 2.45 µM ERK2 IMAP substrate peptides (2.25 µM-unlabeled IPTTPITTTYFFFK—COOH and 200 nM-labeled IPTTPITTTYFFFK-5FAM (5-carboxyfluorescein)-COOH), and 75 µM ATP. The final reaction in each well of 25 µL consists of 0.19 nM mERK2, 900 nM unlabeled peptide, 80 nM labeled-peptide, and 30 uM ATP. Phosphorylation reactions were allowed to proceed for 45 minutes and were immediately quenched by the addition of 60 µL IMAP detection beads (1:1000 dilutions) in IMAP binding buffer (Molecular Devices) with 24 mM NaCl. Plates were read on EnVision reader after 60 minutes binding equilibration using Fluorescence Polarization protocol (Perkin Elmer).

In the Active mouse ERK2 Activity Assay the compounds of Examples 1 to 26 had an AERK2 $IC_{50}$ in the range of 0.1 to 682.2 nM.

In the Active mouse ERK2 Activity Assay the compounds of Examples 2, 4, 5, 6, 8, 9, 10, 11, 14, 15, 19, 20, 22, 25, and 26 had an AERK2 $IC_{50}$ in the range of 0.1 to 1.2 nM.

In the Active human ERK2 Activity Assay the compounds of Examples 27 to 95 had an AERK2 $IC_{50}$ in the range of 0.2 to 899.1 nM.

In the Active human ERK2 Activity Assay the compounds of Examples 27, 29, 30, 31, 34, 43, 49, 51, 52, 53, 56, 57, 58, 59, 60, 62, 63, 64, 65, 66, 67, 69, 71, 72, 74, 87, 88, 89, 91, 93, and 95 had an AERK2 $IC_{50}$ in the range of 0.2 to 1.7 nM.

Table 3 below provides the ERK 2 MAPK1 Mouse $IC_{50}$ (in nM) data for the compounds of Examples 1-26.

TABLE 3

| Ex | $IC_{50}$ |
|---|---|
| 1 | 3.13 |
| 2 | 0.1524 |
| 3 | 36.63 |
| 4 | 1.119 |
| 5 | 0.5018 |
| 6 | 0.1524 |
| 7 | 38.29 |
| 8 | 0.5162 |
| 9 | 0.2223 |
| 10 | 0.2153 |
| 11 | 0.1524 |
| 12 | 3.724 |
| 13 | 10.23 |
| 14 | 1.161 |
| 16 | 3.779 |
| 17 | 107.7 |
| 18 | 9.462 |
| 19 | 0.296 |
| 20 | 0.5369 |
| 21 | 2.232 |
| 22 | 0.9192 |

TABLE 3-continued

| Ex | IC$_{50}$ |
|---|---|
| 23 | 2.223 |
| 24 | 682.2 |
| 26 | 0.4572 |

Table 4 below provides the ERK 2 Human average IC$_{50}$ (in nM) data for the compounds of Examples 2, 6, 9, 11, 15, 19, and 21-95.

TABLE 4

| Ex | IC$_{50}$ |
|---|---|
| 2 | 0.2857 |
| 6 | 0.2045 |
| 9 | 0.8512 |
| 11 | 0.342 |
| 15 | 0.3922 |
| 19 | 0.5556 |
| 21 | 2.534 |
| 22 | 1.608 |
| 23 | 1.997 |
| 24 | 835.5 |
| 25 | 1.956 |
| 26 | 0.5126 |
| 27 | 0.7129 |
| 28 | 3.628 |
| 29 | 0.3336 |
| 30 | 0.8504 |
| 31 | 0.2904 |
| 32 | 3.92 |
| 33 | 15.15 |
| 34 | 1.676 |
| 35 | 2.102 |
| 36 | 32.59 |
| 37 | 9.902 |
| 38 | 480.7 |
| 39 | 60.26 |
| 40 | 2.897 |
| 41 | 4.482 |
| 42 | 14.19 |
| 43 | 0.9342 |
| 44 | 15.95 |
| 45 | 2.737 |
| 46 | 762.9 |
| 47 | 2.337 |
| 48 | 5.577 |
| 49 | 1.04 |
| 50 | 899.1 |
| 51 | 1.001 |
| 52 | 0.6547 |
| 53 | 0.2452 |
| 54 | 6.52 |
| 55 | 35.02 |
| 56 | 0.411 |
| 57 | 1.842 |
| 58 | 1.002 |
| 59 | 0.5141 |
| 60 | 0.2512 |
| 61 | 126.9 |
| 62 | 0.6722 |
| 63 | 0.4045 |
| 64 | 0.5861 |
| 65 | 0.5616 |
| 66 | 1.056 |
| 67 | 0.4285 |
| 68 | 106.2 |
| 69 | 0.432 |
| 70 | 10.23 |
| 71 | 0.1588 |
| 72 | 0.7088 |
| 73 | 9.337 |
| 74 | 0.6032 |
| 75 | 2.636 |
| 76 | 56.07 |
| 77 | 15.07 |
| 78 | 5.386 |

TABLE 4-continued

| Ex | IC$_{50}$ |
|---|---|
| 79 | 34.48 |
| 80 | 3.114 |
| 81 | 1.907 |
| 82 | 10.77 |
| 83 | 3.279 |
| 84 | 6.107 |
| 85 | 29.79 |
| 86 | 455.1 |
| 87 | 0.7479 |
| 88 | 1.156 |
| 89 | 1.333 |
| 90 | 2.188 |
| 91 | 0.8779 |
| 92 | 6.245 |
| 93 | 0.383 |
| 94 | 11.91 |
| 95 | 0.2351 |

Tables 5-10 below provide the ERK 2 Human average IC$_{50}$ (in nM) data for the compounds of Examples 116-161, 163-416, 418-601, and 603-701.

TABLE 5

| Ex | IC$_{50}$ |
|---|---|
| 116 | 10.71 |
| 117 | 5.473 |
| 118 | 501.2 |
| 119 | 210.8 |
| 120 | 60.43 |
| 121 | 3.826 |
| 122 | 2.553 |
| 123 | 4.486 |
| 124 | 6.378 |
| 125 | 6.533 |
| 126 | 8.333 |
| 127 | 14.68 |
| 128 | 19.02 |
| 129 | 13.55 |
| 130 | 1968 |
| 131 | 13.38 |
| 132 | 3.198 |
| 133 | 11.04 |
| 134 | 102.9 |
| 135 | 14.63 |
| 136 | 11.91 |
| 137 | 4.536 |
| 138 | 5.275 |
| 139 | 569.9 |
| 140 | 23.47 |
| 141 | 2.433 |
| 142 | 17.4 |
| 143 | 39.72 |
| 144 | 3.459 |
| 145 | 2.442 |
| 146 | 12.94 |
| 147 | 11.23 |
| 148 | 84.3 |
| 149 | 72.13 |
| 150 | 10.37 |
| 151 | 11.1 |
| 152 | 116.3 |
| 153 | 2.277 |
| 154 | 69.97 |
| 155 | 60.14 |
| 156 | 42.24 |
| 157 | 253 |
| 158 | 2.149 |
| 159 | 609.8 |
| 160 | 1.378 |
| 161 | 5.801 |
| 162 | — |
| 163 | 4.89 |
| 164 | 7.708 |
| 165 | 8.832 |

TABLE 5-continued

| Ex | IC$_{50}$ |
|---|---|
| 166 | 3.646 |
| 167 | 458.3 |
| 168 | 116.8 |
| 169 | 7.333 |
| 170 | 0.7146 |
| 171 | 0.9695 |
| 172 | 242.9 |
| 173 | 39.82 |
| 174 | 1.581 |
| 175 | 6.685 |
| 176 | 40.96 |
| 177 | 0.9142 |
| 178 | 0.5272 |
| 179 | 1.452 |
| 180 | 4.58 |
| 181 | 0.2171 |
| 182 | 18.76 |
| 183 | 0.6619 |
| 184 | 0.1709 |
| 185 | 37.27 |
| 186 | 43.25 |
| 187 | 52.34 |
| 188 | 15.1 |
| 189 | 10.29 |
| 190 | 3.807 |
| 191 | 17.6 |
| 192 | 21.67 |
| 193 | 125.4 |
| 194 | 13.53 |
| 195 | 8.064 |
| 196 | 23.56 |
| 197 | 53.7 |
| 198 | 5.949 |
| 199 | 4.855 |
| 200 | 25.61 |
| 201 | 92.01 |
| 202 | 11.63 |
| 203 | 103.9 |
| 204 | 24.07 |
| 205 | 15.07 |
| 206 | 3.588 |
| 207 | 0.5374 |
| 208 | 6.733 |
| 209 | 8.269 |
| 210 | 96.81 |
| 211 | 0.7313 |
| 212 | 1.757 |
| 213 | 42.06 |
| 214 | 0.3938 |
| 215 | 0.5369 |
| 216 | 66.27 |
| 217 | 41.64 |
| 218 | 0.4872 |
| 219 | 1.677 |
| 220 | 2.459 |
| 221 | 4.492 |
| 222 | 0.9946 |
| 223 | 0.8856 |
| 224 | 24.26 |
| 225 | 2.448 |
| 226 | 1.579 |
| 227 | 25.76 |
| 228 | 70.29 |
| 229 | 1.056 |
| 230 | 649.9 |
| 231 | 1.533 |

TABLE 6

| Ex | IC$_{50}$ |
|---|---|
| 232 | 0.6987 |
| 233 | 42.49 |
| 234 | 0.8612 |
| 235 | 21.87 |

TABLE 6-continued

| Ex | IC$_{50}$ |
|---|---|
| 236 | 1.51 |
| 237 | 0.566 |
| 238 | 0.9352 |
| 239 | 5.883 |
| 240 | 24.2 |
| 241 | 2.732 |
| 242 | 5.54 |
| 243 | 86.79 |
| 244 | 9.85 |
| 245 | 32.49 |
| 246 | 0.5805 |
| 247 | 45.03 |
| 248 | 11.68 |
| 249 | 1258 |
| 250 | 2.358 |
| 251 | 5.258 |
| 252 | 0.7464 |
| 253 | 3.162 |
| 254 | 4.587 |
| 255 | 0.7832 |
| 256 | 1.763 |
| 257 | 378.9 |
| 258 | 1.764 |
| 259 | 0.4687 |
| 260 | 0.309 |
| 261 | 1.489 |
| 262 | 1.253 |
| 263 | 1.801 |
| 264 | 2.079 |
| 265 | 1.641 |
| 266 | 70.59 |
| 267 | 6.331 |
| 268 | 91.6 |
| 269 | 2.807 |
| 270 | 3.726 |
| 271 | 5.934 |
| 272 | 8.355 |
| 273 | 0.9454 |
| 274 | 0.4939 |
| 275 | 1.613 |
| 276 | 14.7 |
| 277 | 1.348 |
| 278 | 43.36 |
| 279 | 113.1 |
| 280 | 9.826 |
| 281 | 1.911 |
| 282 | 0.3037 |
| 283 | 85.97 |
| 284 | 8.283 |
| 285 | 0.3823 |
| 286 | 9.589 |
| 287 | 1.459 |
| 288 | 2286 |
| 289 | 28.03 |
| 290 | 0.3662 |
| 291 | 4.437 |
| 292 | 3.597 |
| 293 | 24.32 |
| 294 | 0.6653 |
| 295 | 2.675 |
| 296 | 0.6014 |
| 297 | 1.051 |
| 298 | 1.172 |
| 299 | 1.159 |
| 300 | 1.344 |
| 301 | 0.5622 |
| 302 | 3.114 |
| 303 | 3.211 |
| 304 | 1.751 |
| 305 | 24.7 |
| 306 | 0.8097 |
| 307 | 1.75 |
| 308 | 1.798 |
| 309 | 44.52 |
| 310 | 6.524 |
| 311 | 26.16 |
| 312 | 0.7508 |
| 313 | 0.7166 |

TABLE 6-continued

| Ex | IC$_{50}$ |
|---|---|
| 314 | 0.88 |
| 315 | 1.934 |
| 316 | 1.845 |
| 317 | 1.133 |
| 318 | 30.24 |
| 319 | 0.5209 |
| 320 | 25.44 |
| 321 | 0.9863 |
| 322 | 1.174 |
| 323 | 9.826 |
| 324 | 0.223 |
| 325 | 3.959 |
| 326 | 3.539 |
| 327 | 0.4475 |
| 328 | 1.574 |
| 329 | 56.5 |
| 330 | 3.057 |
| 331 | 29.11 |
| 332 | 1.336 |
| 333 | 3.381 |
| 334 | 0.3329 |
| 335 | 0.7388 |
| 336 | 1.029 |
| 337 | 1.403 |
| 338 | 0.9977 |
| 339 | 6.078 |
| 340 | 722.7 |
| 341 | 2.914 |
| 342 | 40.92 |
| 343 | 18.66 |
| 344 | 3.148 |
| 345 | 5.372 |
| 346 | 88.21 |
| 347 | 1.344 |

TABLE 7

| Ex | IC$_{50}$ |
|---|---|
| 348 | 2.164 |
| 349 | 6.569 |
| 350 | 10.56 |
| 351 | 91.93 |
| 352 | 30.22 |
| 353 | 1.558 |
| 354 | 0.4741 |
| 355 | 1.537 |
| 356 | 129.8 |
| 357 | 106.2 |
| 358 | 137.2 |
| 359 | 9.272 |
| 360 | 0.3776 |
| 361 | 0.2316 |
| 362 | 0.288 |
| 363 | 25.94 |
| 364 | 1.662 |
| 365 | 0.6026 |
| 366 | 0.3398 |
| 367 | 4.511 |
| 368 | 2.794 |
| 369 | 1.411 |
| 370 | 1.445 |
| 371 | 58.97 |
| 372 | 1.328 |
| 373 | 1.066 |
| 374 | 350.9 |
| 375 | 12.75 |
| 376 | 0.5815 |
| 377 | 0.4776 |
| 378 | 55.65 |
| 379 | 1.507 |
| 380 | 6.177 |
| 381 | 6.712 |
| 382 | 6.259 |
| 383 | 13.29 |

TABLE 7-continued

| Ex | IC$_{50}$ |
|---|---|
| 384 | 24.71 |
| 385 | 0.939 |
| 386 | 4.944 |
| 387 | 4.425 |
| 388 | 6.66 |
| 389 | 4.107 |
| 390 | 2.757 |
| 391 | 22.22 |
| 392 | 22.56 |
| 393 | 13.84 |
| 394 | 0.85 |
| 395 | 7.659 |
| 396 | 8.465 |
| 397 | 48.08 |
| 398 | 1.131 |
| 399 | 2.065 |
| 400 | 5.418 |
| 401 | 20.04 |
| 402 | 12.77 |
| 403 | 53.47 |
| 404 | 11.07 |
| 405 | 14.24 |
| 406 | 1.065 |
| 407 | 5.725 |
| 408 | 1.999 |
| 409 | 5.693 |
| 410 | 2.646 |
| 411 | 34.14 |
| 412 | 0.3033 |
| 413 | 39.23 |
| 414 | 0.7549 |
| 415 | 19.97 |
| 416 | 0.7803 |
| 417 | — |
| 418 | 2.747 |
| 419 | 2.717 |
| 420 | 2.552 |
| 421 | 4.35 |
| 422 | 5.419 |
| 423 | 0.594 |
| 424 | 2.552 |
| 425 | 0.3229 |
| 426 | 5.665 |
| 427 | 1.359 |
| 428 | 1.455 |
| 429 | 1.117 |
| 430 | 2.768 |
| 431 | 2.518 |
| 432 | 0.7445 |
| 433 | 2.973 |
| 434 | 1.142 |
| 435 | 1.082 |
| 436 | 2.141 |
| 437 | 1.949 |
| 438 | 6.596 |
| 439 | 1.296 |
| 440 | 0.4685 |
| 441 | 0.3088 |
| 442 | 0.8152 |
| 443 | 11.81 |
| 444 | 1.116 |
| 445 | 3.735 |
| 446 | 3.301 |
| 447 | 2.621 |
| 448 | 0.8272 |
| 449 | 3.729 |
| 450 | 1.912 |
| 451 | 2.144 |
| 452 | 2244 |
| 453 | 1.625 |
| 454 | 236.7 |
| 455 | 520.4 |
| 456 | 252.7 |
| 457 | 31.15 |
| 458 | 8.455 |
| 459 | 2.74 |
| 460 | 159.7 |
| 461 | 31.16 |

TABLE 7-continued

| Ex | IC$_{50}$ |
|---|---|
| 462 | 356.1 |
| 463 | 1.584 |

TABLE 8

| Ex | IC$_{50}$ |
|---|---|
| 464 | 3.572 |
| 465 | 320.3 |
| 466 | 2.81 |
| 467 | 1.253 |
| 468 | 8.616 |
| 469 | 1.207 |
| 470 | 4.117 |
| 471 | 10.2 |
| 472 | 11.09 |
| 473 | 2.695 |
| 474 | 33.68 |
| 475 | 0.3845 |
| 476 | 0.5869 |
| 477 | 2.614 |
| 478 | 6.012 |
| 479 | 3.024 |
| 480 | 1.221 |
| 481 | 10.84 |
| 482 | 0.2904 |
| 483 | 0.1524 |
| 484 | 376.2 |
| 485 | 0.3067 |
| 486 | 23.52 |
| 487 | 10.13 |
| 488 | 5.853 |
| 489 | 1.201 |
| 490 | 11.29 |
| 491 | 1.413 |
| 492 | 25.97 |
| 493 | 0.4285 |
| 494 | 4.339 |
| 495 | 0.6076 |
| 496 | 1.411 |
| 497 | 1.533 |
| 498 | 2.823 |
| 499 | 1.344 |
| 500 | 0.778 |
| 501 | 0.9578 |
| 502 | 1.309 |
| 503 | 0.8579 |
| 504 | 1.356 |
| 505 | 0.8648 |
| 506 | 0.805 |
| 507 | 0.7618 |
| 508 | 11.58 |
| 509 | 3.071 |
| 510 | 3.661 |
| 511 | 1.199 |
| 512 | 2.939 |
| 513 | 1.561 |
| 514 | 2.868 |
| 515 | 2.454 |
| 516 | 2.346 |
| 517 | 0.7607 |
| 518 | 5.185 |
| 519 | 0.9623 |
| 520 | 0.4398 |
| 521 | 3.306 |
| 522 | 0.357 |
| 523 | 0.6051 |
| 524 | 2.39 |
| 525 | 0.3584 |
| 526 | 0.5461 |
| 527 | 566.7 |
| 528 | 12.67 |
| 529 | 0.2928 |
| 530 | 53.45 |
| 531 | 0.5453 |

TABLE 8-continued

| Ex | IC$_{50}$ |
|---|---|
| 532 | 3.521 |
| 533 | 2.977 |
| 534 | 0.5091 |
| 535 | 0.3036 |
| 536 | 1.138 |
| 537 | 66.6 |
| 538 | 0.2983 |
| 539 | 0.7282 |
| 540 | 945.6 |
| 541 | 305.8 |
| 542 | 0.2688 |
| 543 | 0.2724 |
| 544 | 1.282 |
| 545 | 0.2357 |
| 546 | 0.3577 |
| 547 | 0.1837 |
| 548 | 0.3151 |
| 549 | 2.622 |
| 550 | 2.434 |
| 551 | 41.25 |
| 552 | 23.76 |
| 553 | 0.2599 |
| 554 | 0.2616 |
| 555 | 0.4261 |
| 556 | 232.5 |
| 557 | 1.858 |
| 558 | 0.516 |
| 559 | 14.47 |
| 560 | 81.67 |
| 561 | 15.01 |
| 562 | 25.32 |
| 563 | 251.1 |
| 564 | 50.01 |
| 565 | 3.114 |
| 566 | 0.3132 |
| 567 | 0.4414 |
| 568 | 0.479 |
| 569 | 1.476 |
| 570 | 0.2569 |
| 571 | 3.066 |
| 572 | 1.618 |
| 573 | 7.219 |
| 574 | 1.405 |
| 575 | 1.204 |
| 576 | 2453 |
| 577 | 4.005 |
| 578 | 0.5614 |
| 579 | 10.61 |

TABLE 9

| Ex | IC$_{50}$ |
|---|---|
| 580 | 0.1934 |
| 581 | 0.233 |
| 582 | 0.2339 |
| 583 | 0.9168 |
| 584 | 0.6794 |
| 585 | 1.257 |
| 586 | 1.301 |
| 587 | 12.58 |
| 588 | 30.9 |
| 589 | 0.8229 |
| 590 | 2.061 |
| 591 | 1.54 |
| 592 | 2.877 |
| 593 | 3.336 |
| 594 | 3.778 |
| 595 | 3.465 |
| 596 | 4.872 |
| 597 | 0.9449 |
| 598 | 1.548 |
| 599 | 7.678 |
| 600 | 31.95 |
| 601 | 20.57 |

TABLE 9-continued

| Ex | IC$_{50}$ |
|---|---|
| 602 | — |
| 603 | 3.007 |
| 604 | 16.05 |
| 605 | 0.326 |
| 606 | 3.421 |
| 607 | 0.3352 |
| 608 | 3.815 |
| 609 | 5.83 |
| 610 | 3.119 |
| 611 | 122.5 |
| 612 | 12.62 |
| 613 | 0.2974 |
| 614 | 0.4809 |
| 615 | 6.162 |
| 616 | 0.6099 |
| 617 | 1.067 |
| 618 | 22.75 |
| 619 | 0.1591 |
| 620 | 138.1 |
| 621 | 1.288 |
| 622 | 0.7895 |
| 623 | 1.926 |
| 624 | 4.378 |
| 625 | 13.56 |
| 626 | 0.7996 |
| 627 | 6.09 |
| 628 | 36.43 |
| 629 | 1.505 |
| 630 | 2.124 |
| 631 | 17.4 |
| 632 | 2.194 |
| 633 | 6.208 |
| 634 | 1.302 |
| 635 | 0.8733 |
| 636 | 0.2508 |
| 637 | 4.349 |
| 638 | 8.989 |
| 639 | 0.5352 |
| 640 | 3.595 |
| 641 | 1095 |
| 642 | 326.8 |
| 643 | 1.33 |
| 644 | 1.069 |
| 645 | 0.6208 |
| 646 | 372.9 |
| 647 | 0.464 |
| 648 | 28.21 |
| 649 | 1.062 |
| 650 | 0.3175 |
| 651 | 0.2233 |
| 652 | 0.7204 |
| 653 | 4.161 |
| 654 | 2.201 |
| 655 | 2.265 |
| 656 | 5.057 |
| 657 | 4.671 |
| 658 | 66.87 |
| 659 | 51.88 |
| 660 | 2.664 |
| 661 | 0.9282 |
| 662 | 0.9287 |
| 663 | 9.132 |
| 664 | 2.489 |
| 665 | 193 |
| 666 | 69.91 |
| 667 | 259.4 |
| 668 | 646.9 |
| 669 | 21.58 |
| 670 | 13.59 |
| 671 | 2.325 |
| 672 | 1.549 |
| 673 | 5.41 |
| 674 | 13.2 |
| 675 | 89.24 |
| 676 | 0.9404 |
| 677 | 3.671 |
| 678 | 764.9 |
| 679 | 19.67 |

TABLE 9-continued

| Ex | IC$_{50}$ |
|---|---|
| 680 | 10.11 |
| 681 | 7.701 |
| 682 | 32.42 |
| 683 | 4.355 |
| 684 | 26.83 |
| 685 | 31.36 |
| 686 | 23.84 |
| 687 | 55.95 |
| 688 | 5.39 |
| 689 | 5.147 |
| 690 | 240.3 |
| 691 | 11.09 |
| 692 | 11.98 |
| 693 | 21.36 |
| 694 | 6.029 |
| 695 | 155 |

TABLE 10

| Ex | IC$_{50}$ |
|---|---|
| 696 | 174.6 |
| 697 | 0.2213 |
| 698 | 6.779 |
| 699 | 23.52 |
| 700 | 11.92 |
| 701 | 4.569 |

While the present invention has been described in conjunction with the specific embodiments set forth above, many alternatives, modifications and variations thereof will be apparent to those of ordinary skill in the art. All such alternatives, modifications and variations are intended to fall within the spirit and scope of the present invention.

What is claimed is:

1. A compound of formula (1):

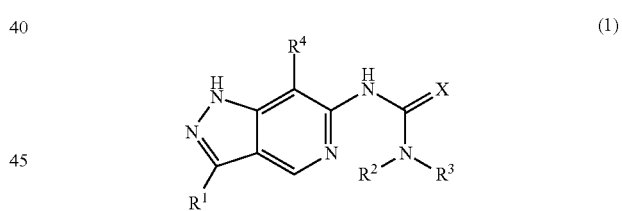

or a pharmaceutically acceptable salt thereof, wherein:
X is S or O;
$R^1$ is selected from the group consisting of: H, halo, —CF$_3$, —CN, ($C_1$-$C_6$)alkyl, substituted ($C_1$-$C_6$)alkyl, ($C_1$-$C_6$) alkenyl, ($C_3$-$C_6$)cycloalkyl, substituted ($C_3$-$C_6$)cycloalkyl, heteroaryl, substituted heteroaryl, heterocycloalkenyl-, substituted heterocycloalkenyl, —($C_1$-$C_6$)alkyl-O—($C_1$-$C_6$)alkyl, aryl, substituted aryl, —C(O)NH($C_1$-$C_6$)alkyl, —C(O)N(($C_1$-$C_6$)alkyl)$_2$ wherein each alkyl is independently selected, —C(O)—($C_1$-$C_6$)alkyl-C(O)—($C_1$-$C_6$)alkyl, —($C_1$-$C_4$)alkyl-C(O)—O—($C_1$-$C_4$)alkyl, —N(($C_1$-$C_6$)alkyl-S(O)$_2$—($C_1$-$C_6$) alkyl, —N(($C_1$-$C_6$)alkyl) -($C_1$-$C_6$)alkyl-O—($C_1$-$C_6$) alkyl, —C(O)NH—($C_1$-$C_2$)alkyl-fused heteroarylheteroaryl, —C(O)NH—($C_1$-$C_2$)alkyl -(substituted fused heteroarylheteroaryl), —C(O)NH—($C_1$-$C_2$)alkyl-($C_3$-$C_6$)cycloalkyl-N(R$^6$)$_2$, —C(O)NH—($C_1$-$C_2$)alkyl-(substituted($C_3$-$C_6$)cycloalkyl)-N(R$^6$)$_2$, —C(O)NH—($C_1$-$C_2$)alkylheterocycloalkyl, —C(O)

NH—($C_1$-$C_2$)alkyl(substituted heterocycloalkyl), —C(O)NH—($C_1$-$C_2$)alkylheteroaryl, —C(O)NH—($C_1$-$C_2$)alkyl(substituted heteroaryl), —C(O)NH—($C_1$-$C_6$)alkyl-($C_3$-$C_6$)cycloalkyl, —C(O)NH—($C_1$-$C_6$) alkyl-(substituted ($C_3$-$C_6$)cycloalkyl), —C(O)NH—($C_1$-$C_6$)alkyl -O—($C_1$-$C_6$)alkyl, —C(O)NH—($C_1$-$C_6$) alkylheterocycloalkyl, —C(O)NH—($C_1$-$C_6$)alkyl (substituted heterocycloalkyl), —C(O)NH—($C_1$-$C_2$)-(bridged multicyclic cycloalkyl), —C(O)NH—($C_1$-$C_2$)-(substituted bridged multicyclic cycloalkyl), —C(O)-heterocycloalkyl-S—($C_1$-$C_6$)alkyl, —C(O)-(substituted heterocycloalkyl-S—($C_1$-$C_6$)alkyl, —C(O)-heterocycloalkyl, —C(O)-(substituted heterocycloalkyl), fused arylheteroaryl, fused (substituted arylheteroaryl), fused heteroarylheteroaryl, fused (substituted heteroarylheteroaryl), —($C_1$-$C_4$)alkyl-$S(O)_2$—($C_1$-$C_6$)alkyl, and —($C_1$-$C_4$)alkyl-NH—($C_1$-$C_6$)alkyl;

and wherein said substituted $R^1$ groups, other than said substituted ($C_1$-$C_6$)alkyl, are substituted with 1 to 3 substituents independently selected from the group consisting of: —($C_1$-$C_6$)alkyl, —($C_1$-$C_6$)alkoxy, halo, CN, —OH, —$CF_3$, =O, —$NH_2$, —NH($C_1$-$C_6$)alkyl, —$S(O)_2$($C_1$-$C_6$)alkyl, —($C_3$-$C_6$)cycloalkyl, —(($C_1$-$C_6$) alkyl)OH, —($C_3$-$C_6$)cycloalkyl-S—($C_3$-$C_6$)cycloalkyl, —N(($C_1$-$C_6$)alkyl)$_2$ wherein each alkyl is independently selected, —C(O)O—($C_1$-$C_6$)alkyl, —C(O)OH, —$OCF_3$, —C(O)NH($C_1$-$C_6$)alkyl, heteroaryl, —($C_1$-$C_6$)alkyl)-O—($C_1$-$C_6$)alkyl, fused heteroarylaryl-, heterocycloalkyl, and heterocycloalkenyl;

and wherein said substituted ($C_1$-$C_6$)alkyl $R^1$ group is substituted with 1 to 3 substituents independently selected from the group consisting of: —($C_1$-$C_6$)alkoxy, halo, CN, —OH, =O, —$CF_3$, —$NH_2$, —NH($C_1$-$C_6$)alkyl, —$S(O)_2$($C_1$-$C_6$)alkyl, fused heteroarylaryl-, heterocycloalkyl, and heterocycloalkenyl;

and wherein the alkyl moieties of the $R^1$ groups, other than ($C_1$-$C_6$)alkyl and substituted ($C_1$-$C_6$)alkyl, are optionally substituted with 1 to 3 substituents independently selected from the group consisting of: —($C_1$-$C_6$)alkoxy, halo, CN, —OH, =O, —$CF_3$, —$NH_2$, —NH($C_1$-C6) alkyl, —$S(O)_2$($C_1$-$C_6$)alkyl, fused heteroarylaryl-, heterocycloalkyl, and heterocycloalkenyl;

$R^2$ is selected from the group consisting of: H, ($C_1$-$C_6$) alkyl, —($C_1$-$C_3$)alkyl-O—($C_1$-$C_2$)alkyl, aryl, arylalkyl-, heteroaryl, heteroarylalkyl-, substituted —($C_1$-$C_6$)alkyl, substituted aryl, substituted arylalkyl-, substituted heteroaryl, and substituted heteroarylalkyl-; wherein said substituted aryl, substituted arylalkyl, substituted heteroaryl and substituted heteroarylalkyl are substituted with 1 to 3 substituents independently selected from the group consisting of: aryl, substituted aryl, arylalkyl-, substituted arylalkyl-, halo, —OH, —C(O)N($R^6$)$_2$, —($C_1$-$C_6$)alkyl, —($C_1$-$C_6$)alkoxy, —$CF_3$, —($C_1$-$C_6$)alkyl-OH, —($C_1$-$C_6$)alkyl-$NH_2$, and —NH—($CH_2$)$_{1-4}$—($C_6$-$C_{10}$)aryl; and wherein said $R^2$ which is substituted —($C_1$-$C_6$)alkyl is substituted with 1-3 substituents independently selected from the group consisting of: aryl, substituted aryl, arylalkyl-, substituted arylalkyl-, halo, —OH, —C(O)N($R^6$)$_2$, —($C_1$-$C_6$) alkoxy, —$CF_3$, —$NH_2$ and —NH—($CH_2$)$_{1-4}$—($C_6$-$C_{10}$)aryl;

$R^3$ is selected from the group consisting of: H, —($C_1$-$C_6$) alkyl, substituted —($C_1$-$C_6$)alkyl, heterocycloalkyl-, substituted heterocycloalkyl-, aryl, substituted aryl, arylalkyl-, substituted arylalkyl-, heteroaryl, substituted heteroaryl, heteroarylalkyl-, substituted heteroarylalkyl-, cycloalkyl, substituted cycloalkyl, cycloalkylalkyl, substituted cycloalkylalkyl-, cycloalkylalkenyl-, substituted cycloalkenyl, heterocycloalkylalkyl-, substituted heterocycloalkylalkyl, —($C_1$-$C_6$)alkyl($CF_3$)—C(O)O—($C_1$-$C_6$)alkyl, cycloalkenylalkyl-, substituted cycloalkenyl, fused cycloalkylheteroaryl, substituted fused cycloalkylheteroaryl, fused heterocycloalkylaryl, substituted fused heterocycloalkylaryl, fused cycloalkylaryl, substituted fused cycloalkylaryl, fused heteroarylaryl, substituted fused heteroarylaryl, —($C_1$-$C_6$)alkyl-heterocycloalkenyl, —($C_1$-$C_6$)alkyl(substituted heterocyloalkenyl), —($C_1$-$C_6$)alkylcycloalkyl-N—(—(C-$C_6$)alkyl)$_2$ (wherein each alkyl is independently selected), —($C_1$-$C_6$)alkylheterocycloalkyl, —$C_1$-$C_6$) alkyl(substituted heterocycloalkyl), —($C_1$-$C_6$)alkylcycloalkylaryl, substituted —($C_1$$C_6$)alkyl(substituted cycloalkylaryl), —($C_1$-$C_6$)alkyl -(fused arylheteroaryl), —($C_1$-$C_6$)alkyl-(substituted used arylheteroaryl), an oxygen bridged ($C_3$-$C_6$) cycloalkyl ring, substituted oxygen bridged ($C_3$-$C_6$) cycloalkyl ring, —(C1-C6) alkyl)-(fused heterocycloalkylaryl), —($C_1$-$C_6$)alkyl)-(substituted fused heterocycloalkylaryl), —($C_1$-$C_6$) alkyl) -(fused heteroarylaryl), —($C_1$-$C_6$)alkyl)-(substituted fused heteroarylaryl), —($C_1$-$C_6$)alkyl)-C(O)—NH-aryl, —($C_1$-$C_6$)alkyl)-C(O)—NH-(substituted aryl), —($C_3$-$C_6$)cycloalkyl-O-aryl, —($C_3$-$C_6$)cycloalkyl-O-(substituted aryl), a 5 and 4 membered heterocycloalkyl spiro ring, a substituted 5 and 4 membered heterocycloalkyl spiro ring, and —($C_1$-$C_6$)alkyl-O—($C_1$-$C_6$)alkyl;

and wherein said $R^3$ 5 and 4 membered heterocycloalkyl spiro ring comprises a 5 membered ring comprising one nitrogen, and a 4 membered (including the carbon common to both rings) ring comprising one oxygen atom;

and wherein said substituted $R^3$ groups, other than substituted —($C_1$-$C_6$)alkyl, are substituted with 1 to 3 substituents independently selected from the group consisting of: aryl, substituted aryl, arylalkyl-, substituted arylalkyl-, halo, —OH, —C(O)N($R^6$)$_2$, —($C_1$-$C_6$)alkyl, —($C_1$-$C_6$)alkoxy, —$CF_3$, —($C_1$-$C_6$)alkyl-OH, —($C_1$-$C_6$)alkyl-$NH_2$, —NH—($CH_2$)$_{1-4}$—($C_6$-$C_{10}$)aryl, —$NH_2$, =O, —CN, —$OCHF_2$, —$OCF_3$, —($C_3$-$C_6$)cycloalkyl, heterocycloalkyl, —($C_1$-$C_6$)alkyl-$CF_3$, —O—C(O)($C_1$-$C_6$)alkyl, —$NHS(O)_2$($C_1$-$C_6$)alkyl, —$S(O)_2$($C_1$-$C_6$)alkyl, —NHaryl, heteroaryl, substituted heteroaryl, —O-heteroaryl, —O-(substituted heteroaryl), —($C_1$-$C_6$)alkyl-N(($C_1$-$C_6$)alkyl)$_2$ wherein each alkyl is independently selected, —($C_1$-$C_6$)alkyl-O—($C_1$-$C_6$)alkyl, —N(($C_1$-$C_6$)alkyl)$_2$ wherein each alkyl is independently selected, —($C_1$-$C_6$)alkyl-$S(O)_2$—($C_1$-$C_6$)alkyl, —(($C_1$-$C_6$)alkyl)(halo)$_{1-3}$, —S($C_1$-$C_6$)alkyl, —($C_1$-$C_6$)alkyl-O—($C_1$-$C_6$)alkyl-($C_3$-$C_6$)cycloalkyl, —($C_1$-$C_6$)alkyl-O—($C_1$-$C_6$)alkyl-O—($C_1$-$C_6$)alkyl, and —($C_1$-$C_6$)alkyl-O—($C_1$-$C_6$) alkyl(halo)$_{1-3}$;

and wherein said $R^3$ substituted —($C_1$-$C_6$)alkyl group is substituted with 1-3 substituents independently selected from the group consisting of: aryl, substituted aryl, arylalkyl-, substituted arylalkyl-, halo, —OH, —C(O)N($R^6$)$_2$, —($C_1$-$C_6$)alkoxy, —$CF_3$, —$NH_2$ and —NH—($CH_2$)$_{1-4}$—($C_6$-$C_{10}$)aryl, —N(($C_1$-$C_6$)alkyl)$_2$ wherein each alkyl is independently selected, —C(O)O($C_1$-$C_6$) alkyl, —C(O)OH, —CN, —O-phenyl;

or said $R^2$ and said $R^3$, taken together with the nitrogen to which they are bonded to, form a 4-6 membered heterocycloalkyl ring, said ring optionally comprising an additional heteroatom selected from the group consisting of: N and O, and wherein said ring is optionally substituted with 1-3 substituents independently selected from the group consisting of: $C_1$-$C_6$)alkyl, aryl, and substituted aryl wherein said substituted aryl is substituted with 1-3 substituents independently selected from the group consisting of halo;

$R^4$ is selected from the group consisting of: H, halo, —($C_1$-$C_6$)alkyl, —OH and —$NH_2$; and each $R^6$ is independently selected from the group consisting of: H and —($C_1$-$C_6$)alkyl.

2. The compound of claim 1, or a pharmaceutically acceptable salt thereof, wherein:

X is S or O;

$R^1$ is selected from the group consisting of: H, halo, ($C_1$-$C_6$)alkyl, ($C_1$-$C_6$)alkenyl, ($C_3$-$C_6$)cycloalkyl, heteroaryl, substituted heteroaryl, heterocycloalkenyl-, substituted heterocycloalkenyl, —($C_1$-$C_6$)alkyl-O—($C_1$-$C_6$)alkyl, aryl, and substituted aryl, and wherein said substituted heteroaryl, substituted heterocycloalkenyl, and substituted aryl are substituted with 1 to 3 substituents independently selected from the group consisting of: —($C_1$-$C_6$)alkyl, —($C_1$-$C_6$)alkoxy, halo, CN, =O, —$NH_2$, —NH($C_1$-$C_6$)alkyl, —S(O)$_2$($C_1$-$C_6$)alkyl, fused heteroarylaryl-, heterocycloalkyl, and heterocycloalkenyl;

$R^2$ is selected from the group consisting of: H, ($C_1$-$C_6$) alkyl, —($C_1$-$C_3$)alkyl-O—($C_1$-$C_2$)alkyl, aryl, arylalkyl-, heteroaryl, heteroarylalkyl-, substituted —($C_1$-$C_6$)alkyl, substituted aryl, substituted arylalkyl-, substituted heteroaryl, and substituted heteroarylalkyl-; wherein said substituted aryl, substituted arylalkyl, substituted heteroaryl and substituted heteroarylalkyl are substituted with 1 to 3 substitutents independently selected from the group consisting of: aryl, substituted aryl, arylalkyl-, substituted arylalkyl-, halo, —OH, —C(O)N($R^6$)$_2$, —($C_1$-$C_6$)alkyl, —($C_1$-$C_6$)alkoxy, —$CF_3$, —($C_1$-$C_6$)alkyl-OH, —($C_1$-$C_6$)alkyl-$NH_2$, and —NH—($CH_2$)$_{1-4}$—($C_6$-$C_{10}$)aryl; and wherein said $R^2$ which is substituted —($C_1$-$C_6$)alkyl is substituted with 1-3 substituents independently selected from the group consisting of: aryl, substituted aryl, arylalkyl-, substituted arylalkyl-, halo, —OH, —C(O)N($R^6$)$_2$, —($C_1$-$C_6$) alkoxy, —$CF_3$, —$NH_2$ and —NH—($CH_2$)$_{1-4}$—($C_6$-$C_{10}$)aryl;

$R^3$ is selected from the group consisting of: H, —($C_1$-$C_6$) alkyl, substituted —($C_1$-$C_6$)alkyl, heterocycloalkyl-, substituted heterocycloalkyl-, aryl, substituted aryl, arylalkyl-, substituted arylalkyl-, heteroaryl, substituted heteroaryl, heteroarylalkyl-, substituted heteroarylalkyl-, cycloalkyl, substituted cycloalkyl, cycloalkylalkyl, substituted cycloalkylalkyl-, cycloalkylalkenyl-, substituted cycloalkenyl, and -alkyl-O-alkyl; and wherein said substituted heteroaryl, substituted heterocycloalkyl, substituted aryl, substituted arylalkyl, substituted heteroarylalkyl, substituted cycloalkyl, substituted cycloalkylalkyl, and substituted cycloalkenyl $R^3$ moieties are substituted with 1 to 3 substituents independently selected from the group consisting of: aryl, substituted aryl, arylalkyl-, substituted arylalkyl-, halo, —OH, —C(O)N($R^6$)$_2$, —($C_1$-$C_6$)alkyl, —($C_1$-$C_6$) alkoxy, —$CF_3$, —($C_1$-$C_6$)alkyl-OH, —($C_1$-$C_6$)alkyl-$NH_2$, and —NH—($CH_2$)$_{1-4}$—($C_6$-$C_{10}$)aryl; and wherein said $R_3$ which is substituted —($C_1$-$C_6$)alkyl is substituted with 1-3 substituents independently selected from the group consisting of: aryl, substituted aryl, arylalkyl-, substituted arylalkyl-, halo, —OH, —C(O)N ($R^6$)$_2$, —($C_1$-$C_6$)alkoxy, —$CF_3$, —$NH_2$ and —NH—($CH_2$)$_{1-4}$—($C_6$-$C_{10}$)aryl;

$R^4$ is selected from the group consisting of: H, halo, —($C_1$-$C_6$)alkyl, —OH and —$NH_2$; and each $R^6$ is independently selected from the group consisting of: —($C_1$-$C_6$)alkyl.

3. The compound of claim 2 wherein X is O.

4. The compound of claim 2 wherein $R^1$ is selected from the group consisting of: propyl, pyridyl, pyridyl-$N^+$—$O^-$, 2-methylpyridyl, dihydropyran, pyrazolyl, N-methylpyrazolyl, fluorophenyl, phenyl, 2,6-dimethylpyridyl, fluoropyridyl, N-methylpyrazolyl-, N-methylpyrazolyl, N-methylindazolyl-, cyanophenyl, propenyl, Br, methyloxodihydropyridyl, pyrazolyl, chloropyridyl, aminopyrimindinyl, methylbenzothiazolyl, dihydrobenzodioxinyl, $CH_3SO_2$-phenyl-, and methylpyridazinyl.

5. The compound of claim 2 wherein $R^1$ is selected from the group consisting of $R^1$ groups (1) to (26).

6. The compound of claim 2 wherein $R^2$ is H.

7. The compound of claim 2 wherein $R^3$ is selected from the group consisting of: (a) piperidinyl, (b) substituted piperidinyl, (c) —$CH_2$-phenyl, (d) substituted —$CH_2$-phenyl, (e) —($CH_2$)-2-phenyl, (f) a hydroxy substituted —CH($CH_3$)-phenyl, (g) a monohalo substituted —CH($CH_3$)-phenyl, (h) a dihalo substituted —CH($CH_3$)-phenyl, (i) —$CH_2$-pyridyl, (j) —$CH_2$-oxadiazolyl, (k) substituted —$CH_2$-oxadiazolyl (l) —$CH_2$-naphthyl, (m) —$CH_2$-cyclopropyl, (n) t-butyl, (o) cyclopropylmethanol, (p) cyclopropylmethylene-, (q) azetidinyl, (r) methoxyethyl, (s) cyclopropyl-CH($CF_3$)—, (t) N-methylimidazolyl-$CH_2$—, (u) methylthiazolyl-$CH_2$—, (v) pyrimindinyl-$CH_2$—, (w) pyridyl-$CH_2$—, (x) pyridyl-($CH_2$)$_2$—, (y) pyrazinyl-$CH_2$—, (z) pyridyl -CH($CH_3$)—, (aa) fluoropyridyl-$CH_2$—, (ab) phenylethylaminopyridazinyl-, (ac) phenyl, (ad) chlorophenyl-C($CH_3$)$_2$—, (ae) chlorophenyltetrahydropyranyl-, (af) dihydroindenyl, (ag) phenyl-CH($CH_3$)—, and (ah) chlorophenylcyclopropyl-.

8. The compound of claim 2 wherein $R^3$ is selected from the group consisting of $R^3$ groups (27) to (81).

9. The compound of claim 2 wherein $R^4$ is selected from the group consisting of H, Cl, and F.

10. The compound of claim 2 wherein $R^4$ is H.

11. The compound of claim 2 wherein $R^2$ is H and $R^3$ is other than H.

12. The compound of claim 2 wherein $R^2$ is H, $R^3$ is other than H, $R^4$ is H, and X is O.

13. The compound of claim 2 wherein $R^3$ is selected from the group consisting of: $R^3$ groups

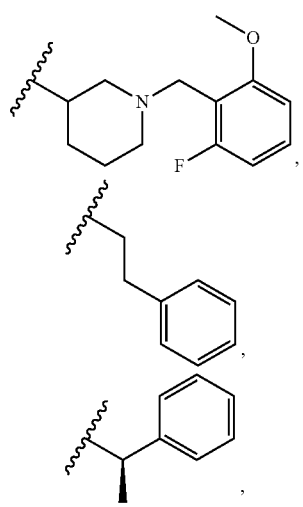

-continued
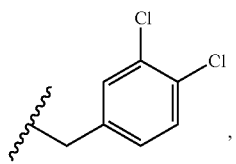,
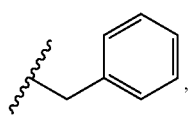,
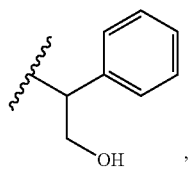,
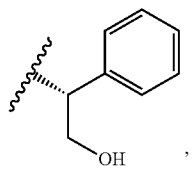,
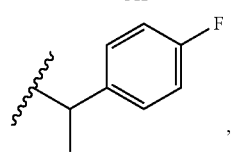,
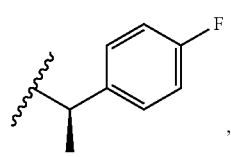,
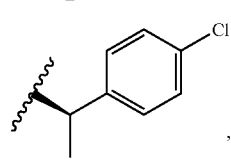,
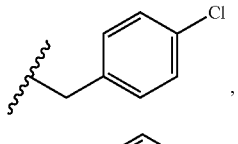,
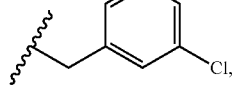,
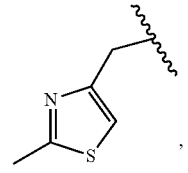,
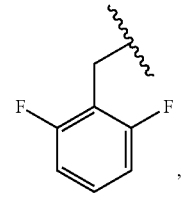,
-continued
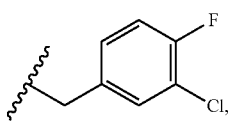,
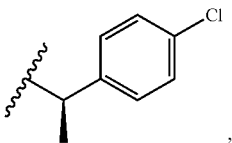,
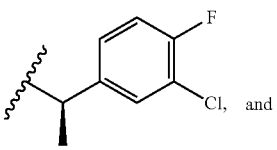 and
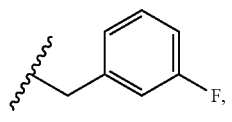,
$R^1$ is selected from the group consisting of $R^1$ groups $CH_3CH_2CH_2-$, $CH_3CH=CH-$
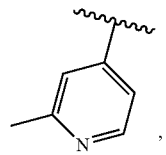,
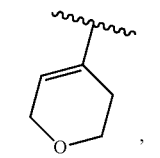,
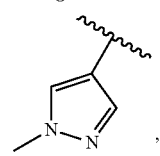,
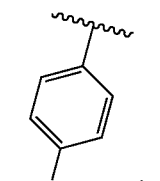,
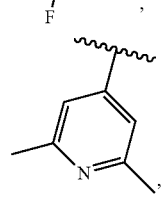,
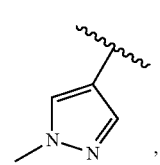, -continued

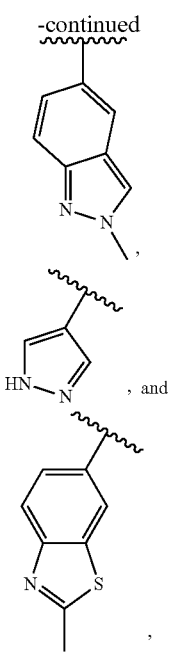
, and

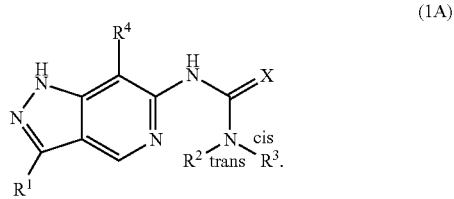
, $R^2$ is H, $R^4$ is H, and X is O.

14. The compound of claim 2 wherein said compound of formula (1) is a compound of formula (1A):

(1A)

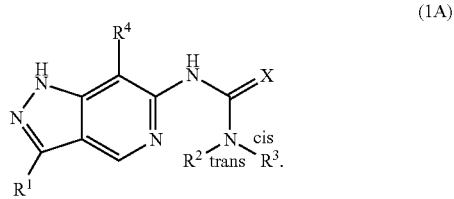

15. A compound selected from the group consisting of
1-[3-(2-methylpyridin-4-yl)-1H-pyrazolo[4,3-c]pyridin-6-yl]-3-piperidin-3-ylurea,
1-[(3R)-1-(2-fluoro-6-methoxybenzyl)-piperidin-3-yl]-3-[3-(2-methylpyridin-4-yl)-1H -pyrazolo[4,3-c]pyridin-6-yl]urea,
1-[(3S)-1-(2-fluoro-6-methoxybenzyl)-piperidin-3-yl]-3-[3-(2-methylpyridin-4-yl)-1H -pyrazolo[4,3-c]pyridin-6-yl]urea
1-[1-(2-fluoro-6-methoxybenzyl)-piperidin-3-yl]-3-[3-(2-methylpyridin-4-yl)-1H-pyrazolo[4,3-c]pyridin-6-yl]urea,
1-[3-(2-methylpyridin-4-yl)-1H-pyrazolo[4,3-c]pyridin-6-yl]-3-(2-phenylethyl)urea,
1-[3-(2-methylpyridin-4-yl)-1H-pyrazolo[4,3-c]pyridin-6-yl]-3-[(1R)-1-phenylethyl]urea,
1-[3-(2-methylpyridin-4-yl)-1H-pyrazolo[4,3-c]pyridin-6-yl]-3-[(1S)-1-phenylethyl]urea,
1-(3,4-dichlorobenzyl)-3-[3-(2-methylpyridin-4-yl)-1H-pyrazolo[4,3-c]pyridin-6-yl]urea,
1-benzyl-3-[3-(2-methylpyridin-4-yl)-1H-pyrazolo[4,3-c]pyridin-6-yl]urea,
1-(2-hydroxy-1-phenylethyl)-3-[3-(2-methylpyridin-4-yl)-1H-pyrazolo[4,3-c]pyridin-6-yl]urea,
1-[(1S)-1-(4-fluorophenyl)ethyl]-3-[3-(2-methylpyridin-4-yl)-1H-pyrazolo[4,3-c]pyridin-6-yl]urea,
1[3-(2-methylpyridin-4-yl)-1H-pyrazolo[4,3-c]pyridin-6-yl]-3-(pyridin-4-ylmethyl)urea,
1-[5-methyl-1,3,4-oxadiazol-2-yl)methyl]-3-[3-(2-methylpyridin-4-yl)-1H-pyrazolo[4,3-c]urea,
1-[3-(2-methylpyridin-4-yl)-1H-pyrazolo[4,3-c]pyridin-6-yl]-3-(pyridin-3-ylmethyl)urea,
1-[(1S)-2-hydroxy-1-phenylethyl]-3-[3-(2-methylpyridin-4-yl)-1H-pyrazolo[4,3-c]pyridin-6-yl]urea,
1-[3-(2-methylpyridin-4-yl)-1H-pyrazolo[4,3-c]pyridin-6-yl]-3-[(1S)-2,2,2-trifluoro-1-phenylethyl]urea,
1-[(1R)-2-hydroxy-1-phenylethyl]-3-[3-(2-methylpyridin-4-yl)-1H-pyrazolo[4,3-c]pyridin-6-yl]urea,
1-[3-(2-methylpyridin-4-yl)-1H-pyrazolo[4,3-c]pyridin-6-yl]-3-[(1R)-2,2,2-trifluoro-1-phenylethyl]urea,
1-[(1R)-1-(4-chlorophenyl)ethyl]-3-[3-(2-methylpyridin-4-yl)-1H-pyrazolo[4,3-c]pyridin-6-yl]urea,
1-[3-(3,6-dihydro-2H-pyran-4-yl)-1H-pyrazolo[4,3-c]pyridin-6-yl]-3-[(1R)-1-phenylethyl]urea,
1[3-(3 -methoxypropyl)-1H-pyrazolo[4,3-c]pyridin-6-yl]-3-[(1R)-1-phenylethyl]urea,
1-[(1R)-1-phenylethyl]-3-(3-propyl-1H-pyrazolo[4,3-c]pyridin-6-yl)urea,
1-[3-(2-methylpyridin-4-yl)-1H-pyrazolo[4,3-c]pyridin-6-yl]urea,
1-[(1R)-1-(4-fluorophenyl)ethyl]-3-(1H-pyrazolo[4,3-c]pyridin-6-yl)urea,
1-(3-cyclopropyl-1H-pyrazolo[4,3-c]pyridin-6-yl)-3-[(1R)-1-phenylethyl]urea,
1-(4-chlorobenzyl)-3-[3-(2-methylpyridin-4-yl)-1H-pyrazolo[4,3-c]pyridin-6-yl]urea,
1-(3-chlorobenzyl)-3-[3-(2-methylpyridin-4-yl)-1H-pyrazolo[4,3-c]pyridin-6-yl]urea,
1-{3-[6-(1-methylethoxy)pyridin-3-yl]-1H-pyrazolo[4,3-c]pyridin-6-yl}-3-[(1R)-1-phenylethyl]urea,
1-[3-(1-methyl-1H-pyrazol-4-yl)-1H-pyrazolo[4,3-c]pyridin-6-yl]-3-[(1R)-1-phenylethyl]urea,
1-[3-(4-fluorophenyl)-1H-pyrazolo[4,3-c]pyridin-6-yl]-3-[(1R)-1-phenylethyl]urea,
1-[3-(2,6-dimethylpyridin-4-yl)-1H-pyrazolo[4,3-c]pyridin-6-yl]-3-[(1R)-1-phenylethyl]urea,
1-[3-(2-methylpyridin-4-yl)-1H-pyrazolo[4,3-c]pyridin-6-yl]-3-(naphthalen-1-ylmethyl)urea,
1-(3,4-dimethoxybenzyl)-3-[3-(4-fluorophenyl)-1H-pyrazolo[4,3-c]pyridin-6-yl]urea,
1-[3-(4-fluorophenyl)-1H-pyrazolo[4,3-c]pyridin-6-yl]urea,
1-(cyclopropylmethyl)-3-[3-(2-methylpyridin-4-yl)-1H-pyrazolo[4,3-c]pyridin-6-yl]urea,
1-tert-butyl-3-[3-(2-methylpyridin-4-yl)-1H-pyrazolo[4,3-c]pyridin-6-yl]urea,
hydroxycyclopropyl)methyl]-3-[3-(2-methylpyridin-4-yl)-1H-pyrazolo[4,3-c]pyridin-6-yl]urea,
1-(cyclopropylidenemethyl)-3-[3-(2-methylpyridin-4-yl)-1H-pyrazolo[4,3-c]pyridin-6-yl]urea,
1-azetidin-3-yl-3-[3-(2-methylpyridin-4-yl)-1H-pyrazolo[4,3-c]pyridin-6-yl]urea,
1-(2-methoxyethyl)-3-[3-(2-methylpyridin-4-yl)-1H-pyrazolo[4,3-c]pyridin-6-yl]urea,
1-(1-cyclopropyl-2,2,2-trifluoroethyl)-3[3-(2-methylpyridin-4-yl)-1H-pyrazolo[4,3-c]pyridin -6-yl]urea,
1-[(1-methyl-1H-imidazol-5-yl)methyl]-3-[3-(2-methylpyridin-4-yl)-1H-pyrazolo[4,3-c]pyridin-6-yl]urea,
1-[3-(2-methylpyridin-4-yl)-1H-pyrazolo[4,3-c]pyridin-6-yl]-3-[(2-methyl-1,3-thiazol-4-yl)methyl]urea,
1-[3-(2-methylpyridin-4-yl)-1H-pyrazolo[4,3-c]pyridin-6-yl]-3-(pyrimidin-2-ylmethyl)urea, 1-[3-(2-methylpyridin-4-yl)-1H-pyrazolo[4,3-c]pyridin-6-yl]-3-(naphthalen-2-ylmethyl)urea,
1-methyl-3-[3-(2-methylpyridin-4-yl)-1H-pyrazolo[4,3-c]pyridin-6-yl]-1-(pyridin-3-ylmethyl)urea,
1-[3-(2-methylpyridin-4-yl)-1H-pyrazolo[4,3-c]pyridin-6-yl]-3-(2-pyridin-2-ylethyl)urea,
1-[3-(2-methylpyridin-4-yl)-1H-pyrazolo[4,3-c]pyridin-6-yl]-3-(pyrazin-2-ylmethyl)urea,
1-[3-(2-methylpyridin-4-yl)-1H-pyrazolo[4,3-c]pyridin-6-yl]-3-(1-pyridin-3-ylethyl)urea
1-(2-methoxyethyl)-3-[3-(2-methylpyridin-4-yl)-1H-pyrazolo[4,3-c]pyridin-6-yl]-1-(pyridin-3-ylmethyl)urea,
1-[(5-fluoropyridin-3-yl)methyl]-3[3-(2-methylpyridin-4-yl)-1H-pyrazolo[4,3-c]pyridin-6-yl]urea,
1-(2,6-difluorobenzyl)-3-[3-(2-methylpyridin-4-yl)-1H-pyrazolo[4,3-c]pyridin-6-yl]urea,
1-(3-fluorobenzyl)-3-[3-(2-methylpyridin-4-yl)-1H-pyrazolo[4,3-c]pyridin-6-yl]urea,
1-[3-(2-methylpyridin-4-yl)-1H-pyrazolo[4,3-c]pyridin-6-yl]-3-[4-(trifluoromethyl)-benzyl]urea,
1[3-(2-methylpyridin-4-yl)-1H-pyrazolo[4,3-c]pyridin-6-yl]-3-{6-[(2-phenylethyl)-amino]pyridazin-3-yl}urea,
1-(3-chloro-4-fluorobenzyl)-3-[3-(2-methylpyridin-4-yl)-1H-pyrazolo[4,3-c]pyridin-6-yl]urea,
1-[(1R)-1-(4-chlorophenyl)ethyl]-3-[3-(2-fluoropyridin-4-yl)-1H-pyrazolo[4,3-c]pyridin-6-yl]urea,
1-(3-chloro-4-fluorobenzyl)-3-[3-(2-fluoropyridin-4-yl)-1H-pyrazolo[4,3-c]pyridin-6-yl]urea,
1-[(1R)-1-(4-chlorophenyl)ethyl]-3-[3-(1-methyl-1H-pyrazol-4-yl)-1H-pyrazolo[4,3-c]pyridin-6-yl]urea,
1-(3-chloro-4-fluorobenzyl)-3-[3-(1-methyl-1H-pyrazol-4-yl)-1H-pyrazolo[4,3-c]pyridin-6-yl]urea,
1-[3-(2-methylpyridin-4-yl)-1H-pyrazolo[4,3-c]pyridin-6-yl]-3-phenylurea,
1-[(1R)-1-(3-chlorophenyl)ethyl]-3-[3-(2-methyl-2H-indazol-5-yl)-1H-pyrazolo[4,3-c]pyridin-6-yl]urea,
1-[(1R)-1-(4-fluorophenyl)ethyl]-3-[3-(2-methyl-2H-indazol-5-yl)-1H-pyrazolo[4,3-c]pyridin-6-yl]urea,
1-(3-chloro-4-fluorobenzyl)-3-[3-(2-methyl-2H-indazol-5-yl)-1H-pyrazolo[4,3-c]pyridin-6-yl]urea,
1-[(1R)-1-(4-chlorophenyl)ethyl]-3-[3-(2-methyl-2H-indazol-5-yl)-1H-pyrazolo[4,3-c]pyridin-6-yl]urea,
1-[3-(4-cyanophenyl)-1H-pyrazolo[4,3-c]pyridin-6-yl]-3-[(1R)-1-phenylethyl]urea,
1-[(1R)-1-phenylethyl]-3-{3-[(1E)-prop-1-en-1-yl]-1H-pyrazolo[4,3-c]pyridin-6-yl}urea,
1-(3-bromo-1H-pyrazolo[4,3-c]pyridin-6-yl)-3-[(1R)-1-(3-chloro-4-fluorophenyl)ethyl]urea,
1-[(1R)-1-(3-chloro-4-fluorophenyl)ethyl]-3-[3-(2-methylpyridin-4-yl)-1H-pyrazolo[4,3-c]pyridin-6-yl]urea,
1-[1-(4-chlorophenyl)-1-methylethyl]-3-[3-(2-methylpyridin-4-yl)-1H-pyrazolo[4,3-c]pyridin-6-yl]urea,
1-[(1R)-1-(4-fluorophenyl)ethyl]-3-[3-(1-methyl-6-oxo-1,6-dihydropyridin-3-yl)-1H-pyrazolo[4,3-c]pyridin-6-yl]urea,
1-[(1R)-1-(3-chloro-4-fluorophenyl)ethyl]-3-[3-(1-methyl-1H-pyrazol-4-yl)-1H-pyrazolo[4,3-c]pyridin-6-yl]urea,
1-[(1R)-1-(3-chloro-4-fluorophenyl)ethyl]-3-[3-(4-fluorophenyl)-1H-pyrazolo[4,3-c]pyridin-6-yl]urea,
1-[(1R)-1-(3-chloro-4-fluorophenyl)ethyl]-3-[3-(1H-pyrazol-4-yl)-1H-pyrazolo[4,3-c]pyridin-6-yl]urea,
1-[(1R)-1-(3-chloro-4-fluorophenyl)ethyl]-3-[3-(2-chloropyridin-4-yl)-1H-pyrazolo[4,3-c]pyridin-6-yl]urea,
1-[(1R)-1-(3-chloro-4-fluorophenyl)ethyl]-3-[3-(3-chlorophenyl)-1H-pyrazolo[4,3-c]pyridin-6-yl]urea,
1[4-(4-chlorophenyl)tetrahydro-2H-pyran-4-yl]-3-[3-(2-methylpyridin-4-yl)-1H-pyrazolo[4,3-c]pyridin-6-yl]urea,
1-(2,3-dihydro-1H-inden-1-yl)-3-[3-(2-methylpyridin-4-yl)-1H-pyrazolo[4,3-c]pyridin-6-yl]urea,
1[7-bromo-3-(2-methylpyridin-4-yl)-1H-pyrazolo[4,3-c]pyridin-6-yl]-3-[(1R)-1-phenylethyl]urea,
1-[3-(2-aminopyrimidin-5-yl)-1H-pyrazolo[4,3-c]pyridin-6-yl]-3-[(1R)-1-(3-chloro-4-fluorophenyl)ethyl]urea,
1-[(1R)-1-(3-chloro-4-fluorophenyl)ethyl]-3-[3-(2-fluoropyridin-4-yl)-1H-pyrazolo[4,3-c]pyridin-6-yl]urea,
1-[(1R)-1-(3-chloro-4-fluorophenyl)ethyl]-3-(3-cyclopropyl-1H-pyrazolo[4,3-c]pyridin-6-yl)urea,
1-[3-(4-cyanophenyl)-1H-pyrazolo[4,3-c]pyridin-6-yl]-3-[(1R)-1-(4-fluorophenyl)ethyl]urea,
1-[(1R)-1-(3-chlorophenyl)ethyl]-3-[3-(4-cyanophenyl)-1H-pyrazolo[4,3-c]pyridin-6-yl]urea,
1-[1-(4-chlorophenyl)cyclopropyl]-3[3-(2-methylpyridin-4-yl)-1H-pyrazolo[4,3-c]pyridin-6-yl]urea,
1-[7-bromo-3-(2-methylpyridin-4-yl)-1H-pyrazolo[4,3-c]pyridin-6-yl]-3-[(1R)-1-(4-chlorophenyl)ethyl]urea,
1-[3-(2-methyl-1,3-benzothiazol-6-yl)-1H-pyrazolo[4,3-c]pyridin-6-yl]-3-[(1R)-1-phenylethyl]urea,
1-[3-(2,3-dihydro-1,4-benzodioxin-6-yl)-1H-pyrazolo[4,3-c]pyridin-6-yl]-3-[1R)-1-phenylethyl]urea,
1-{3-[4-(methylsulfonyl)phenyl]-1H-pyrazolo[4,3-c]pyridin-6-yl}-3-[(1R)-1-phenylethyl]urea,
1-[3-(1-methyl-1H-pyrazol-3-yl)-1H-pyrazolo[4,3-c]pyridin-6-yl]-3-[(1R)-1-phenylethyl]urea,
1-[3-(6-methylpyridazin-4-yl)-1H-pyrazolo[4,3-c]pyridin-6-yl]-3-[(1R)-1-phenylethyl]urea,
1-benzyl-3-[7-chloro-3-(2-methylpyridin-4-yl)-1H-pyrazolo[4,3-c]pyridin-6-yl]urea,
1-[3-(1-oxidopyridin-4-yl)-1H-pyrazolo[4,3-c]pyridin-6-yl]-3-[(1R)-1-phenylethyl]urea,
1-benzyl-3-[3-(2-methylpyridin-4-yl)-1H-pyrazolo[4,3-c]pyridin-6-yl]thiourea, and
1-[7-fluoro-3-(2-methylpyridin-4-yl)-1H-pyrazolo[4,3-c]pyridin-6-yl1-3-[(1R)-1-phenylethyl]urea.

16. The compound of claim 15 selected from the group consisting of

1-[(3R)-1-(2-fluoro-6-methoxybenzyl)-piperidin-3-yl]-3-[3-(2-methylpyridin-4-yl)-1H -pyrazolo[4,3-c]pyridin-6-yl]urea,
1-[(3S)-1-(2-fluoro-6-methoxybenzyl)-piperidin-3-yl]-3-[3-(2-methylpyridin-4-yl)-1H -pyrazolo[4,3-c]pyridin-6-yl]urea,
1-[1-(2-fluoro-6-methoxybenzyl)-piperidin-3-yl]-3-[3-(2-methylpyridin-4-yl)-1H-pyrazolo[4,3-c]pyridin-6-yl]urea,
1[3-(2-methylpyridin-4-yl)-1H-pyrazolo[4,3-c]pyridin-6-yl]-3-(2-phenylethyl)urea,
1[3-(2-methylpyridin-4-yl)-1H-pyrazolo[4,3-c]pyridin-6-yl]-3-[(1R)-1-phenylethyl]urea,
1-[3-(2-methylpyridin-4-yl)-1H-pyrazolo[4,3-c]pyridin-6-yl]-3-[(1S)-1-phenylethyl]urea,
1-(3,4-dichlorobenzyl)-3-[3-(2-methylpyridin-4-yl)-1H-pyrazolo[4,3-c]pyridin-6-yl]urea,
1-benzyl-3-[3-(2-methylpyridin-4-yl)-1H-pyrazolo[4,3-c]pyridin-6-yl]urea,
1-(2-hydroxy-1-phenylethyl)-3-[3-(2-methylpyridin-4-yl)-1H-pyrazolo[4,3-c]pyridin-6-yl]urea,
1-[(1S)-1-(4-fluorophenyl)ethyl]-3-[3-(2-methylpyridin-4-yl)-1H-pyrazolo[4,3-c]pyridin-6-yl]urea,
1-[3-(2-methylpyridin-4-yl)-1H-pyrazolo[4,3-c]pyridin-6-yl]-3-(pyridin-4-ylmethyl)urea, 1-[(5-methyl-1,3,4-oxadiazol-2-yl)methyl]-3-[3-(2-methylpyridin-4-yl)-1H-pyrazolo[4,3-c]urea
1-[3-(2-methylpyridin-4-yl)-1H-pyrazolo[4,3-c]pyridin-6-yl]-3-(pyridin-3-ylmethyl)urea,
1-[(1R)-2-hydroxy-1-phenylethyl]-3-[3-(2-methylpyridin-4-yl)-1H-pyrazolo[4,3-c]pyridin-6-yl]urea,
1-[3-(2-methylpyridin-4-yl)-1H-pyrazolo[4,3-c]pyridin-6-yl]-3-[(1R)-2,2,2-trifluoro-1-phenylethyl]urea,
1-[1-(4-chlorophenyl)-1-methylethyl]-3-[3-(2-methylpyridin-4-yl)-1H-pyrazolo[4,3-c]pyridin-6-yl]urea,
1-[7-bromo-3-(2-methylpyridin-4-yl)-1H-pyrazolo[4,3-c]pyridin-6-yl]-3-[(1R)-1-(4-chlorophenyl)ethyl]urea, and
1-benzyl-3-[7-chloro-3-(2-methylpyridin-4-yl)-1H-pyrazolo[4,3-c]pyridin-6-yl]urea, and the free base form of
1[3-(2-methylpyridin-4-yl)-1H-pyrazolo[4,3-c]pyridin-6-yl]-3-piperidin-3-ylurea,
1-[(1S)-2-hydroxy-1-phenylethyl]-3-[3-(2-methylpyridin-4-yl)-1H-pyrazolo[4,3-c]pyridin-6-yl]urea,
1-[3-(2-methylpyridin-4-yl)-1H-pyrazolo[4,3-c]pyridin-6-yl]-3-[(1S)-2,2,2-trifluoro-1-phenylethyl]urea,
1-[(1R)-1-(4-chlorophenyl)ethyl]-3-[3-(2-methylpyridin-4-yl)-1H-pyrazolo[4,3-c]pyridin-6-yl]urea,
1-[3-(3,6-dihydro-2H-pyran-4-yl)-1H-pyrazolo[4,3-c]pyridin-6-yl]-3-[(1R)-1-phenylethyl]urea,
1-[3-(3-methoxypropyl)-1H-pyrazolo[4,3-c]pyridin-6-yl]-3-[(1R)-1-phenylethyl]urea,
1-[(1R)-1-phenylethyl]-3-(3-propyl-1H-pyrazolo[4,3-c]pyridin-6-yl)urea,
1-[3-(2-methylpyridin-4-yl)-1H-pyrazolo[4,3-c]pyridin-6-yl]urea,
1-[(1R)-1-(4-fluorophenyl)ethyl]-3-(1H-pyrazolo [4,3-c]pyridin-6-yl)urea,
1-(3-cyclopropyl-1H-pyrazolo [4,3-c]pyridin-6-yl)-3-[(1R)-1-phenylethyl]urea,
1-(4-chlorobenzyl)-3-[3-(2-methylpyridin-4-yl)-1H-pyrazolo[4,3-c]pyridin-6-yl]urea,
1-(3-chlorobenzyl)-3-[3-(2-methylpyridin-4-yl)-1H-pyrazolo[4,3-c]pyridin-6-yl]urea,
1-{3-[6-(1-methylethoxy)pyridin-3-yl]-1H-pyrazolo[4,3-c]pyridin-6-yl}-3-[(1R)-1-phenylethyl]urea,
1-[3-(1-methyl-1H-pyrazol-4-yl)-1H-pyrazolo[4,3-c]pyridin-6-yl]-3-[(1R)-1-phenylethyl]urea,
1-[3-(4-fluorophenyl)-1H-pyrazolo[4,3 -c]pyridin-6-yl]-3-[(1R)-1-phenylethyl]urea,
1-[3-(2,6-dimethylpyridin-4-yl)-1H-pyrazolo[4,3-c]pyridin-6-yl]-3-[(1R)-1-phenylethyl]urea,
1-[3-(2-methylpyridin-4-yl)-1H-pyrazolo[4,3-c]pyridin-6-yl]-3-(naphthalen-1-ylmethyl)urea,
1-(3,4-dimethoxybenzyl)-3-[3-(4-fluorophenyl)-1H-pyrazolo[4,3-c]pyridin-6-yl]urea,
1-[3-(4-fluorophenyl)-1H-pyrazolo[4,3-c]pyridin-6-yl]urea,
1-(cyclopropylmethyl)-3-[3-(2-methylpyridin-4-yl)-1H-pyrazolo[4,3-c]pyridin-6-yl]urea,
1-tert-butyl-3-[3-(2-methylpyridin-4-yl)-1H-pyrazolo[4,3-c]pyridin-6-yl]urea,
hydroxycyclopropyl)methyl]-3-[3-(2-methylpyridin-4-yl)-1H-pyrazolo[4,3-c]pyridin-6-yl]urea,
1-(cyclopropylidenemethyl)-3-[3-(2-methylpyridin-4-yl)-1H-pyrazolo[4,3-c]pyridin-6-yl]urea,
1-azetidin-3-yl-3-[3-(2-methylpyridin-4-yl)-1H-pyrazolo[4,3-c]pyridin-6-yl]urea,
1-(2-methoxyethyl)-3-[3-(2-methylpyridin-4-yl)-1H-pyrazolo[4,3-c]pyridin-6-yl]urea,
1-(1-cyclopropyl-2,2,2-trifluoroethyl)-3-[3-(2-methylpyridin-4-yl)-1H-pyrazolo[4,3-c]pyridin-6-yl]urea,
1-[(1-methyl-1H-imidazol-5-yl)methyl]-3-[3-(2-methylpyridin-4-yl)-1H-pyrazolo[4,3-c]pyridin-6-yl]urea,
1-[3-(2-methylpyridin-4-yl)-1H-pyrazolo[4,3-c]pyridin-6-yl]-3-[(2-methyl-1,3-thiazol-4-yl)methyl]urea,
1-[3-(2-methylpyridin-4-yl)-1H-pyrazolo[4,3-c]pyridin-6-yl]-3-(pyrimidin-2-ylmethyl)urea,
1-[3-(2-methylpyridin-4-yl)-1H-pyrazolo[4,3-c]pyridin-6-yl]-3-(naphthalen-2-ylmethyl)urea,
1-methyl-3-[3-(2-methylpyridin-4-yl)-1H-pyrazolo[4,3-c]pyridin-6-yl]-1-(pyridin-3-ylmethyl)urea,
1-[3-(2-methylpyridin-4-yl)-1H-pyrazolo[4,3-c]pyridin-6-yl]-3-(2-pyridin-2-ylethyl)urea,
1-[3-(2-methylpyridin-4-yl)-1H-pyrazolo[4,3-c]pyridin-6-yl]-3-(pyrazin-2-ylmethyl)urea,
1-[3-(2-methylpyridin-4-yl)-1H-pyrazolo[4,3-c]pyridin-6-yl]-3-(1-pyridin-3-ylethyl)urea
1-(2-methoxyethyl)-3-[3-(2-methylpyridin-4-yl)-1H-pyrazolo[4,3-c]pyridin-6-yl]-1-(pyridin-3-ylmethyl)urea,
1-[(5-fluoropyridin-3-yl)methyl]-3-[3-(2-methylpyridin-4-yl)-1H-pyrazolo[4,3-c]pyridin-6-yl]urea,
1-(2,6-difluorobenzyl)-3-[3-(2-methylpyridin-4-yl)-1H-pyrazolo[4,3-c]pyridin-6-yl]urea,
1-(3-fluorobenzyl)-3-[3-(2-methylpyridin-4-yl)-1H-pyrazolo[4,3-c]pyridin-6-yl]urea,
1-[3-(2-methylpyridin-4-yl)-1H-pyrazolo[4,3-c]pyridin-6-yl]-3-[4-(trifluoromethyl) -benzyl]urea,
1-[3-(2-methylpyridin-4-yl)-1H-pyrazolo[4,3-c]pyridin-6-yl]-3-{6-[(2-phenylethyl) -amino]pyridazin-3-yl}urea,
1-(3-chloro-4-fluorobenzyl)-3-[3-(2-methylpyridin-4-yl)-1H-pyrazolo[4,3-c]pyridin-6-yl]urea,
1-[(1R)-1-(4-chlorophenyl)ethyl]-3-[3-(2-fluoropyridin-4-yl)-1H-pyrazolo[4,3-c]pyridin-6-yl]urea,
1-(3-chloro-4-fluorobenzyl)-3-[3-(2-fluoropyridin-4-yl)-1H-pyrazolo[4,3-c]pyridin-6-yl]urea,
1-[(1R)-1-(4-chlorophenyl)ethyl]-3-[3-(1-methyl-1H-pyrazol-4-yl)-1H-pyrazolo[4,3-c]pyridin-6-yl]urea,
1-(3-chloro-4-fluorobenzyl)-3-[3-(1-methyl-1H-pyrazol-4-yl)-1H-pyrazolo[4,3-c]pyridin-6-yl]urea,
1-[3-(2-methylpyridin-4-yl)-1H-pyrazolo[4,3-c]pyridin-6-yl]-3-phenylurea,
1-[(1R)-1-(3-chlorophenyl)ethyl]-3-[3-(2-methyl-2H-indazol-5-yl)-1H-pyrazolo[4,3-c]pyridin-6-yl]urea,
1-[(1R)-1-(4-fluorophenyl)ethyl]-3-[3-(2-methyl-2H-indazol-5-yl)-1H-pyrazolo[4,3-c]pyridin-6-yl]urea,
1-(3-chloro-4-fluorobenzyl)-3-[3-(2-methyl-2H-indazol-5-yl)-1H-pyrazolo[4,3-c]pyridin-6-yl]urea,
1-[(1R)-1-(4-chlorophenyl)ethyl]-3-[3-(2-methyl-2H-indazol-5-yl)-1H-pyrazolo[4,3-c]pyridin-6-yl]urea,
1-[3-(4-cyanophenyl)-1H-pyrazolo[4,3-c]pyridin-6-yl]-3-[(1R)-1-phenylethyl]urea,
1-[(1R)-1-phenylethyl]-3-{3-[(1E)-prop-1-en-1-yl]-1H-pyrazolo[4,3-c]pyridin-6-yl}urea,
1-(3-bromo-1H-pyrazolo[4,3-c]pyridin-6-yl)-3-[(1R)-1-(3-chloro-4-fluorophenyl)ethyl]urea,
1-[(1R)-1-(3-chloro-4-fluorophenyl)ethyl]-3-[3-(2-methylpyridin-4-yl)-1H-pyrazolo[4,3-c]pyridin-6-yl]urea,
1-[(1R)-1-(4-fluorophenyl)ethyl]-3-[3-(1-methyl-6-oxo-1,6-dihydropyridin-3-yl)-1H -pyrazolo[4,3-c]pyridin-6-yl]urea,
1-[(1R)-1-(3-chloro-4-fluorophenyl)ethyl]-3-[3-(1-methyl-1H-pyrazol-4-yl)-1H-pyrazolo[4,3-c]pyridin-6-yl]urea,
1-[(1R)-1-(3-chloro-4-fluorophenyl)ethyl]-3-[3-(4-fluorophenyl)-1H-pyrazolo[4,3-c]pyridin-6-yl]urea, 1-[(1R)-1-(3-chloro-4-fluorophenyl)ethyl]-3-[3-(1H-pyrazol-4-yl)-1H-pyrazolo[4,3-c]pyridin-6-yl]urea,
1-[(1R)-1-(3-chloro-4-fluorophenyl)ethyl]-3-[3-(2-chloropyridin-4-yl)-1H-pyrazolo[4,3-c]pyridin-6-yl]urea,
1-[(1R)-1-(3-chloro-4-fluorophenyl)ethyl]-3-[3-(3-chlorophenyl)-1H-pyrazolo[4,3-c]pyridin-6-yl]urea,
1-[4-(4-chlorophenyl)tetrahydro-2H-pyran-4-yl]-3-[3-(2-methylpyridin-4-yl)-1H-pyrazolo[4,3-c]pyridin-6-yl]urea,
1-(2,3-dihydro-1H-inden-1-yl)-3-[3-(2-methylpyridin-4-yl)-1H-pyrazolo[4,3-c]pyridin-6-yl]urea,
1-[7-bromo-3-(2-methylpyridin-4-yl)-1H-pyrazolo[4,3-c]pyridin-6-yl]-3-[(1R)-1-phenylethyl]urea,
1-[3-(2-aminopyrimidin-5-yl)-1H-pyrazolo[4,3-c]pyridin-6-yl]-3-[(1R)-1-(3-chloro-4-fluorophenyl)ethyl]urea,
1-[(1R)-1-(3-chloro-4-fluorophenyl)ethyl]-3-[3-(2-fluoropyridin-4-yl)-1H-pyrazolo[4,3-c]pyridin-6-yl]urea,
1-[(1R)-1-(3-chloro-4-fluorophenyl)ethyl]-3-(3-cyclopropyl-1H-pyrazolo[4,3-c]pyridin-6-yl)urea,
1-[3-(4-cyanophenyl)-1H-pyrazolo[4,3-c]pyridin-6-yl]-3-[(1R)-1-(4-fluorophenyl)ethyl]urea,
1-[(1R)-1-(3-chlorophenyl)ethyl]-3-[3-(4-cyanophenyl)-1H-pyrazolo[4,3-c]pyridin-6-yl]urea,
1-[1-(4-chlorophenyl)cyclopropyl]-3-[3-(2-methylpyridin-4-yl)-1H-pyrazolo[4,3-c]pyridin-6-yl]urea,
1-[3-(2-methyl-1,3-benzothiazol-6-yl)-1H-pyrazolo[4,3-c]pyridin-6-yl]-3-[(1R)-1-phenylethyl]urea,
1-[3-(2,3-dihydro-1,4-benzodioxin-6-yl)-1H-pyrazolo[4,3-c]pyridin-6-yl]-3-[(1R)-1-phenylethyl]urea,
1-{3-[4-(methylsulfonyl)phenyl]-1H-pyrazolo[4,3-c]pyridin-6-yl}-3-[(1R)-1-phenylethyl]urea, 1-[3-(1-methyl-1H-pyrazol-3-yl)-1H-pyrazolo[4,3-c]pyridin-6-yl]-3-[(1R)-1-phenylethyl]urea,
1-[3-(6-methylpyridazin-4-yl)-1H-pyrazolo[4,3-c]pyridin-6-yl]-3-[(1R)-1-phenylethyl]urea,
1-[3-(1-oxidopyridin-4-yl)-1H-pyrazolo[4,3-c]pyridin-6-yl]-3-[(1R)-1-phenylethyl]urea,
1-benzyl-3-[3-(2-methylpyridin-4-yl)-1H-pyrazolo[4,3-c]pyridin-6-yl]thiourea, and
1-[7-fluoro-3-(2-methylpyridin-4-yl)-1H-pyrazolo[4,3-c]pyridin-6-yl]-3-[(1R)-1-phenylethyl]urea,
or a pharmaceutically acceptable salt thereof 17. The compound of claim 15 selected from the group consisting of
1-[(3R)-1-(2-fluoro-6-methoxybenzyl)-piperidin-3-yl]-3-[3-(2-methylpyridin-4-yl)-1H -pyrazolo[4,3-c]pyridin-6-yl]urea,
1-[1-(2-fluoro-6-methoxybenzyl)-piperidin-3-yl]-3-[3-(2-methylpyridin-4-yl)-1H-pyrazolo[4,3-c]pyridin-6-yl]urea,
1-[3-(2-methylpyridin-4-yl)-1H-pyrazolo[4,3-c]pyridin-6-yl]-3-(2-phenylethyl)urea,
1-[3-(2-methylpyridin-4-yl)-1H-pyrazolo[4,3-c]pyridin-6-yl]-3-[(1R)-1-phenylethyl]urea,
1-(3,4-dichlorobenzyl)-3-[3-(2-methylpyridin-4-yl)-1H-pyrazolo[4,3-c]pyridin-6-yl]urea,
1-benzyl-3-[3-(2-methylpyridin-4-yl)-1H-pyrazolo[4,3-c]pyridin-6-yl]urea,
1-(2-hydroxy-1-phenylethyl)-3-[3-(2-methylpyridin-4-yl)-1H-pyrazolo[4,3-c]pyridin-6-yl]urea,
1-[(1S)-1-(4-fluorophenyl)ethyl]-3-[3-(2-methylpyridin-4-yl)-1H-pyrazolo[4,3-c]pyridin-6-yl]urea, and
1-[3-(2-methylpyridin-4-yl)-1H-pyrazolo[4,3-c]pyridin-6-yl]-3-(pyridin-3-ylmethyl)urea, and the free base form of
1-[(1S)-2-hydroxy-1-phenylethyl]-3-[3-(2-methylpyridin-4-yl)-1H-pyrazolo[4,3-c]pyridin-6-yl]urea,
1-[(1R)-1-(4-chlorophenyl)ethyl]-3-[3-(2-methylpyridin-4-yl)-1H-pyrazolo[4,3-c]pyridin-6-yl]urea,
1-[3-(3,6-dihydro-2H-pyran-4-yl)-1H-pyrazolo[4,3-c]pyridin-6-yl]-3-[(1R)-1-phenylethyl]urea,
1-[(1R)-1-phenylethyl]-3-(3-propyl-1H-pyrazolo[4,3-c]pyridin-6-yl)urea,
1-(3-cyclopropyl-1H-pyrazolo[4,3-c]pyridin-6-yl)-3-[(1R)-1-phenylethyl]urea, and
1-(4-chlorobenzyl)-3-[3-(2-methylpyridin-4-yl)-1H-pyrazolo[4,3-c]pyridin-6-yl]urea,
or a pharmaceutically salt of thereof.

18. The compound of claim 15 selected from the group consisting of:
1-(3-chlorobenzyl)-3-[3-(2-methylpyridin-4-yl)-1H-pyrazolo[4,3-c]pyridin-6-yl]urea,
1-[3-(1-methyl-1H-pyrazol-4-yl)-1H-pyrazolo[4,3-c]pyridin-6-yl]-3-[(1R)-1-phenylethyl]urea,
1-[3-(4-fluorophenyl)-1H-pyrazolo[4,3-c]pyridin-6-yl]-3-[(1R)-1-phenylethyl]urea,
1-[3-(2,6-dimethylpyridin-4-yl)-1H-pyrazolo[4,3-c]pyridin-6-yl]-3-[(1R)-1-phenylethyl]urea, 1-[3-(4-fluorophenyl)-1H-pyrazolo[4,3-c]pyridin-6-yl]urea,
1-[3-(2-methylpyridin-4-yl)-1H-pyrazolo[4,3-c]pyridin-6-yl]-3-[(2-methyl-1,3-thiazol-4-yl)methyl]urea,
1-[3-(2-methylpyridin-4-yl)-1H-pyrazolo[4,3-c]pyridin-6-yl]-3-(1-pyridin-3-ylethyl)urea
1-[(5-fluoropyridin-3-yl)methyl]-3-[3-(2-methylpyridin-4-yl)-1H-pyrazolo[4,3-c]pyridin-6-yl ]urea,
1-(2,6-difluorobenzyl)-3-[3-(2-methylpyridin-4-yl)-1H-pyrazolo[4,3-c]pyridin-6-yl]urea,
1-(3-fluorobenzyl)-3-[3-(2-methylpyridin-4-yl)-1H-pyrazolo[4,3-c]pyridin-6-yl]urea,
1-(3-chloro-4-fluorobenzyl)-3-[3-(2-methylpyridin-4-yl)-1H-pyrazolo[4,3-c]pyridin-6-yl]urea,
1-[(1R)-1-(4-chlorophenyl)ethyl]-3-[1-(2-fluoropyridin-4-yl)-1H-pyrazolo[4,3-c]pyridin-6-yl]urea,
1-(3-chloro-4-fluorobenzyl)-3-[3-(2-fluoropyridin-4-yl)-1H-pyrazolo[4,3-c]pyridin-6-yl]urea,
1-[(1R)-1-(4-chlorophenyl)ethyl]-3-[3-(1-methyl-1H-pyrazol-4-yl)-1H-pyrazolo[4,3-c]pyridin-6-yl]urea,
1-(3-chloro-4-fluorobenzyl)-3-[3-(1-methyl-1H-pyrazol-4-yl)-1H-pyrazolo[4,3-c]pyridin-6-yl]urea,
1-[(1R)-1-(3-chlorophenyl)ethyl]-3-[3-(2-methyl-2H-indazol-5-yl)-1H-pyrazolo[4,3-c]pyridin-6-yl]urea,
1-[(1R)-1-(4-fluorophenyl)ethyl]-3-[3-(2-methyl-2H-indazol-5-yl)-1H-pyrazolo[4,3-c]pyridin-6-yl]urea,
1-(3-chloro-4-fluorobenzyl)-3-[3-(2-methyl-2H-indazol-5-yl)-1H-pyrazolo[4,3-c]pyridin-6-yl]urea,
1-[(1R)-1-(4-chlorophenyl)ethyl]-3-[3-(2-methyl-2H-indazol-5-yl)-1H-pyrazolo[4,3-c]pyridin-6-yl]urea,
1-[3-(4-cyanophenyl)-1H-pyrazolo[4,3-c]pyridin-6-yl]-3-[(1R)-1-phenylethyl]urea,
1-[(1R)-1-phenylethyl]-3-{3-[(1E)-prop-1-en-1-yl]-1H-pyrazolo[4,3-c]pyridin-6-yl}urea,
1-[(1R)-1-(3-chloro-4-fluorophenyl)ethyl]-3-[3-(2-methylpyridin-4-yl)-1H-pyrazolo[4,3-c]pyridin-6-yl]urea,
1-[(1R)-1-(4-fluorophenyl)ethyl]-3-[3-(1-methyl-6-oxo-1,6-dihydropyridin-3-yl)-1H -pyrazolo[4,3-c]pyridin-6-yl]urea,
1-[(1R)-1-(3-chloro-4-fluorophenyl)ethyl]-3-[3-(1-methyl-1H-pyrazol-4-yl)-1H-pyrazolo[4,3-c]pyridin-6-yl]urea,
1-[(1R)-1-(3-chloro-4-fluorophenyl)ethyl]-3-[3-(1H-pyrazol-4-yl)-1H-pyrazolo[4,3-c]pyridin-6-yl]urea, 1-[3-(2-methyl-1,3-benzothiazol-6-yl)-1H-pyrazolo[4,3-c]pyridin-6-yl]-3-[(1R)-1-phenylethyl]urea, 1-[3-(2,3-dihydro-1,4-benzodioxin-6-yl)-1H-pyrazolo[4,3-c]pyridin-6-yl]-3-[(1R)-1-phenylethyl]urea, 1-{3-[4-(methylsulfonyl)phenyl]-1H-pyrazolo[4,3-c]pyridin-6-yl}-3-[(1R)-1-phenylethyl]urea, 1-[3-(6-methylpyridazin-4-yl)-1H-pyrazolo[4,3-c]pyridin-6-yl]-3-[(1R)-1-phenylethyl]urea, 1-[3-(1-oxidopyridin-4-yl)-1H-pyrazolo[4,3-c]pyridin-6-yl]-3-[(1R)-1-phenylethyl]urea, and 1-[7-fluoro-3-(2-methylpyridin-4-yl)-1H-pyrazolo[4,3-c]pyridin-6-yl]-3-[(1R)-1-phenylethyl]urea, or a pharmaceutically acceptable salt thereof.

19. A pharmaceutical composition comprising a compound of claim 1 and a pharmaceutically acceptable carrier.

20. A method for inhibiting ERK2 in a patient in need of such inhibition, said method comprising administering to said patient an effective amount of at least one compound of claim 1.

* * * * *